United States Patent
Mohammadi et al.

(10) Patent No.: US 6,682,921 B1
(45) Date of Patent: Jan. 27, 2004

(54) CRYSTALS OF THE TYROSINE KINASE DOMAIN OF NON-INSULIN RECEPTOR TYROSINE KINASES

(75) Inventors: Moosa Mohammadi, New York, NY (US); Joseph Schlessinger, New York, NY (US); Stevan R. Hubbard, Riverdale, NY (US)

(73) Assignee: New York University, New York, NY (US)

( * ) Notice: Subject to any disclaimer, the term of this patent is extended or adjusted under 35 U.S.C. 154(b) by 442 days.

(21) Appl. No.: 09/664,526

(22) Filed: Sep. 18, 2000

Related U.S. Application Data

(63) Continuation of application No. 09/188,809, filed on Nov. 9, 1998, now abandoned, which is a continuation of application No. 08/701,191, filed on Aug. 21, 1996, now Pat. No. 5,942,428.

(51) Int. Cl.$^7$ ............................ C12N 9/12; C12N 5/10; C07H 21/04

(52) U.S. Cl. ...................... 435/194; 435/325; 435/348; 435/320.1; 536/23.1; 536/23.2

(58) Field of Search ................................ 435/194, 325, 435/348, 320.1; 536/23.2, 23.1

(56) References Cited

U.S. PATENT DOCUMENTS

| | | | |
|---|---|---|---|
| 5,217,999 A | 6/1993 | Levitzki et al. | 514/613 |
| 5,229,501 A | 7/1993 | Keifer et al. | 530/399 |
| 5,302,606 A | 4/1994 | Spada et al. | 514/357 |
| 5,330,992 A | 7/1994 | Eissenstat et al. | 514/312 |

FOREIGN PATENT DOCUMENTS

| | | |
|---|---|---|
| WO | WO 91/15495 | 10/1991 |
| WO | WO 92/13870 | 8/1992 |
| WO | WO 92/20642 | 11/1992 |
| WO | WO 92/21660 | 12/1992 |
| WO | WO 94/03427 | 2/1994 |
| WO | WO 94/14808 | 7/1994 |
| WO | WO 96/40116 | 12/1996 |

OTHER PUBLICATIONS

Ausubel et al. (editor), *Current Protocols in Molecular Biology*, John Wiley & Sons (1994) (Table Of Contents For vols. 1 & 2).

Basilico et al., "The FGF family of growth factors and oncogenes," *Advances in Cancer Research* 59:116–165 (1992).

Bellot et al., "Ligand–induced transphosphorylation between different FGF receptors," *EMBO J.* 10:2849–2854 (1991).

Bellus et al., "A recurrent mutation in the tyrosine kinase domain of fibroblast growth factor receptor 3 causes hypochondroplasia," *Nature Genetics* 10:357–359 (1995).

Blaikie et al., "A Region in Shc Distinct from the SH2 Domain Can Bind Tyrosine–phosphorylated Growth Factor Receptors," *The Journal of Biological Chemistry* 269(51):32031–32034 (1994).

Blundell et al., *Protein Crystallography*, Academic Press (1976)(Table of Contents).

Bossemeyer et al., "Phosphotransferase and substrate binding mechanism of the cAMP–dependent protein kinase catalytic subunit from porcine heart as deduced from 2.0 A structure of the complex with $Mn^{2+}$ adenylyl imidodiphosphate and inhibitor peptide PKI (5–24)," *EMBO J.* 12:849–859 (1993).

Branden et al., "Introduction of Protein Structure" *Garland Publishing Inc.*, (1991) *New York*, pp. 269–273.

Brunger, "Free R value: A novel statistical quantity for assessing the accuracy of crystal structures," *Nature*, 355:472–475 (1992).

Brunger, *X–Plor (version 3.1) Manual* (1992)(Table of Contents).

Burgess et al., "The heparin–binding (fibroblast) growth factor family of proteins," *Ann. Rev. Biochem.* 58:575–606 (1989).

Burgess et al., "The fibroblast growth factor family: Multifunctional regulators of cell proliferation," *Cell Proliferation in Cancer*, Pusztai et al., eds. Oxford University Press, Oxford; Ch. 7 pp. 154–195 (1994).

Cantley et al., "Oncogenes and Signal Transduction," *Cell* 64:281–302 (1991).

Chan et al., "Activation ZAP–70 kinase activity by phosphorylation of tyrosine 493 is required for lymphocyte antigen receptor function," *EMBO J.* 14(11):2499–2508 (1995).

Clark et al., "Loss of three major auto phosphorylation sites in the EGF receptor does not block the mitogenic action of EGF," *Cell. Physiol.* 134(3):421–428 (1988).

Cowtan, "'dm': An automated procedure for phase improvement by density modification," *CCP4 and ESF–EACBM Newsletter* (joint) 31:34–38 (1994).

Creighton, *Proteins: Structures and Molecular Principles* pp. 79–86, W.H. Freeman and Co., New York (1983).

(List continued on next page.)

Primary Examiner—Nashaat T. Nashed
(74) Attorney, Agent, or Firm—Beth A. Burrous; Foley & Lardner

(57) ABSTRACT

Crystals of the tyrosine kinase domain of cytoplasmic tyrosine kinases and receptor tyrosine kinases that undergo ligand-mediated receptor dimerization are provided. In particular, crystals of a mutant of the tyrosine kinase domain of fibroblast growth factor receptor 1 (FLGK), alone and in complex with a non-hydrolyzable adenosine triphosphate analogue, are provided. Also provided are the high resolution three dimensional structures of crystalline FLGK, both alone and in co-complex with the adenosine triphosphate analogue, as determined by X-ray diffraction.

4 Claims, 9 Drawing Sheets

OTHER PUBLICATIONS

Figure 1:
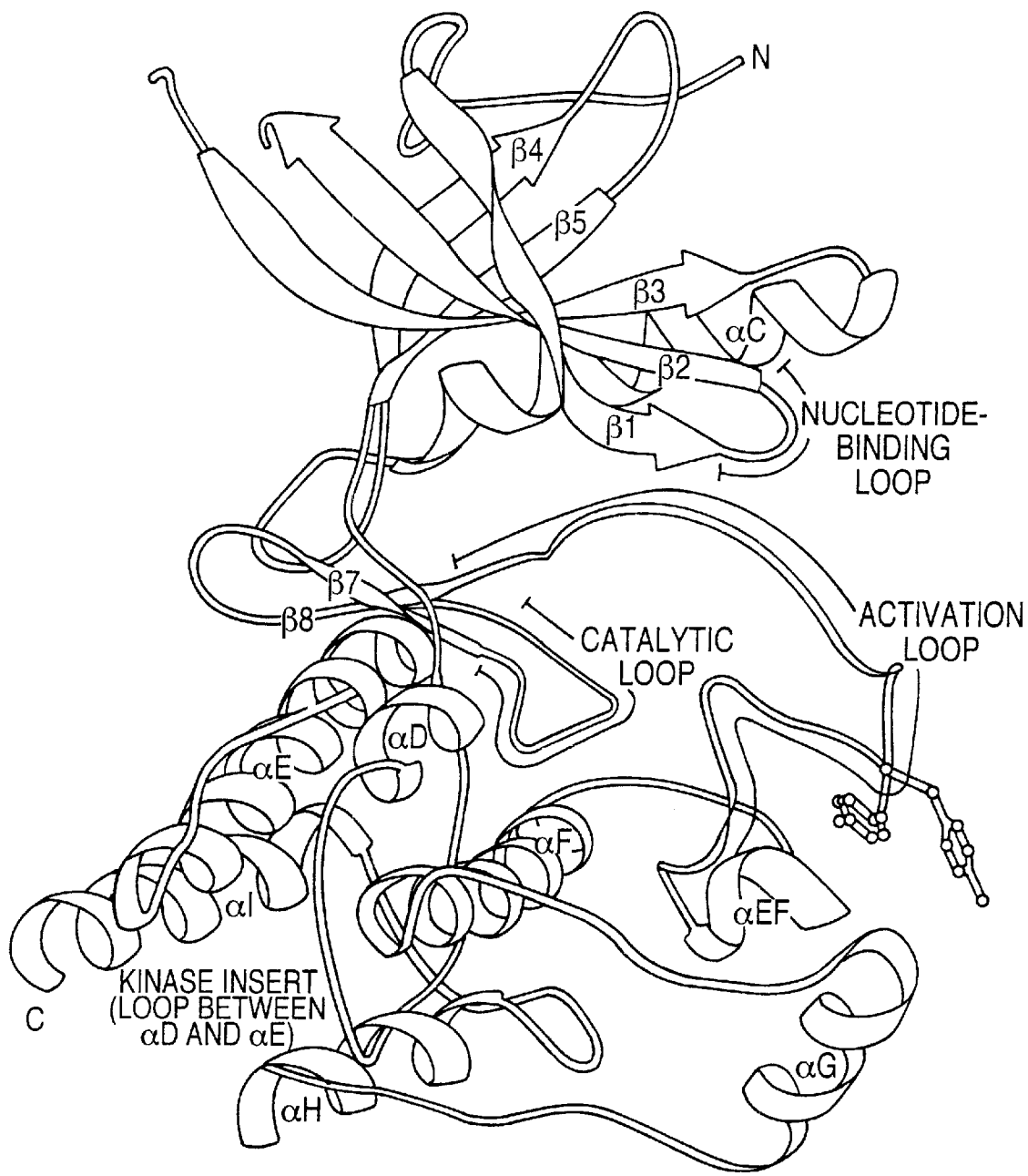

Debondt et al., 1993, "Crystal Structure of Cyclin–Dependent Kinase 2," *Nature* 363:595–602.

Devore et al., "An FGF Receptor Signaling Pathway is Required for the Normal Cell Migrations of the Sex Myoblasts in *C. elegans* Hermaphrodites," *Cell* 83:611–620 (1995).

Ducruix et al., *Crystallization of Nucleic Acids and Proteins: A Practical Approach*, IRL Press, Oxford, England (1992)(Table of Contents).

Ellis et al., "Replacement of insulin receptor tyrosine residues 1162 and 1163 comprises insulin–stimulated kinase activity and uptake of 2–deoxyglucose," *Cell* 45:721–732 (1986).

Flores–Riveros et al., *J. Biol. Chem.* 264:21557–21572 (1989).

Friesel et al., "Spatially restricted expression of fibroblast growth factor receptor–2 during Xenopus development," *Development* 116(4):1051–1058 (1992).

Friesel et al., "cDNA cloning and developmental expression of fibroblast growth factor receptors from *Xenopus laevis*," *Mol. Cell. Biol.* 11(5):2481–2488 (1991).

Givol et al., "Complexity of FGF receptors: Genetic basis for structural diversity and functional specificity," *FASEB J.* 6(15):3362–3369 (1992).

Goldsmith et al., "Protein Kinases," *Current Opinion in Structural Biology* 4(6):833–840 (1994).

Gotoh et al., "A highly conserved tyrosine residue at codon 845 within the kinase domain is not required for the transforming activity of human epidermal growth factor receptor," *Biochem. Biophys. Res. Commun.* 186(2):768–774 (1992).

Hendrickson, "Transformations to optimize the superposition of similar structures," *Acta Crystallogr.* A35:158–163 (1979).

Honegger et al., "Kinetic parameters of the protein tyrosine kinase activity of Egf–receptor mutants with individually altered autophosphorylation sites," *EMBO J.* 7:3053–3060 (1988).

Honegger et al., "Biological activities of EGF–receptor mutants with individually altered autophosphorylation sites," *EMBO J.* 7(10):3045–3052 (1988).

Hu et al., 1994, "Insights Into Autoregulation from the Crystal Structure of Twitchin Kinase," *Nature* 369:581–584.

Hubbard et al., 1994, "Crystal Structure of Tyrosine Kinase Domain of the Human Insulin Receptor," *Nature* 372:746–754.

Hunter, "Protein kinase classification," *Methods Enzymol.* 200:3–37 (1991).

Jeffrey et al., "Mechanism of CDK activation revealed by the structure of a cyclinA–CDK2 complex," *Nature* 376:313–320 (1995).

Johnson et al., "Active and inactive protein kinases: Structural basis for regulation" *Cell* 85:149–158 (1996).

Johnson et al., "Structural and functional diversity in the FGF receptor multigene family," *Adv. Cancer Res.* 60:1–41 (1993).

Jones, "Interactive computer graphics: FRODO," *Methods in Enzymology* 115:157–171 (1985).

Kabsch et al., "Dictionary of protein secondary structure: Pattern recognition of hydrogen bonded and geometrical features," *Biopolymers* 22:2577–2637 (1983).

Klagsbrun et al., "A dual receptor system is required for basic fibroblast growth factor activity," *Cell* 67(2):229–231 (1991).

Klambt et al., "Breathless, A Drosophila FGF receptor homolog, is essential for migration of tracheal and specific midline glial cells," *Genes & Development* 6:1668–1678 (1992).

Kmiecik et al., "Activation and suppression of pp60$^{c-src}$ transforming ability by mutation of its primary sites of tyrosine phosphorylation," *Cell* 49:65–73 (1987).

Knighton et al., 1991, "Crystal Structure of the Catalytic Subunit of Cyclic Adenosine Monophosphate–Dependent Protein Kinase," *Science* 253:407–414.

Komada et al., "Regulatory role of major tyrosine autophosphorylation site of kinase domain of c–Met receptor (scatter factor/hepatocyte growth factor receptor)," *J. Biol. Chem.* 269:16131–16136 (1994).

Kusari et al., "Insulin resistance an diabetes due to different mutations in the tyrosine kinase domain of both insulin receptor gene alleles," *J. Biol. Chem.* 266:5260–5267 (1991).

Laskowski et al., "Computer programs," *J. Appl. Cryst.* 26:283–291 (1993).

Lattman, "Use of the rotation and translation functions," *Methods in Enzymology*, 115:55–77 (1985).

Levitzki and Gazit, "Tyrosine Kinase Inhibition: An Approach to Drug Development," *Science* 267:1782–1788 (1995).

Longati et al., Tyrosine $^{1234-1235}$ are critical for activation of the tyrosine kinase encoded by the MET proto–oncogene (HGF receptor) *Oncogene* 9:49–57 (1994).

McPherson, "Current approaches to macromolecular crystallization," *Eur. J. Biochem.* 189:1–23 (1990).

McPherson, *Preparation and Analysis of Protein Crystals*, John Wiley, New York (1982) (Table of Contents).

Middlemas et al., "Identification of TrkB autophosphorylation sites and evidence that phospholipase C–γ1 is a substrate of the TrkB receptor," *J. Biol. Chem.* 269:5458–5466 (1994).

Mohammadi et al., "A tyrosine–phosphorylated carboxy–terminal peptide of the fibroblast growth factor receptor (FIg) is a binding site for the SH2 domain of phospholipase C–γ1," *Mol. Cell. Biol.* 11:5068–5078 (1991).

Mohammadi et al., "Structure of the FGF Receptor Tyrosine Kinase Domain Reveals a Novel Autoinhibitory Mechanism" *Cell* 86, 577–587 (1996).

Naski, "Graded activation of fibroblast growth factor receptor 3 by mutations causing achondroplasia and thanatophoric dysplasia," *Nature Genetics* 13:233–237 (1996).

Navaza, "AmoRe: An automated package for molecular replacement," *Acta Crystallogr.* A50:157–163 (1994).

Nicholls et al., "Protein folding and association: Insights from the interfacial and thermodynamic properties of hydrocarbons," *Proteins* 11:281–296 (1991).

Ornitz et al., "Heparin is required for cell–free binding of basic fibroblast growth factor to a soluble receptor and for mitogenesis in whole cells," *Mol. Cell. Biol.* 12(1):240–247 (1992).

Otwinowski, *Isomorphous Replacement and Anomalous Scattering*, Evans and Leslie eds. (Daresbury, United Kingdom: Daresbury Laboratory), 80–86 (1991).

Otwinowski, *Proceedings of the CCP4 Study Weekend*, Sawyer et al., eds. (Daresbury, United Kingdom: SERC Daresbury Laboratory), 56–62 (1993).

Pawson and Schlessinger, "SH2 and SH3 domains," *Current Biology* 3(7):434–442 (1993).

Peters et al., "Point mutation of an FGF receptor abolishes phosphatidylinositol turnover and $ca^{2+}$ flux but not mitogenesis," *Nature* 358:678–781 (1992).

Piwnica–Worms et al., "Tyrosine phosphorylation regulates the biochemical and biological properties of $pp60^{c-src}$," *Cell* 49:75–82 (1987).

Rodrigues et al., "Autophosphorylation modulates the kinase activity and oncogenic potential of the Met receptor tyrosine kinase," *Oncogene* 9:2019–2027 (1994).

Rossman (ed.), "The molecular replacement method A collection of papers on the use of non–crystallographic symmetry," *Int. Sci. Rev. Ser*. No. 13, Gordon & Breach, New York (1972) (Table of Contents).

Shishido et al., "Two FGF–receptor homologues of Drosophila: one is expressed in mesodermal primordiumin early embryos," *Development* 117:751–761 (1993).

Spivak–Kroizman et al., "Heparin–induced oligomerization of FGF molecules is responsible for FGF receptor dimerization, activation, and cell prolifertion," *Cell* 79:1015–1024 (1994).

Stephens et al., "Trk receptors use redundant signal transduction pathways involving SHC and PLC–γ1 to mediate NGF response," *Neuron* 12:691–705 (1994).

Taylor et al., "How do protein kinases discriminate between serine/threonine and tyrosine? Structural insights from the insulin receptor protein–tyrosine kinase," *FASEB J*. 9(13):1255–1266 (1995).

Taylor et al., "Three protein kinase structures define a common motif," *Structure* 2(5):345–355 (*1994*).

Ueno et al., "A truncated form of fibroblast growth factor receptor 1 inhibits signal transduction by multiple types of fibroblast growth factor receptor," *J. Biol. Chem*. 267:1470–1476 (1992).

Ullrich and Schlessinger, "Signal Transduction by Receptors with Tyrosine Kinase Activity," *Cell* 61:203–212 (1990).

Van Der Geer et al., 1994, "Receptor Protein–Tyrosine Kinases and Their Signal Transduction Pathways," *Ann. Rev. Cell Biol.* 10:251–337.

Venkataraman et al., "Preferential self–association basic fibroblast growth factor is stabilized by heparin during receptor dimerization and activation," *Proc. Natl. Acad. Sci. USA* 93(2):845–850 (1996).

Wange et al., "Activating and inhibitory mutations in adjacent tyrosines in the kinase domain of ZAP–70," *J. Biol. Chim.* 270(32):18730–18733 (1995).

Weber, "Physical principles of protein characterization," *Adv. Protein Chem.* 41:1–36 (1991).

Wei et al., 1994, "Protein Kinase Superfamily—Comparisons of Sequence Data With Three–Dimensional Structures," *Curr. Opin. Struct. Biol.* 4:450–455.

Zhang et al., 1994, "Atomic Structure of the MAP Kinase ERK2 at 2.3 A Resolution," *Nature* 367:704–711.

Zhang et al., "The regulatory role of known tyrosine autophosphorylation sites of the insulin receptor kinase domain," *J. Biol. Chem.* 266:990–996 (1991).

Zheng et al., 1993 "Crystal Structure of the Catalytic Subunit of cAMP–Dependent Protein Kinase Complexed with MgATP and Peptide Inhibitor," *Biochemistry* 32:2154–2161.

Adnane et al., "BEK and FLG, two receptors to members of the FGF family, are amplified in subsets of human breast cancers," *Oncogene*, 6:659–663 (1991), ©Macmillan Press, Ltd.

Akbasak & Sunar–Akbasak et al., "Oncogenes: cause or consequence in the development of glial tumors," *J. Neurol. Sci.*111:119–133 (1992), ©Elsevier Science Publishers B.V.

Arteaga et al., "Blockade of the Type I Somatomedin Receptor Inhibits Growth of Human Breast Cancer Cells in Athymic Mice," *J. Clin. Invest.*84:1418–1423, Nov. 1989, © The American Society for Clinical Investigation, Inc.

Bartlett et al., "Caveat: A Program to Facilitate the Structure–derived Design of Biologically Active Molecules," *Chemical and Biochemical Problems*182–196 (1989).

Baserga, "Oncogenes and the Strategy of Growth Factors," *Cell*79:927–930, Dec. 16, 1994, ©Cell Press.

Baserga, "The Insulin–like Growth Factor I Receptor: A Key to Tumor Growth!" *Cancer Research*55:249–252, Jan. 15, 1995.

Basilico & Moscatelli, "The FGF Family of Growth Factors and Oncongenes," *Adv. Cancer Res.*59:115–165 (1992).

Blundell et al., "Knowledge–based protein modeling and design," *Eur. J. Biochem.*172:513–520 (1988).

Bohm, "On the use of LUDI to search the Fine Chemicals Directory for ligands of proteins of known three–dimensional structure," *J. Comp. Aided Molec. Design*8:623–632 (1994).

Bolen et al., "The Src family of tyrosine kinase in hemopoietic signal transduction," *Faseb J.*6:3403–3409, Dec. 1992.

Clark et al., "Pro Ligand: An approach to de novo molecular design. 1. Application to the design of organic molecules," *J. Comp. Aided Molec. Design*9:13–32 (1995).

Colman, "Structure–based drug design," *Current Opinion in Struc. Biol.*4:868–874 (1994).

Coppola et al., "A Functional Insulin–Like Growth Factor I Receptor is Required for the Mitogenic and Transforming Activities of the Epidermal Growth Factor Receptor," *Molecular and Cellular Biology*14(7):4588–4595, Jul. 1994, ©American Society for Microbiology.

Cowtan, "Protein Crystallography," *CCP4 and ESF–EACBM Newsletter*(joint) 31:34–38.

DeVries et al., "The fms–like Tyrosine Kinase, a Receptor for Vascular Endothelial Growth Factor," *Science*255:989–991, Feb. 21, 1992.

Deng, et al., "Fibroblast growth factor receptor 3 is a negative regulator of bone growth," *Cell*84:911–92, Mar. 22, 1996, ©Cell Press.

Dickson et al., "Tyrosine kinase receptor–nuclear protooncogene interactions in breast cancer," *Cancer Treatment Res.*61:249–273 (1992) ©Kluwer Academic Publishers, Boston, MA, USA.

Fantl et al., "Distinct Phosphotyrosines on a Growth Factor Receptor Bind to Specific Molecules that Mediate Different Signaling Pathways," *Cell*413–423, May 1, 1992, ©Cell Press.

Ferrara & Henzel, "Pituitary Follicular Cells Secrete a Novel Heparin–Binding Growth Factor Specific for Vascular Endothelial Cells," *Biochemical Biophysical Research Communicationsn*161(2):851–858, Jun. 15, 1989, ©Academic Press, Inc.

Floege et al., "Factors involved in the regulation of mesangial cell proliferation in vitro and in vivo," *Kidney International*43:S47–S54, ©International Society of Nephrology.

Folkman & Klagsbrun, "Angiogenic Factors," *Science*235:442–447, Jan. 23, 1987.

Folkman & Shing, "Angiogenesis," *J. Biol. Chem.* 267(16):10931–10934, Jun. 5, 1992, ©The Americah Society for Biochemistry and Molecular Biology, Inc., USA.

Folkman, "Ch. 24. Angiogenesis," *Congress of Thrombosis and Haemostasis*(Verstraete et al., eds.) Leuven University Press, Leuven, 583–296 (1987).

Folkman, "What is the Evidence that Tumors are Angiogensis Dependent!" *Journal of the natiional Cancer Institute*, 82(1):4–6, Jan. 3, 1990.

Goodford, "A Computational Procedure for Determining Energetically Favorable Binding Sites on Biologically Important macromolecules," *J. Med. Chem.*, 28:849–857 (1985).

Goodsell and Olson, "Automated Docking of Substrates to Proteins by Simulated Annealing," *Proteins: Structure, Function, and Genetics*, 8:195–202 (1990).

Greer, "Model Structure for the Inflammatory Protein C5a," *Science*, 228:1055–1060 (1985).

Houck et al., "Dual Regulation of Vascular Endothelial Growth Factor Bioavailability by Genetic and Proteolytic Mechanisms," *J. Biol. Chem.*, 267(36):26031–26037, Dec. 25, 1992, ©The American Society for Biochemistry and Molecular Biology, Inc., USA.

JABS et al., "Jackson–Waeiss and Crouzon syndromes are allelic with mutations in fiborblast growth factor receptor 2," *Nature Genetics*, 8:275–279, Nov. 1994.

Jaye et al., "Fibroblast growth factor receptor tyrosine kinases: Molecular analysis and signal transduction," *Biochimica et Biophysica Acta*, 1135:185–199 (1992), ©Elsevier Science Publishers B.V.

Jones et al., "Crystallization of authentic recombinant human growth hormone," *Biotechnology*, 5:499–500 (1987).

Klagsbrun and Edelman, "Biological and biochemical properties of fibroblast growth factors," *Arterioschlerosis*, 9:269–278, May/Jun. 1989.

Klagsbrun and Soker, "VEGF/NPF: the angiogenesis factor found!" *Current biology*, 3(10):699–7023 (1993).

Kline et al., "Studies by 1H Nuclear Magnetic Resonance and Distance Geometry of the Solution Conformation of the α–Amylase Inhibitor Tendamistat," *J. Molecular Biology*, 189:377–382 (1986).

Knighton et al., "Crystal Structure of the Catalytic Subunit of Cyclic Adenosine Monophosphate–Dependent Protein Kinase," *Science*, 253:407–414, Jul. 26, 1991.

Knighton et al., "Structural Basis of the Intrasteric Regulation of Myosin Light Chain Kinases," *Science*258:130–135 (1992).

Koch et al., "SH2 and SH3 Domains: Elements that control interactions of cytoplasmic signaling proteins," *Science*252:668–674, May 3, 1991.

Korc et al., "Overexpression of the epidermal growth factor in human panreatic cancer is associated with concomitant increases in the levels of epidermal growth factor and transforming growth factor alpha," *J. Clin. Invest.*90:1352–1360, Oct. 1992, ©The American Society for Clinical Investigation, Inc.

Kumabe et al., "Amplification of α–platelet–derived growth factor receptor gene lacking an exon coding for a portion of the extracellular region in a primary brain tumor of glial origin," *Oncogene*7:627–633, (1992), ©Macmillan Press Ltd.

Kuntz et al., "A geometric approach to macromolecule–ligand interactions," *J. Mol. Biol.*162:269–288 (1982).

Kuntz et al., "Structure–based molecular design," *Acc. Chem. Res.*27:117–123 (1994).

Laskowski et al., "Procheck: a computer program to check the stereochemical quality of protein structures," *J. Appl. Cryst.*26:283–2291 (1993).

Lee and Donoghue, "Intracellular retention of membrane–anchored v–sis protein abrogates autocrine signal transduction,," *Journal of Cell Biology*118(5):1057–1070, Sep. 1992, ©The Rockefeller University Press.

Macauley et al., "Autocrine function for insulin–like growth factor I in human small cell lung cancer cell lines and fresh tumor cells," *Cancer Research*50:2511–2517, Apr. 15, 1990.

March et al., *Advanced Organic Chemistry; Reactions, Mechanism, and Structure*, New York, McGraw Hill (Mar. 1994) (Table of Contents), John Wiley & Sons.

Meng, et al., "Automated docking with grid–based energy evaluation," *J. Compt. Chem.*13:505–524 (1992).

Miller et al., "FLOG: A system to select 'quasi–flexible'ligands complementary to a receptor of known three–dimensional structure," *J. Comp. Aided Molec. Design.* 8:153–174 (1994).

Miranker and Karplus, "Functionally maps of binding sites: A multiple copy of simultaneous search method," *Proteins: Structure, Function, and Genetics*11:29–34 (1991).

Mohammadi e tal., "Identification of six novel autophosphorylatio sites on fibroblast growth factor receptor 1 and elucidation of their importance in receptor activation and signal transduction," *Mol. Cell Biol.*16:977–989, Mar. 1996, ©American Society for Microbiology.

Muenke et al., "A common mutation in the fibroblast growth factor receptor 1 gene in Pfeiffer syndome," *Nature Genetics*8:269–274, Nov. 1994.

Nicholls et al., "Protein folding and association: Insights from the interfacial and thermodynamic properties of hydrocarbons," *Proteins: Structure Function and Genetics*11:281–296 (1991).

Pflugrath et al., "Crystal Structure Determination Refinement and the Molecular Model of the α–Amylase Inhibitor hoe–467 A," *J. Mol. Biology*189:383–385 (1986).

Plate et al., "Vascular endothelial growth factor is potential tumor angiogenesis factor in human gliomas in vivo," *Nature*359:845–848, Oct. 29, 1994.

Plowoman et al., "Receptor Tyrosine kinases as Targets for Drug Intervention," *DN&P*7(6):334–339, Aug. 1994.

Sandberg–Nordqvist et al., "Characterization of Insulin–Like Growth Factor 1 in Human Primary Brain Tumors," *Cancer Research*53:2475–2478, Jun. 1, 1993.

Schlessinger and Ullrich, "Growth Factor Signaling by Receptor Tyrosine Kinases," *Neuron*9:383–391, Sep. 1992, ©Cell Press.

Schlessinger et al., "Regulation of growth factor activation by proteoglycans: What is the role of thel ow affinity receptors!" *Cell*83:357–360, Nov. 3, 1995, ©Cell Press.

Shiang et al., "Mutations in the transmembrane domain of FGFR3 cause the most common genetic form of dwarfism, anchondroplasis," *Cell*78:335–342, Jul. 29, 1994, ©Cell Press.

Shibuya et al., "Nucleotide sequence and expression of a novel human receptor–type tyrosine kinase gene (fit) closely related to the fms family," *Oncogene*5:519–524 (1990).

Slamon et al., "Studies of the Her–2/neu photo–oncogene in human breast and ovarian cancer," *Science* 244:707–712, May 12, 1989.

Songyang et al., "SH2 domains recognize specific phosphopeptide sequences," *Cell* 72: 767–778, Mar. 23, 1993, ©Cell Press.

Songyang et al., "Specific motifs recognized by the SH2 domains of Csk, 3BP2, fps/fes, GRB–2, HCP, SHC, Syk and Vav," *Molecular and Cellular Biology*, 14(4):2777–2785, Apr. 1994, ©American Society for Microbiology.

Shweiki et al., "Vascular endothelial growth factor induced by hypoxia may mediate hypoxia–initiated angiogenesis," *Natur* 359:843–845, Oct. 29, 1992.

Tavormina et al., "Thanatophoric dysplasia (types I and II) caused by distinct mutations in fibroblast growth factor receptor 3," *Nature Genetics* 9:321–328, Mar. 1995.

Torp et al., "Expression of the epidermal growth factor receptor gene in human brain metastases," *AMPIS* 100:713–719 (1992).

Tuzi et al., "Expression of growth factor receptors in human brain tumours," *Br. J. Cancer* 63:227–233 (1991).

Vaisman et al., "Characterization of the receptors for vascular endothelial growth factor," *J. Biol. Chem.* 265: 19461–19466, Nov. 15, 1990, ©The American Society for Biochemistry and Molecular Biology.

Weber, "Physical Principles of Protein Crystallization," *Adv. Protein Chem.* 41:1–36 (1991).

Webster et al., "Constitutive activation of fibroblast growth factor receptor 3 by the transmembrane domain point mutation found in achondroplasia," *Embo J.* 15(3):520–527 (1996), ©Oxford University Press.

Wei et al., "Expression, Characterization, and Crystallization of the Catalytic Fore of the Human Insulin Receptor Protein–tyrosine Kinase Domain," *Journal of Biological Chemistry* 270(14):8122–8130, Apr. 7, 1995, ©The American Society for Biochemistry and Molecular Biology, Inc., USA.

Weidner et al., "Tumor Angiogenesis and Metastasis–Correlation in Invasive Breast Carcinoma," *New England J. Medicine* 324(1):1–7, Jan. 3, 1991, ©the Massachusetts Medical Society, USA.

Wuthrich, "Chapter 10, Three–Dimensional Protein Structures by NMR", *NMR of Protein and Nucleic Acids* 176–199 (1986).

FIG. 6A-1

FIG. 6B

```
         465
FGFR1_h  LPEDPRWELP RDRLVLGK-P LGEGCFGQVV LAEAIGLDKD KPNRVTKVAV KMLKSDATEK DLSDLISEME MMKMI-GKHK
  SRC_h  GLAKDAWEIP RESLRLEV-K LGQGCFGEVW MGTW------ NGT--TRVAI KTLKPGTMSP -E--AFLQ-E AQVMKKLRHE
  BRK_h  LPHWDDWERP REEFTLCR_K LGSGYFGEVF EGLW------ KDR--VQVAI KVISRDNLLH -Q--QMLQSE IQAMKKLRHK
  BTK_h  GLGYGSWEID PKDLTFLK-E LGTGQFGVVK YGKW------ RGQYD--VAI KMIKEGSMSE -D--EFIE-E AKVMMNLSHE
  CSK_h  EFYRSGWALN MKELKLLQ-T IGKGEFGDVM LGDY------ RGN---KVAV KCIKNDA-TA -Q--AFL-AE ASVMTQLRHS
  ABL_h  SPNYDKWEME RTDITMKH-K LGGGQYGEVY EGVW------ K-KYSLTVAV KTLKEDTMEV -E--EFLK-E AAVMKEIKHP
ZAP70_h  LKDKKLF-LK RDNLLIADIE LGCGNFGSVR QGVY-----RM RKKQ-IDVAI KVLKQG--TE KADTEEMMRE AQIMHQLDNP
  FES_h  AVPKDKWVLN HEDLVLGE-Q IGRGNFGEVF SGR------- LRADNTLVAV KSCRETLPPD LKAK-FLQ-E ARILKQYSHP
  FAK_h  MPSTRDYEIQ RERIELGRC- IGEGQFGDVH QGIY----MS PENPALAVAI KTCKNC--TS DSVREKFLQE ALTMRQFDHP
 JAK1_h  PTEVDPTHFE KRFLKRIR-Q LGEGHFGKVE LCRY----DP EDNTGEQVAV KSLKPE--SG GNHIADLKKE IEILRNLYHE
  ACK_h  PLQSLTCLIG EKDLRLLE-K LGDGSFGVVR RGEW----DA PSGKTVSVAV KCLKPDVLSQ PEAMDDFIRE VNAMHSLDHR
              I                                           II                  III

543
FGFR1_h  NIINLLGACT -QDGP-LYVI VEYASKGNLR EYLQARRPPG LEYCYNPSHN PEEQLSSKDL VSCAYQVARG MEYLASKKCI
  SRC_h  KLVQLYAVVS -E-EP-IYIV TEYMSKGSLL DFLKGET--- ---------- -GKYLRLPQL VDMAAQIASG MAYVERMNYV
  BRK_h  HILALYAVVS VG-DP-VYII TELMAKGSLL ELLRDSD--- ---------- -EKVLPVSEL LDIAWQVAEG MCYLESQNYI
  BTK_h  KLVQLYGVCT KQR-P-IFII TEYMANGCLL NYLRE-M--- ---------- -RHRFQTQQL LEMCKDVCEA MEYLESKQFL
  CSK_h  NLVQLLGVIV EEKGG-LYIV TEYMAKGSLV DYLRSRG--- ---------- -RSVLGGDCL LKFSLDVCEA MEYLEGNNFV
  ABL_h  NLVQLLGVCT REP-P-FYII TEFMTYGNLL DYLRECN--- ---------- -RQEVNAVVL LYMATQISSA MEYLEKKNFI
ZAP70_h  YIVRLIGVCQ AEA---LMLV MEMAGGGPLH KFLVGK---- ---------- -REEIPVSNV AELLHQVSMG MKYLEEKNFV
  FES_h  NIVRLIGVCT -QKQP-IYIV MELVQGGDFL TFLRTE---- ---------- -GARLRVKTL LQMVGDAAAG MEYLESKCCI
  FAK_h  HIVKLIGVIT ENP---VWII MELCTLGELR SFLQVR---- ---------- -KYSLDLASL ILYAYQLSTA LAYLESKRFV
 JAK1_h  NIVKYKGICT EDGGNGIKLI MEFLPSGSLK EYLPKN---- ---------- -KNKINLKQQ LKYAVQICKG MDYLGSRQYV
  ACK_h  NLIRLYGVVL TPP---MKMV TELAPLGSLL DRLRKH---- ---------- -QGHFLLGTL SRYAVQVAEG MGYLESKRFI
              IV             V                                      VIa                 VIb

621
FGFR1_h  HRDLAARNVL VTEDNVMKIA DFGLARDIH- HIDYYKKTTN GRLPVKWMAP EAL-FDRIYT HQSDVWSFGV LLWEIFTLGG
  SRC_h  HRDLRAANIL VGENLVCKVA DFGLARLIE- DNEYTARQGA -KFPIKWTAP EAALYGR-FT IKSDVWSFGI LLTELTTKGR
  BRK_h  HRDLAARNIL VGENTLCKVG DFGLARLIK- EDVYLSHD-H -NIPYKWTAP EALSRGH-YS TKSDVWSFGI LLHEMFSRGQ
  BTK_h  HRDLAARNCL VNDQGVVKVS DFGLSRYVL- DDEYTSSVGS -KFPVRWSPP EVLMYSK-FS SKSDIWAFGV LMWEIYSLGK
  CSK_h  HRDLAARNVL VSEDNVAKVS DFGLTK---- -EASSTQDTG -KLPVKWTAP EALREKK-TK TKSDVWSFGI LLWEIYSFGR
  ABL_h  HRDLAARNCL VGENHLVKVA DFGLSRLMT- GDTYTAHAGA -KFPIKWTAP ESLAYNK-FS IKSDVWAFGV LLWEIATYGM
ZAP70_h  HRDLAARNVL LVNRHYAKIS DFGLSKALGA DDSYYTARSA GKWPLKWYAP ECINFRK-FS SRSDVWSYGC TMWEALSYGQ
  FES_h  HRDLAARNCL VTEKNVLKIS DFGMSREEA- DGVYAASGGS RQVPVKWTAP EALNYGR-YS SESDVWSFGI LLWETFSLGA
  FAK_h  HRDIAARNVL VSSNDCVKLG DFGLSRYME- DSTYYKA-SK GKLPIKWMAP ESINFRR-FT SASDVWMFGV CMWEILMHGV
 JAK1_h  HRDLAARNVL VESEHQVKIG DFGLTKAIET DKEYYTVKDD RDSPVFWYAP ECLMQSK-FY IASDVWSFGV TLHELLTYCD
  ACK_h  HRDLAARNLL LATRDLVKIG DFGLMRALPQ NDDHYVMQEH RKVPFAWCAP ESLKTRT-FS HASDTWMFGV TLWEMFTYGQ
              VII                                                     VIII         IX 699                                                                                 764
FGFR1_h  S--------- ----PYPGVP VEELFKLLKE -GHRMDKPSN CTNELYMMMR DCWHAVPSQR PTFKQLVEDL DRIVALTSNQ
  SRC_h  V--------- ----PYPGMV NREVLDQVER -GYRMPCPPE CPESLHDLMC QCWRKEPEER PTFEYLQAFL EDYFTSTEPQ
  BRK_h  V--------- ----PYPGMS NHEAFLRVDA -GYRMPCPLE CPPSVHKLML TCWCRDPEQR PCFKALRERL SSFTSYENPT
  BTK_h  M--------- ----PYERFT NSETAEHIAQ -GLRLYRPHL ASEKVYTIMY SCWHEKADER PTFKILLSNI LDVMDEES--
  CSK_h  V--------- ----PYPRIP LKDVVPRVEK -GYKMDAPDG CPPAVYEVMK NCWHLDAAMR PSFLQLREQL EHIKTHELHL
  ABL_h  S--------- ----PYPGID LSQVYELLEK -DYRMERPEG CPEKVYELMR ACWQWNPSDR PSFAEIHQAF ETMFQESSIS
ZAP70_h  K--------- ----PYKKMK GPEVMAFIE- QGKRMECPPE CPPELYALMS DCWIYKWEDR PDFLTVEQRM RACYYSLASK
  FES_h  S--------- ----PYPNLS NQQTREFVEK -GGRLPCPEL CPDAVFRLME QCWAYEPGQR PSFSTIYQEL QSIR--KRHR
  FAK_h  K--------- ----PFQGVK NNDVIGRIE- NGERLPMPPN CPPTLYSLMT KCWAYDPSRR PRFTELKAQL STILEEEKAQ
 JAK1_h  SDSSPMALFL KMIGPTHGQM TVTRLVNTLK EGKRLPCPPN CPDEVYQLMR KCWEFQPSNR TSFQNLIEGF -----EALLK
  ACK_h  E--------- ----PWIGLN GSQILHKIDK EGERLPRPED CPQDIYNVMV QCWAHKPEDR PTFVALRDFL LEAQPTDMRA
              X                                                     XI
```

US 6,682,921 B1

CRYSTALS OF THE TYROSINE KINASE DOMAIN OF NON-INSULIN RECEPTOR TYROSINE KINASES

This application is a continuation of U.S. Ser. No. 09/188,809 filed Nov. 9, 1998, now abandoned, which is continuation of U.S. Ser. No. 08/701,191 filed Aug. 21, 1996, now U.S. Pat. No. 5,942,428. The entirety of these applications are hereby incorporated by reference.

1. INTRODUCTION

The present invention concerns crystalline forms of polypeptides corresponding to the catalytic domain of receptor tyrosine kinases of the non-insulin receptor type. Such tyrosine kinases include receptors of a class that are not covalently cross-linked but are understood to undergo ligand-induced dimerization (such as the FGF-receptor), as well as cytoplasmic tyrosine-kinases. The invention also concerns methods for obtaining such crystals and to the high-resolution X-ray diffraction structures and atomic structure coordinates obtained therefrom. The crystals of the invention, and the atomic structure coordinates obtained therefrom, are useful for solving the crystal and solution structures of the tyrosine kinase domains and for identifying compounds that bind to domains of receptor and non-receptor tyrosine kinases.

2. BACKGROUND OF THE INVENTION

Growth factors play important roles in the control of cell growth, differentiation, metabolism and oncogenesis. The signals generated by a growth factor are transduced across the cellular membrane by transmembrane receptors specific for the growth factor. The diverse biological effects of growth factors are mediated by a large family of cell surface transmembrane receptors with intrinsic protein tyrosine kinase (PTK) activity. The extracellular portion of receptor PTKs contain the binding site for its particular growth factor/ligand, whereas the tyrosine kinase activity resides in the cytoplasmic portion. Binding of a growth factor to the extracellular domain of this receptor results in autophosphorylation of specific tyrosine residues in the cytoplasmic domain. These phosphotyrosines either stimulate PTK activity or serve as binding sites for downstream signalling proteins containing Src-homology 2 (SH2) or phosphotyrosine binding (PTB) domains.

Eighteen classes or subfamilies of human receptor PTKs have been identified to date, including the insulin-receptor (IR), EGF-receptor, PDGF receptor and FGF-receptor. Ligand-induced dimerization of receptors such as the EGF, PDGF and FGF receptors is thought to be essential for activation. Growth factors, such as PDGF are dimeric molecules which, by themselves, are able to induce PDGF-receptor dimerization. However, FGFs are monomeric and are unable, by themselves; to induce receptor dimerization. Dimerization of FGF receptors is thought to be mediated by FGF in concert with heparin sulfate proteoglycans (soluble or cell surface bound).

In contrast to the EGF, PDGF and FGF receptors, which are monomeric and dimerize upon ligand binding, the insulin receptor exists as a "dimer." In fact, the insulin receptor is a disulphide-linked $\alpha_2\beta_2$ heterotetramer. Binding of insulin to the extracellular $\alpha$-chains is thought to cause a change within the quaternary structure of the receptor that results in autophosphorylation of specific tyrosines in the cytoplasmic portion of the $\beta$ chains.

In an effort to elucidate the mechanisms underlying kinase activation, the crystal structure of such proteins is often sought to be determined. The crystal structures of several protein serine/threonine kinases have been reported: cyclic-AMP-dependent protein kinase (CAPK; Knighton et al., 1994); cyclin-dependent kinase 2 (CDK2; DeBondt et al., 1993); mitogen-activated protein kinase (MAPK; Zhang et al., 1994); and twitchin kinase (Hu et al., 1994). However, the crystalline structure of only one receptor tyrosine kinase has been determined—the unphosphorylated apo form of the tyrosine kinase domain of the insulin receptor (Hubbard et al., 1994).

Despite these reports, the ability to obtain crystalline forms of the tyrosine kinase domains of non-insulin receptor tyrosine kinases; i.e., cytoplasmic tyrosine kinases and/or receptor tyrosine kinases that undergo ligand-mediated dimerization, has not been realized. A particularly illuminating example is the EGF receptor; to the Applicant's knowledge, researchers armed with the knowledge of how to obtain crystals of the tyrosine kinase domains of both the insulin receptor and serine/threonine kinases have attempted to obtain crystals of the tyrosine kinase domain of EGF receptor without success.

3. SUMMARY OF THE INVENTION

The invention relates to crystalline forms of polypeptides corresponding to the catalytic domains of receptor tyrosine kinases of the non-insulin receptor type. Such tyrosine kinases include receptors that are not covalently cross-linked, but are believed to undergo ligand-induced dimerization, as well as cytoplasmic tyrosine kinases. The polypeptides of the invention include, but are not limited to, crystallized polypeptides corresponding to the native or mutated catalytic domain of tyrosine kinases (ie., the non-insulin receptor-type described above), derivative crystals (i.e., heavy atom derivatives), and co-crystals of the native or mutated catalytic domain in association with one or more compounds, including but not limited to cofactors, substrates, substrate analogs, inhibitors, allosteric effectors, etc., and preferably compounds that bind the catalytic site.

Preferably, the crystalline catalytic domains of the invention are of sufficient quality to provide for a determination of the three-dimensional X-ray diffraction structure of the crystalline polypeptide to a resolution of about 1.5 Å to about 2.5 Å.

The invention is based, in part, on the Applicants' discovery and elucidation of the sequence requirements for the successful crystallization of polypeptides corresponding to catalytic domains of receptor tyrosine kinases that are not covalently cross-linked and are believed to undergo ligand-induced dimerization—a goal which heretofore remained elusive. In this regard, the Applicants have determined that at least about 20 amino acid residues (+/−5 amino acid residues) upstream of the first glycine in the conserved glycine-rich region of the catalytic domain, and at least about 17 amino acid residues (+/−5 amino acid residues) downstream of the conserved arginine located at the C-terminal boundary of the catalytic domain are required to engineer a polypeptide suitable for crystallization.

In those cases where the resulting polypeptide contains cysteine residues that interfere with crystallization, such cysteine residues can be substituted with an appropriate amino acid that does not readily form covalent bonds with other amino acid residues under crystallization conditions, e.g., such substitutions include, but are not limited to Ala, Ser, or Gly. Any cysteines located in a non-helical or non-β-strand segment based on secondary structural assignments are candidates for replacement. Cysteines located in domains corresponding to the glycine-rich loop, the kinase insert, the juxtamembrane region or the activation loop are prime candidates for replacement. However, substitutions of cysteine residues that are conserved among the kinases should be avoided (e.g., substitutions of the highly conserved cysteine residues located at the C-terminus, positions 725 and 736 in FIG. 6A, should be avoided).

The invention is demonstrated by way of example, for the fibroblast growth factor (FGF) receptor-1 (FGF-R1). The examples demonstrate that the crystal structure of the tyrosine kinase domain of the FGF-R1 has been determined to 2.0 Å resolution; the crystal structure of the FGF-R1 catalytic domain in complex with an ATP analog is described to 2.3 Å resolution.

The crystalline catalytic domains are useful for elucidating the mechanism by which the receptor tyrosine kinases are activated by ligand-induced dimerization, and for the identification of compounds that bind to the catalytic domain.

3.1 Definitions

As used herein, the following terms shall have the following meanings:

"Native Tyrosine Kinase Domain or Native Catalytic Domain:" As used herein, "native tyrosine kinase domain" or "native catalytic domain" refers to that portion or domain of a naturally occurring cytoplasmic tyrosine kinase or non-insulin receptor tyrosine kinase which possesses protein tyrosine kinase ("PTK") activity as described in Mohammadi et al., 1991 and 1996.

"Human FLGK:" As used herein, "human FLGK" refers to the tyrosine kinase domain of human fibroblast growth factor receptor 1 ("FGFR1") having the amino acid sequence of SEQ ID NO:1. Generally, human FLGK comprises a 310 amino acid residue fragment (residues 456 to 765) of human FGFR1.

"FLGK:" As used herein, "FLGK" refers to a mutant of human FLGK which is characterized by the amino acid sequence of SEQ ID NO:2. As compared to human FLGK, FLGK contains the following amino acid substitutions: Cys-488→Ala, Cys-584→Ser, Leu-457→Val, and has an additional five amino acid residues at the N-terminus (residues 1–5 of SEQ ID NO:2) (Ser-Ala:Ala-Gly-Thr).

"Mutant:" As used herein, "mutant" refers to a polypeptide which is obtained by replacing at least one amino acid residue in a native tyrosine kinase domain with a different amino acid residue and/or by adding and/or deleting amino acid residues within the native polypeptide or at the N- and/or C-terminus of a polypeptide corresponding to a native tyrosine kinase domain and which has substantially the same three-dimensional structure as the native tyrosine kinase domain from which it is derived. By having substantially the same three-dimensional structure is meant having a set of atomic structure coordinates that have a root mean square deviation (r.m.s.d.) of less than or equal to about 2 Å when superimposed with the atomic structure coordinates of the native tyrosine kinase domain from which the mutant is derived when at least about 50% to 100% of the Cα atoms of the native tyrosine kinase are included in the superposition.

A mutant may have, but need not have, PTK activity.

"Crystal:" As used herein, "crystal" refers to a polypeptide-in crystalline form. The term "crystal" includes native crystals, derivative crystals and co-crystals, as described herein.

"Native Crystal:" As used herein, "native crystal"refers to a crystal wherein the polypeptide is substantially pure.

"Derivative Crystal:" As used herein, "derivative crystal" refers to a crystal wherein the polypeptide is in covalent association with one or more heavy-metal atoms.

"Co-Crystal:" As used herein, "co-crystal" refers to a crystal wherein the polypeptide is in association with one or more compounds. Such compounds include, by way of example and not limitation, cofactors, substrates, substrate analogues, inhibitors, allosteric effectors, etc. Preferred compounds include AMP-PCP and AMP-PNP.

"Co-Complex:" As used herein, "co-complex" refers to a polypeptide in association with one or more compounds as enumerated above.

"Association:" As used herein, "association" refers to a condition of proximity between α-chemical entity or compound, or portions or fragments thereof, and tyrosine 35 kinase domain protein, or portions or fragments thereof. The association may be non-covalent, i.e., where the juxtaposition is energetically favored by, e.g., hydrogen-bonding, van der Waals, electrostatic or hydrophobic interactions, or it may be covalent.

Figure 3A:
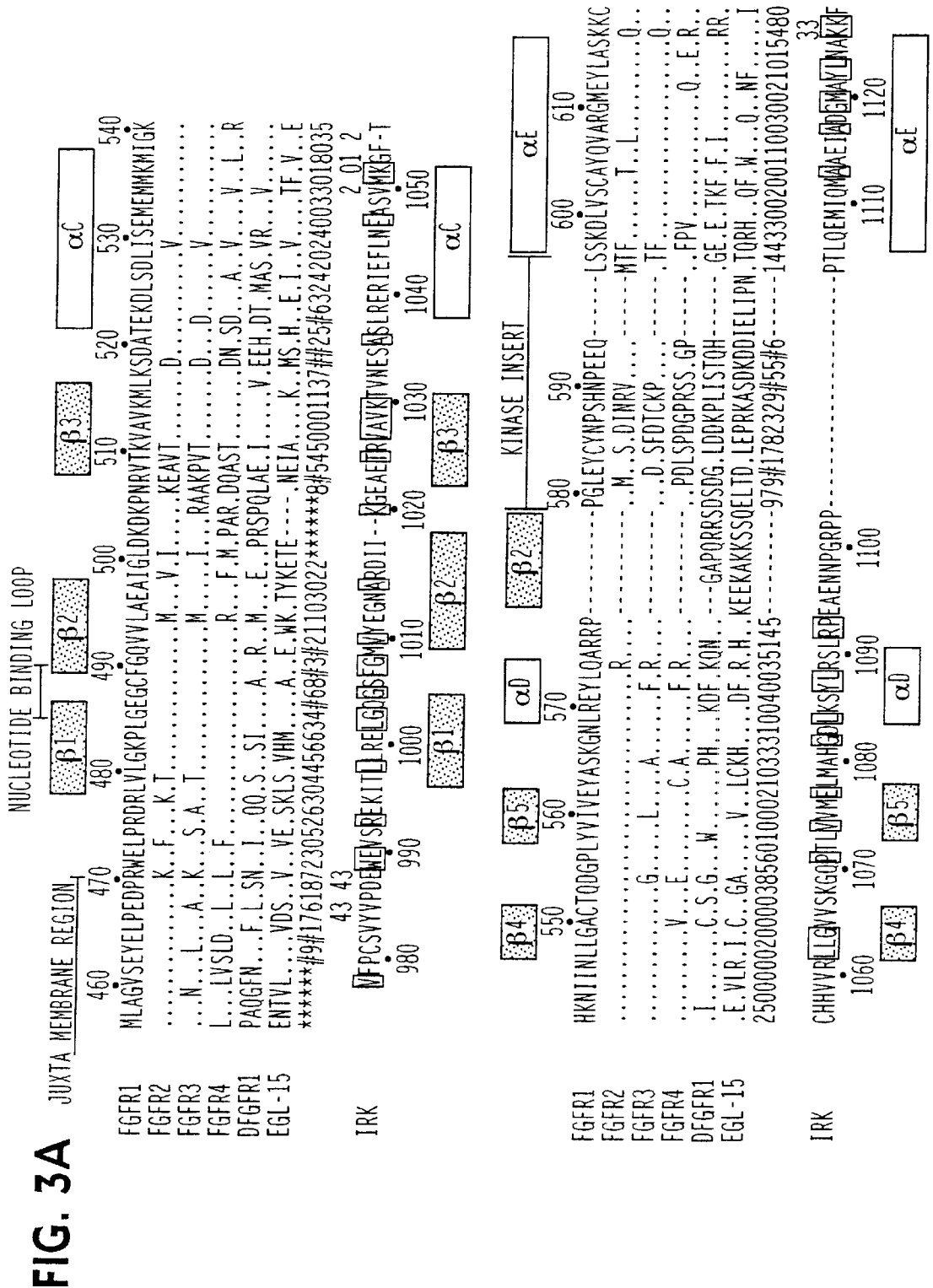
Figure 3B:
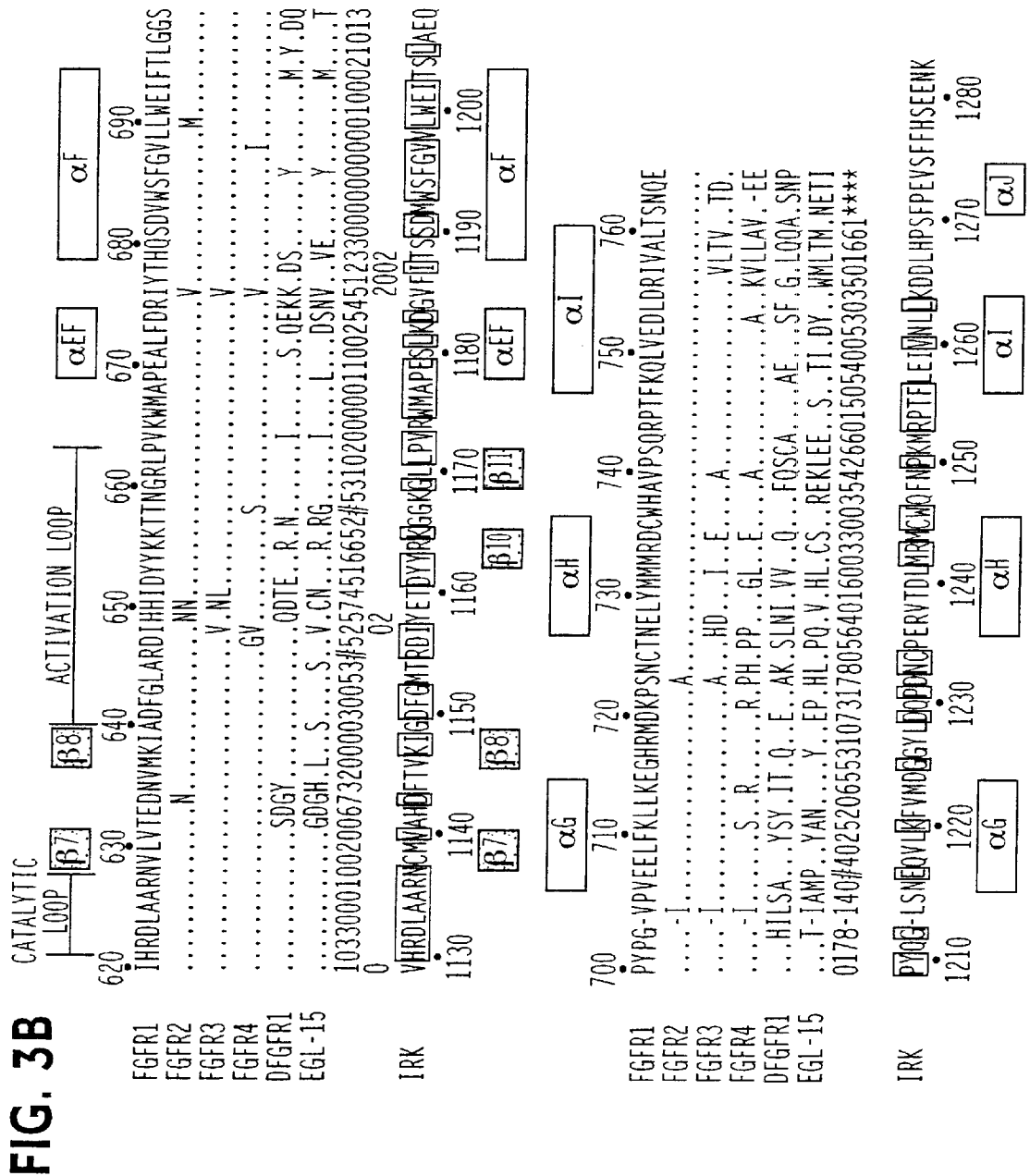

"Active Site:" As used herein, "active site" refers to that site in tyrosine kinase domains where substrate peptide binding, ATP binding and cleavage occur. For human FLGK and FLGK, the active site comprises the catalytic loop, the activation loop-and the nucleotide binding loop and is characterized by at least amino acid residues Lys-514, Glu-531, Asp-623, Asn-628, the glycine-rich loop (amino acid residues 485–490), Asp-641 and Arg-627 (FIG. 3).

"Catalytic Loon:" As used herein, "catalytic loop" refers to a loop in tyrosine kinase domains between αE and β7 containing conserved amino acid residues that are believed to be important in the phosphotransfer reaction or enzymatic process. For human FLGK and FLGK the catalytic loop contains aspartic acid residue Asp-623, which acts as a catalytic base, and is characterized by at least amino acid residues 621 to 628 (FIG. 3).

"Activation Loop:" As used herein, "activation loop" refers to a loop in tyrosine kinase domains between β8 and αEF that is believed to act as a regulatory loop. For human FLGK and FLGK, the activation loop contains two autophosphorylation sites and is characterized by at least amino acid residues 640 to 663 (FIG. 3).

"Nucleotide Binding Loon or Glycine-Rich Loop:" As used herein, "nucleotide-binding loop" or "glycine-rich loop" refers to a loop in tyrosine kinase domains between β1 and β2 which contains the protein kinase-conserved glycine-rich GXGXXG consensus sequence (where X is any amino acid). For human FLGK and FLGK the nucleotide binding loop is characterized by at least amino acid residues 485 to 490 (FIG. 3).

"Autophosphorylation Site:" As used herein, "autophosphorylation site" refers to those tyrosine residues in tyrosine kinase domains that are phosphorylated by a tyrosine kinase domain. Human FLGK and FLGK have six (6) autophosphorylation sites: two in the activation loop (Tyr-653 and Tyr-654), one in the juxtamembrane region (Tyr-463), two in the kinase insert (Tyr-583 and Tyr-585) and one in the C-terminal lobe (Tyr-730) (Mohammadi et al., 1996).

"Juxtamembrane Region:" As used herein, "juxtamembrane region" refers to that portion of receptor tyrosine kinases located between the transmembrane helix and the tyrosine kinase domain. For human FGFR1 the juxtamembrane region is characterized by at least amino acid residues 398 to 470 (FIG. 6).

"Kinase Insert:" As used herein, "kinase insert" refers a stretch of up to about one hundred amino acid residues which divides the tyrosine kinase domain of certain tyrosine kinases in two. For human FLGK and FLGK, the kinase insert is located between helices αD and αE (FIGS. 1 and 3), contains autophosphorylation sites Tyr-583 and Tyr-585, and is characterized by at least amino acid residues 575 to 596 (FIG. 3).

"Unit Cell:" As used herein, "unit cell" refers to the smallest and simplest volume element (i.e., parallelpiped-shaped block) of a crystal that is completely representative of the unit of pattern of the crystal. The dimensions of the unit cell are defined by six numbers: dimensions a, b and c and angles α, β and γ (Blundel et al., 1976). A crystal is an efficiently packed array of many unit cells.

"Monoclinic Unit Cell:" As used herein, "monoclinic unit cell" refers to a unit cell wherein a≠b≠c; α=γ=90°; and β>90°.

"Crystal Lattice:" As used herein, "crystal lattice" refers to the array of points defined by the vertices of packed unit cells.

"Space Group:" As used herein, "space group" refers to the symmetry of a unit cell. In a space group designation (e.g., C2) the capital letter indicates the lattice type and the other symbols represent symmetry operations that can be carried out on the unit cell without changing its appearance.

"Asymmetric Unit:" As used herein, "asymmetric unit" refers to the largest aggregate of molecules in the unit cell that possesses no symmetry elements, but that can be juxtaposed on other identical entities by symmetry operations.

"Crystallopraphically-Related Dimer:" As used herein, "crystallographically-related dimer" refers to a dimer of two molecules wherein the symmetry axes or planes that relate the two molecules comprising the dimer coincide with the symmetry axes or planes of the crystal lattice.

"Non-Crystallographically-Related Dimer:" As used herein, "non-crystallographically-related dimer" refers to a dimer of two molecules wherein the symmetry axes or planes that relate the two molecules comprising the dimer do not coincide with the symmetry axes or planes of the crystal lattice.

"Isomorphous Replacement:" As used-herein, "isomorphous replacement" refers to the method of using heavy-atom derivative crystals to obtain the phase information necessary to elucidate the three-dimensional structure of a native crystal (Blundel et al., 1976). The phrase "heavy-atom derivatization" is synonymous with "isomorphous replacement."

"Molecular Replacement:" As used herein, "molecular replacement" refers to the method of calculating initial phases for a new crystal whose structure coordinates are unknown by orienting and positioning a molecule whose structure coordinates are known within the unit cell of the new crystal so as to best account for the observed diffraction pattern of the new crystal. Phases are then calculated from this model and combined with observed amplitudes to provide an approximate Fourier synthesis of the structure of the molecules comprising the new crystal. This, in turn, is subject to any of several methods of refinement to provide a final, accurate set of structure coordinates for the new crystal (Lattman, 1985; Rossman, 1972).

3.2 Abbreviations

The amino acid notations used herein for the twenty genetically encoded L-amino acids are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

"ATP:" As used herein, "ATP" refers to adenosine triphosphate.

"AMP-PCP:" As used herein, "AMP-PCP" refers to adenylyl diphosphonate, a non-hydrolyzable analogue of ATP.

"AMP-PNP:" As used herein, "AMP-PNP" refers to adenylyl imidodiphosphate, a non-hydrolyzable analogue of ATP.

"$C_\alpha$:" As used herein, "$C_\alpha$" refers to the alpha carbon of an amino acid residue.

4. BRIEF DESCRIPTION OF THE FIGURES

FIG. 1 provides a ribbon diagram of the structure of FLGK showing the side chains of tyrosines Tyr-653 and Tyr-654 and the α helical (αC, αD, αE, αEF, αF–αI), β strand (β1–β5, β7, β8), nucleotide-binding loop, catalytic loop, activation loop and kinase insert regions of the molecule. The termini are denoted by N and C. The loop between β2 and β3 is disordered, indicated by a break in the chain in-this region.

Figure 2:
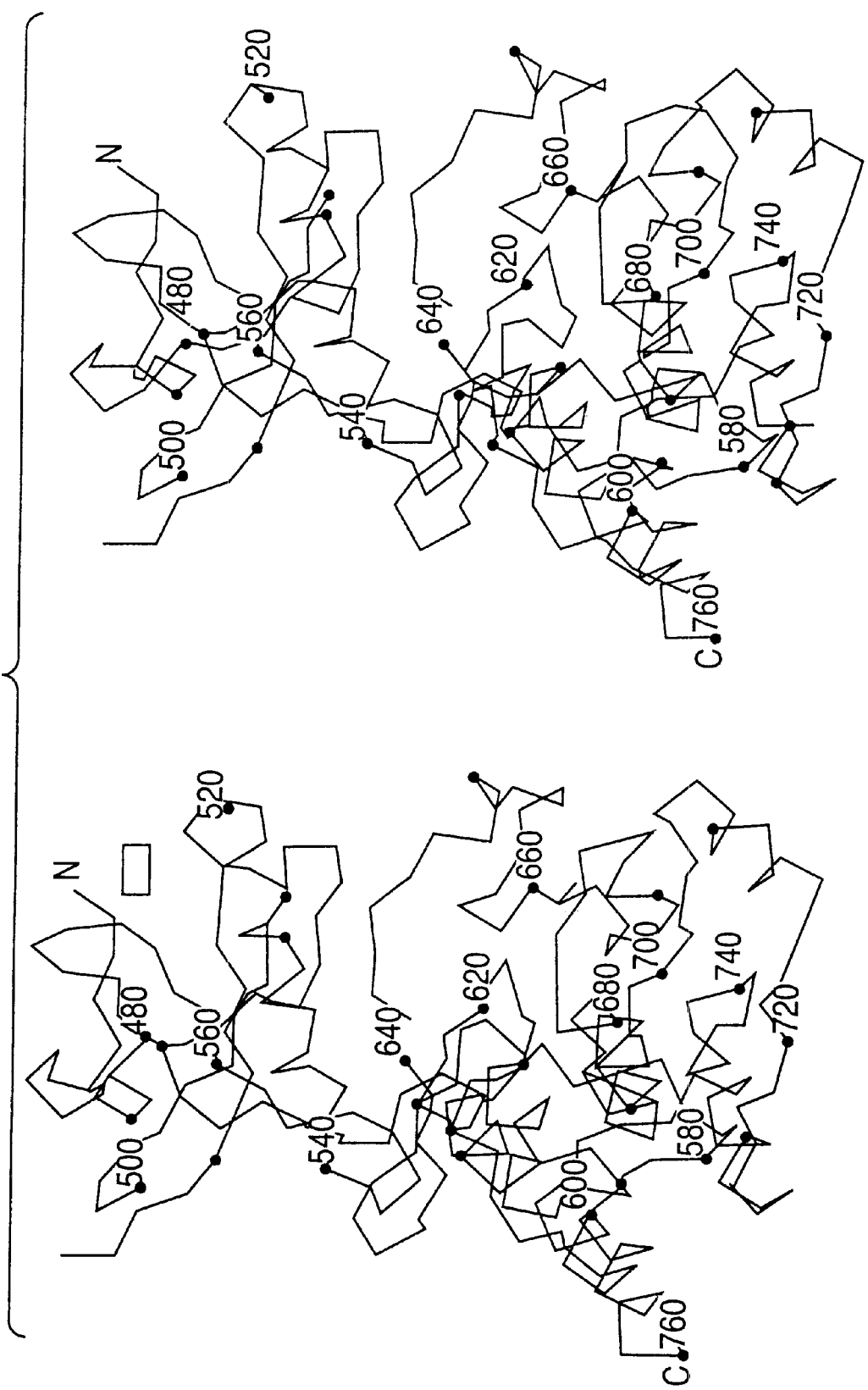

FIG. 2 provides a stereo view of a $C_\alpha$ trace of FLGK shown in the same orientation as FIG. 1, with every tenth amino acid residue marked with a filled circle and every twentieth amino acid residue labeled with a residue number.

FIG. 3 provides a structure-based sequence alignment of human fibroblast growth factor receptor 1 (FGFR1) (SEQ ID NO:6), human fibroblast growth factor receptor 2 (FGFR2) (SEQ ID NO:7), human fibroblast growth factor receptor 3 (FGFP3) (SEQ ID NO:8), human fibroblast growth factor receptor 4 (FGFR4) (SEQ ID NO:9), a D. malanogaster homolog (DFGFR1) (SEQ ID NO:10), a C. elegans homolog (EGL-15) (SEQ ID NO:11) and insulin receptor tyrosine kinase (IRK) (SEQ ID NO:12).

Figure 4A:
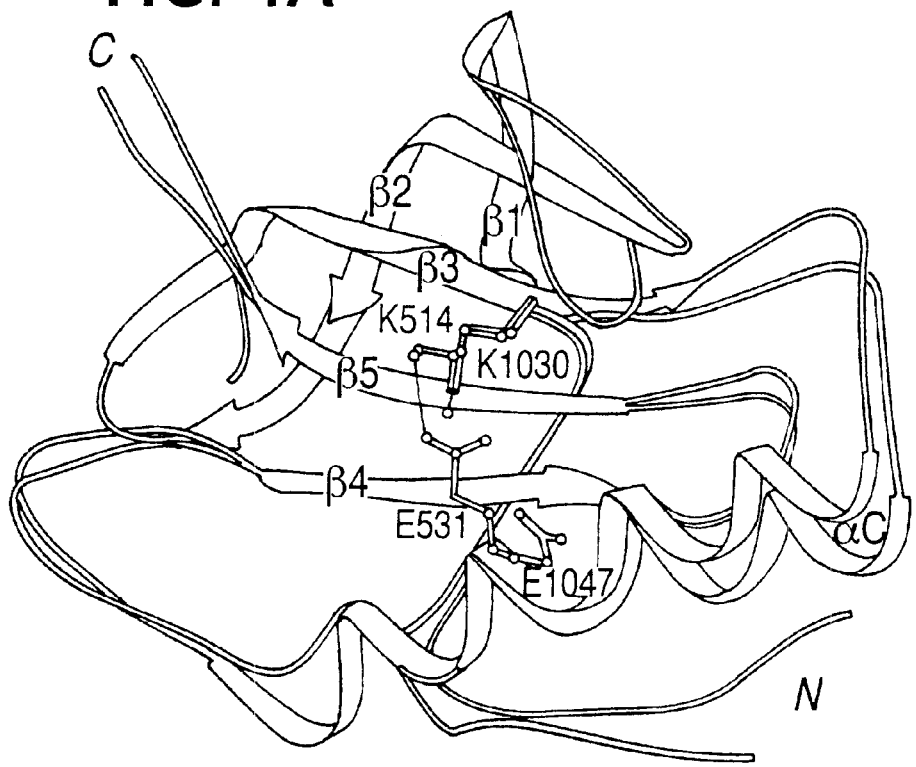
Figure 4B:
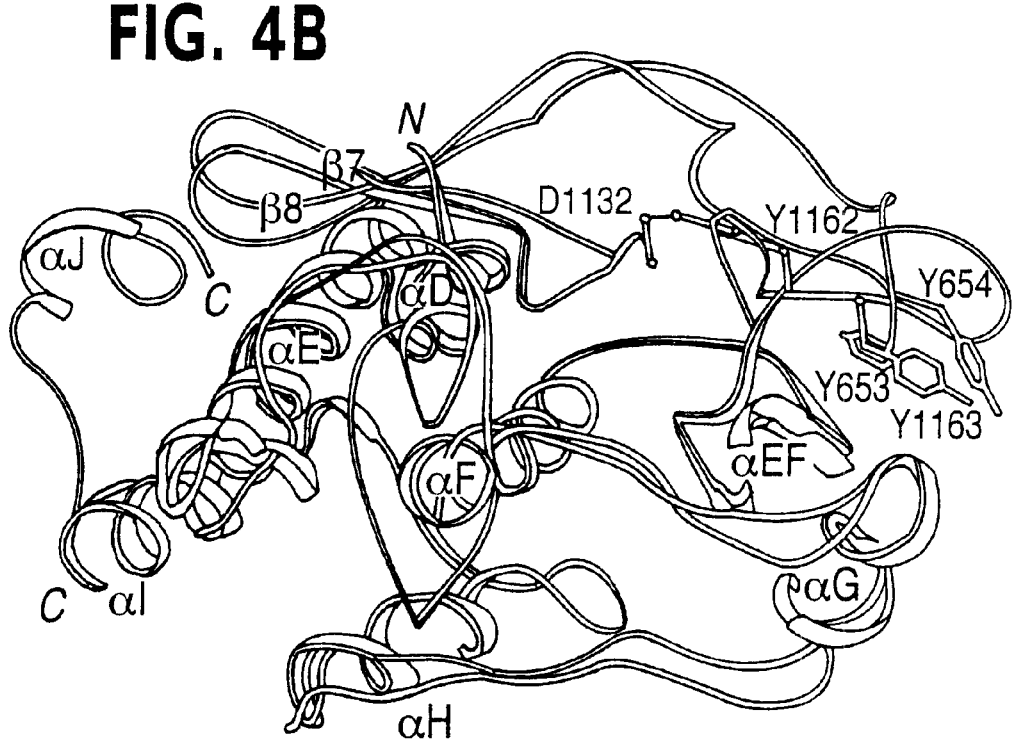

FIGS. 4A and 4B provide ribbon diagrams of the N-terminal lobes (4A) and C-terminal lobes (4B) of FLGK and IRK in which the $C_\alpha$ atoms of the β sheets (4A) or α-helices (4B) of the two proteins have been superimposed.

Figure 5:
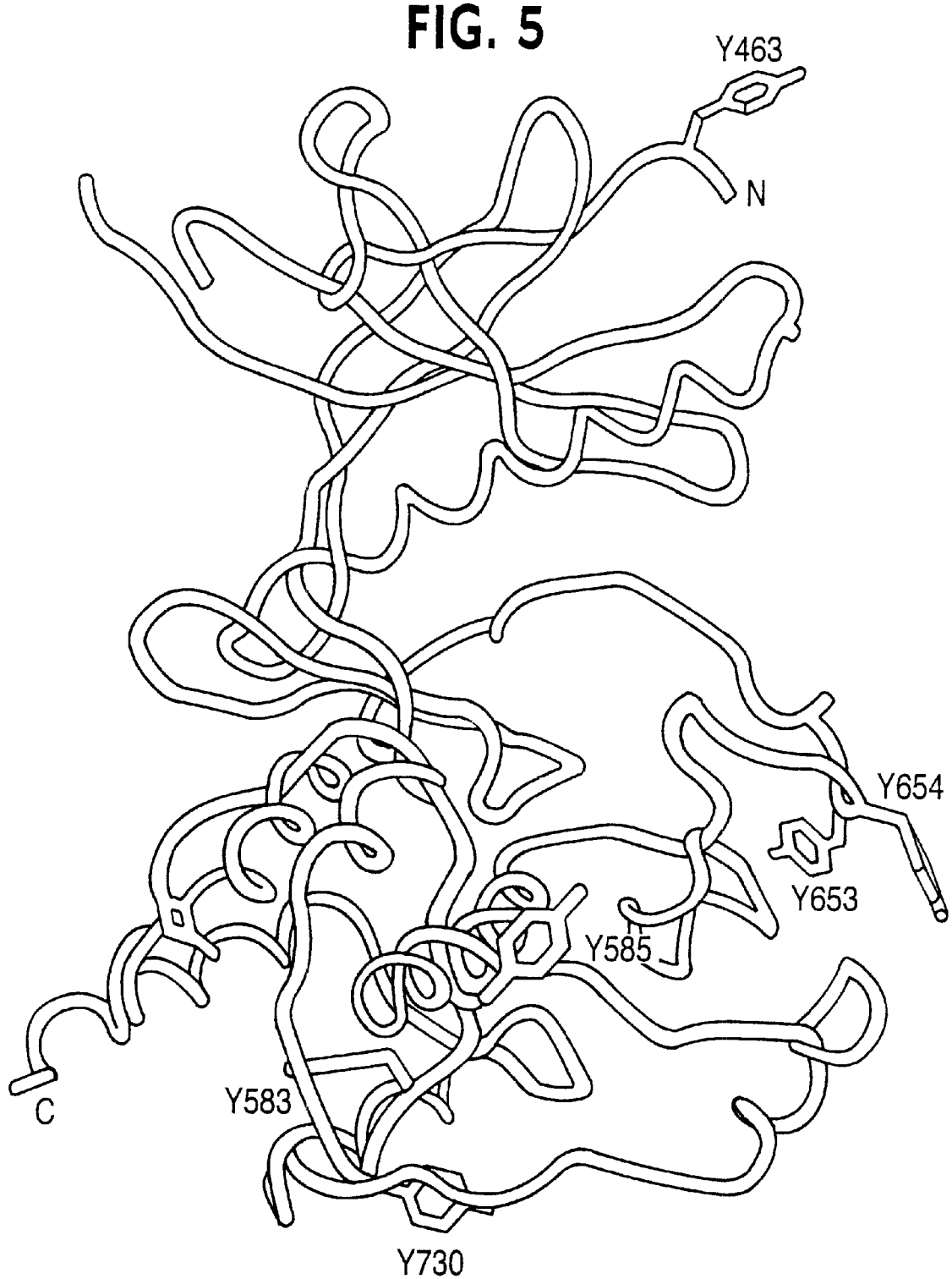

FIG. 5 illustrates the side-chain positions of the tyrosine autophosphorylation sites of FLGK on the backbone representation of FLGK.

Figures 2, 6A:
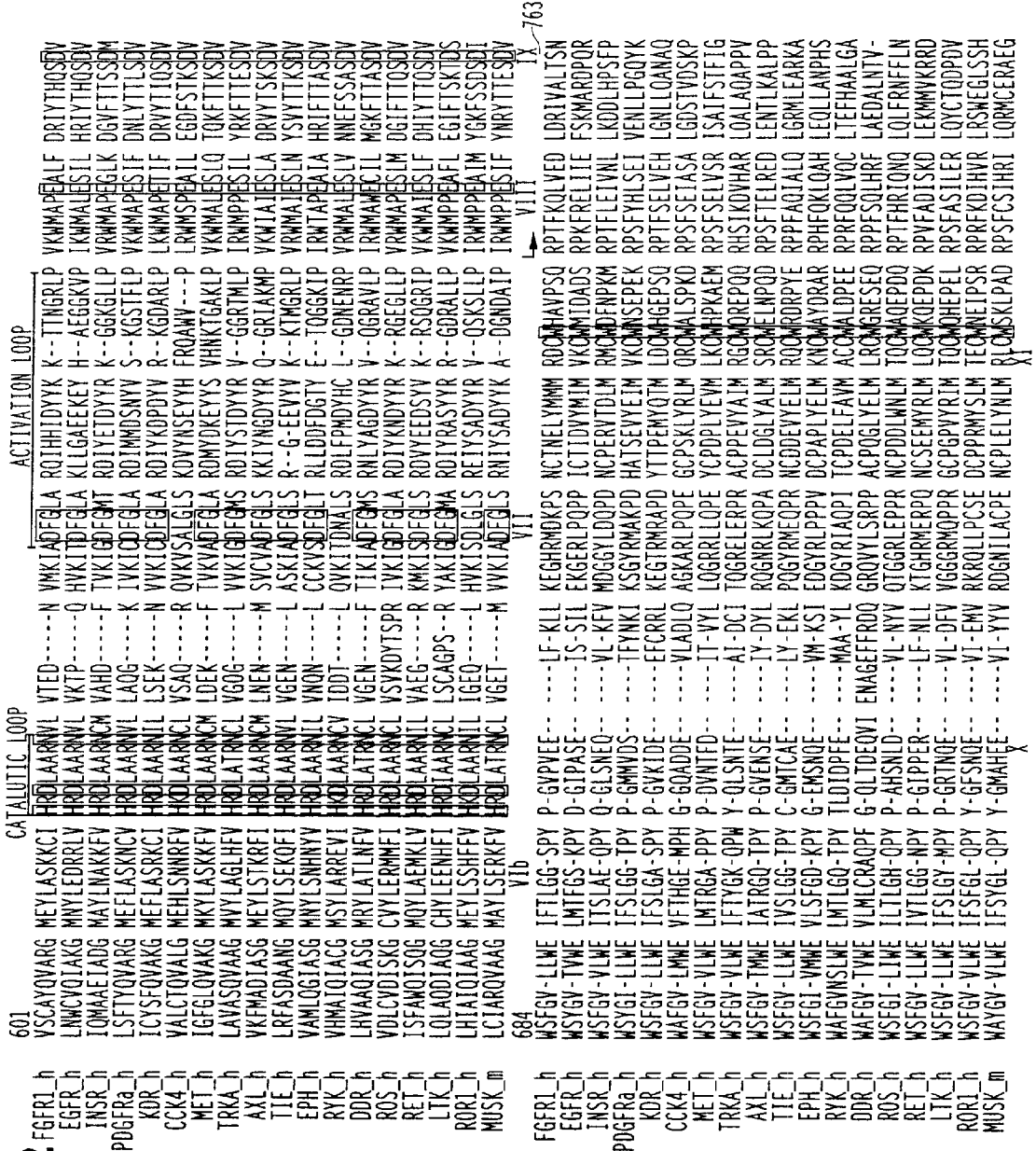

FIGS. 6A (SEQ ID NOS. 13–30, respectively, in order of appearance) and 6B (SEQ ID NOS 31–41, respectively, in order of appearance) are amino acid sequence alignments of the catalytic domains of PTKs, including receptor and non-receptor type PTKs. FIG. 6A depicts one representative member from each of the eighteen subfamilies of receptor tyrosine kinases. FIG. 6B depicts one representative member from each of the subfamilies of cytoplasmic tyrosine kinases. In FIGS. 6A and 6B highly conserved residues are boxed. The position of the glycine-rich domain, kinase insert, catalytic loop, and activation loop are indicated. The numbering is for human FGF-receptor.

4.1. BRIEF DESCRIPTION OF THE TABLES

Table 1 summarizes the X-ray crystallography data sets of FLGK derivative crystals that were used to determine the structures of crystalline FLGK and crystalline FLGK:AMP-PCP co-complex of the invention;

Table 2 summarizes the X-ray crystallography refinement parameters of the structures of crystalline FLGK and crystalline FLGK:AMP-PCP co-complex of the invention;

Table 3 provides the atomic structure coordinates of native FLGK crystals of the invention as determined by X-ray crystallography; and Table 4 provides the atomic structure coordinates of FLGK:AMP-PCP co-crystals of the invention as determined by X-ray crystallography.

5. DETAILED DESCRIPTION OF THE INVENTION

The present invention relates to crystalline polypeptides corresponding to the catalytic domain of receptor tyrosine kinases of the non-insulin receptor type. Such tyrosine kinases include receptors of a class that are not covalently cross-linked but are understood to undergo ligand-induced dimerization, as well as cytoplasmic tyrosine kinases. Preferably, the crystalline catalytic domains are of sufficient quality to allow for the determination of the three-dimensional X-ray diffraction structure to a resolution of about 1.5 Å to about 2.5 Å. The invention also relates to methods for preparing and crystallizing the polypeptides. The polypeptides themselves, as well as information derived from their crystal structures can be used to analyze and modify tyrosine kinase activity as well as to identify compounds that interact with the catalytic domain.

The polypeptides of the invention are designed on the basis of the structure of a region in the cytoplasmic domain of the receptor tyrosine kinase that contains the catalytic domain. By way of illustration, FIG. 6A shows the amino acid sequence alignment of the catalytic domains of eighteen human receptor tyrosine kinases; one representative member from each of the eighteen subfamilies is shown. FIG. 6B shows the alignment for cytoplasmic kinases. The applicants have discovered and determined the boundaries of the domain required for crystallization of the resulting polypeptide. Surprisingly, these boundaries differ from that required for catalytic activity. For example, referring to FIG. 6A, the domain required for catalytic activity is generally believed to span about 7 amino acid residues upstream of the first glycine (FIG. 6A residue number 485) of the N-terminal glycine-rich region through about 10 residues beyond the C-terminal conserved arginine (FIG. 6A, residue number 744). However, the Applicants have found that additional sequence upstream of the N-terminal glycine-rich region and downstream of the C-terminal conserved arginine are required for crystallization. In particular, the Applicants have determined that at least about 20 amino acid residues (+/−5 amino acid residues) upstream of the first glycine (i.e., FIG. 6A, residue number 485) in the conserved glycine-rich region of the catalytic domain, and at least about 17 amino acid residues (+/−5 amino acid residues) downstream of the conserved arginine (i.e., FIG. 6A, residue number 744) located at the C-terminal boundary of the catalytic domain are required to engineer a polypeptide suitable for crystallization.

In those situations where the resulting polypeptide contains cysteine residues that interfere with crystallization (e.g., cysteine residue numbers 488 and 584 in the FGF-R1 sequence shown in FIG. 6A), such cysteine residues can be substituted with an appropriate amino acid that does not readily form covalent bonds with other amino acid residues under crystallization conditions; e.g., by substituting the cysteine with Ala, Ser or Gly. Any cysteine located in a non-helical or non-β-stranded segment, based on secondary structure assignments, are good candidates for replacement. For example, cysteines located in regions corresponding to the glycine-rich-loop, the kinase insert, the juxtamembrane region or the activation loop are prime candidates for replacement. However, substitutions of cysteine residues that are conserved among the kinases (e.g., FIG. 6A at positions 725 and 736) are preferably avoided.

5.1 Crystalline Tyrosine Kinases

The crystals of the invention include native crystals, derivative crystals and co-crystals. The native crystals of the invention generally comprise substantially pure polypeptides corresponding to the tyrosine kinase domain in crystalline form.

It is to be understood that the crystalline tyrosine kinase domains of the invention are not limited to naturally occurring or native tyrosine kinase domains. Indeed, the crystals of the invention include mutants of native tyrosine kinase domains. Mutants of native tyrosine kinase domains are obtained by replacing at least one amino acid residue in a native tyrosine kinase domain with a different amino acid residue, or by adding or deleting amino acid residues within the native polypeptide or at the N- or C-terminus of the native polypeptide, and have substantially the same three-dimensional structure as the native tyrosine kinase domain from which the mutant is derived.

By having substantially the same three-dimensional structure is meant having a set of atomic structure coordinates that have a root mean square deviation of less than or equal to about 2Å when superimposed with the atomic structure coordinates of the native tyrosine kinase domain from which the mutant is derived when at least about 50% to 100% of the Cβ atoms of the native tyrosine kinase domain are included in the superposition.

Amino acid substitutions, deletions and additions which do not significantly interfere with the three-dimensional structure of the tyrosine kinase domain will depend, in part, on the region of the tyrosine kinase domain where the substitution, addition or deletion occurs. In highly variable regions of the molecule, such as those shown in FIG. 6, non-conservative substitutions as well as conservative substitutions may be tolerated without significantly disrupting the three-dimensional structure of the molecule. In highly conserved regions, or regions containing significant secondary structure, such as those regions shown in FIG. 6, conservative amino acid substitutions are preferred.

Conservative amino acid substitutions are well-known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

Of course, it is to be understood that for tyrosine kinase domains obtained in whole or in part by chemical synthesis, the selection of amino acids available for substitution or addition is not limited to the genetically encoded amino acids. Indeed, the mutants described herein may contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues to a native tyrosine kinase domain in order to provide convenient cloning sites in cDNA encoding the polypeptide, to aid in purification of the polypeptide, etc. Such substitutions, deletions and/or additions which do not substantially alter the three dimensional structure of the native tyrosine kinase domain will be apparent to those having skills in the art.

It should be noted that the mutants contemplated herein need not exhibit PTK activity. Indeed, amino acid substitutions, additions or deletions that interfere with the kinase activity of the tyrosine kinase domain but which do not significantly alter the three-dimensional structure of the domain are specifically contemplated by the invention. Such crystalline polypeptides, or the atomic structure coordinates obtained therefrom, can be used to identify compounds that-bind to the native domain. These compounds may affect the activity or the native domain.

The derivative crystals of the invention generally comprise a crystalline tyrosine kinase domain polypeptide in covalent association with one or more heavy metal atoms. The polypeptide may correspond to a native or a mutated tyrosine kinase domain. Heavy metal atoms useful for providing derivative crystals include, by way of example and not limitation, gold, mercury, etc.

The co-crystals of the invention generally comprise a crystalline tyrosine kinase domain polypeptide in association with one or more compounds. The association may be covalent or non-covalent. Such compounds include, but are not limited to, cofactors, substrates, substrate analogues, inhibitors, allosteric effectors, etc.

5.2 Production of Polypeptides

The native and mutated tyrosine kinase domain polypeptides described herein may be chemically synthesized in whole or part using techniques that are well-known in the art (see, e.g., Creighton, 1983). Alternatively, methods which are well known to those skilled in the art can be used to construct expression vectors containing the native or mutated tyrosine kinase domain polypeptide coding sequence and appropriate transcriptional/translational control signals. These methods include in vitro recombinant DNA techniques, synthetic techniques and in vivo recombination/genetic recombination. See, for example, the techniques described in Maniatis et al., 1989 and Ausubel et al., 1989.

A variety of-host-expression vector systems may be utilized to express the tyrosine kinase domain coding sequence. These include but are not limited to microorganisms such as bacteria transformed with recombinant bacteriophage DNA, plasmid DNA or cosmid DNA expression vectors containing the tyrosine kinase domain coding sequence; yeast transformed with recombinant yeast expression vectors containing the tyrosine kinase domain coding sequence; insect cell systems infected with recombinant virus expression vectors (e.g., baculovirus) containing the tyrosine kinase domain coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the tyrosine kinase domain coding sequence; or animal cell systems. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used.; when cloning in plant cell systems, promoters derived from the genome of plant cells (e.c., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the tyrosine kinase domain DNA, SV40-, BPV- and EBV-based vectors may be used with an appropriate selectable marker.

5.3 Crystallization of Polypeptides and Characterization of Crystal Structure The native, derivative and co-crystals of the invention can be obtained by conventional means as are well-known in the art of protein crystallography, including batch, liquid bridge, dialysis, vapor diffusion and hanging drop methods. (see, e.a., McPherson, 1982; McPherson, 1990; Webber, 1991).

Generally, the native crystals of the invention are grown by dissolving substantially pure tyrosine kinase domain polypeptide in an aqueous buffer containing a precipitant at a concentration just below that necessary to precipitate the protein. Water is removed by controlled evaporation to produce precipitating conditions, which are maintained until crystal growth ceases.

In a preferred embodiment of the invention, native crystals are grown by vapor diffusion in hanging drops (McPherson, 1982 and 1990). In this method, the polypeptide/precipitant solution is allowed to equilibrate in a closed container with a larger aqueous reservoir having a precipitant concentration optimal for producing crystals. Generally, less than about 25 µL of substantially pure polypeptide solution is mixed with an equal volume of reservoir solution, giving a precipitant concentration about half that required for crystallization. This solution is suspended as a droplet underneath a coverslip, which is sealed onto the top of the reservoir. The sealed container is allowed to stand, usually for about 2–6 weeks, until crystals grow.

For crystals of the invention, it has been found that hanging drops containing about 2.0 µL of tyrosine kinase domain polypeptide (10 mg/mL in 10 mM Tris-HCl, pH 8.0, 10 mM NaCl and 2 mM dithiothreitol) and 2.0 µL reservoir solution (16% w/v polyethylene glycol MW 10000, 0.3 M $(NH_4)_2SO_4$, 5% v/v ethylene glycol or glycerol and 100 mM bis-Tris, pH 6.5) suspended over 0.5 mL reservoir buffer for about 3–4 weeks at 4° C. provide crystals suitable for high resolution X-ray structure determination.

Of course, those having skill in the art will recognize that the above-described crystallization conditions can be varied. Such variations may be used alone or in combination, and include polypeptide solutions containing polypeptide concentrations between 1 mg/mL and 60 mg/mL, Tris-HCl concentrations between 10 mM and 200 mM, dithiothreitol concentrations between 0 mM and 20 mM, pH ranges between 5.5 and 7.5; and reservoir solutions containing polyethylene glycol concentrations between 10% and 30% (w/v), polyethylene glycol molecular weights between 1000 and 20,000, $(NH_4)_2SO_4$ concentrations between 0.1 M and 0.5 M, ethylene glycol or glycerol concentrations between 0% and 20% (v/v), bis-Tris concentrations between 10 mM and 200 mM, pH ranges between 5.5 and 7.5 and temperature ranges between 0° C. and 25° C. Other buffer solutions may be used such as HEPES buffer, so long as the desired pH range is maintained.

Derivative crystals of the invention can be obtained by soaking native crystals in mother liquor containing salts of heavy metal atoms. It has been found that soaking a native crystal in a solution containing about 0.1 mM to about 5 mM thimerosal, 4-chloromeruribenzoic acid or $KAu(CN)_2$ for about 2 hr to about 72 hr provides derivative crystals suitable for use as isomorphous replacements in determining the X-ray crystal structure of the tyrosine kinase domain polypeptide.

Co-crystals of the invention can be obtained by soaking a native crystal in mother liquor containing compound that bind the kinase domain, or described above, or can be obtained by co-crystallizing the kinase domain polypeptide in the presence of one or more binding compounds.

For co-crystals of tyrosine kinase domain polypeptide in co-complex with AMP-PCP, it has been found that co-crystallizing the kinase domain polypeptide in the presence of AMP-PCP using the above-described crystallization conditions for obtaining native crystals with a polypeptide solution additionally containing 10 mM AMP-PCP and 20 mM $MgCl_2$ yields co-crystals suitable for the high resolution structure determination by X-ray crystallography. Of course, those having skill in the art will recognize that the concentrations of AMP-PCP and $MgCl_2$ in the polypeptide solution can be varied, alone or in combination with the variations described above for native crystals. Such variations include polypeptide solutions containing AMP-PCP concentrations between 0.1 mM and 50 mM and $MgCl_2$ concentrations between 0 mM and 50 mM.

Methods for obtaining the three-dimensional structure of the crystalline tyrosine kinase domains described herein, as well as the atomic structure coordinates, are well-known in the art (see, e.g., Ducruix and Geige, 1992, and references cited therein).

5.4 Uses of the Crystals and Atomic Structure Coordinates

The crystals of the invention, and particularly the atomic structure coordinates obtained therefrom, have a wide variety of uses. For example, the crystals described herein can be used as a starting material in any of the art-known methods of use for receptor and non-receptor tyrosine kinases. Such methods of use include, for example, identifying molecules that bind to the native or mutated catalytic domain of tyrosine kinases. The crystals and structure coordinates are particularly useful for identifying compounds that inhibit receptor and non-receptor tyrosine kinases as an approach towards developing new therapeutic agents (see, e.g., Levitzki and Gazit, 1995).

The structure coordinates described herein can be used as phasing models in determining the crystal structures of additional native or mutated tyrosine kinase domains, as well as the structures of co-crystals of such domains with ligands such as inhibitors, agonists, antagonists, etc. The structure coordinates, as well as models of the three-dimensional structures obtained therefrom, can also be used to aid the elucidation of solution-based structures of native or mutated tyrosine kinase domains, such as those obtained via NMR. Thus, the crystals and atomic structure coordinates of the invention provide a convenient means for elucidating the structures and functions of receptor and non-receptor tyrosine kinases.

For purposes of clarity and discussion, the crystals of the invention will be described by reference to specific FLGK exemplary crystals. Those skilled in the art will appreciate that the principles described herein are generally applicable to crystals of the tyrosine kinase domain of any cytoplasmic tyrosine kinase that undergoes ligand-induced dimerization or receptor tyrosine kinase, including but not limited to the tyrosine kinases of FIG. 6.

5.5 Crystalline FLGK

In one illustrative embodiment, the invention provides crystals of FLGK. The crystals were obtained by the methods provided in the Examples. The FLGK crystals, which may be native crystals, derivative crystals or co-crystals, have monoclinic unit cells (i.e., unit cells wherein a≠b≠c; α=γ=90°; and β>90°) and space group symmetry C2. There are two FLGK molecules in the asymmetric unit, related by an approximate two-fold axis.

Two forms of crystalline FLGK were obtained. In one form (designated "C2-A form"), the unit cell has dimensions of a=208.3 +/−0.2 Å, b=57.8 +/−0.2 Å, c=65.5 +/−0.2 Å and β=107.2 °+/−0.2°. In another form (designated "C2-B form"), the unit cell has dimensions of a=211.6 +/−0.2 Å, b=51.3 +/−0.2 Å, c=66.1 +/−0.2 Å and β=107.7° +/−0.2°.

Three distinct two-fold related FLGK dimers are observed in both the C2-A and C2-B forms of the FLGK crystal, one non-crystallographically related dimer and two crystallographically related dimers. The non-crystallographically related dimer comprises the two molecules in the asymmetric unit. The residues making up the dimer interface are located in C-terminal lobe. In this dimer, the C-terminal lobes abut with the N-terminal lobes distal to one another. The total amount of surface area buried in the surface is about 950 $Å^2$. Very few of the interactions in the interface are of a specific nature, e.g., hydrogen-bonding or close packing of hydrophobic residues.

There are two crystallographically-related dimers in the C2 lattice. In the first dimer, the residues that constitute the dimer interface are limited to those in the β-sheet of the N-terminal lobe (amino acid residues 477, 479, 498, 506, 508 and 496). The total surface area buried in this interface is about 670 $Å^2$. The interactions are rather specific. Three hydrophobic residues which are partially solvent-exposed in the monomer, Val-479, Ile-498 and Val-508, come together with their two-fold-related residues to form a compact hydrophobic plug. This plug is capped on either side by a salt bridge between Arg-477 and Glu-496. In addition, two main-chain hydrogen-bonds connect the β-sheets of the two monomers at the start of β3 (amino acid residues 506 and 508). The residues in this dimer interface, or their residue character, are generally conserved in the mammalian FGF receptors, but not in the invertebrate homologues.

The other crystallographically-related dimer buries about 1650 Å² in its interface. In this dimer, the αC helices of the two monomers are nearly parallel and contact each other at their C-terminal ends. Met-534 and Met-537 are in van der Waals contact with their two-fold-related residues. Other hydrophobic contacts involve Pro-466 with Ile-648 and Pro-469 with Ile-676 and Thr-678. In addition, hydrogen bonds (side-chain to main-chain) are made between Arg-470 and Lys-618 and between His-649 and Glu-464, and there are several water molecules that bridge the two monomers through hydrogen bonding.

In the C2-B form of the crystal, the monomers of this second crystallographically-related dimer are shifted slightly with respect to one another (6° rotation), indicating that this interface is somewhat fluid.

In both of the crystallographically-related dimers, the N-termini of the two molecules comprising the dimer point in the same direction and are reasonably close to one another.

5.5.1 Structures of FLGK and FLGK:AMP-PCP Co-Complex

The present invention also provides, for the first time, the high-resolution three-dimensional structures and atomic structure coordinates of crystalline FLGK and crystalline FLGK:AMP-PCP co-complex as determined by X-ray crystallography. The specific methods used to obtain the structure coordinates are provided in the examples. The atomic structure coordinates of crystalline FLGK, obtained from the C2-A form of the crystal to 2.0 Å resolution, are listed in Table 3; the coordinates of crystalline FLGK:AMP-PCP co-complex, obtained from the C2-A form of the crystal to 2.3 Å resolution are listed in Table 4.

Those having skill in the art will recognize that atomic structure coordinates as determined by X-ray crystallography are not without error. Thus, it is to be understood that any set of structure coordinates obtained for crystals of FLGK, whether native crystals, derivative crystals or co-crystals, that have a root mean square deviation ("r.m.s.d.") of less than or equal to about 1.5 Å when superimposed, using backbone atoms (N, $C_\alpha$, C and O), on the structure coordinates listed in Table 3 or Table 4 are considered to be identical with the structure coordinates listed in the Tables when at least about 50% to 100% of the backbone atoms of FLGK are included in the superposition.

Referring now to FIG. 1, the overall structure of FLGK is bi-lobate. The N-terminal lobe of FLGK spans amino acid residues 456–567 (FIG. 3) and comprises a curled β-sheet of five anti-parallel strands (β1–β5) and one β-helix (βC). The C-terminal lobe spans amino acid residues 568–765 (FIG. 3) and comprises two β-strands (β7, β8) and seven α-helices (βD, αE, αEF, αF–αI). The secondary structure nomenclature follows that used for IRK (Hubbard et al., 1994) which in turn is based on the assignments for CAPK (Knighton et al., 1991). FIG. 2 shows a stereo view of a $C_\alpha$ trace of FLGK in the same orientation as FIG. 1.

A structure-based sequence alignment of the tyrosine kinase domains of human fibroblast growth factor receptor 1 (human FLGK; labelled FGFR1), human fibroblast growth factor receptors 2, 3 and 4 (labelled FGFR2, FGFR3 and FGFR4, respectively), a *D. melanogaster* homologue (labelled DFDFR1), a *C elegans* homologue (labelled EGL-15) and insulin receptor kinase (labelled IRK), is shown in FIG. 3. The sequence of FLGK, which is not shown in FIG. 3 is identical to the sequence of FGFR1 except that FLGK has the following amino acid substitutions and additions: Cys-488→Ala, Cys-584→Ser, Leu-457→Val and an additional five N-terminal amino acids (residues 1–5 of SEQ ID NO:2) (Ser-Ala-Ala-Gly-Thr). The secondary structure assignments for FGFR1 and JRK were obtained using the Kabsch and Sander algorithm (Kabsch and Sander, 1983) as impiemented in PROCHECK (Laskowski et al., 1993). In the FGF receptor sequences, a period represents sequence identity to FGFR1. In the IRK sequence, residues that are identical to FGFR1 are highlighted. A hyphen denotes an insertion.

The numbers under the EGL-15 sequence represent the fractional solvent accessibility (FSA2) of the residue in the FLGK structure. The FSA ratio is the ratio of the solvent-accessible surface area of a residue in a Gly-X-Gly tripeptide compared to that in the FLGK structure. A value of 0 represents an FSA between 0.00 and 0.09; 1 represents an FSA between 0.10 and 0.19, etc. The higher the value, the more solvent-exposed the residue. An asterisk or pound sign in the FSA line indicates that the residue (asterisk) or side chain (pound sign) is not included in the atom model due to disorder. The numbers below the FSA line are the FSAs for those residues that form part of a dimer interface.

The amino acid residue numbers for FGFR1, and hence FLGK, and IRK provided in FIG. 3 are used in the discussion that follows. Significant differences in the N-terminal lobe of FLGK as compared to IRK are found in the loops between β strands and in αC. Residues from the end of β1 through the beginning of β2 (amino acid residues 485–490) form the nucleotide-binding loop, named because of its role in ATP coordination. This residue stretch contains the protein kinase-conserved GXGXXG sequence motif, where X is any amino acid. This loop is poorly ordered in one FLGK molecule in the asymmetric unit and disordered (i.e., not included in the atomic model) in the other FLGK molecule in the asymmetric unit. The loop between β1 and β3 is disordered in both FLGK molecules comprising the asymmetric unit.

Referring now to FIG. 4A, which provides a ribbon diagram of the N-terminal lobes of FLGK and IRK in which the $C_a$ atoms of the β-sheets have been superimposed, it can be seen that in FLGK αC is longer by one helical turn than in IRK and is oriented such that residues Lys-514 and Glu-531, which are conserved in protein kinases, form a salt bridge (represented by a black line). While not intending to be bound by theory, this salt bridge is believed to be important for proper positioning of the conserved lysine side chain, which coordinates two phosphate oxygens of ATP. The salt bridge is observed in the structures of cAPK (Knighton et al., 1991) and mitogen-activated protein kinase (MAPK) (Zhang et al., 1994).

Referring now to FIG. 4B, which provides a ribbon diagram of the C-terminal lobes of FLGK and IRK in which the $C_\alpha$ atoms of the α-helices have been superimposed, a significant difference is found in the C-terminal helix of FLGK when compared to IRK; helix αI of FLGK is longer by seven residues (two helical turns) than its counterpart in IRK. The extended length of αI is presumably important in the biological functioning of FGF receptors, since the tyrosine autophosphorylation site to which an SH2 domain of PLCγ binds is six residues C-terminal to this helix.

The structure of FLGK displays an open disposition of the N- and C-terminal lobes. Despite having different sets of lattice contacts, the two FLGK molecules in the asymmetric unit have only a 2° difference in relative lobe orientation. It appears as though the stearic interaction between residues in αC (Glu-531 and Met-534) with Phe-642 and Gly-643 of the protein kinase-conserved DFG sequence at the beginning of the activation loop accounts for the open conformation of FLGK.

The active site of FLGK is characterized by at least amino acid residues spanning the catalytic loop, activation loop and nucleotide binding loop. Unlike the structure of IRK, in which Tyr-1162 occupies the active site of the molecule, the active sites of both FLGK molecules in the asymmetric unit are unoccupied.

The activation loop, which regulates phosphorylation, is characterized by at least resides 640 to 663. Quite surprisingly, while the activation loops of FLGK and IRK contain the same number of amino acid residues and share greater than 50% sequence homology, the paths of the polypeptide chains are strikingly dissimilar, diverging at Ala-640 (Gly-1149 in IRK) and reconverging at Val-664 (Val-1173 in IRK). Tyr-653 and Tyr 564 are not bound in the active site. Instead, these residues point away from it. Tyr-653 is in van der Waals contact with several hydrophobic residues (Val-664, Leu-672 and Phe-710) and is hydrogen-bonded via its hydroxyl group to a backbone carbonyl oxygen (Leu-672). Tyr-654 is more solvent exposed than Tyr-653, and its only van der Waals contact is with Val-706. Temperature factor data suggest that the activation loop is relatively mobile and adopts multiple conformations.

The catalytic loop of protein kinases lies between secondary structure elements αE and β7 and contains an invariant aspartic acid residue (Asp-623 in FLGK) which serves as the catalytic base in the phosphotransfer reaction, abstracting the proton from the hydroxyl group of the substrate tyrosine, serine or threonine. The catalytic loop sequence of FLGK comprises at least residues His-621 to Asn-628 (amino acid sequence residues 166–173 of SEQ ID NO:1 HRDLAARN), and is identical to that for IRK and most receptor and non-receptor PTKs.

In addition to the two tyrosine autophosphorylation sites in the activation loop (Tyr-653 and Tyr-654), there are four other autophosphorylation sites present in the FLGK crystals of the invention: one in the juxtamembrane region (Tyr-463), two in the kinase insert (Tyr-583 and Tyr-585) and one in-the C-terminal lobe (Tyr-730) (Mohammadi et al., 1996). They exhibit varying degrees of conservation in mammalian FGF receptors:. Tyr-463 and Tyr-585 in FGFR1 and 2; Tyr-583 in FGFR1, 2 and 3; and Tyr-730 in FGFR 1, 2, 3 and 4 (FIG. 3).

Referring now to FIG. 5, the positions of the autophosphorylation sites are mapped onto the FLGK structure. The juxtamembrane site (Tyr-463) and the residues N-terminal to it are disordered in one of the FLGK molecules in the asymmetric unit. In the other molecule in the asymmetric unit Tyr-463 is involved in a lattice contact.

The kinase insert region (the region between helices αD and αE) contains autophosphorylation sites Tyr-583 and Tyr-585 and is disordered in both FLGK molecules in the asymmetric unit of the C2-A form of the crystal. In the C2-B form, several lattice contacts partially pin down this region in one of the two FLGK molecules in the asymmetric unit, allowing a trace of the polypeptide chain to be made. There is no well-defined secondary structure for these residues. Tyr-730, situated in αH in the C-terminal lobe, is nearly buried and the side-chain hydroxyl group makes two hydrogen-bonds. The side chains of neighboring Met-732 and Met-733 are both buried. Therefore, phosphorylation of Tyr-730 would presumably require prior unfolding of αH.

Aside from Tyr-730, the five other autophosphorylation sites (including Tyr-653 and Tyr-654) are found in relatively mobile segments of the FLGK molecule. While not intending to be bound by theory, the spatial positions of the autophosphorylation sites relative to the active site suggest that autophosphorylation occurs by a trans mechanism between two kinase domains, supporting the hypothesis that ligand-induced receptor dimerization is critical for the initiation of autophosphorylation events.

The structure of crystalline FLGK:AMP-PCP co-complex is essentially similar to that observed for crystalline FLGK. There are no significant changes in the structure of FLGK induced by AMP-PCP binding. In particular, binding of AMP-PCP, and by extension ATP, does not by itself promote lobe closure under the crystallization conditions used. Furthermore, complexation did not result in any noticeable changes in the conformations of the activation and nucleotide-binding loops.

The crystalline FLGK:AMP-PCP co-complex contains hydrogen bonds that are present between N1 of adenine and the amide nitrogen of Ala-564 and between N6 of adenine and the carbonyl oxygen of Glu-562. The adenine ring is flanked on one side by Leu-484 and-Val-492 (N-terminal lobe) and on the other side by Leu-630 (C-terminal lobe). The ribose hydroxyl groups make no direct hydrogen bonds with protein atoms. Lys-514 is hydrogen-bonded to oxygens of the β- and γ-phosphates. There is no unambiguous electron density that would indicate the positions of $Mg^{2+}$ ions. Generally, AMP-PCP appears to be coordinated rather loosely to unphosphorylated FLGK, being bound to the "roof" of the cleft rather than being tightly sandwiched between the two kinase lobes.

5.5.2 Structural Differences Between FGF-R and IRK

Several features distinguish the FGF-receptor structure from that of the insulin-receptor tyrosine kinase. These distinctions are likely to be important in signalling by FGF-receptors, and other monomeric receptors that are believed to undergo ligand-induced dimerization.

The most significant difference between the structures of FGFR1K and IRK is the conformation of the activation loop. In FGFR1K, the activation loop is disposed such that the binding site for substrate peptides is blocked not by an activation loop tyrosine, as in IRK, but by Arg-661 and PTK-invariant Pro-663, while the ATP binding site is accessible. This represents another molecular mechanism by which a receptor PTK may be autoinhibited. The observed autoinhibition in FGFR1K would appear to be weaker than that in IRK because of fewer specific interactions made by residues in the FGFR1K activation loop (manifested in the relatively higher B-values) and the accessibility of the ATP site. One obvious distinction between the insulin and FGF receptor families is that in the former, receptors are covalently linked heterotetramers ($\alpha_2\beta_2$), whereas in the latter, receptor dimerization is ligand dependent. Receptors whose kinase domains are always in close proximity may require a stronger autoinhibition mechanism than those receptors that associate only upon ligand binding (Taylor et al., 1995). Since most growth factor receptors undergo ligand-dependent dimerization and activation, the FGF receptor autoinhibition mechanism appears to be a more general one.

6. EXAMPLE

Preparation of Crystals of the Catalytic Domain of the FGF-R-1

The subsections below describe the production of a polypeptide containing the catalytic domain of the FGF-receptor-1, and the preparation and characterization of crystals, derivative crystals and co-crystals of sufficient quality for X-ray diffraction analysis.

Production and Purification of FLGK

A recombinant baculoviras (Pharmingen, CA) was engineered to encode the protein of SEQ ID NO:3. Compared to tie sequence of humann FLGK (SEQ ID NO:1), the protein of SEQ ID NO:3 has a cleavable histidine tag (MRGSHHHHHHGMASMTGBQQMGRDLYDDDDKD TSSR) fused to the N-terminus to aid in protein purification. The protein of SEQ ID NO:3 is encoded by the nucleic acid sequence of SEQ ID NO:5. Also, three amino acid substitutions were introduced: Cys-488→Ala, Cys-584→Ser and Leu-457→Val. The two cysteine substitutions were made to prevent the formation of disulfide-linked oligomers, which occurs for the native protein. The substitution Leu-457→Val was necessary to introduce a NcoI cloning site near Met-456. The codon fox Tyr-766 (TAC) was changed to a stop codon (TAG) and a HindIII-cloning site was generated following this stop codon. These substitutions were introduced into the full length cDNA of hman FLGK (SEQ ID NO:4) in ml3MP19 by site-directed mutagenesis using an in vitro mutagenesis kit according to the manufacturer's protocol (Amersham). The resulting construct was digested with NcoI and HindIII and was ligated into appropriately digested pBlueBac HistagB (Invitrogen). Transfection of insect cells (Sf9) was performed with the BaculoGold transfection system according to the manufacturet's protocol (Pharmingen). Following identification of positive plaques, the recombinant baculovirus was amplified to high titer ($5 \times 10^7$ virus particles/ml). Sf9 cells were grown in 175-cm² flasks to a density of $2-3 \times 10^7$ per flask and infected with recombinant baculovirus with a multiplicity of infection (MOI) of ten (10). After 48 hrs., cells were harvested by centrifugation at 3,000 g for 35 min. at 4° C. and then lysed in lysis buffer (25 mM HEPES, pH 7.5, 150 mM NaCl, 10% glycerol, 1.5 mN $MgCl_2$, 1% Triton X-100, 10 µg/rnl aprotonin, 10 µg/ml leupeptin and 1 mM phenylmethylsulfonyl fluoride (PMSF)). Lysates were centriflged in a Sorval RC 5C centriftge (Dupont) for 1 hr at 4° C. at 40,000 g followed by ultracentriftigation in an XL-80 ultracentrifuge (Beckman) at 100,000 g for 1 hr. After centrifugation, the clarified lysate was passed over a $Ni^{2+}$chelating column (Pharmacia), and the bound histidine-tagged fiusion protein was cluted with 100 mM imidazole (pH 7.5). Pooled fractions were loaded onto a Mono Q anion exchange column (Pharmacia) and eluted with a NaCl gradient fom 0 to 500 mM. The fractions contaning the fusion protein were concentrated in a Centricon-30 (Amicon), and the histidine tag was removed by overnight digestion with enterokinase (Biozyme) at 20° C. The digestion was terminated by the addition of aprotonin, leupeptin, PMSF, TPCK (tosyl-L-phenylalanine chloromethyl ketone) and bovine pancreatic trypsin ininbitor (BPTI). The cleaved kinase domain was then separated from the histidine tag on a Superose 12 size-exclusion column (Pharmacia). The eltited kinase domain was further purified on a Mono Q column. The purified kinase domain was analyzed by N-terminal sequencing and-mass spectrometry. Five amino acids (SAAGT) remained from the histidine tag. The predicted molecular mass was confirmed by mass spectrometry. The amino acid sequence of the pified poein (FLGK) is provided in SEQ ID NO:2.

6.1.1 Preparation of FLGK Native Crystals

FLGK native crystals (C2-A form) were grown at 4° C. by vapor diffusion in hanging drops (McPherson, 1990). 2 µL FLGK (SEQ ID NO:2) (20-mg/mL in 10 mM Tris-HCl, 10 mM NaCl, 2 mM DTT, pH 8.0) was mixed with an equal volume (2 µL) of reservoir buffer (16% w/v polyethylene glycol MW 10,000, 0.3 M $(NH_4)_2SO_4$, 5% v/v ethylene glycol, 100 mM bis-Tris, pH 6.5) and allowed to stand over 0.5 ml reservoir solution at 4° C. Irregular crystals typically grew to 0.6×0.3×0.2 mm over a period of 3–4 weeks. The solvent content of the crystal was 55% (assuming a partial specific volume of 0.73 cm³/gm).

FLGK native crystals (C2-B form) were grown as described above using a reservoir buffer containing 5% v/v glycerol instead of ethylene glycol. The solvent content of the crystal was 50% (assuming a partial specific volume of 0.73 cm³/gm).

6.1.2 Preparation of Heavy Atom Derivative Crystals

Heavy atom derivative crystals were obtained by soaking FLGK native crystals (C2-A form) in a solution containing ethylmercurithiosalicylic acid (thimerosal), $KAu(CN)_2$ or 4-chloromercuribenzoic acid, as provided in Table 1, infra, and containing 25% PEG 10000, 0.3 M $(NH_4)_2SO_4$, 5% ethylene glycol or glycerol, and 100 mM bis-Tris (pH 6.5), and were flash-cooled either in liquid nitrogen directly (Synchrotron) or in a dry nitrogen stream at −175° C. (rotating anode).

6.1.3 Preparation of FLGK:AMP-PCP Co-Crystals

Crystals of FLGK complexed with AMP-PCP were obtained as described in Example 6.1.1, except that the protein solution additionally contained 10 mM AMP-PCP and 20 mM $MgCl_2$.

6.2 Analysis and Characterization of FLGK Crystals

6.2.1 Diffraction Data Collection

Data were collected either on a Rigaku RU-200 rotating anode operated at 50 kV and 100 mA (Cu Kα) and equipped with double-focusing mirrors and an R-AXIS IIC image plate detector, or at beamline X-4A at the National Synchrotron Light Source, Brookhaven National Laboratory. Synchrotron data (λ=1.07 Å) were collected on Fuji image plates and read with a Fuji scanner. One cryo-cooled crystal was used for each of the data sets. To obtain cryo-cooled crystals, crystals were soaked in a cryo-protectant solution containing 25% PEG 10000, 0.3 M $(NH_4)_2SO_4$, 5% ethylene glycol or glycerol and 100 mM bis-Tris (pH 6.5), and were flash-cooled either in liquid nitrogen directly (synchrotron data) or in a dry nitrogen stream at −175° C. (rotating anode data). All data were processed using DENZO and SCALEPACK (Otwinowski, 1993).

6.2.2 Structure Determination

A molecular replacement solution was found initially for the C2-B crystal form using an IRK search model that consisted of polyalanine plus the common side chains for residues 993–1263 (FLGK residues 475–754), excluding residues 1094–1105 (kinase insert) and 1153–1170 (activation loop). With AMORE (Navaza, 1994), using 80% of the structure factor amplitudes between 15.0 and 3.5 Å, one of the two molecules in the asymmetric unit was located. The correlation coefficient (c.c.) for the correct 1-molecule solution was 0.23 (versus 0.20 for the highest incorrect solution). This molecule was rigid body-refined in X-PLOR (Brunger, 1992), first as one rigid body unit, then as two units each comprising a lobe of the kinase. Rigid body refinement (12.0–3.5 Å, F>3σ) resulted in a relative rotation of the two lobes of ~10° and an increase of the c.c. from 0.20 to 0.25. The rigid body-refined molecule was then used as a new search model in AMORE, and this time both molecules in the asymmetric unit were located. The c.c. for the correct 2-molecule solution was 0.35 (versus 0.27 for the highest incorrect solution).

Multiple cycles of model building and refinement against 6.0–2.4 Å data resulted in the addition to the model of many of the side chains and some of the missing polypeptide chain. Model building was performed using TOM/FRODO (Jones, 1985) and conjugate-gradient minimization and simulated annealing were performed using X-PLOR (Brunger, 1992). At this stage, the R-value was 30% (free R-value of 36%). To help expedite model building and refinement, experimental phases were obtained. Because crystals grown in the presence of ethylene glycol were easier to manipulate than those grown in glycerol, several heavy-atom derivative data sets were collected from C2-A crystals that had been soaked in various heavy atom solutions. The C2-B structure was subsequently refined against 6.0–2.4 Å data to an R-value of 23.8% (free R-value of 30.4%) with r.m.s.d. values of 0.008 Å for bond distances and 1.4° for bond angles.

Molecular replacement was used to locate the two FLGK molecules (designated FLGK-A and FLGK-B) in the asymmetric unit of the C2-A crystal form. Using AMORE with 80% of structure factor amplitudes between 15.0 and 3.5 Å and the C2-B model, the c.c. for the correct 2-molecule solution was 0.62 (versus 0.35 for the highest incorrect solution). Heavy atom positions were determined from difference Fourier maps using the calculated phases from the partial model. Refinement of heavy atom parameters and phase determination were performed with MLPHARE (Otwinowski, 1991). An initial molecular isomorphous replacement (MIR)-phased electron density map was calculated with data between 2.0. and 2.8 Å resolution. This map was improved by solvent flattening, histogram matching, and non-crystallographic symmetry (NCS) averaging using DM (Cowtan, 1994).

Refinement of the C2-A FLGK structure against 6.0–2.0 Å data proceeded by conjugate-gradient minimization and simulated annealing using X-PLOR. Tight NCS restraints were imposed until data to 2.0 Å resolution were included in the refinement, at which point the restraints were lifted. An overall anisotropic B-value was calculated using X-PLOR and applied to the observed structure factors, reducing the R-value by ~3%. Water molecules whose B-values refined to ≧70 ÅA$^2$ were omitted from the subsequent refinement round. The average B-value is 37.5 Å$^2$ for all protein atoms, 35.4 Å$^2$ for protein atoms in FLGK-A, 39.7 Å$^2$ for protein atoms in FLGK-B, and 40.2 Å$^2$ for water molecules. The side chains for Cys-603 in FLGK-A and FLGK-B and for Met-534 in FLGK-B have been modeled in two different conformations. Residues that are not included in the atomic model due to poor supporting electron density are for FLGK-A: 456–463, 486–490, 501–504, 580–591, 763–765; and for FLG-B: 456–460, 501–504, 578–593, 646–651, 657–659, 762–765.

The positions of the two AMP-PCP molecules (one per FLGK molecule) were easily identified in $2F_{obs(co-complex)} - F_{calc(FLGK)}$ difference Fourier maps. The AMP-PCP molecule bound to FLGK-B is less tightly bound and has been modeled with an occupancy of 0.5.

The following table summarizes the X-ray crystallography data sets of FLGK derivative crystals that were used to determine the structures of crystalline FLGK and crystalline FLGK:AMP-PCP co-complex of the invention.

TABLE 1

Data Collection and MIR Phasing Summary

| | Native | AMP-PCP | Thi-1[a] | Thi-2[a] | PCMB[a] | KAu(CN)$_2$ |
|---|---|---|---|---|---|---|
| X-ray source | X-4A | RU-200 | RU-200 | RU-200 | RU-200 | RU-200 |
| Resolution limit (Å) | 2.0 | 2.3 | 2.6 | 2.8 | 2.8 | 2.8 |
| Number of sites | — | — | 4 | 7 | 2 | 2 |
| Conc. (mM)/time (h) | — | — | 0.1/24 | 0.1/48 | 0.2/2 | 5.0/72 |
| $R_{sym}$[b] (%) | 4.8(19.7)[c] | 4.5(23.3)[c] | 5.5 | 9.8 | 6.8 | 6.8 |
| Total observations | 122569 | 91324 | 55456 | 59488 | 67988 | 45303 |
| Unique reflections | 50771 | 31997 | 42820[d] | 35538[d] | 18619 | 18202 |
| Completeness (%) | 97.3(96.3)[c] | 95.5(93.7)[c] | 95.0 | 96.7 | 98.0 | 97.7 |
| Signal (% 1 > 3σ) | 80.7(50.3)[c] | 79.6(51.7)[c] | 69.8 | 66.8 | 84.7 | 77.6 |
| $R_{iso}$[e] (%) | — | — | 17.1 | 31.2 | 15.4 | 15.2 |
| Phasing power[f] | — | — | 1.8 | 2.0 | 1.0 | 0.9 |
| $R_{cullis}$[g] (%) | — | — | 0.55 | 0.50 | 0.81 | 0.84 |
| Overall FOM[h] | | | | 0.60 | | |

[a]Thi-1, Thi-2; ethylmercurithiosalicylic acid (thimerosal); PCMB: 4-chloromercuribenzoic acid.
[b]$R_{sym} = 100 \times \Sigma_h\Sigma_i|I_i(h) - <I(h)>|/\Sigma_h\Sigma_iI_i(h)$
[c]Value in parentheses is for the highest resolution shell.
[d]I(+h) and I(−h) processed as independent reflections. Anomalous scattering contributions were included.
[e]$R_{iso} = 100 \times \Sigma_h ||F_p(h) \pm F_{PH}(h)| - |F_{PH}(h)||/\Sigma_h|F_p(h)|$, where $F_p$ and $F_{PH}$ are the native and derivative structure factors, respectively.
[f]Phasing power: r.m.s. heavy atom structure factor / r.m.s. lack of closure (for acentric reflections from 20.0 to 2.8 Å).
[g]$R_{cullis} = 100 \times \Sigma_h ||F_{PH}(h)| - F_{H(calc)}(h)|/\Sigma_h|F_{PH}(h) \pm F_p(h)|$ (for centric reflections from 20.0 to 2.8 Å).
[h]Figure of merit: $\int P(\phi)\exp(i\phi)d\phi / \int P(\phi)d(\phi)$, where P is the probability distribution of the phase angle $\phi$.

6.2.3 Structure Analyses

Atomic superpositions were performed with TOSS (Hendrickson, 1979). Per residue solvent accessible surface calculations were done with X-PLOR. The surface area buried in a dimer interface was calculated with GRASP (Nicholls et al., 1991) using a probe radius of 1.4 Å. The stereochemical quality of the atomic model was monitored using PROCHECK (Laskowski et al., 1993). As defined in PROCHECK, 93% of the residues in the model have main-chain torsion angles in the most favored Ramachandran regions. There are no residues in disallowed regions, and three residues in generously allowed regions: Arg-622 in FLGK-A and FLGK-B and Arg-554 in FLGK-A. The overall G-factor score is 0.42.

The following table summarizes the X-ray crystallography refinement parameters of the structures of crystalline FLGK and crystalline FLGK:AMP-PCP co-complex of the invention.

TABLE 2

Refinement Parameters
FLGK: 550 residues, 252 water molecules (4589 atoms)
FLGK:AMP-PCP: 550 residues, 238 water molecules, 2 AMP-PCP molecules (4638 atoms)

| Model | d-spacings (Å) | Reflections (N) | R-value[a] (%) | R.m.s.d. bonds (Å) | R.m.s.d. angles (°) | B-values[b] (Å$^2$) |
|---|---|---|---|---|---|---|
| FLGK: | 6.0–2.0 | 42548 | 21.3 (26.2)[c] | 0.008 | 1.3 | 1.6 |
| FLGK:AMP-PCP: | 6.0–2.3 | 26729 | 20.1 (27.5)[c] | 0.009 | 1.4 | 1.7 |

[a]R-value = $100 \times \Sigma_h \|F_{obs}(h)\| - \|F_{calc}(h)\| / \Sigma_h |F_{obs}(h)|$ for reflections with $F_{obs} > 2\sigma$.
[b]For bonded protein atoms.
[c]Value in parentheses is the free R-value (Brünger, 1993) determined from 5% of the data.

Tables 3 and 4, following this page, provide the atomic structure coordinates of unphosphorylated FLGK and unphosphorylated FLGK:AMP-PCP co-complex, respectively. In the Tables, coordinates for both of the FLGK molecules of the dimer comprising the asymmetric unit are provided. The amino acid residue numbers coincide with those used in FIG. 3. In the first FLGK molecule of the dimer the residue number is preceded by a 1, i.e., residue number 464 of the first FLGK molecule of the dimer is denoted by "1464".

TABLE 3

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1 | N | GLU | 1464 | −13.639 | 16.975 | 8.571 | 1.00 | 54.29 |
| ATOM 3 | CA | GLU | 1464 | −12.479 | 17.105 | 7.695 | 1.00 | 52.62 |
| ATOM 4 | CB | GLU | 1464 | −11.400 | 17.974 | 8.349 | 1.00 | 54.64 |
| ATOM 5 | C | GLU | 1464 | −11.914 | 15.738 | 7.319 | 1.00 | 49.74 |
| ATOM 6 | O | GLU | 1464 | −11.845 | 15.407 | 6.136 | 1.00 | 52.04 |
| ATOM 7 | N | LEU | 1465 | −11.562 | 14.925 | 8.310 | 1.00 | 44.95 |
| ATOM 9 | CA | LEU | 1465 | −11.018 | 13.599 | 8.037 | 1.00 | 41.04 |
| ATOM 10 | CB | LEU | 1465 | −10.236 | 13.066 | 9.235 | 1.00 | 40.18 |
| ATOM 11 | CG | LEU | 1465 | −8.719 | 13.196 | 9.130 | 1.00 | 43.70 |
| ATOM 12 | CD1 | LEU | 1465 | −8.346 | 14.654 | 8.891 | 1.00 | 46.74 |
| ATOM 13 | CD2 | LEU | 1465 | −8.061 | 12.671 | 10.395 | 1.00 | 40.72 |
| ATOM 14 | C | LEU | 1465 | −12.092 | 12.594 | 7.656 | 1.00 | 39.18 |
| ATOM 15 | O | LEU | 1465 | −13.187 | 12.590 | 8.219 | 1.00 | 38.05 |
| ATOM 16 | N | PRO | 1466 | −11.802 | 11.748 | 6.657 | 1.00 | 37.20 |
| ATOM 17 | CD | PRO | 1466 | −10.597 | 11.793 | 5.810 | 1.00 | 36.41 |
| ATOM 18 | CA | PRO | 1466 | −12.741 | 10.727 | 6.189 | 1.00 | 36.13 |
| ATOM 19 | CB | PRO | 1466 | −12.110 | 10.262 | 4.878 | 1.00 | 37.50 |
| ATOM 20 | CG | PRO | 1466 | −10.629 | 10.459 | 5.135 | 1.00 | 36.20 |
| ATOM 21 | C | PRO | 1466 | −12.846 | 9.595 | 7.201 | 1.00 | 35.61 |
| ATOM 22 | O | PRO | 1466 | −11.847 | 9.174 | 7.788 | 1.00 | 35.18 |
| ATOM 23 | N | GLU | 1467 | −14.060 | 9.121 | 7.429 | 1.00 | 35.38 |
| ATOM 25 | CA | GLU | 1467 | −14.268 | 8.053 | 8.377 | 1.00 | 35.43 |
| ATOM 26 | CB | GLU | 1467 | −15.744 | 7.965 | 8.746 | 1.00 | 41.10 |
| ATOM 27 | CG | GLU | 1467 | −16.375 | 9.280 | 9.098 | 1.00 | 48.25 |
| ATOM 28 | CD | GLU | 1467 | −17.819 | 9.145 | 9.596 | 1.00 | 50.24 |
| ATOM 29 | OE1 | GLU | 1467 | −18.446 | 8.071 | 9.378 | 1.00 | 52.82 |
| ATOM 30 | OE2 | GLU | 1467 | −18.314 | 10.109 | 10.230 | 1.00 | 51.26 |
| ATOM 31 | C | GLU | 1467 | −13.838 | 6.714 | 7.801 | 1.00 | 32.65 |
| ATOM 32 | O | GLU | 1467 | −13.899 | 6.511 | 6.591 | 1.00 | 35.06 |
| ATOM 33 | N | ASP | 1468 | −13.299 | 5.854 | 8.659 | 1.00 | 30.46 |
| ATOM 35 | CA | ASP | 1468 | −12.883 | 4.516 | 8.262 | 1.00 | 28.85 |
| ATOM 36 | CB | ASP | 1468 | −11.384 | 4.424 | 7.975 | 1.00 | 29.34 |
| ATOM 37 | CG | ASP | 1468 | −10.985 | 3.072 | 7.408 | 1.00 | 27.57 |
| ATOM 38 | OD1 | ASP | 1468 | −11.833 | 2.159 | 7.359 | 1.00 | 27.78 |
| ATOM 39 | OD2 | ASP | 1468 | −9.817 | 2.916 | 7.003 | 1.00 | 30.64 |
| ATOM 40 | C | ASP | 1468 | −13.252 | 3.564 | 9.384 | 1.00 | 29.29 |
| ATOM 41 | O | ASP | 1468 | −12.481 | 3.364 | 10.336 | 1.00 | 27.76 |
| ATOM 42 | N | PRO | 1469 | −14.435 | 2.939 | 9.268 | 1.00 | 28.99 |
| ATOM 43 | CD | PRO | 1469 | −15.354 | 3.091 | 8.120 | 1.00 | 28.09 |
| ATOM 44 | CA | PRO | 1469 | −14.971 | 1.987 | 10.244 | 1.00 | 30.01 |
| ATOM 45 | CB | PRO | 1469 | −16.244 | 1.473 | 9.553 | 1.00 | 33.33 |
| ATOM 46 | CG | PRO | 1469 | −16.665 | 2.630 | 8.690 | 1.00 | 30.53 |
| ATOM 47 | C | PRO | 1469 | −14.012 | 0.848 | 10.563 | 1.00 | 28.96 |
| ATOM 48 | O | PRO | 1469 | −14.085 | 0.251 | 11.636 | 1.00 | 28.52 |
| ATOM 49 | N | ARG | 1470 | −13.106 | 0.556 | 9.631 | 1.00 | 27.59 |
| ATOM 51 | CA | ARG | 1470 | −12.139 | −0.520 | 9.810 | 1.00 | 27.37 |
| ATOM 52 | CB | ARG | 1470 | −11.301 | −0.707 | 8.533 | 1.00 | 28.84 |
| ATOM 53 | CG | ARG | 1470 | −12.049 | −1.279 | 7.317 | 1.00 | 30.57 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 54 | CD | ARG | 1470 | −11.137 | −1.352 | 6.068 | 1.00 | 26.71 |
| ATOM 55 | NE | ARG | 1470 | −10.489 | −0.068 | 5.793 | 1.00 | 31.26 |
| ATOM 57 | CZ | ARG | 1470 | −9.603 | 0.151 | 4.823 | 1.00 | 32.60 |
| ATOM 58 | NH1 | ARG | 1470 | −9.241 | −0.828 | 3.999 | 1.00 | 33.19 |
| ATOM 61 | NH2 | ARG | 1470 | −9.067 | 1.359 | 4.686 | 1.00 | 28.65 |
| ATOM 64 | C | ARG | 1470 | −11.180 | −0.285 | 10.981 | 1.00 | 29.21 |
| ATOM 65 | O | ARG | 1470 | −10.757 | −1.230 | 11.641 | 1.00 | 28.47 |
| ATOM 66 | N | TRP | 1471 | −10.909 | 0.977 | 11.280 | 1.00 | 27.80 |
| ATOM 68 | CA | TRP | 1471 | −9.940 | 1.314 | 12.306 | 1.00 | 28.62 |
| ATOM 69 | CB | TRP | 1471 | −8.729 | 1.944 | 11.609 | 1.00 | 24.97 |
| ATOM 70 | CG | TRP | 1471 | −8.044 | 0.976 | 10.728 | 1.00 | 24.86 |
| ATOM 71 | CD2 | TRP | 1471 | −7.156 | −0.060 | 11.144 | 1.00 | 28.00 |
| ATOM 72 | CE2 | TRP | 1471 | −6.782 | −0.776 | 9.989 | 1.00 | 29.23 |
| ATOM 73 | CE3 | TRP | 1471 | −6.642 | −0.460 | 12.389 | 1.00 | 26.59 |
| ATOM 74 | CD1 | TRP | 1471 | −8.166 | 0.860 | 9.374 | 1.00 | 27.23 |
| ATOM 75 | NE1 | TRP | 1471 | −7.413 | −0.192 | 8.922 | 1.00 | 30.10 |
| ATOM 77 | CZ2 | TRP | 1471 | −5.912 | −1.866 | 10.036 | 1.00 | 28.70 |
| ATOM 78 | CZ3 | TRP | 1471 | −5.778 | −1.545 | 12.435 | 1.00 | 27.18 |
| ATOM 79 | CH2 | TRP | 1471 | −5.424 | −2.237 | 11.266 | 1.00 | 27.23 |
| ATOM 80 | C | TRP | 1471 | −10.371 | 2.223 | 13.440 | 1.00 | 28.42 |
| ATOM 81 | O | TRP | 1471 | −9.664 | 2.321 | 14.442 | 1.00 | 26.48 |
| ATOM 82 | N | GLU | 1472 | −11.521 | 2.874 | 13.293 | 1.00 | 28.62 |
| ATOM 84 | CA | GLU | 1472 | −11.981 | 3.823 | 14.297 | 1.00 | 27.16 |
| ATOM 85 | CB | GLU | 1472 | −13.245 | 4.534 | 13.799 | 1.00 | 28.89 |
| ATOM 86 | CG | GLU | 1472 | −13.552 | 5.869 | 14.520 | 1.00 | 29.09 |
| ATOM 87 | CD | GLU | 1472 | −12.692 | 7.042 | 14.054 | 1.00 | 26.43 |
| ATOM 88 | OE1 | GLU | 1472 | −12.134 | 7.009 | 12.938 | 1.00 | 28.59 |
| ATOM 89 | OE2 | GLU | 1472 | −12.596 | 8.024 | 14.801 | 1.00 | 27.28 |
| ATOM 90 | C | GLU | 1472 | −12.217 | 3.269 | 15.701 | 1.00 | 25.10 |
| ATOM 91 | O | GLU | 1472 | −12.763 | 2.196 | 15.861 | 1.00 | 26.48 |
| ATOM 92 | N | LEU | 1473 | −11.750 | 3.991 | 16.711 | 1.00 | 24.65 |
| ATOM 94 | CA | LEU | 1473 | −11.962 | 3.608 | 18.104 | 1.00 | 26.27 |
| ATOM 95 | CB | LEU | 1473 | −10.645 | 3.266 | 18.817 | 1.00 | 28.24 |
| ATOM 96 | CG | LEU | 1473 | −10.750 | 3.025 | 20.337 | 1.00 | 27.23 |
| ATOM 97 | CD1 | LEU | 1473 | −11.323 | 1.636 | 20.642 | 1.00 | 25.23 |
| ATOM 98 | CD2 | LEU | 1473 | −9.390 | 3.183 | 21.000 | 1.00 | 26.33 |
| ATOM 99 | C | LEU | 1473 | −12.546 | 4.856 | 18.740 | 1.00 | 26.52 |
| ATOM 100 | O | LEU | 1473 | −12.122 | 5.973 | 18.411 | 1.00 | 25.16 |
| ATOM 101 | N | PRO | 1474 | −13.610 | 4.703 | 19.554 | 1.00 | 28.52 |
| ATOM 102 | CD | PRO | 1474 | −14.435 | 3.500 | 19.770 | 1.00 | 29.65 |
| ATOM 103 | CA | PRO | 1474 | −14.215 | 5.870 | 20.207 | 1.00 | 29.18 |
| ATOM 104 | CB | PRO | 1474 | −15.368 | 5.251 | 21.003 | 1.00 | 28.58 |
| ATOM 105 | CG | PRO | 1474 | −15.768 | 4.097 | 20.154 | 1.00 | 28.17 |
| ATOM 106 | C | PRO | 1474 | −13.173 | 6.528 | 21.124 | 1.00 | 29.75 |
| ATOM 107 | O | PRO | 1474 | −12.427 | 5.841 | 21.828 | 1.00 | 31.78 |
| ATOM 108 | N | ARG | 1475 | −13.107 | 7.849 | 21.097 | 1.00 | 30.76 |
| ATOM 110 | CA | ARG | 1475 | −12.149 | 8.588 | 21.900 | 1.00 | 32.26 |
| ATOM 111 | CB | ARG | 1475 | −12.362 | 10.083 | 21.743 | 1.00 | 31.58 |
| ATOM 112 | CG | ARG | 1475 | −12.178 | 10.536 | 20.342 | 1.00 | 37.54 |
| ATOM 113 | CD | ARG | 1475 | −12.048 | 12.027 | 20.206 | 1.00 | 36.96 |
| ATOM 114 | NE | ARG | 1475 | −11.733 | 12.317 | 18.813 | 1.00 | 40.07 |
| ATOM 116 | CZ | ARG | 1475 | −10.503 | 12.501 | 18.352 | 1.00 | 37.59 |
| ATOM 117 | NH1 | ARG | 1475 | −9.470 | 12.447 | 19.186 | 1.00 | 34.89 |
| ATOM 120 | NH2 | ARG | 1475 | −10.308 | 12.669 | 17.049 | 1.00 | 34.54 |
| ATOM 123 | C | ARG | 1475 | −12.173 | 8.261 | 23.371 | 1.00 | 35.58 |
| ATOM 124 | O | ARG | 1475 | −11.135 | 8.318 | 24.036 | 1.00 | 37.03 |
| ATOM 125 | N | ASP | 1476 | −13.356 | 7.958 | 23.889 | 1.00 | 36.68 |
| ATOM 127 | CA | ASP | 1476 | −13.498 | 7.647 | 25.307 | 1.00 | 37.07 |
| ATOM 128 | CB | ASP | 1476 | −14.967 | 7.759 | 25.740 | 1.00 | 37.87 |
| ATOM 129 | CG | ASP | 1476 | −15.851 | 6.704 | 25.115 | 1.00 | 38.93 |
| ATOM 130 | OD1 | ASP | 1476 | −15.412 | 6.015 | 24.179 | 1.00 | 43.75 |
| ATOM 131 | OD2 | ASP | 1476 | −17.003 | 6.558 | 25.563 | 1.00 | 45.77 |
| ATOM 132 | C | ASP | 1476 | −12.922 | 6.292 | 25.701 | 1.00 | 35.86 |
| ATOM 133 | O | ASP | 1476 | −12.923 | 5.928 | 26.878 | 1.00 | 37.98 |
| ATOM 134 | N | ARG | 1477 | −12.478 | 5.527 | 24.711 | 1.00 | 33.37 |
| ATOM 136 | CA | ARG | 1477 | −11.889 | 4.221 | 24.961 | 1.00 | 31.84 |
| ATOM 137 | CB | ARG | 1477 | −12.214 | 3.262 | 23.809 | 1.00 | 31.84 |
| ATOM 138 | CG | ARG | 1477 | −13.693 | 2.965 | 23.580 | 1.00 | 29.70 |
| ATOM 139 | CD | ARG | 1477 | −14.366 | 2.365 | 24.809 | 1.00 | 33.88 |
| ATOM 140 | NE | ARG | 1477 | −14.596 | 3.372 | 25.838 | 1.00 | 33.86 |
| ATOM 142 | CZ | ARG | 1477 | −14.845 | 3.102 | 27.113 | 1.00 | 34.14 |
| ATOM 143 | NH1 | ARG | 1477 | −14.906 | 1.846 | 27.542 | 1.00 | 30.58 |
| ATOM 146 | NH2 | ARG | 1477 | −15.024 | 4.102 | 27.961 | 1.00 | 33.14 |
| ATOM 149 | C | ARG | 1477 | −10.373 | 4.338 | 25.105 | 1.00 | 31.30 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 150 | O | ARG | 1477 | −9.679 | 3.362 | 25.365 | 1.00 | 32.32 |
| ATOM 151 | N | LEU | 1478 | −9.856 | 5.544 | 24.978 | 1.00 | 32.85 |
| ATOM 153 | CA | LEU | 1478 | −8.426 | 5.739 | 25.054 | 1.00 | 35.64 |
| ATOM 154 | CB | LEU | 1478 | −7.964 | 6.360 | 23.737 | 1.00 | 34.96 |
| ATOM 155 | CG | LEU | 1478 | −6.498 | 6.291 | 23.331 | 1.00 | 36.36 |
| ATOM 156 | CD1 | LEU | 1478 | −6.059 | 4.833 | 23.192 | 1.00 | 30.71 |
| ATOM 157 | CD2 | LEU | 1478 | −6.335 | 7.048 | 22.020 | 1.00 | 33.97 |
| ATOM 158 | C | LEU | 1478 | −8.054 | 6.625 | 26.243 | 1.00 | 37.60 |
| ATOM 159 | O | LEU | 1478 | −8.366 | 7.815 | 26.263 | 1.00 | 41.20 |
| ATOM 160 | N | VAL | 1479 | −7.442 | 6.023 | 27.257 | 1.00 | 36.52 |
| ATOM 162 | CA | VAL | 1479 | −7.008 | 6.745 | 28.449 | 1.00 | 35.59 |
| ATOM 163 | CB | VAL | 1479 | −7.041 | 5.829 | 29.688 | 1.00 | 35.92 |
| ATOM 164 | CG1 | VAL | 1479 | −6.712 | 6.627 | 30.926 | 1.00 | 39.40 |
| ATOM 165 | CG2 | VAL | 1479 | −8.404 | 5.163 | 29.825 | 1.00 | 34.46 |
| ATOM 166 | C | VAL | 1479 | −5.577 | 7.224 | 28.197 | 1.00 | 35.36 |
| ATOM 167 | O | VAL | 1479 | −4.622 | 6.443 | 28.269 | 1.00 | 32.50 |
| ATOM 168 | N | LEU | 1480 | −5.439 | 8.506 | 27.878 | 1.00 | 37.77 |
| ATOM 170 | CA | LEU | 1480 | −4.132 | 9.086 | 27.572 | 1.00 | 42.77 |
| ATOM 171 | CB | LEU | 1480 | −4.298 | 10.421 | 26.842 | 1.00 | 41.84 |
| ATOM 172 | CG | LEU | 1480 | −4.991 | 10.369 | 25.471 | 1.00 | 42.45 |
| ATOM 173 | CD1 | LEU | 1480 | −5.135 | 11.774 | 24.924 | 1.00 | 42.58 |
| ATOM 174 | CD2 | LEU | 1480 | −4.200 | 9.508 | 24.502 | 1.00 | 43.09 |
| ATOM 175 | C | LEU | 1480 | −3.211 | 9.233 | 28.778 | 1.00 | 45.25 |
| ATOM 176 | O | LEU | 1480 | −3.621 | 9.739 | 29.822 | 1.00 | 45.47 |
| ATOM 177 | N | GLY | 1481 | −1.958 | 8.816 | 28.612 | 1.00 | 46.82 |
| ATOM 179 | CA | GLY | 1481 | −1.016 | 8.889 | 29.708 | 1.00 | 50.47 |
| ATOM 180 | C | GLY | 1481 | 0.296 | 9.617 | 29.472 | 1.00 | 52.24 |
| ATOM 181 | O | GLY | 1481 | 0.360 | 10.638 | 28.781 | 1.00 | 53.41 |
| ATOM 182 | N | LYS | 1482 | 1.349 | 9.070 | 30.068 | 1.00 | 53.64 |
| ATOM 184 | CA | LYS | 1482 | 2.697 | 9.627 | 30.000 | 1.00 | 56.19 |
| ATOM 185 | CB | LYS | 1482 | 3.636 | 8.776 | 30.859 | 1.00 | 57.19 |
| ATOM 186 | CG | LYS | 1482 | 5.115 | 9.023 | 30.628 | 1.00 | 61.02 |
| ATOM 187 | CD | LYS | 1482 | 5.938 | 7.831 | 31.089 | 1.00 | 63.12 |
| ATOM 188 | CE | LYS | 1482 | 5.494 | 6.547 | 30.395 | 1.00 | 61.98 |
| ATOM 189 | NZ | LYS | 1482 | 6.252 | 5.368 | 30.899 | 1.00 | 63.38 |
| ATOM 193 | C | LYS | 1482 | 3.297 | 9.795 | 28.604 | 1.00 | 56.56 |
| ATOM 194 | O | LYS | 1482 | 3.291 | 8.868 | 27.791 | 1.00 | 55.03 |
| ATOM 195 | N | PRO | 1483 | 3.852 | 10.983 | 28.323 | 1.00 | 58.31 |
| ATOM 196 | CD | PRO | 1483 | 3.859 | 12.191 | 29.167 | 1.00 | 56.98 |
| ATOM 197 | CA | PRO | 1483 | 4.465 | 11.254 | 27.020 | 1.00 | 59.52 |
| ATOM 198 | CB | PRO | 1483 | 4.910 | 12.711 | 27.155 | 1.00 | 58.75 |
| ATOM 199 | CG | PRO | 1483 | 3.927 | 13.278 | 28.141 | 1.00 | 58.79 |
| ATOM 200 | C | PRO | 1483 | 5.673 | 10.335 | 26.834 | 1.00 | 61.17 |
| ATOM 201 | O | PRO | 1483 | 6.509 | 10.216 | 27.731 | 1.00 | 61.31 |
| ATOM 202 | N | LEU | 1484 | 5.728 | 9.643 | 25.702 | 1.00 | 64.31 |
| ATOM 204 | CA | LEU | 1484 | 6.838 | 8.738 | 25.408 | 1.00 | 67.77 |
| ATOM 205 | CB | LEU | 1484 | 6.349 | 7.512 | 24.640 | 1.00 | 67.66 |
| ATOM 206 | CG | LEU | 1484 | 5.415 | 6.558 | 25.386 | 1.00 | 69.00 |
| ATOM 207 | CD1 | LEU | 1484 | 4.943 | 5.457 | 24.445 | 1.00 | 66.76 |
| ATOM 208 | CD2 | LEU | 1484 | 6.126 | 5.972 | 26.604 | 1.00 | 67.77 |
| ATOM 209 | C | LEU | 1484 | 7.934 | 9.431 | 24.608 | 1.00 | 70.82 |
| ATOM 210 | O | LEU | 1484 | 9.117 | 9.115 | 24.759 | 1.00 | 71.82 |
| ATOM 211 | N | GLY | 1485 | 7.534 | 10.357 | 23.742 | 1.00 | 73.28 |
| ATOM 213 | CA | GLY | 1485 | 8.492 | 11.077 | 22.922 | 1.00 | 74.53 |
| ATOM 214 | C | GLY | 1485 | 7.819 | 11.754 | 21.747 | 1.00 | 75.19 |
| ATOM 215 | O | GLY | 1485 | 6.635 | 12.090 | 21.822 | 1.00 | 75.61 |
| ATOM 216 | N | GLN | 1491 | 4.406 | 14.274 | 18.638 | 1.00 | 50.72 |
| ATOM 218 | CA | GLN | 1491 | 4.042 | 13.876 | 19.994 | 1.00 | 47.33 |
| ATOM 219 | CB | GLN | 1491 | 3.033 | 14.869 | 20.587 | 1.00 | 46.67 |
| ATOM 220 | C | GLN | 1491 | 3.486 | 12.449 | 20.073 | 1.00 | 46.66 |
| ATOM 221 | O | GLN | 1491 | 2.581 | 12.074 | 19.323 | 1.00 | 45.20 |
| ATOM 222 | N | VAL | 1492 | 4.072 | 11.650 | 20.960 | 1.00 | 45.41 |
| ATOM 224 | CA | VAL | 1492 | 3.646 | 10.274 | 21.184 | 1.00 | 43.83 |
| ATOM 225 | CB | VAL | 1492 | 4.680 | 9.244 | 20.709 | 1.00 | 41.60 |
| ATOM 226 | CG1 | VAL | 1492 | 4.138 | 7.849 | 20.937 | 1.00 | 41.35 |
| ATOM 227 | CG2 | VAL | 1492 | 5.007 | 9.445 | 19.237 | 1.00 | 42.72 |
| ATOM 228 | C | VAL | 1492 | 3.458 | 10.084 | 22.683 | 1.00 | 44.45 |
| ATOM 229 | O | VAL | 1492 | 4.335 | 10.437 | 23.482 | 1.00 | 43.86 |
| ATOM 230 | N | VAL | 1493 | 2.309 | 9.548 | 23.070 | 1.00 | 42.67 |
| ATOM 232 | CA | VAL | 1493 | 2.029 | 9.321 | 24.477 | 1.00 | 41.05 |
| ATOM 233 | CB | VAL | 1493 | 0.884 | 10.242 | 25.013 | 1.00 | 40.64 |
| ATOM 234 | CG1 | VAL | 1493 | 1.177 | 11.693 | 24.722 | 1.00 | 42.40 |
| ATOM 235 | CG2 | VAL | 1493 | −0.459 | 9.844 | 24.427 | 1.00 | 43.36 |
| ATOM 236 | C | VAL | 1493 | 1.626 | 7.880 | 24.704 | 1.00 | 40.09 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 237 | O | VAL | 1493 | 1.129 | 7.212 | 23.796 | 1.00 | 39.99 |
| ATOM 238 | N | LEU | 1494 | 1.927 | 7.374 | 25.890 | 1.00 | 37.10 |
| ATOM 240 | CA | LEU | 1494 | 1.535 | 6.036 | 26.250 | 1.00 | 35.08 |
| ATOM 241 | CB | LEU | 1494 | 2.359 | 5.542 | 27.440 | 1.00 | 35.57 |
| ATOM 242 | CG | LEU | 1494 | 2.036 | 4.161 | 28.007 | 1.00 | 36.87 |
| ATOM 243 | CD1 | LEU | 1494 | 2.123 | 3.085 | 26.931 | 1.00 | 36.90 |
| ATOM 244 | CD2 | LEU | 1494 | 2.998 | 3.860 | 29.143 | 1.00 | 41.99 |
| ATOM 245 | C | LEU | 1494 | 0.077 | 6.236 | 26.648 | 1.00 | 33.31 |
| ATOM 246 | O | LEU | 1494 | −0.311 | 7.318 | 27.097 | 1.00 | 32.93 |
| ATOM 247 | N | ALA | 1495 | −0.740 | 5.219 | 26.435 | 1.00 | 33.35 |
| ATOM 249 | CA | ALA | 1495 | −2.147 | 5.292 | 26.773 | 1.00 | 30.67 |
| ATOM 250 | CB | ALA | 1495 | −2.923 | 5.937 | 25.637 | 1.00 | 30.35 |
| ATOM 251 | C | ALA | 1495 | −2.661 | 3.893 | 27.025 | 1.00 | 29.97 |
| ATOM 252 | O | ALA | 1495 | −1.944 | 2.909 | 26.840 | 1.00 | 28.15 |
| ATOM 253 | N | GLU | 1496 | −3.898 | 3.813 | 27.488 | 1.00 | 30.37 |
| ATOM 255 | CA | GLU | 1496 | −4.537 | 2.536 | 27.745 | 1.00 | 31.47 |
| ATOM 256 | CB | GLU | 1496 | −4.862 | 2.392 | 29.223 | 1.00 | 32.48 |
| ATOM 257 | CG | GLU | 1496 | −3.627 | 2.239 | 30.093 | 1.00 | 37.81 |
| ATOM 258 | CD | GLU | 1496 | −3.938 | 2.426 | 31.565 | 1.00 | 41.09 |
| ATOM 259 | OE1 | GLU | 1496 | −4.328 | 3.548 | 31.944 | 1.00 | 41.53 |
| ATOM 260 | OE2 | GLU | 1496 | −3.797 | 1.453 | 32.341 | 1.00 | 44.12 |
| ATOM 261 | C | GLU | 1496 | −5.806 | 2.524 | 26.916 | 1.00 | 32.72 |
| ATOM 262 | O | GLU | 1496 | −6.586 | 3.478 | 26.954 | 1.00 | 33.91 |
| ATOM 263 | N | ALA | 1497 | −5.953 | 1.494 | 26.094 | 1.00 | 31.06 |
| ATOM 265 | CA | ALA | 1497 | −7.117 | 1.353 | 25.239 | 1.00 | 32.33 |
| ATOM 266 | CB | ALA | 1497 | −6.691 | 0.879 | 23.859 | 1.00 | 29.56 |
| ATOM 267 | C | ALA | 1497 | −8.056 | 0.343 | 25.885 | 1.00 | 32.26 |
| ATOM 268 | O | ALA | 1497 | −7.648 | −0.773 | 26.197 | 1.00 | 33.55 |
| ATOM 269 | N | ILE | 1498 | −9.286 | 0.759 | 26.160 | 1.00 | 32.99 |
| ATOM 271 | CA | ILE | 1498 | −10.276 | −0.126 | 26.766 | 1.00 | 34.00 |
| ATOM 272 | CB | ILE | 1498 | −11.329 | 0.668 | 27.592 | 1.00 | 34.69 |
| ATOM 273 | CG2 | ILE | 1498 | −12.341 | −0.288 | 28.240 | 1.00 | 34.24 |
| ATOM 274 | CG1 | ILE | 1498 | −10.647 | 1.496 | 28.686 | 1.00 | 33.56 |
| ATOM 275 | CD1 | ILE | 1498 | −11.543 | 2.572 | 29.258 | 1.00 | 31.25 |
| ATOM 276 | C | ILE | 1498 | −10.994 | −0.830 | 25.624 | 1.00 | 35.71 |
| ATOM 277 | O | ILE | 1498 | −11.618 | −0.181 | 24.786 | 1.00 | 34.88 |
| ATOM 278 | N | GLY | 1499 | −10.890 | −2.147 | 25.573 | 1.00 | 40.43 |
| ATOM 280 | CA | GLY | 1499 | −11.553 | −2.884 | 24.516 | 1.00 | 47.63 |
| ATOM 281 | C | GLY | 1499 | −10.670 | −3.233 | 23.330 | 1.00 | 53.08 |
| ATOM 282 | O | GLY | 1499 | −9.934 | −4.226 | 23.380 | 1.00 | 54.97 |
| ATOM 283 | N | LEU | 1500 | −10.713 | −2.394 | 22.294 | 1.00 | 54.18 |
| ATOM 285 | CA | LEU | 1500 | −9.957 | −2.603 | 21.055 | 1.00 | 55.26 |
| ATOM 286 | CB | LEU | 1500 | −8.444 | −2.726 | 21.305 | 1.00 | 55.39 |
| ATOM 287 | CG | LEU | 1500 | −7.562 | −1.472 | 21.241 | 1.00 | 54.27 |
| ATOM 288 | CD1 | LEU | 1500 | −6.110 | −1.891 | 21.367 | 1.00 | 52.89 |
| ATOM 289 | CD2 | LEU | 1500 | −7.768 | −0.711 | 19.935 | 1.00 | 50.91 |
| ATOM 290 | C | LEU | 1500 | −10.453 | −3.830 | 20.288 | 1.00 | 55.39 |
| ATOM 291 | O | LEU | 1500 | −10.376 | −4.963 | 20.774 | 1.00 | 56.23 |
| ATOM 292 | N | PRO | 1505 | −13.315 | −5.836 | 25.394 | 1.00 | 53.03 |
| ATOM 293 | CD | PRO | 1505 | −13.945 | −7.148 | 25.167 | 1.00 | 55.12 |
| ATOM 294 | CA | PRO | 1505 | −14.306 | −4.848 | 25.846 | 1.00 | 50.62 |
| ATOM 295 | CB | PRO | 1505 | −15.635 | −5.607 | 25.715 | 1.00 | 50.09 |
| ATOM 296 | CG | PRO | 1505 | −15.241 | −7.031 | 25.950 | 1.00 | 52.18 |
| ATOM 297 | C | PRO | 1505 | −14.039 | −4.348 | 27.273 | 1.00 | 46.35 |
| ATOM 298 | O | PRO | 1505 | −14.065 | −3.143 | 27.524 | 1.00 | 45.82 |
| ATOM 299 | N | ASN | 1506 | −13.711 | −5.261 | 28.181 | 1.00 | 42.76 |
| ATOM 301 | CA | ASN | 1506 | −13.433 | −4.892 | 29.566 | 1.00 | 45.29 |
| ATOM 302 | CB | ASN | 1506 | −14.283 | −5.728 | 30.529 | 1.00 | 45.92 |
| ATOM 303 | CG | ASN | 1506 | −15.752 | −5.395 | 30.441 | 1.00 | 46.17 |
| ATOM 304 | OD1 | ASN | 1506 | −16.132 | −4.232 | 30.390 | 1.00 | 48.57 |
| ATOM 305 | ND2 | ASN | 1506 | −16.589 | −6.418 | 30.406 | 1.00 | 48.63 |
| ATOM 308 | C | ASN | 1506 | −11.954 | −5.008 | 29.939 | 1.00 | 45.33 |
| ATOM 309 | O | ASN | 1506 | −11.597 | −5.084 | 31.121 | 1.00 | 44.53 |
| ATOM 310 | N | ARG | 1507 | −11.100 | −5.010 | 28.924 | 1.00 | 45.63 |
| ATOM 312 | CA | ARG | 1507 | −9.660 | −5.122 | 29.117 | 1.00 | 45.57 |
| ATOM 313 | CB | ARG | 1507 | −9.131 | −6.354 | 28.375 | 1.00 | 53.33 |
| ATOM 314 | CG | ARG | 1507 | −9.407 | −7.685 | 29.043 | 1.00 | 61.39 |
| ATOM 315 | CD | ARG | 1507 | −8.336 | −8.028 | 30.063 | 1.00 | 67.74 |
| ATOM 316 | NE | ARG | 1507 | −8.525 | −9.376 | 30.585 | 1.00 | 74.64 |
| ATOM 318 | CZ | ARG | 1507 | −7.970 | −9.842 | 31.701 | 1.00 | 80.01 |
| ATOM 319 | NH1 | ARG | 1507 | −7.166 | −9.075 | 32.433 | 1.00 | 80.04 |
| ATOM 322 | NH2 | ARG | 1507 | −8.268 | −11.068 | 32.115 | 1.00 | 83.41 |
| ATOM 325 | C | ARG | 1507 | −8.964 | −3.897 | 28.555 | 1.00 | 40.94 |
| ATOM 326 | O | ARG | 1507 | −9.370 | −3.375 | 27.517 | 1.00 | 37.60 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 327 | N | VAL | 1508 | −7.956 | −3.409 | 29.267 | 1.00 | 39.33 |
| ATOM 329 | CA | VAL | 1508 | −7.190 | −2.269 | 28.789 | 1.00 | 37.26 |
| ATOM 330 | CB | VAL | 1508 | −6.854 | −1.224 | 29.905 | 1.00 | 36.25 |
| ATOM 331 | CG1 | VAL | 1508 | −8.124 | −0.739 | 30.571 | 1.00 | 39.63 |
| ATOM 332 | CG2 | VAL | 1508 | −5.903 | −1.796 | 30.928 | 1.00 | 36.92 |
| ATOM 333 | C | VAL | 1508 | −5.898 | −2.818 | 28.188 | 1.00 | 34.38 |
| ATOM 334 | O | VAL | 1508 | −5.387 | −3.851 | 28.630 | 1.00 | 32.85 |
| ATOM 335 | N | THR | 1509 | −5.406 | −2.140 | 27.159 | 1.00 | 30.47 |
| ATOM 337 | CA | THR | 1509 | −4.174 | −2.523 | 26.491 | 1.00 | 31.65 |
| ATOM 338 | CB | THR | 1509 | −4.455 | −2.959 | 25.027 | 1.00 | 34.13 |
| ATOM 339 | CG1 | THR | 1509 | −5.426 | −4.013 | 25.018 | 1.00 | 40.74 |
| ATOM 341 | CG2 | THR | 1509 | −3.184 | −3.458 | 24.345 | 1.00 | 31.06 |
| ATOM 342 | C | THR | 1509 | −3.270 | −1.299 | 26.461 | 1.00 | 28.38 |
| ATOM 343 | O | THR | 1509 | −3.716 | −0.219 | 26.104 | 1.00 | 27.78 |
| ATOM 344 | N | LYS | 1510 | −2.023 | −1.442 | 26.896 | 1.00 | 29.48 |
| ATOM 346 | CA | LYS | 1510 | −1.101 | −0.312 | 26.835 | 1.00 | 30.54 |
| ATOM 347 | CB | LYS | 1510 | 0.172 | −0.558 | 27.635 | 1.00 | 27.88 |
| ATOM 348 | CG | LYS | 1510 | −0.037 | −0.600 | 29.118 | 1.00 | 33.91 |
| ATOM 349 | CD | LYS | 1510 | 1.284 | −0.759 | 29.840 | 1.00 | 40.30 |
| ATOM 350 | CE | LYS | 1510 | 1.145 | −1.674 | 31.062 | 1.00 | 46.24 |
| ATOM 351 | NZ | LYS | 1510 | 0.338 | −1.096 | 32.187 | 1.00 | 49.09 |
| ATOM 355 | C | LYS | 1510 | −0.757 | −0.166 | 25.365 | 1.00 | 28.64 |
| ATOM 356 | O | LYS | 1510 | −0.402 | −1.142 | 24.704 | 1.00 | 28.76 |
| ATOM 357 | N | VAL | 1511 | −0.902 | 1.048 | 24.856 | 1.00 | 29.34 |
| ATOM 359 | CA | VAL | 1511 | −0.627 | 1.347 | 23.463 | 1.00 | 29.79 |
| ATOM 360 | CB | VAL | 1511 | −1.951 | 1.457 | 22.658 | 1.00 | 27.14 |
| ATOM 361 | CG1 | VAL | 1511 | −2.681 | 0.111 | 22.657 | 1.00 | 24.56 |
| ATOM 362 | CG2 | VAL | 1511 | −2.837 | 2.561 | 23.243 | 1.00 | 22.15 |
| ATOM 363 | C | VAL | 1511 | 0.123 | 2.672 | 23.361 | 1.00 | 29.83 |
| ATOM 364 | O | VAL | 1511 | 0.213 | 3.413 | 24.338 | 1.00 | 33.14 |
| ATOM 365 | N | ALA | 1512 | 0.705 | 2.939 | 22.196 | 1.00 | 27.86 |
| ATOM 367 | CA | ALA | 1512 | 1.405 | 4.192 | 21.962 | 1.00 | 25.55 |
| ATOM 368 | CB | ALA | 1512 | 2.743 | 3.935 | 21.297 | 1.00 | 24.69 |
| ATOM 369 | C | ALA | 1512 | 0.500 | 5.009 | 21.057 | 1.00 | 25.25 |
| ATOM 370 | O | ALA | 1512 | −0.061 | 4.483 | 20.107 | 1.00 | 27.18 |
| ATOM 371 | N | VAL | 1513 | 0.340 | 6.289 | 21.360 | 1.00 | 29.63 |
| ATOM 373 | CA | VAL | 1513 | −0.520 | 7.165 | 20.573 | 1.00 | 32.66 |
| ATOM 374 | CB | VAL | 1513 | −1.704 | 7.713 | 21.422 | 1.00 | 32.47 |
| ATOM 375 | CG1 | VAL | 1513 | −2.609 | 8.585 | 20.574 | 1.00 | 32.29 |
| ATOM 376 | CG2 | VAL | 1513 | −2.508 | 6.559 | 22.031 | 1.00 | 32.15 |
| ATOM 377 | C | VAL | 1513 | 0.238 | 8.334 | 19.938 | 1.00 | 34.67 |
| ATOM 378 | O | VAL | 1513 | 0.792 | 9.185 | 20.635 | 1.00 | 34.65 |
| ATOM 379 | N | LYS | 1514 | 0.207 | 8.367 | 18.605 | 1.00 | 36.88 |
| ATOM 381 | CA | LYS | 1514 | 0.859 | 9.390 | 17.789 | 1.00 | 36.43 |
| ATOM 382 | CB | LYS | 1514 | 1.349 | 8.764 | 16.489 | 1.00 | 36.37 |
| ATOM 383 | CG | LYS | 1514 | 2.250 | 7.563 | 16.697 | 1.00 | 39.49 |
| ATOM 384 | CD | LYS | 1514 | 2.559 | 6.854 | 15.390 | 1.00 | 45.29 |
| ATOM 385 | CE | LYS | 1514 | 3.080 | 7.815 | 14.331 | 1.00 | 50.70 |
| ATOM 386 | NZ | LYS | 1514 | 4.212 | 8.685 | 14.798 | 1.00 | 51.41 |
| ATOM 390 | C | LYS | 1514 | −0.121 | 10.496 | 17.459 | 1.00 | 36.75 |
| ATOM 391 | O | LYS | 1514 | −1.228 | 10.234 | 16.978 | 1.00 | 35.42 |
| ATOM 392 | N | MET | 1515 | 0.294 | 11.731 | 17.700 | 1.00 | 38.12 |
| ATOM 394 | CA | MET | 1515 | −0.545 | 12.882 | 17.432 | 1.00 | 41.90 |
| ATOM 395 | CB | MET | 1515 | −1.371 | 13.238 | 18.668 | 1.00 | 43.08 |
| ATOM 396 | CG | MET | 1515 | −0.536 | 13.601 | 19.880 | 1.00 | 45.01 |
| ATOM 397 | SD | MET | 1515 | −1.561 | 13.784 | 21.324 | 1.00 | 46.03 |
| ATOM 398 | CE | MET | 1515 | −1.675 | 12.072 | 21.885 | 1.00 | 44.02 |
| ATOM 399 | C | MET | 1515 | 0.314 | 14.065 | 17.021 | 1.00 | 44.65 |
| ATOM 400 | O | MET | 1515 | 1.543 | 14.013 | 17.094 | 1.00 | 45.64 |
| ATOM 401 | N | LEU | 1516 | −0.347 | 15.123 | 16.568 | 1.00 | 47.08 |
| ATOM 403 | CA | LEU | 1516 | 0.329 | 16.337 | 16.134 | 1.00 | 48.08 |
| ATOM 404 | CB | LEU | 1516 | −0.500 | 17.033 | 15.054 | 1.00 | 45.50 |
| ATOM 405 | CG | LEU | 1516 | −0.764 | 16.265 | 13.764 | 1.00 | 43.22 |
| ATOM 406 | CD1 | LEU | 1516 | −1.783 | 17.014 | 12.946 | 1.00 | 40.32 |
| ATOM 407 | CD2 | LEU | 1516 | 0.540 | 16.072 | 12.991 | 1.00 | 43.78 |
| ATOM 408 | C | LEU | 1516 | 0.516 | 17.302 | 17.297 | 1.00 | 51.27 |
| ATOM 409 | O | LEU | 1516 | −0.214 | 17.249 | 18.291 | 1.00 | 50.37 |
| ATOM 410 | N | LYS | 1517 | 1.491 | 18.191 | 17.157 | 1.00 | 55.47 |
| ATOM 412 | CA | LYS | 1517 | 1.757 | 19.207 | 18.168 | 1.00 | 59.10 |
| ATOM 413 | CB | LYS | 1517 | 3.203 | 19.702 | 18.068 | 1.00 | 61.61 |
| ATOM 414 | CG | LYS | 1517 | 4.251 | 18.669 | 18.462 | 1.00 | 64.82 |
| ATOM 415 | CD | LYS | 1517 | 5.635 | 19.109 | 18.018 | 1.00 | 67.42 |
| ATOM 416 | CE | LYS | 1517 | 6.696 | 18.102 | 18.432 | 1.00 | 71.76 |
| ATOM 417 | NZ | LYS | 1517 | 8.021 | 18.411 | 17.812 | 1.00 | 73.57 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 421 | C | LYS | 1517 | 0.794 | 20.365 | 17.920 | 1.00 | 59.91 |
| ATOM 422 | O | LYS | 1517 | 0.187 | 20.456 | 16.852 | 1.00 | 59.88 |
| ATOM 423 | N | SER | 1518 | 0.686 | 21.267 | 18.886 | 1.00 | 61.85 |
| ATOM 425 | CA | SER | 1518 | -0.216 | 22.409 | 18.760 | 1.00 | 63.70 |
| ATOM 426 | CB | SER | 1518 | -0.158 | 23.274 | 20.024 | 1.00 | 64.21 |
| ATOM 427 | C | SER | 1518 | 0.079 | 23.263 | 17.529 | 1.00 | 64.37 |
| ATOM 428 | O | SER | 1518 | -0.841 | 23.757 | 16.875 | 1.00 | 66.16 |
| ATOM 429 | N | ASP | 1519 | 1.359 | 23.410 | 17.202 | 1.00 | 64.15 |
| ATOM 431 | CA | ASP | 1519 | 1.767 | 24.217 | 16.054 | 1.00 | 64.55 |
| ATOM 432 | CB | ASP | 1519 | 3.109 | 24.897 | 16.343 | 1.00 | 65.84 |
| ATOM 433 | C | ASP | 1519 | 1.858 | 23.441 | 14.742 | 1.00 | 63.95 |
| ATOM 434 | O | ASP | 1519 | 2.432 | 23.931 | 13.769 | 1.00 | 64.95 |
| ATOM 435 | N | ALA | 1520 | 1.303 | 22.232 | 14.719 | 1.00 | 62.57 |
| ATOM 437 | CA | ALA | 1520 | 1.329 | 21.398 | 13.521 | 1.00 | 60.34 |
| ATOM 438 | CB | ALA | 1520 | 0.704 | 20.039 | 13.810 | 1.00 | 60.53 |
| ATOM 439 | C | ALA | 1520 | 0.616 | 22.062 | 12.353 | 1.00 | 58.21 |
| ATOM 440 | O | ALA | 1520 | -0.464 | 22.631 | 12.506 | 1.00 | 58.32 |
| ATOM 441 | N | THR | 1521 | 1.241 | 22.001 | 11.186 | 1.00 | 55.96 |
| ATOM 443 | CA | THR | 1521 | 0.673 | 22.582 | 9.981 | 1.00 | 54.98 |
| ATOM 444 | CB | THR | 1521 | 1.783 | 23.013 | 9.031 | 1.00 | 53.84 |
| ATOM 445 | OG1 | THR | 1521 | 2.554 | 21.862 | 8.659 | 1.00 | 55.84 |
| ATOM 447 | CG2 | THR | 1521 | 2.693 | 24.026 | 9.703 | 1.00 | 55.01 |
| ATOM 448 | C | THR | 1521 | -0.184 | 21.545 | 9.261 | 1.00 | 54.25 |
| ATOM 449 | O | THR | 1521 | -0.190 | 20.371 | 9.629 | 1.00 | 54.74 |
| ATOM 450 | N | GLU | 1522 | -0.877 | 21.974 | 8.212 | 1.00 | 53.32 |
| ATOM 452 | CA | GLU | 1522 | -1.702 | 21.066 | 7.423 | 1.00 | 52.64 |
| ATOM 453 | CB | GLU | 1522 | -2.472 | 21.829 | 6.339 | 1.00 | 53.55 |
| ATOM 454 | C | GLU | 1522 | -0.793 | 20.012 | 6.780 | 1.00 | 51.95 |
| ATOM 455 | O | GLU | 1522 | -1.226 | 18.895 | 6.504 | 1.00 | 53.28 |
| ATOM 456 | N | LYS | 1523 | 0.464 | 20.377 | 6.544 | 1.00 | 48.66 |
| ATOM 458 | CA | LYS | 1523 | 1.429 | 19.460 | 5.963 | 1.00 | 46.30 |
| ATOM 459 | CB | LYS | 1523 | 2.730 | 20.201 | 5.620 | 1.00 | 48.30 |
| ATOM 460 | CG | LYS | 1523 | 3.889 | 19.308 | 5.164 | 1.00 | 49.58 |
| ATOM 461 | CD | LYS | 1523 | 3.487 | 18.388 | 4.016 | 1.00 | 50.87 |
| ATOM 462 | CE | LYS | 1523 | 4.688 | 17.635 | 3.466 | 1.00 | 54.08 |
| ATOM 463 | NZ | LYS | 1523 | 4.271 | 16.629 | 2.440 | 1.00 | 57.87 |
| ATOM 467 | C | LYS | 1523 | 1.699 | 18.391 | 7.006 | 1.00 | 43.89 |
| ATOM 468 | O | LYS | 1523 | 1.747 | 17.202 | 6.697 | 1.00 | 43.92 |
| ATOM 469 | N | ASP | 1524 | 1.857 | 18.828 | 8.249 | 1.00 | 42.71 |
| ATOM 471 | CA | ASP | 1524 | 2.114 | 17.915 | 9.351 | 1.00 | 42.11 |
| ATOM 472 | CB | ASP | 1524 | 2.313 | 18.701 | 10.653 | 1.00 | 44.94 |
| ATOM 473 | CG | ASP | 1524 | 3.623 | 19.490 | 10.673 | 1.00 | 48.90 |
| ATOM 474 | OD1 | ASP | 1524 | 3.692 | 20.512 | 11.392 | 1.00 | 51.88 |
| ATOM 475 | OD2 | ASP | 1524 | 4.590 | 19.084 | 9.990 | 1.00 | 50.06 |
| ATOM 476 | C | ASP | 1524 | 0.956 | 16.931 | 9.481 | 1.00 | 39.85 |
| ATOM 477 | O | ASP | 1524 | 1.164 | 15.738 | 9.748 | 1.00 | 39.01 |
| ATOM 478 | N | LEU | 1525 | -0.261 | 17.438 | 9.296 | 1.00 | 38.32 |
| ATOM 480 | CA | LEU | 1525 | -1.461 | 16.610 | 9.355 | 1.00 | 36.16 |
| ATOM 481 | CB | LEU | 1525 | -2.720 | 17.470 | 9.200 | 1.00 | 35.13 |
| ATOM 482 | CG | LEU | 1525 | -4.081 | 16.760 | 9.186 | 1.00 | 34.70 |
| ATOM 483 | CD1 | LEU | 1525 | -4.184 | 15.668 | 10.252 | 1.00 | 36.15 |
| ATOM 484 | CD2 | LEU | 1525 | -5.162 | 17.789 | 9.395 | 1.00 | 32.96 |
| ATOM 485 | C | LEU | 1525 | -1.406 | 15.560 | 8.254 | 1.00 | 34.31 |
| ATOM 486 | O | LEU | 1525 | -1.575 | 14.377 | 8.518 | 1.00 | 33.34 |
| ATOM 487 | N | SER | 1526 | -1.136 | 16.005 | 7.030 | 1.00 | 36.40 |
| ATOM 489 | CA | SER | 1526 | -1.039 | 15.128 | 5.865 | 1.00 | 37.16 |
| ATOM 490 | CB | SER | 1526 | -0.669 | 15.931 | 4.618 | 1.00 | 38.84 |
| ATOM 491 | OG | SER | 1526 | -1.736 | 16.779 | 4.245 | 1.00 | 49.61 |
| ATOM 493 | C | SER | 1526 | -0.021 | 14.016 | 6.044 | 1.00 | 35.90 |
| ATOM 494 | O | SER | 1526 | -0.273 | 12.873 | 5.670 | 1.00 | 36.68 |
| ATOM 495 | N | ASP | 1527 | 1.142 | 14.349 | 6.591 | 1.00 | 35.89 |
| ATOM 497 | CA | ASP | 1527 | 2.177 | 13.342 | 6.796 | 1.00 | 35.25 |
| ATOM 498 | CB | ASP | 1527 | 3.497 | 13.998 | 7.201 | 1.00 | 35.58 |
| ATOM 499 | CG | ASP | 1527 | 4.100 | 14.850 | 6.081 | 1.00 | 37.19 |
| ATOM 500 | OD1 | ASP | 1527 | 3.750 | 14.653 | 4.895 | 1.00 | 37.38 |
| ATOM 501 | OD2 | ASP | 1527 | 4.932 | 15.726 | 6.395 | 1.00 | 42.93 |
| ATOM 502 | C | ASP | 1527 | 1.749 | 12.274 | 7.799 | 1.00 | 31.77 |
| ATOM 503 | O | ASP | 1527 | 2.000 | 11.090 | 7.594 | 1.00 | 30.58 |
| ATOM 504 | N | LEU | 1528 | 1.055 | 12.684 | 8.853 | 1.00 | 31.80 |
| ATOM 506 | CA | LEU | 1528 | 0.581 | 11.730 | 9.857 | 1.00 | 33.53 |
| ATOM 507 | CB | LEU | 1528 | -0.002 | 12.471 | 11.076 | 1.00 | 32.20 |
| ATOM 508 | CG | LEU | 1528 | -0.440 | 11.623 | 12.275 | 1.00 | 32.63 |
| ATOM 509 | CD1 | LEU | 1528 | 0.705 | 10.708 | 12.709 | 1.00 | 33.09 |
| ATOM 510 | CD2 | LEU | 1528 | -0.891 | 12.512 | 13.426 | 1.00 | 31.52 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 511 | C | LEU | 1528 | −0.468 | 10.792 | 9.235 | 1.00 | 32.89 |
| ATOM 512 | O | LEU | 1528 | −0.494 | 9.589 | 9.521 | 1.00 | 32.39 |
| ATOM 513 | N | ILE | 1529 | −1.336 | 11.357 | 8.393 | 1.00 | 33.72 |
| ATOM 515 | CA | ILE | 1529 | −2.376 | 10.591 | 7.711 | 1.00 | 30.48 |
| ATOM 516 | CB | ILE | 1529 | −3.336 | 11.505 | 6.895 | 1.00 | 28.85 |
| ATOM 517 | CG2 | ILE | 1529 | −4.229 | 10.662 | 5.997 | 1.00 | 28.54 |
| ATOM 518 | CG1 | ILE | 1529 | −4.200 | 12.344 | 7.843 | 1.00 | 29.52 |
| ATOM 519 | CD1 | ILE | 1529 | −5.143 | 13.308 | 7.133 | 1.00 | 32.07 |
| ATOM 520 | C | ILE | 1529 | −1.698 | 9.608 | 6.768 | 1.00 | 31.50 |
| ATOM 521 | O | ILE | 1529 | −2.009 | 8.419 | 6.780 | 1.00 | 30.75 |
| ATOM 522 | N | SER | 1530 | −0.749 | 10.100 | 5.974 | 1.00 | 33.28 |
| ATOM 524 | CA | SER | 1530 | −0.011 | 9.250 | 5.038 | 1.00 | 32.48 |
| ATOM 525 | CB | SER | 1530 | 1.114 | 10.042 | 4.368 | 1.00 | 37.20 |
| ATOM 526 | OG | SER | 1530 | 0.604 | 11.218 | 3.766 | 1.00 | 49.93 |
| ATOM 528 | C | SER | 1530 | 0.583 | 8.045 | 5.756 | 1.00 | 29.05 |
| ATOM 529 | O | SER | 1530 | 0.397 | 6.909 | 5.316 | 1.00 | 28.66 |
| ATOM 530 | N | GLU | 1531 | 1.259 | 8.290 | 6.878 | 1.00 | 28.21 |
| ATOM 532 | CA | GLU | 1531 | 1.880 | 7.207 | 7.631 | 1.00 | 27.30 |
| ATOM 533 | CB | GLU | 1531 | 2.656 | 7.733 | 8.839 | 1.00 | 28.90 |
| ATOM 534 | CG | GLU | 1531 | 3.271 | 6.609 | 9.672 | 1.00 | 27.17 |
| ATOM 535 | CD | GLU | 1531 | 4.047 | 7.081 | 10.886 | 1.00 | 30.07 |
| ATOM 536 | OE1 | GLU | 1531 | 4.779 | 6.244 | 11.448 | 1.00 | 34.78 |
| ATOM 537 | OE2 | GLU | 1531 | 3.931 | 8.256 | 11.291 | 1.00 | 31.96 |
| ATOM 538 | C | GLU | 1531 | 0.870 | 6.162 | 8.072 | 1.00 | 27.73 |
| ATOM 539 | O | GLU | 1531 | 1.160 | 4.961 | 8.028 | 1.00 | 28.72 |
| ATOM 540 | N | MET | 1532 | −0.286 | 6.621 | 8.555 | 1.00 | 29.78 |
| ATOM 542 | CA | MET | 1532 | −1.373 | 5.734 | 8.990 | 1.00 | 28.79 |
| ATOM 543 | CB | MET | 1532 | −2.501 | 6.553 | 9.646 | 1.00 | 28.90 |
| ATOM 544 | CG | MET | 1532 | −3.763 | 5.741 | 9.993 | 1.00 | 29.73 |
| ATOM 545 | SD | MET | 1532 | −5.089 | 6.693 | 10.765 | 1.00 | 30.19 |
| ATOM 546 | CE | MET | 1532 | −5.455 | 7.870 | 9.494 | 1.00 | 26.70 |
| ATOM 547 | C | MET | 1532 | −1.935 | 4.937 | 7.796 | 1.00 | 28.34 |
| ATOM 548 | O | MET | 1532 | −2.166 | 3.730 | 7.893 | 1.00 | 26.62 |
| ATOM 549 | N | GLU | 1533 | −2.165 | 5.624 | 6.678 | 1.00 | 28.85 |
| ATOM 551 | CA | GLU | 1533 | −2.684 | 4.984 | 5.467 | 1.00 | 28.24 |
| ATOM 552 | CB | GLU | 1533 | −2.936 | 6.027 | 4.384 | 1.00 | 25.42 |
| ATOM 553 | CG | GLU | 1533 | −4.099 | 6.956 | 4.719 | 1.00 | 30.05 |
| ATOM 554 | CD | GLU | 1533 | −5.393 | 6.201 | 5.021 | 1.00 | 29.47 |
| ATOM 555 | OE1 | GLU | 1533 | −5.794 | 5.336 | 4.211 | 1.00 | 29.01 |
| ATOM 556 | OE2 | GLU | 1533 | −6.011 | 6.472 | 6.073 | 1.00 | 33.98 |
| ATOM 557 | C | GLU | 1533 | −1.694 | 3.944 | 4.968 | 1.00 | 28.01 |
| ATOM 558 | O | GLU | 1533 | −2.072 | 2.845 | 4.573 | 1.00 | 27.39 |
| ATOM 559 | N | MET | 1534 | −0.416 | 4.293 | 5.036 | 1.00 | 29.06 |
| ATOM 561 | CA | MET | 1534 | 0.662 | 3.413 | 4.621 | 1.00 | 29.74 |
| ATOM 562 | CB | MET | 1534 | 1.992 | 4.155 | 4.755 | 1.00 | 33.16 |
| ATOM 563 | CG | MET | 1534 | 3.198 | 3.270 | 4.682 | 1.00 | 42.88 |
| ATOM 564 | SD | MET | 1534 | 3.805 | 3.127 | 3.042 | 1.00 | 50.20 |
| ATOM 565 | CE | MET | 1534 | 5.137 | 4.169 | 3.159 | 1.00 | 42.64 |
| ATOM 566 | C | MET | 1534 | 0.641 | 2.156 | 5.493 | 1.00 | 26.90 |
| ATOM 567 | O | MET | 1534 | 0.755 | 1.038 | 4.990 | 1.00 | 27.05 |
| ATOM 568 | N | MET | 1535 | 0.512 | 2.348 | 6.803 | 1.00 | 25.42 |
| ATOM 570 | CA | MET | 1535 | 0.437 | 1.233 | 7.737 | 1.00 | 25.88 |
| ATOM 571 | CB | MET | 1535 | 0.325 | 1.741 | 9.181 | 1.00 | 27.63 |
| ATOM 572 | CG | MET | 1535 | 1.607 | 2.391 | 9.737 | 1.00 | 27.26 |
| ATOM 573 | SD | MET | 1535 | 1.584 | 2.561 | 11.564 | 1.00 | 29.49 |
| ATOM 574 | CE | MET | 1535 | 1.294 | 4.255 | 11.699 | 1.00 | 28.22 |
| ATOM 575 | C | MET | 1535 | −0.754 | 0.324 | 7.396 | 1.00 | 26.28 |
| ATOM 576 | O | MET | 1535 | −0.645 | −0.908 | 7.469 | 1.00 | 25.93 |
| ATOM 577 | N | LYS | 1536 | −1.890 | 0.928 | 7.032 | 1.00 | 27.19 |
| ATOM 579 | CA | LYS | 1536 | −3.087 | 0.162 | 6.647 | 1.00 | 27.20 |
| ATOM 580 | CB | LYS | 1536 | −4.257 | 1.088 | 6.310 | 1.00 | 25.29 |
| ATOM 581 | CG | LYS | 1536 | −4.897 | 1.770 | 7.491 | 1.00 | 23.86 |
| ATOM 582 | CD | LYS | 1536 | −5.884 | 2.820 | 7.017 | 1.00 | 22.16 |
| ATOM 583 | CE | LYS | 1536 | −6.460 | 3.588 | 8.174 | 1.00 | 22.25 |
| ATOM 584 | NZ | LYS | 1536 | −7.484 | 4.541 | 7.713 | 1.00 | 23.40 |
| ATOM 588 | C | LYS | 1536 | −2.785 | −0.699 | 5.423 | 1.00 | 24.52 |
| ATOM 589 | O | LYS | 1536 | −3.069 | −1.889 | 5.403 | 1.00 | 26.61 |
| ATOM 590 | N | MET | 1537 | −2.183 | −0.093 | 4.411 | 1.00 | 27.12 |
| ATOM 592 | CA | MET | 1537 | −1.843 | −0.815 | 3.194 | 1.00 | 28.06 |
| ATOM 593 | CB | MET | 1537 | −1.269 | 0.147 | 2.147 | 1.00 | 30.36 |
| ATOM 594 | CG | MET | 1537 | −2.265 | 1.164 | 1.591 | 1.00 | 36.31 |
| ATOM 595 | SD | MET | 1537 | −3.699 | 0.444 | 0.727 | 1.00 | 42.19 |
| ATOM 596 | CE | MET | 1537 | −2.912 | −0.057 | −0.793 | 1.00 | 36.22 |
| ATOM 597 | C | MET | 1537 | −0.857 | −1.952 | 3.447 | 1.00 | 26.98 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 598 | O | MET | 1537 | −1.060 | −3.065 | 2.963 | 1.00 | 25.34 |
| ATOM 599 | N | ILE | 1538 | 0.188 | −1.678 | 4.229 | 1.00 | 27.69 |
| ATOM 601 | CA | ILE | 1538 | 1.234 | −2.674 | 4.535 | 1.00 | 25.39 |
| ATOM 602 | CB | ILE | 1538 | 2.454 | −2.006 | 5.255 | 1.00 | 24.42 |
| ATOM 603 | CG2 | ILE | 1538 | 3.424 | −3.051 | 5.811 | 1.00 | 25.28 |
| ATOM 604 | CG1 | ILE | 1538 | 3.223 | −1.131 | 4.269 | 1.00 | 23.88 |
| ATOM 605 | CD1 | ILE | 1538 | 4.373 | −0.372 | 4.901 | 1.00 | 27.19 |
| ATOM 606 | C | ILE | 1538 | 0.760 | −3.922 | 5.292 | 1.00 | 25.59 |
| ATOM 607 | O | ILE | 1538 | 1.242 | −5.033 | 5.035 | 1.00 | 26.11 |
| ATOM 608 | N | GLY | 1539 | −0.193 | −3.767 | 6.208 | 1.00 | 26.13 |
| ATOM 610 | CA | GLY | 1539 | −0.661 | −4.940 | 6.934 | 1.00 | 25.25 |
| ATOM 611 | C | GLY | 1539 | 0.191 | −5.280 | 8.149 | 1.00 | 26.77 |
| ATOM 612 | O | GLY | 1539 | 1.214 | −4.637 | 8.414 | 1.00 | 25.42 |
| ATOM 613 | N | LYS | 1540 | −0.204 | −6.327 | 8.862 | 1.00 | 25.62 |
| ATOM 615 | CA | LYS | 1540 | 0.467 | −6.716 | 10.092 | 1.00 | 26.38 |
| ATOM 616 | CB | LYS | 1540 | −0.552 | −7.283 | 11.084 | 1.00 | 27.15 |
| ATOM 617 | CG | LYS | 1540 | −1.573 | −6.303 | 11.550 | 1.00 | 34.23 |
| ATOM 618 | CD | LYS | 1540 | −2.528 | −6.943 | 12.546 | 1.00 | 40.69 |
| ATOM 619 | CE | LYS | 1540 | −3.559 | −5.927 | 13.057 | 1.00 | 44.08 |
| ATOM 620 | NZ | LYS | 1540 | −2.956 | −4.800 | 13.833 | 1.00 | 44.05 |
| ATOM 624 | C | LYS | 1540 | 1.609 | −7.705 | 10.014 | 1.00 | 24.37 |
| ATOM 625 | O | LYS | 1540 | 1.627 | −8.600 | 9.181 | 1.00 | 26.12 |
| ATOM 626 | N | HIS | 1541 | 2.545 | −7.538 | 10.936 | 1.00 | 24.41 |
| ATOM 628 | CA | HIS | 1541 | 3.666 | −8.440 | 11.091 | 1.00 | 25.41 |
| ATOM 629 | CB | HIS | 1541 | 4.772 | −8.228 | 10.057 | 1.00 | 21.88 |
| ATOM 630 | CG | HIS | 1541 | 5.798 | −9.320 | 10.068 | 1.00 | 22.68 |
| ATOM 631 | CD2 | HIS | 1541 | 5.823 | −10.522 | 9.444 | 1.00 | 21.40 |
| ATOM 632 | ND1 | HIS | 1541 | 6.939 | −9.268 | 10.843 | 1.00 | 22.12 |
| ATOM 634 | CE1 | HIS | 1541 | 7.619 | −10.389 | 10.697 | 1.00 | 24.78 |
| ATOM 635 | NE2 | HIS | 1541 | 6.966 | −11.167 | 9.854 | 1.00 | 27.00 |
| ATOM 637 | C | HIS | 1541 | 4.234 | −8.328 | 12.494 | 1.00 | 25.47 |
| ATOM 638 | O | HIS | 1541 | 4.364 | −7.239 | 13.050 | 1.00 | 26.77 |
| ATOM 639 | N | LYS | 1542 | 4.560 | −9.476 | 13.063 | 1.00 | 26.38 |
| ATOM 641 | CA | LYS | 1542 | 5.127 | −9.552 | 14.401 | 1.00 | 30.07 |
| ATOM 642 | CB | LYS | 1542 | 5.515 | −11.003 | 14.692 | 1.00 | 31.38 |
| ATOM 643 | CG | LYS | 1542 | 6.061 | −11.252 | 16.077 | 1.00 | 42.79 |
| ATOM 644 | CD | LYS | 1542 | 6.289 | −12.735 | 16.294 | 1.00 | 50.84 |
| ATOM 645 | CE | LYS | 1542 | 7.041 | −13.374 | 15.114 | 1.00 | 56.75 |
| ATOM 646 | NZ | LYS | 1542 | 7.511 | −14.763 | 15.424 | 1.00 | 61.29 |
| ATOM 650 | C | LYS | 1542 | 6.342 | −8.652 | 14.624 | 1.00 | 27.65 |
| ATOM 651 | O | LYS | 1542 | 6.519 | −8.113 | 15.711 | 1.00 | 26.83 |
| ATOM 652 | N | ASN | 1543 | 7.146 | −8.445 | 13.585 | 1.00 | 27.20 |
| ATOM 654 | CA | ASN | 1543 | 8.354 | −7.642 | 13.735 | 1.00 | 25.50 |
| ATOM 655 | CB | ASN | 1543 | 9.578 | −8.431 | 13.260 | 1.00 | 25.59 |
| ATOM 656 | CG | ASN | 1543 | 9.712 | −9.767 | 13.974 | 1.00 | 22.64 |
| ATOM 657 | OD1 | ASN | 1543 | 9.522 | −10.821 | 13.371 | 1.00 | 26.76 |
| ATOM 658 | ND2 | ASN | 1543 | 9.970 | −9.727 | 15.273 | 1.00 | 25.56 |
| ATOM 661 | C | ASN | 1543 | 8.374 | −6.213 | 13.226 | 1.00 | 25.48 |
| ATOM 662 | O | ASN | 1543 | 9.417 | −5.692 | 12.842 | 1.00 | 24.58 |
| ATOM 663 | N | ILE | 1544 | 7.209 | −5.575 | 13.244 | 1.00 | 24.60 |
| ATOM 665 | CA | ILE | 1544 | 7.065 | −4.177 | 12.868 | 1.00 | 22.32 |
| ATOM 666 | CB | ILE | 1544 | 6.524 | −3.972 | 11.409 | 1.00 | 25.82 |
| ATOM 667 | CG2 | ILE | 1544 | 7.401 | −4.720 | 10.403 | 1.00 | 24.24 |
| ATOM 668 | CG1 | ILE | 1544 | 5.057 | −4.411 | 11.279 | 1.00 | 26.04 |
| ATOM 669 | CD1 | ILE | 1544 | 4.446 | −4.121 | 9.901 | 1.00 | 23.20 |
| ATOM 670 | C | ILE | 1544 | 6.075 | −3.598 | 13.881 | 1.00 | 22.37 |
| ATOM 671 | O | ILE | 1544 | 5.364 | −4.345 | 14.559 | 1.00 | 21.68 |
| ATOM 672 | N | ILE | 1545 | 6.111 | −2.290 | 14.076 | 1.00 | 23.72 |
| ATOM 674 | CA | ILE | 1545 | 5.169 | −1.650 | 14.989 | 1.00 | 25.92 |
| ATOM 675 | CB | ILE | 1545 | 5.602 | −0.199 | 15.364 | 1.00 | 27.24 |
| ATOM 676 | CG2 | ILE | 1545 | 4.452 | 0.554 | 16.035 | 1.00 | 22.76 |
| ATOM 677 | CG1 | ILE | 1545 | 6.839 | −0.219 | 16.285 | 1.00 | 25.57 |
| ATOM 678 | CD1 | ILE | 1545 | 6.591 | −0.797 | 17.686 | 1.00 | 24.66 |
| ATOM 679 | C | ILE | 1545 | 3.877 | −1.612 | 14.179 | 1.00 | 26.03 |
| ATOM 680 | O | ILE | 1545 | 3.823 | −0.988 | 13.122 | 1.00 | 25.70 |
| ATOM 681 | N | ASN | 1546 | 2.849 | −2.293 | 14.669 | 1.00 | 24.79 |
| ATOM 683 | CA | ASN | 1546 | 1.577 | −2.354 | 13.956 | 1.00 | 25.51 |
| ATOM 684 | CB | ASN | 1546 | 0.922 | −3.727 | 14.137 | 1.00 | 25.17 |
| ATOM 685 | CG | ASN | 1546 | 1.730 | −4.839 | 13.539 | 1.00 | 21.67 |
| ATOM 686 | OD1 | ASN | 1546 | 1.856 | −4.947 | 12.329 | 1.00 | 24.29 |
| ATOM 687 | ND2 | ASN | 1546 | 2.278 | −5.686 | 14.384 | 1.00 | 22.24 |
| ATOM 690 | C | ASN | 1546 | 0.578 | −1.276 | 14.349 | 1.00 | 26.85 |
| ATOM 691 | O | ASN | 1546 | 0.630 | −0.724 | 15.453 | 1.00 | 28.67 |
| ATOM 692 | N | LEU | 1547 | −0.301 | −0.956 | 13.407 | 1.00 | 27.70 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 694 | CA | LEU | 1547 | −1.357 | 0.019 | 13.622 | 1.00 | 27.64 |
| ATOM 695 | CB | LEU | 1547 | −1.945 | 0.481 | 12.284 | 1.00 | 24.87 |
| ATOM 696 | CG | LEU | 1547 | −3.173 | 1.400 | 12.337 | 1.00 | 23.25 |
| ATOM 697 | CD1 | LEU | 1547 | −2.790 | 2.763 | 12.929 | 1.00 | 23.76 |
| ATOM 698 | CD2 | LEU | 1547 | −3.757 | 1.569 | 10.923 | 1.00 | 23.47 |
| ATOM 699 | C | LEU | 1547 | −2.415 | −0.771 | 14.396 | 1.00 | 27.27 |
| ATOM 700 | O | LEU | 1547 | −2.663 | −1.952 | 14.103 | 1.00 | 25.27 |
| ATOM 701 | N | LEU | 1548 | −3.000 | −0.130 | 15.400 | 1.00 | 27.94 |
| ATOM 703 | CA | LEU | 1548 | −4.017 | −0.770 | 16.223 | 1.00 | 26.98 |
| ATOM 704 | CB | LEU | 1548 | −3.623 | −0.735 | 17.708 | 1.00 | 24.65 |
| ATOM 705 | CG | LEU | 1548 | −2.327 | −1.450 | 18.108 | 1.00 | 25.38 |
| ATOM 706 | CD1 | LEU | 1548 | −2.189 | −1.428 | 19.613 | 1.00 | 25.73 |
| ATOM 707 | CD2 | LEU | 1548 | −2.337 | −2.886 | 17.621 | 1.00 | 23.92 |
| ATOM 708 | C | LEU | 1548 | −5.369 | −0.113 | 16.042 | 1.00 | 26.65 |
| ATOM 709 | O | LEU | 1548 | −6.392 | −0.752 | 16.238 | 1.00 | 27.11 |
| ATOM 710 | N | GLY | 1549 | −5.378 | 1.163 | 15.684 | 1.00 | 25.04 |
| ATOM 712 | CA | GLY | 1549 | −6.643 | 1.855 | 15.516 | 1.00 | 25.47 |
| ATOM 713 | C | GLY | 1549 | −6.417 | 3.336 | 15.367 | 1.00 | 26.23 |
| ATOM 714 | O | GLY | 1549 | −5.267 | 3.781 | 15.287 | 1.00 | 28.41 |
| ATOM 715 | N | ALA | 1550 | −7.501 | 4.104 | 15.349 | 1.00 | 25.49 |
| ATOM 717 | CA | ALA | 1550 | −7.408 | 5.550 | 15.198 | 1.00 | 24.81 |
| ATOM 718 | CB | ALA | 1550 | −7.176 | 5.913 | 13.724 | 1.00 | 21.79 |
| ATOM 719 | C | ALA | 1550 | −8.645 | 6.271 | 15.691 | 1.00 | 25.51 |
| ATOM 720 | O | ALA | 1550 | −9.738 | 5.702 | 15.726 | 1.00 | 24.09 |
| ATOM 721 | N | CYS | 1551 | −8.440 | 7.527 | 16.080 | 1.00 | 24.90 |
| ATOM 723 | CA | CYS | 1551 | −9.492 | 8.438 | 16.511 | 1.00 | 26.80 |
| ATOM 724 | CB | CYS | 1551 | −9.243 | 8.932 | 17.944 | 1.00 | 26.32 |
| ATOM 725 | SG | CYS | 1551 | −9.333 | 7.655 | 19.223 | 1.00 | 32.31 |
| ATOM 726 | C | CYS | 1551 | −9.341 | 9.585 | 15.502 | 1.00 | 28.31 |
| ATOM 727 | O | CYS | 1551 | −3.361 | 10.338 | 15.537 | 1.00 | 28.42 |
| ATOM 728 | N | THR | 1552 | −10.261 | 9.660 | 14.547 | 1.00 | 28.38 |
| ATOM 730 | CA | THR | 1552 | −10.198 | 10.671 | 13.498 | 1.00 | 31.26 |
| ATOM 731 | CB | THR | 1552 | −10.159 | 9.977 | 12.095 | 1.00 | 30.07 |
| ATOM 732 | OG1 | THR | 1552 | −11.406 | 9.309 | 11.836 | 1.00 | 29.64 |
| ATOM 734 | CG2 | THR | 1552 | −9.044 | 8.945 | 12.053 | 1.00 | 28.65 |
| ATOM 735 | C | THR | 1552 | −11.355 | 11.662 | 13.509 | 1.00 | 33.31 |
| ATOM 736 | O | THR | 1552 | −11.295 | 12.722 | 12.874 | 1.00 | 31.94 |
| ATOM 737 | N | GLN | 1553 | −12.420 | 11.309 | 14.214 | 1.00 | 36.09 |
| ATOM 739 | CA | GLN | 1553 | −13.598 | 12.158 | 14.245 | 1.00 | 39.26 |
| ATOM 740 | CB | GLN | 1553 | −14.864 | 11.299 | 14.145 | 1.00 | 36.61 |
| ATOM 741 | CG | GLN | 1553 | −14.932 | 10.436 | 12.881 | 1.00 | 37.72 |
| ATOM 742 | CD | GLN | 1553 | −14.762 | 11.247 | 11.601 | 1.00 | 38.41 |
| ATOM 743 | OE1 | GLN | 1553 | −15.491 | 12.210 | 11.363 | 1.00 | 37.88 |
| ATOM 744 | NE2 | GLN | 1553 | −13.798 | 10.858 | 10.770 | 1.00 | 37.67 |
| ATOM 747 | C | GLN | 1553 | −13.671 | 13.079 | 15.451 | 1.00 | 41.28 |
| ATOM 748 | O | GLN | 1553 | −13.150 | 12.758 | 16.513 | 1.00 | 41.37 |
| ATOM 749 | N | ASP | 1554 | −14.282 | 14.246 | 15.243 | 1.00 | 44.93 |
| ATOM 751 | CA | ASP | 1554 | −14.487 | 15.254 | 16.281 | 1.00 | 48.05 |
| ATOM 752 | CB | ASP | 1554 | −15.828 | 15.009 | 16.975 | 1.00 | 50.80 |
| ATOM 753 | CG | ASP | 1554 | −17.007 | 15.281 | 16.067 | 1.00 | 56.88 |
| ATOM 754 | OD1 | ASP | 1554 | −17.921 | 16.019 | 16.491 | 1.00 | 63.89 |
| ATOM 755 | OD2 | ASP | 1554 | −17.016 | 14.776 | 14.925 | 1.00 | 58.98 |
| ATOM 756 | C | ASP | 1554 | −13.367 | 15.366 | 17.316 | 1.00 | 48.04 |
| ATOM 757 | O | ASP | 1554 | −13.556 | 15.056 | 18.502 | 1.00 | 48.73 |
| ATOM 758 | N | GLY | 1555 | −12.205 | 15.819 | 16.860 | 1.00 | 44.30 |
| ATOM 760 | CA | GLY | 1555 | −11.080 | 15.960 | 17.756 | 1.00 | 42.32 |
| ATOM 761 | C | GLY | 1555 | −9.761 | 15.713 | 17.052 | 1.00 | 40.69 |
| ATOM 762 | O | GLY | 1555 | −9.740 | 15.465 | 15.848 | 1.00 | 40.71 |
| ATOM 763 | N | PRO | 1556 | −8.644 | 15.776 | 17.782 | 1.00 | 39.49 |
| ATOM 764 | CD | PRO | 1556 | −8.585 | 15.983 | 19.235 | 1.00 | 40.36 |
| ATOM 765 | CA | PRO | 1556 | −7.298 | 15.566 | 17.250 | 1.00 | 38.37 |
| ATOM 766 | CB | PRO | 1556 | −6.405 | 15.771 | 18.470 | 1.00 | 38.47 |
| ATOM 767 | CG | PRO | 1556 | −7.226 | 16.573 | 19.388 | 1.00 | 41.77 |
| ATOM 768 | C | PRO | 1556 | −7.140 | 14.154 | 16.746 | 1.00 | 36.92 |
| ATOM 769 | O | PRO | 1556 | −7.606 | 13.208 | 17.371 | 1.00 | 37.04 |
| ATOM 770 | N | LEU | 1557 | −6.447 | 14.017 | 15.627 | 1.00 | 36.70 |
| ATOM 772 | CA | LEU | 1557 | −6.201 | 12.719 | 15.037 | 1.00 | 34.81 |
| ATOM 773 | CB | LEU | 1557 | −5.528 | 12.885 | 13.664 | 1.00 | 32.49 |
| ATOM 774 | CG | LEU | 1557 | −5.004 | 11.623 | 12.954 | 1.00 | 30.83 |
| ATOM 775 | CD1 | LEU | 1557 | −6.146 | 10.655 | 12.664 | 1.00 | 26.28 |
| ATOM 776 | CD2 | LEU | 1557 | −4.283 | 12.014 | 11.672 | 1.00 | 25.55 |
| ATOM 777 | C | LEU | 1557 | −5.290 | 11.925 | 15.961 | 1.00 | 33.63 |
| ATOM 778 | O | LEU | 1557 | −4.229 | 12.410 | 16.369 | 1.00 | 33.62 |
| ATOM 779 | N | TYR | 1558 | −5.718 | 10.724 | 16.319 | 1.00 | 31.97 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 781 | CA | TYR | 1558 | −4.902 | 9.863 | 17.147 | 1.00 | 31.81 |
| ATOM 782 | CB | TYR | 1558 | −5.614 | 9.500 | 18.462 | 1.00 | 33.55 |
| ATOM 783 | CG | TYR | 1558 | −5.710 | 10.638 | 19.461 | 1.00 | 35.33 |
| ATOM 784 | CD1 | TYR | 1558 | −6.644 | 10.608 | 20.499 | 1.00 | 35.68 |
| ATOM 785 | CE1 | TYR | 1558 | −6.757 | 11.670 | 21.394 | 1.00 | 38.60 |
| ATOM 786 | CD2 | TYR | 1558 | −4.883 | 11.759 | 19.349 | 1.00 | 38.62 |
| ATOM 787 | CE2 | TYR | 1558 | −4.985 | 12.824 | 20.235 | 1.00 | 40.33 |
| ATOM 788 | CZ | TYR | 1558 | −5.924 | 12.781 | 21.254 | 1.00 | 41.70 |
| ATOM 789 | OH | TYR | 1558 | −6.040 | 13.867 | 22.104 | 1.00 | 42.66 |
| ATOM 791 | C | TYR | 1558 | −4.607 | 8.604 | 16.345 | 1.00 | 31.08 |
| ATOM 792 | O | TYR | 1558 | −5.527 | 7.937 | 15.857 | 1.00 | 31.28 |
| ATOM 793 | N | VAL | 1559 | −3.328 | 8.336 | 16.116 | 1.00 | 28.34 |
| ATOM 795 | CA | VAL | 1559 | −2.934 | 7.132 | 15.403 | 1.00 | 26.39 |
| ATOM 796 | CB | VAL | 1559 | −1.830 | 7.401 | 14.364 | 1.00 | 29.17 |
| ATOM 797 | CG1 | VAL | 1559 | −1.463 | 6.103 | 13.648 | 1.00 | 26.25 |
| ATOM 798 | CG2 | VAL | 1559 | −2.297 | 8.461 | 13.360 | 1.00 | 29.56 |
| ATOM 799 | C | VAL | 1559 | −2.411 | 6.226 | 16.498 | 1.00 | 25.14 |
| ATOM 800 | O | VAL | 1559 | −1.396 | 6.522 | 17.120 | 1.00 | 28.04 |
| ATOM 801 | N | ILE | 1560 | −3.164 | 5.171 | 16.783 | 1.00 | 25.28 |
| ATOM 803 | CA | ILE | 1560 | −2.832 | 4.208 | 17.831 | 1.00 | 24.81 |
| ATOM 804 | CB | ILE | 1560 | −4.133 | 3.669 | 18.496 | 1.00 | 24.63 |
| ATOM 805 | CG2 | ILE | 1560 | −3.790 | 2.812 | 19.728 | 1.00 | 20.93 |
| ATOM 806 | CG1 | ILE | 1560 | −5.044 | 4.854 | 18.869 | 1.00 | 22.94 |
| ATOM 807 | CD1 | ILE | 1560 | −6.499 | 4.502 | 19.028 | 1.00 | 25.34 |
| ATOM 808 | C | ILE | 1560 | −1.994 | 3.051 | 17.286 | 1.00 | 26.38 |
| ATOM 809 | O | ILE | 1560 | −2.429 | 2.301 | 16.398 | 1.00 | 26.14 |
| ATOM 810 | N | VAL | 1561 | −0.782 | 2.911 | 17.809 | 1.00 | 27.31 |
| ATOM 812 | CA | VAL | 1561 | 0.112 | 1.852 | 17.359 | 1.00 | 27.32 |
| ATOM 813 | CB | VAL | 1561 | 1.309 | 2.435 | 16.527 | 1.00 | 25.01 |
| ATOM 814 | CG1 | VAL | 1561 | 0.785 | 3.220 | 15.338 | 1.00 | 19.39 |
| ATOM 815 | CG2 | VAL | 1561 | 2.170 | 3.340 | 17.397 | 1.00 | 26.08 |
| ATOM 816 | C | VAL | 1561 | 0.615 | 1.029 | 18.548 | 1.00 | 25.89 |
| ATOM 817 | O | VAL | 1561 | 0.364 | 1.373 | 19.713 | 1.00 | 25.64 |
| ATOM 818 | N | GLU | 1562 | 1.288 | −0.076 | 18.250 | 1.00 | 24.49 |
| ATOM 820 | CA | GLU | 1562 | 1.806 | −0.949 | 19.284 | 1.00 | 25.00 |
| ATOM 821 | CB | GLU | 1562 | 2.357 | −2.231 | 18.677 | 1.00 | 23.69 |
| ATOM 822 | CG | GLU | 1562 | 1.272 | −3.170 | 18.219 | 1.00 | 24.29 |
| ATOM 823 | CD | GLU | 1562 | 1.814 | −4.393 | 17.514 | 1.00 | 27.65 |
| ATOM 824 | OE1 | GLU | 1562 | 1.218 | −5.480 | 17.649 | 1.00 | 29.50 |
| ATOM 825 | OE2 | GLU | 1562 | 2.832 | −4.270 | 16.807 | 1.00 | 32.34 |
| ATOM 826 | C | GLU | 1562 | 2.840 | −0.279 | 20.170 | 1.00 | 27.27 |
| ATOM 827 | O | GLU | 1562 | 3.596 | 0.576 | 19.729 | 1.00 | 26.18 |
| ATOM 828 | N | TYR | 1563 | 2.822 | −0.663 | 21.441 | 1.00 | 30.39 |
| ATOM 830 | CA | TYR | 1563 | 3.715 | −0.121 | 22.454 | 1.00 | 32.48 |
| ATOM 831 | CB | TYR | 1563 | 2.932 | 0.132 | 23.750 | 1.00 | 33.91 |
| ATOM 832 | CG | TYR | 1563 | 3.788 | 0.535 | 24.928 | 1.00 | 34.93 |
| ATOM 833 | CD1 | TYR | 1563 | 4.606 | 1.664 | 24.871 | 1.00 | 34.50 |
| ATOM 834 | CE1 | TYR | 1563 | 5.374 | 2.051 | 25.967 | 1.00 | 37.77 |
| ATOM 835 | CD2 | TYR | 1563 | 3.758 | −0.201 | 26.108 | 1.00 | 33.54 |
| ATOM 836 | CE2 | TYR | 1563 | 4.519 | 0.171 | 27.205 | 1.00 | 34.94 |
| ATOM 837 | CZ | TYR | 1563 | 5.321 | 1.296 | 27.128 | 1.00 | 37.22 |
| ATOM 838 | OH | TYR | 1563 | 6.087 | 1.648 | 28.206 | 1.00 | 45.36 |
| ATOM 840 | C | TYR | 1563 | 4.896 | −1.039 | 22.730 | 1.00 | 31.53 |
| ATOM 841 | O | TYR | 1563 | 4.737 | −2.252 | 22.895 | 1.00 | 30.43 |
| ATOM 842 | N | ALA | 1564 | 6.082 | −0.444 | 22.761 | 1.00 | 32.28 |
| ATOM 844 | CA | ALA | 1564 | 7.326 | −1.167 | 23.026 | 1.00 | 32.59 |
| ATOM 845 | CB | ALA | 1564 | 8.308 | −0.957 | 21.863 | 1.00 | 30.11 |
| ATOM 846 | C | ALA | 1564 | 7.897 | −0.608 | 24.334 | 1.00 | 31.81 |
| ATOM 847 | O | ALA | 1564 | 8.563 | 0.427 | 24.345 | 1.00 | 34.11 |
| ATOM 848 | N | SER | 1565 | 7.619 | −1.296 | 25.434 | 1.00 | 34.09 |
| ATOM 850 | CA | SER | 1565 | 8.039 | −0.853 | 26.763 | 1.00 | 35.05 |
| ATOM 851 | CB | SER | 1565 | 7.400 | −1.725 | 27.829 | 1.00 | 30.13 |
| ATOM 852 | OG | SER | 1565 | 7.689 | −3.084 | 27.579 | 1.00 | 38.17 |
| ATOM 854 | C | SER | 1565 | 9.526 | −0.769 | 27.041 | 1.00 | 35.03 |
| ATOM 855 | O | SER | 1565 | 9.947 | −0.001 | 27.902 | 1.00 | 37.12 |
| ATOM 856 | N | LYS | 1566 | 10.321 | −1.557 | 26.330 | 1.00 | 34.55 |
| ATOM 858 | CA | LYS | 1566 | 11.756 | −1.559 | 26.562 | 1.00 | 33.48 |
| ATOM 859 | CB | LYS | 1566 | 12.291 | −2.990 | 26.508 | 1.00 | 31.90 |
| ATOM 860 | CG | LYS | 1566 | 11.674 | −3.865 | 27.586 | 1.00 | 28.63 |
| ATOM 861 | CD | LYS | 1566 | 12.162 | −5.287 | 27.508 | 1.00 | 34.97 |
| ATOM 862 | CE | LYS | 1566 | 11.763 | −6.042 | 28.761 | 1.00 | 36.82 |
| ATOM 863 | NZ | LYS | 1566 | 12.288 | −7.433 | 28.748 | 1.00 | 41.32 |
| ATOM 867 | C | LYS | 1566 | 12.567 | −0.613 | 25.691 | 1.00 | 34.98 |
| ATOM 868 | O | LYS | 1566 | 13.785 | −0.740 | 25.607 | 1.00 | 38.03 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 869 | N | GLY | 1567 | 11.892 | 0.338 | 25.049 | 1.00 | 36.00 |
| ATOM 871 | CA | GLY | 1567 | 12.582 | 1.322 | 24.222 | 1.00 | 34.14 |
| ATOM 872 | C | GLY | 1567 | 13.245 | 0.864 | 22.933 | 1.00 | 32.01 |
| ATOM 873 | O | GLY | 1567 | 12.975 | -0.222 | 22.439 | 1.00 | 31.95 |
| ATOM 874 | N | ASN | 1568 | 14.091 | 1.719 | 22.360 | 1.00 | 33.51 |
| ATOM 876 | CA | ASN | 1568 | 14.774 | 1.375 | 21.121 | 1.00 | 34.20 |
| ATOM 877 | CB | ASN | 1568 | 15.203 | 2.627 | 20.332 | 1.00 | 34.07 |
| ATOM 878 | CG | ASN | 1568 | 16.420 | 3.321 | 20.910 | 1.00 | 35.09 |
| ATOM 879 | OD1 | ASN | 1568 | 17.453 | 2.709 | 21.156 | 1.00 | 34.36 |
| ATOM 880 | ND2 | ASN | 1568 | 16.317 | 4.624 | 21.066 | 1.00 | 38.38 |
| ATOM 883 | C | ASN | 1568 | 15.927 | 0.401 | 21.325 | 1.00 | 33.38 |
| ATOM 884 | O | ASN | 1568 | 16.490 | 0.315 | 22.414 | 1.00 | 34.93 |
| ATOM 885 | N | LEU | 1569 | 16.276 | -0.317 | 20.263 | 1.00 | 31.11 |
| ATOM 887 | CA | LEU | 1569 | 17.333 | -1.316 | 20.298 | 1.00 | 30.44 |
| ATOM 888 | CB | LEU | 1569 | 17.437 | -2.008 | 18.928 | 1.00 | 29.46 |
| ATOM 889 | CG | LEU | 1569 | 18.438 | -3.148 | 18.741 | 1.00 | 29.01 |
| ATOM 890 | CD1 | LEU | 1569 | 18.285 | -4.219 | 19.840 | 1.00 | 28.81 |
| ATOM 891 | CD2 | LEU | 1569 | 18.263 | -3.740 | 17.338 | 1.00 | 26.62 |
| ATOM 892 | C | LEU | 1569 | 18.706 | -0.805 | 20.762 | 1.00 | 30.16 |
| ATOM 893 | O | LEU | 1569 | 19.400 | -1.501 | 21.496 | 1.00 | 27.32 |
| ATOM 894 | N | ARG | 1570 | 19.097 | 0.396 | 20.344 | 1.00 | 30.74 |
| ATOM 896 | CA | ARG | 1570 | 20.386 | 0.951 | 20.758 | 1.00 | 33.72 |
| ATOM 897 | CB | ARG | 1570 | 20.597 | 2.349 | 20.160 | 1.00 | 32.82 |
| ATOM 898 | CG | ARG | 1570 | 21.873 | 3.009 | 20.662 | 1.00 | 36.90 |
| ATOM 899 | CD | ARG | 1570 | 21.966 | 4.481 | 20.332 | 1.00 | 39.32 |
| ATOM 900 | NE | ARG | 1570 | 20.749 | 5.222 | 20.664 | 1.00 | 50.32 |
| ATOM 902 | CZ | ARG | 1570 | 20.376 | 5.600 | 21.889 | 1.00 | 51.90 |
| ATOM 903 | NH1 | ARG | 1570 | 21.118 | 5.316 | 22.960 | 1.00 | 50.15 |
| ATOM 906 | NH2 | ARG | 1570 | 19.246 | 6.284 | 22.033 | 1.00 | 53.67 |
| ATOM 909 | C | ARG | 1570 | 20.434 | 1.022 | 22.298 | 1.00 | 35.75 |
| ATOM 910 | O | ARG | 1570 | 21.324 | 0.444 | 22.939 | 1.00 | 35.67 |
| ATOM 911 | N | GLU | 1571 | 19.444 | 1.695 | 22.880 | 1.00 | 35.56 |
| ATOM 913 | CA | GLU | 1571 | 19.331 | 1.835 | 24.328 | 1.00 | 36.50 |
| ATOM 914 | CB | GLU | 1571 | 18.055 | 2.607 | 24.667 | 1.00 | 39.08 |
| ATOM 915 | CG | GLU | 1571 | 18.061 | 4.056 | 24.208 | 1.00 | 46.75 |
| ATOM 916 | CD | GLU | 1571 | 16.694 | 4.721 | 24.311 | 1.00 | 51.36 |
| ATOM 917 | OE1 | GLU | 1571 | 15.676 | 3.996 | 24.417 | 1.00 | 55.22 |
| ATOM 918 | OE2 | GLU | 1571 | 16.635 | 5.972 | 24.267 | 1.00 | 53.59 |
| ATOM 919 | C | GLU | 1571 | 19.314 | 0.469 | 25.022 | 1.00 | 34.82 |
| ATOM 920 | O | GLU | 1571 | 20.018 | 0.242 | 26.013 | 1.00 | 35.05 |
| ATOM 921 | N | TYR | 1572 | 18.520 | -0.441 | 24.469 | 1.00 | 33.35 |
| ATOM 923 | CA | TYR | 1572 | 18.366 | -1.796 | 24.986 | 1.00 | 31.83 |
| ATOM 924 | CB | TYR | 1572 | 17.365 | -2.544 | 24.102 | 1.00 | 30.77 |
| ATOM 925 | CG | TYR | 1572 | 17.170 | -4.008 | 24.408 | 1.00 | 28.50 |
| ATOM 926 | CD1 | TYR | 1572 | 16.193 | -4.420 | 25.313 | 1.00 | 30.48 |
| ATOM 927 | CE1 | TYR | 1572 | 15.977 | -5.760 | 25.574 | 1.00 | 30.97 |
| ATOM 928 | CD2 | TYR | 1572 | 17.933 | -4.985 | 23.772 | 1.00 | 26.14 |
| ATOM 929 | CE2 | TYR | 1572 | 17.725 | -6.329 | 24.027 | 1.00 | 26.21 |
| ATOM 930 | CZ | TYR | 1572 | 16.742 | -6.708 | 24.935 | 1.00 | 30.30 |
| ATOM 931 | OH | TYR | 1572 | 16.518 | -8.041 | 25.214 | 1.00 | 33.52 |
| ATOM 933 | C | TYR | 1572 | 19.692 | -2.556 | 25.044 | 1.00 | 34.83 |
| ATOM 934 | O | TYR | 1572 | 19.959 | -3.308 | 25.992 | 1.00 | 34.93 |
| ATOM 935 | N | LEU | 1573 | 20.517 | -2.370 | 24.020 | 1.00 | 34.34 |
| ATOM 937 | CA | LEU | 1573 | 21.803 | -3.053 | 23.961 | 1.00 | 35.38 |
| ATOM 938 | CB | LEU | 1573 | 22.357 | -3.027 | 22.531 | 1.00 | 32.71 |
| ATOM 939 | CG | LEU | 1573 | 21.669 | -3.891 | 21.464 | 1.00 | 29.16 |
| ATOM 940 | CD1 | LEU | 1573 | 22.161 | -3.503 | 20.087 | 1.00 | 26.98 |
| ATOM 941 | CD2 | LEU | 1573 | 21.932 | -5.351 | 21.710 | 1.00 | 28.85 |
| ATOM 942 | C | LEU | 1573 | 22.799 | -2.420 | 24.933 | 1.00 | 37.54 |
| ATOM 943 | O | LEU | 1573 | 23.511 | -3.123 | 25.659 | 1.00 | 36.67 |
| ATOM 944 | N | GLN | 1574 | 22.814 | -1.092 | 24.969 | 1.00 | 37.90 |
| ATOM 946 | CA | GLN | 1574 | 23.729 | -0.368 | 25.838 | 1.00 | 39.77 |
| ATOM 947 | CB | GLN | 1574 | 23.624 | 1.138 | 25.572 | 1.00 | 40.09 |
| ATOM 948 | CG | GLN | 1574 | 24.208 | 1.549 | 24.217 | 1.00 | 42.28 |
| ATOM 949 | CD | GLN | 1574 | 24.030 | 3.018 | 23.896 | 1.00 | 44.28 |
| ATOM 950 | OE1 | GLN | 1574 | 23.362 | 3.755 | 24.615 | 1.00 | 47.55 |
| ATOM 951 | NE2 | GLN | 1574 | 24.613 | 3.448 | 22.790 | 1.00 | 46.09 |
| ATOM 954 | C | GLN | 1574 | 23.490 | -0.697 | 27.310 | 1.00 | 40.75 |
| ATOM 955 | O | GLN | 1574 | 24.440 | -0.939 | 28.059 | 1.00 | 41.29 |
| ATOM 956 | N | ALA | 1575 | 22.220 | -0.783 | 27.696 | 1.00 | 40.10 |
| ATOM 958 | CA | ALA | 1575 | 21.842 | -1.088 | 29.069 | 1.00 | 38.81 |
| ATOM 959 | CB | ALA | 1575 | 20.349 | -0.819 | 29.273 | 1.00 | 35.69 |
| ATOM 960 | C | ALA | 1575 | 22.192 | -2.514 | 29.503 | 1.00 | 40.63 |
| ATOM 961 | O | ALA | 1575 | 22.098 | -2.843 | 30.690 | 1.00 | 43.39 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 962 | N | ARG | 1576 | 22.602 | −3.357 | 28.561 | 1.00 | 38.39 |
| ATOM 964 | CA | ARG | 1576 | 22.945 | −4.729 | 28.896 | 1.00 | 37.69 |
| ATOM 965 | CB | ARG | 1576 | 22.034 | −5.689 | 28.137 | 1.00 | 38.16 |
| ATOM 966 | CG | ARG | 1576 | 20.594 | −5.547 | 28.589 | 1.00 | 37.89 |
| ATOM 967 | CD | ARG | 1576 | 19.622 | −6.281 | 27.711 | 1.00 | 37.36 |
| ATOM 968 | NE | ARG | 1576 | 18.267 | −6.255 | 28.265 | 1.00 | 34.99 |
| ATOM 970 | CZ | ARG | 1576 | 17.565 | −5.150 | 28.484 | 1.00 | 36.94 |
| ATOM 971 | NH1 | ARG | 1576 | 18.083 | −3.960 | 28.209 | 1.00 | 36.18 |
| ATOM 974 | NH2 | ARG | 1576 | 16.310 | −5.237 | 28.909 | 1.00 | 40.93 |
| ATOM 977 | C | ARG | 1576 | 24.413 | −5.073 | 28.704 | 1.00 | 38.93 |
| ATOM 978 | O | ARG | 1576 | 24.801 | −6.249 | 28.699 | 1.00 | 39.75 |
| ATOM 979 | N | ARG | 1577 | 25.233 | −4.036 | 28.570 | 1.00 | 39.21 |
| ATOM 981 | CA | ARG | 1577 | 26.671 | −4.196 | 28.413 | 1.00 | 38.97 |
| ATOM 982 | CB | ARG | 1577 | 27.307 | −2.870 | 28.000 | 1.00 | 36.06 |
| ATOM 983 | CG | ARG | 1577 | 26.992 | −2.408 | 26.610 | 1.00 | 36.41 |
| ATOM 984 | CD | ARG | 1577 | 27.695 | −1.094 | 26.337 | 1.00 | 36.17 |
| ATOM 985 | NE | ARG | 1577 | 27.776 | −0.806 | 24.907 | 1.00 | 38.45 |
| ATOM 987 | CZ | ARG | 1577 | 28.284 | 0.309 | 24.387 | 1.00 | 39.00 |
| ATOM 988 | NH1 | ARG | 1577 | 28.764 | 1.262 | 25.175 | 1.00 | 38.88 |
| ATOM 991 | NH2 | ARG | 1577 | 28.311 | 0.469 | 23.071 | 1.00 | 37.76 |
| ATOM 994 | C | ARG | 1577 | 27.247 | −4.571 | 29.772 | 1.00 | 40.59 |
| ATOM 995 | O | ARG | 1577 | 26.680 | −4.217 | 30.800 | 1.00 | 38.52 |
| ATOM 996 | N | PRO | 1578 | 28.358 | −5.327 | 29.796 | 1.00 | 43.19 |
| ATOM 997 | CD | PRO | 1578 | 29.077 | −5.980 | 28.692 | 1.00 | 44.84 |
| ATOM 998 | CA | PRO | 1578 | 28.952 | −5.692 | 31.088 | 1.00 | 45.06 |
| ATOM 999 | CB | PRO | 1578 | 30.065 | −6.673 | 30.689 | 1.00 | 44.86 |
| ATOM 1000 | CG | PRO | 1578 | 30.431 | −6.229 | 29.308 | 1.00 | 44.56 |
| ATOM 1001 | C | PRO | 1578 | 29.513 | −4.420 | 31.734 | 1.00 | 44.93 |
| ATOM 1002 | O | PRO | 1578 | 29.809 | −3.439 | 31.043 | 1.00 | 43.13 |
| ATOM 1003 | N | PRO | 1579 | 29.649 | −4.414 | 33.067 | 1.00 | 47.61 |
| ATOM 1004 | CD | PRO | 1579 | 29.315 | −5.492 | 34.012 | 1.00 | 48.39 |
| ATOM 1005 | CA | PRO | 1579 | 30.173 | −3.247 | 33.784 | 1.00 | 48.74 |
| ATOM 1006 | CB | PRO | 1579 | 30.138 | −3.706 | 35.238 | 1.00 | 49.73 |
| ATOM 1007 | CG | PRO | 1579 | 29.027 | −4.711 | 35.259 | 1.00 | 49.21 |
| ATOM 1008 | C | PRO | 1579 | 31.591 | −2.888 | 33.357 | 1.00 | 49.67 |
| ATOM 1009 | O | PRO | 1579 | 32.483 | −3.733 | 33.361 | 1.00 | 52.07 |
| ATOM 1010 | N | GLU | 1592 | 19.165 | −5.411 | 32.444 | 1.00 | 64.83 |
| ATOM 1012 | CA | GLU | 1592 | 20.603 | −5.147 | 32.491 | 1.00 | 64.82 |
| ATOM 1013 | CB | GLU | 1592 | 20.969 | −4.421 | 33.784 | 1.00 | 67.61 |
| ATOM 1014 | C | GLU | 1592 | 21.448 | −6.413 | 32.335 | 1.00 | 63.99 |
| ATOM 1015 | O | GLU | 1592 | 22.653 | −6.336 | 32.098 | 1.00 | 65.67 |
| ATOM 1016 | N | GLU | 1593 | 20.821 | −7.575 | 32.485 | 1.00 | 62.41 |
| ATOM 1018 | CA | GLU | 1593 | 21.534 | −8.844 | 32.342 | 1.00 | 61.23 |
| ATOM 1019 | CB | GLU | 1593 | 20.595 | −10.017 | 32.600 | 1.00 | 61.20 |
| ATOM 1020 | C | GLU | 1593 | 22.141 | −8.953 | 30.944 | 1.00 | 59.26 |
| ATOM 1021 | O | GLU | 1593 | 21.494 | −8.631 | 29.945 | 1.00 | 59.84 |
| ATOM 1022 | N | GLN | 1594 | 23.388 | −9.405 | 30.888 | 1.00 | 57.94 |
| ATOM 1024 | CA | GLN | 1594 | 24.101 | −9.558 | 29.625 | 1.00 | 54.91 |
| ATOM 1025 | CB | GLN | 1594 | 25.501 | −10.141 | 29.865 | 1.00 | 55.13 |
| ATOM 1026 | CG | GLN | 1594 | 26.439 | −9.252 | 30.679 | 1.00 | 56.93 |
| ATOM 1027 | CD | GLN | 1594 | 27.682 | −9.997 | 31.180 | 1.00 | 59.60 |
| ATOM 1028 | OE1 | GLN | 1594 | 28.241 | −10.858 | 30.488 | 1.00 | 58.45 |
| ATOM 1029 | NE2 | GLN | 1594 | 28.117 | −9.662 | 32.393 | 1.00 | 58.95 |
| ATOM 1032 | C | GLN | 1594 | 23.331 | −10.438 | 28.640 | 1.00 | 52.30 |
| ATOM 1033 | O | GLN | 1594 | 22.637 | −11.389 | 29.025 | 1.00 | 52.03 |
| ATOM 1034 | N | LEU | 1595 | 23.438 | −10.091 | 27.366 | 1.00 | 49.60 |
| ATOM 1036 | CA | LEU | 1595 | 22.782 | −10.836 | 26.308 | 1.00 | 45.16 |
| ATOM 1037 | CB | LEU | 1595 | 22.459 | −9.907 | 25.135 | 1.00 | 41.36 |
| ATOM 1038 | CG | LEU | 1595 | 21.463 | −8.815 | 25.523 | 1.00 | 39.43 |
| ATOM 1039 | CD1 | LEU | 1595 | 21.617 | −7.583 | 24.644 | 1.00 | 36.21 |
| ATOM 1040 | CD2 | LEU | 1595 | 20.060 | −9.389 | 25.480 | 1.00 | 34.91 |
| ATOM 1041 | C | LEU | 1595 | 23.747 | −11.900 | 25.858 | 1.00 | 43.30 |
| ATOM 1042 | O | LEU | 1595 | 24.953 | −11.675 | 25.841 | 1.00 | 43.62 |
| ATOM 1043 | N | SER | 1596 | 23.230 | −13.081 | 25.553 | 1.00 | 42.92 |
| ATOM 1045 | CA | SER | 1596 | 24.085 | −14.150 | 25.077 | 1.00 | 41.86 |
| ATOM 1046 | CB | SER | 1596 | 23.410 | −15.502 | 25.298 | 1.00 | 40.86 |
| ATOM 1047 | OG | SER | 1596 | 22.188 | −15.596 | 24.595 | 1.00 | 37.88 |
| ATOM 1049 | C | SER | 1596 | 24.322 | −13.914 | 23.587 | 1.00 | 41.59 |
| ATOM 1050 | O | SER | 1596 | 23.657 | −13.077 | 22.966 | 1.00 | 41.94 |
| ATOM 1051 | N | SER | 1597 | 25.275 | −14.637 | 23.018 | 1.00 | 39.60 |
| ATOM 1053 | CA | SER | 1597 | 25.557 | −14.518 | 21.603 | 1.00 | 39.74 |
| ATOM 1054 | CB | SER | 1597 | 26.729 | −15.409 | 21.223 | 1.00 | 41.38 |
| ATOM 1055 | OG | SER | 1597 | 27.824 | −15.147 | 22.077 | 1.00 | 50.59 |
| ATOM 1057 | C | SER | 1597 | 24.315 | −14.921 | 20.818 | 1.00 | 38.16 |

TABLE 3-continued

Atomic Structure Coordinates of Unphosphorylated FLGK

| Atom No. | Atom Type | A.A. Type | A.A. No. | X | Y | Z | OCC | B | |
|---|---|---|---|---|---|---|---|---|---|
| ATOM 1058 | O | SER | 1597 | 24.036 | −14.353 | 19.769 | 1.00 | 38.03 | |
| ATOM 1059 | N | LYS | 1598 | 23.560 | −15.891 | 21.327 | 1.00 | 36.40 | |
| ATOM 1061 | CA | LYS | 1598 | 22.362 | −16.312 | 20.634 | 1.00 | 35.97 | |
| ATOM 1062 | CB | LYS | 1598 | 21.791 | −17.594 | 21.228 | 1.00 | 36.69 | |
| ATOM 1063 | CG | LYS | 1598 | 20.989 | −18.402 | 20.198 | 1.00 | 40.42 | |
| ATOM 1064 | CD | LYS | 1598 | 20.164 | −19.499 | 20.838 | 1.00 | 40.37 | |
| ATOM 1065 | CE | LYS | 1598 | 19.792 | −20.572 | 19.829 | 1.00 | 46.34 | |
| ATOM 1066 | NZ | LYS | 1598 | 20.993 | −21.338 | 19.362 | 1.00 | 45.29 | |
| ATOM 1070 | C | LYS | 1598 | 21.324 | −15.194 | 20.696 | 1.00 | 37.49 | |
| ATOM 1071 | O | LYS | 1598 | 20.567 | −14.983 | 19.738 | 1.00 | 38.10 | |
| ATOM 1072 | N | ASP | 1599 | 21.316 | −14.458 | 21.807 | 1.00 | 35.21 | |
| ATOM 1074 | CA | ASP | 1599 | 20.380 | −13.352 | 21.983 | 1.00 | 34.02 | |
| ATOM 1075 | CB | ASP | 1599 | 20.556 | −12.686 | 23.346 | 1.00 | 37.78 | |
| ATOM 1076 | CG | ASP | 1599 | 19.970 | −13.493 | 24.483 | 1.00 | 40.05 | |
| ATOM 1077 | OD1 | ASP | 1599 | 20.270 | −13.143 | 25.642 | 1.00 | 42.73 | |
| ATOM 1078 | OD2 | ASP | 1599 | 19.204 | −14.450 | 24.235 | 1.00 | 42.39 | |
| ATOM 1079 | C | ASP | 1599 | 20.633 | −12.306 | 20.922 | 1.00 | 32.84 | |
| ATOM 1080 | O | ASP | 1599 | 19.694 | −11.779 | 20.311 | 1.00 | 30.59 | |
| ATOM 1081 | N | LEU | 1600 | 21.912 | −11.999 | 20.724 | 1.00 | 31.11 | |
| ATOM 1083 | CA | LEU | 1600 | 22.323 | −10.998 | 19.744 | 1.00 | 32.17 | |
| ATOM 1084 | CB | LEU | 1600 | 23.823 | −10.722 | 19.875 | 1.00 | 32.30 | |
| ATOM 1085 | CG | LEU | 1600 | 24.275 | −10.162 | 21.235 | 1.00 | 31.08 | |
| ATOM 1086 | CD1 | LEU | 1600 | 25.794 | −9.931 | 21.242 | 1.00 | 30.59 | |
| ATOM 1087 | CD2 | LEU | 1600 | 23.549 | −8.863 | 21.514 | 1.00 | 28.89 | |
| ATOM 1088 | C | LEU | 1600 | 21.949 | −11.390 | 18.311 | 1.00 | 30.77 | |
| ATOM 1089 | O | LEU | 1600 | 21.352 | −10.601 | 17.574 | 1.00 | 29.87 | |
| ATOM 1090 | N | VAL | 1601 | 22.269 | −12.623 | 17.933 | 1.00 | 30.19 | |
| ATOM 1092 | CA | VAL | 1601 | 21.954 | −13.115 | 16.602 | 1.00 | 29.25 | |
| ATOM 1093 | CB | VAL | 1601 | 22.593 | −14.497 | 16.349 | 1.00 | 31.27 | |
| ATOM 1094 | CG1 | VAL | 1601 | 22.355 | −14.936 | 14.914 | 1.00 | 31.60 | |
| ATOM 1095 | CG2 | VAL | 1601 | 24.093 | −14.434 | 16.622 | 1.00 | 31.91 | |
| ATOM 1096 | C | VAL | 1601 | 20.438 | −13.181 | 16.405 | 1.00 | 29.06 | |
| ATOM 1097 | O | VAL | 1601 | 19.946 | −12.914 | 15.310 | 1.00 | 27.71 | |
| ATOM 1098 | N | SER | 1602 | 19.702 | −13.511 | 17.468 | 1.00 | 29.10 | |
| ATOM 1100 | CA | SER | 1602 | 18.243 | −13.585 | 17.400 | 1.00 | 29.29 | |
| ATOM 1101 | CB | SER | 1602 | 17.680 | −14.189 | 18.679 | 1.00 | 30.81 | |
| ATOM 1102 | OG | SER | 1602 | 16.266 | −14.074 | 18.692 | 1.00 | 35.78 | |
| ATOM 1104 | C | SER | 1602 | 17.649 | −12.199 | 17.156 | 1.00 | 28.98 | |
| ATOM 1105 | O | SER | 1602 | 16.662 | −12.039 | 16.426 | 1.00 | 26.82 | |
| ATOM 1106 | N | CYS | 1603 | 18.274 | −11.202 | 17.765 | 1.00 | 29.06 | |
| ATOM 1108 | CA | CYS | 1603 | 17.870 | −9.823 | 17.599 | 1.00 | 29.22 | |
| ATOM 1109 | CB | CYS | 1603 | 18.784 | −8.943 | 18.438 | 1.00 | 29.66 | |
| ATOM 1110 | SG | CYS | 1603 | 18.575 | −7.212 | 18.103 | 0.50 | 23.69 | PRT1 |
| ATOM 1111 | C | CYS | 1603 | 17.988 | −9.422 | 16.112 | 1.00 | 29.23 | |
| ATOM 1112 | O | CYS | 1603 | 17.087 | −8.796 | 15.552 | 1.00 | 27.52 | |
| ATOM 1113 | N | ALA | 1604 | 19.113 | −9.778 | 15.491 | 1.00 | 27.87 | |
| ATOM 1115 | CA | ALA | 1604 | 19.376 | −9.484 | 14.077 | 1.00 | 26.37 | |
| ATOM 1116 | CB | ALA | 1604 | 20.783 | −9.941 | 13.690 | 1.00 | 23.88 | |
| ATOM 1117 | C | ALA | 1604 | 18.349 | −10.203 | 13.223 | 1.00 | 25.82 | |
| ATOM 1118 | O | ALA | 1604 | 17.788 | −9.631 | 12.289 | 1.00 | 25.84 | |
| ATOM 1119 | N | TYR | 1605 | 18.119 | −11.468 | 13.544 | 1.00 | 25.56 | |
| ATOM 1121 | CA | TYR | 1605 | 17.152 | −12.276 | 12.827 | 1.00 | 27.81 | |
| ATOM 1122 | CB | TYR | 1605 | 17.080 | −13.662 | 13.456 | 1.00 | 26.66 | |
| ATOM 1123 | CG | TYR | 1605 | 15.974 | −14.515 | 12.886 | 1.00 | 30.75 | |
| ATOM 1124 | CD1 | TYR | 1605 | 16.111 | −15.141 | 11.640 | 1.00 | 30.20 | |
| ATOM 1125 | CE1 | TYR | 1605 | 15.088 | −15.944 | 11.126 | 1.00 | 30.03 | |
| ATOM 1126 | CD2 | TYR | 1605 | 14.790 | −14.707 | 13.596 | 1.00 | 30.73 | |
| ATOM 1127 | CE2 | TYR | 1605 | 13.775 | −15.500 | 13.097 | 1.00 | 30.71 | |
| ATOM 1128 | CZ | TYR | 1605 | 13.930 | −16.117 | 11.867 | 1.00 | 30.93 | |
| ATOM 1129 | OH | TYR | 1605 | 12.923 | −16.928 | 11.417 | 1.00 | 32.31 | |
| ATOM 1131 | C | TYR | 1605 | 15.748 | −11.641 | 12.775 | 1.00 | 26.15 | |
| ATOM 1132 | O | TYR | 1605 | 15.147 | −11.551 | 11.702 | 1.00 | 26.64 | |
| ATOM 1133 | N | GLN | 1606 | 15.244 | −11.200 | 13.926 | 1.00 | 25.48 | |
| ATOM 1135 | CA | GLN | 1606 | 13.921 | −10.581 | 14.023 | 1.00 | 26.86 | |
| ATOM 1136 | CB | GLN | 1606 | 13.589 | −10.269 | 15.482 | 1.00 | 26.83 | |
| ATOM 1137 | CG | GLN | 1606 | 13.357 | −11.508 | 16.332 | 1.00 | 25.84 | |
| ATOM 1138 | CD | GLN | 1606 | 13.151 | −11.167 | 17.791 | 1.00 | 30.86 | |
| ATOM 1139 | OE1 | GLN | 1606 | 12.202 | −10.471 | 18.150 | 1.00 | 31.87 | |
| ATOM 1140 | NE2 | GLN | 1606 | 14.056 | −11.631 | 18.640 | 1.00 | 31.67 | |
| ATOM 1143 | C | GLN | 1606 | 13.835 | −9.310 | 13.186 | 1.00 | 27.52 | |
| ATOM 1144 | O | GLN | 1606 | 12.831 | −9.058 | 12.506 | 1.00 | 26.05 | |
| ATOM 1145 | N | VAL | 1607 | 14.904 | −8.523 | 13.216 | 1.00 | 26.68 | |
| ATOM 1147 | CA | VAL | 1607 | 14.963 | −7.301 | 12.435 | 1.00 | 25.66 | |
| ATOM 1148 | CB | VAL | 1607 | 16.225 | −6.485 | 12.787 | 1.00 | 28.50 | |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1149 | CG1 | VAL | 1607 | 16.363 | −5.274 | 11.853 | 1.00 | 26.04 |
| ATOM 1150 | CG2 | VAL | 1607 | 16.151 | −6.031 | 14.246 | 1.00 | 24.45 |
| ATOM 1151 | C | VAL | 1607 | 14.934 | −7.641 | 10.938 | 1.00 | 24.89 |
| ATOM 1152 | O | VAL | 1607 | 14.184 | −7.033 | 10.177 | 1.00 | 25.86 |
| ATOM 1153 | N | ALA | 1608 | 15.738 | −8.619 | 10.522 | 1.00 | 25.24 |
| ATOM 1155 | CA | ALA | 1608 | 15.773 | −9.039 | 9.120 | 1.00 | 22.95 |
| ATOM 1156 | CB | ALA | 1608 | 16.813 | −10.117 | 8.920 | 1.00 | 20.24 |
| ATOM 1157 | C | ALA | 1608 | 14.383 | −9.541 | 8.679 | 1.00 | 25.71 |
| ATOM 1158 | O | ALA | 1608 | 13.963 | −9.319 | 7.532 | 1.00 | 27.48 |
| ATOM 1159 | N | ARG | 1609 | 13.676 | −10.216 | 9.585 | 1.00 | 27.10 |
| ATOM 1161 | CA | ARG | 1609 | 12.327 | −10.708 | 9.301 | 1.00 | 28.55 |
| ATOM 1162 | CB | ARG | 1609 | 11.840 | −11.640 | 10.397 | 1.00 | 31.53 |
| ATOM 1163 | CG | ARG | 1609 | 12.407 | −13.005 | 10.290 | 1.00 | 36.05 |
| ATOM 1164 | CD | ARG | 1609 | 11.537 | −13.931 | 11.056 | 1.00 | 40.28 |
| ATOM 1165 | NE | ARG | 1609 | 10.849 | −14.874 | 10.190 | 1.00 | 42.06 |
| ATOM 1167 | CZ | ARG | 1609 | 9.974 | −15.771 | 10.632 | 1.00 | 42.08 |
| ATOM 1168 | NH1 | ARG | 1609 | 9.678 | −15.834 | 11.928 | 1.00 | 40.32 |
| ATOM 1171 | NH2 | ARG | 1609 | 9.416 | −16.620 | 9.784 | 1.00 | 43.27 |
| ATOM 1174 | C | ARG | 1609 | 11.329 | −9.569 | 9.124 | 1.00 | 25.55 |
| ATOM 1175 | O | ARG | 1609 | 10.469 | −9.621 | 8.231 | 1.00 | 26.98 |
| ATOM 1176 | N | GLY | 1610 | 11.418 | −8.565 | 9.996 | 1.00 | 23.92 |
| ATOM 1178 | CA | GLY | 1610 | 10.555 | −7.406 | 9.870 | 1.00 | 22.19 |
| ATOM 1179 | C | GLY | 1610 | 10.800 | −6.747 | 8.512 | 1.00 | 25.92 |
| ATOM 1180 | O | GLY | 1610 | 9.855 | −6.424 | 7.772 | 1.00 | 23.49 |
| ATOM 1181 | N | MET | 1611 | 12.076 | −6.589 | 8.163 | 1.00 | 23.15 |
| ATOM 1183 | CA | MET | 1611 | 12.456 | −5.989 | 6.888 | 1.00 | 22.57 |
| ATOM 1184 | CB | MET | 1611 | 13.956 | −5.710 | 6.849 | 1.00 | 22.18 |
| ATOM 1185 | CG | MET | 1611 | 14.398 | −4.542 | 7.729 | 1.00 | 22.63 |
| ATOM 1186 | SD | MET | 1611 | 13.478 | −3.006 | 7.426 | 1.00 | 25.23 |
| ATOM 1187 | CE | MET | 1611 | 13.812 | −2.688 | 5.675 | 1.00 | 21.38 |
| ATOM 1188 | C | MET | 1611 | 12.050 | −6.848 | 5.681 | 1.00 | 23.96 |
| ATOM 1189 | O | MET | 1611 | 11.673 | −6.326 | 4.633 | 1.00 | 25.26 |
| ATOM 1190 | N | GLU | 1612 | 12.130 | −8.163 | 5.822 | 1.00 | 24.34 |
| ATOM 1192 | CA | GLU | 1612 | 11.755 | −9.043 | 4.733 | 1.00 | 25.56 |
| ATOM 1193 | CB | GLU | 1612 | 12.018 | −10.494 | 5.121 | 1.00 | 24.96 |
| ATOM 1194 | CG | GLU | 1612 | 11.703 | −11.488 | 4.009 | 1.00 | 26.79 |
| ATOM 1195 | CD | GLU | 1612 | 11.812 | −12.931 | 4.450 | 1.00 | 26.96 |
| ATOM 1196 | OE1 | GLU | 1612 | 11.557 | −13.212 | 5.636 | 1.00 | 30.98 |
| ATOM 1197 | OE2 | GLU | 1612 | 12.154 | −13.791 | 3.611 | 1.00 | 32.31 |
| ATOM 1198 | C | GLU | 1612 | 10.267 | −8.829 | 4.415 | 1.00 | 25.70 |
| ATOM 1199 | O | GLU | 1612 | 9.860 | −8.753 | 3.252 | 1.00 | 24.30 |
| ATOM 1200 | N | TYR | 1613 | 9.463 | −8.723 | 5.465 | 1.00 | 23.55 |
| ATOM 1202 | CA | TYR | 1613 | 8.037 | −8.501 | 5.294 | 1.00 | 22.94 |
| ATOM 1203 | CB | TYR | 1613 | 7.314 | −8.586 | 6.650 | 1.00 | 24.00 |
| ATOM 1204 | CG | TYR | 1613 | 5.841 | −8.281 | 6.549 | 1.00 | 22.93 |
| ATOM 1205 | CD1 | TYR | 1613 | 4.945 | −9.245 | 6.097 | 1.00 | 21.60 |
| ATOM 1206 | CE1 | TYR | 1613 | 3.582 | −8.962 | 5.963 | 1.00 | 21.14 |
| ATOM 1207 | CD2 | TYR | 1613 | 5.347 | −7.018 | 6.869 | 1.00 | 25.81 |
| ATOM 1208 | CE2 | TYR | 1613 | 3.979 | −6.718 | 6.733 | 1.00 | 24.45 |
| ATOM 1209 | CZ | TYR | 1613 | 3.112 | −7.697 | 6.281 | 1.00 | 23.28 |
| ATOM 1210 | OH | TYR | 1613 | 1.775 | −7.411 | 6.126 | 1.00 | 22.95 |
| ATOM 1212 | C | TYR | 1613 | 7.803 | −7.138 | 4.637 | 1.00 | 22.57 |
| ATOM 1213 | O | TYR | 1613 | 7.022 | −7.024 | 3.699 | 1.00 | 24.72 |
| ATOM 1214 | N | LEU | 1614 | 8.460 | −6.101 | 5.156 | 1.00 | 22.16 |
| ATOM 1216 | CA | LEU | 1614 | 8.334 | −4.755 | 4.615 | 1.00 | 22.60 |
| ATOM 1217 | CB | LEU | 1614 | 9.175 | −3.772 | 5.440 | 1.00 | 22.56 |
| ATOM 1218 | CG | LEU | 1614 | 8.577 | −3.415 | 6.802 | 1.00 | 24.92 |
| ATOM 1219 | CD1 | LEU | 1614 | 9.535 | −2.541 | 7.580 | 1.00 | 21.46 |
| ATOM 1220 | CD2 | LEU | 1614 | 7.218 | −2.711 | 6.611 | 1.00 | 21.87 |
| ATOM 1221 | C | LEU | 1614 | 8.699 | −4.683 | 3.124 | 1.00 | 23.76 |
| ATOM 1222 | O | LEU | 1614 | 7.975 | −4.077 | 2.326 | 1.00 | 23.84 |
| ATOM 1223 | N | ALA | 1615 | 9.809 | −5.314 | 2.744 | 1.00 | 23.48 |
| ATOM 1225 | CA | ALA | 1615 | 10.232 | −5.340 | 1.352 | 1.00 | 22.70 |
| ATOM 1226 | CB | ALA | 1615 | 11.591 | −6.019 | 1.215 | 1.00 | 21.52 |
| ATOM 1227 | C | ALA | 1615 | 9.188 | −6.063 | 0.505 | 1.00 | 22.87 |
| ATOM 1228 | O | ALA | 1615 | 8.854 | −5.591 | −0.581 | 1.00 | 24.23 |
| ATOM 1229 | N | SER | 1616 | 8.652 | −7.176 | 1.015 | 1.00 | 22.76 |
| ATOM 1231 | CA | SER | 1616 | 7.638 | −7.954 | 0.295 | 1.00 | 22.88 |
| ATOM 1232 | CB | SER | 1616 | 7.315 | −9.251 | 1.039 | 1.00 | 21.39 |
| ATOM 1233 | OG | SER | 1616 | 6.400 | −9.036 | 2.102 | 1.00 | 26.24 |
| ATOM 1235 | C | SER | 1616 | 6.360 | −7.131 | 0.044 | 1.00 | 24.88 |
| ATOM 1236 | O | SER | 1616 | 5.635 | −7.358 | −0.927 | 1.00 | 24.73 |
| ATOM 1237 | N | LYS | 1617 | 6.104 | −6.173 | 0.927 | 1.00 | 23.82 |
| ATOM 1239 | CA | LYS | 1617 | 4.970 | −5.287 | 0.810 | 1.00 | 22.47 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1240 | CB | LYS | 1617 | 4.455 | −4.914 | 2.199 | 1.00 | 23.62 |
| ATOM 1241 | CG | LYS | 1617 | 3.792 | −6.072 | 2.927 | 1.00 | 27.16 |
| ATOM 1242 | CD | LYS | 1617 | 2.551 | −6.487 | 2.169 | 1.00 | 30.84 |
| ATOM 1243 | CE | LYS | 1617 | 1.810 | −7.602 | 2.852 | 1.00 | 33.57 |
| ATOM 1244 | NZ | LYS | 1617 | 2.484 | −8.894 | 2.653 | 1.00 | 44.30 |
| ATOM 1248 | C | LYS | 1617 | 5.346 | −4.034 | 0.035 | 1.00 | 23.56 |
| ATOM 1249 | O | LYS | 1617 | 4.639 | −3.030 | 0.091 | 1.00 | 25.16 |
| ATOM 1250 | N | LYS | 1618 | 6.495 | −4.066 | −0.638 | 1.00 | 24.69 |
| ATOM 1252 | CA | LYS | 1618 | 6.953 | −2.943 | −1.468 | 1.00 | 24.04 |
| ATOM 1253 | CB | LYS | 1618 | 5.863 | −2.581 | −2.492 | 1.00 | 26.96 |
| ATOM 1254 | CG | LYS | 1618 | 5.775 | −3.491 | −3.709 | 1.00 | 29.14 |
| ATOM 1255 | CD | LYS | 1618 | 5.567 | −4.942 | −3.345 | 1.00 | 33.91 |
| ATOM 1256 | CE | LYS | 1618 | 5.662 | −5.858 | −4.558 | 1.00 | 32.98 |
| ATOM 1257 | NZ | LYS | 1618 | 4.431 | −5.821 | −5.380 | 1.00 | 36.73 |
| ATOM 1261 | C | LYS | 1618 | 7.406 | −1.686 | −0.713 | 1.00 | 24.01 |
| ATOM 1262 | O | LYS | 1618 | 7.557 | −0.606 | −1.302 | 1.00 | 23.73 |
| ATOM 1263 | N | CYS | 1619 | 7.689 | −1.842 | 0.573 | 1.00 | 25.91 |
| ATOM 1265 | CA | CYS | 1619 | 8.108 | −0.731 | 1.418 | 1.00 | 25.65 |
| ATOM 1266 | CB | CYS | 1619 | 7.444 | −0.885 | 2.792 | 1.00 | 24.93 |
| ATOM 1267 | SG | CYS | 1619 | 7.941 | 0.313 | 4.064 | 1.00 | 24.14 |
| ATOM 1268 | C | CYS | 1619 | 9.631 | −0.628 | 1.573 | 1.00 | 23.07 |
| ATOM 1269 | O | CYS | 1619 | 10.304 | −1.630 | 1.809 | 1.00 | 20.98 |
| ATOM 1270 | N | ILE | 1620 | 10.170 | 0.573 | 1.363 | 1.00 | 22.95 |
| ATOM 1272 | CA | ILE | 1620 | 11.604 | 0.841 | 1.524 | 1.00 | 23.81 |
| ATOM 1273 | CB | ILE | 1620 | 12.202 | 1.607 | 0.276 | 1.00 | 24.36 |
| ATOM 1274 | CG2 | ILE | 1620 | 13.670 | 1.995 | 0.506 | 1.00 | 17.24 |
| ATOM 1275 | CG1 | ILE | 1620 | 12.108 | 0.739 | −0.987 | 1.00 | 23.13 |
| ATOM 1276 | CD1 | ILE | 1620 | 12.171 | 1.544 | −2.286 | 1.00 | 25.37 |
| ATOM 1277 | C | ILE | 1620 | 11.633 | 1.729 | 2.771 | 1.00 | 24.70 |
| ATOM 1278 | O | ILE | 1620 | 10.981 | 2.763 | 2.806 | 1.00 | 25.21 |
| ATOM 1279 | N | HIS | 1621 | 12.348 | 1.297 | 3.804 | 1.00 | 25.62 |
| ATOM 1281 | CA | HIS | 1621 | 12.427 | 2.041 | 5.057 | 1.00 | 25.53 |
| ATOM 1282 | CB | HIS | 1621 | 13.181 | 1.237 | 6.132 | 1.00 | 22.76 |
| ATOM 1283 | CG | HIS | 1621 | 13.004 | 1.773 | 7.528 | 1.00 | 26.42 |
| ATOM 1284 | CD2 | HIS | 1621 | 12.356 | 1.260 | 8.601 | 1.00 | 24.74 |
| ATOM 1285 | ND1 | HIS | 1621 | 13.474 | 3.011 | 7.927 | 1.00 | 26.62 |
| ATOM 1287 | CE1 | HIS | 1621 | 13.119 | 3.233 | 9.179 | 1.00 | 25.70 |
| ATOM 1288 | NE2 | HIS | 1621 | 12.439 | 2.187 | 9.616 | 1.00 | 26.23 |
| ATOM 1290 | C | HIS | 1621 | 13.073 | 3.401 | 4.914 | 1.00 | 26.36 |
| ATOM 1291 | O | HIS | 1621 | 12.528 | 4.405 | 5.370 | 1.00 | 25.89 |
| ATOM 1292 | N | ARG | 1622 | 14.271 | 3.406 | 4.341 | 1.00 | 25.35 |
| ATOM 1294 | CA | ARG | 1622 | 15.082 | 4.608 | 4.140 | 1.00 | 25.05 |
| ATOM 1295 | CB | ARG | 1622 | 14.268 | 5.766 | 3.540 | 1.00 | 20.89 |
| ATOM 1296 | CG | ARG | 1622 | 13.709 | 5.444 | 2.175 | 1.00 | 19.03 |
| ATOM 1297 | CD | ARG | 1622 | 13.089 | 6.656 | 1.488 | 0.50 | 14.06 |
| ATOM 1298 | NE | ARG | 1622 | 12.684 | 6.300 | 0.131 | 0.50 | 11.96 |
| ATOM 1300 | CZ | ARG | 1622 | 11.606 | 5.577 | −0.166 | 0.50 | 11.83 |
| ATOM 1301 | NH1 | ARG | 1622 | 10.801 | 5.137 | 0.797 | 0.50 | 10.20 |
| ATOM 1304 | NH2 | ARG | 1622 | 11.366 | 5.239 | −1.425 | 0.50 | 8.63 |
| ATOM 1307 | C | ARG | 1622 | 15.877 | 5.058 | 5.379 | 1.00 | 24.37 |
| ATOM 1308 | O | ARG | 1622 | 16.787 | 5.863 | 5.268 | 1.00 | 25.17 |
| ATOM 1309 | N | ASP | 1623 | 15.555 | 4.527 | 6.552 | 1.00 | 24.61 |
| ATOM 1311 | CA | ASP | 1623 | 16.315 | 4.899 | 7.748 | 1.00 | 28.82 |
| ATOM 1312 | CB | ASP | 1623 | 15.777 | 6.173 | 8.410 | 1.00 | 32.33 |
| ATOM 1313 | CG | ASP | 1623 | 16.733 | 6.735 | 9.469 | 1.00 | 36.67 |
| ATOM 1314 | OD1 | ASP | 1623 | 16.276 | 7.520 | 10.321 | 1.00 | 43.56 |
| ATOM 1315 | OD2 | ASP | 1623 | 17.937 | 6.385 | 9.463 | 1.00 | 36.29 |
| ATOM 1316 | C | ASP | 1623 | 16.408 | 3.766 | 8.766 | 1.00 | 28.22 |
| ATOM 1317 | O | ASP | 1623 | 16.118 | 3.937 | 9.956 | 1.00 | 26.87 |
| ATOM 1318 | N | LEU | 1624 | 16.783 | 2.592 | 8.278 | 1.00 | 26.34 |
| ATOM 1320 | CA | LEU | 1624 | 16.941 | 1.428 | 9.132 | 1.00 | 26.59 |
| ATOM 1321 | CB | LEU | 1624 | 16.996 | 0.168 | 8.265 | 1.00 | 24.59 |
| ATOM 1322 | CG | LEU | 1624 | 17.082 | −1.175 | 8.978 | 1.00 | 24.72 |
| ATOM 1323 | CD1 | LEU | 1624 | 15.844 | −1.408 | 9.856 | 1.00 | 24.35 |
| ATOM 1324 | CD2 | LEU | 1624 | 17.258 | −2.261 | 7.931 | 1.00 | 24.63 |
| ATOM 1325 | C | LEU | 1624 | 18.210 | 1.595 | 10.004 | 1.00 | 26.87 |
| ATOM 1326 | O | LEU | 1624 | 19.322 | 1.777 | 9.497 | 1.00 | 28.19 |
| ATOM 1327 | N | ALA | 1625 | 18.009 | 1.570 | 11.317 | 1.00 | 27.77 |
| ATOM 1329 | CA | ALA | 1625 | 19.069 | 1.741 | 12.309 | 1.00 | 24.54 |
| ATOM 1330 | CB | ALA | 1625 | 19.355 | 3.210 | 12.494 | 1.00 | 19.81 |
| ATOM 1331 | C | ALA | 1625 | 18.498 | 1.173 | 13.592 | 1.00 | 26.44 |
| ATOM 1332 | O | ALA | 1625 | 17.289 | 0.961 | 13.679 | 1.00 | 27.58 |
| ATOM 1333 | N | ALA | 1626 | 19.342 | 0.940 | 14.594 | 1.00 | 25.38 |
| ATOM 1335 | CA | ALA | 1626 | 18.872 | 0.397 | 15.865 | 1.00 | 24.65 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1336 | CB | ALA | 1626 | 20.054 | 0.023 | 16.774 | 1.00 | 23.35 |
| ATOM 1337 | C | ALA | 1626 | 17.929 | 1.373 | 16.578 | 1.00 | 25.54 |
| ATOM 1338 | O | ALA | 1626 | 17.057 | 0.951 | 17.325 | 1.00 | 27.70 |
| ATOM 1339 | N | ARG | 1627 | 18.104 | 2.671 | 16.344 | 1.00 | 25.06 |
| ATOM 1341 | CA | ARG | 1627 | 17.242 | 3.675 | 16.959 | 1.00 | 25.48 |
| ATOM 1342 | CB | ARG | 1627 | 17.706 | 5.089 | 16.597 | 1.00 | 28.15 |
| ATOM 1343 | CG | ARG | 1627 | 17.759 | 5.370 | 15.084 | 1.00 | 33.13 |
| ATOM 1344 | CD | ARG | 1627 | 18.157 | 6.811 | 14.774 | 1.00 | 33.29 |
| ATOM 1345 | NE | ARG | 1627 | 18.442 | 7.011 | 13.351 | 1.00 | 35.74 |
| ATOM 1347 | CZ | ARG | 1627 | 19.652 | 6.889 | 12.813 | 1.00 | 37.40 |
| ATOM 1348 | NH1 | ARG | 1627 | 20.695 | 6.585 | 13.575 | 1.00 | 39.73 |
| ATOM 1351 | NH2 | ARG | 1627 | 19.817 | 7.012 | 11.507 | 1.00 | 36.90 |
| ATOM 1354 | C | ARG | 1627 | 15.812 | 3.491 | 16.479 | 1.00 | 24.81 |
| ATOM 1355 | O | ARG | 1627 | 14.871 | 3.853 | 17.173 | 1.00 | 24.05 |
| ATOM 1356 | N | ASN | 1628 | 15.667 | 2.910 | 15.293 | 1.00 | 24.80 |
| ATOM 1358 | CA | ASN | 1628 | 14.368 | 2.686 | 14.685 | 1.00 | 25.97 |
| ATOM 1359 | CB | ASN | 1628 | 14.383 | 3.132 | 13.225 | 1.00 | 30.08 |
| ATOM 1360 | CG | ASN | 1628 | 14.417 | 4.640 | 13.096 | 1.00 | 33.62 |
| ATOM 1361 | OD1 | ASN | 1628 | 13.775 | 5.347 | 13.864 | 1.00 | 35.11 |
| ATOM 1362 | ND2 | ASN | 1628 | 15.212 | 5.141 | 12.169 | 1.00 | 36.31 |
| ATOM 1365 | C | ASN | 1628 | 13.802 | 1.288 | 14.824 | 1.00 | 26.03 |
| ATOM 1366 | O | ASN | 1628 | 12.951 | 0.869 | 14.031 | 1.00 | 26.87 |
| ATOM 1367 | N | VAL | 1629 | 14.330 | 0.550 | 15.797 | 1.00 | 26.04 |
| ATOM 1369 | CA | VAL | 1629 | 13.854 | −0.783 | 16.128 | 1.00 | 25.09 |
| ATOM 1370 | CB | VAL | 1629 | 14.924 | −1.876 | 15.959 | 1.00 | 27.00 |
| ATOM 1371 | CG1 | VAL | 1629 | 14.390 | −3.197 | 16.546 | 1.00 | 20.99 |
| ATOM 1372 | CG2 | VAL | 1629 | 15.295 | −2.051 | 14.462 | 1.00 | 23.26 |
| ATOM 1373 | C | VAL | 1629 | 13.504 | −0.671 | 17.600 | 1.00 | 27.59 |
| ATOM 1374 | O | VAL | 1629 | 14.340 | −0.285 | 18.418 | 1.00 | 25.81 |
| ATOM 1375 | N | LEU | 1630 | 12.245 | −0.929 | 17.923 | 1.00 | 28.17 |
| ATOM 1377 | CA | LEU | 1630 | 11.768 | −0.845 | 19.296 | 1.00 | 30.20 |
| ATOM 1378 | CB | LEU | 1630 | 10.445 | −0.077 | 19.332 | 1.00 | 30.26 |
| ATOM 1379 | CG | LEU | 1630 | 10.484 | 1.285 | 18.626 | 1.00 | 29.81 |
| ATOM 1380 | CD1 | LEU | 1630 | 9.119 | 1.983 | 18.745 | 1.00 | 28.46 |
| ATOM 1381 | CD2 | LEU | 1630 | 11.576 | 2.141 | 19.233 | 1.00 | 28.37 |
| ATOM 1382 | C | LEU | 1630 | 11.639 | −2.242 | 19.904 | 1.00 | 29.32 |
| ATOM 1383 | O | LEU | 1630 | 11.414 | −3.219 | 19.189 | 1.00 | 30.84 |
| ATOM 1384 | N | VAL | 1631 | 11.800 | −2.342 | 21.221 | 1.00 | 28.90 |
| ATOM 1386 | CA | VAL | 1631 | 11.732 | −3.629 | 21.905 | 1.00 | 26.84 |
| ATOM 1387 | CB | VAL | 1631 | 13.067 | −3.919 | 22.670 | 1.00 | 28.88 |
| ATOM 1388 | CG1 | VAL | 1631 | 13.077 | −5.341 | 23.236 | 1.00 | 21.54 |
| ATOM 1389 | CG2 | VAL | 1631 | 14.259 | −3.699 | 21.744 | 1.00 | 24.30 |
| ATOM 1390 | C | VAL | 1631 | 10.561 | −3.645 | 22.881 | 1.00 | 29.02 |
| ATOM 1391 | O | VAL | 1631 | 10.406 | −2.737 | 23.706 | 1.00 | 29.31 |
| ATOM 1392 | N | THR | 1632 | 9.733 | −4.674 | 22.764 | 1.00 | 30.84 |
| ATOM 1394 | CA | THR | 1632 | 8.562 | −4.830 | 23.616 | 1.00 | 32.24 |
| ATOM 1395 | CB | THR | 1632 | 7.488 | −5.685 | 22.912 | 1.00 | 31.45 |
| ATOM 1396 | OG1 | THR | 1632 | 7.896 | −7.064 | 22.910 | 1.00 | 30.86 |
| ATOM 1398 | CG2 | THR | 1632 | 7.268 | −5.194 | 21.470 | 1.00 | 28.04 |
| ATOM 1399 | C | THR | 1632 | 8.919 | −5.493 | 24.943 | 1.00 | 34.17 |
| ATOM 1400 | O | THR | 1632 | 10.017 | −6.019 | 25.105 | 1.00 | 35.02 |
| ATOM 1401 | N | GLU | 1633 | 7.959 | −5.524 | 25.866 | 1.00 | 36.16 |
| ATOM 1403 | CA | GLU | 1633 | 8.155 | −6.138 | 27.177 | 1.00 | 36.34 |
| ATOM 1404 | CB | GLU | 1633 | 6.865 | −6.063 | 27.996 | 1.00 | 37.07 |
| ATOM 1405 | CG | GLU | 1633 | 6.957 | −6.649 | 29.414 | 1.00 | 44.57 |
| ATOM 1406 | CD | GLU | 1633 | 8.035 | −6.000 | 30.301 | 1.00 | 49.38 |
| ATOM 1407 | OE1 | GLU | 1633 | 8.124 | −4.753 | 30.352 | 1.00 | 51.03 |
| ATOM 1408 | OE2 | GLU | 1633 | 8.788 | −6.750 | 30.968 | 1.00 | 51.63 |
| ATOM 1409 | C | GLU | 1633 | 8.600 | −7.585 | 27.042 | 1.00 | 36.42 |
| ATOM 1410 | O | GLU | 1633 | 9.347 | −8.085 | 27.874 | 1.00 | 38.56 |
| ATOM 1411 | N | ASP | 1634 | 8.185 | −8.240 | 25.964 | 1.00 | 37.70 |
| ATOM 1413 | CA | ASP | 1634 | 8.550 | −9.637 | 25.737 | 1.00 | 38.53 |
| ATOM 1414 | CB | ASP | 1634 | 7.408 | −10.378 | 25.027 | 1.00 | 44.08 |
| ATOM 1415 | CG | ASP | 1634 | 6.041 | −10.106 | 25.657 | 1.00 | 51.60 |
| ATOM 1416 | OD1 | ASP | 1634 | 5.865 | −10.367 | 26.867 | 1.00 | 52.37 |
| ATOM 1417 | OD2 | ASP | 1634 | 5.137 | −9.631 | 24.933 | 1.00 | 57.23 |
| ATOM 1418 | C | ASP | 1634 | 9.826 | −9.776 | 24.905 | 1.00 | 36.56 |
| ATOM 1419 | O | ASP | 1634 | 10.127 | −10.865 | 24.430 | 1.00 | 36.74 |
| ATOM 1420 | N | ASN | 1635 | 10.569 | −8.683 | 24.739 | 1.00 | 36.56 |
| ATOM 1422 | CA | ASN | 1635 | 11.819 | −8.662 | 23.945 | 1.00 | 37.10 |
| ATOM 1423 | CB | ASN | 1635 | 12.888 | −9.587 | 24.548 | 1.00 | 36.92 |
| ATOM 1424 | CG | ASN | 1635 | 13.226 | −9.226 | 25.978 | 1.00 | 36.54 |
| ATOM 1425 | OD1 | ASN | 1635 | 13.275 | −8.058 | 26.340 | 1.00 | 38.84 |
| ATOM 1426 | ND2 | ASN | 1635 | 13.423 | −10.235 | 26.806 | 1.00 | 39.58 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1429 | C | ASN | 1635 | 11.632 | −8.980 | 22.451 | 1.00 | 34.78 |
| ATOM 1430 | O | ASN | 1635 | 12.446 | −9.677 | 21.834 | 1.00 | 34.00 |
| ATOM 1431 | N | VAL | 1636 | 10.533 | −8.498 | 21.880 | 1.00 | 31.35 |
| ATOM 1433 | CA | VAL | 1636 | 10.279 | −8.711 | 20.469 | 1.00 | 29.76 |
| ATOM 1434 | CB | VAL | 1636 | 8.778 | −8.946 | 20.181 | 1.00 | 30.60 |
| ATOM 1435 | CG1 | VAL | 1636 | 8.538 | −9.081 | 18.675 | 1.00 | 30.38 |
| ATOM 1436 | CG2 | VAL | 1636 | 8.315 | −10.209 | 20.897 | 1.00 | 28.51 |
| ATOM 1437 | C | VAL | 1636 | 10.768 | −7.449 | 19.781 | 1.00 | 28.02 |
| ATOM 1438 | O | VAL | 1636 | 10.506 | −6.351 | 20.254 | 1.00 | 25.87 |
| ATOM 1439 | N | MET | 1637 | 11.575 | −7.624 | 18.738 | 1.00 | 28.15 |
| ATOM 1440 | CA | MET | 1637 | 12.119 | −6.508 | 17.980 | 1.00 | 26.01 |
| ATOM 1442 | CB | MET | 1637 | 13.366 | −6.953 | 17.204 | 1.00 | 27.82 |
| ATOM 1443 | CG | MET | 1637 | 14.479 | −7.554 | 18.051 | 1.00 | 29.73 |
| ATOM 1444 | SD | MET | 1637 | 15.124 | −6.410 | 19.288 | 1.00 | 29.96 |
| ATOM 1445 | CE | MET | 1637 | 15.120 | −7.459 | 20.689 | 1.00 | 27.19 |
| ATOM 1446 | C | MET | 1637 | 11.040 | −6.087 | 16.993 | 1.00 | 24.77 |
| ATOM 1447 | O | MET | 1637 | 10.480 | −6.929 | 16.303 | 1.00 | 24.50 |
| ATOM 1448 | N | LYS | 1638 | 10.755 | −4.791 | 16.931 | 1.00 | 25.74 |
| ATOM 1450 | CA | LYS | 1638 | 9.746 | −4.258 | 16.029 | 1.00 | 23.67 |
| ATOM 1451 | CB | LYS | 1638 | 8.486 | −3.888 | 16.799 | 1.00 | 21.78 |
| ATOM 1452 | CG | LYS | 1638 | 7.715 | −5.092 | 17.298 | 1.00 | 24.60 |
| ATOM 1453 | CD | LYS | 1638 | 6.406 | −4.683 | 18.005 | 1.00 | 23.87 |
| ATOM 1454 | CE | LYS | 1638 | 5.486 | −5.897 | 18.256 | 1.00 | 23.06 |
| ATOM 1455 | NZ | LYS | 1638 | 4.871 | −6.398 | 16.976 | 1.00 | 24.60 |
| ATOM 1459 | C | LYS | 1638 | 10.260 | −3.042 | 15.293 | 1.00 | 24.37 |
| ATOM 1460 | O | LYS | 1638 | 10.658 | −2.055 | 15.901 | 1.00 | 26.58 |
| ATOM 1461 | N | ILE | 1639 | 10.271 | −3.119 | 13.971 | 1.00 | 25.69 |
| ATOM 1463 | CA | ILE | 1639 | 10.721 | −2.005 | 13.148 | 1.00 | 25.94 |
| ATOM 1464 | CB | ILE | 1639 | 10.935 | −2.447 | 11.668 | 1.00 | 26.49 |
| ATOM 1465 | CG2 | ILE | 1639 | 11.218 | −1.236 | 10.762 | 1.00 | 21.19 |
| ATOM 1466 | CG1 | ILE | 1639 | 12.103 | −3.433 | 11.604 | 1.00 | 27.58 |
| ATOM 1467 | CD1 | ILE | 1639 | 12.120 | −4.232 | 10.355 | 1.00 | 32.96 |
| ATOM 1468 | C | ILE | 1639 | 9.675 | −0.892 | 13.242 | 1.00 | 27.32 |
| ATOM 1469 | O | ILE | 1639 | 8.466 | −1.133 | 13.103 | 1.00 | 25.45 |
| ATOM 1470 | N | ALA | 1640 | 10.156 | 0.320 | 13.498 | 1.00 | 27.43 |
| ATOM 1472 | CA | ALA | 1640 | 9.321 | 1.499 | 13.632 | 1.00 | 26.96 |
| ATOM 1473 | CB | ALA | 1640 | 9.557 | 2.133 | 15.006 | 1.00 | 25.21 |
| ATOM 1474 | C | ALA | 1640 | 9.641 | 2.510 | 12.538 | 1.00 | 26.80 |
| ATOM 1475 | O | ALA | 1640 | 10.691 | 2.446 | 11.896 | 1.00 | 27.55 |
| ATOM 1476 | N | ASP | 1641 | 8.716 | 3.440 | 12.328 | 1.00 | 27.06 |
| ATOM 1478 | CA | ASP | 1641 | 8.862 | 4.526 | 11.349 | 1.00 | 30.54 |
| ATOM 1479 | CB | ASP | 1641 | 9.993 | 5.484 | 11.753 | 1.00 | 33.12 |
| ATOM 1480 | CG | ASP | 1641 | 9.668 | 6.310 | 12.999 | 1.00 | 36.17 |
| ATOM 1481 | OD1 | ASP | 1641 | 10.477 | 7.203 | 13.334 | 1.00 | 42.24 |
| ATOM 1482 | OD2 | ASP | 1641 | 8.633 | 6.076 | 13.648 | 1.00 | 33.22 |
| ATOM 1483 | C | ASP | 1641 | 9.049 | 4.107 | 9.898 | 1.00 | 29.94 |
| ATOM 1484 | O | ASP | 1641 | 9.598 | 4.861 | 9.102 | 1.00 | 30.13 |
| ATOM 1485 | N | PHE | 1642 | 8.569 | 2.920 | 9.553 | 1.00 | 30.22 |
| ATOM 1487 | CA | PHE | 1642 | 8.680 | 2.426 | 8.191 | 1.00 | 30.91 |
| ATOM 1488 | CB | PHE | 1642 | 8.462 | 0.909 | 8.159 | 1.00 | 26.24 |
| ATOM 1489 | CG | PHE | 1642 | 7.156 | 0.470 | 8.750 | 1.00 | 27.82 |
| ATOM 1490 | CD1 | PHE | 1642 | 5.986 | 0.495 | 7.988 | 1.00 | 27.08 |
| ATOM 1491 | CD2 | PHE | 1642 | 7.089 | 0.026 | 10.066 | 1.00 | 26.70 |
| ATOM 1492 | CE1 | PHE | 1642 | 4.761 | 0.088 | 8.532 | 1.00 | 25.18 |
| ATOM 1493 | CE2 | PHE | 1642 | 5.872 | −0.383 | 10.624 | 1.00 | 27.59 |
| ATOM 1494 | CZ | PHE | 1642 | 4.705 | −0.354 | 9.855 | 1.00 | 28.05 |
| ATOM 1495 | C | PHE | 1642 | 7.729 | 3.139 | 7.219 | 1.00 | 33.35 |
| ATOM 1496 | O | PHE | 1642 | 7.983 | 3.165 | 6.018 | 1.00 | 36.19 |
| ATOM 1497 | N | GLY | 1643 | 6.661 | 3.746 | 7.736 | 1.00 | 32.76 |
| ATOM 1499 | CA | GLY | 1643 | 5.710 | 4.419 | 6.863 | 1.00 | 31.44 |
| ATOM 1500 | C | GLY | 1643 | 5.805 | 5.927 | 6.910 | 1.00 | 32.94 |
| ATOM 1501 | O | GLY | 1643 | 4.945 | 6.636 | 6.399 | 1.00 | 33.10 |
| ATOM 1502 | N | LEU | 1644 | 6.872 | 6.407 | 7.525 | 1.00 | 35.45 |
| ATOM 1504 | CA | LEU | 1644 | 7.124 | 7.828 | 7.684 | 1.00 | 39.04 |
| ATOM 1505 | CB | LEU | 1644 | 8.387 | 8.011 | 8.514 | 1.00 | 37.80 |
| ATOM 1506 | CG | LEU | 1644 | 8.414 | 9.120 | 9.549 | 1.00 | 42.51 |
| ATOM 1507 | CD1 | LEU | 1644 | 7.301 | 8.887 | 10.563 | 1.00 | 44.08 |
| ATOM 1508 | CD2 | LEU | 1644 | 9.779 | 9.127 | 10.243 | 1.00 | 44.47 |
| ATOM 1509 | C | LEU | 1644 | 7.259 | 8.580 | 6.357 | 1.00 | 42.20 |
| ATOM 1510 | O | LEU | 1644 | 7.895 | 8.107 | 5.414 | 1.00 | 44.14 |
| ATOM 1511 | N | ALA | 1645 | 6.607 | 9.732 | 6.267 | 1.00 | 43.89 |
| ATOM 1513 | CA | ALA | 1645 | 6.677 | 10.569 | 5.082 | 1.00 | 45.62 |
| ATOM 1514 | CB | ALA | 1645 | 5.463 | 11.493 | 5.028 | 1.00 | 45.06 |
| ATOM 1515 | C | ALA | 1645 | 7.966 | 11.388 | 5.186 | 1.00 | 45.82 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1516 | O | ALA | 1645 | 8.240 | 11.994 | 6.228 | 1.00 | 45.85 |
| ATOM 1517 | N | ARG | 1646 | 8.766 | 11.389 | 4.129 | 1.00 | 45.16 |
| ATOM 1519 | CA | ARG | 1646 | 10.015 | 12.140 | 4.138 | 1.00 | 47.06 |
| ATOM 1520 | CB | ARG | 1646 | 11.126 | 11.318 | 4.794 | 1.00 | 48.00 |
| ATOM 1521 | C | ARG | 1646 | 10.445 | 12.546 | 2.742 | 1.00 | 46.83 |
| ATOM 1522 | O | ARG | 1646 | 10.429 | 11.729 | 1.823 | 1.00 | 45.76 |
| ATOM 1523 | N | ASP | 1647 | 10.807 | 13.814 | 2.578 | 1.00 | 48.96 |
| ATOM 1525 | CA | ASP | 1647 | 11.278 | 14.291 | 1.288 | 1.00 | 50.93 |
| ATOM 1526 | CB | ASP | 1647 | 10.938 | 15.769 | 1.073 | 1.00 | 52.33 |
| ATOM 1527 | CG | ASP | 1647 | 11.191 | 16.228 | −0.360 | 1.00 | 55.93 |
| ATOM 1528 | OD1 | ASP | 1647 | 12.231 | 15.850 | −0.956 | 1.00 | 52.58 |
| ATOM 1529 | OD2 | ASP | 1647 | 10.340 | 16.980 | −0.896 | 1.00 | 59.54 |
| ATOM 1530 | C | ASP | 1647 | 12.789 | 14.104 | 1.336 | 1.00 | 50.78 |
| ATOM 1531 | O | ASP | 1647 | 13.491 | 14.803 | 2.077 | 1.00 | 48.32 |
| ATOM 1532 | N | ILE | 1648 | 13.274 | 13.144 | 0.556 | 1.00 | 50.84 |
| ATOM 1534 | CA | ILE | 1648 | 14.696 | 12.833 | 0.516 | 1.00 | 52.58 |
| ATOM 1535 | CB | ILE | 1648 | 14.984 | 11.571 | −0.324 | 1.00 | 50.85 |
| ATOM 1536 | CG2 | ILE | 1648 | 14.204 | 10.386 | 0.241 | 1.00 | 49.34 |
| ATOM 1537 | CG1 | ILE | 1648 | 14.638 | 11.813 | −1.801 | 1.00 | 48.22 |
| ATOM 1538 | CD1 | ILE | 1648 | 15.233 | 10.806 | −2.754 | 1.00 | 42.86 |
| ATOM 1539 | C | ILE | 1648 | 15.523 | 13.999 | −0.018 | 1.00 | 55.57 |
| ATOM 1540 | O | ILE | 1648 | 16.648 | 14.222 | 0.423 | 1.00 | 57.24 |
| ATOM 1541 | N | HIS | 1649 | 14.944 | 14.766 | −0.936 | 1.00 | 56.80 |
| ATOM 1543 | CA | HIS | 1649 | 15.650 | 15.895 | −1.520 | 1.00 | 58.03 |
| ATOM 1544 | CB | HIS | 1649 | 15.013 | 16.302 | −2.859 | 1.00 | 58.71 |
| ATOM 1545 | CG | HIS | 1649 | 15.221 | 15.308 | −3.958 | 1.00 | 60.28 |
| ATOM 1546 | CD2 | HIS | 1649 | 16.303 | 14.566 | −4.306 | 1.00 | 60.74 |
| ATOM 1547 | ND1 | HIS | 1649 | 14.241 | 14.986 | −4.874 | 1.00 | 61.70 |
| ATOM 1549 | CE1 | HIS | 1649 | 14.708 | 14.104 | −5.742 | 1.00 | 61.86 |
| ATOM 1550 | NE2 | HIS | 1649 | 15.959 | 13.833 | −5.417 | 1.00 | 60.98 |
| ATOM 1552 | C | HIS | 1649 | 15.721 | 17.093 | −0.591 | 1.00 | 58.49 |
| ATOM 1553 | O | HIS | 1649 | 16.129 | 18.175 | −1.004 | 1.00 | 60.56 |
| ATOM 1554 | N | HIS | 1650 | 15.285 | 16.916 | 0.654 | 1.00 | 59.58 |
| ATOM 1556 | CA | HIS | 1650 | 15.306 | 18.001 | 1.635 | 1.00 | 61.38 |
| ATOM 1557 | CB | HIS | 1650 | 13.898 | 18.540 | 1.863 | 1.00 | 65.28 |
| ATOM 1558 | CG | HIS | 1650 | 13.404 | 19.433 | 0.738 | 1.00 | 72.62 |
| ATOM 1559 | CD2 | HIS | 1650 | 13.492 | 20.752 | 0.536 | 1.00 | 76.23 |
| ATOM 1560 | ND1 | HIS | 1650 | 12.710 | 18.904 | −0.339 | 1.00 | 77.05 |
| ATOM 1562 | CE1 | HIS | 1650 | 12.402 | 19.907 | −1.157 | 1.00 | 78.51 |
| ATOM 1563 | NE2 | HIS | 1650 | 12.863 | 21.015 | −0.647 | 1.00 | 78.82 |
| ATOM 1565 | C | HIS | 1650 | 15.925 | 17.575 | 2.972 | 1.00 | 60.63 |
| ATOM 1566 | O | HIS | 1650 | 15.796 | 18.271 | 3.969 | 1.00 | 60.20 |
| ATOM 1567 | N | ILE | 1651 | 16.584 | 16.419 | 2.987 | 1.00 | 60.22 |
| ATOM 1569 | CA | ILE | 1651 | 17.197 | 15.920 | 4.204 | 1.00 | 60.03 |
| ATOM 1570 | CB | ILE | 1651 | 17.574 | 14.434 | 4.069 | 1.00 | 62.54 |
| ATOM 1571 | CG2 | ILE | 1651 | 18.280 | 13.920 | 5.323 | 1.00 | 63.48 |
| ATOM 1572 | CG1 | ILE | 1651 | 16.329 | 13.584 | 3.800 | 1.00 | 65.18 |
| ATOM 1573 | CD1 | ILE | 1651 | 16.635 | 12.124 | 3.603 | 1.00 | 67.18 |
| ATOM 1574 | C | ILE | 1651 | 18.457 | 16.698 | 4.557 | 1.00 | 59.16 |
| ATOM 1575 | O | ILE | 1651 | 19.326 | 16.907 | 3.716 | 1.00 | 59.25 |
| ATOM 1576 | N | ASP | 1652 | 18.532 | 17.176 | 5.793 | 1.00 | 58.91 |
| ATOM 1578 | CA | ASP | 1652 | 19.702 | 17.915 | 6.260 | 1.00 | 58.25 |
| ATOM 1579 | CB | ASP | 1652 | 19.312 | 18.788 | 7.444 | 1.00 | 61.14 |
| ATOM 1580 | CG | ASP | 1652 | 20.506 | 19.569 | 8.028 | 1.00 | 65.33 |
| ATOM 1581 | OD1 | ASP | 1652 | 21.614 | 19.574 | 7.411 | 1.00 | 67.11 |
| ATOM 1582 | OD2 | ASP | 1652 | 20.337 | 20.191 | 9.126 | 1.00 | 69.04 |
| ATOM 1583 | C | ASP | 1652 | 20.786 | 16.922 | 6.676 | 1.00 | 56.75 |
| ATOM 1584 | O | ASP | 1652 | 20.699 | 16.307 | 7.741 | 1.00 | 56.06 |
| ATOM 1585 | N | TYR | 1653 | 21.794 | 16.762 | 5.826 | 1.00 | 55.40 |
| ATOM 1587 | CA | TYR | 1653 | 22.900 | 15.849 | 6.088 | 1.00 | 54.50 |
| ATOM 1588 | CB | TYR | 1653 | 23.825 | 15.783 | 4.872 | 1.00 | 52.80 |
| ATOM 1589 | CG | TYR | 1653 | 23.334 | 14.854 | 3.796 | 1.00 | 52.10 |
| ATOM 1590 | CD1 | TYR | 1653 | 24.123 | 14.566 | 2.685 | 1.00 | 51.50 |
| ATOM 1591 | CE1 | TYR | 1653 | 23.701 | 13.658 | 1.724 | 1.00 | 53.52 |
| ATOM 1592 | CD2 | TYR | 1653 | 22.099 | 14.214 | 3.917 | 1.00 | 52.88 |
| ATOM 1593 | CE2 | TYR | 1653 | 21.664 | 13.302 | 2.966 | 1.00 | 54.63 |
| ATOM 1594 | CZ | TYR | 1653 | 22.469 | 13.025 | 1.870 | 1.00 | 54.35 |
| ATOM 1595 | OH | TYR | 1653 | 22.049 | 12.107 | 0.933 | 1.00 | 53.23 |
| ATOM 1597 | C | TYR | 1653 | 23.717 | 16.158 | 7.339 | 1.00 | 55.40 |
| ATOM 1598 | O | TYR | 1653 | 24.381 | 15.284 | 7.900 | 1.00 | 54.47 |
| ATOM 1599 | N | TYR | 1654 | 23.673 | 17.409 | 7.773 | 1.00 | 56.72 |
| ATOM 1601 | CA | TYR | 1654 | 24.421 | 17.826 | 8.947 | 1.00 | 58.87 |
| ATOM 1602 | CB | TYR | 1654 | 24.978 | 19.235 | 8.733 | 1.00 | 57.91 |
| ATOM 1603 | CG | TYR | 1654 | 26.068 | 19.269 | 7.685 | 1.00 | 60.49 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1604 | CD1 | TYR | 1654 | 25.760 | 19.301 | 6.325 | 1.00 | 61.37 |
| ATOM 1605 | CE1 | TYR | 1654 | 26.769 | 19.289 | 5.356 | 1.00 | 63.72 |
| ATOM 1606 | CD2 | TYR | 1654 | 27.412 | 19.227 | 8.053 | 1.00 | 61.74 |
| ATOM 1607 | CE2 | TYR | 1654 | 28.425 | 19.216 | 7.099 | 1.00 | 64.08 |
| ATOM 1608 | CZ | TYR | 1654 | 28.102 | 19.248 | 5.753 | 1.00 | 65.12 |
| ATOM 1609 | OH | TYR | 1654 | 29.117 | 19.248 | 4.817 | 1.00 | 64.17 |
| ATOM 1611 | C | TYR | 1654 | 23.628 | 17.732 | 10.245 | 1.00 | 60.17 |
| ATOM 1612 | O | TYR | 1654 | 24.173 | 17.935 | 11.335 | 1.00 | 61.09 |
| ATOM 1613 | N | LYS | 1655 | 22.348 | 17.393 | 10.133 | 1.00 | 60.54 |
| ATOM 1615 | CA | LYS | 1655 | 21.493 | 17.277 | 11.306 | 1.00 | 62.12 |
| ATOM 1616 | CB | LYS | 1655 | 20.019 | 17.382 | 10.910 | 1.00 | 64.32 |
| ATOM 1617 | CG | LYS | 1655 | 19.054 | 17.346 | 12.079 | 1.00 | 67.17 |
| ATOM 1618 | CD | LYS | 1655 | 17.644 | 17.608 | 11.602 | 1.00 | 73.05 |
| ATOM 1619 | CE | LYS | 1655 | 16.626 | 17.243 | 12.660 | 1.00 | 77.36 |
| ATOM 1620 | NZ | LYS | 1655 | 15.230 | 17.494 | 12.186 | 1.00 | 81.10 |
| ATOM 1624 | C | LYS | 1655 | 21.754 | 15.976 | 12.057 | 1.00 | 62.19 |
| ATOM 1625 | O | LYS | 1655 | 21.902 | 14.907 | 11.454 | 1.00 | 61.36 |
| ATOM 1626 | N | LYS | 1656 | 21.822 | 16.084 | 13.380 | 1.00 | 62.26 |
| ATOM 1628 | CA | LYS | 1656 | 22.069 | 14.933 | 14.236 | 1.00 | 62.28 |
| ATOM 1629 | CB | LYS | 1656 | 23.027 | 15.310 | 15.372 | 1.00 | 62.05 |
| ATOM 1630 | CG | LYS | 1656 | 24.474 | 15.489 | 14.957 | 1.00 | 62.62 |
| ATOM 1631 | CD | LYS | 1656 | 25.320 | 15.889 | 16.157 | 1.00 | 66.45 |
| ATOM 1632 | CE | LYS | 1656 | 26.803 | 15.666 | 15.908 | 1.00 | 67.28 |
| ATOM 1633 | NZ | LYS | 1656 | 27.619 | 16.007 | 17.109 | 1.00 | 68.45 |
| ATOM 1637 | C | LYS | 1656 | 20.774 | 14.381 | 14.824 | 1.00 | 61.86 |
| ATOM 1638 | O | LYS | 1656 | 19.714 | 15.007 | 14.733 | 1.00 | 62.95 |
| ATOM 1639 | N | THR | 1657 | 20.875 | 13.198 | 15.420 | 1.00 | 60.10 |
| ATOM 1641 | CA | THR | 1657 | 19.743 | 12.541 | 16.053 | 1.00 | 57.73 |
| ATOM 1642 | CB | THR | 1657 | 19.973 | 11.012 | 16.121 | 1.00 | 56.04 |
| ATOM 1643 | CG1 | THR | 1657 | 21.150 | 10.730 | 16.896 | 1.00 | 55.21 |
| ATOM 1645 | CG2 | THR | 1657 | 20.152 | 10.431 | 14.731 | 1.00 | 53.07 |
| ATOM 1646 | C | THR | 1657 | 19.664 | 13.102 | 17.472 | 1.00 | 57.74 |
| ATOM 1647 | O | THR | 1657 | 20.513 | 13.899 | 17.870 | 1.00 | 57.76 |
| ATOM 1648 | N | THR | 1658 | 18.678 | 12.667 | 18.249 | 1.00 | 58.80 |
| ATOM 1650 | CA | THR | 1658 | 18.548 | 13.140 | 19.627 | 1.00 | 60.33 |
| ATOM 1651 | CB | THR | 1658 | 17.318 | 12.517 | 20.290 | 1.00 | 61.37 |
| ATOM 1652 | C | THR | 1658 | 19.811 | 12.779 | 20.406 | 1.00 | 60.43 |
| ATOM 1653 | O | THR | 1658 | 20.350 | 13.599 | 21.155 | 1.00 | 60.59 |
| ATOM 1654 | N | ASN | 1659 | 20.311 | 11.567 | 20.161 | 1.00 | 59.97 |
| ATOM 1656 | CA | ASN | 1659 | 21.508 | 11.058 | 20.827 | 1.00 | 58.28 |
| ATOM 1657 | CB | ASN | 1659 | 21.607 | 9.545 | 20.645 | 1.00 | 59.95 |
| ATOM 1658 | CG | ASN | 1659 | 22.444 | 8.883 | 21.723 | 1.00 | 60.10 |
| ATOM 1659 | OD1 | ASN | 1659 | 22.382 | 9.265 | 22.891 | 1.00 | 61.26 |
| ATOM 1660 | ND2 | ASN | 1659 | 23.210 | 7.867 | 21.341 | 1.00 | 57.09 |
| ATOM 1663 | C | ASN | 1659 | 22.781 | 11.717 | 20.311 | 1.00 | 57.13 |
| ATOM 1664 | O | ASN | 1659 | 23.868 | 11.418 | 20.793 | 1.00 | 57.34 |
| ATOM 1665 | N | GLY | 1660 | 22.643 | 12.570 | 19.299 | 1.00 | 56.48 |
| ATOM 1667 | CA | GLY | 1660 | 23.781 | 13.276 | 18.733 | 1.00 | 54.87 |
| ATOM 1668 | C | GLY | 1660 | 24.539 | 12.570 | 17.623 | 1.00 | 53.04 |
| ATOM 1669 | O | GLY | 1660 | 25.716 | 12.855 | 17.394 | 1.00 | 54.11 |
| ATOM 1670 | N | ARG | 1661 | 23.879 | 11.659 | 16.918 | 1.00 | 51.37 |
| ATOM 1672 | CA | ARG | 1661 | 24.536 | 10.930 | 15.833 | 1.00 | 48.96 |
| ATOM 1673 | CB | ARG | 1661 | 24.283 | 9.428 | 15.961 | 1.00 | 48.48 |
| ATOM 1674 | CG | ARG | 1661 | 24.848 | 8.796 | 17.215 | 1.00 | 50.03 |
| ATOM 1675 | CD | ARG | 1661 | 24.492 | 7.325 | 17.234 | 1.00 | 50.78 |
| ATOM 1676 | NE | ARG | 1661 | 25.013 | 6.614 | 18.396 | 1.00 | 50.11 |
| ATOM 1678 | CZ | ARG | 1661 | 24.902 | 5.299 | 18.566 | 1.00 | 50.08 |
| ATOM 1679 | NH1 | ARG | 1661 | 24.286 | 4.560 | 17.645 | 1.00 | 46.57 |
| ATOM 1682 | NH2 | ARG | 1661 | 25.426 | 4.717 | 19.643 | 1.00 | 47.88 |
| ATOM 1685 | C | ARG | 1661 | 24.076 | 11.422 | 14.459 | 1.00 | 46.53 |
| ATOM 1686 | O | ARG | 1661 | 23.031 | 12.029 | 14.325 | 1.00 | 45.01 |
| ATOM 1687 | N | LEU | 1662 | 24.839 | 11.094 | 13.432 | 1.00 | 42.39 |
| ATOM 1689 | CA | LEU | 1662 | 24.546 | 11.503 | 12.076 | 1.00 | 40.71 |
| ATOM 1690 | CB | LEU | 1662 | 25.823 | 12.031 | 11.399 | 1.00 | 40.25 |
| ATOM 1691 | CG | LEU | 1662 | 26.408 | 13.332 | 11.965 | 1.00 | 42.44 |
| ATOM 1692 | CD1 | LEU | 1662 | 27.853 | 13.478 | 11.537 | 1.00 | 40.42 |
| ATOM 1693 | CD2 | LEU | 1662 | 25.591 | 14.536 | 11.514 | 1.00 | 41.16 |
| ATOM 1694 | C | LEU | 1662 | 23.946 | 10.362 | 11.258 | 1.00 | 38.45 |
| ATOM 1695 | O | LEU | 1662 | 24.647 | 9.436 | 10.862 | 1.00 | 36.67 |
| ATOM 1696 | N | PRO | 1663 | 22.632 | 10.428 | 10.987 | 1.00 | 37.09 |
| ATOM 1697 | CD | PRO | 1663 | 21.717 | 11.475 | 11.489 | 1.00 | 38.18 |
| ATOM 1698 | CA | PRO | 1663 | 21.894 | 9.424 | 10.207 | 1.00 | 35.59 |
| ATOM 1699 | CB | PRO | 1663 | 20.535 | 10.098 | 9.983 | 1.00 | 35.90 |
| ATOM 1700 | CG | PRO | 1663 | 20.343 | 10.856 | 11.258 | 1.00 | 39.13 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1701 | C | PRO | 1663 | 22.556 | 9.045 | 8.876 | 1.00 | 33.05 |
| ATOM 1702 | O | PRO | 1663 | 22.362 | 7.933 | 8.378 | 1.00 | 31.16 |
| ATOM 1703 | N | VAL | 1664 | 23.333 | 9.960 | 8.299 | 1.00 | 32.07 |
| ATOM 1705 | CA | VAL | 1664 | 24.020 | 9.669 | 7.034 | 1.00 | 32.49 |
| ATOM 1706 | CB | VAL | 1664 | 24.831 | 10.886 | 6.477 | 1.00 | 32.68 |
| ATOM 1707 | CG1 | VAL | 1664 | 23.898 | 11.906 | 5.864 | 1.00 | 32.25 |
| ATOM 1708 | CG2 | VAL | 1664 | 25.670 | 11.523 | 7.571 | 1.00 | 33.22 |
| ATOM 1709 | C | VAL | 1664 | 24.957 | 8.469 | 7.171 | 1.00 | 29.57 |
| ATOM 1710 | O | VAL | 1664 | 25.328 | 7.864 | 6.175 | 1.00 | 27.39 |
| ATOM 1711 | N | LYS | 1665 | 25.303 | 8.116 | 8.409 | 1.00 | 28.82 |
| ATOM 1713 | CA | LYS | 1665 | 26.189 | 6.991 | 8.673 | 1.00 | 27.87 |
| ATOM 1714 | CB | LYS | 1665 | 26.815 | 7.100 | 10.065 | 1.00 | 26.99 |
| ATOM 1715 | CG | LYS | 1665 | 27.967 | 8.089 | 10.079 | 1.00 | 29.23 |
| ATOM 1716 | CD | LYS | 1665 | 28.283 | 8.619 | 11.466 | 1.00 | 30.64 |
| ATOM 1717 | CE | LYS | 1665 | 29.543 | 9.478 | 11.426 | 1.00 | 30.94 |
| ATOM 1718 | NZ | LYS | 1665 | 29.826 | 10.128 | 12.737 | 1.00 | 31.63 |
| ATOM 1722 | C | LYS | 1665 | 25.546 | 5.637 | 8.465 | 1.00 | 26.76 |
| ATOM 1723 | O | LYS | 1665 | 26.211 | 4.615 | 8.589 | 1.00 | 26.78 |
| ATOM 1724 | N | TRP | 1666 | 24.260 | 5.630 | 8.137 | 1.00 | 25.79 |
| ATOM 1726 | CA | TRP | 1666 | 23.561 | 4.381 | 7.865 | 1.00 | 26.56 |
| ATOM 1727 | CB | TRP | 1666 | 22.299 | 4.273 | 8.724 | 1.00 | 25.63 |
| ATOM 1728 | CG | TRP | 1666 | 22.564 | 3.872 | 10.174 | 1.00 | 26.95 |
| ATOM 1729 | CD2 | TRP | 1666 | 23.052 | 4.717 | 11.232 | 1.00 | 24.83 |
| ATOM 1730 | CE2 | TRP | 1666 | 23.134 | 3.920 | 12.398 | 1.00 | 24.49 |
| ATOM 1731 | CE3 | TRP | 1666 | 23.433 | 6.062 | 11.306 | 1.00 | 24.54 |
| ATOM 1732 | CD1 | TRP | 1666 | 22.376 | 2.636 | 10.730 | 1.00 | 20.10 |
| ATOM 1733 | NE1 | TRP | 1666 | 22.716 | 2.660 | 12.063 | 1.00 | 21.86 |
| ATOM 1734 | CZ2 | TRP | 1666 | 23.575 | 4.433 | 13.627 | 1.00 | 25.71 |
| ATOM 1736 | CZ3 | TRP | 1666 | 23.870 | 6.569 | 12.523 | 1.00 | 26.00 |
| ATOM 1737 | CH2 | TRP | 1666 | 23.939 | 5.754 | 13.665 | 1.00 | 26.04 |
| ATOM 1738 | C | TRP | 1666 | 23.188 | 4.263 | 6.386 | 1.00 | 23.62 |
| ATOM 1739 | O | TRP | 1666 | 22.754 | 3.214 | 5.931 | 1.00 | 24.87 |
| ATOM 1740 | N | MET | 1667 | 23.404 | 5.330 | 5.631 | 1.00 | 22.78 |
| ATOM 1742 | CA | MET | 1667 | 23.046 | 5.361 | 4.215 | 1.00 | 23.73 |
| ATOM 1743 | CB | MET | 1667 | 22.894 | 6.802 | 3.744 | 1.00 | 26.24 |
| ATOM 1744 | CG | MET | 1667 | 21.823 | 7.621 | 4.434 | 1.00 | 35.55 |
| ATOM 1745 | SD | MET | 1667 | 21.795 | 9.276 | 3.706 | 1.00 | 42.23 |
| ATOM 1746 | CE | MET | 1667 | 21.019 | 8.904 | 2.238 | 1.00 | 40.57 |
| ATOM 1747 | C | MET | 1667 | 23.991 | 4.693 | 3.239 | 1.00 | 22.77 |
| ATOM 1748 | O | MET | 1667 | 25.205 | 4.894 | 3.294 | 1.00 | 24.25 |
| ATOM 1749 | N | ALA | 1668 | 23.420 | 3.963 | 2.286 | 1.00 | 22.73 |
| ATOM 1751 | CA | ALA | 1668 | 24.217 | 3.337 | 1.237 | 1.00 | 23.54 |
| ATOM 1752 | CB | ALA | 1668 | 23.339 | 2.495 | 0.340 | 1.00 | 21.80 |
| ATOM 1753 | C | ALA | 1668 | 24.805 | 4.495 | 0.430 | 1.00 | 25.53 |
| ATOM 1754 | O | ALA | 1668 | 24.181 | 5.551 | 0.316 | 1.00 | 23.66 |
| ATOM 1755 | N | PRO | 1669 | 26.006 | 4.314 | −0.153 | 1.00 | 26.86 |
| ATOM 1756 | CD | PRO | 1669 | 26.899 | 3.144 | −0.095 | 1.00 | 26.35 |
| ATOM 1757 | CA | PRO | 1669 | 26.611 | 5.390 | −0.942 | 1.00 | 27.78 |
| ATOM 1758 | CB | PRO | 1669 | 27.864 | 4.731 | −1.518 | 1.00 | 25.51 |
| ATOM 1759 | CG | PRO | 1669 | 28.225 | 3.741 | −0.471 | 1.00 | 25.36 |
| ATOM 1760 | C | PRO | 1669 | 25.686 | 5.900 | −2.057 | 1.00 | 26.47 |
| ATOM 1761 | O | PRO | 1669 | 25.617 | 7.099 | −2.288 | 1.00 | 28.42 |
| ATOM 1762 | N | GLU | 1670 | 24.951 | 5.010 | −2.724 | 1.00 | 26.88 |
| ATOM 1764 | CA | GLU | 1670 | 24.057 | 5.459 | −3.796 | 1.00 | 29.03 |
| ATOM 1765 | CB | GLU | 1670 | 23.597 | 4.293 | −4.693 | 1.00 | 31.79 |
| ATOM 1766 | CG | GLU | 1670 | 22.588 | 3.325 | −4.065 | 1.00 | 32.47 |
| ATOM 1767 | CD | GLU | 1670 | 23.212 | 2.184 | −3.255 | 1.00 | 32.43 |
| ATOM 1768 | OE1 | GLU | 1670 | 22.429 | 1.297 | −2.822 | 1.00 | 25.01 |
| ATOM 1769 | OE2 | GLU | 1670 | 24.458 | 2.157 | −3.069 | 1.00 | 28.75 |
| ATOM 1770 | C | GLU | 1670 | 22.864 | 6.274 | −3.294 | 1.00 | 28.37 |
| ATOM 1771 | O | GLU | 1670 | 22.358 | 7.146 | −4.001 | 1.00 | 25.72 |
| ATOM 1772 | N | ALA | 1671 | 22.451 | 6.028 | −2.053 | 1.00 | 30.08 |
| ATOM 1774 | CA | ALA | 1671 | 21.347 | 6.779 | −1.465 | 1.00 | 31.24 |
| ATOM 1775 | CB | ALA | 1671 | 20.751 | 6.031 | −0.287 | 1.00 | 26.42 |
| ATOM 1776 | C | ALA | 1671 | 21.899 | 8.125 | −1.013 | 1.00 | 31.36 |
| ATOM 1777 | O | ALA | 1671 | 21.298 | 9.167 | −1.249 | 1.00 | 33.11 |
| ATOM 1778 | N | LEU | 1672 | 23.068 | 8.096 | −0.387 | 1.00 | 32.73 |
| ATOM 1780 | CA | LEU | 1672 | 23.715 | 9.304 | 0.100 | 1.00 | 33.96 |
| ATOM 1781 | CB | LEU | 1672 | 24.931 | 8.935 | 0.940 | 1.00 | 33.89 |
| ATOM 1782 | CG | LEU | 1672 | 25.783 | 10.071 | 1.502 | 1.00 | 37.62 |
| ATOM 1783 | CD1 | LEU | 1672 | 25.010 | 10.800 | 2.581 | 1.00 | 39.57 |
| ATOM 1784 | CD2 | LEU | 1672 | 27.054 | 9.491 | 2.087 | 1.00 | 32.30 |
| ATOM 1785 | C | LEU | 1672 | 24.157 | 10.207 | −1.042 | 1.00 | 36.83 |
| ATOM 1786 | O | LEU | 1672 | 23.769 | 11.369 | −1.102 | 1.00 | 37.87 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1787 | N | PHE | 1673 | 24.959 | 9.669 | −1.954 | 1.00 | 35.82 |
| ATOM 1789 | CA | PHE | 1673 | 25.466 | 10.449 | −3.071 | 1.00 | 35.82 |
| ATOM 1790 | CB | PHE | 1673 | 26.738 | 9.802 | −3.639 | 1.00 | 34.66 |
| ATOM 1791 | CG | PHE | 1673 | 27.850 | 9.642 | −2.634 | 1.00 | 33.84 |
| ATOM 1792 | CD1 | PHE | 1673 | 28.503 | 8.422 | −2.494 | 1.00 | 32.65 |
| ATOM 1793 | CD2 | PHE | 1673 | 28.242 | 10.709 | −1.827 | 1.00 | 36.98 |
| ATOM 1794 | CE1 | PHE | 1673 | 29.540 | 8.257 | −1.555 | 1.00 | 37.95 |
| ATOM 1795 | CE2 | PHE | 1673 | 29.279 | 10.557 | −0.881 | 1.00 | 39.90 |
| ATOM 1796 | CZ | PHE | 1673 | 29.927 | 9.325 | −0.748 | 1.00 | 37.09 |
| ATOM 1797 | C | PHE | 1673 | 24.483 | 10.692 | −4.210 | 1.00 | 36.34 |
| ATOM 1798 | O | PHE | 1673 | 24.430 | 11.788 | −4.754 | 1.00 | 37.18 |
| ATOM 1799 | N | ASP | 1674 | 23.705 | 9.677 | −4.568 | 1.00 | 38.22 |
| ATOM 1801 | CA | ASP | 1674 | 22.780 | 9.777 | −5.693 | 1.00 | 38.51 |
| ATOM 1802 | CB | ASP | 1674 | 23.008 | 8.597 | −6.633 | 1.00 | 40.34 |
| ATOM 1803 | CG | ASP | 1674 | 24.439 | 8.511 | −7.122 | 1.00 | 43.87 |
| ATOM 1804 | OD1 | ASP | 1674 | 25.092 | 9.571 | −7.254 | 1.00 | 42.79 |
| ATOM 1805 | OD2 | ASP | 1674 | 24.906 | 7.376 | −7.369 | 1.00 | 47.94 |
| ATOM 1806 | C | ASP | 1674 | 21.298 | 9.853 | −5.360 | 1.00 | 40.21 |
| ATOM 1807 | O | ASP | 1674 | 20.457 | 9.872 | −6.271 | 1.00 | 39.07 |
| ATOM 1808 | N | ARG | 1675 | 20.975 | 9.836 | −4.072 | 1.00 | 39.83 |
| ATOM 1810 | CA | ARG | 1675 | 19.589 | 9.900 | −3.631 | 1.00 | 42.25 |
| ATOM 1811 | CB | ARG | 1675 | 18.992 | 11.271 | −3.964 | 1.00 | 48.19 |
| ATOM 1812 | CG | ARG | 1675 | 19.691 | 12.420 | −3.267 | 1.00 | 59.20 |
| ATOM 1813 | CD | ARG | 1675 | 19.462 | 13.729 | −4.019 | 1.00 | 67.81 |
| ATOM 1814 | NE | ARG | 1675 | 20.079 | 14.876 | −3.352 | 1.00 | 75.11 |
| ATOM 1816 | CZ | ARG | 1675 | 19.688 | 16.136 | −3.525 | 1.00 | 78.74 |
| ATOM 1817 | NH1 | ARG | 1675 | 18.680 | 16.429 | −4.341 | 1.00 | 79.91 |
| ATOM 1820 | NH2 | ARG | 1675 | 20.311 | 17.115 | −2.890 | 1.00 | 81.24 |
| ATOM 1823 | C | ARG | 1675 | 18.730 | 8.777 | −4.221 | 1.00 | 39.00 |
| ATOM 1824 | O | ARG | 1675 | 17.544 | 8.956 | −4.488 | 1.00 | 39.71 |
| ATOM 1825 | N | ILE | 1676 | 19.345 | 7.624 | −4.434 | 1.00 | 35.50 |
| ATOM 1827 | CA | ILE | 1676 | 18.636 | 6.471 | −4.958 | 1.00 | 33.51 |
| ATOM 1828 | CB | ILE | 1676 | 19.434 | 5.759 | −6.039 | 1.00 | 34.59 |
| ATOM 1829 | CG2 | ILE | 1676 | 18.582 | 4.678 | −6.649 | 1.00 | 33.90 |
| ATOM 1830 | CG1 | ILE | 1676 | 19.848 | 6.752 | −7.120 | 1.00 | 37.60 |
| ATOM 1831 | CD1 | ILE | 1676 | 20.861 | 6.197 | −8.109 | 1.00 | 42.67 |
| ATOM 1832 | C | ILE | 1676 | 18.390 | 5.501 | −3.809 | 1.00 | 30.94 |
| ATOM 1833 | O | ILE | 1676 | 19.326 | 4.926 | −3.252 | 1.00 | 28.62 |
| ATOM 1834 | N | TYR | 1677 | 17.124 | 5.351 | −3.443 | 1.00 | 30.60 |
| ATOM 1836 | CA | TYR | 1677 | 16.724 | 4.467 | −2.359 | 1.00 | 25.87 |
| ATOM 1837 | CB | TYR | 1677 | 15.781 | 5.197 | −1.413 | 1.00 | 26.40 |
| ATOM 1838 | CG | TYR | 1677 | 16.483 | 6.220 | −0.555 | 1.00 | 27.67 |
| ATOM 1839 | CD1 | TYR | 1677 | 16.663 | 7.533 | −0.999 | 1.00 | 27.45 |
| ATOM 1840 | CE1 | TYR | 1677 | 17.269 | 8.483 | −0.191 | 1.00 | 26.55 |
| ATOM 1841 | CD2 | TYR | 1677 | 16.935 | 5.883 | 0.721 | 1.00 | 24.58 |
| ATOM 1842 | CE2 | TYR | 1677 | 17.536 | 6.828 | 1.538 | 1.00 | 26.35 |
| ATOM 1843 | CZ | TYR | 1677 | 17.698 | 8.122 | 1.080 | 1.00 | 28.80 |
| ATOM 1844 | OH | TYR | 1677 | 18.270 | 9.059 | 1.914 | 1.00 | 34.97 |
| ATOM 1846 | C | TYR | 1677 | 16.055 | 3.235 | −2.911 | 1.00 | 22.70 |
| ATOM 1847 | O | TYR | 1677 | 15.144 | 3.335 | −3.728 | 1.00 | 26.22 |
| ATOM 1848 | N | THR | 1678 | 16.477 | 2.076 | −2.420 | 1.00 | 21.83 |
| ATOM 1850 | CA | THR | 1678 | 15.968 | 0.791 | −2.865 | 1.00 | 22.14 |
| ATOM 1851 | CB | THR | 1678 | 16.907 | 0.191 | −3.928 | 1.00 | 23.91 |
| ATOM 1852 | OG1 | THR | 1678 | 18.229 | 0.105 | −3.373 | 1.00 | 27.47 |
| ATOM 1854 | CG2 | THR | 1678 | 16.949 | 1.053 | −5.188 | 1.00 | 24.94 |
| ATOM 1855 | C | THR | 1678 | 15.999 | −0.176 | −1.692 | 1.00 | 22.79 |
| ATOM 1856 | O | THR | 1678 | 16.427 | 0.170 | −0.592 | 1.00 | 23.39 |
| ATOM 1857 | N | HIS | 1679 | 15.563 | −1.402 | −1.929 | 1.00 | 21.98 |
| ATOM 1859 | CA | HIS | 1679 | 15.613 | −2.417 | −0.888 | 1.00 | 22.97 |
| ATOM 1860 | CB | HIS | 1679 | 14.872 | −3.671 | −1.351 | 1.00 | 22.04 |
| ATOM 1861 | CG | HIS | 1679 | 13.421 | −3.444 | −1.621 | 1.00 | 25.41 |
| ATOM 1862 | CD2 | HIS | 1679 | 12.674 | −3.611 | −2.740 | 1.00 | 26.60 |
| ATOM 1863 | ND1 | HIS | 1679 | 12.556 | −2.954 | −0.663 | 1.00 | 26.13 |
| ATOM 1865 | CE1 | HIS | 1679 | 11.348 | −2.830 | −1.178 | 1.00 | 28.66 |
| ATOM 1866 | NE2 | HIS | 1679 | 11.394 | −3.221 | −2.441 | 1.00 | 29.66 |
| ATOM 1868 | C | HIS | 1679 | 17.097 | −2.719 | −0.650 | 1.00 | 23.14 |
| ATOM 1869 | O | HIS | 1679 | 17.511 | −3.074 | 0.459 | 1.00 | 21.69 |
| ATOM 1870 | N | GLN | 1680 | 17.895 | −2.506 | −1.697 | 1.00 | 22.38 |
| ATOM 1872 | CA | GLN | 1680 | 19.335 | −2.726 | −1.658 | 1.00 | 22.33 |
| ATOM 1873 | CB | GLN | 1680 | 19.948 | −2.594 | −3.058 | 1.00 | 22.52 |
| ATOM 1874 | CG | GLN | 1680 | 19.895 | −3.872 | −3.879 | 1.00 | 29.15 |
| ATOM 1875 | CD | GLN | 1680 | 18.865 | −3.847 | −4.991 | 1.00 | 33.60 |
| ATOM 1876 | OE1 | GLN | 1680 | 17.819 | −3.212 | −4.871 | 1.00 | 38.43 |
| ATOM 1877 | NE2 | GLN | 1680 | 19.159 | −4.542 | −6.085 | 1.00 | 33.44 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1880 | C | GLN | 1680 | 20.007 | −1.740 | −0.732 | 1.00 | 22.61 |
| ATOM 1881 | O | GLN | 1680 | 20.943 | −2.093 | −0.027 | 1.00 | 22.00 |
| ATOM 1882 | N | SER | 1681 | 19.562 | −0.490 | −0.745 | 1.00 | 22.06 |
| ATOM 1884 | CA | SER | 1681 | 20.184 | 0.479 | 0.137 | 1.00 | 23.41 |
| ATOM 1885 | CB | SER | 1681 | 19.886 | 1.923 | −0.306 | 1.00 | 20.06 |
| ATOM 1886 | OG | SER | 1681 | 18.503 | 2.166 | −0.479 | 1.00 | 22.90 |
| ATOM 1888 | C | SER | 1681 | 19.778 | 0.206 | 1.583 | 1.00 | 23.08 |
| ATOM 1889 | O | SER | 1681 | 20.528 | 0.531 | 2.506 | 1.00 | 24.13 |
| ATOM 1890 | N | ASP | 1682 | 18.608 | −0.412 | 1.770 | 1.00 | 23.19 |
| ATOM 1892 | CA | ASP | 1682 | 18.107 | −0.775 | 3.104 | 1.00 | 22.37 |
| ATOM 1893 | CB | ASP | 1682 | 16.660 | −1.275 | 3.018 | 1.00 | 24.55 |
| ATOM 1894 | CG | ASP | 1682 | 15.616 | −0.172 | 3.222 | 1.00 | 24.22 |
| ATOM 1895 | OD1 | ASP | 1682 | 14.428 | −0.479 | 3.005 | 1.00 | 25.02 |
| ATOM 1896 | OD2 | ASP | 1682 | 15.949 | 0.968 | 3.625 | 1.00 | 24.82 |
| ATOM 1897 | C | ASP | 1682 | 18.980 | −1.888 | 3.690 | 1.00 | 20.47 |
| ATOM 1898 | O | ASP | 1682 | 19.172 | −1.984 | 4.906 | 1.00 | 21.83 |
| ATOM 1899 | N | VAL | 1683 | 19.480 | −2.746 | 2.806 | 1.00 | 20.14 |
| ATOM 1901 | CA | VAL | 1683 | 20.340 | −3.856 | 3.179 | 1.00 | 20.49 |
| ATOM 1902 | CB | VAL | 1683 | 20.493 | −4.842 | 2.003 | 1.00 | 22.38 |
| ATOM 1903 | CG1 | VAL | 1683 | 21.757 | −5.691 | 2.159 | 1.00 | 19.57 |
| ATOM 1904 | CG2 | VAL | 1683 | 19.264 | −5.740 | 1.942 | 1.00 | 22.35 |
| ATOM 1905 | C | VAL | 1683 | 21.677 | −3.315 | 3.683 | 1.00 | 20.22 |
| ATOM 1906 | O | VAL | 1683 | 22.202 | −3.789 | 4.684 | 1.00 | 21.41 |
| ATOM 1907 | N | TRP | 1684 | 22.210 | −2.311 | 3.003 | 1.00 | 21.33 |
| ATOM 1909 | CA | TRP | 1684 | 23.440 | −1.666 | 3.449 | 1.00 | 22.21 |
| ATOM 1910 | CB | TRP | 1684 | 23.768 | −0.473 | 2.540 | 1.00 | 18.78 |
| ATOM 1911 | CG | TRP | 1684 | 24.924 | 0.391 | 3.037 | 1.00 | 22.80 |
| ATOM 1912 | CD2 | TRP | 1684 | 26.237 | 0.477 | 2.472 | 1.00 | 24.60 |
| ATOM 1913 | CE2 | TRP | 1684 | 26.989 | 1.364 | 3.286 | 1.00 | 24.34 |
| ATOM 1914 | CE3 | TRP | 1684 | 26.853 | −0.099 | 1.352 | 1.00 | 24.32 |
| ATOM 1915 | CD1 | TRP | 1684 | 24.933 | 1.208 | 4.138 | 1.00 | 22.28 |
| ATOM 1916 | NE1 | TRP | 1684 | 26.169 | 1.791 | 4.297 | 1.00 | 22.32 |
| ATOM 1918 | CZ2 | TRP | 1684 | 28.324 | 1.669 | 3.022 | 1.00 | 24.77 |
| ATOM 1919 | CZ3 | TRP | 1684 | 28.193 | 0.213 | 1.090 | 1.00 | 24.46 |
| ATOM 1920 | CH2 | TRP | 1684 | 28.906 | 1.088 | 1.918 | 1.00 | 24.00 |
| ATOM 1921 | C | TRP | 1684 | 23.198 | −1.183 | 4.899 | 1.00 | 23.26 |
| ATOM 1922 | O | TRP | 1684 | 23.982 | −1.475 | 5.805 | 1.00 | 24.52 |
| ATOM 1923 | N | SER | 1685 | 22.108 | −0.447 | 5.113 | 1.00 | 22.88 |
| ATOM 1925 | CA | SER | 1685 | 21.744 | 0.057 | 6.444 | 1.00 | 24.01 |
| ATOM 1926 | CB | SER | 1685 | 20.398 | 0.783 | 6.385 | 1.00 | 21.90 |
| ATOM 1927 | OG | SER | 1685 | 20.424 | 1.787 | 5.388 | 1.00 | 24.75 |
| ATOM 1929 | C | SER | 1685 | 21.659 | −1.087 | 7.464 | 1.00 | 24.28 |
| ATOM 1930 | O | SER | 1685 | 22.077 | −0.933 | 8.625 | 1.00 | 23.94 |
| ATOM 1931 | N | PHE | 1686 | 21.099 | −2.221 | 7.037 | 1.00 | 23.20 |
| ATOM 1933 | CA | PHE | 1686 | 20.993 | −3.393 | 7.898 | 1.00 | 23.87 |
| ATOM 1934 | CB | PHE | 1686 | 20.216 | −4.519 | 7.216 | 1.00 | 19.56 |
| ATOM 1935 | CG | PHE | 1686 | 20.062 | −5.734 | 8.075 | 1.00 | 22.19 |
| ATOM 1936 | CD1 | PHE | 1686 | 19.240 | −5.701 | 9.203 | 1.00 | 21.55 |
| ATOM 1937 | CD2 | PHE | 1686 | 20.773 | −6.899 | 7.793 | 1.00 | 21.94 |
| ATOM 1938 | CE1 | PHE | 1686 | 19.125 | −6.801 | 10.033 | 1.00 | 21.66 |
| ATOM 1939 | CE2 | PHE | 1686 | 20.663 | −8.012 | 8.623 | 1.00 | 22.47 |
| ATOM 1940 | CZ | PHE | 1686 | 19.842 | −7.961 | 9.743 | 1.00 | 23.14 |
| ATOM 1941 | C | PHE | 1686 | 22.389 | −3.890 | 8.300 | 1.00 | 22.62 |
| ATOM 1942 | O | PHE | 1686 | 22.579 | −4.424 | 9.407 | 1.00 | 23.09 |
| ATOM 1943 | N | GLY | 1687 | 23.354 | −3.726 | 7.401 | 1.00 | 23.50 |
| ATOM 1945 | CA | GLY | 1687 | 24.718 | −4.110 | 7.721 | 1.00 | 23.83 |
| ATOM 1946 | C | GLY | 1687 | 25.230 | −3.247 | 8.867 | 1.00 | 21.95 |
| ATOM 1947 | O | GLY | 1687 | 25.901 | −3.749 | 9.778 | 1.00 | 23.76 |
| ATOM 1948 | N | VAL | 1688 | 24.928 | −1.947 | 8.817 | 1.00 | 20.60 |
| ATOM 1950 | CA | VAL | 1688 | 25.331 | −1.009 | 9.877 | 1.00 | 22.34 |
| ATOM 1951 | CB | VAL | 1688 | 25.020 | 0.481 | 9.488 | 1.00 | 20.94 |
| ATOM 1952 | CG1 | VAL | 1688 | 25.547 | 1.438 | 10.543 | 1.00 | 21.65 |
| ATOM 1953 | CG2 | VAL | 1688 | 25.675 | 0.832 | 8.160 | 1.00 | 22.71 |
| ATOM 1954 | C | VAL | 1688 | 24.598 | −1.400 | 11.182 | 1.00 | 22.71 |
| ATOM 1955 | O | VAL | 1688 | 25.199 | −1.479 | 12.255 | 1.00 | 22.78 |
| ATOM 1956 | N | LEU | 1689 | 23.310 | −1.706 | 11.082 | 1.00 | 22.81 |
| ATOM 1958 | CA | LEU | 1689 | 22.534 | −2.111 | 12.253 | 1.00 | 25.21 |
| ATOM 1959 | CB | LEU | 1689 | 21.064 | −2.357 | 11.866 | 1.00 | 25.78 |
| ATOM 1960 | CG | LEU | 1689 | 20.006 | −2.491 | 12.976 | 1.00 | 29.18 |
| ATOM 1961 | CD1 | LEU | 1689 | 18.643 | −2.109 | 12.408 | 1.00 | 28.57 |
| ATOM 1962 | CD2 | LEU | 1689 | 19.959 | −3.895 | 13.553 | 1.00 | 26.77 |
| ATOM 1963 | C | LEU | 1689 | 23.158 | −3.375 | 12.871 | 1.00 | 25.88 |
| ATOM 1964 | O | LEU | 1689 | 23.249 | −3.483 | 14.099 | 1.00 | 26.50 |
| ATOM 1965 | N | LEU | 1690 | 23.588 | −4.323 | 12.031 | 1.00 | 25.84 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 1967 | CA | LEU | 1690 | 24.221 | −5.544 | 12.523 | 1.00 | 24.43 |
| ATOM 1968 | CB | LEU | 1690 | 24.669 | −6.444 | 11.377 | 1.00 | 26.35 |
| ATOM 1969 | CG | LEU | 1690 | 23.672 | −7.309 | 10.604 | 1.00 | 26.57 |
| ATOM 1970 | CD1 | LEU | 1690 | 24.415 | −7.962 | 9.446 | 1.00 | 26.33 |
| ATOM 1971 | CD2 | LEU | 1690 | 23.042 | −8.380 | 11.502 | 1.00 | 24.66 |
| ATOM 1972 | C | LEU | 1690 | 25.430 | −5.168 | 13.349 | 1.00 | 25.22 |
| ATOM 1973 | O | LEU | 1690 | 25.646 | −5.706 | 14.435 | 1.00 | 24.84 |
| ATOM 1974 | N | TRP | 1691 | 26.211 | −4.227 | 12.826 | 1.00 | 26.92 |
| ATOM 1976 | CA | TRP | 1691 | 27.405 | −3.728 | 13.504 | 1.00 | 25.77 |
| ATOM 1977 | CB | TRP | 1691 | 28.072 | −2.659 | 12.631 | 1.00 | 24.82 |
| ATOM 1978 | CG | TRP | 1691 | 29.394 | −2.195 | 13.154 | 1.00 | 27.98 |
| ATOM 1979 | CD2 | TRP | 1691 | 29.623 | −1.104 | 14.056 | 1.00 | 26.95 |
| ATOM 1980 | CE2 | TRP | 1691 | 31.022 | −1.015 | 14.259 | 1.00 | 27.64 |
| ATOM 1981 | CE3 | TRP | 1691 | 28.783 | −0.191 | 14.708 | 1.00 | 26.28 |
| ATOM 1982 | CD1 | TRP | 1691 | 30.634 | −2.715 | 12.856 | 1.00 | 28.38 |
| ATOM 1983 | NE1 | TRP | 1691 | 31.609 | −2.009 | 13.518 | 1.00 | 29.56 |
| ATOM 1985 | CZ2 | TRP | 1691 | 31.599 | −0.045 | 15.086 | 1.00 | 27.78 |
| ATOM 1986 | CZ3 | TRP | 1691 | 29.356 | 0.769 | 15.533 | 1.00 | 27.63 |
| ATOM 1987 | CH2 | TRP | 1691 | 30.753 | 0.835 | 15.713 | 1.00 | 30.68 |
| ATOM 1988 | C | TRP | 1691 | 27.025 | −3.147 | 14.876 | 1.00 | 26.38 |
| ATOM 1989 | O | TRP | 1691 | 27.686 | −3.414 | 15.883 | 1.00 | 24.82 |
| ATOM 1990 | N | GLU | 1692 | 25.926 | −2.393 | 14.916 | 1.00 | 27.62 |
| ATOM 1992 | CA | GLU | 1692 | 25.442 | −1.790 | 16.162 | 1.00 | 27.02 |
| ATOM 1993 | CB | GLU | 1692 | 24.193 | −0.963 | 15.919 | 1.00 | 29.27 |
| ATOM 1994 | CG | GLU | 1692 | 24.345 | 0.236 | 15.028 | 1.00 | 24.77 |
| ATOM 1995 | CD | GLU | 1692 | 23.046 | 0.992 | 14.962 | 1.00 | 25.98 |
| ATOM 1996 | OE1 | GLU | 1692 | 22.238 | 0.694 | 14.058 | 1.00 | 22.29 |
| ATOM 1997 | OE2 | GLU | 1692 | 22.803 | 1.837 | 15.850 | 1.00 | 25.12 |
| ATOM 1998 | C | GLU | 1692 | 25.092 | −2.856 | 17.191 | 1.00 | 27.88 |
| ATOM 1999 | O | GLU | 1692 | 25.333 | −2.673 | 18.379 | 1.00 | 30.18 |
| ATOM 2000 | N | ILE | 1693 | 24.500 | −3.956 | 16.734 | 1.00 | 26.65 |
| ATOM 2002 | CA | ILE | 1693 | 24.118 | −5.054 | 17.618 | 1.00 | 26.14 |
| ATOM 2003 | CB | ILE | 1693 | 23.279 | −6.144 | 16.858 | 1.00 | 25.37 |
| ATOM 2004 | CG2 | ILE | 1693 | 23.144 | −7.445 | 17.704 | 1.00 | 21.48 |
| ATOM 2005 | CG1 | ILE | 1693 | 21.897 | −5.563 | 16.496 | 1.00 | 24.80 |
| ATOM 2006 | CD1 | ILE | 1693 | 21.017 | −6.479 | 15.642 | 1.00 | 22.40 |
| ATOM 2007 | C | ILE | 1693 | 25.345 | −5.698 | 18.239 | 1.00 | 27.17 |
| ATOM 2008 | O | ILE | 1693 | 25.424 | −5.864 | 19.452 | 1.00 | 27.30 |
| ATOM 2009 | N | PHE | 1694 | 26.329 | −6.017 | 17.414 | 1.00 | 29.98 |
| ATOM 2011 | CA | PHE | 1694 | 27.518 | −6.674 | 17.925 | 1.00 | 30.61 |
| ATOM 2012 | CB | PHE | 1694 | 28.140 | −7.556 | 16.843 | 1.00 | 28.30 |
| ATOM 2013 | CG | PHE | 1694 | 27.197 | −8.611 | 16.353 | 1.00 | 30.91 |
| ATOM 2014 | CD1 | PHE | 1694 | 26.627 | −8.526 | 15.088 | 1.00 | 34.46 |
| ATOM 2015 | CD2 | PHE | 1694 | 26.743 | −9.601 | 17.224 | 1.00 | 32.71 |
| ATOM 2016 | CE1 | PHE | 1694 | 25.622 | −9.409 | 14.701 | 1.00 | 34.24 |
| ATOM 2017 | CE2 | PHE | 1694 | 25.737 | −10.490 | 16.844 | 1.00 | 32.44 |
| ATOM 2018 | CZ | PHE | 1694 | 25.170 | −10.387 | 15.592 | 1.00 | 32.70 |
| ATOM 2019 | C | PHE | 1694 | 28.512 | −5.796 | 18.689 | 1.00 | 31.74 |
| ATOM 2020 | O | PHE | 1694 | 29.469 | −6.299 | 19.276 | 1.00 | 35.15 |
| ATOM 2021 | N | THR | 1695 | 28.275 | −4.489 | 18.698 | 1.00 | 31.12 |
| ATOM 2023 | CA | THR | 1695 | 29.101 | −3.575 | 19.473 | 1.00 | 29.96 |
| ATOM 2024 | CB | THR | 1695 | 29.532 | −2.351 | 18.657 | 1.00 | 28.09 |
| ATOM 2025 | OG1 | THR | 1695 | 28.373 | −1.685 | 18.150 | 1.00 | 30.65 |
| ATOM 2027 | CG2 | THR | 1695 | 30.450 | −2.767 | 17.510 | 1.00 | 23.37 |
| ATOM 2028 | C | THR | 1695 | 28.240 | −3.128 | 20.664 | 1.00 | 30.01 |
| ATOM 2029 | O | THR | 1695 | 28.617 | −2.233 | 21.427 | 1.00 | 31.14 |
| ATOM 2030 | N | LEU | 1696 | 27.078 | −3.766 | 20.797 | 1.00 | 27.96 |
| ATOM 2032 | CA | LEU | 1696 | 26.113 | −3.490 | 21.862 | 1.00 | 30.25 |
| ATOM 2033 | CB | LEU | 1696 | 26.633 | −3.985 | 23.216 | 1.00 | 33.54 |
| ATOM 2034 | CG | LEU | 1696 | 26.899 | −5.482 | 23.339 | 1.00 | 32.61 |
| ATOM 2035 | CD1 | LEU | 1696 | 27.473 | −5.777 | 24.711 | 1.00 | 33.54 |
| ATOM 2036 | CD2 | LEU | 1696 | 25.602 | −6.233 | 23.126 | 1.00 | 36.37 |
| ATOM 2037 | C | LEU | 1696 | 25.717 | −2.031 | 21.958 | 1.00 | 28.19 |
| ATOM 2038 | O | LEU | 1696 | 25.792 | −1.431 | 23.018 | 1.00 | 29.18 |
| ATOM 2039 | N | GLY | 1697 | 25.251 | −1.472 | 20.853 | 1.00 | 28.24 |
| ATOM 2041 | CA | GLY | 1697 | 24.851 | −0.082 | 20.858 | 1.00 | 28.29 |
| ATOM 2042 | C | GLY | 1697 | 25.990 | 0.845 | 20.499 | 1.00 | 27.68 |
| ATOM 2043 | O | GLY | 1697 | 25.960 | 2.022 | 20.846 | 1.00 | 29.79 |
| ATOM 2044 | N | GLY | 1698 | 26.986 | 0.324 | 19.790 | 1.00 | 29.23 |
| ATOM 2046 | CA | GLY | 1698 | 28.115 | 1.143 | 19.396 | 1.00 | 30.79 |
| ATOM 2047 | C | GLY | 1698 | 27.743 | 2.212 | 18.388 | 1.00 | 32.38 |
| ATOM 2048 | O | GLY | 1698 | 26.817 | 2.044 | 17.601 | 1.00 | 33.26 |
| ATOM 2049 | N | SER | 1699 | 28.480 | 3.314 | 18.411 | 1.00 | 30.81 |
| ATOM 2051 | CA | SER | 1699 | 28.268 | 4.437 | 17.510 | 1.00 | 32.03 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2052 | CB | SER | 1699 | 28.528 | 5.728 | 18.288 | 1.00 | 34.81 |
| ATOM 2053 | OG | SER | 1699 | 28.559 | 6.862 | 17.440 | 1.00 | 40.03 |
| ATOM 2055 | C | SER | 1699 | 29.198 | 4.325 | 16.282 | 1.00 | 32.20 |
| ATOM 2056 | O | SER | 1699 | 30.428 | 4.325 | 16.408 | 1.00 | 31.67 |
| ATOM 2057 | N | PRO | 1700 | 28.620 | 4.148 | 15.082 | 1.00 | 32.62 |
| ATOM 2058 | CD | PRO | 1700 | 27.178 | 4.142 | 14.773 | 1.00 | 34.19 |
| ATOM 2059 | CA | PRO | 1700 | 29.422 | 4.028 | 13.856 | 1.00 | 31.76 |
| ATOM 2060 | CB | PRO | 1700 | 28.357 | 3.830 | 12.759 | 1.00 | 32.04 |
| ATOM 2061 | CG | PRO | 1700 | 27.145 | 3.351 | 13.502 | 1.00 | 33.17 |
| ATOM 2062 | C | PRO | 1700 | 30.214 | 5.309 | 13.609 | 1.00 | 28.70 |
| ATOM 2063 | O | PRO | 1700 | 29.715 | 6.391 | 13.871 | 1.00 | 28.57 |
| ATOM 2064 | N | TYR | 1701 | 31.459 | 5.181 | 13.164 | 1.00 | 28.61 |
| ATOM 2066 | CA | TYR | 1701 | 32.311 | 6.338 | 12.870 | 1.00 | 29.92 |
| ATOM 2067 | CB | TYR | 1701 | 31.920 | 6.946 | 11.510 | 1.00 | 30.15 |
| ATOM 2068 | CG | TYR | 1701 | 31.965 | 5.994 | 10.339 | 1.00 | 36.17 |
| ATOM 2069 | CD1 | TYR | 1701 | 30.799 | 5.630 | 9.664 | 1.00 | 39.26 |
| ATOM 2070 | CE1 | TYR | 1701 | 30.839 | 4.767 | 8.571 | 1.00 | 41.51 |
| ATOM 2071 | CD2 | TYR | 1701 | 33.176 | 5.467 | 9.893 | 1.00 | 37.48 |
| ATOM 2072 | CE2 | TYR | 1701 | 33.229 | 4.607 | 8.805 | 1.00 | 42.94 |
| ATOM 2073 | CZ | TYR | 1701 | 32.059 | 4.263 | 8.146 | 1.00 | 45.72 |
| ATOM 2074 | OH | TYR | 1701 | 32.110 | 3.431 | 7.043 | 1.00 | 53.99 |
| ATOM 2076 | C | TYR | 1701 | 32.279 | 7.448 | 13.941 | 1.00 | 31.09 |
| ATOM 2077 | O | TYR | 1701 | 31.935 | 8.592 | 13.649 | 1.00 | 31.93 |
| ATOM 2078 | N | PRO | 1702 | 32.649 | 7.135 | 15.189 | 1.00 | 34.66 |
| ATOM 2079 | CD | PRO | 1702 | 33.212 | 5.879 | 15.708 | 1.00 | 36.83 |
| ATOM 2080 | CA | PRO | 1702 | 32.631 | 8.173 | 16.231 | 1.00 | 33.54 |
| ATOM 2081 | CB | PRO | 1702 | 33.116 | 7.432 | 17.479 | 1.00 | 32.18 |
| ATOM 2082 | CG | PRO | 1702 | 32.903 | 6.001 | 17.175 | 1.00 | 40.82 |
| ATOM 2083 | C | PRO | 1702 | 33.628 | 9.274 | 15.883 | 1.00 | 34.78 |
| ATOM 2084 | O | PRO | 1702 | 34.750 | 8.981 | 15.455 | 1.00 | 33.97 |
| ATOM 2085 | N | GLY | 1703 | 33.220 | 10.528 | 16.074 | 1.00 | 36.45 |
| ATOM 2087 | CA | GLY | 1703 | 34.085 | 11.667 | 15.788 | 1.00 | 34.40 |
| ATOM 2088 | C | GLY | 1703 | 34.245 | 12.006 | 14.317 | 1.00 | 34.34 |
| ATOM 2089 | O | GLY | 1703 | 34.977 | 12.933 | 13.969 | 1.00 | 34.20 |
| ATOM 2090 | N | VAL | 1704 | 33.552 | 11.275 | 13.445 | 1.00 | 35.02 |
| ATOM 2092 | CA | VAL | 1704 | 33.641 | 11.512 | 12.007 | 1.00 | 32.77 |
| ATOM 2093 | CB | VAL | 1704 | 33.614 | 10.176 | 11.221 | 1.00 | 31.32 |
| ATOM 2094 | CG1 | VAL | 1704 | 33.628 | 10.435 | 9.709 | 1.00 | 31.46 |
| ATOM 2095 | CG2 | VAL | 1704 | 34.796 | 9.297 | 11.637 | 1.00 | 27.62 |
| ATOM 2096 | C | VAL | 1704 | 32.510 | 12.410 | 11.513 | 1.00 | 33.35 |
| ATOM 2097 | O | VAL | 1704 | 31.337 | 12.070 | 11.640 | 1.00 | 33.94 |
| ATOM 2098 | N | PRO | 1705 | 32.849 | 13.589 | 10.974 | 1.00 | 32.43 |
| ATOM 2099 | CD | PRO | 1705 | 34.181 | 14.221 | 10.949 | 1.00 | 32.77 |
| ATOM 2100 | CA | PRO | 1705 | 31.826 | 14.505 | 10.472 | 1.00 | 33.61 |
| ATOM 2101 | CB | PRO | 1705 | 32.545 | 15.853 | 10.509 | 1.00 | 33.21 |
| ATOM 2102 | CG | PRO | 1705 | 33.935 | 15.482 | 10.141 | 1.00 | 35.53 |
| ATOM 2103 | C | PRO | 1705 | 31.395 | 14.138 | 9.052 | 1.00 | 33.91 |
| ATOM 2104 | O | PRO | 1705 | 32.113 | 13.409 | 8.354 | 1.00 | 32.65 |
| ATOM 2105 | N | VAL | 1706 | 30.255 | 14.684 | 8.619 | 1.00 | 33.82 |
| ATOM 2107 | CA | VAL | 1706 | 29.689 | 14.447 | 7.280 | 1.00 | 33.97 |
| ATOM 2108 | CB | VAL | 1706 | 28.617 | 15.513 | 6.943 | 1.00 | 37.41 |
| ATOM 2109 | CG1 | VAL | 1706 | 28.045 | 15.282 | 5.556 | 1.00 | 41.12 |
| ATOM 2110 | CG2 | VAL | 1706 | 27.507 | 15.484 | 7.971 | 1.00 | 38.89 |
| ATOM 2111 | C | VAL | 1706 | 30.712 | 14.428 | 6.135 | 1.00 | 32.32 |
| ATOM 2112 | O | VAL | 1706 | 30.819 | 13.450 | 5.398 | 1.00 | 32.58 |
| ATOM 2113 | N | GLU | 1707 | 31.477 | 15.504 | 6.004 | 1.00 | 31.15 |
| ATOM 2115 | CA | GLU | 1707 | 32.478 | 15.630 | 4.956 | 1.00 | 29.82 |
| ATOM 2116 | CB | GLU | 1707 | 33.172 | 16.989 | 5.048 | 1.00 | 30.05 |
| ATOM 2117 | C | GLU | 1707 | 33.531 | 14.541 | 4.959 | 1.00 | 28.52 |
| ATOM 2118 | O | GLU | 1707 | 33.995 | 14.134 | 3.896 | 1.00 | 30.85 |
| ATOM 2119 | N | GLU | 1708 | 33.958 | 14.110 | 6.143 | 1.00 | 28.70 |
| ATOM 2121 | CA | GLU | 1708 | 34.978 | 13.073 | 6.235 | 1.00 | 29.50 |
| ATOM 2122 | CB | GLU | 1708 | 35.590 | 13.010 | 7.641 | 1.00 | 31.28 |
| ATOM 2123 | CG | GLU | 1708 | 36.281 | 14.289 | 8.103 | 1.00 | 41.63 |
| ATOM 2124 | CD | GLU | 1708 | 37.454 | 14.718 | 7.237 | 1.00 | 49.91 |
| ATOM 2125 | OE1 | GLU | 1708 | 38.020 | 13.876 | 6.498 | 1.00 | 53.57 |
| ATOM 2126 | OE2 | GLU | 1708 | 37.821 | 15.916 | 7.308 | 1.00 | 58.45 |
| ATOM 2127 | C | GLU | 1708 | 34.365 | 11.730 | 5.878 | 1.00 | 30.00 |
| ATOM 2128 | O | GLU | 1708 | 35.016 | 10.874 | 5.257 | 1.00 | 28.43 |
| ATOM 2129 | N | LEU | 1709 | 33.103 | 11.559 | 6.257 | 1.00 | 30.08 |
| ATOM 2131 | CA | LEU | 1709 | 32.392 | 10.324 | 3.964 | 1.00 | 29.19 |
| ATOM 2132 | CB | LEU | 1709 | 30.995 | 10.347 | 6.592 | 1.00 | 28.97 |
| ATOM 2133 | CG | LEU | 1709 | 30.109 | 9.186 | 6.137 | 1.00 | 30.66 |
| ATOM 2134 | CD1 | LEU | 1709 | 30.664 | 7.866 | 6.659 | 1.00 | 29.24 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2135 | CD2 | LEU | 1709 | 28.684 | 9.403 | 6.593 | 1.00 | 29.29 |
| ATOM 2136 | C | LEU | 1709 | 32.294 | 10.130 | 4.449 | 1.00 | 28.26 |
| ATOM 2137 | O | LEU | 1709 | 32.450 | 9.011 | 3.948 | 1.00 | 28.86 |
| ATOM 2138 | N | PHE | 1710 | 32.016 | 11.220 | 3.735 | 1.00 | 26.86 |
| ATOM 2140 | CA | PHE | 1710 | 31.903 | 11.192 | 2.285 | 1.00 | 28.86 |
| ATOM 2141 | CB | PHE | 1710 | 31.632 | 12.593 | 1.743 | 1.00 | 31.88 |
| ATOM 2142 | CG | PHE | 1710 | 30.249 | 13.095 | 2.014 | 1.00 | 37.62 |
| ATOM 2143 | CD1 | PHE | 1710 | 29.265 | 12.247 | 2.509 | 1.00 | 42.63 |
| ATOM 2144 | CD2 | PHE | 1710 | 29.931 | 14.424 | 1.792 | 1.00 | 43.53 |
| ATOM 2145 | CE1 | PHE | 1710 | 27.977 | 12.718 | 2.783 | 1.00 | 45.99 |
| ATOM 2146 | CE2 | PHE | 1710 | 28.648 | 14.905 | 2.061 | 1.00 | 46.25 |
| ATOM 2147 | CZ | PHE | 1710 | 27.670 | 14.045 | 2.559 | 1.00 | 44.45 |
| ATOM 2148 | C | PHE | 1710 | 33.193 | 10.660 | 1.681 | 1.00 | 30.42 |
| ATOM 2149 | O | PHE | 1710 | 33.174 | 9.807 | 0.792 | 1.00 | 29.01 |
| ATOM 2150 | N | LYS | 1711 | 34.309 | 11.152 | 2.212 | 1.00 | 30.64 |
| ATOM 2152 | CA | LYS | 1711 | 35.650 | 10.762 | 1.786 | 1.00 | 32.89 |
| ATOM 2153 | CB | LYS | 1711 | 36.670 | 11.655 | 2.502 | 1.00 | 37.91 |
| ATOM 2154 | CG | LYS | 1711 | 38.108 | 11.479 | 2.088 | 1.00 | 42.99 |
| ATOM 2155 | CD | LYS | 1711 | 38.976 | 12.528 | 2.752 | 1.00 | 47.45 |
| ATOM 2156 | CE | LYS | 1711 | 40.380 | 12.505 | 2.182 | 1.00 | 52.35 |
| ATOM 2157 | NZ | LYS | 1711 | 41.104 | 11.272 | 2.587 | 1.00 | 58.47 |
| ATOM 2161 | C | LYS | 1711 | 35.913 | 9.273 | 2.071 | 1.00 | 32.23 |
| ATOM 2162 | O | LYS | 1711 | 36.445 | 8.559 | 1.216 | 1.00 | 30.79 |
| ATOM 2163 | N | LEU | 1712 | 35.533 | 8.807 | 3.264 | 1.10 | 31.37 |
| ATOM 2165 | CA | LEU | 1712 | 35.704 | 7.399 | 3.630 | 1.00 | 29.46 |
| ATOM 2166 | CB | LEU | 1712 | 35.220 | 7.117 | 5.065 | 1.00 | 28.57 |
| ATOM 2167 | CG | LEU | 1712 | 36.045 | 7.662 | 6.242 | 1.00 | 30.18 |
| ATOM 2168 | CD1 | LEU | 1712 | 35.395 | 7.349 | 7.569 | 1.00 | 26.92 |
| ATOM 2169 | CD2 | LEU | 1712 | 37.452 | 7.083 | 6.210 | 1.00 | 30.88 |
| ATOM 2170 | C | LEU | 1712 | 34.922 | 6.539 | 2.651 | 1.00 | 28.99 |
| ATOM 2171 | O | LEU | 1712 | 35.438 | 5.551 | 2.136 | 1.00 | 30.73 |
| ATOM 2172 | N | LEU | 1713 | 33.675 | 6.915 | 2.388 | 1.00 | 30.13 |
| ATOM 2174 | CA | LEU | 1713 | 32.851 | 6.158 | 1.456 | 1.00 | 32.10 |
| ATOM 2175 | CB | LEU | 1713 | 31.411 | 6.685 | 1.443 | 1.00 | 35.23 |
| ATOM 2176 | CG | LEU | 1713 | 30.612 | 6.292 | 2.691 | 1.00 | 37.47 |
| ATOM 2177 | CD1 | LEU | 1713 | 29.265 | 6.982 | 2.720 | 1.00 | 40.85 |
| ATOM 2178 | CD2 | LEU | 1713 | 30.447 | 4.788 | 2.723 | 1.00 | 39.61 |
| ATOM 2179 | C | LEU | 1713 | 33.441 | 6.147 | 0.047 | 1.00 | 32.70 |
| ATOM 2180 | O | LEU | 1713 | 33.548 | 5.090 | −0.578 | 1.00 | 31.86 |
| ATOM 2181 | N | LYS | 1714 | 33.859 | 7.309 | −0.444 | 1.00 | 32.42 |
| ATOM 2183 | CA | LYS | 1714 | 34.440 | 7.387 | −1.776 | 1.00 | 32.56 |
| ATOM 2184 | CB | LYS | 1714 | 34.826 | 8.824 | −2.112 | 1.00 | 33.02 |
| ATOM 2185 | CG | LYS | 1714 | 33.640 | 9.736 | −2.297 | 1.00 | 35.56 |
| ATOM 2186 | CD | LYS | 1714 | 32.736 | 9.235 | −3.396 | 1.00 | 37.94 |
| ATOM 2187 | CE | LYS | 1714 | 31.635 | 10.246 | −3.682 | 1.00 | 42.57 |
| ATOM 2188 | NZ | LYS | 1714 | 30.727 | 9.805 | −4.779 | 1.00 | 47.40 |
| ATOM 2192 | C | LYS | 1714 | 35.664 | 6.488 | −1.885 | 1.00 | 35.36 |
| ATOM 2193 | O | LYS | 1714 | 35.927 | 5.898 | −2.937 | 1.00 | 36.68 |
| ATOM 2194 | N | GLU | 1715 | 36.376 | 6.338 | −0.775 | 1.00 | 34.51 |
| ATOM 2196 | CA | GLU | 1715 | 37.577 | 5.527 | −0.749 | 1.00 | 35.31 |
| ATOM 2197 | CB | GLU | 1715 | 38.566 | 6.125 | 0.250 | 1.00 | 37.07 |
| ATOM 2198 | CG | GLU | 1715 | 38.967 | 7.537 | −0.163 | 1.00 | 43.62 |
| ATOM 2199 | CD | GLU | 1715 | 39.735 | 8.310 | 0.893 | 1.00 | 49.75 |
| ATOM 2200 | OE1 | GLU | 1715 | 39.906 | 7.814 | 2.029 | 1.00 | 49.71 |
| ATOM 2201 | OE2 | GLU | 1715 | 40.163 | 9.442 | 0.572 | 1.00 | 55.13 |
| ATOM 2202 | C | GLU | 1715 | 37.321 | 4.048 | −0.487 | 1.00 | 34.08 |
| ATOM 2203 | O | GLU | 1715 | 38.259 | 3.260 | −0.438 | 1.00 | 34.82 |
| ATOM 2204 | N | GLY | 1716 | 36.049 | 3.674 | −0.366 | 1.00 | 31.53 |
| ATOM 2206 | CA | GLY | 1716 | 35.695 | 2.288 | −0.133 | 1.00 | 27.58 |
| ATOM 2207 | C | GLY | 1716 | 35.966 | 1.765 | 1.262 | 1.00 | 28.60 |
| ATOM 2208 | O | GLY | 1716 | 36.069 | 0.560 | 1.464 | 1.00 | 27.81 |
| ATOM 2209 | N | HIS | 1717 | 36.062 | 2.663 | 2.236 | 1.00 | 29.10 |
| ATOM 2211 | CA | HIS | 1717 | 36.319 | 2.263 | 3.617 | 1.00 | 29.30 |
| ATOM 2212 | CB | HIS | 1717 | 36.501 | 3.510 | 4.486 | 1.00 | 30.54 |
| ATOM 2213 | CG | HIS | 1717 | 36.788 | 3.213 | 5.930 | 1.00 | 32.88 |
| ATOM 2214 | CD2 | HIS | 1717 | 37.961 | 3.023 | 6.586 | 1.00 | 32.21 |
| ATOM 2215 | ND1 | HIS | 1717 | 35.798 | 3.108 | 6.881 | 1.00 | 34.22 |
| ATOM 2217 | CE1 | HIS | 1717 | 36.342 | 2.865 | 8.061 | 1.00 | 31.51 |
| ATOM 2218 | NE2 | HIS | 1717 | 37.651 | 2.809 | 7.907 | 1.00 | 31.94 |
| ATOM 2220 | C | HIS | 1717 | 35.180 | 1.416 | 4.183 | 1.00 | 28.42 |
| ATOM 2221 | O | HIS | 1717 | 34.017 | 1.666 | 3.885 | 1.00 | 30.71 |
| ATOM 2222 | N | ARG | 1718 | 35.526 | 0.450 | 5.028 | 1.00 | 27.75 |
| ATOM 2224 | CA | ARG | 1718 | 34.559 | −0.423 | 5.688 | 1.00 | 27.58 |
| ATOM 2225 | CB | ARG | 1718 | 34.562 | −1.813 | 5.048 | 1.00 | 29.07 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2226 | CG | ARG | 1718 | 34.078 | −1.860 | 3.597 | 1.00 | 28.39 |
| ATOM 2227 | CD | ARG | 1718 | 32.609 | −1.412 | 3.475 | 1.00 | 27.64 |
| ATOM 2228 | NE | ARG | 1718 | 32.091 | −1.467 | 2.096 | 1.00 | 24.37 |
| ATOM 2230 | CZ | ARG | 1718 | 32.173 | −0.476 | 1.210 | 1.00 | 24.26 |
| ATOM 2231 | NH1 | ARG | 1718 | 32.768 | 0.668 | 1.532 | 1.00 | 23.98 |
| ATOM 2234 | NH2 | ARG | 1718 | 31.595 | −0.603 | 0.019 | 1.00 | 21.60 |
| ATOM 2237 | C | ARG | 1718 | 35.005 | −0.521 | 7.148 | 1.00 | 30.11 |
| ATOM 2238 | O | ARG | 1718 | 36.201 | −0.623 | 7.428 | 1.00 | 30.60 |
| ATOM 2239 | N | MET | 1719 | 34.056 | −0.430 | 8.074 | 1.00 | 30.69 |
| ATOM 2241 | CA | MET | 1719 | 34.350 | −0.490 | 9.501 | 1.00 | 31.77 |
| ATOM 2242 | CB | MET | 1719 | 33.072 | −0.302 | 10.335 | 1.00 | 34.56 |
| ATOM 2243 | CG | MET | 1719 | 32.408 | 1.060 | 10.194 | 1.00 | 36.71 |
| ATOM 2244 | SD | MET | 1719 | 31.015 | 1.307 | 11.314 | 1.00 | 38.66 |
| ATOM 2245 | CE | MET | 1719 | 29.797 | 0.338 | 10.544 | 1.00 | 36.99 |
| ATOM 2246 | C | MET | 1719 | 34.998 | −1.810 | 9.854 | 1.00 | 30.20 |
| ATOM 2247 | O | MET | 1719 | 34.802 | −2.802 | 9.169 | 1.00 | 31.41 |
| ATOM 2248 | N | ASP | 1720 | 35.778 | −1.809 | 10.926 | 1.00 | 32.49 |
| ATOM 2250 | CA | ASP | 1720 | 36.473 | −3.008 | 11.385 | 1.00 | 33.60 |
| ATOM 2251 | CB | ASP | 1720 | 37.593 | −2.630 | 12.358 | 1.00 | 37.65 |
| ATOM 2252 | CG | ASP | 1720 | 38.628 | −1.688 | 11.747 | 1.00 | 44.69 |
| ATOM 2253 | OD1 | ASP | 1720 | 38.442 | −1.223 | 10.596 | 1.00 | 50.97 |
| ATOM 2254 | OD2 | ASP | 1720 | 39.632 | −1.398 | 12.443 | 1.00 | 48.67 |
| ATOM 2255 | C | ASP | 1720 | 35.524 | −3.977 | 12.079 | 1.00 | 31.26 |
| ATOM 2256 | O | ASP | 1720 | 34.466 | −3.581 | 12.561 | 1.00 | 32.69 |
| ATOM 2257 | N | LYS | 1721 | 35.943 | −5.231 | 12.191 | 1.00 | 32.76 |
| ATOM 2259 | CA | LYS | 1721 | 35.133 | −6.261 | 12.825 | 1.00 | 32.28 |
| ATOM 2260 | CB | LYS | 1721 | 35.726 | −7.649 | 12.575 | 1.00 | 33.63 |
| ATOM 2261 | CG | LYS | 1721 | 34.854 | −8.773 | 13.125 | 1.00 | 35.68 |
| ATOM 2262 | CD | LYS | 1721 | 35.392 | −10.126 | 12.784 | 1.00 | 36.22 |
| ATOM 2263 | CE | LYS | 1721 | 36.054 | −10.749 | 13.988 | 1.00 | 42.65 |
| ATOM 2264 | NZ | LYS | 1721 | 36.354 | −12.189 | 13.756 | 1.00 | 46.15 |
| ATOM 2268 | C | LYS | 1721 | 35.039 | −6.051 | 14.315 | 1.00 | 35.55 |
| ATOM 2269 | O | LYS | 1721 | 36.064 | −5.926 | 14.986 | 1.00 | 37.78 |
| ATOM 2270 | N | PRO | 1722 | 33.807 | −6.017 | 14.861 | 1.00 | 36.91 |
| ATOM 2271 | CD | PRO | 1722 | 32.504 | −6.105 | 14.179 | 1.00 | 34.43 |
| ATOM 2272 | CA | PRO | 1722 | 33.630 | −5.827 | 16.305 | 1.00 | 37.77 |
| ATOM 2273 | CB | PRO | 1722 | 32.107 | −5.846 | 16.465 | 1.00 | 36.32 |
| ATOM 2274 | CG | PRO | 1722 | 31.603 | −5.375 | 15.122 | 1.00 | 34.53 |
| ATOM 2275 | C | PRO | 1722 | 34.246 | −7.026 | 17.023 | 1.00 | 39.31 |
| ATOM 2276 | O | PRO | 1722 | 34.274 | −8.136 | 16.477 | 1.00 | 38.78 |
| ATOM 2277 | N | SER | 1723 | 34.777 | −6.820 | 18.222 | 1.00 | 42.72 |
| ATOM 2279 | CA | SER | 1723 | 35.336 | −7.954 | 18.940 | 1.00 | 45.01 |
| ATOM 2280 | CB | SER | 1723 | 36.152 | −7.508 | 20.160 | 1.00 | 46.88 |
| ATOM 2281 | OG | SER | 1723 | 35.327 | −7.027 | 21.208 | 1.00 | 53.47 |
| ATOM 2283 | C | SER | 1723 | 34.088 | −8.731 | 19.359 | 1.00 | 46.67 |
| ATOM 2284 | O | SER | 1723 | 32.982 | −8.172 | 19.417 | 1.00 | 46.21 |
| ATOM 2285 | N | ASN | 1724 | 34.237 | −10.025 | 19.590 | 1.00 | 47.80 |
| ATOM 2287 | CA | ASN | 1724 | 33.092 | −10.826 | 19.999 | 1.00 | 52.78 |
| ATOM 2288 | CB | ASN | 1724 | 32.559 | −10.319 | 21.355 | 1.00 | 57.86 |
| ATOM 2289 | CG | ASN | 1724 | 33.679 | −10.091 | 22.370 | 1.00 | 61.99 |
| ATOM 2290 | OD1 | ASN | 1724 | 34.531 | −10.959 | 22.585 | 1.00 | 63.17 |
| ATOM 2291 | ND2 | ASN | 1724 | 33.712 | −8.899 | 22.953 | 1.00 | 63.56 |
| ATOM 2294 | C | ASN | 1724 | 32.015 | −10.779 | 18.893 | 1.00 | 51.43 |
| ATOM 2295 | O | ASN | 1724 | 30.859 | −10.423 | 19.108 | 1.00 | 51.56 |
| ATOM 2296 | N | CYS | 1725 | 32.454 | −11.087 | 17.683 | 1.00 | 48.91 |
| ATOM 2298 | CA | CYS | 1725 | 31.600 | −11.136 | 16.508 | 1.00 | 45.62 |
| ATOM 2299 | CB | CYS | 1725 | 31.526 | −9.771 | 15.811 | 1.00 | 44.83 |
| ATOM 2300 | SG | CYS | 1725 | 30.693 | −9.816 | 14.194 | 1.00 | 41.83 |
| ATOM 2301 | C | CYS | 1725 | 32.341 | −12.135 | 15.640 | 1.00 | 42.30 |
| ATOM 2302 | O | CYS | 1725 | 33.566 | −12.045 | 15.493 | 1.00 | 44.63 |
| ATOM 2303 | N | THR | 1726 | 31.627 | −13.134 | 15.141 | 1.00 | 37.46 |
| ATOM 2305 | CA | THR | 1726 | 32.259 | −14.153 | 14.320 | 1.00 | 35.29 |
| ATOM 2306 | CB | THR | 1726 | 31.339 | −15.367 | 14.132 | 1.00 | 33.44 |
| ATOM 2307 | OG1 | THR | 1726 | 30.109 | −14.952 | 13.523 | 1.00 | 34.77 |
| ATOM 2308 | CG2 | THR | 1726 | 31.070 | −16.019 | 15.454 | 1.00 | 30.22 |
| ATOM 2310 | C | THR | 1726 | 32.668 | −13.622 | 12.963 | 1.00 | 33.53 |
| ATOM 2311 | O | THR | 1726 | 32.158 | −12.593 | 12.518 | 1.00 | 32.93 |
| ATOM 2312 | N | ASN | 1727 | 33.619 | −14.294 | 12.319 | 1.00 | 32.72 |
| ATOM 2314 | CA | ASN | 1727 | 34.030 | −13.867 | 10.983 | 1.00 | 35.91 |
| ATOM 2315 | CB | ASN | 1727 | 35.166 | −14.724 | 10.422 | 1.00 | 40.64 |
| ATOM 2316 | CG | ASN | 1727 | 36.463 | −14.533 | 11.168 | 1.00 | 46.52 |
| ATOM 2317 | OD1 | ASN | 1727 | 37.047 | −13.453 | 11.158 | 1.00 | 49.98 |
| ATOM 2318 | ND2 | ASN | 1727 | 36.931 | −15.592 | 11.814 | 1.00 | 49.04 |
| ATOM 2321 | C | ASN | 1727 | 32.824 | −14.006 | 10.058 | 1.00 | 34.27 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2322 | O | ASN | 1727 | 32.681 | −13.236 | 9.116 | 1.00 | 32.96 |
| ATOM 2323 | N | GLU | 1728 | 31.969 | −14.997 | 10.326 | 1.00 | 32.49 |
| ATOM 2325 | CA | GLU | 1728 | 30.778 | −15.235 | 9.510 | 1.00 | 31.99 |
| ATOM 2326 | CB | GLU | 1728 | 30.064 | −16.504 | 9.975 | 1.00 | 34.15 |
| ATOM 2327 | CG | GLU | 1728 | 28.836 | −16.866 | 9.156 | 1.00 | 35.63 |
| ATOM 2328 | CD | GLU | 1728 | 28.187 | −18.169 | 9.608 | 1.00 | 39.72 |
| ATOM 2329 | OE1 | GLU | 1728 | 28.200 | −18.463 | 10.824 | 1.00 | 42.25 |
| ATOM 2330 | OE2 | GLU | 1728 | 27.654 | −16.896 | 8.742 | 1.00 | 39.87 |
| ATOM 2331 | C | GLU | 1728 | 29.814 | −14.049 | 9.549 | 1.00 | 30.76 |
| ATOM 2332 | O | GLU | 1728 | 29.309 | −13.602 | 8.512 | 1.00 | 29.58 |
| ATOM 2333 | N | LEU | 1729 | 29.559 | −13.544 | 10.750 | 1.00 | 30.01 |
| ATOM 2335 | CA | LEU | 1729 | 28.670 | −12.408 | 10.911 | 1.00 | 30.21 |
| ATOM 2336 | CB | LEU | 1729 | 28.225 | −12.272 | 12.364 | 1.00 | 30.13 |
| ATOM 2337 | CG | LEU | 1729 | 27.208 | −13.350 | 12.748 | 1.00 | 33.61 |
| ATOM 2338 | CD1 | LEU | 1729 | 27.119 | −13.483 | 14.262 | 1.00 | 33.71 |
| ATOM 2339 | CD2 | LEU | 1729 | 25.844 | −13.021 | 12.139 | 1.00 | 30.31 |
| ATOM 2340 | C | LEU | 1729 | 29.316 | −11.133 | 10.390 | 1.00 | 30.26 |
| ATOM 2341 | O | LEU | 1729 | 28.619 | −10.229 | 9.938 | 1.00 | 28.89 |
| ATOM 2342 | N | TYR | 1730 | 30.648 | −11.063 | 10.435 | 1.00 | 28.91 |
| ATOM 2344 | CA | TYR | 1730 | 31.343 | −9.893 | 9.912 | 1.00 | 28.91 |
| ATOM 2345 | CB | TYR | 1730 | 32.804 | −9.861 | 10.359 | 1.00 | 29.09 |
| ATOM 2346 | CG | TYR | 1730 | 33.537 | −8.639 | 9.857 | 1.00 | 30.15 |
| ATOM 2347 | CD1 | TYR | 1730 | 33.037 | −7.358 | 10.103 | 1.00 | 29.97 |
| ATOM 2348 | CE1 | TYR | 1730 | 33.688 | −6.227 | 9.626 | 1.00 | 28.99 |
| ATOM 2349 | CD2 | TYR | 1730 | 34.716 | −8.757 | 9.119 | 1.00 | 29.24 |
| ATOM 2350 | CE2 | TYR | 1730 | 35.386 | −7.620 | 8.632 | 1.00 | 28.25 |
| ATOM 2351 | CZ | TYR | 1730 | 34.861 | −6.362 | 8.889 | 1.00 | 28.41 |
| ATOM 2352 | OH | TYR | 1730 | 35.485 | −5.227 | 8.405 | 1.00 | 31.64 |
| ATOM 2354 | C | TYR | 1730 | 31.260 | −9.943 | 8.379 | 1.00 | 27.10 |
| ATOM 2355 | O | TYR | 1730 | 31.078 | −8.920 | 7.726 | 1.00 | 27.46 |
| ATOM 2356 | N | MET | 1731 | 31.390 | −11.138 | 7.813 | 1.00 | 26.68 |
| ATOM 2358 | CA | MET | 1731 | 31.298 | −11.315 | 6.372 | 1.00 | 28.68 |
| ATOM 2359 | CB | MET | 1731 | 31.526 | −12.778 | 5.989 | 1.00 | 35.43 |
| ATOM 2360 | CG | MET | 1731 | 31.158 | −13.087 | 4.545 | 1.00 | 46.19 |
| ATOM 2361 | SD | MET | 1731 | 31.441 | −14.804 | 4.064 | 1.00 | 60.10 |
| ATOM 2362 | CE | MET | 1731 | 32.603 | −14.550 | 2.678 | 1.00 | 58.31 |
| ATOM 2363 | C | MET | 1731 | 29.917 | −10.858 | 5.912 | 1.00 | 27.42 |
| ATOM 2364 | O | MET | 1731 | 29.782 | −10.227 | 4.871 | 1.00 | 30.80 |
| ATOM 2365 | N | MET | 1732 | 28.893 | −11.191 | 6.688 | 1.00 | 28.53 |
| ATOM 2367 | CA | MET | 1732 | 27.522 | −10.777 | 6.389 | 1.00 | 26.47 |
| ATOM 2368 | CB | MET | 1732 | 26.562 | −11.308 | 7.458 | 1.00 | 25.79 |
| ATOM 2369 | CG | MET | 1732 | 25.116 | −10.838 | 7.274 | 1.00 | 26.01 |
| ATOM 2370 | SD | MET | 1732 | 24.004 | −11.550 | 8.469 | 1.00 | 26.22 |
| ATOM 2371 | CE | MET | 1732 | 23.787 | −13.195 | 7.783 | 1.00 | 23.74 |
| ATOM 2372 | C | MET | 1732 | 27.445 | −9.243 | 6.319 | 1.00 | 25.15 |
| ATOM 2373 | O | MET | 1732 | 26.886 | −8.691 | 5.379 | 1.00 | 25.41 |
| ATOM 2374 | N | MET | 1733 | 28.024 | −8.564 | 7.308 | 1.00 | 26.48 |
| ATOM 2376 | CA | MET | 1733 | 28.057 | −7.104 | 7.331 | 1.00 | 27.09 |
| ATOM 2377 | CB | MET | 1733 | 28.903 | −6.594 | 8.488 | 1.00 | 25.91 |
| ATOM 2378 | CG | MET | 1733 | 28.235 | −6.556 | 9.824 | 1.00 | 31.64 |
| ATOM 2379 | SD | MET | 1733 | 29.442 | −6.111 | 11.094 | 1.00 | 29.59 |
| ATOM 2380 | CE | MET | 1733 | 28.886 | −7.126 | 12.420 | 1.00 | 28.14 |
| ATOM 2381 | C | MET | 1733 | 28.720 | −6.613 | 6.056 | 1.00 | 28.43 |
| ATOM 2382 | O | MET | 1733 | 28.185 | −5.753 | 5.372 | 1.00 | 31.37 |
| ATOM 2383 | N | ARG | 1734 | 29.891 | −7.169 | 5.747 | 1.00 | 28.57 |
| ATOM 2385 | CA | ARG | 1734 | 30.642 | −6.783 | 4.551 | 1.00 | 27.00 |
| ATOM 2386 | CB | ARG | 1734 | 32.007 | −7.488 | 4.510 | 1.00 | 25.98 |
| ATOM 2387 | CG | ARG | 1734 | 32.927 | −7.154 | 5.707 | 1.00 | 28.13 |
| ATOM 2388 | CD | ARG | 1734 | 33.229 | −5.672 | 5.765 | 1.00 | 29.97 |
| ATOM 2389 | NE | ARG | 1734 | 33.922 | −5.256 | 4.553 | 1.00 | 40.49 |
| ATOM 2391 | CZ | ARG | 1734 | 35.238 | −5.361 | 4.363 | 1.00 | 43.95 |
| ATOM 2392 | NH1 | ARG | 1734 | 36.023 | −5.853 | 5.318 | 1.00 | 41.81 |
| ATOM 2395 | NH2 | ARG | 1734 | 35.760 | −5.048 | 3.184 | 1.00 | 46.20 |
| ATOM 2398 | C | ARG | 1734 | 29.859 | −7.037 | 3.268 | 1.00 | 24.57 |
| ATOM 2399 | O | ARG | 1734 | 29.992 | −6.290 | 2.314 | 1.00 | 24.94 |
| ATOM 2400 | N | ASP | 1735 | 29.071 | −8.107 | 3.235 | 1.00 | 24.79 |
| ATOM 2402 | CA | ASP | 1735 | 28.254 | −8.420 | 2.061 | 1.00 | 23.88 |
| ATOM 2403 | CB | ASP | 1735 | 27.669 | −9.830 | 2.150 | 1.00 | 25.95 |
| ATOM 2404 | CG | ASP | 1735 | 28.724 | −10.913 | 2.024 | 1.00 | 27.60 |
| ATOM 2405 | OD1 | ASP | 1735 | 29.842 | −10.632 | 1.529 | 1.00 | 27.75 |
| ATOM 2406 | OD2 | ASP | 1735 | 28.432 | −12.051 | 2.430 | 1.00 | 28.90 |
| ATOM 2407 | C | ASP | 1735 | 27.139 | −7.396 | 1.941 | 1.00 | 22.61 |
| ATOM 2408 | O | ASP | 1735 | 26.777 | −6.996 | 0.833 | 1.00 | 22.66 |
| ATOM 2409 | N | CYS | 1736 | 26.611 | −6.965 | 3.085 | 1.00 | 20.61 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2411 | CA | CYS | 1736 | 25.561 | −5.952 | 3.109 | 1.00 | 23.63 |
| ATOM 2412 | CB | CYS | 1736 | 25.007 | −5.767 | 4.534 | 1.00 | 21.98 |
| ATOM 2413 | SG | CYS | 1736 | 23.934 | −7.126 | 5.111 | 1.00 | 22.95 |
| ATOM 2414 | C | CYS | 1736 | 26.129 | −4.633 | 2.599 | 1.00 | 23.62 |
| ATOM 2415 | O | CYS | 1736 | 25.403 | −3.797 | 2.047 | 1.00 | 22.15 |
| ATOM 2416 | N | TRP | 1737 | 27.438 | −4.461 | 2.775 | 1.00 | 24.37 |
| ATOM 2418 | CA | TRP | 1737 | 28.123 | −3.247 | 2.342 | 1.00 | 23.77 |
| ATOM 2419 | CB | TRP | 1737 | 29.162 | −2.810 | 3.371 | 1.00 | 19.38 |
| ATOM 2420 | CG | TRP | 1737 | 28.601 | −2.520 | 4.718 | 1.00 | 21.62 |
| ATOM 2421 | CD2 | TRP | 1737 | 29.268 | −2.688 | 5.971 | 1.00 | 24.81 |
| ATOM 2422 | CE2 | TRP | 1737 | 28.371 | −2.278 | 6.980 | 1.00 | 25.95 |
| ATOM 2423 | CE3 | TRP | 1737 | 30.534 | −3.165 | 6.340 | 1.00 | 29.02 |
| ATOM 2424 | CD1 | TRP | 1737 | 27.359 | −2.024 | 5.007 | 1.00 | 23.21 |
| ATOM 2425 | NE1 | TRP | 1737 | 27.213 | −1.876 | 6.362 | 1.00 | 21.80 |
| ATOM 2427 | CZ2 | TRP | 1737 | 28.710 | −2.305 | 8.347 | 1.00 | 26.68 |
| ATOM 2428 | CZ3 | TRP | 1737 | 30.873 | −3.198 | 7.699 | 1.00 | 31.06 |
| ATOM 2429 | CH2 | TRP | 1737 | 29.959 | −2.774 | 8.685 | 1.00 | 30.18 |
| ATOM 2430 | C | TRP | 1737 | 28.788 | −3.372 | 0.978 | 1.00 | 24.88 |
| ATOM 2431 | O | TRP | 1737 | 29.737 | −2.646 | 0.689 | 1.00 | 25.11 |
| ATOM 2432 | N | HIS | 1738 | 28.303 | −4.278 | 0.132 | 1.00 | 25.27 |
| ATOM 2434 | CA | HIS | 1738 | 28.888 | −4.406 | −1.191 | 1.00 | 24.27 |
| ATOM 2435 | CB | HIS | 1738 | 28.280 | −5.573 | −1.986 | 1.00 | 25.24 |
| ATOM 2436 | CG | HIS | 1738 | 29.179 | −6.073 | −3.081 | 1.00 | 26.28 |
| ATOM 2437 | CD2 | HIS | 1738 | 29.727 | −5.437 | −4.147 | 1.00 | 25.67 |
| ATOM 2438 | ND1 | HIS | 1738 | 29.697 | −7.352 | −3.098 | 1.00 | 27.55 |
| ATOM 2440 | CE1 | HIS | 1738 | 30.528 | −7.478 | −4.117 | 1.00 | 27.51 |
| ATOM 2441 | NE2 | HIS | 1738 | 30.564 | −6.329 | −4.770 | 1.00 | 30.93 |
| ATOM 2443 | C | HIS | 1738 | 28.715 | −3.087 | −1.953 | 1.00 | 25.59 |
| ATOM 2444 | O | HIS | 1738 | 27.659 | −2.451 | −1.905 | 1.00 | 22.01 |
| ATOM 2445 | N | ALA | 1739 | 29.784 | −2.651 | −2.612 | 1.00 | 23.84 |
| ATOM 2447 | CA | ALA | 1739 | 29.759 | −1.418 | −3.388 | 1.00 | 24.93 |
| ATOM 2448 | CB | ALA | 1739 | 31.131 | −1.177 | −4.024 | 1.00 | 26.39 |
| ATOM 2449 | C | ALA | 1739 | 28.671 | −1.508 | −4.462 | 1.00 | 25.35 |
| ATOM 2450 | O | ALA | 1739 | 27.963 | −0.535 | −4.727 | 1.00 | 28.20 |
| ATOM 2451 | N | VAL | 1740 | 28.543 | −2.680 | −5.073 | 1.00 | 22.68 |
| ATOM 2453 | CA | VAL | 1740 | 27.528 | −2.904 | −6.101 | 1.00 | 26.46 |
| ATOM 2454 | CB | VAL | 1740 | 27.995 | −3.968 | −7.117 | 1.00 | 29.70 |
| ATOM 2455 | CG1 | VAL | 1740 | 27.063 | −4.003 | −8.334 | 1.00 | 26.01 |
| ATOM 2456 | CG2 | VAL | 1740 | 29.433 | −3.686 | −7.537 | 1.00 | 31.22 |
| ATOM 2457 | C | VAL | 1740 | 26.213 | −3.358 | −5.443 | 1.00 | 25.07 |
| ATOM 2458 | O | VAL | 1740 | 26.138 | −4.474 | −4.903 | 1.00 | 23.55 |
| ATOM 2459 | N | PRO | 1741 | 25.155 | −2.519 | −5.514 | 1.00 | 25.30 |
| ATOM 2460 | CD | PRO | 1741 | 25.133 | −1.190 | −6.153 | 1.00 | 22.43 |
| ATOM 2461 | CA | PRO | 1741 | 23.844 | −2.833 | −4.921 | 1.00 | 24.09 |
| ATOM 2462 | CB | PRO | 1741 | 22.962 | −1.675 | −5.402 | 1.00 | 23.12 |
| ATOM 2463 | CG | PRO | 1741 | 23.928 | −0.527 | −5.491 | 1.00 | 22.04 |
| ATOM 2464 | C | PRO | 1741 | 23.272 | −4.191 | −5.313 | 1.00 | 22.18 |
| ATOM 2465 | O | PRO | 1741 | 22.727 | −4.900 | −4.466 | 1.00 | 21.23 |
| ATOM 2466 | N | SER | 1742 | 23.437 | −4.570 | −6.580 | 1.00 | 23.87 |
| ATOM 2468 | CA | SER | 1742 | 22.928 | −5.847 | −7.088 | 1.00 | 24.36 |
| ATOM 2469 | CB | SER | 1742 | 23.071 | −5.907 | −8.612 | 1.00 | 27.39 |
| ATOM 2470 | OG | SER | 1742 | 24.436 | −6.025 | −8.986 | 1.00 | 29.25 |
| ATOM 2472 | C | SER | 1742 | 23.636 | −7.058 | −6.488 | 1.00 | 23.96 |
| ATOM 2473 | O | SER | 1742 | 23.145 | −8.179 | −6.575 | 1.00 | 24.30 |
| ATOM 2474 | N | GLN | 1743 | 24.810 | −6.839 | −5.915 | 1.00 | 24.39 |
| ATOM 2476 | CA | GLN | 1743 | 25.558 | −7.934 | −5.345 | 1.00 | 23.15 |
| ATOM 2477 | CB | GLN | 1743 | 27.046 | −7.755 | −5.638 | 1.00 | 23.83 |
| ATOM 2478 | CG | GLN | 1743 | 27.359 | −7.784 | −7.126 | 1.00 | 22.84 |
| ATOM 2479 | CD | GLN | 1743 | 26.816 | −9.036 | −7.808 | 1.00 | 24.20 |
| ATOM 2480 | OE1 | GLN | 1743 | 27.318 | −10.135 | −7.590 | 1.00 | 21.50 |
| ATOM 2481 | NE2 | GLN | 1743 | 25.775 | −8.871 | −8.628 | 1.00 | 22.45 |
| ATOM 2484 | C | GLN | 1743 | 25.309 | −8.171 | −3.868 | 1.00 | 23.12 |
| ATOM 2485 | O | GLN | 1743 | 25.816 | −9.135 | −3.317 | 1.00 | 24.96 |
| ATOM 2486 | N | ARG | 1744 | 24.557 | −7.280 | −3.225 | 1.00 | 23.67 |
| ATOM 2488 | CA | ARG | 1744 | 24.242 | −7.424 | −1.806 | 1.00 | 22.11 |
| ATOM 2489 | CB | ARG | 1744 | 23.699 | −6.110 | −1.231 | 1.00 | 19.70 |
| ATOM 2490 | CG | ARG | 1744 | 24.672 | −4.959 | −1.338 | 1.00 | 21.26 |
| ATOM 2491 | CD | ARG | 1744 | 24.049 | −3.640 | −0.890 | 1.00 | 20.68 |
| ATOM 2492 | NE | ARG | 1744 | 24.923 | −2.552 | −1.305 | 1.00 | 25.21 |
| ATOM 2494 | CZ | ARG | 1744 | 24.540 | −1.313 | −1.583 | 1.00 | 24.30 |
| ATOM 2495 | NH1 | ARG | 1744 | 23.257 | −0.955 | −1.481 | 1.00 | 22.04 |
| ATOM 2498 | NH2 | ARG | 1744 | 25.450 | −0.448 | −2.036 | 1.00 | 21.29 |
| ATOM 2501 | C | ARG | 1744 | 23.184 | −8.505 | −1.640 | 1.00 | 22.53 |
| ATOM 2502 | O | ARG | 1744 | 22.437 | −8.800 | −2.588 | 1.00 | 23.08 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2503 | N | PRO | 1745 | 23.162 | −9.170 | −0.467 | 1.00 | 20.76 |
| ATOM 2504 | CD | PRO | 1745 | 24.087 | −9.078 | 0.681 | 1.00 | 21.71 |
| ATOM 2505 | CA | PRO | 1745 | 22.160 | −10.207 | −0.243 | 1.00 | 22.34 |
| ATOM 2506 | CB | PRO | 1745 | 22.632 | −10.859 | 1.057 | 1.00 | 20.58 |
| ATOM 2507 | CG | PRO | 1745 | 23.298 | −9.727 | 1.783 | 1.00 | 20.36 |
| ATOM 2508 | C | PRO | 1745 | 20.814 | −9.512 | −0.048 | 1.00 | 23.62 |
| ATOM 2509 | O | PRO | 1745 | 20.759 | −8.318 | 0.255 | 1.00 | 25.29 |
| ATOM 2510 | N | THR | 1746 | 19.731 | −10.235 | −0.275 | 1.00 | 23.39 |
| ATOM 2512 | CA | THR | 1746 | 18.404 | −9.675 | −0.080 | 1.00 | 22.77 |
| ATOM 2513 | CB | THR | 1746 | 17.386 | −10.368 | −1.004 | 1.00 | 23.24 |
| ATOM 2514 | OG1 | THR | 1746 | 17.409 | −11.783 | −0.763 | 1.00 | 23.11 |
| ATOM 2516 | CG2 | THR | 1746 | 17.724 | −10.103 | −2.475 | 1.00 | 24.96 |
| ATOM 2517 | C | THR | 1746 | 18.009 | −9.954 | 1.365 | 1.00 | 24.98 |
| ATOM 2518 | O | THR | 1746 | 18.664 | −10.758 | 2.043 | 1.00 | 24.30 |
| ATOM 2519 | N | PHE | 1747 | 16.944 | −9.318 | 1.853 | 1.00 | 24.95 |
| ATOM 2521 | CA | PHE | 1747 | 16.501 | −9.596 | 3.221 | 1.00 | 25.16 |
| ATOM 2522 | CB | PHE | 1747 | 15.395 | −8.628 | 3.661 | 1.00 | 23.64 |
| ATOM 2523 | CG | PHE | 1747 | 15.916 | −7.283 | 4.089 | 1.00 | 24.34 |
| ATOM 2524 | CD1 | PHE | 1747 | 16.715 | −7.167 | 5.226 | 1.00 | 21.21 |
| ATOM 2525 | CD2 | PHE | 1747 | 15.649 | −6.137 | 3.334 | 1.00 | 21.42 |
| ATOM 2526 | CE1 | PHE | 1747 | 17.252 | −5.932 | 5.597 | 1.00 | 20.99 |
| ATOM 2527 | CE2 | PHE | 1747 | 16.178 | −4.907 | 3.699 | 1.00 | 20.36 |
| ATOM 2628 | CZ | PHE | 1747 | 16.985 | −4.807 | 4.840 | 1.00 | 19.30 |
| ATOM 2529 | C | PHE | 1747 | 16.034 | −11.049 | 3.311 | 1.00 | 23.57 |
| ATOM 2530 | O | PHE | 1747 | 16.182 | −11.702 | 4.344 | 1.00 | 25.32 |
| ATOM 2531 | N | LYS | 1748 | 15.520 | −11.573 | 2.202 | 1.00 | 23.19 |
| ATOM 2533 | CA | LYS | 1748 | 15.066 | −12.958 | 2.167 | 1.00 | 23.67 |
| ATOM 2534 | CB | LYS | 1748 | 14.462 | −13.285 | 0.799 | 1.00 | 26.67 |
| ATOM 2535 | CG | LYS | 1748 | 14.018 | −14.739 | 0.622 | 1.00 | 30.49 |
| ATOM 2536 | CD | LYS | 1748 | 13.642 | −14.996 | −0.837 | 1.00 | 38.98 |
| ATOM 2537 | CE | LYS | 1748 | 13.182 | −16.432 | −1.087 | 1.00 | 44.52 |
| ATOM 2538 | NZ | LYS | 1748 | 11.997 | −16.790 | −0.245 | 1.00 | 52.75 |
| ATOM 2542 | C | LYS | 1748 | 16.264 | −13.865 | 2.445 | 1.00 | 25.65 |
| ATOM 2543 | O | LYS | 1748 | 16.184 | −14.778 | 3.270 | 1.00 | 27.19 |
| ATOM 2544 | N | GLN | 1749 | 17.378 | −13.603 | 1.762 | 1.00 | 24.56 |
| ATOM 2546 | CA | GLN | 1749 | 18.588 | −14.397 | 1.950 | 1.00 | 26.33 |
| ATOM 2547 | CB | GLN | 1749 | 19.702 | −13.953 | 0.993 | 1.00 | 27.97 |
| ATOM 2548 | CG | GLN | 1749 | 19.416 | −14.066 | −0.484 | 1.00 | 37.31 |
| ATOM 2549 | CD | GLN | 1749 | 20.518 | −13.415 | −1.315 | 1.00 | 40.24 |
| ATOM 2550 | OE1 | GLN | 1749 | 20.296 | −12.408 | −1.970 | 1.00 | 38.83 |
| ATOM 2551 | NE2 | GLN | 1749 | 21.726 | −13.983 | −1.259 | 1.00 | 47.83 |
| ATOM 2554 | C | GLN | 1749 | 19.099 | −14.223 | 3.377 | 1.00 | 23.92 |
| ATOM 2555 | O | GLN | 1749 | 19.459 | −15.196 | 4.040 | 1.00 | 25.27 |
| ATOM 2556 | N | LEU | 1750 | 19.155 | −12.976 | 3.829 | 1.00 | 23.12 |
| ATOM 2558 | CA | LEU | 1750 | 19.641 | −12.662 | 5.175 | 1.00 | 24.34 |
| ATOM 2559 | CB | LEU | 1750 | 19.607 | −11.149 | 5.427 | 1.00 | 23.08 |
| ATOM 2560 | CG | LEU | 1750 | 20.633 | −10.311 | 4.665 | 1.00 | 23.84 |
| ATOM 2561 | CD1 | LEU | 1750 | 20.274 | −8.806 | 4.724 | 1.00 | 22.10 |
| ATOM 2562 | CD2 | LEU | 1750 | 22.013 | −10.586 | 5.246 | 1.00 | 24.91 |
| ATOM 2563 | C | LEU | 1750 | 18.840 | −13.400 | 6.236 | 1.00 | 27.40 |
| ATOM 2564 | O | LEU | 1750 | 39.408 | −13.915 | 7.211 | 1.00 | 27.11 |
| ATOM 2565 | N | VAL | 1751 | 17.527 | −13.482 | 6.031 | 1.00 | 26.83 |
| ATOM 2567 | CA | VAL | 1751 | 16.665 | −14.174 | 6.970 | 1.00 | 25.31 |
| ATOM 2568 | CB | VAL | 1751 | 15.176 | −13.994 | 6.599 | 1.00 | 25.87 |
| ATOM 2569 | CG1 | VAL | 1751 | 14.304 | −14.975 | 7.382 | 1.00 | 28.43 |
| ATOM 2570 | CG2 | VAL | 1751 | 14.746 | −12.593 | 6.934 | 1.00 | 21.52 |
| ATOM 2571 | C | VAL | 1751 | 17.047 | −15.642 | 7.025 | 1.00 | 25.87 |
| ATOM 2572 | O | VAL | 1751 | 17.178 | −16.218 | 8.106 | 1.00 | 23.41 |
| ATOM 2573 | N | GLU | 1752 | 17.253 | −16.243 | 5.858 | 1.00 | 29.98 |
| ATOM 2575 | CA | GLU | 1752 | 17.631 | −17.651 | 5.799 | 1.00 | 33.12 |
| ATOM 2576 | CB | GLU | 1752 | 17.653 | −18.134 | 4.346 | 1.00 | 35.99 |
| ATOM 2577 | CG | GLU | 1752 | 16.284 | −18.077 | 3.670 | 1.00 | 43.58 |
| ATOM 2578 | CD | GLU | 1752 | 16.300 | −18.575 | 2.230 | 1.00 | 48.64 |
| ATOM 2579 | OE1 | GLU | 1752 | 15.453 | −18.124 | 1.431 | 1.00 | 48.99 |
| ATOM 2580 | OE2 | GLU | 1752 | 17.157 | −19.426 | 1.902 | 1.00 | 55.41 |
| ATOM 2581 | C | GLU | 1752 | 18.995 | −17.891 | 6.467 | 1.00 | 33.15 |
| ATOM 2582 | O | GLU | 1752 | 19.173 | −18.847 | 7.236 | 1.00 | 30.71 |
| ATOM 2583 | N | ASP | 1753 | 19.951 | −17.011 | 6.186 | 1.00 | 31.12 |
| ATOM 2585 | CA | ASP | 1753 | 21.279 | −17.131 | 6.770 | 1.00 | 30.51 |
| ATOM 2586 | CB | ASP | 1753 | 22.243 | −16.108 | 6.155 | 1.00 | 29.15 |
| ATOM 2587 | CG | ASP | 1753 | 22.488 | −16.344 | 4.672 | 1.00 | 33.53 |
| ATOM 2588 | OD1 | ASP | 1753 | 22.361 | −17.494 | 4.215 | 1.00 | 34.92 |
| ATOM 2589 | OD2 | ASP | 1753 | 22.815 | −15.371 | 3.955 | 1.00 | 38.26 |
| ATOM 2590 | C | ASP | 1753 | 21.215 | −16.968 | 8.287 | 1.00 | 28.54 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2591 | O | ASP | 1753 | 21.739 | −17.800 | 9.025 | 1.00 | 28.95 |
| ATOM 2592 | N | LEU | 1754 | 20.537 | −15.926 | 8.753 | 1.00 | 27.25 |
| ATOM 2594 | CA | LEU | 1754 | 20.421 | −15.673 | 10.193 | 1.00 | 28.08 |
| ATOM 2595 | CB | LEU | 1754 | 19.754 | −14.328 | 10.455 | 1.00 | 23.31 |
| ATOM 2596 | CG | LEU | 1754 | 20.733 | −13.199 | 10.160 | 1.00 | 24.47 |
| ATOM 2597 | CD1 | LEU | 1754 | 20.007 | −11.863 | 10.094 | 1.00 | 19.58 |
| ATOM 2598 | CD2 | LEU | 1754 | 21.846 | −13.207 | 11.216 | 1.00 | 21.17 |
| ATOM 2599 | C | LEU | 1754 | 19.688 | −16.789 | 10.921 | 1.00 | 31.61 |
| ATOM 2600 | O | LEU | 1754 | 20.037 | −17.135 | 12.048 | 1.00 | 32.64 |
| ATOM 2601 | N | ASP | 1755 | 18.690 | −17.367 | 10.259 | 1.00 | 32.61 |
| ATOM 2603 | CA | ASP | 1755 | 17.931 | −18.460 | 10.833 | 1.00 | 34.20 |
| ATOM 2604 | CB | ASP | 1755 | 16.823 | −18.883 | 9.872 | 1.00 | 37.70 |
| ATOM 2605 | CG | ASP | 1755 | 15.808 | −19.780 | 10.526 | 1.00 | 44.27 |
| ATOM 2606 | OD1 | ASP | 1755 | 15.445 | −19.521 | 11.692 | 1.00 | 47.16 |
| ATOM 2607 | OD2 | ASP | 1755 | 15.370 | −20.745 | 9.876 | 1.00 | 51.35 |
| ATOM 2608 | C | ASP | 1755 | 18.894 | −19.616 | 11.073 | 1.00 | 34.63 |
| ATOM 2609 | O | ASP | 1755 | 18.858 | −20.273 | 12.119 | 1.00 | 36.24 |
| ATOM 2610 | N | ARG | 1756 | 19.782 | −19.826 | 10.108 | 1.00 | 32.60 |
| ATOM 2612 | CA | ARG | 1756 | 20.784 | −20.870 | 10.190 | 1.00 | 33.69 |
| ATOM 2613 | CB | ARG | 1756 | 21.548 | −20.939 | 8.867 | 1.00 | 35.42 |
| ATOM 2614 | CG | ARG | 1756 | 22.639 | −22.003 | 8.800 | 1.00 | 40.87 |
| ATOM 2615 | CD | ARG | 1756 | 23.212 | −22.094 | 7.395 | 1.00 | 42.73 |
| ATOM 2616 | NE | ARG | 1756 | 23.739 | −20.813 | 6.926 | 1.00 | 48.45 |
| ATOM 2618 | CZ | ARG | 1756 | 24.882 | −20.274 | 7.340 | 1.00 | 49.90 |
| ATOM 2619 | NH1 | ARG | 1756 | 25.634 | −20.905 | 8.243 | 1.00 | 49.63 |
| ATOM 2622 | NH2 | ARG | 1756 | 25.276 | −19.105 | 6.844 | 1.00 | 50.86 |
| ATOM 2625 | C | ARG | 1756 | 21.748 | −20.598 | 11.345 | 1.00 | 34.78 |
| ATOM 2626 | O | ARG | 1756 | 21.929 | −21.436 | 12.228 | 1.00 | 36.24 |
| ATOM 2627 | N | ILE | 1757 | 22.325 | −19.402 | 11.363 | 1.00 | 35.35 |
| ATOM 2629 | CA | ILE | 1757 | 23.281 | −19.018 | 12.392 | 1.00 | 35.54 |
| ATOM 2630 | CB | ILE | 1757 | 23.905 | −17.631 | 12.103 | 1.00 | 34.99 |
| ATOM 2631 | CG2 | ILE | 1757 | 24.955 | −17.303 | 13.159 | 1.00 | 32.06 |
| ATOM 2632 | CG1 | ILE | 1757 | 24.547 | −17.626 | 10.711 | 1.00 | 33.77 |
| ATOM 2633 | CD1 | ILE | 1757 | 24.908 | −16.247 | 10.185 | 1.00 | 31.44 |
| ATOM 2634 | C | ILE | 1757 | 22.698 | −19.036 | 13.803 | 1.00 | 36.49 |
| ATOM 2635 | O | ILE | 1757 | 23.337 | −19.548 | 14.716 | 1.00 | 36.40 |
| ATOM 2636 | N | VAL | 1758 | 21.487 | −18.515 | 13.988 | 1.00 | 36.91 |
| ATOM 2638 | CA | VAL | 1758 | 20.881 | −18.498 | 15.322 | 1.00 | 38.68 |
| ATOM 2639 | CB | VAL | 1758 | 19.425 | −17.962 | 15.312 | 1.00 | 37.77 |
| ATOM 2640 | CG1 | VAL | 1758 | 18.806 | −18.059 | 16.708 | 1.00 | 38.39 |
| ATOM 2641 | CG2 | VAL | 1758 | 19.392 | −16.524 | 14.854 | 1.00 | 36.69 |
| ATOM 2642 | C | VAL | 1758 | 20.891 | −19.908 | 15.895 | 1.00 | 41.38 |
| ATOM 2643 | O | VAL | 1758 | 21.405 | −20.138 | 16.997 | 1.00 | 42.41 |
| ATOM 2644 | N | ALA | 1759 | 20.379 | −20.851 | 15.111 | 1.00 | 40.59 |
| ATOM 2646 | CA | ALA | 1759 | 20.325 | −22.247 | 15.508 | 1.00 | 40.84 |
| ATOM 2647 | CB | ALA | 1759 | 19.741 | −23.074 | 14.384 | 1.00 | 40.20 |
| ATOM 2648 | C | ALA | 1759 | 21.703 | −22.787 | 15.897 | 1.00 | 42.52 |
| ATOM 2649 | O | ALA | 1759 | 21.822 | −23.594 | 16.809 | 1.00 | 44.78 |
| ATOM 2650 | N | LEU | 1760 | 22.740 | −22.339 | 15.208 | 1.00 | 43.16 |
| ATOM 2652 | CA | LEU | 1760 | 24.095 | −22.800 | 15.493 | 1.00 | 46.98 |
| ATOM 2653 | CB | LEU | 1760 | 24.921 | −22.761 | 14.203 | 1.00 | 47.66 |
| ATOM 2654 | CG | LEU | 1760 | 24.286 | −23.545 | 13.060 | 1.00 | 52.77 |
| ATOM 2655 | CD1 | LEU | 1760 | 24.973 | −23.222 | 11.745 | 1.00 | 56.58 |
| ATOM 2656 | CD2 | LEU | 1760 | 24.343 | −25.038 | 13.369 | 1.00 | 53.06 |
| ATOM 2657 | C | LEU | 1760 | 24.811 | −21.986 | 16.573 | 1.00 | 47.43 |
| ATOM 2658 | O | LEU | 1760 | 25.917 | −22.335 | 16.989 | 1.00 | 46.58 |
| ATOM 2659 | N | THR | 1761 | 24.183 | −20.914 | 17.034 | 1.00 | 48.65 |
| ATOM 2661 | CA | THR | 1761 | 24.814 | −20.055 | 18.021 | 1.00 | 49.69 |
| ATOM 2662 | CB | THR | 1761 | 24.382 | −18.570 | 17.831 | 1.00 | 50.15 |
| ATOM 2663 | OG1 | THR | 1761 | 24.783 | −18.127 | 16.529 | 1.00 | 49.87 |
| ATOM 2665 | CG2 | THR | 1761 | 25.063 | −17.671 | 18.843 | 1.00 | 48.64 |
| ATOM 2666 | C | THR | 1761 | 24.673 | −20.497 | 19.475 | 1.00 | 50.33 |
| ATOM 2667 | O | THR | 1761 | 23.584 | −20.825 | 19.947 | 1.00 | 48.81 |
| ATOM 2668 | N | SER | 1762 | 25.811 | −20.511 | 20.166 | 1.00 | 50.25 |
| ATOM 2670 | CA | SER | 1762 | 25.891 | −20.890 | 21.566 | 1.00 | 50.98 |
| ATOM 2671 | CB | SER | 1762 | 27.362 | −20.887 | 22.002 | 1.00 | 54.71 |
| ATOM 2672 | OG | SER | 1762 | 27.537 | −21.423 | 23.308 | 1.00 | 57.99 |
| ATOM 2674 | C | SER | 1762 | 25.083 | −19.914 | 22.425 | 1.00 | 49.39 |
| ATOM 2675 | O | SER | 1762 | 25.297 | −18.694 | 22.370 | 1.00 | 48.00 |
| ATOM 3474 | N | SER | 461 | 79.623 | 25.766 | 14.533 | 1.00 | 48.84 |
| ATOM 3476 | CA | SER | 461 | 79.566 | 24.645 | 13.593 | 1.00 | 46.93 |
| ATOM 3477 | CB | SER | 461 | 78.276 | 23.838 | 13.809 | 1.00 | 46.66 |
| ATOM 3478 | C | SER | 461 | 79.676 | 25.114 | 12.138 | 1.00 | 43.02 |
| ATOM 3479 | O | SER | 461 | 79.692 | 24.301 | 11.210 | 1.00 | 40.19 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 3480 | N | GLU | 462 | 79.791 | 26.427 | 11.956 | 1.00 | 41.48 |
| ATOM 3482 | CA | GLU | 462 | 79.904 | 27.034 | 10.628 | 1.00 | 39.59 |
| ATOM 3483 | CB | GLU | 462 | 80.021 | 28.560 | 10.744 | 1.00 | 40.66 |
| ATOM 3484 | C | GLU | 462 | 81.054 | 26.480 | 9.796 | 1.00 | 36.60 |
| ATOM 3485 | O | GLU | 462 | 80.852 | 26.121 | 8.641 | 1.00 | 35.10 |
| ATOM 3486 | N | TYR | 463 | 82.252 | 26.416 | 10.380 | 1.00 | 36.07 |
| ATOM 3488 | CA | TYR | 463 | 83.430 | 25.916 | 9.673 | 1.00 | 35.60 |
| ATOM 3489 | CB | TYR | 463 | 84.597 | 26.906 | 9.755 | 1.00 | 38.15 |
| ATOM 3490 | CG | TYR | 463 | 84.372 | 28.104 | 8.861 | 1.00 | 44.08 |
| ATOM 3491 | CD1 | TYR | 463 | 84.137 | 29.366 | 9.406 | 1.00 | 44.99 |
| ATOM 3492 | CE1 | TYR | 463 | 83.833 | 30.451 | 8.193 | 1.00 | 46.88 |
| ATOM 3493 | CD2 | TYR | 463 | 84.305 | 27.959 | 7.464 | 1.00 | 43.95 |
| ATOM 3494 | CE2 | TYR | 463 | 84.003 | 29.044 | 6.642 | 1.00 | 41.86 |
| ATOM 3495 | CZ | TYR | 463 | 83.768 | 30.282 | 7.215 | 1.00 | 43.89 |
| ATOM 3496 | OH | TYR | 463 | 83.468 | 31.364 | 6.431 | 1.00 | 44.37 |
| ATOM 3498 | C | TYR | 463 | 83.903 | 24.520 | 10.014 | 1.00 | 33.90 |
| ATOM 3499 | O | TYR | 463 | 84.440 | 23.828 | 9.147 | 1.00 | 33.90 |
| ATOM 3500 | N | GLU | 464 | 83.742 | 24.098 | 11.260 | 1.00 | 32.81 |
| ATOM 3502 | CA | GLU | 464 | 84.167 | 22.753 | 11.633 | 1.00 | 34.64 |
| ATOM 3503 | CB | GLU | 464 | 85.663 | 22.727 | 11.919 | 1.00 | 37.48 |
| ATOM 3504 | CG | GLU | 464 | 86.075 | 23.633 | 13.049 | 1.00 | 45.48 |
| ATOM 3505 | CD | GLU | 464 | 87.552 | 23.987 | 13.015 | 1.00 | 55.80 |
| ATOM 3506 | OE1 | GLU | 464 | 87.920 | 24.996 | 13.659 | 1.00 | 61.78 |
| ATOM 3507 | OE2 | GLU | 464 | 88.344 | 23.271 | 2.351 | 1.00 | 58.34 |
| ATOM 3508 | C | GLU | 464 | 83.426 | 22.296 | 12.858 | 1.00 | 33.05 |
| ATOM 3509 | O | GLU | 464 | 83.083 | 23.119 | 13.705 | 1.00 | 34.54 |
| ATOM 3510 | N | LEU | 465 | 83.147 | 21.001 | 12.943 | 1.00 | 32.59 |
| ATOM 3512 | CA | LEU | 465 | 82.462 | 20.463 | 14.114 | 1.00 | 33.74 |
| ATOM 3513 | CB | LEU | 465 | 81.484 | 19.341 | 13.747 | 1.00 | 31.20 |
| ATOM 3514 | CG | LEU | 465 | 80.510 | 19.433 | 12.577 | 1.00 | 32.77 |
| ATOM 3515 | CD1 | LEU | 465 | 79.355 | 18.492 | 12.858 | 1.00 | 26.21 |
| ATOM 3516 | CD2 | LEU | 465 | 80.021 | 20.846 | 12.359 | 1.00 | 31.59 |
| ATOM 3517 | C | LEU | 465 | 83.511 | 19.889 | 15.059 | 1.00 | 35.64 |
| ATOM 3518 | O | LEU | 465 | 84.641 | 19.574 | 14.642 | 1.00 | 33.77 |
| ATOM 3519 | N | PRO | 466 | 83.150 | 19.734 | 16.349 | 1.00 | 36.71 |
| ATOM 3520 | CD | PRO | 466 | 81.865 | 20.104 | 16.967 | 1.00 | 36.97 |
| ATOM 3521 | CA | PRO | 466 | 84.074 | 19.185 | 17.346 | 1.00 | 36.17 |
| ATOM 3522 | CB | PRO | 466 | 83.247 | 19.196 | 18.626 | 1.00 | 36.83 |
| ATOM 3523 | CG | PRO | 466 | 82.274 | 20.326 | 18.394 | 1.00 | 40.80 |
| ATOM 3524 | C | PRO | 466 | 84.419 | 17.765 | 16.950 | 1.00 | 37.39 |
| ATOM 3525 | O | PRO | 466 | 83.626 | 17.077 | 16.297 | 1.00 | 34.71 |
| ATOM 3526 | N | GLU | 467 | 85.611 | 17.330 | 17.315 | 1.00 | 38.40 |
| ATOM 3528 | CA | GLU | 467 | 86.030 | 15.987 | 16.976 | 1.00 | 42.59 |
| ATOM 3529 | CB | GLU | 467 | 87.493 | 15.987 | 16.540 | 1.00 | 49.21 |
| ATOM 3530 | CG | GLU | 467 | 87.922 | 14.682 | 15.891 | 1.00 | 58.93 |
| ATOM 3531 | CD | GLU | 467 | 89.276 | 14.769 | 15.213 | 1.00 | 64.76 |
| ATOM 3532 | OE1 | GLU | 467 | 90.013 | 15.767 | 15.426 | 1.00 | 63.57 |
| ATOM 3533 | OE2 | GLU | 467 | 89.592 | 13.823 | 14.458 | 1.00 | 69.03 |
| ATOM 3534 | C | GLU | 467 | 85.825 | 15.037 | 18.146 | 1.00 | 40.74 |
| ATOM 3535 | O | GLU | 467 | 85.938 | 15.430 | 19.309 | 1.00 | 41.52 |
| ATOM 3536 | N | ASP | 468 | 85.472 | 13.802 | 17.831 | 1.00 | 38.57 |
| ATOM 3538 | CA | ASP | 468 | 85.273 | 12.776 | 18.851 | 1.00 | 40.86 |
| ATOM 3539 | CB | ASP | 468 | 83.793 | 12.640 | 19.224 | 1.00 | 40.27 |
| ATOM 3540 | CG | ASP | 468 | 83.566 | 11.697 | 20.397 | 1.00 | 41.36 |
| ATOM 3541 | OD1 | ASP | 468 | 82.429 | 11.670 | 20.919 | 1.00 | 42.50 |
| ATOM 3542 | OD2 | ASP | 468 | 84.514 | 10.992 | 20.807 | 1.00 | 38.55 |
| ATOM 3543 | C | ASP | 468 | 85.803 | 11.470 | 18.278 | 1.00 | 40.75 |
| ATOM 3544 | O | ASP | 468 | 85.068 | 10.701 | 17.650 | 1.00 | 41.80 |
| ATOM 3545 | N | PRO | 469 | 87.100 | 11.209 | 18.481 | 1.00 | 41.71 |
| ATOM 3546 | CD | PRO | 469 | 88.00I | 12.062 | 19.276 | 1.00 | 41.87 |
| ATOM 3547 | CA | PRO | 469 | 87.801 | 10.011 | 18.012 | 1.00 | 40.07 |
| ATOM 3548 | CB | PRO | 469 | 89.091 | 10.042 | 18.831 | 1.00 | 40.42 |
| ATOM 3549 | CG | PRO | 469 | 89.366 | 11.505 | 18.938 | 1.00 | 39.42 |
| ATOM 3550 | C | PRO | 469 | 87.033 | 8.720 | 18.260 | 1.00 | 41.00 |
| ATOM 3551 | O | PRO | 469 | 87.032 | 7.822 | 17.414 | 1.00 | 41.75 |
| ATOM 3552 | N | ARG | 470 | 86.361 | 8.639 | 19.411 | 1.00 | 40.70 |
| ATOM 3554 | CA | ARG | 470 | 85.600 | 7.446 | 19.779 | 1.00 | 41.03 |
| ATOM 3555 | CB | ARG | 470 | 84.827 | 7.677 | 21.075 | 1.00 | 44.18 |
| ATOM 3556 | CG | ARG | 470 | 85.628 | 8.240 | 22.211 | 1.00 | 47.89 |
| ATOM 3557 | CD | ARG | 470 | 84.719 | 8.518 | 23.400 | 1.00 | 50.56 |
| ATOM 3558 | NE | ARG | 470 | 83.576 | 9.345 | 23.023 | 1.00 | 51.20 |
| ATOM 3560 | CZ | ARG | 470 | 82.695 | 9.845 | 23.881 | 1.00 | 52.24 |
| ATOM 3561 | NH1 | ARG | 470 | 82.818 | 9.608 | 25.183 | 1.00 | 51.31 |
| ATOM 3564 | NH2 | ARG | 470 | 81.672 | 10.564 | 23.432 | 1.00 | 52.73 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 3567 | C | ARG | 470 | 84.596 | 7.004 | 18.723 | 1.00 | 39.03 |
| ATOM 3568 | O | ARG | 470 | 84.401 | 5.813 | 18.518 | 1.00 | 40.72 |
| ATOM 3569 | N | TRP | 471 | 83.972 | 7.965 | 18.050 | 1.00 | 37.77 |
| ATOM 3571 | CA | TRP | 471 | 82.948 | 7.656 | 17.059 | 1.00 | 36.73 |
| ATOM 3572 | CB | TRP | 471 | 81.672 | 8.401 | 17.432 | 1.00 | 35.05 |
| ATOM 3573 | CG | TRP | 471 | 81.044 | 7.862 | 18.673 | 1.00 | 34.85 |
| ATOM 3574 | CD2 | TRP | 471 | 80.235 | 6.687 | 18.766 | 1.00 | 34.96 |
| ATOM 3575 | CE2 | TRP | 471 | 79.831 | 6.564 | 20.116 | 1.00 | 35.12 |
| ATOM 3576 | CE3 | TRP | 471 | 79.810 | 5.721 | 17.838 | 1.00 | 33.25 |
| ATOM 3577 | CD1 | TRP | 471 | 81.106 | 8.390 | 19.933 | 1.00 | 29.97 |
| ATOM 3578 | NE1 | TRP | 471 | 80.377 | 7.616 | 20.805 | 1.00 | 32.18 |
| ATOM 3580 | CZ2 | TRP | 471 | 79.017 | 5.512 | 20.560 | 1.00 | 33.98 |
| ATOM 3581 | CZ3 | TRP | 471 | 79.002 | 4.673 | 18.282 | 1.00 | 33.71 |
| ATOM 3582 | CH2 | TRP | 471 | 78.618 | 4.580 | 19.632 | 1.00 | 33.28 |
| ATOM 3583 | C | TRP | 471 | 83.275 | 7.930 | 15.599 | 1.00 | 37.27 |
| ATOM 3584 | O | TRP | 471 | 82.580 | 7.445 | 14.695 | 1.00 | 36.61 |
| ATOM 3585 | N | GLU | 472 | 84.341 | 8.680 | 15.361 | 1.00 | 37.93 |
| ATOM 3587 | CA | GLU | 472 | 84.706 | 9.054 | 14.004 | 1.00 | 37.08 |
| ATOM 3588 | CB | GLU | 472 | 85.865 | 10.049 | 14.045 | 1.00 | 36.30 |
| ATOM 3589 | CG | GLU | 472 | 86.026 | 10.851 | 12.773 | 1.00 | 33.51 |
| ATOM 3590 | CD | GLU | 472 | 84.931 | 11.895 | 12.580 | 1.00 | 33.80 |
| ATOM 3591 | OE1 | GLU | 472 | 84.385 | 12.408 | 13.581 | 1.00 | 35.19 |
| ATOM 3592 | OE2 | GLU | 472 | 84.641 | 12.226 | 11.412 | 1.00 | 32.51 |
| ATOM 3593 | C | GLU | 472 | 85.021 | 7.923 | 13.032 | 1.00 | 37.88 |
| ATOM 3594 | O | GLU | 472 | 85.774 | 7.000 | 13.351 | 1.00 | 38.20 |
| ATOM 3595 | N | LEU | 473 | 84.422 | 7.992 | 11.846 | 1.00 | 37.55 |
| ATOM 3597 | CA | LEU | 473 | 84.678 | 7.004 | 10.813 | 1.00 | 36.93 |
| ATOM 3598 | CB | LEU | 473 | 83.404 | 6.244 | 10.443 | 1.00 | 37.08 |
| ATOM 3599 | CG | LEU | 473 | 83.680 | 5.086 | 9.470 | 1.00 | 39.14 |
| ATOM 3600 | CD1 | LEU | 473 | 84.196 | 3.877 | 10.250 | 1.00 | 38.39 |
| ATOM 3601 | CD2 | LEU | 473 | 82.433 | 4.716 | 8.672 | 1.00 | 39.46 |
| ATOM 3602 | C | LEU | 473 | 85.207 | 7.732 | 9.577 | 1.00 | 38.52 |
| ATOM 3603 | O | LEU | 473 | 84.660 | 8.764 | 9.182 | 1.00 | 38.67 |
| ATOM 3604 | N | PRO | 474 | 86.334 | 7.259 | 9.005 | 1.00 | 39.02 |
| ATOM 3605 | CD | PRO | 474 | 87.259 | 6.259 | 9.571 | 1.00 | 38.39 |
| ATOM 3606 | CA | PRO | 474 | 86.918 | 7.877 | 7.809 | 1.00 | 38.24 |
| ATOM 3607 | CB | PRO | 474 | 88.188 | 7.049 | 7.590 | 1.00 | 38.40 |
| ATOM 3608 | CG | PRO | 474 | 88.580 | 6.680 | 8.979 | 1.00 | 35.50 |
| ATOM 3609 | C | PRO | 474 | 85.942 | 7.727 | 6.642 | 1.00 | 37.56 |
| ATOM 3610 | O | PRO | 474 | 85.415 | 6.641 | 6.400 | 1.00 | 37.88 |
| ATOM 3611 | N | ARG | 475 | 85.720 | 8.809 | 5.907 | 1.00 | 37.73 |
| ATOM 3613 | CA | ARG | 475 | 84.779 | 8.790 | 4.795 | 1.00 | 40.01 |
| ATOM 3614 | CB | ARG | 475 | 84.655 | 10.183 | 4.182 | 1.00 | 38.31 |
| ATOM 3615 | CG | ARG | 475 | 84.217 | 11.236 | 5.198 | 1.00 | 35.15 |
| ATOM 3616 | CD | ARG | 475 | 84.069 | 12.631 | 4.586 | 1.00 | 33.92 |
| ATOM 3617 | NE | ARG | 475 | 83.718 | 13.603 | 5.616 | 1.00 | 30.45 |
| ATOM 3619 | CZ | ARG | 475 | 82.475 | 13.880 | 5.993 | 1.00 | 26.48 |
| ATOM 3620 | NH1 | ARG | 475 | 81.444 | 13.284 | 5.407 | 1.00 | 24.80 |
| ATOM 3623 | NH2 | ARG | 475 | 82.271 | 14.650 | 7.056 | 1.00 | 25.16 |
| ATOM 3626 | C | ARG | 475 | 85.054 | 7.735 | 3.728 | 1.00 | 42.18 |
| ATOM 3627 | O | ARG | 475 | 84.125 | 7.197 | 3.128 | 1.00 | 41.43 |
| ATOM 3628 | N | ASP | 476 | 86.322 | 7.391 | 3.535 | 1.00 | 45.44 |
| ATOM 3630 | CA | ASP | 476 | 86.676 | 6.387 | 2.541 | 1.00 | 49.80 |
| ATOM 3631 | CB | ASP | 476 | 88.192 | 6.343 | 2.329 | 1.00 | 50.95 |
| ATOM 3632 | CG | ASP | 476 | 88.944 | 5.975 | 3.585 | 1.00 | 53.89 |
| ATOM 3633 | OD1 | ASP | 476 | 89.303 | 4.789 | 3.731 | 1.00 | 59.71 |
| ATOM 3634 | OD2 | ASP | 476 | 89.176 | 6.867 | 4.427 | 1.00 | 57.39 |
| ATOM 3635 | C | ASP | 476 | 86.149 | 5.010 | 2.950 | 1.00 | 51.23 |
| ATOM 3636 | O | ASP | 476 | 86.051 | 4.102 | 2.121 | 1.00 | 53.54 |
| ATOM 3637 | N | ARG | 477 | 85.814 | 4.664 | 4.230 | 1.00 | 50.49 |
| ATOM 3639 | CA | ARG | 477 | 85.285 | 3.610 | 4.753 | 1.00 | 49.32 |
| ATOM 3640 | CB | ARG | 477 | 85.834 | 3.364 | 6.152 | 1.00 | 49.79 |
| ATOM 3641 | CG | ARG | 477 | 87.237 | 2.806 | 6.112 | 1.00 | 53.06 |
| ATOM 3642 | CD | ARG | 477 | 87.960 | 2.981 | 7.420 | 1.00 | 56.76 |
| ATOM 3643 | NE | ARG | 477 | 87.310 | 2.293 | 8.529 | 1.00 | 59.35 |
| ATOM 3645 | CZ | ARG | 477 | 87.728 | 2.371 | 9.789 | 1.00 | 62.23 |
| ATOM 3646 | NH1 | ARG | 477 | 88.793 | 3.103 | 10.101 | 1.00 | 63.66 |
| ATOM 3649 | NH2 | ARG | 477 | 87.067 | 1.741 | 10.745 | 1.00 | 64.35 |
| ATOM 3652 | C | ARG | 477 | 83.755 | 3.547 | 4.750 | 1.00 | 48.04 |
| ATOM 3653 | O | ARG | 477 | 83.160 | 2.693 | 5.404 | 1.00 | 48.09 |
| ATOM 3654 | N | LEU | 478 | 83.129 | 4.412 | 3.958 | 1.00 | 45.38 |
| ATOM 3656 | CA | LEU | 478 | 81.685 | 4.469 | 3.870 | 1.00 | 41.60 |
| ATOM 3657 | CB | LEU | 478 | 81.168 | 5.578 | 4.790 | 1.00 | 38.39 |
| ATOM 3658 | CG | LEU | 478 | 79.651 | 5.699 | 4.894 | 1.00 | 36.38 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 3659 | CD1 | LEU | 478 | 79.113 | 4.595 | 5.802 | 1.00 | 33.98 |
| ATOM 3660 | CD2 | LEU | 478 | 79.293 | 7.068 | 5.441 | 1.00 | 40.06 |
| ATOM 3661 | C | LEU | 478 | 81.279 | 4.774 | 2.433 | 1.00 | 41.92 |
| ATOM 3662 | O | LEU | 478 | 81.696 | 5.780 | 1.870 | 1.00 | 43.99 |
| ATOM 3663 | N | VAL | 479 | 80.466 | 3.904 | 1.844 | 1.00 | 42.29 |
| ATOM 3665 | CA | VAL | 479 | 79.992 | 4.082 | 0.471 | 1.00 | 41.07 |
| ATOM 3666 | CB | VAL | 479 | 80.227 | 2.816 | −0.397 | 1.00 | 41.13 |
| ATOM 3667 | CG1 | VAL | 479 | 79.719 | 3.057 | 1.810 | 1.00 | 40.19 |
| ATOM 3668 | CG2 | VAL | 479 | 61.700 | 2.448 | −0.420 | 1.00 | 41.36 |
| ATOM 3669 | C | VAL | 479 | 78.500 | 4.345 | 0.540 | 1.00 | 40.44 |
| ATOM 3670 | O | VAL | 479 | 77.719 | 3.451 | 0.885 | 1.00 | 39.86 |
| ATOM 3671 | N | LEU | 480 | 78.112 | 5.582 | 0.253 | 1.00 | 41.37 |
| ATOM 3673 | CA | LEU | 480 | 76.706 | 5.973 | 0.293 | 1.00 | 41.63 |
| ATOM 3674 | CB | LEU | 480 | 76.568 | 7.492 | 0.166 | 1.00 | 39.91 |
| ATOM 3675 | CG | LEU | 480 | 77.236 | 8.332 | 1.261 | 1.00 | 39.23 |
| ATOM 3676 | CD1 | LEU | 480 | 76.890 | 9.800 | 1.039 | 1.00 | 37.73 |
| ATOM 3677 | CD2 | LEU | 480 | 76.791 | 7.877 | 2.647 | 1.00 | 35.18 |
| ATOM 3678 | C | LEU | 480 | 75.899 | 5.273 | −0.788 | 1.00 | 42.21 |
| ATOM 3679 | O | LEU | 480 | 76.395 | 5.048 | −1.890 | 1.00 | 45.27 |
| ATOM 3680 | N | GLY | 481 | 74.650 | 4.947 | −0.476 | 1.00 | 41.51 |
| ATOM 3682 | CA | GLY | 481 | 73.812 | 4.257 | −1.433 | 1.00 | 40.19 |
| ATOM 3683 | C | GLY | 481 | 72.446 | 4.872 | −1.640 | 1.00 | 41.58 |
| ATOM 3684 | O | GLY | 481 | 72.262 | 6.091 | −1.550 | 1.00 | 41.35 |
| ATOM 3685 | N | LYS | 482 | 71.474 | 4.009 | −1.908 | 1.00 | 42.65 |
| ATOM 3687 | CA | LYS | 482 | 70.105 | 4.429 | −2.166 | 1.00 | 44.17 |
| ATOM 3688 | CB | LYS | 482 | 69.240 | 3.221 | −2.542 | 1.00 | 45.66 |
| ATOM 3689 | C | LYS | 482 | 69.475 | 5.148 | −0.994 | 1.00 | 44.86 |
| ATOM 3690 | O | LYS | 482 | 69.638 | 4.752 | 0.155 | 1.00 | 45.23 |
| ATOM 3691 | N | PRO | 483 | 68.749 | 6.234 | −1.273 | 1.00 | 45.94 |
| ATOM 3692 | CD | PRO | 483 | 68.518 | 6.880 | −2.576 | 1.00 | 46.96 |
| ATOM 3693 | CA | PRO | 483 | 68.099 | 6.983 | −0.206 | 1.00 | 47.79 |
| ATOM 3694 | CB | PRO | 483 | 67.542 | 8.200 | −0.947 | 1.00 | 47.02 |
| ATOM 3695 | CG | PRO | 483 | 67.269 | 7.666 | −2.307 | 1.00 | 46.65 |
| ATOM 3696 | C | PRO | 483 | 66.991 | 6.151 | 0.429 | 1.00 | 48.74 |
| ATOM 3697 | O | PRO | 483 | 66.314 | 5.376 | −0.251 | 1.00 | 48.01 |
| ATOM 3698 | N | LEU | 484 | 66.858 | 6.268 | 1.742 | 1.00 | 49.91 |
| ATOM 3700 | CA | LEU | 484 | 65.837 | 5.547 | 2.477 | 1.00 | 53.93 |
| ATOM 3701 | CB | LEU | 484 | 66.433 | 4.883 | 3.720 | 1.00 | 50.17 |
| ATOM 3702 | CG | LEU | 484 | 67.517 | 3.844 | 3.445 | 1.00 | 48.93 |
| ATOM 3703 | CD1 | LEU | 484 | 68.226 | 3.460 | 4.731 | 1.00 | 49.05 |
| ATOM 3704 | CD2 | LEU | 484 | 66.906 | 2.630 | 2.784 | 1.00 | 47.03 |
| ATOM 3705 | C | LEU | 484 | 64.715 | 6.501 | 2.878 | 1.00 | 58.70 |
| ATOM 3706 | O | LEU | 484 | 63.571 | 6.075 | 3.055 | 1.00 | 61.95 |
| ATOM 3707 | N | GLY | 485 | 65.027 | 7.788 | 3.006 | 1.00 | 60.35 |
| ATOM 3709 | CA | GLY | 485 | 63.998 | 8.737 | 3.397 | 1.00 | 64.00 |
| ATOM 3710 | C | GLY | 485 | 64.445 | 10.183 | 3.476 | 1.00 | 66.09 |
| ATOM 3711 | O | GLY | 485 | 65.643 | 10.468 | 3.577 | 1.00 | 65.26 |
| ATOM 3712 | N | GLU | 486 | 63.471 | 11.090 | 3.458 | 1.00 | 67.18 |
| ATOM 3714 | CA | GLU | 486 | 63.733 | 12.525 | 3.508 | 1.00 | 68.69 |
| ATOM 3715 | CB | GLU | 486 | 63.873 | 13.084 | 2.091 | 1.00 | 69.88 |
| ATOM 3716 | C | GLU | 486 | 62.618 | 13.249 | 4.245 | 1.00 | 68.80 |
| ATOM 3717 | O | GLU | 486 | 61.481 | 12.775 | 4.295 | 1.00 | 69.26 |
| ATOM 3718 | N | GLY | 487 | 62.943 | 14.415 | 4.791 | 1.00 | 68.47 |
| ATOM 3720 | CA | GLY | 487 | 61.960 | 15.188 | 5.520 | 1.00 | 67.56 |
| ATOM 3721 | C | GLY | 487 | 62.373 | 16.635 | 5.634 | 1.00 | 66.71 |
| ATOM 3722 | O | GLY | 487 | 63.040 | 17.172 | 4.747 | 1.00 | 66.48 |
| ATOM 3723 | N | ALA | 488 | 61.979 | 17.265 | 6.735 | 1.00 | 67.22 |
| ATOM 3725 | CA | ALA | 488 | 62.304 | 18.661 | 6.992 | 1.00 | 67.78 |
| ATOM 3726 | CB | ALA | 488 | 61.637 | 19.121 | 8.283 | 1.00 | 68.97 |
| ATOM 3727 | C | ALA | 488 | 63.817 | 18.830 | 7.085 | 1.00 | 67.38 |
| ATOM 3728 | O | ALA | 488 | 64.413 | 18.597 | 8.141 | 1.00 | 67.14 |
| ATOM 3729 | N | PHE | 489 | 64.429 | 19.155 | 5.946 | 1.00 | 66.22 |
| ATOM 3731 | CA | PHE | 489 | 65.677 | 19.364 | 5.831 | 1.00 | 65.49 |
| ATOM 3732 | CB | PHE | 489 | 61.277 | 20.699 | 6.467 | 1.00 | 66.11 |
| ATOM 3733 | C | PHE | 489 | 66.749 | 18.207 | 6.368 | 1.00 | 64.07 |
| ATOM 3734 | O | PHE | 489 | 67.924 | 18.399 | 6.731 | 1.00 | 61.56 |
| ATOM 3735 | N | GLY | 490 | 66.171 | 17.005 | 6.349 | 1.00 | 60.79 |
| ATOM 3737 | CA | GLY | 490 | 66.852 | 15.803 | 6.797 | 1.00 | 54.72 |
| ATOM 3738 | C | GLY | 490 | 66.787 | 14.760 | 5.692 | 1.00 | 51.78 |
| ATOM 3739 | O | GLY | 490 | 65.765 | 14.624 | 5.013 | 1.00 | 49.17 |
| ATOM 3740 | N | GLN | 491 | 67.874 | 14.015 | 5.528 | 1.00 | 49.97 |
| ATOM 3742 | CA | GLN | 491 | 68.000 | 12.984 | 4.504 | 1.00 | 48.06 |
| ATOM 3743 | CB | GLN | 491 | 68.891 | 13.520 | 3.371 | 1.00 | 51.02 |
| ATOM 3744 | CG | GLN | 491 | 69.286 | 12.518 | 2.289 | 1.00 | 56.00 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 3745 | CD | GLN | 491 | 70.155 | 13.143 | 1.202 | 1.00 | 58.93 |
| ATOM 3746 | OE1 | GLN | 491 | 70.483 | 14.330 | 1.255 | 1.00 | 60.31 |
| ATOM 3747 | NE2 | GLN | 491 | 70.529 | 12.341 | 0.202 | 1.00 | 60.19 |
| ATOM 3750 | C | GLN | 491 | 68.623 | 11.720 | 5.114 | 1.00 | 45.59 |
| ATOM 3751 | O | GLN | 491 | 69.511 | 11.792 | 5.959 | 1.00 | 45.22 |
| ATOM 3752 | N | VAL | 492 | 68.148 | 10.561 | 4.693 | 1.00 | 43.19 |
| ATOM 3754 | CA | VAL | 492 | 68.676 | 9.304 | 5.193 | 1.00 | 41.54 |
| ATOM 3755 | CB | VAL | 492 | 67.655 | 8.584 | 6.087 | 1.00 | 41.74 |
| ATOM 3756 | CG1 | VAL | 492 | 68.217 | 7.248 | 6.561 | 1.00 | 43.70 |
| ATOM 3757 | CG2 | VAL | 492 | 67.283 | 9.463 | 7.269 | 1.00 | 44.07 |
| ATOM 3758 | C | VAL | 492 | 68.971 | 8.424 | 3.993 | 1.00 | 39.72 |
| ATOM 3759 | O | VAL | 492 | 68.125 | 8.271 | 3.108 | 1.00 | 39.81 |
| ATOM 3760 | N | VAL | 493 | 70.176 | 7.872 | 3.942 | 1.00 | 36.38 |
| ATOM 3762 | CA | VAL | 493 | 70.545 | 7.001 | 2.844 | 1.00 | 35.88 |
| ATOM 3763 | CB | VAL | 493 | 71.580 | 7.666 | 1.869 | 1.00 | 36.92 |
| ATOM 3764 | CG1 | VAL | 493 | 71.142 | 9.069 | 1.485 | 1.00 | 36.64 |
| ATOM 3765 | CG2 | VAL | 493 | 72.978 | 7.670 | 2.469 | 1.00 | 38.29 |
| ATOM 3766 | C | VAL | 493 | 71.131 | 5.689 | 3.351 | 1.00 | 36.03 |
| ATOM 3767 | O | VAL | 493 | 71.693 | 5.617 | 4.443 | 1.00 | 36.57 |
| ATOM 3768 | N | LEU | 494 | 70.947 | 4.637 | 2.571 | 1.00 | 34.91 |
| ATOM 3770 | CA | LEU | 494 | 71.500 | 3.344 | 2.909 | 1.00 | 36.04 |
| ATOM 3771 | CB | LEU | 494 | 70.809 | 2.244 | 2.094 | 1.00 | 37.43 |
| ATOM 3772 | CG | LEU | 494 | 71.312 | 0.814 | 2.269 | 1.00 | 36.62 |
| ATOM 3773 | CD1 | LEU | 494 | 71.327 | 0.437 | 3.735 | 1.00 | 36.37 |
| ATOM 3774 | CD2 | LEU | 494 | 70.419 | −0.118 | 1.479 | 1.00 | 40.70 |
| ATOM 3775 | C | LEU | 494 | 72.967 | 3.451 | 2.510 | 1.00 | 37.08 |
| ATOM 3776 | O | LEU | 494 | 73.308 | 4.160 | 1.560 | 1.00 | 34.90 |
| ATOM 3777 | N | ALA | 495 | 73.839 | 2.779 | 3.243 | 1.00 | 37.18 |
| ATOM 3779 | CA | ALA | 495 | 75.246 | 2.810 | 2.918 | 1.00 | 39.84 |
| ATOM 3780 | CB | ALA | 495 | 75.885 | 4.066 | 3.541 | 1.00 | 39.29 |
| ATOM 3781 | C | ALA | 495 | 75.949 | 1.578 | 3.400 | 1.00 | 41.68 |
| ATOM 3782 | O | ALA | 495 | 75.400 | 0.808 | 4.189 | 1.00 | 41.53 |
| ATOM 3783 | N | GLU | 496 | 77.149 | 1.348 | 2.881 | 1.00 | 43.44 |
| ATOM 3785 | CA | GLU | 496 | 77.936 | 0.202 | 3.297 | 1.00 | 42.86 |
| ATOM 3786 | CB | GLU | 496 | 78.328 | −0.663 | 2.101 | 1.00 | 44.63 |
| ATOM 3787 | CG | GLU | 496 | 77.120 | −1.167 | 1.320 | 1.00 | 53.31 |
| ATOM 3788 | CD | GLU | 496 | 77.386 | −2.450 | 0.545 | 1.00 | 59.48 |
| ATOM 3789 | OE1 | GLU | 496 | 76.494 | −3.332 | 0.534 | 1.00 | 62.39 |
| ATOM 3790 | OE2 | GLU | 496 | 78.477 | −2.580 | −0.053 | 1.00 | 62.15 |
| ATOM 3791 | C | GLU | 496 | 79.150 | 0.750 | 4.006 | 1.00 | 40.96 |
| ATOM 3792 | O | GLU | 496 | 79.889 | 1.568 | 3.455 | 1.00 | 40.81 |
| ATOM 3793 | N | ALA | 497 | 79.267 | 0.411 | 5.280 | 1.00 | 40.79 |
| ATOM 3795 | CA | ALA | 497 | 80.381 | 0.857 | 6.096 | 1.00 | 41.84 |
| ATOM 3796 | CB | ALA | 497 | 79.888 | 1.240 | 7.478 | 1.00 | 38.80 |
| ATOM 3797 | C | ALA | 497 | 81.394 | −0.280 | 6.181 | 1.00 | 44.72 |
| ATOM 3798 | O | ALA | 497 | 81.019 | −1.445 | 6.215 | 1.00 | 44.78 |
| ATOM 3799 | N | ILE | 498 | 82.678 | 0.054 | 6.183 | 1.00 | 48.03 |
| ATOM 3801 | CA | ILE | 498 | 83.729 | −0.952 | 6.255 | 1.00 | 48.78 |
| ATOM 3802 | CB | ILE | 498 | 84.654 | −0.894 | 5.014 | 1.00 | 50.57 |
| ATOM 3803 | CG2 | ILE | 498 | 85.748 | −1.954 | 5.119 | 1.00 | 51.32 |
| ATOM 3804 | CG1 | ILE | 498 | 83.851 | −1.103 | 3.726 | 1.00 | 51.90 |
| ATOM 3805 | CD1 | ILE | 498 | 83.139 | 0.146 | 3.198 | 1.00 | 55.47 |
| ATOM 3806 | C | ILE | 498 | 84.573 | −0.754 | 7.511 | 1.00 | 48.31 |
| ATOM 3807 | O | ILE | 498 | 85.005 | 0.359 | 7.805 | 1.00 | 47.90 |
| ATOM 3808 | N | GLY | 499 | 84.754 | −1.829 | 8.271 | 1.30 | 49.29 |
| ATOM 3810 | CA | GLY | 499 | 85.563 | −1.774 | 9.479 | 1.00 | 53.17 |
| ATOM 3811 | C | GLY | 499 | 85.076 | −0.944 | 10.657 | 1.00 | 57.22 |
| ATOM 3812 | O | GLY | 499 | 85.885 | −0.341 | 11.364 | 1.00 | 59.20 |
| ATOM 3813 | N | LEU | 500 | 83.768 | −0.948 | 10.909 | 1.00 | 58.51 |
| ATOM 3815 | CA | LEU | 500 | 83.193 | −0.189 | 12.023 | 1.00 | 57.80 |
| ATOM 3816 | CB | LEU | 500 | 81.705 | −0.519 | 12.181 | 1.00 | 55.67 |
| ATOM 3817 | CG | LEU | 500 | 80.789 | 0.036 | 11.086 | 1.00 | 54.81 |
| ATOM 3818 | CD1 | LEU | 500 | 79.361 | −0.445 | 11.293 | 1.00 | 53.00 |
| ATOM 3819 | CD2 | LEU | 500 | 80.854 | 1.561 | 11.089 | 1.00 | 53.27 |
| ATOM 3820 | C | LEU | 500 | 83.926 | −0.466 | 13.333 | 1.00 | 58.15 |
| ATOM 3821 | O | LEU | 500 | 84.461 | −1.560 | 13.529 | 1.00 | 60.29 |
| ATOM 3822 | N | PRO | 505 | 87.397 | −6.022 | 10.511 | 1.00 | 77.18 |
| ATOM 3823 | CD | PRO | 505 | 88.509 | −6.651 | 11.242 | 1.00 | 78.26 |
| ATOM 3824 | CA | PRO | 505 | 87.755 | −4.660 | 10.097 | 1.00 | 75.62 |
| ATOM 3825 | CB | PRO | 505 | 89.166 | −4.487 | 10.669 | 1.00 | 75.77 |
| ATOM 3826 | CG | PRO | 505 | 89.696 | −5.884 | 10.715 | 1.00 | 77.07 |
| ATOM 3827 | C | PRO | 505 | 87.709 | −4.440 | 8.583 | 1.00 | 73.15 |
| ATOM 3828 | O | PRO | 505 | 87.772 | −3.308 | 8.105 | 1.00 | 72.63 |
| ATOM 3829 | N | ASN | 506 | 87.595 | −5.524 | 7.830 | 1.00 | 71.27 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 3831 | CA | ASN | 506 | 87.518 | −5.421 | 6.380 | 1.00 | 69.14 |
| ATOM 3832 | CB | ASN | 506 | 88.577 | −6.313 | 5.728 | 1.00 | 70.76 |
| ATOM 3833 | C | ASN | 506 | 86.119 | −5.840 | 5.940 | 1.00 | 67.30 |
| ATOM 3834 | O | ASN | 506 | 85.834 | −5.957 | 4.750 | 1.00 | 67.03 |
| ATOM 3835 | N | ARG | 507 | 85.250 | −6.064 | 6.921 | 1.00 | 65.27 |
| ATOM 3837 | CA | ARG | 507 | 83.876 | −6.479 | 6.669 | 1.00 | 62.86 |
| ATOM 3838 | CB | ARG | 507 | 83.335 | −7.267 | 7.864 | 1.00 | 65.45 |
| ATOM 3839 | C | ARG | 507 | 82.991 | −5.274 | 6.443 | 1.00 | 59.56 |
| ATOM 3840 | O | ARG | 507 | 83.161 | −4.247 | 7.100 | 1.00 | 59.70 |
| ATOM 3841 | N | VAL | 508 | 82.057 | −5.397 | 5.509 | 1.00 | 56.65 |
| ATOM 3843 | CA | VAL | 508 | 81.135 | −4.310 | 5.226 | 1.00 | 55.48 |
| ATOM 3844 | CB | VAL | 508 | 80.850 | −4.157 | 3.719 | 1.00 | 55.71 |
| ATOM 3845 | CG1 | VAL | 508 | 82.146 | −3.962 | 2.962 | 1.00 | 58.18 |
| ATOM 3846 | CG2 | VAL | 508 | 80.096 | −5.356 | 3.188 | 1.00 | 58.76 |
| ATOM 3847 | C | VAL | 508 | 79.833 | −4.537 | 5.979 | 1.00 | 53.10 |
| ATOM 3848 | O | VAL | 508 | 79.352 | −5.665 | 6.091 | 1.00 | 54.25 |
| ATOM 3849 | N | THR | 509 | 79.282 | −3.460 | 6.514 | 1.00 | 50.06 |
| ATOM 3851 | CA | THR | 509 | 78.041 | −3.512 | 7.260 | 1.00 | 45.70 |
| ATOM 3852 | CB | THR | 509 | 78.256 | −3.029 | 8.715 | 1.00 | 45.59 |
| ATOM 3853 | OG1 | THR | 509 | 79.395 | −3.696 | 9.279 | 1.00 | 43.86 |
| ATOM 3855 | CG2 | THR | 509 | 77.028 | −3.328 | 9.573 | 1.00 | 44.19 |
| ATOM 3856 | C | THR | 509 | 77.064 | −2.574 | 6.564 | 1.00 | 43.57 |
| ATOM 3857 | O | THR | 509 | 77.416 | −1.444 | 6.221 | 1.00 | 41.15 |
| ATOM 3858 | N | LYS | 510 | 75.871 | −3.073 | 6.268 | 1.00 | 42.96 |
| ATOM 3860 | CA | LYS | 510 | 74.847 | −2.253 | 3.640 | 1.00 | 41.91 |
| ATOM 3861 | CB | LYS | 510 | 73.740 | −3.144 | 5.091 | 1.00 | 44.74 |
| ATOM 3862 | CG | LYS | 510 | 72.864 | −2.461 | 4.069 | 1.00 | 51.83 |
| ATOM 3863 | CD | LYS | 510 | 73.392 | −2.645 | 2.659 | 1.00 | 55.00 |
| ATOM 3864 | CE | LYS | 510 | 72.769 | −3.879 | 2.020 | 1.00 | 58.36 |
| ATOM 3865 | NZ | LYS | 510 | 73.069 | −5.131 | 2.769 | 1.00 | 58.57 |
| ATOM 3869 | C | LYS | 510 | 74.322 | −1.367 | 6.789 | 1.00 | 40.74 |
| ATOM 3870 | O | LYS | 510 | 73.909 | −1.874 | 7.837 | 1.00 | 40.26 |
| ATOM 3871 | N | VAL | 511 | 74.413 | −0.052 | 6.624 | 1.00 | 37.21 |
| ATOM 3873 | CA | VAL | 511 | 73.989 | 0.577 | 7.661 | 1.00 | 33.44 |
| ATOM 3874 | CB | VAL | 511 | 75.227 | 1.515 | 8.362 | 1.00 | 34.53 |
| ATOM 3875 | CG1 | VAL | 511 | 76.100 | 0.436 | 9.014 | 1.00 | 31.98 |
| ATOM 3876 | CG2 | VAL | 511 | 76.048 | 2.322 | 7.358 | 1.00 | 34.82 |
| ATOM 3877 | C | VAL | 511 | 73.134 | 1.989 | 7.087 | 1.00 | 31.34 |
| ATOM 3878 | O | VAL | 511 | 73.025 | 2.130 | 5.871 | 1.00 | 31.33 |
| ATOM 3879 | N | ALA | 512 | 72.485 | 2.748 | 7.961 | 1.00 | 30.70 |
| ATOM 3881 | CA | ALA | 512 | 71.671 | 3.376 | 7.523 | 1.00 | 30.81 |
| ATOM 3882 | CB | ALA | 512 | 70.305 | 3.879 | 8.206 | 1.00 | 29.85 |
| ATOM 3883 | C | ALA | 512 | 72.453 | 5.124 | 7.904 | 1.00 | 31.30 |
| ATOM 3884 | O | ALA | 512 | 73.036 | 5.197 | 8.996 | 1.00 | 30.24 |
| ATOM 3885 | N | VAL | 513 | 72.480 | 6.096 | 6.999 | 1.00 | 30.86 |
| ATOM 3887 | CA | VAL | 513 | 73.208 | 7.332 | 7.238 | 1.00 | 30.58 |
| ATOM 3888 | CB | VAL | 513 | 74.358 | 7.525 | 6.223 | 1.00 | 31.11 |
| ATOM 3869 | CG1 | VAL | 513 | 75.132 | 8.788 | 6.547 | 1.00 | 29.63 |
| ATOM 3890 | CG2 | VAL | 513 | 75.290 | 6.317 | 6.223 | 1.00 | 28.70 |
| ATOM 3891 | C | VAL | 513 | 72.300 | 8.556 | 7.189 | 1.00 | 31.28 |
| ATOM 3892 | O | VAL | 513 | 71.645 | 8.824 | 6.167 | 1.00 | 30.12 |
| ATOM 3893 | N | LYS | 514 | 72.229 | 9.257 | 8.321 | 1.00 | 31.03 |
| ATOM 3895 | CA | LYS | 514 | 71.439 | 10.479 | 8.451 | 1.00 | 32.56 |
| ATOM 3896 | CB | LYS | 514 | 70.881 | 10.635 | 9.870 | 1.00 | 34.31 |
| ATOM 3897 | CG | LYS | 514 | 69.977 | 9.516 | 10.326 | 1.00 | 38.25 |
| ATOM 3898 | CD | LYS | 514 | 69.513 | 9.774 | 11.753 | 1.00 | 47.74 |
| ATOM 3899 | CE | LYS | 514 | 68.514 | 8.719 | 12.230 | 1.00 | 51.60 |
| ATOM 3900 | NZ | LYS | 514 | 67.226 | 8.755 | 11.468 | 1.00 | 58.53 |
| ATOM 3904 | C | LYS | 514 | 72.357 | 11.659 | 8.137 | 1.00 | 30.29 |
| ATOM 3905 | O | LYS | 514 | 73.485 | 11.736 | 8.628 | 1.00 | 28.14 |
| ATOM 3906 | N | MET | 515 | 71.867 | 12.580 | 7.320 | 1.00 | 30.67 |
| ATOM 3908 | CA | MET | 515 | 72.643 | 13.747 | 6.920 | 1.00 | 29.94 |
| ATOM 3909 | CB | MET | 515 | 73.435 | 13.442 | 5.648 | 1.00 | 30.64 |
| ATOM 3910 | CG | MET | 515 | 72.557 | 13.038 | 4.464 | 1.00 | 32.16 |
| ATOM 3911 | SD | MET | 515 | 73.525 | 12.522 | 3.036 | 1.00 | 37.59 |
| ATOM 3912 | CE | MET | 515 | 74.015 | 10.933 | 3.563 | 1.00 | 29.11 |
| ATOM 3913 | C | MET | 515 | 71.675 | 14.869 | 6.635 | 1.00 | 29.71 |
| ATOM 3914 | O | MET | 515 | 70.462 | 14.664 | 6.598 | 1.00 | 30.04 |
| ATOM 3915 | N | LEU | 516 | 72.212 | 16.060 | 6.445 | 1.00 | 29.56 |
| ATOM 3917 | CA | LEU | 516 | 71.381 | 17.206 | 6.136 | 1.00 | 30.76 |
| ATOM 3918 | CD | LEU | 516 | 72.093 | 18.508 | 6.526 | 1.00 | 28.20 |
| ATOM 3919 | CG | LEU | 516 | 72.396 | 18.724 | 8.011 | 1.00 | 28.48 |
| ATOM 3920 | CD1 | LEU | 516 | 73.202 | 19.983 | 8.185 | 1.00 | 27.55 |
| ATOM 3921 | CD2 | LEU | 516 | 71.114 | 18.814 | 8.794 | 1.00 | 25.49 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 3922 | C | LEU | 516 | 71.081 | 17.225 | 4.647 | 1.00 | 30.97 |
| ATOM 3923 | O | LEU | 516 | 71.728 | 16.534 | 3.851 | 1.00 | 29.93 |
| ATOM 3924 | N | LYS | 517 | 70.030 | 17.946 | 4.291 | 1.00 | 31.57 |
| ATOM 3926 | CA | LYS | 517 | 69.677 | 18.117 | 2.899 | 1.00 | 31.44 |
| ATOM 3927 | CB | LYS | 517 | 68.169 | 18.310 | 2.752 | 1.00 | 34.79 |
| ATOM 3928 | CG | LYS | 517 | 67.375 | 17.098 | 3.194 | 1.00 | 38.42 |
| ATOM 3929 | CD | LYS | 547 | 66.148 | 16.888 | 2.343 | 1.00 | 46.52 |
| ATOM 3930 | CE | LYS | 517 | 65.087 | 17.950 | 2.582 | 1.00 | 53.77 |
| ATOM 3931 | NZ | LYS | 517 | 63.901 | 17.740 | 1.690 | 1.00 | 56.38 |
| ATOM 3935 | C | LYS | 517 | 70.457 | 19.377 | 2.499 | 1.00 | 30.18 |
| ATOM 3936 | O | LYS | 517 | 70.892 | 20.134 | 3.370 | 1.00 | 27.47 |
| ATOM 3937 | N | SER | 518 | 70.646 | 19.594 | 1.201 | 1.00 | 31.13 |
| ATOM 3939 | CA | SER | 518 | 71.394 | 20.747 | 0.693 | 1.00 | 32.11 |
| ATOM 3940 | CB | SER | 518 | 71.518 | 20.652 | −0.824 | 1.00 | 33.45 |
| ATOM 3941 | OG | SER | 518 | 70.242 | 20.567 | −1.428 | 1.00 | 34.51 |
| ATOM 3943 | C | SER | 518 | 70.814 | 22.103 | 1.073 | 1.00 | 32.81 |
| ATOM 3944 | O | SER | 518 | 71.515 | 23.123 | 1.027 | 1.00 | 34.03 |
| ATOM 3945 | N | ASP | 519 | 69.540 | 22.117 | 1.449 | 1.00 | 29.80 |
| ATOM 3947 | CA | ASP | 519 | 68.886 | 23.354 | 1.836 | 1.00 | 28.94 |
| ATOM 3948 | CB | ASP | 519 | 67.473 | 23.421 | 1.237 | 1.00 | 33.90 |
| ATOM 3949 | CG | ASP | 519 | 66.542 | 22.332 | 1.771 | 1.00 | 34.42 |
| ATOM 3950 | OD1 | ASP | 519 | 67.020 | 21.328 | 2.333 | 1.00 | 35.58 |
| ATOM 3951 | OD2 | ASP | 519 | 65.313 | 22.485 | 1.617 | 1.00 | 41.83 |
| ATOM 3952 | C | ASP | 519 | 68.829 | 23.559 | 3.342 | 1.00 | 29.08 |
| ATOM 3953 | O | ASP | 519 | 68.177 | 24.485 | 3.816 | 1.00 | 29.79 |
| ATOM 3954 | N | ALA | 520 | 69.514 | 22.710 | 4.099 | 1.00 | 29.73 |
| ATOM 3956 | CA | ALA | 520 | 69.488 | 22.824 | 5.558 | 1.00 | 29.16 |
| ATOM 3957 | CB | ALA | 520 | 70.171 | 21.639 | 6.190 | 1.00 | 28.13 |
| ATOM 3958 | C | ALA | 520 | 70.122 | 24.108 | 6.040 | 1.00 | 28.06 |
| ATOM 3959 | O | ALA | 520 | 70.880 | 24.741 | 5.309 | 1.00 | 28.84 |
| ATOM 3960 | N | THR | 521 | 69.800 | 24.491 | 7.272 | 1.00 | 27.84 |
| ATOM 3962 | CA | THR | 521 | 70.357 | 25.692 | 7.885 | 1.00 | 30.45 |
| ATOM 3963 | CB | THR | 521 | 69.254 | 26.635 | 8.463 | 1.00 | 33.56 |
| ATOM 3964 | CG1 | THR | 521 | 68.547 | 25.968 | 9.520 | 1.00 | 36.27 |
| ATOM 3966 | CG2 | THR | 521 | 68.275 | 27.074 | 7.379 | 1.00 | 36.06 |
| ATOM 3967 | C | THR | 521 | 71.251 | 25.263 | 9.048 | 1.00 | 30.04 |
| ATOM 3968 | O | THR | 521 | 71.348 | 24.072 | 9.369 | 1.00 | 28.16 |
| ATOM 3969 | N | GLU | 522 | 71.876 | 26.241 | 9.696 | 1.00 | 31.42 |
| ATOM 3971 | CA | GLU | 522 | 72.745 | 25.978 | 10.832 | 1.00 | 36.94 |
| ATOM 3972 | CB | GLU | 522 | 73.404 | 27.282 | 11.299 | 1.00 | 44.74 |
| ATOM 3973 | CG | GLU | 522 | 74.414 | 27.130 | 12.450 | 1.00 | 58.34 |
| ATOM 3974 | CD | GLU | 522 | 75.769 | 26.579 | 12.009 | 1.00 | 64.50 |
| ATOM 3975 | OE1 | GLU | 522 | 76.798 | 27.261 | 12.231 | 1.00 | 64.89 |
| ATOM 3976 | OE2 | GLU | 522 | 75.806 | 25.461 | 11.452 | 1.00 | 70.26 |
| ATOM 3977 | C | GLU | 522 | 71.932 | 25.345 | 11.969 | 1.00 | 34.02 |
| ATOM 3978 | O | GLU | 522 | 72.428 | 24.480 | 12.684 | 1.00 | 31.11 |
| ATOM 3979 | N | LYS | 523 | 70.670 | 25.750 | 12.097 | 1.00 | 32.53 |
| ATOM 3981 | CA | LYS | 523 | 69.805 | 25.210 | 13.135 | 1.00 | 34.06 |
| ATOM 3982 | C3 | LYS | 523 | 68.481 | 25.970 | 13.188 | 1.00 | 39.54 |
| ATOM 3983 | CG | LYS | 523 | 67.560 | 25.541 | 14.322 | 1.00 | 45.55 |
| ATOM 3984 | CD | LYS | 523 | 66.360 | 24.776 | 13.789 | 1.00 | 52.08 |
| ATOM 3985 | CE | LYS | 523 | 65.443 | 24.312 | 14.914 | 1.00 | 54.16 |
| ATOM 3986 | NZ | LYS | 523 | 64.313 | 23.509 | 14.373 | 1.00 | 54.38 |
| ATOM 3990 | C | LYS | 523 | 69.572 | 23.733 | 12.861 | 1.00 | 31.73 |
| ATOM 3991 | O | LYS | 523 | 69.589 | 22.922 | 13.788 | 1.00 | 31.15 |
| ATOM 3992 | N | ASP | 524 | 69.374 | 23.383 | 11.590 | 1.00 | 29.22 |
| ATOM 3994 | CA | ASP | 524 | 69.182 | 21.980 | 11.214 | 1.00 | 28.79 |
| ATOM 3995 | CB | ASP | 524 | 68.928 | 21.831 | 9.714 | 1.00 | 27.65 |
| ATOM 3996 | CG | ASP | 524 | 67.586 | 22.396 | 9.286 | 1.00 | 33.89 |
| ATOM 3997 | OD1 | ASP | 524 | 66.568 | 22.106 | 9.954 | 1.00 | 34.66 |
| ATOM 3998 | OD2 | ASP | 524 | 67.549 | 23.120 | 8.270 | 1.00 | 30.04 |
| ATOM 3999 | C | ASP | 524 | 70.424 | 21.190 | 11.606 | 1.00 | 28.00 |
| ATOM 4000 | O | ASP | 524 | 70.317 | 20.104 | 12.162 | 1.00 | 30.83 |
| ATOM 4001 | N | LEU | 525 | 71.603 | 21.761 | 11.347 | 1.00 | 29.87 |
| ATOM 4003 | CA | LEU | 525 | 72.873 | 21.121 | 11.700 | 1.00 | 27.60 |
| ATOM 4004 | CB | LEU | 525 | 74.064 | 21.997 | 11.282 | 1.00 | 24.08 |
| ATOM 4005 | CG | LEU | 525 | 75.462 | 21.433 | 11.593 | 1.00 | 26.11 |
| ATOM 4006 | CD1 | LEU | 525 | 75.597 | 19.979 | 11.098 | 1.00 | 23.67 |
| ATOM 4007 | CD2 | LEU | 525 | 76.530 | 22.321 | 10.967 | 1.00 | 21.28 |
| ATOM 4008 | C | LEU | 525 | 72.909 | 20.869 | 13.200 | 1.00 | 26.38 |
| ATOM 4009 | O | LEU | 525 | 73.249 | 19.777 | 13.653 | 1.00 | 26.09 |
| ATOM 4010 | N | SER | 526 | 72.560 | 21.902 | 13.956 | 1.00 | 29.72 |
| ATOM 4012 | CA | SER | 526 | 72.500 | 21.861 | 15.422 | 1.00 | 32.16 |
| ATOM 4013 | CH | SER | 526 | 71.980 | 23.209 | 15.939 | 1.00 | 33.45 |

TABLE 3-continued

Atomic Structure Coordinates of Unphosphorylated FLGK

| Atom No. | Atom Type | A.A. Type | A.A. No. | X | Y | Z | OCC | B | |
|---|---|---|---|---|---|---|---|---|---|
| ATOM 4014 | OG | SER | 526 | 71.793 | 23.213 | 17.343 | 1.00 | 40.42 | |
| ATOM 4016 | C | SER | 526 | 71.572 | 20.728 | 15.902 | 1.00 | 31.64 | |
| ATOM 4017 | O | SER | 526 | 71.869 | 20.030 | 16.889 | 1.00 | 32.54 | |
| ATOM 4018 | N | ASP | 527 | 70.454 | 20.561 | 15.201 | 1.00 | 27.92 | |
| ATOM 4020 | CA | ASP | 527 | 69.492 | 19.527 | 15.524 | 1.00 | 28.60 | |
| ATOM 4021 | CB | ASP | 527 | 68.187 | 19.767 | 14.765 | 1.00 | 29.35 | |
| ATOM 4022 | CG | ASP | 527 | 67.418 | 20.984 | 15.278 | 1.00 | 31.37 | |
| ATOM 4023 | OD1 | ASP | 527 | 67.759 | 21.549 | 16.353 | 1.00 | 31.96 | |
| ATOM 4024 | OD2 | ASP | 527 | 66.456 | 21.369 | 14.591 | 1.00 | 32.58 | |
| ATOM 4025 | C | ASP | 527 | 70.038 | 18.131 | 15.246 | 1.00 | 28.82 | |
| ATOM 4026 | O | ASP | 527 | 69.854 | 17.212 | 16.047 | 1.00 | 29.65 | |
| ATOM 4027 | N | LEU | 528 | 70.721 | 17.962 | 14.120 | 1.00 | 29.29 | |
| ATOM 4029 | CA | LEU | 528 | 71.302 | 16.658 | 13.794 | 1.00 | 29.94 | |
| ATOM 4030 | CB | LEU | 528 | 71.780 | 16.621 | 12.336 | 1.00 | 26.45 | |
| ATOM 4031 | CG | LEU | 528 | 72.315 | 15.276 | 11.840 | 1.00 | 28.34 | |
| ATOM 4032 | CD1 | LEU | 528 | 71.240 | 14.189 | 12.035 | 1.00 | 27.16 | |
| ATOM 4033 | CD2 | LEU | 528 | 72.756 | 15.387 | 10.372 | 1.00 | 25.91 | |
| ATOM 4034 | C | LEU | 528 | 72.449 | 16.319 | 14.776 | 1.00 | 29.72 | |
| ATOM 4035 | O | LEU | 528 | 72.617 | 15.162 | 15.178 | 1.10 | 28.98 | |
| ATOM 4036 | N | ILE | 529 | 73.224 | 17.329 | 15.168 | 1.00 | 30.15 | |
| ATOM 4038 | CA | ILE | 529 | 74.305 | 17.131 | 16.134 | 1.00 | 28.88 | |
| ATOM 4039 | CB | ILE | 529 | 75.188 | 18.382 | 16.268 | 1.00 | 26.91 | |
| ATOM 4040 | CG2 | ILE | 529 | 76.175 | 18.221 | 17.423 | 1.00 | 24.82 | |
| ATOM 4041 | CG1 | ILE | 529 | 75.960 | 18.613 | 14.984 | 1.00 | 23.98 | |
| ATOM 4042 | CD1 | ILE | 529 | 76.663 | 19.932 | 14.973 | 1.00 | 28.33 | |
| ATOM 4043 | C | ILE | 529 | 73.709 | 16.799 | 17.516 | 1.00 | 29.71 | |
| ATOM 4044 | O | ILE | 529 | 74.172 | 15.880 | 18.193 | 1.00 | 29.19 | |
| ATOM 4045 | N | SER | 530 | 72.672 | 17.524 | 17.926 | 1.00 | 26.84 | |
| ATOM 4047 | CA | SER | 530 | 72.061 | 17.247 | 19.214 | 1.00 | 31.46 | |
| ATOM 4048 | CB | SER | 530 | 70.948 | 18.251 | 19.521 | 1.00 | 36.17 | |
| ATOM 4049 | OG | SER | 530 | 70.045 | 18.363 | 18.431 | 1.00 | 47.58 | |
| ATOM 4051 | C | SER | 530 | 71.526 | 15.822 | 19.248 | 1.00 | 30.05 | |
| ATOM 4052 | O | SER | 530 | 71.646 | 15.136 | 20.270 | 1.00 | 29.61 | |
| ATOM 4053 | N | GLU | 531 | 70.972 | 15.357 | 18.132 | 1.00 | 27.74 | |
| ATOM 4055 | CA | GLU | 531 | 70.458 | 13.999 | 18.090 | 1.00 | 28.71 | |
| ATOM 4056 | CB | GLU | 531 | 69.709 | 13.727 | 16.789 | 1.00 | 29.72 | |
| ATOM 4057 | CG | GLU | 531 | 69.147 | 12.319 | 16.737 | 1.00 | 32.21 | |
| ATOM 4058 | CD | GLU | 531 | 68.510 | 11.979 | 15.414 | 1.00 | 33.88 | |
| ATOM 4059 | OE1 | GLU | 531 | 68.026 | 10.846 | 15.281 | 1.00 | 37.60 | |
| ATOM 4060 | OE2 | GLU | 531 | 68.483 | 12.833 | 14.510 | 1.00 | 34.70 | |
| ATOM 4061 | C | GLU | 531 | 71.578 | 12.974 | 18.271 | 1.00 | 28.91 | |
| ATOM 4062 | O | GLU | 531 | 71.428 | 12.007 | 19.019 | 1.00 | 29.46 | |
| ATOM 4063 | N | MET | 532 | 72.686 | 13.179 | 17.567 | 1.00 | 28.84 | |
| ATOM 4065 | CA | MET | 532 | 73.851 | 12.296 | 17.648 | 1.00 | 29.35 | |
| ATOM 4066 | CB | MET | 532 | 74.948 | 12.786 | 16.689 | 1.00 | 27.41 | |
| ATOM 4067 | CG | MET | 532 | 76.299 | 12.117 | 16.872 | 1.00 | 26.71 | |
| ATOM 4068 | SD | MET | 532 | 77.503 | 12.675 | 15.640 | 1.00 | 32.27 | |
| ATOM 4069 | CE | MET | 532 | 77.732 | 14.400 | 16.117 | 1.00 | 24.10 | |
| ATOM 4070 | C | MET | 532 | 74.389 | 12.280 | 19.078 | 1.00 | 28.80 | |
| ATOM 4071 | O | MET | 532 | 74.700 | 11.230 | 19.630 | 1.00 | 29.74 | |
| ATOM 4072 | N | GLU | 533 | 74.481 | 13.454 | 19.681 | 1.00 | 28.83 | |
| ATOM 4074 | CA | GLU | 533 | 74.985 | 13.546 | 21.033 | 1.00 | 29.66 | |
| ATOM 4075 | CB | GLU | 533 | 75.182 | 15.008 | 21.423 | 1.00 | 32.23 | |
| ATOM 4076 | CG | GLU | 533 | 76.331 | 15.687 | 20.651 | 1.00 | 34.47 | |
| ATOM 4077 | CD | GLU | 533 | 77.656 | 14.937 | 20.714 | 1.00 | 38.03 | |
| ATOM 4078 | OE1 | GLU | 533 | 78.168 | 14.780 | 21.903 | 1.00 | 39.75 | |
| ATOM 4079 | OE2 | GLU | 533 | 78.192 | 14.497 | 19.736 | 1.00 | 38.75 | |
| ATOM 4080 | C | GLU | 533 | 74.058 | 12.815 | 22.005 | 1.00 | 31.55 | |
| ATOM 4081 | O | GLU | 533 | 74.521 | 12.083 | 22.889 | 1.00 | 30.63 | |
| ATOM 4082 | N | MET | 534 | 72.750 | 12.958 | 21.799 | 1.00 | 31.31 | |
| ATOM 4084 | CA | MET | 534 | 71.789 | 12.289 | 22.664 | 1.00 | 30.78 | |
| ATOM 4085 | CB | MET | 534 | 70.348 | 12.672 | 22.319 | 1.00 | 31.23 | |
| ATOM 4086 | CG | MET | 534 | 69.453 | 12.648 | 23.551 | 0.50 | 29.35 | PRT1 |
| ATOM 4087 | SD | MET | 534 | 67.688 | 12.563 | 23.246 | 0.50 | 28.79 | PRT1 |
| ATOM 4088 | CE | MET | 534 | 67.290 | 14.230 | 22.875 | 0.50 | 26.96 | PRT1 |
| ATOM 4089 | C | MET | 534 | 71.991 | 10.773 | 22.560 | 1.00 | 28.82 | |
| ATOM 4090 | O | MET | 534 | 72.053 | 10.083 | 23.568 | 1.00 | 30.10 | |
| ATOM 4091 | N | MET | 535 | 72.149 | 10.271 | 21.339 | 1.00 | 29.16 | |
| ATOM 4093 | CA | MET | 535 | 72.381 | 8.852 | 21.110 | 1.00 | 29.37 | |
| ATOM 4094 | CB | MET | 535 | 72.546 | 8.551 | 19.617 | 1.00 | 27.35 | |
| ATOM 4095 | CG | MET | 535 | 71.281 | 8.790 | 18.817 | 1.00 | 28.40 | |
| ATOM 4096 | SD | MET | 535 | 71.255 | 7.955 | 17.255 | 1.00 | 30.26 | |
| ATOM 4097 | CE | MET | 535 | 71.336 | 9.279 | 16.188 | 1.00 | 35.50 | |
| ATOM 4098 | C | MET | 535 | 73.612 | 8.388 | 21.887 | 1.00 | 30.36 | |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4099 | O | MET | 535 | 73.626 | 7.287 | 22.460 | 1.00 | 26.13 |
| ATOM 4100 | N | LYS | 536 | 74.640 | 9.233 | 21.909 | 1.00 | 30.70 |
| ATOM 4102 | CA | LYS | 536 | 75.850 | 8.913 | 22.649 | 1.00 | 31.76 |
| ATOM 4103 | CB | LYS | 536 | 76.934 | 9.954 | 22.388 | 1.00 | 31.05 |
| ATOM 4104 | CG | LYS | 536 | 77.550 | 9.883 | 21.004 | 1.00 | 26.80 |
| ATOM 4105 | CD | LYS | 536 | 78.534 | 11.017 | 20.860 | 1.00 | 31.05 |
| ATOM 4106 | CE | LYS | 536 | 79.132 | 11.138 | 19.466 | 1.00 | 29.83 |
| ATOM 4107 | NZ | LYS | 536 | 79.957 | 12.377 | 19.440 | 1.00 | 29.32 |
| ATOM 4111 | C | LYS | 536 | 75.550 | 8.834 | 24.150 | 1.00 | 31.99 |
| ATOM 4112 | O | LYS | 536 | 75.920 | 7.859 | 24.806 | 1.00 | 31.92 |
| ATOM 4113 | N | MET | 537 | 74.837 | 9.826 | 24.676 | 1.00 | 31.81 |
| ATOM 4115 | CA | MET | 537 | 74.517 | 9.835 | 26.090 | 1.00 | 35.37 |
| ATOM 4116 | CB | MET | 537 | 73.860 | 11.154 | 26.506 | 1.00 | 41.32 |
| ATOM 4117 | CG | MET | 537 | 74.828 | 12.335 | 26.610 | 1.00 | 51.50 |
| ATOM 4118 | SD | MET | 537 | 76.234 | 12.090 | 27.776 | 1.00 | 57.48 |
| ATOM 4119 | CE | MET | 537 | 75.460 | 12.637 | 29.334 | 1.00 | 56.91 |
| ATOM 4120 | C | MET | 537 | 73.630 | 8.679 | 26.499 | 1.00 | 36.11 |
| ATOM 4121 | O | MET | 537 | 73.845 | 8.084 | 27.548 | 1.00 | 38.54 |
| ATOM 4122 | N | ILE | 538 | 72.652 | 8.347 | 25.661 | 1.00 | 33.69 |
| ATOM 4124 | CA | ILE | 538 | 71.704 | 7.277 | 25.954 | 1.00 | 31.62 |
| ATOM 4125 | CB | ILE | 538 | 70.492 | 7.314 | 24.974 | 1.00 | 28.21 |
| ATOM 4126 | CG2 | ILE | 538 | 69.681 | 6.018 | 25.034 | 1.00 | 28.22 |
| ATOM 4127 | CG1 | ILE | 538 | 69.590 | 8.488 | 25.338 | 1.00 | 23.74 |
| ATOM 4128 | CD1 | ILE | 538 | 68.487 | 8.728 | 24.344 | 1.00 | 27.14 |
| ATOM 4129 | C | ILE | 538 | 72.322 | 5.894 | 26.008 | 1.00 | 31.07 |
| ATOM 4130 | O | ILE | 538 | 71.952 | 5.080 | 26.860 | 1.00 | 33.13 |
| ATOM 4131 | N | GLY | 539 | 73.239 | 5.611 | 25.094 | 1.00 | 29.52 |
| ATOM 4133 | CA | GLY | 539 | 73.871 | 4.309 | 25.093 | 1.00 | 28.40 |
| ATOM 4134 | C | GLY | 539 | 73.111 | 3.275 | 24.289 | 1.00 | 30.21 |
| ATOM 4135 | O | GLY | 539 | 72.018 | 3.554 | 23.788 | 1.00 | 29.66 |
| ATOM 4136 | N | LYS | 540 | 73.679 | 2.074 | 24.199 | 1.00 | 28.44 |
| ATOM 4138 | CA | LYS | 540 | 73.105 | 0.984 | 23.426 | 1.00 | 31.09 |
| ATOM 4139 | CB | LYS | 540 | 74.215 | 0.089 | 22.895 | 1.00 | 33.15 |
| ATOM 4140 | CG | LYS | 540 | 75.116 | 0.776 | 21.906 | 1.00 | 39.54 |
| ATOM 4141 | CD | LYS | 540 | 76.125 | −0.175 | 21.329 | 1.00 | 43.98 |
| ATOM 4142 | CE | LYS | 540 | 77.033 | 0.562 | 20.349 | 1.00 | 50.79 |
| ATOM 4143 | NZ | LYS | 540 | 76.338 | 0.977 | 19.086 | 1.00 | 51.09 |
| ATOM 4147 | C | LYS | 540 | 72.053 | 0.087 | 24.059 | 1.00 | 32.78 |
| ATOM 4148 | O | LYS | 540 | 72.068 | −0.195 | 25.266 | 1.00 | 32.41 |
| ATOM 4149 | N | HIS | 541 | 71.137 | −0.374 | 23.208 | 1.00 | 31.20 |
| ATOM 4151 | CA | HIS | 541 | 70.080 | −1.304 | 23.591 | 1.00 | 31.53 |
| ATOM 4152 | CB | HIS | 541 | 68.911 | −0.630 | 24.298 | 1.00 | 30.69 |
| ATOM 4153 | CG | HIS | 541 | 67.948 | −1.613 | 24.882 | 1.00 | 31.18 |
| ATOM 4154 | CD2 | HIS | 541 | 67.938 | −2.255 | 26.072 | 1.00 | 33.02 |
| ATOM 4155 | NDZ | HIS | 541 | 66.882 | −2.123 | 24.165 | 1.00 | 30.56 |
| ATOM 4157 | CE1 | HIS | 541 | 66.268 | −3.037 | 24.869 | 1.00 | 32.95 |
| ATOM 4158 | NE2 | HIS | 541 | 66.886 | −3.140 | 26.053 | 1.00 | 31.79 |
| ATOM 4160 | C | HIS | 541 | 69.590 | −2.013 | 22.340 | 1.00 | 32.72 |
| ATOM 4161 | O | HIS | 541 | 69.495 | −1.404 | 21.275 | 1.00 | 30.34 |
| ATOM 4162 | N | LYS | 542 | 69.282 | −3.305 | 22.475 | 1.00 | 32.32 |
| ATOM 4164 | CA | LYS | 542 | 68.828 | −4.131 | 21.359 | 1.00 | 30.29 |
| ATOM 4165 | CB | LYS | 542 | 68.637 | −5.587 | 21.798 | 1.00 | 29.34 |
| ATOM 4166 | C | LYS | 542 | 67.560 | −3.661 | 20.692 | 1.00 | 29.09 |
| ATOM 4167 | O | LYS | 542 | 67.369 | −3.903 | 19.507 | 1.00 | 29.12 |
| ATOM 4168 | N | ASN | 543 | 66.683 | −3.012 | 21.446 | 1.00 | 28.54 |
| ATOM 4170 | CA | ASN | 543 | 65.425 | −2.559 | 20.869 | 1.00 | 29.10 |
| ATOM 4171 | CB | ASN | 543 | 64.245 | −3.047 | 21.712 | 1.00 | 29.69 |
| ATOM 4172 | CG | ASN | 543 | 64.253 | −4.556 | 21.900 | 1.00 | 29.62 |
| ATOM 4173 | OD1 | ASN | 543 | 64.510 | −5.050 | 23.000 | 1.00 | 31.63 |
| ATOM 4174 | ND2 | ASN | 543 | 64.020 | −5.291 | 20.828 | 1.00 | 28.66 |
| ATOM 4177 | C | ASN | 543 | 65.299 | −1.073 | 20.532 | 1.00 | 29.61 |
| ATOM 4178 | O | ASN | 543 | 64.207 | −0.507 | 20.578 | 1.00 | 28.00 |
| ATOM 4179 | N | ILE | 544 | 66.432 | −0.442 | 20.222 | 1.00 | 28.39 |
| ATOM 4181 | CA | ILE | 544 | 66.466 | 0.958 | 19.804 | 1.00 | 25.73 |
| ATOM 4182 | CB | ILE | 544 | 66.903 | 1.952 | 20.935 | 1.00 | 25.98 |
| ATOM 4183 | CG2 | ILE | 544 | 66.083 | 1.721 | 22.215 | 1.00 | 22.04 |
| ATOM 4184 | CG1 | ILE | 544 | 68.412 | 1.860 | 21.209 | 1.00 | 24.30 |
| ATOM 4185 | CD1 | ILE | 544 | 68.901 | 2.846 | 22.274 | 1.00 | 22.83 |
| ATOM 4186 | C | ILE | 544 | 67.463 | 1.020 | 18.639 | 1.00 | 26.20 |
| ATOM 4187 | O | ILE | 544 | 68.276 | 0.106 | 18.467 | 1.00 | 25.46 |
| ATOM 4188 | N | ILE | 545 | 67.307 | 2.016 | 17.771 | 1.00 | 26.26 |
| ATOM 4190 | CA | ILE | 545 | 68.223 | 2.209 | 16.641 | 1.00 | 27.62 |
| ATOM 4191 | CB | ILE | 545 | 67.647 | 3.195 | 15.585 | 1.00 | 28.33 |
| ATOM 4192 | CG2 | ILE | 545 | 68.726 | 3.595 | 14.562 | 1.00 | 28.00 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4193 | CG1 | ILE | 545 | 66.453 | 2.565 | 14.856 | 1.00 | 24.69 |
| ATOM 4194 | CD1 | ILE | 545 | 66.850 | 1.467 | 13.875 | 1.00 | 26.17 |
| ATOM 4195 | C | ILE | 545 | 69.492 | 2.794 | 17.267 | 1.00 | 28.23 |
| ATOM 4196 | O | ILE | 545 | 69.468 | 3.872 | 17.846 | 1.00 | 28.97 |
| ATOM 4197 | N | ASN | 546 | 70.595 | 2.069 | 17.164 | 1.00 | 29.45 |
| ATOM 4199 | CA | ASN | 546 | 71.845 | 2.508 | 17.774 | 1.00 | 28.58 |
| ATOM 4200 | CB | ASN | 546 | 72.580 | 1.309 | 18.384 | 1.00 | 26.34 |
| ATOM 4201 | CG | ASN | 546 | 71.812 | 0.673 | 19.527 | 1.00 | 25.52 |
| ATOM 4202 | OD1 | ASN | 546 | 71.634 | 1.277 | 20.580 | 1.00 | 28.82 |
| ATOM 4203 | ND2 | ASN | 546 | 71.341 | −0.541 | 19.318 | 1.00 | 26.57 |
| ATOM 4206 | C | ASN | 546 | 72.810 | 3.264 | 16.881 | 1.00 | 28.74 |
| ATOM 4207 | O | ASN | 546 | 72.858 | 3.041 | 15.675 | 1.00 | 29.26 |
| ATOM 4208 | N | LEU | 547 | 73.578 | 4.155 | 17.504 | 1.00 | 29.90 |
| ATOM 4210 | CA | LEU | 547 | 74.618 | 4.936 | 16.834 | 1.00 | 30.27 |
| ATOM 4211 | CB | LEU | 547 | 75.075 | 6.081 | 17.745 | 1.00 | 25.85 |
| ATOM 4212 | CG | LEU | 547 | 76.161 | 1.034 | 17.232 | 1.00 | 27.73 |
| ATOM 4213 | CD1 | LEU | 547 | 75.670 | 7.851 | 16.033 | 1.00 | 27.38 |
| ATOM 4214 | CD2 | LEU | 547 | 76.545 | 7.966 | 18.345 | 1.00 | 29.14 |
| ATOM 4215 | C | LEU | 547 | 75.811 | 4.004 | 16.567 | 1.00 | 32.22 |
| ATOM 4216 | O | LEU | 547 | 76.256 | 3.291 | 17.471 | 1.00 | 33.38 |
| ATOM 4217 | N | LEU | 548 | 76.317 | 4.005 | 15.335 | 1.00 | 32.12 |
| ATOM 4219 | CA | LEU | 548 | 77.452 | 3.159 | 14.960 | 1.00 | 32.94 |
| ATOM 4220 | CB | LEU | 548 | 77.103 | 2.310 | 13.740 | 1.00 | 29.97 |
| ATOM 4221 | CG | LEU | 548 | 75.839 | 1.458 | 13.840 | 1.00 | 31.55 |
| ATOM 4222 | CD1 | LEU | 548 | 75.662 | 0.71 3 | 12.540 | 1.00 | 27.85 |
| ATOM 4223 | CD2 | LEU | 548 | 75.917 | 0.500 | 15.025 | 1.00 | 26.34 |
| ATOM 4224 | C | LEU | 548 | 78.726 | 3.955 | 14.654 | 1.00 | 36.06 |
| ATOM 4225 | O | LEU | 548 | 79.836 | 3.410 | 14.668 | 1.00 | 36.42 |
| ATOM 4226 | N | GLY | 549 | 78.562 | 5.219 | 14.298 | 1.00 | 35.78 |
| ATOM 4228 | CA | GLY | 549 | 79.713 | 6.042 | 13.987 | 1.00 | 36.22 |
| ATOM 4229 | C | GLY | 549 | 79.267 | 7.376 | 13.433 | 1.00 | 35.30 |
| ATOM 4230 | O | GLY | 549 | 78.062 | 7.646 | 13.362 | 1.00 | 33.46 |
| ATOM 4231 | N | ALA | 550 | 80.232 | 8.206 | 13.042 | 1.00 | 34.94 |
| ATOM 4233 | CA | ALA | 550 | 79.945 | 9.525 | 12.490 | 1.00 | 31.91 |
| ATOM 4234 | CB | ALA | 550 | 79.588 | 10.495 | 13.613 | 1.00 | 30.54 |
| ATOM 4235 | C | ALA | 550 | 81.128 | 10.077 | 11.715 | 1.00 | 31.58 |
| ATOM 4236 | O | ALA | 550 | 82.281 | 9.832 | 12.080 | 1.00 | 31.23 |
| ATOM 4237 | N | CYS | 551 | 80.818 | 11.812 | 10.643 | 1.00 | 31.13 |
| ATOM 4239 | CA | CYS | 551 | 81.805 | 11.503 | 9.804 | 1.00 | 28.28 |
| ATOM 4240 | CB | CYS | 551 | 81.621 | 11.180 | 8.316 | 1.00 | 27.27 |
| ATOM 4241 | SG | CYS | 551 | 81.771 | 9.449 | 7.839 | 1.00 | 30.33 |
| ATOM 4242 | C | CYS | 551 | 81.450 | 12.960 | 10.074 | 1.00 | 25.88 |
| ATOM 4243 | O | CYS | 551 | 80.432 | 13.458 | 9.605 | 1.00 | 27.73 |
| ATOM 4244 | N | THR | 552 | 82.214 | 13.586 | 10.954 | 1.00 | 25.35 |
| ATOM 4246 | CA | THR | 552 | 81.988 | 14.967 | 11.353 | 1.00 | 26.79 |
| ATOM 4247 | CB | THR | 552 | 82.051 | 15.092 | 12.899 | 1.00 | 27.76 |
| ATOM 4248 | CG1 | THR | 552 | 83.392 | 14.839 | 13.338 | 1.00 | 27.62 |
| ATOM 4250 | CG2 | THR | 552 | 81.119 | 14.086 | 13.575 | 1.00 | 29.17 |
| ATOM 4251 | C | THR | 552 | 83.036 | 15.931 | 10.790 | 1.00 | 25.03 |
| ATOM 4252 | O | THR | 552 | 82.825 | 17.137 | 10.746 | 1.00 | 25.34 |
| ATOM 4253 | N | GLN | 553 | 84.174 | 15.385 | 10.381 | 1.00 | 27.34 |
| ATOM 4255 | CA | GLN | 553 | 85.285 | 16.190 | 9.888 | 1.00 | 26.31 |
| ATOM 4256 | CB | GLN | 553 | 86.601 | 15.639 | 10.468 | 1.00 | 25.05 |
| ATOM 4257 | CG | GLN | 553 | 86.581 | 15.491 | 11.993 | 1.00 | 24.78 |
| ATOM 4258 | CD | GLN | 553 | 86.382 | 16.823 | 12.709 | 1.00 | 25.40 |
| ATOM 4259 | OE1 | GLN | 553 | 87.175 | 17.748 | 12.546 | 1.00 | 33.74 |
| ATOM 4260 | NE2 | GLN | 553 | 85.338 | 16.920 | 13.516 | 1.00 | 25.61 |
| ATOM 4263 | C | GLN | 553 | 85.390 | 16.274 | 8.379 | 1.00 | 27.08 |
| ATOM 4264 | O | GLN | 553 | 85.083 | 15.318 | 1.669 | 1.00 | 28.76 |
| ATOM 4265 | N | ASP | 554 | 85.804 | 17.438 | 7.819 | 1.00 | 28.63 |
| ATOM 4267 | CA | ASP | 554 | 86.015 | 17.677 | 6.471 | 1.00 | 29.70 |
| ATOM 4268 | CB | ASP | 554 | 87.335 | 17.050 | 6.051 | 1.00 | 29.73 |
| ATOM 4269 | CG | ASP | 554 | 88.480 | 17.587 | 6.857 | 1.00 | 33.38 |
| ATOM 4270 | OD1 | ASP | 554 | 88.794 | 18.780 | 6.711 | 1.00 | 36.53 |
| ATOM 4271 | OD2 | ASP | 554 | 19.024 | 16.841 | 7.687 | 1.00 | 36.40 |
| ATOM 4272 | C | ASP | 554 | 84.908 | 17.258 | 5.522 | 1.00 | 29.64 |
| ATOM 4273 | O | ASP | 554 | 85.112 | 16.422 | 4.643 | 1.00 | 32.06 |
| ATOM 4274 | N | GLY | 555 | 83.748 | 17.881 | 5.679 | 1.00 | 28.59 |
| ATOM 4276 | CA | GLY | 555 | 92.620 | 17.571 | 4.825 | 1.00 | 26.85 |
| ATOM 4277 | C | GLY | 555 | 81.313 | 17.434 | 5.607 | 1.00 | 25.30 |
| ATOM 4278 | O | GLY | 555 | 81.319 | 17.593 | 6.834 | 1.00 | 23.96 |
| ATOM 4279 | N | PRO | 556 | 80.229 | 17.113 | 4.920 | 1.00 | 24.84 |
| ATOM 4280 | CD | PRO | 556 | 80.159 | 16.850 | 3.472 | 1.00 | 21.36 |
| ATOM 4281 | CA | PRO | 556 | 78.920 | 16.942 | 5.550 | 1.00 | 25.26 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4282 | CB | PRO | 556 | 78.033 | 16.494 | 4.386 | 1.00 | 23.37 |
| ATOM 4283 | CG | PRO | 556 | 79.025 | 15.881 | 3.399 | 1.00 | 24.44 |
| ATOM 4284 | C | PRO | 556 | 78.885 | 15.941 | 6.700 | 1.00 | 26.50 |
| ATOM 4285 | O | PRO | 556 | 79.515 | 14.875 | 6.654 | 1.00 | 27.38 |
| ATOM 4286 | N | LEU | 557 | 78.171 | 16.314 | 7.754 | 1.00 | 26.25 |
| ATOM 4288 | CA | LEU | 557 | 78.032 | 15.452 | 8.917 | 1.00 | 28.25 |
| ATOM 4289 | CB | LEU | 557 | 77.403 | 16.217 | 10.092 | 1.00 | 27.09 |
| ATOM 4290 | CG | LEU | 557 | 76.922 | 15.414 | 11.310 | 1.00 | 28.35 |
| ATOM 4291 | CD1 | LEU | 557 | 78.088 | 14.733 | 12.011 | 1.00 | 25.54 |
| ATOM 4292 | CD2 | LEU | 557 | 76.204 | 16.340 | 12.271 | 1.00 | 26.91 |
| ATOM 4293 | C | LEU | 557 | 77.169 | 14.246 | 8.514 | 1.00 | 29.06 |
| ATOM 4294 | O | LEU | 557 | 76.060 | 14.385 | 8.011 | 1.00 | 29.05 |
| ATOM 4295 | N | TYR | 558 | 77.717 | 13.065 | 8.807 | 1.00 | 29.43 |
| ATOM 4297 | CA | TYR | 558 | 77.018 | 11.823 | 8.573 | 1.00 | 28.02 |
| ATOM 4298 | CB | TYR | 558 | 77.813 | 10.918 | 7.632 | 1.00 | 27.83 |
| ATOM 4299 | CG | TYR | 558 | 77.969 | 11.414 | 6.203 | 1.00 | 31.70 |
| ATOM 4300 | CD1 | TXR | 558 | 78.966 | 10.893 | 5.383 | 1.00 | 32.90 |
| ATOM 4301 | CE1 | TYR | 558 | 79.121 | 11.315 | 4.073 | 1.00 | 32.69 |
| ATOM 4302 | CD2 | TYR | 558 | 77.122 | 12.386 | 5.666 | 1.00 | 30.23 |
| ATOM 4303 | CE2 | TYR | 558 | 77.271 | 12.815 | 4.350 | 1.00 | 29.97 |
| ATOM 4304 | CZ | TYR | 558 | 78.280 | 12.272 | 3.560 | 1.00 | 33.20 |
| ATOM 4305 | OH | TYR | 558 | 78.452 | 12.681 | 2.253 | 1.00 | 35.32 |
| ATOM 4307 | C | TYR | 558 | 76.848 | 11.131 | 9.932 | 1.00 | 28.42 |
| ATOM 4308 | O | TYR | 558 | 17.823 | 10.902 | 10.647 | 1.00 | 27.81 |
| ATOM 4309 | N | VAL | 559 | 75.601 | 10.870 | 10.313 | 1.00 | 29.20 |
| ATOM 4311 | CA | VAL | 559 | 75.286 | 10.175 | 11.564 | 1.00 | 29.17 |
| ATOM 4312 | CB | VAL | 559 | 74.102 | 10.832 | 12.329 | 1.00 | 28.53 |
| ATOM 4313 | CG1 | VAL | 559 | 73.802 | 10.036 | 13.607 | 1.00 | 27.08 |
| ATOM 4314 | CG2 | VAL | 559 | 74.456 | 12.281 | 12.687 | 1.00 | 23.27 |
| ATOM 4315 | C | VAL | 559 | 74.911 | 8.772 | 11.137 | 1.00 | 26.41 |
| ATOM 4316 | O | VAL | 559 | 73.834 | 8.536 | 10.593 | 1.00 | 25.91 |
| ATOM 4317 | N | ILE | 560 | 75.824 | 7.846 | 11.371 | 1.00 | 26.71 |
| ATOM 4319 | CA | ILE | 560 | 75.638 | 6.465 | 10.966 | 1.00 | 27.55 |
| ATOM 4320 | CB | ILE | 560 | 77.012 | 5.829 | 10.619 | 1.00 | 28.48 |
| ATOM 4321 | CG2 | ILE | 560 | 76.819 | 4.468 | 9.979 | 1.00 | 29.18 |
| ATOM 4322 | CG1 | ILE | 560 | 77.793 | 6.745 | 9.657 | 1.00 | 27.99 |
| ATOM 4323 | CD1 | ILE | 560 | 79.274 | 6.399 | 9.525 | 1.00 | 28.97 |
| ATOM 4324 | C | ILE | 560 | 74.917 | 5.644 | 12.034 | 1.00 | 29.17 |
| ATOM 4325 | O | ILE | 560 | 75.404 | 5.497 | 13.160 | 1.00 | 28.92 |
| ATOM 4326 | N | VAL | 561 | 73.743 | 5.129 | 11.681 | 1.00 | 28.60 |
| ATOM 4328 | CA | VAL | 561 | 72.957 | 4.325 | 12.606 | 1.00 | 28.58 |
| ATOM 4329 | CB | VAL | 561 | 71.634 | 5.061 | 13.047 | 1.00 | 27.53 |
| ATOM 4330 | CG1 | VAL | 561 | 71.951 | 6.400 | 13.701 | 1.00 | 22.44 |
| ATOM 4331 | CG2 | VAL | 561 | 70.697 | 5.246 | 11.874 | 1.00 | 23.19 |
| ATOM 4332 | C | VAL | 561 | 72.618 | 2.956 | 12.006 | 1.00 | 28.20 |
| ATOM 4333 | O | VAL | 561 | 72.875 | 2.694 | 10.825 | 1.00 | 27.99 |
| ATOM 4334 | N | GLU | 562 | 72.057 | 2.079 | 12.834 | 1.00 | 29.17 |
| ATOM 4336 | CA | GLU | 562 | 71.666 | 0.744 | 12.399 | 1.00 | 28.96 |
| ATOM 4337 | CB | GLU | 562 | 71.199 | −0.086 | 13.589 | 1.00 | 27.34 |
| ATOM 4338 | CG | GLU | 562 | 72.308 | −0.331 | 14.583 | 1.00 | 30.12 |
| ATOM 4339 | CD | GLU | 562 | 71.838 | −1.075 | 15.808 | 1.00 | 32.29 |
| ATOM 4340 | OE1 | GLU | 562 | 72.526 | −2.030 | 16.217 | 1.00 | 32.45 |
| ATOM 4341 | OE2 | GLU | 562 | 70.785 | −0.702 | 16.362 | 1.00 | 30.16 |
| ATOM 4342 | C | GLU | 562 | 70.580 | 0.794 | 11.340 | 1.00 | 29.79 |
| ATOM 4343 | O | GLU | 562 | 69.690 | 1.653 | 11.386 | 1.00 | 29.75 |
| ATOM 4344 | N | TYR | 563 | 70.684 | −0.106 | 10.369 | 1.00 | 30.51 |
| ATOM 4346 | CA | TYR | 563 | 69.735 | −0.209 | 9.267 | 1.00 | 33.76 |
| ATOM 4347 | CB | TYR | 563 | 70.494 | −0.602 | 7.988 | 1.00 | 31.04 |
| ATOM 4348 | CG | TYR | 563 | 69.624 | −0.928 | 6.806 | 1.00 | 33.40 |
| ATOM 4349 | CD1 | TYR | 563 | 68.693 | −0.019 | 6.340 | 1.00 | 33.07 |
| ATOM 4350 | CE1 | TYR | 563 | 67.908 | −0.301 | 5.243 | 1.00 | 34.71 |
| ATOM 4351 | CD2 | TYR | 563 | 69.749 | −2.141 | 6.147 | 1.00 | 34.61 |
| ATOM 4352 | CE2 | TYR | 563 | 68.970 | −2.446 | 5.035 | 1.00 | 36.54 |
| ATOM 4353 | CZ | TYR | 563 | 68.047 | −1.518 | 4.589 | 1.00 | 36.83 |
| ATOM 4354 | OH | TYR | 563 | 67.261 | −1.805 | 3.501 | 1.00 | 38.81 |
| ATOM 4356 | C | TYR | 563 | 68.655 | −1.269 | 9.588 | 1.00 | 36.14 |
| ATOM 4357 | O | TYR | 563 | 68.946 | −2.365 | 10.023 | 1.00 | 37.70 |
| ATOM 4358 | N | ALA | 564 | 67.406 | −0.948 | 9.309 | 1.00 | 37.87 |
| ATOM 4360 | CA | ALA | 564 | 66.276 | −1.832 | 9.534 | 1.00 | 38.49 |
| ATOM 4361 | CB | ALA | 564 | 65.278 | −1.167 | 10.458 | 1.10 | 42.57 |
| ATOM 4362 | C | ALA | 564 | 65.645 | −2.153 | 8.179 | 1.00 | 39.65 |
| ATOM 4363 | O | ALA | 564 | 64.796 | −1.423 | 7.687 | 1.00 | 39.74 |
| ATOM 4364 | N | SER | 565 | 66.039 | −3.280 | 7.607 | 1.00 | 40.06 |
| ATOM 4366 | CA | SER | 565 | 65.567 | −3.699 | 6.295 | 1.00 | 40.67 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4367 | CB | SER | 565 | 66.267 | −4.986 | 5.883 | 1.00 | 38.71 |
| ATOM 4368 | OG | SER | 565 | 66.107 | −5.964 | 6.889 | 1.00 | 41.35 |
| ATOM 4370 | C | SER | 565 | 64.081 | −3.884 | 6.106 | 1.00 | 42.17 |
| ATOM 4371 | O | SER | 565 | 63.585 | −3.741 | 4.992 | 1.00 | 44.25 |
| ATOM 4372 | N | LYS | 566 | 63.360 | −4.207 | 7.167 | 1.00 | 41.71 |
| ATOM 4374 | CA | LYS | 566 | 61.928 | −4.427 | 7.015 | 1.00 | 40.22 |
| ATOM 4375 | CB | LYS | 566 | 61.525 | −5.668 | 7.800 | 1.00 | 39.51 |
| ATOM 4376 | CG | LYS | 566 | 62.202 | −6.910 | 7.226 | 1.00 | 41.48 |
| ATOM 4377 | CD | LYS | 566 | 62.113 | −8.094 | 8.149 | 1.00 | 41.53 |
| ATOM 4378 | CE | LYS | 566 | 62.710 | −9.312 | 7.491 | 1.00 | 41.18 |
| ATOM 4379 | NZ | LYS | 566 | 62.763 | −10.458 | 8.438 | 1.00 | 46.17 |
| ATOM 4383 | C | LYS | 566 | 61.007 | −3.220 | 7.263 | 1.00 | 40.47 |
| ATOM 4384 | O | LYS | 566 | 59.800 | −3.367 | 7.486 | 1.00 | 42.68 |
| ATOM 4385 | N | GLY | 567 | 61.584 | −2.026 | 7.167 | 1.00 | 38.90 |
| ATOM 4387 | CA | GLY | 567 | 60.826 | −0.799 | 7.336 | 1.00 | 37.13 |
| ATOM 4388 | C | GLY | 567 | 60.199 | −0.592 | 8.694 | 1.00 | 36.72 |
| ATOM 4389 | O | GLY | 567 | 60.644 | −1.172 | 9.683 | 1.00 | 38.48 |
| ATOM 4390 | N | ASN | 568 | 59.191 | 0.273 | 8.753 | 1.00 | 35.77 |
| ATOM 4392 | CA | ASN | 568 | 58.518 | 0.549 | 10.015 | 1.00 | 35.36 |
| ATOM 4393 | CB | ASN | 568 | 57.883 | 1.957 | 10.045 | 1.00 | 36.30 |
| ATOM 4394 | CG | ASN | 568 | 56.635 | 2.088 | 9.169 | 1.00 | 38.06 |
| ATOM 4395 | OD1 | ASN | 568 | 55.623 | 1.421 | 9.383 | 1.00 | 38.66 |
| ATOM 4396 | ND2 | ASN | 568 | 56.686 | 3.010 | 8.221 | 1.00 | 37.29 |
| ATOM 4399 | C | ASN | 568 | 57.504 | −0.532 | 10.341 | 1.00 | 33.04 |
| ATOM 4400 | O | ASN | 568 | 57.061 | −1.265 | 9.461 | 1.00 | 32.10 |
| ATOM 4401 | N | LEU | 569 | 57.142 | −0.612 | 11.617 | 1.00 | 33.59 |
| ATOM 4403 | CA | LEU | 569 | 56.199 | −1.604 | 12.132 | 1.00 | 32.91 |
| ATOM 4404 | CB | LEU | 569 | 56.045 | −1.428 | 13.647 | 1.00 | 33.84 |
| ATOM 4405 | CG | LEU | 569 | 55.088 | −2.343 | 14.403 | 1.00 | 31.96 |
| ATOM 4406 | CD1 | LEU | 569 | 55.522 | −3.797 | 14.216 | 1.00 | 33.20 |
| ATOM 4407 | CD2 | LEU | 569 | 55.069 | −1.967 | 15.868 | 1.00 | 30.81 |
| ATOM 4408 | C | LEU | 569 | 54.820 | −1.591 | 11.478 | 1.00 | 32.12 |
| ATOM 4409 | O | LEU | 569 | 54.214 | −2.645 | 11.300 | 1.00 | 33.08 |
| ATOM 4410 | N | ARG | 570 | 54.315 | −0.409 | 11.148 | 1.00 | 32.05 |
| ATOM 4412 | CA | ARG | 570 | 52.999 | −0.293 | 10.529 | 1.00 | 35.21 |
| ATOM 4413 | CB | ARG | 570 | 52.659 | 1.173 | 10.256 | 1.00 | 36.77 |
| ATOM 4414 | CG | ARG | 570 | 51.282 | 1.370 | 9.653 | 1.00 | 43.11 |
| ATOM 4415 | CO | ARG | 570 | 51.203 | 2.690 | 8.926 | 1.00 | 49.24 |
| ATOM 4416 | NE | ARG | 570 | 52.154 | 2.775 | 7.815 | 1.00 | 55.77 |
| ATOM 4418 | CZ | ARG | 570 | 52.995 | 3.790 | 7.619 | 1.00 | 58.89 |
| ATOM 4419 | NH1 | ARG | 570 | 53.016 | 4.820 | 8.463 | 1.00 | 61.61 |
| ATOM 4422 | NH2 | ARG | 570 | 53.804 | 3.786 | 6.566 | 1.00 | 59.16 |
| ATOM 4425 | C | ARG | 570 | 52.992 | −1.063 | 9.220 | 1.00 | 35.16 |
| ATOM 4426 | O | ARG | 570 | 52.145 | −1.922 | 8.990 | 1.00 | 35.50 |
| ATOM 4427 | N | GLU | 571 | 53.971 | −0.760 | 8.383 | 1.00 | 36.29 |
| ATOM 4429 | CA | GLU | 571 | 54.111 | −1.400 | 7.089 | 1.00 | 37.51 |
| ATOM 4430 | CB | GLU | 571 | 15.219 | 0.701 | 6.308 | 1.00 | 41.27 |
| ATOM 4431 | CG | GLU | 571 | 54.945 | 0.778 | 6.110 | 1.00 | 49.88 |
| ATOM 4432 | CD | GLU | 571 | 56.087 | 1.516 | 5.436 | 1.00 | 57.58 |
| ATOM 4433 | OE1 | GLU | 571 | 57.264 | 1.122 | 5.636 | 1.00 | 60.59 |
| ATOM 4434 | OE2 | GLU | 571 | 55.804 | 2.504 | 4.714 | 1.00 | 61.14 |
| ATOM 4435 | C | GLU | 571 | 54.399 | −2.896 | 7.228 | 1.00 | 36.24 |
| ATOM 4436 | O | GLU | 571 | 53.889 | −3.716 | 6.459 | 1.00 | 34.22 |
| ATOM 4437 | N | TYR | 572 | 55.202 | −3.238 | 8.232 | 1.00 | 35.98 |
| ATOM 4439 | CA | TYR | 572 | 55.570 | −4.619 | 8.517 | 1.00 | 35.34 |
| ATOM 4440 | CB | TYR | 572 | 56.526 | −4.656 | 9.714 | 1.00 | 30.94 |
| ATOM 4441 | CG | TYR | 572 | 56.959 | −6.034 | 11.180 | 1.00 | 32.71 |
| ATOM 4442 | CD1 | TYR | 572 | 58.009 | −6.714 | 9.547 | 1.00 | 12.33 |
| ATOM 4443 | CE1 | TYR | 572 | 58.464 | −7.940 | 10.026 | 1.00 | 30.31 |
| ATOM 4444 | CD2 | TYR | 572 | 56.369 | −6.626 | 11.303 | 1.00 | 33.43 |
| ATOM 4445 | CE2 | TYR | 572 | 56.813 | −7.551 | 11.791 | 1.00 | 31.46 |
| ATOM 4446 | CZ | TYR | 572 | 57.064 | −8.502 | 11.148 | 1.00 | 33.99 |
| ATOM 4447 | OH | TYR | 572 | 58.311 | −9.706 | 11.640 | 1.00 | 36.30 |
| ATOM 4449 | C | TYR | 572 | 54.312 | 5.425 | 8.526 | 1.00 | 37.26 |
| ATOM 4450 | O | TYR | 572 | 54.121 | −6.530 | 8.314 | 1.00 | 36.91 |
| ATOM 4451 | N | LEU | 573 | 53.457 | −4.850 | 9.665 | 1.00 | 36.82 |
| ATOM 4453 | CA | LEU | 573 | 52.208 | −1.476 | 10.075 | 1.00 | 35.56 |
| ATOM 4454 | CB | LEU | 573 | 51.537 | −4.629 | 11.165 | 1.00 | 34.03 |
| ATOM 4455 | CG | LEU | 573 | 52.238 | −4.527 | 12.519 | 1.00 | 32.82 |
| ATOM 4456 | CD1 | LEU | 573 | 51.621 | −3.423 | 13.377 | 1.00 | 28.95 |
| ATOM 4457 | CD2 | LEU | 573 | 52.168 | −5.856 | 13.207 | 1.00 | 29.46 |
| ATOM 4458 | C | LEU | 573 | 51.237 | −5.658 | 8.915 | 1.00 | 34.56 |
| ATOM 4459 | O | LEU | 573 | 50.670 | −6.729 | 8.726 | 1.00 | 34.80 |
| ATOM 4460 | N | GLN | 574 | 51.030 | −4.602 | 8.150 | 1.00 | 37.10 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4462 | CA | GLN | 574 | 50.101 | −4.666 | 7.031 | 1.00 | 41.15 |
| ATOM 4463 | CB | GLN | 574 | 49.875 | −3.278 | 6.457 | 1.00 | 41.63 |
| ATOM 4464 | CG | GLN | 574 | 49.089 | −2.375 | 7.366 | 1.00 | 43.13 |
| ATOM 4465 | CD | GLN | 574 | 49.063 | −0.959 | 6.860 | 1.00 | 47.77 |
| ATOM 4466 | OE1 | GLN | 574 | 49.655 | −0.647 | 5.827 | 1.00 | 50.00 |
| ATOM 4467 | NE2 | GLN | 574 | 48.378 | −0.086 | 7.582 | 1.00 | 49.67 |
| ATOM 4470 | C | GLN | 574 | 50.529 | −5.627 | 5.934 | 1.00 | 42.38 |
| ATOM 4471 | O | GLN | 574 | 49.685 | −6.284 | 5.318 | 1.00 | 44.56 |
| ATOM 4472 | N | ALA | 575 | 51.835 | −5.717 | 5.697 | 1.00 | 41.99 |
| ATOM 4474 | CA | ALA | 575 | 52.367 | −6.608 | 4.676 | 1.00 | 41.29 |
| ATOM 4475 | CB | ALA | 575 | 53.841 | −6.325 | 4.446 | 1.00 | 40.43 |
| ATOM 4476 | C | ALA | 575 | 52.186 | −8.058 | 5.066 | 1.00 | 41.42 |
| ATOM 4477 | O | ALA | 575 | 52.392 | −8.949 | 4.249 | 1.00 | 43.65 |
| ATOM 4478 | N | ARG | 576 | 51.815 | −8.294 | 6.319 | 1.00 | 42.56 |
| ATOM 4480 | CA | ARG | 576 | 51.642 | −9.646 | 6.824 | 1.00 | 42.51 |
| ATOM 4481 | CB | ARG | 576 | 52.676 | −9.910 | 7.920 | 1.00 | 40.14 |
| ATOM 4482 | CG | ARG | 576 | 54.100 | −9.896 | 7.377 | 1.00 | 40.32 |
| ATOM 4483 | CD | ARG | 576 | 55.172 | −9.836 | 8.460 | 1.00 | 40.78 |
| ATOM 4484 | NE | ARG | 576 | 56.513 | −9.783 | 7.874 | 1.00 | 42.13 |
| ATOM 4486 | CZ | ARG | 576 | 56.975 | −8.785 | 7.120 | 1.00 | 40.73 |
| ATOM 4487 | NH1 | ARG | 576 | 56.215 | −7.732 | 6.851 | 1.00 | 39.21 |
| ATOM 4490 | NH2 | ARG | 576 | 58.201 | −8.846 | 6.622 | 1.00 | 37.62 |
| ATOM 4493 | C | ARG | 576 | 50.242 | −9.931 | 7.326 | 1.00 | 44.48 |
| ATOM 4494 | O | ARG | 576 | 50.028 | −10.869 | 8.098 | 1.00 | 46.84 |
| ATOM 4495 | N | ARG | 577 | 49.275 | −9.146 | 6.866 | 1.00 | 46.26 |
| ATOM 4497 | CA | ARG | 577 | 47.893 | −9.344 | 7.292 | 1.00 | 46.89 |
| ATOM 4498 | CB | ARG | 577 | 47.027 | −8.170 | 6.845 | 1.00 | 46.16 |
| ATOM 4499 | CG | ARG | 577 | 47.189 | −6.939 | 7.696 | 1.00 | 44.93 |
| ATOM 4500 | CD | ARG | 577 | 46.463 | −5.766 | 7.080 | 1.00 | 44.60 |
| ATOM 4501 | NE | ARG | 577 | 46.284 | −4.613 | 8.039 | 1.00 | 41.05 |
| ATOM 4503 | CZ | ARG | 577 | 45.612 | −3.565 | 7.793 | 1.00 | 45.95 |
| ATOM 4504 | NH1 | ARG | 577 | 45.052 | −3.372 | 6.606 | 1.00 | 47.39 |
| ATOM 4507 | NH2 | ARG | 577 | 45.466 | −2.655 | 8.749 | 1.00 | 45.49 |
| ATOM 4510 | C | ARG | 577 | 47.334 | −10.649 | 6.740 | 1.00 | 46.60 |
| ATOM 4511 | O | ARG | 577 | 47.478 | −10.933 | 5.551 | 1.00 | 47.15 |
| ATOM 4512 | N | GLN | 594 | 53.312 | −14.007 | 7.967 | 1.00 | 63.97 |
| ATOM 4514 | CA | GLN | 594 | 52.110 | −14.068 | 8.799 | 1.00 | 63.06 |
| ATOM 4515 | CB | GLN | 594 | 51.175 | −15.183 | 8.319 | 1.00 | 64.16 |
| ATOM 4516 | C | GLN | 594 | 52.501 | −14.278 | 10.258 | 1.00 | 61.68 |
| ATOM 4517 | O | GLN | 594 | 53.101 | −15.292 | 10.619 | 1.00 | 60.95 |
| ATOM 4518 | N | LEU | 595 | 52.140 | −13.313 | 11.092 | 1.00 | 58.58 |
| ATOM 4520 | CA | LEU | 595 | 52.470 | −13.335 | 12.505 | 1.00 | 55.58 |
| ATOM 4521 | CB | LEU | 595 | 52.619 | −11.902 | 13.020 | 1.00 | 54.05 |
| ATOM 4522 | CG | LEU | 595 | 53.570 | −11.074 | 12.153 | 1.00 | 56.23 |
| ATOM 4523 | CD1 | LEU | 595 | 53.496 | −9.609 | 12.524 | 1.00 | 58.84 |
| ATOM 4524 | CD2 | LEU | 595 | 54.977 | −11.596 | 12.301 | 1.00 | 55.93 |
| ATOM 4525 | C | LEU | 595 | 51.480 | −14.093 | 13.372 | 1.00 | 53.77 |
| ATOM 4526 | O | LEU | 595 | 50.276 | −14.046 | 13.139 | 1.00 | 54.31 |
| ATOM 4527 | N | SER | 596 | 52.012 | −14.780 | 14.377 | 1.00 | 51.04 |
| ATOM 4529 | CA | SER | 596 | 53.206 | −15.541 | 15.316 | 1.00 | 48.97 |
| ATOM 4530 | CB | SER | 596 | 52.004 | −16.737 | 15.834 | 1.00 | 48.89 |
| ATOM 4531 | OG | SER | 596 | 52.945 | −16.345 | 16.820 | 1.00 | 48.59 |
| ATOM 4531 | C | SER | 396 | 50.853 | −14.641 | 16.488 | 1.00 | 47.56 |
| ATOM 4534 | O | SER | 596 | 51.470 | −13.590 | 16.676 | 1.00 | 46.71 |
| ATOM 4535 | N | SER | 597 | 49.888 | −15.070 | 17.292 | 1.00 | 47.11 |
| ATOM 4537 | CA | SER | 597 | 49.462 | −14.315 | 18.461 | 1.00 | 47.88 |
| ATOM 4538 | CB | SER | 597 | 48.386 | −15.084 | 19.229 | 1.00 | 50.66 |
| ATOM 4539 | OG | SER | 597 | 47.574 | −15.839 | 18.343 | 1.00 | 57.08 |
| ATOM 4541 | C | SER | 597 | 50.666 | −14.068 | 19.372 | 1.00 | 46.03 |
| ATOM 4542 | O | SER | 597 | 50.735 | −13.045 | 20.047 | 1.00 | 46.49 |
| ATOM 4543 | N | LYS | 598 | 51.607 | −15.007 | 19.399 | 1.00 | 46.08 |
| ATOM 4545 | CA | LYS | 598 | 52.798 | −14.844 | 20.229 | 1.00 | 46.33 |
| ATOM 4546 | CB | LYS | 598 | 53.558 | −16.163 | 20.384 | 1.00 | 46.67 |
| ATOM 4547 | CG | LYS | 598 | 54.449 | −16.224 | 21.623 | 1.00 | 49.61 |
| ATOM 4548 | CD | LYS | 598 | 55.240 | −17.539 | 21.668 | 1.00 | 53.69 |
| ATOM 4549 | CE | LYS | 598 | 55.899 | −17.797 | 23.026 | 1.00 | 53.15 |
| ATOM 4550 | NZ | LYS | 598 | 54.891 | −18.076 | 24.093 | 1.00 | 52.02 |
| ATOM 4554 | C | LYS | 598 | 53.706 | −13.790 | 19.599 | 1.00 | 45.43 |
| ATOM 4555 | O | LYS | 598 | 54.292 | −12.968 | 20.311 | 1.00 | 44.18 |
| ATOM 4556 | N | ASP | 599 | 53.780 | −13.804 | 18.264 | 1.00 | 44.16 |
| ATOM 4558 | CA | ASP | 599 | 54.598 | −12.851 | 17.513 | 1.00 | 43.46 |
| ATOM 4559 | CS | ASP | 599 | 54.523 | −13.098 | 16.001 | 1.00 | 44.83 |
| ATOM 4560 | CG | ASP | 599 | 55.288 | −14.336 | 15.560 | 1.00 | 48.24 |
| ATOM 4561 | OD1 | ASP | 599 | 56.228 | −14.754 | 16.260 | 1.00 | 52.90 |

TABLE 3-continued

Atomic Structure Coordinates of Unphosphorylated FLGK

| Atom No. | Atom Type | A.A. Type | A.A. No. | X | Y | Z | OCC | B | |
|---|---|---|---|---|---|---|---|---|---|
| ATOM 4562 | OD2 | ASP | 599 | 54.958 | −14.894 | 14.493 | 1.00 | 51.43 | |
| ATOM 4563 | C | ASP | 599 | 54.120 | −11.437 | 17.796 | 1.00 | 42.71 | |
| ATOM 4564 | O | ASP | 599 | 54.937 | −10.550 | 18.059 | 1.00 | 45.00 | |
| ATOM 4565 | N | LEU | 600 | 52.803 | −11.235 | 17.776 | 1.00 | 37.69 | |
| ATOM 4567 | CA | LEU | 600 | 52.246 | −9.918 | 18.030 | 1.00 | 34.03 | |
| ATOM 4568 | CB | LEU | 600 | 50.747 | −9.882 | 17.747 | 1.00 | 34.06 | |
| ATOM 4569 | CG | LEU | 600 | 50.332 | 10.068 | 16.281 | 1.00 | 33.13 | |
| ATOM 4570 | CD1 | LEU | 600 | 48.814 | −9.992 | 16.190 | 1.00 | 37.38 | |
| ATOM 4571 | CD2 | LEU | 600 | 50.974 | −9.012 | 15.373 | 1.00 | 25.63 | |
| ATOM 4572 | C | LEU | 600 | 52.537 | −9.452 | 19.439 | 1.00 | 34.58 | |
| ATOM 4573 | O | LEU | 600 | 52.910 | −8.294 | 19.636 | 1.00 | 33.18 | |
| ATOM 4574 | N | VAL | 601 | 52.415 | −10.348 | 20.419 | 1.00 | 34.24 | |
| ATOM 4576 | CA | VAL | 601 | 52.692 | −9.969 | 21.808 | 1.00 | 35.80 | |
| ATOM 4577 | CS | VAL | 601 | 52.214 | −11.036 | 22.827 | 1.00 | 37.50 | |
| ATOM 4578 | CG1 | VAL | 601 | 52.331 | −10.483 | 24.252 | 1.00 | 38.08 | |
| ATOM 4579 | CG2 | VAL | 601 | 50.766 | −11.409 | 22.560 | 1.00 | 40.77 | |
| ATOM 4580 | C | VAL | 601 | 54.198 | −9.741 | 21.982 | 1.00 | 35.04 | |
| ATOM 4581 | O | VAL | 601 | 54.634 | −8.856 | 22.731 | 1.00 | 34.33 | |
| ATOM 4582 | N | SER | 602 | 54.981 | −10.531 | 21.262 | 1.00 | 32.58 | |
| ATOM 4584 | CA | SER | 602 | 56.421 | −10.421 | 21.307 | 1.00 | 36.01 | |
| ATOM 4585 | C1 | SER | 602 | 57.045 | −11.504 | 20.439 | 1.00 | 38.43 | |
| ATOM 4586 | CG | SER | 602 | 58.453 | −11.387 | 20.419 | 1.00 | 43.36 | |
| ATOM 4588 | C | SER | 602 | 56.809 | −9.038 | 20.800 | 1.00 | 35.21 | |
| ATOM 4589 | O | SER | 602 | 57.651 | −8.363 | 21.394 | 1.00 | 35.03 | |
| ATOM 4590 | N | CYS | 603 | 56.183 | −8.614 | 19.707 | 1.00 | 34.35 | |
| ATOM 4592 | CA | CYS | 603 | 56.438 | −7.294 | 19.141 | 1.00 | 34.04 | |
| ATOM 4593 | CB | CYS | 603 | 55.543 | −7.055 | 17.925 | 1.00 | 33.45 | |
| ATOM 4594 | SG | CYS | 603 | 55.653 | −5.423 | 17.229 | 0.50 | 32.19 | PRT1 |
| ATOM 4595 | C | CYS | 603 | 56.198 | −6.211 | 20.191 | 3.00 | 32.79 | |
| ATOM 4596 | O | CYS | 603 | 57.023 | −5.316 | 20.362 | 1.00 | 33.36 | |
| ATOM 4597 | N | ALA | 604 | 55.088 | −6.321 | 20.917 | 3.00 | 31.31 | |
| ATOM 4599 | CA | ALA | 604 | 54.743 | −5.358 | 21.965 | 1.00 | 32.36 | |
| ATOM 4600 | CB | ALA | 604 | 53.321 | −5.610 | 22.481 | 1.00 | 32.0 | |
| ATOM 4601 | C | ALA | 604 | 55.741 | −5.394 | 23.128 | 1.00 | 32.8J | |
| ATOM 4602 | O | ALA | 604 | 56.050 | −4.358 | 23.727 | 1.00 | 30.89 | |
| ATOM 4603 | N | TYR | 605 | 56.212 | −6.592 | 23.465 | 1.00 | 32.95 | |
| ATOM 4605 | CA | TYR | 605 | 57.189 | −6.758 | 24.539 | 1.00 | 33.34 | |
| ATOM 4606 | CB | TYR | 605 | 57.500 | −8.236 | 24.737 | 1.00 | 32.58 | |
| ATOM 4607 | CG | TYR | 605 | 58.640 | −8.495 | 25.690 | 1.00 | 32.51 | |
| ATOM 4608 | CD1 | TYR | 605 | 58.511 | −8.236 | 27.053 | 1.00 | 33.50 | |
| ATOM 4609 | CE1 | TYR | 605 | 59.556 | −8.507 | 27.943 | 1.00 | 37.08 | |
| ATOM 4610 | CD2 | TYR | 605 | 59.841 | −9.026 | 25.230 | 1.00 | 34.22 | |
| ATOM 4611 | CE2 | TYR | 605 | 60.896 | −9.300 | 26.109 | 1.00 | 36.64 | |
| ATOM 4612 | CZ | TYR | 605 | 60.746 | −9.042 | 27.464 | 1.00 | 37.56 | |
| ATOM 4613 | OH | TYR | 605 | 61.776 | −9.342 | 28.336 | 1.00 | 38.0 | |
| ATOM 4615 | C | TYR | 605 | 56.480 | −6.006 | 24.191 | 1.00 | 32.42 | |
| ATOM 4616 | O | TYR | 605 | 55.975 | −5.203 | 24.991 | 1.00 | 33.34 | |
| ATOM 4617 | N | GLN | 606 | 58.997 | −6.267 | 22.989 | 1.00 | 30.61 | |
| ATOM 4619 | CA | GLN | 606 | 60.218 | −5.643 | 22.474 | 1.00 | 31.12 | |
| ATOM 4620 | CB | GLN | 606 | 60.499 | −6.143 | 21.058 | 1.00 | 30.57 | |
| ATOM 4621 | CG | GLN | 606 | 61.044 | −7.568 | 21.008 | 1.00 | 33.90 | |
| ATOM 4622 | CD | GLN | 606 | 61.240 | −8.080 | 19.593 | 1.00 | 32.17 | |
| ATOM 4623 | OE1 | GLN | 606 | 62.155 | −7.652 | 18.883 | 1.00 | 32.55 | |
| ATOM 4624 | NE2 | GLN | 606 | 60.374 | −8.998 | 19.171 | 1.00 | 33.10 | |
| ATOM 4627 | C | GLN | 606 | 60.157 | −4.114 | 22.487 | 1.00 | 31.69 | |
| ATOM 4628 | O | GLN | 606 | 61.111 | −3.453 | 22.910 | 1.00 | 31.18 | |
| ATOM 4629 | N | VAL | 607 | 59.035 | −3.564 | 22.020 | 1.00 | 29.50 | |
| ATOM 4631 | CA | VAL | 607 | 58.816 | −2.122 | 22.000 | 1.00 | 27.54 | |
| ATOM 4632 | CB | VAL | 607 | 57.454 | −1.751 | 21.306 | 1.00 | 26.79 | |
| ATOM 4633 | CG1 | VAL | 607 | 57.131 | −0.291 | 21.516 | 1.00 | 24.80 | |
| ATOM 4634 | CG2 | VAL | 607 | 57.505 | −2.050 | 19.815 | 1.00 | 22.95 | |
| ATOM 4635 | C | VAL | 607 | 58.827 | −1.576 | 23.432 | 1.00 | 28.30 | |
| ATOM 4636 | O | VAL | 607 | 59.469 | −0.548 | 23.705 | 1.00 | 28.32 | |
| ATOM 4637 | N | ALA | 608 | 58.110 | −2.247 | 24.340 | 1.00 | 27.21 | |
| ATOM 4639 | CA | ALA | 608 | 58.061 | −1.805 | 25.735 | 1.00 | 26.54 | |
| ATOM 4640 | CB | ALA | 608 | 57.070 | −2.649 | 26.510 | 1.00 | 26.70 | |
| ATOM 4641 | C | ALA | 608 | 59.457 | −1.850 | 26.365 | 1.00 | 25.97 | |
| ATOM 4642 | O | ALA | 608 | 59.802 | −0.993 | 27.183 | 1.00 | 25.88 | |
| ATOM 4643 | N | ARG | 609 | 60.250 | −2.848 | 25.994 | 1.00 | 26.02 | |
| ATOM 4645 | CA | ARG | 609 | 61.606 | −2.977 | 26.512 | 1.00 | 30.44 | |
| ATOM 4646 | CB | ARG | 609 | 62.234 | −4.285 | 26.058 | 1.00 | 34.09 | |
| ATOM 4647 | CG | ARG | 609 | 61.642 | −5.516 | 26.682 | 1.00 | 39.24 | |
| ATOM 4648 | CD | ARG | 609 | 62.659 | −6.615 | 26.615 | 1.00 | 42.75 | |
| ATOM 4649 | NE | ARG | 609 | 63.405 | −6.704 | 27.860 | 1.00 | 45.52 | |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4651 | CZ | ARG | 609 | 64.525 | −7.405 | 26.019 | 1.00 | 46.24 |
| ATOM 4652 | NH1 | ARG | 609 | 65.055 | −8.079 | 27.001 | 1.00 | 41.48 |
| ATOM 4655 | NH2 | ARG | 609 | 65.079 | −7.482 | 29.225 | 1.00 | 47.49 |
| ATOM 4658 | C | ARG | 609 | 62.478 | −1.829 | 26.015 | 1.00 | 34.20 |
| ATOM 4659 | O | ARG | 609 | 63.265 | −1.255 | 26.788 | 1.00 | 35.24 |
| ATOM 4660 | N | GLY | 610 | 62.368 | −1.528 | 24.717 | 1.00 | 33.25 |
| ATOM 4662 | CA | GLY | 610 | 63.130 | −0.439 | 24.138 | 1.00 | 29.57 |
| ATOM 4663 | C | GLY | 610 | 62.802 | 0.614 | 24.901 | 1.00 | 29.31 |
| ATOM 4664 | O | GLY | 610 | 63.695 | 1.543 | 25.335 | 1.00 | 27.46 |
| ATOM 4665 | N | MET | 611 | 61.507 | 1.020 | 25.147 | 1.00 | 31.07 |
| ATOM 4667 | CA | MET | 611 | 61.016 | 2.178 | 25.889 | 1.00 | 30.09 |
| ATOM 4668 | CB | MET | 611 | 59.493 | 2.280 | 25.782 | 1.00 | 29.51 |
| ATOM 4669 | CG | MET | 611 | 58.997 | 2.655 | 24.404 | 1.00 | 28.21 |
| ATOM 4670 | SD | MET | 611 | 59.760 | 4.175 | 23.787 | 1.00 | 29.00 |
| ATOM 4671 | CE | MET | 611 | 59.350 | 5.335 | 25.039 | 1.00 | 25.91 |
| ATOM 4672 | C | MET | 611 | 61.439 | 2.189 | 27.361 | 1.00 | 30.47 |
| ATOM 4673 | O | MET | 611 | 61.734 | 3.242 | 27.919 | 1.00 | 29.43 |
| ATOM 4674 | N | GLU | 612 | 61.429 | 1.031 | 28.002 | 1.00 | 31.97 |
| ATOM 4676 | CA | GLU | 612 | 61.836 | 0.947 | 29.402 | 1.00 | 35.34 |
| ATOM 4677 | CB | GLU | 612 | 61.707 | −0.490 | 29.904 | 1.00 | 36.17 |
| ATOM 4678 | CG | GLU | 612 | 62.305 | −0.729 | 31.278 | 1.00 | 34.87 |
| ATOM 4679 | CD | GLU | 612 | 62.259 | −2.185 | 31.705 | 1.00 | 32.68 |
| ATOM 4680 | OE1 | GLU | 612 | 62.641 | −3.070 | 30.904 | 1.00 | 35.01 |
| ATOM 4681 | OE2 | GLU | 612 | 61.848 | −2.443 | 32.858 | 1.00 | 36.56 |
| ATOM 4662 | C | GLU | 612 | 63.296 | 1.425 | 29.490 | 1.00 | 35.26 |
| ATOM 4683 | O | GLU | 612 | 63.677 | 2.162 | 30.417 | 1.00 | 31.21 |
| ATOM 4684 | N | TYR | 613 | 64.092 | 1.040 | 28.491 | 1.00 | 36.10 |
| ATOM 4686 | CA | TYR | 613 | 65.491 | 1.458 | 28.440 | 1.00 | 34.76 |
| ATOM 4687 | CB | TYR | 613 | 66.249 | 0.788 | 27.301 | 1.00 | 31.15 |
| ATOM 4688 | CG | TYR | 613 | 67.700 | 1.195 | 27.284 | 1.00 | 34.28 |
| ATOM 4689 | CD1 | TYR | 613 | 68.600 | 0.654 | 28.207 | 1.00 | 36.50 |
| ATOM 4690 | CE1 | TYR | 613 | 69.949 | 1.035 | 28.219 | 1.00 | 38.20 |
| ATOM 4691 | CD2 | TYR | 613 | 68.179 | 2.135 | 26.366 | 1.00 | 32.99 |
| ATOM 4692 | CE2 | TYR | 613 | 69.520 | 2.526 | 26.372 | 1.00 | 33.32 |
| ATOM 4693 | CZ | TYR | 613 | 70.399 | 1.968 | 27.302 | 1.00 | 36.59 |
| ATOM 4694 | OH | TYR | 613 | 71.721 | 2.340 | 27.333 | 1.00 | 35.73 |
| ATOM 4696 | C | TYR | 613 | 65.583 | 2.970 | 28.273 | 1.00 | 34.03 |
| ATOM 4697 | O | TYR | 613 | 66.231 | 2.643 | 29.075 | 1.00 | 35.26 |
| ATOM 4698 | N | LEU | 614 | 64.916 | 3.503 | 27.250 | 1.00 | 31.78 |
| ATOM 4700 | CA | LEU | 614 | 64.945 | 4.937 | 26.998 | 1.00 | 29.50 |
| ATOM 4701 | CB | LEU | 614 | 64.095 | 5.297 | 25.775 | 1.00 | 28.26 |
| ATOM 4702 | CG | LEU | 614 | 64.564 | 4.742 | 24.422 | 1.00 | 31.29 |
| ATOM 4703 | CD1 | LEU | 614 | 63.564 | 5.089 | 23.321 | 1.00 | 28.09 |
| ATOM 4704 | CD2 | LEU | 614 | 65.951 | 5.282 | 24.079 | 1.00 | 29.52 |
| ATOM 4705 | C | LEU | 614 | 64.489 | 5.715 | 28.224 | 1.00 | 32.49 |
| ATOM 4706 | O | LEU | 614 | 65.108 | 6.117 | 28.598 | 1.00 | 31.73 |
| ATOM 4707 | N | ALA | 615 | 63.431 | 5.232 | 28.872 | 1.00 | 33.06 |
| ATOM 4709 | CA | ALA | 615 | 62.906 | 5.870 | 30.070 | 1.00 | 35.16 |
| ATOM 4710 | CB | ALA | 615 | 61.598 | 5.192 | 30.511 | 1.00 | 36.64 |
| ATOM 4711 | C | ALA | 615 | 63.942 | 5.838 | 31.202 | 1.00 | 35.36 |
| ATOM 4712 | O | ALA | 615 | 64.065 | 6.805 | 31.952 | 1.00 | 36.80 |
| ATOM 4713 | N | SER | 616 | 64.690 | 4.739 | 31.315 | 1.00 | 35.91 |
| ATOM 4715 | CA | SER | 616 | 65.716 | 4.621 | 32.354 | 1.00 | 35.78 |
| ATOM 4716 | CB | SER | 616 | 66.287 | 3.199 | 32.424 | 1.00 | 32.52 |
| ATOM 4717 | OG | SER | 616 | 67.133 | 2.899 | 31.324 | 1.00 | 29.64 |
| ATOM 4719 | C | SER | 616 | 66.832 | 5.623 | 32.063 | 1.00 | 37.48 |
| ATOM 4720 | O | SER | 616 | 67.556 | 6.048 | 32.967 | 1.00 | 38.76 |
| ATOM 4721 | N | LYS | 617 | 66.971 | 5.980 | 30.790 | 1.00 | 34.74 |
| ATOM 4723 | CA | LYS | 617 | 67.973 | 6.931 | 30.357 | 1.00 | 32.44 |
| ATOM 4724 | CB | LYS | 617 | 68.540 | 6.520 | 28.998 | 1.00 | 32.94 |
| ATOM 4725 | CG | LYS | 617 | 69.330 | 5.232 | 19.041 | 1.00 | 32.64 |
| ATOM 4726 | CD | LYS | 617 | 70.539 | 5.402 | 29.933 | 1.00 | 38.45 |
| ATOM 4727 | CE | LYS | 617 | 71.252 | 4.091 | 30.139 | 1.00 | 40.84 |
| ATOM 4728 | NZ | LYS | 617 | 72.552 | 4.306 | 30.812 | 1.00 | 46.49 |
| ATOM 4732 | C | LYS | 617 | 67.376 | 8.325 | 30.281 | 1.00 | 33.29 |
| ATOM 4733 | O | LYS | 617 | 67.909 | 9.188 | 29.598 | 1.00 | 33.95 |
| ATOM 4734 | N | LYS | 618 | 66.245 | 6.528 | 30.952 | 1.00 | 34.87 |
| ATOM 4736 | CA | LYS | 618 | 65.569 | 9.822 | 30.997 | 1.00 | 35.44 |
| ATOM 4737 | CB | LYS | 618 | 66.512 | 10.866 | 31.581 | 1.00 | 40.44 |
| ATOM 4738 | CG | LYS | 618 | 67.192 | 10.446 | 32.877 | 1.00 | 48.19 |
| ATOM 4739 | CD | LYS | 618 | 66.234 | 10.363 | 34.037 | 1.00 | 55.47 |
| ATOM 4740 | CE | LYS | 618 | 66.962 | 9.939 | 35.310 | 1.00 | 61.56 |
| ATOM 4741 | NZ | LYS | 618 | 66.070 | 10.032 | 36.514 | 1.00 | 68.82 |
| ATOM 4745 | C | LYS | 618 | 65.015 | 10.327 | 29.663 | 1.00 | 35.62 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4746 | O | LYS | 618 | 64.557 | 11.463 | 29.569 | 1.00 | 36.44 |
| ATOM 4747 | N | CYS | 619 | 65.006 | 9.472 | 28.647 | 1.00 | 34.24 |
| ATOM 4749 | CA | CYS | 619 | 64.525 | 9.848 | 27.323 | 1.00 | 31.62 |
| ATOM 4750 | CB | CYS | 619 | 65.279 | 9.033 | 26.263 | 1.00 | 31.17 |
| ATOM 4751 | SG | CYS | 619 | 64.816 | 9.306 | 24.541 | 1.00 | 30.02 |
| ATOM 4752 | C | CYS | 619 | 63.004 | 9.701 | 27.149 | 1.00 | 30.45 |
| ATOM 4753 | O | CYS | 619 | 62.418 | 8.649 | 27.368 | 1.00 | 29.24 |
| ATOM 4754 | N | ILE | 620 | 62.359 | 10.798 | 26.800 | 1.00 | 30.14 |
| ATOM 4756 | CA | ILE | 620 | 60.935 | 10.822 | 26.542 | 1.00 | 31.76 |
| ATOM 4757 | CB | ILE | 620 | 60.268 | 12.040 | 27.193 | 1.00 | 31.26 |
| ATOM 4758 | CG2 | ILE | 620 | 58.799 | 12.116 | 26.774 | 1.00 | 31.66 |
| ATOM 4759 | CG1 | ILE | 620 | 60.392 | Z1.957 | 28.712 | 1.00 | 29.71 |
| ATOM 4760 | CD1 | ILE | 620 | 60.016 | 13.236 | 29.396 | 1.00 | 27.40 |
| ATOM 4761 | C | ILE | 620 | 60.864 | 10.961 | 25.023 | 1.00 | 31.86 |
| ATOM 4762 | O | ILE | 620 | 61.384 | 11.920 | 24.465 | 1.00 | 32.70 |
| ATOM 4763 | N | HIS | 621 | 60.249 | 9.986 | 24.366 | 1.00 | 31.70 |
| ATOM 4765 | CA | HIS | 621 | 60.133 | 9.973 | 22.906 | 1.00 | 32.12 |
| ATOM 4766 | CB | HIS | 621 | 59.708 | 8.578 | 22.430 | 1.00 | 29.61 |
| ATOM 4767 | CG | HIS | 621 | 59.903 | 8.344 | 20.961 | 1.00 | 28.62 |
| ATOM 4768 | CD2 | HIS | 621 | 60.511 | 7.336 | 20.300 | 1.00 | 27.49 |
| ATOM 4769 | ND1 | HIS | 621 | 59.373 | 9.168 | 19.988 | 1.00 | 30.08 |
| ATOM 4771 | CE1 | HIS | 621 | 59.637 | 8.669 | 18.795 | 1.00 | 25.00 |
| ATOM 4772 | NE2 | HIS | 621 | 60.325 | 7.554 | 18.956 | 1.00 | 26.55 |
| ATOM 4774 | C | HIS | 621 | 59.194 | 11.026 | 22.321 | 1.00 | 34.51 |
| ATOM 4775 | O | HIS | 621 | 59.466 | 11.570 | 21.251 | 1.00 | 36.79 |
| ATOM 4776 | N | ARG | 622 | 58.048 | 11.248 | 22.960 | 1.00 | 35.26 |
| ATOM 4778 | CA | ARG | 622 | 57.068 | 12.239 | 22.490 | 1.00 | 34.68 |
| ATOM 4779 | CB | ARG | 622 | 57.705 | 13.628 | 22.370 | 1.00 | 33.43 |
| ATOM 4780 | CG | ARG | 622 | 58.285 | 14.135 | 23.674 | 1.00 | 31.52 |
| ATOM 4781 | CD | ARG | 622 | 58.781 | 15.563 | 23.570 | 0.50 | 27.82 |
| ATOM 4782 | NE | ARG | 622 | 59.216 | 16.050 | 24.876 | 0.50 | 28.82 |
| ATOM 4784 | CZ | ARG | 622 | 60.362 | 15.715 | 25.463 | 0.50 | 30.41 |
| ATOM 4785 | NH1 | ARG | 622 | 61.215 | 14.891 | 24.860 | 0.50 | 31.15 |
| ATOM 4788 | NH2 | ARG | 622 | 60.640 | 16.168 | 26.680 | 0.50 | 30.83 |
| ATOM 4791 | C | ARG | 622 | 56.283 | 11.891 | 21.213 | 1.00 | 34.71 |
| ATOM 4792 | O | ARG | 622 | 55.289 | 12.544 | 20.912 | 1.00 | 35.58 |
| ATOM 4793 | N | ASP | 623 | 56.719 | 10.884 | 20.459 | 1.00 | 34.90 |
| ATOM 4795 | CA | ASP | 623 | 55.986 | 10.468 | 19.261 | 1.00 | 34.30 |
| ATOM 4796 | CB | ASP | 623 | 56.443 | 11.212 | 17.994 | 1.00 | 36.76 |
| ATOM 4797 | CG | ASP | 623 | 55.535 | 10.9Z8 | 16.772 | 1.00 | 43.35 |
| ATOM 4798 | OD1 | ASP | 623 | 55.980 | 11.131 | 15.624 | 1.00 | 47.64 |
| ATOM 4799 | OD2 | ASP | 623 | 54.376 | 10.469 | 16.954 | 1.00 | 43.30 |
| ATOM 4800 | C | ASP | 623 | 56.094 | 8.967 | 19.051 | 1.00 | 32.24 |
| ATOM 4801 | O | ASP | 623 | 56.406 | 8.494 | 17.957 | 1.00 | 31.19 |
| ATOM 4802 | N | LEU | 624 | 55.895 | 8.209 | 20.118 | 1.00 | 32.27 |
| ATOM 4804 | CA | LEU | 624 | 55.964 | 6.759 | 20.005 | 1.00 | 33.18 |
| ATOM 4805 | CB | LEU | 624 | 56.013 | 6.118 | 21.390 | 1.00 | 31.16 |
| ATOM 4806 | CG | LEU | 624 | 56.019 | 4.592 | 21.452 | 1.00 | 32.74 |
| ATOM 4807 | CD1 | LEU | 624 | 57.257 | 4.020 | 20.765 | 1.00 | 30.64 |
| ATOM 4808 | CD2 | LEU | 624 | 55.974 | 4.177 | 22.904 | Z.00 | 34.51 |
| ATOM 4809 | C | LEU | 624 | 54.738 | 6.274 | 19.2Z7 | 1.00 | 35.18 |
| ATOM 4810 | O | LEU | 624 | 53.559 | 6.511 | 19.612 | 1.00 | 35.72 |
| ATOM 4811 | N | ALA | 625 | 54.997 | 5.632 | 18.084 | 1.00 | 32.37 |
| ATOM 4813 | CA | ALA | 625 | 53.946 | 5.113 | 17.223 | 1.00 | 30.60 |
| ATOM 4814 | CB | ALA | 625 | 53.447 | 6.205 | 16.298 | 1.00 | 25.26 |
| ATOM 4815 | C | ALA | 625 | 54.618 | 4.020 | 16.427 | 1.00 | 29.87 |
| ATOM 4816 | O | ALA | 625 | 55.839 | 3.978 | 16.378 | 1.00 | 32.01 |
| ATOM 4817 | N | ALA | 626 | 53.834 | 3.163 | 15.779 | 1.00 | 30.12 |
| ATOM 4819 | CA | ALA | 626 | 54.373 | 2.057 | 14.978 | 1.00 | 29.62 |
| ATOM 4820 | CB | ALA | 626 | 53.231 | 1.159 | 14.441 | 1.00 | 27.11 |
| ATOM 4821 | C | ALA | 626 | 55.255 | 2.552 | 13.838 | 1.00 | 26.57 |
| ATOM 4822 | O | ALA | 626 | 56.193 | 1.671 | 13.434 | 1.00 | 26.29 |
| ATOM 4823 | N | ARG | 627 | 54.935 | 3.730 | 13.317 | 1.00 | 26.74 |
| ATOM 4825 | CA | ARG | 627 | 55.706 | 4.352 | 12.244 | 1.00 | 26.73 |
| ATOM 4826 | CB | ARG | 627 | 55.056 | 5.671 | 11.827 | 1.00 | 29.62 |
| ATOM 4827 | CG | ARG | 627 | 54.894 | 6.659 | 12.972 | 1.00 | 31.84 |
| ATOM 4828 | CD | ARG | 627 | 54.435 | 8.032 | 12.485 | 1.00 | 38.54 |
| ATOM 4829 | NE | ARG | 627 | 53.987 | 8.878 | 13.590 | 1.00 | 38.59 |
| ATOM 4831 | CZ | ARG | 627 | 52.745 | 8.879 | 14.064 | 1.00 | 39.55 |
| ATOM 4832 | NH1 | ARG | 627 | 51.822 | 8.094 | 13.525 | 1.00 | 35.96 |
| ATOM 4835 | NH2 | ARG | 627 | 52.447 | 9.604 | 15.127 | 1.00 | 41.05 |
| ATOM 4838 | C | ARG | 627 | 57.151 | 4.632 | 12.676 | 1.00 | 30.79 |
| ATOM 4839 | O | ARG | 627 | 58.058 | 4.687 | 11.838 | 1.00 | 30.16 |
| ATOM 4840 | N | ASN | 628 | 57.347 | 4.822 | 13.985 | 1.00 | 30.31 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4842 | CA | ASN | 628 | 58.661 | 5.109 | 14.550 | 1.01 | 28.50 |
| ATOM 4843 | CB | ASN | 628 | 58.587 | 6.257 | 15.549 | 1.00 | 27.84 |
| ATOM 4844 | CG | ASN | 628 | 58.369 | 7.571 | 14.868 | 1.00 | 31.41 |
| ATOM 4845 | OD1 | ASN | 628 | 58.893 | 7.796 | 13.782 | 1.0a | 33.45 |
| ATOM 4846 | ND2 | ASN | 628 | 57.551 | 8.429 | 15.460 | 1.00 | 28.53 |
| ATOM 4849 | C | ASN | 628 | 59.352 | 3.919 | 15.169 | 1.00 | 28.10 |
| ATOM 4850 | O | ASN | 628 | 60.232 | 4.076 | 16.021 | 1.00 | 28.64 |
| ATOM 4851 | N | VAL | 629 | 58.887 | 2.733 | 14.803 | 1.00 | 27.79 |
| ATOM 4853 | CA | VAL | 629 | 59.484 | 1.482 | 15.253 | 1.00 | 28.30 |
| ATOM 4854 | CB | VAL | 629 | 58.475 | 0.577 | 15.983 | 1.00 | 25.38 |
| ATOM 4855 | CG1 | VAL | 629 | 59.118 | −0.753 | 16.284 | 1.00 | 23.07 |
| ATOM 4856 | CG2 | VAL | 629 | 57.980 | 1.246 | 17.265 | 1.00 | 22.48 |
| ATOM 4857 | C | VAL | 629 | 59.925 | 0.810 | 13.949 | 1.00 | 28.69 |
| ATOM 4858 | O | VAL | 629 | 59.114 | 0.616 | 13.043 | 1.00 | 27.07 |
| ATOM 4859 | N | LEU | 630 | 61.220 | 0.542 | 13.823 | 1.00 | 29.54 |
| ATOM 4861 | CA | LEU | 630 | 61.749 | −0.081 | 12.616 | 1.00 | 30.17 |
| ATOM 4862 | CB | LEU | 630 | 62.999 | 0.659 | 12.142 | 1.00 | 29.62 |
| ATOM 4863 | CG | LEU | 630 | 62.831 | 2.180 | 12.035 | 1.00 | 29.14 |
| ATOM 4864 | CD1 | LEU | 630 | 64.121 | 2.795 | 11.579 | 1.00 | 29.83 |
| ATOM 4865 | CD2 | LEU | 630 | 61.693 | 2.543 | 11.086 | 1.00 | 32.59 |
| ATOM 4866 | C | LEU | 630 | 62.036 | −1.541 | 12.899 | 1.00 | 30.56 |
| ATOM 4867 | O | LEU | 630 | 62.290 | −1.910 | 14.042 | 1.00 | 31.06 |
| ATOM 4868 | N | VAL | 631 | 61.966 | −2.376 | 11.866 | 1.00 | 33.03 |
| ATOM 4870 | CA | VAL | 631 | 62.174 | −3.813 | 12.022 | 1.00 | 31.83 |
| ATOM 4871 | CB | VAL | 631 | 60.902 | −4.605 | 11.582 | 1.00 | 29.48 |
| ATOM 4872 | CG1 | VAL | 631 | 61.017 | −6.067 | 11.980 | 1.00 | 29.39 |
| ATOM 4873 | CG2 | VAL | 631 | 59.644 | −3.984 | 12.196 | 1.00 | 25.38 |
| ATOM 4874 | C | VAL | 631 | 63.379 | −4.242 | 11.196 | 1.00 | 32.37 |
| ATOM 4875 | O | VAL | 631 | 63.508 | −3.865 | 10.024 | 1.00 | 33.57 |
| ATOM 4876 | N | THR | 632 | 64.285 | −4.987 | 11.820 | 1.00 | 34.39 |
| ATOM 4878 | CA | THR | 632 | 65.504 | −5.453 | 11.145 | 1.00 | 35.84 |
| ATOM 4879 | CB | THR | 632 | 66.659 | −5.685 | 12.148 | 1.00 | 33.11 |
| ATOM 4880 | OG1 | THR | 632 | 66.328 | −6.774 | 13.020 | 1.00 | 34.88 |
| ATOM 4882 | CG2 | THR | 632 | 66.922 | −4.426 | 12.972 | 1.00 | 28.85 |
| ATOM 4883 | C | THR | 632 | 65.272 | −6.738 | 10.350 | 1.00 | 37.63 |
| ATOM 4884 | O | THR | 632 | 64.195 | −7.347 | 10.439 | 1.00 | 37.20 |
| ATOM 4885 | N | GLU | 633 | 66.289 | −7.163 | 9.609 | 1.00 | 39.78 |
| ATOM 4887 | CA | GLU | 633 | 66.182 | −8.379 | 8.794 | 1.00 | 43.30 |
| ATOM 4888 | CB | GLU | 633 | 67.437 | −8.590 | 7.933 | 1.00 | 46.66 |
| ATOM 4889 | CG | GLU | 633 | 67.336 | −9.729 | 6.876 | 1.00 | 51.37 |
| ATOM 4890 | CD | GLU | 633 | 66.490 | −9.404 | 5.6Z2 | 1.00 | 54.30 |
| ATOM 4891 | OE1 | GLU | 633 | 65.859 | −8.327 | 5.523 | 1.00 | 55.85 |
| ATOM 4892 | OE2 | GLU | 633 | 66.460 | −10.256 | 4.710 | 1.00 | 55.95 |
| ATOM 4893 | C | GLU | 633 | 65.919 | −9.592 | 9.677 | 1.00 | 42.72 |
| ATOM 4894 | O | GLU | 633 | 65.360 | −10.582 | 9.222 | 1.00 | 45.10 |
| ATOM 4895 | N | ASP | 634 | 66.287 | −9.494 | 10.949 | 1.00 | 42.83 |
| ATOM 4897 | CA | ASP | 634 | 66.075 | −10.585 | 11.884 | 1.00 | 43.03 |
| ATOM 4898 | CB | ASP | 634 | 67.324 | −10.809 | 12.743 | 1.00 | 49.02 |
| ATOM 4899 | CG | ASP | 634 | 68.539 | −11.240 | 11.916 | 1.00 | 55.95 |
| ATOM 4900 | OD1 | ASP | 634 | 68.462 | −12.292 | 11.237 | 1.00 | 59.10 |
| ATOM 4901 | OD2 | ASP | 634 | 69.568 | −10.525 | 11.943 | 1.00 | 59.41 |
| ATOM 4902 | C | ASP | 634 | 64.848 | −10.340 | 12.751 | 1.00 | 41.75 |
| ATOM 4903 | O | ASP | 634 | 64.737 | −10.873 | 13.847 | 1.00 | 42.79 |
| ATOM 4904 | N | ASN | 635 | 63.937 | −9.508 | 12.257 | 1.00 | 42.51 |
| ATOM 4906 | CA | ASN | 635 | 62.686 | −9.186 | 12.939 | 1.00 | 42.53 |
| ATOM 4907 | CB | ASN | 635 | 61.768 | −10.417 | 12.992 | 1.00 | 45.07 |
| ATOM 4908 | CG | ASN | 635 | 61.483 | −10.985 | 11.624 | 1.00 | 46.54 |
| ATOM 4909 | OD1 | ASN | 635 | 60.868 | −10.336 | 10.786 | 1.00 | 49.77 |
| ATOM 4910 | ND2 | ASN | 635 | 61.949 | −12.192 | 11.383 | 1.00 | 49.29 |
| ATOM 4913 | C | ASN | 635 | 62.801 | −8.577 | 14.331 | 1.00 | 40.51 |
| ATOM 4914 | O | ASN | 635 | 61.939 | −8.800 | 15.187 | 1.00 | 41.80 |
| ATOM 4915 | N | VAL | 636 | 63.844 | −7.795 | 14.561 | 1.00 | 37.98 |
| ATOM 4917 | CA | VAL | 636 | 64.016 | −7.164 | 15.856 | 1.00 | 33.92 |
| ATOM 4918 | CB | VAL | 636 | 65.517 | −7.005 | 16.195 | 1.00 | 32.21 |
| ATOM 4919 | CG1 | VAL | 636 | 65.697 | −6.284 | 17.530 | 1.00 | 31.40 |
| ATOM 4920 | CG2 | VAL | 636 | 66.169 | −8.367 | 16.242 | 1.00 | 30.93 |
| ATOM 4921 | C | VAL | 636 | 63.349 | −5.797 | 15.811 | 1.00 | 31.85 |
| ATOM 4922 | O | VAL | 636 | 63.531 | −5.061 | 14.849 | 1.00 | 33.47 |
| ATOM 4923 | N | MET | 637 | 62.525 | −5.492 | 16.807 | 1.00 | 31.69 |
| ATOM 4925 | CA | MET | 637 | 61.860 | −4.194 | 16.879 | 1.00 | 31.44 |
| ATOM 4926 | CB | MET | 637 | 60.642 | −4.241 | 17.820 | 1.00 | 34.97 |
| ATOM 4927 | CG | MET | 637 | 59.559 | −5.264 | 17.455 | 1.00 | 36.80 |
| ATOM 4928 | SD | MET | 637 | 58.860 | −5.048 | 15.803 | 1.00 | 35.45 |
| ATOM 4929 | CE | MET | 637 | 59.030 | −6.709 | 15.116 | 1.00 | 32.12 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 4930 | C | MET | 637 | 62.874 | −3.209 | 17.454 | 1.00 | 31.86 |
| ATOM 4931 | O | MET | 637 | 63.512 | −3.496 | 18.479 | 1.00 | 29.47 |
| ATOM 4932 | N | LYS | 638 | 62.985 | −2.041 | 16.820 | 1.00 | 30.87 |
| ATOM 4934 | CA | LYS | 636 | 63.915 | −0.994 | 17.244 | 1.00 | 29.66 |
| ATOM 4935 | CB | LYS | 638 | 65.161 | −0.983 | 16.349 | 1.00 | 27.51 |
| ATOM 4936 | CG | LYS | 638 | 66.171 | −2.059 | 16.691 | 1.00 | 27.29 |
| ATOM 4937 | CD | LYS | 638 | 67.370 | −1.984 | 15.781 | 1.00 | 28.55 |
| ATOM 4938 | CE | LYS | 638 | 68.409 | −3.029 | 16.150 | 1.00 | 24.75 |
| ATOM 4939 | NZ | LYS | 638 | 68.964 | −2.785 | 17.498 | 1.00 | 25.59 |
| ATOM 4943 | C | LYS | 638 | 63.283 | 0.383 | 17.215 | 1.00 | 27.72 |
| ATOM 4944 | O | LYS | 638 | 62.918 | 0.869 | 16.146 | 1.00 | 27.66 |
| ATOM 4945 | N | ILE | 639 | 63.163 | 1.004 | 18.387 | 1.00 | 26.21 |
| ATOM 4947 | CA | ILE | 639 | 62.597 | 2.343 | 18.501 | 1.00 | 26.27 |
| ATOM 4948 | CB | ILE | 639 | 62.580 | 2.862 | 19.965 | 1.00 | 26.52 |
| ATOM 4949 | CG2 | ILE | 639 | 61.896 | 4.206 | 20.017 | 1.00 | 21.50 |
| ATOM 4950 | CG1 | ILE | 639 | 61.918 | 1.854 | 20.926 | 1.00 | 25.70 |
| ATOM 4951 | CD1 | ILE | 639 | 60.496 | 1.494 | 20.599 | 1.00 | 25.62 |
| ATOM 4952 | C | ILE | 639 | 63.505 | 3.288 | 17.718 | 1.00 | 29.56 |
| ATOM 4953 | O | ILE | 639 | 64.730 | 3.281 | 17.906 | 1.00 | 27.74 |
| ATOM 4954 | N | ALA | 640 | 62.897 | 4.101 | 16.857 | 1.00 | 27.91 |
| ATOM 4956 | CA | ALA | 640 | 63.620 | 5.071 | 16.042 | 1.00 | 28.79 |
| ATOM 4957 | CB | ALA | 640 | 63.377 | 4.796 | 14.563 | 1.00 | 26.74 |
| ATOM 4958 | C | ALA | 640 | 63.164 | 6.487 | 16.385 | 1.00 | 28.91 |
| ATOM 4959 | O | ALA | 640 | 62.087 | 6.683 | 16.956 | 1.00 | 28.67 |
| ATOM 4960 | N | ASP | 641 | 64.007 | 7.464 | 16.067 | 1.00 | 28.25 |
| ATOM 4962 | CA | ASP | 641 | 63.708 | 8.876 | 16.296 | 1.00 | 30.80 |
| ATOM 4963 | CB | ASP | 641 | 62.520 | 9.319 | 15.428 | 1.00 | 33.44 |
| ATOM 4964 | CG | ASP | 641 | 62.869 | 9.393 | 13.948 | 1.00 | 38.01 |
| ATOM 4965 | 001 | ASP | 641 | 64.002 | 9.001 | 13.574 | 1.00 | 42.41 |
| ATOM 4966 | OD2 | ASP | 641 | 62.006 | 9.847 | 13.160 | 1.00 | 41.74 |
| ATOM 4967 | C | ASP | 641 | 63.501 | 9.311 | 17.745 | 1.00 | 29.07 |
| ATOM 4968 | O | ASP | 641 | 62.847 | 10.309 | 18.020 | 1.00 | 28.42 |
| ATOM 4969 | n | PHE | 642 | 64.138 | 8.604 | 18.663 | 1.00 | 29.69 |
| ATOM 4971 | CA | PHE | 642 | 64.036 | 8.914 | 20.074 | 1.00 | 29.62 |
| ATOM 4972 | CB | PHE | 642 | 64.347 | 7.656 | 20.890 | 1.00 | 27.18 |
| ATOM 4973 | CG | PHE | 642 | 65.702 | 7.058 | 20.603 | 1.00 | 23.96 |
| ATOM 4974 | CD1 | PHE | 642 | 66.848 | 7.559 | 21.219 | 1.00 | 23.66 |
| ATOM 4975 | CD2 | PHE | 642 | 65.828 | 5.974 | 19.742 | 1.00 | 24.08 |
| ATOM 4976 | CE1 | PHE | 642 | 68.090 | 6.992 | 20.980 | 1.00 | 23.02 |
| ATOM 4977 | CE2 | PHE | 642 | 67.069 | 5.403 | 19.501 | 1.00 | 23.20 |
| ATOM 4978 | CZ | PHE | 642 | 68.200 | 5.909 | 20.121 | 1.00 | 21.68 |
| ATOM 4979 | C | PHE | 642 | 64.948 | 10.075 | 20.502 | 1.00 | 32.99 |
| ATOM 4980 | O | PHE | 642 | 64.755 | 10.664 | 21.574 | 1.00 | 32.10 |
| ATOM 4981 | N | GLY | 643 | 65.940 | 10.396 | 19.671 | 1.00 | 34.66 |
| ATOM 4983 | CA | GLY | 643 | 66.869 | 11.463 | 20.003 | 1.00 | 35.29 |
| ATOM 4984 | C | GLY | 643 | 66.639 | 12.755 | 19.250 | 1.00 | 39.13 |
| ATOM 4985 | O | GLY | 643 | 67.464 | 13.666 | 19.333 | 1.00 | 39.83 |
| ATOM 4986 | N | LEU | 644 | 65.520 | 12.650 | 18.532 | 1.00 | 42.26 |
| ATOM 4988 | CA | LEU | 644 | 65.202 | 14.043 | 17.745 | 1.00 | 46.25 |
| ATOM 4989 | CB | LEU | 644 | 63.935 | 13.843 | 16.911 | 1.00 | 44.59 |
| ATOM 4990 | CG | LEU | 644 | 63.911 | 12.839 | 15.763 | 1.00 | 43.00 |
| ATOM 4991 | CD1 | LEU | 644 | 62.653 | 13.068 | 14.940 | 1.00 | 42.61 |
| ATOM 4992 | CD2 | LEU | 644 | 65.119 | 13.016 | 14.889 | 1.00 | 45.65 |
| ATOM 4993 | C | LEU | 644 | 65.037 | 15.298 | 18.578 | 1.00 | 49.59 |
| ATOM 4994 | O | LEU | 644 | 64.391 | 15.281 | 19.623 | 1.00 | 51.90 |
| ATOM 4995 | N | ALA | 645 | 65.585 | 16.401 | 18.080 | 1.00 | 52.08 |
| ATOM 4997 | CA | ALA | 645 | 65.495 | 17.677 | 18.777 | 1.00 | 54.71 |
| ATOM 4998 | CB | ALA | 645 | 66.414 | 1B.699 | 18.124 | 1.00 | 54.38 |
| ATOM 4999 | C | ALA | 645 | 64.053 | 18.184 | 18.790 | 1.00 | 55.44 |
| ATOM 5000 | O | ALA | 645 | 63.534 | 18.582 | 19.832 | 1.00 | 56.69 |
| ATOM 5001 | N | ASP | 652 | 52.389 | 21.543 | 14.759 | 1.00 | 73.74 |
| ATOM 5003 | CA | ASP | 652 | 51.207 | 21.745 | 13.934 | 1.00 | 73.83 |
| ATOM 5004 | CB | ASP | 652 | 51.601 | 21.995 | 12.472 | 1.00 | 73.22 |
| ATOM 5005 | CG | ASP | 652 | 50.398 | 22.241 | 11.569 | 1.00 | 72.95 |
| ATOM 5006 | OD1 | ASP | 652 | 49.354 | 22.715 | 12.065 | 1.00 | 73.71 |
| ATOM 5007 | OD2 | ASP | 652 | 50.497 | 21.956 | 10.357 | 1.00 | 73.02 |
| ATOM 5008 | C | ASP | 652 | 50.321 | 20.514 | 14.042 | 1.00 | 75.11 |
| ATOM 5009 | O | ASP | 652 | 50.568 | 19.495 | 13.394 | 1.00 | 75.96 |
| ATOM 5010 | N | TYR | 653 | 49.272 | 20.628 | 14.849 | 1.00 | 75.57 |
| ATOM 5012 | CA | TYR | 653 | 48.348 | 19.524 | 15.064 | 1.00 | 75.68 |
| ATOM 5013 | CB | TYR | 653 | 47.274 | 19.914 | 16.088 | 1.00 | 76.85 |
| ATOM 5014 | CG | TYR | 653 | 47.771 | 19.995 | 17.519 | 1.00 | 79.55 |
| ATOM 5015 | CD1 | TYR | 653 | 46.983 | 20.567 | 18.518 | 1.00 | 80.89 |
| ATOM 5016 | CE1 | TYR | 653 | 47.438 | 20.648 | 19.836 | 1.00 | 83.02 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5017 | CD2 | TYR | 653 | 49.032 | 19.503 | 17.874 | 1.00 | 80.87 |
| ATOM 5018 | CE2 | TYR | 653 | 49.496 | 19.578 | 19.183 | 1.00 | 81.70 |
| ATOM 5019 | CZ | TYR | 653 | 48.698 | 20.152 | 20.160 | 1.00 | 83.09 |
| ATOM 5020 | OH | TYR | 653 | 49.165 | 20.243 | 21.451 | 1.00 | 83.73 |
| ATOM 5022 | C | TYR | 653 | 47.685 | 19.038 | 13.787 | 1.00 | 75.03 |
| ATOM 5023 | O | TYR | 653 | 47.232 | 17.897 | 13.711 | 1.00 | 75.97 |
| ATOM 5024 | N | TYR | 654 | 47.679 | 19.885 | 12.767 | 1.00 | 73.85 |
| ATOM 5026 | CA | TYR | 654 | 47.039 | 19.538 | 11.507 | 1.00 | 73.32 |
| ATOM 5027 | CB | TYR | 654 | 46.276 | 20.750 | 10.972 | 1.00 | 71.97 |
| ATOM 5028 | CG | TYR | 654 | 45.259 | 21.276 | 11.954 | 1.00 | 70.94 |
| ATOM 5029 | CD1 | TYR | 654 | 45.659 | 21.801 | 13.185 | 1.00 | 71.41 |
| ATOM 5030 | CEI | TYR | 654 | 44.733 | 22.234 | 14.121 | 1.00 | 73.60 |
| ATOM 5031 | CD2 | TYR | 654 | 43.899 | 21.206 | 11.680 | 1.00 | 71.81 |
| ATOM 5032 | CE2 | TYR | 654 | 42.956 | 21.642 | 12.610 | 1.00 | 74.81 |
| ATOM 5033 | CZ | TYR | 654 | 43.380 | 22.152 | 13.832 | 1.00 | 74.84 |
| ATOM 5034 | OH | TYR | 654 | 42.457 | 22.571 | 14.769 | 1.00 | 76.60 |
| ATOM 5036 | C | TYR | 654 | 47.975 | 18.967 | 10.446 | 1.00 | 73.82 |
| ATOM 5037 | O | TYR | 654 | 47.545 | 18.671 | 9.329 | 1.00 | 74.25 |
| ATOM 5038 | N | LYS | 655 | 49.249 | 18.806 | 10.784 | 1.00 | 74.04 |
| ATOM 5040 | CA | LYS | 655 | 50.195 | 18.256 | 9.827 | 1.00 | 75.41 |
| ATOM 5041 | CB | LYS | 655 | 51.626 | 18.680 | 10.164 | 1.00 | 78.45 |
| ATOM 5042 | CG | LYS | 655 | 52.647 | 18.198 | 9.151 | 1.00 | 83.01 |
| ATOM 5043 | CD | LYS | 655 | 54.062 | 18.589 | 9.537 | 1.00 | 87.72 |
| ATOM 5044 | CE | LYS | 655 | 55.076 | 17.813 | 8.703 | 1.00 | 91.45 |
| ATOM 5045 | NZ | LYS | 655 | 56.489 | 18.133 | 9.074 | 1.00 | 94.17 |
| ATOM 5049 | C | LYS | 655 | 50.075 | 16.736 | 9.832 | 1.00 | 75.50 |
| ATOM 5050 | O | LYS | 655 | 50.245 | 16.092 | 10.872 | 1.00 | 75.90 |
| ATOM 5051 | N | LYS | 656 | 49.750 | 16.173 | 8.672 | 1.00 | 75.26 |
| ATOM 5053 | CA | LYS | 656 | 49.597 | 14.730 | 8.533 | 1.00 | 74.97 |
| ATOM 5054 | CB | LYS | 656 | 48.723 | 14.406 | 7.323 | 1.00 | 75.40 |
| ATOM 5055 | CG | LYS | 656 | 47.266 | 14.753 | 7.519 | 1.00 | 76.87 |
| ATOM 5056 | CD | LYS | 656 | 46.489 | 14.535 | 6.239 | 1.00 | 80.75 |
| ATOM 5057 | CE | LYS | 656 | 45.001 | 14.655 | 6.483 | 1.00 | 83.60 |
| ATOM 5058 | NZ | LYS | 656 | 44.236 | 14.637 | 5.204 | 1.00 | 87.14 |
| ATOM 5062 | C | LYS | 656 | 50.939 | 14.016 | 8.414 | 1.00 | 74.58 |
| ATOM 5063 | O | LYS | 656 | 51.904 | 14.578 | 7.897 | 1.00 | 75.01 |
| ATOM 5064 | N | GLY | 660 | 49.137 | 9.764 | 5.736 | 1.00 | 59.18 |
| ATOM 5066 | CA | GLY | 660 | 48.106 | 10.781 | 5.548 | 1.00 | 56.19 |
| ATOM 5067 | C | GLY | 660 | 47.407 | 10.761 | 7.192 | 1.00 | 55.31 |
| ATOM 5068 | O | GLY | 660 | 46.289 | 11.263 | 7.328 | 1.00 | 56.96 |
| ATOM 5069 | N | ARG | 661 | 48.059 | 10.163 | 8.183 | 1.00 | 53.02 |
| ATOM 5071 | CA | ARG | 661 | 47.493 | 10.083 | 9.527 | 1.00 | 49.80 |
| ATOM 5072 | CS | ARG | 661 | 47.944 | 8.799 | 10.229 | 1.00 | 51.79 |
| ATOM 5073 | CG | ARG | 661 | 47.683 | 7.523 | 9.450 | 1.00 | 50.59 |
| ATOM 5074 | CD | ARG | 661 | 47.822 | 6.323 | 10.367 | 1.00 | 53.68 |
| ATOM 5075 | NE | ARG | 661 | 47.714 | 5.044 | 9.665 | 1.00 | 52.66 |
| ATOM 5077 | CZ | ARG | 661 | 47.928 | 3.863 | 10.236 | 1.00 | 51.73 |
| ATOM 5078 | NH1 | ARG | 661 | 48.264 | 3.794 | 11.518 | 1.00 | 50.23 |
| ATOM 5081 | NH2 | ARG | 661 | 47.800 | 2.751 | 9.528 | 1.00 | 52.58 |
| ATOM 5084 | C | ARG | 661 | 47.915 | 11.297 | 10.346 | 1.00 | 44.80 |
| ATOM 5085 | O | ARG | 661 | 48.865 | 11.998 | 9.986 | 1.00 | 43.61 |
| ATOM 5086 | N | LEU | 662 | 47.221 | 11.528 | 11.453 | 1.00 | 40.74 |
| ATOM 5088 | CA | LEU | 662 | 47.518 | 12.654 | 12.333 | 1.00 | 37.88 |
| ATOM 5089 | CB | LEU | 662 | 46.234 | 13.415 | 12.611 | 1.00 | 36.19 |
| ATOM 5090 | CG | LEU | 662 | 45.515 | 14.074 | 11.499 | 1.00 | 35.32 |
| ATOM 5091 | CD1 | LEU | 662 | 44.045 | 14.278 | 11.831 | 1.00 | 31.05 |
| ATOM 5092 | CD2 | LEU | 662 | 46.217 | 15.383 | 11.156 | 1.00 | 34.37 |
| ATOM 5093 | C | LEU | 662 | 48.162 | 12.170 | 13.622 | 1.00 | 35.34 |
| ATOM 5094 | O | LEU | 662 | 47.529 | 11.479 | 14.417 | 1.00 | 33.06 |
| ATOM 5095 | N | PRO | 663 | 49.441 | 12.518 | 13.843 | 1.00 | 36.39 |
| ATOM 5096 | CD | PRO | 663 | 50.375 | 13.113 | 12.868 | 1.0o | 37.57 |
| ATOM 5097 | CA | PRO | 663 | 50.158 | 12.107 | 15.054 | 1.00 | 36.39 |
| ATOM 5098 | CB | PRO | 663 | 51.516 | 12.787 | 14.885 | 1.00 | 36.98 |
| ATOM 5099 | CG | PRO | 663 | 51.728 | 12.657 | 13.401 | 1.00 | 38.48 |
| ATOM 5100 | C | PRO | 663 | 49.477 | 12.491 | 16.371 | 1.00 | 35.47 |
| ATOM 5101 | O | PRO | 663 | 49.699 | 11.841 | 17.392 | 1.00 | 35.08 |
| ATOM 5102 | N | VAL | 664 | 48.646 | 13.532 | 16.362 | 1.00 | 34.28 |
| ATOM 5104 | CA | VAL | 664 | 47.951 | 13.931 | 17.583 | 1.00 | 34.43 |
| ATOM 5105 | CB | VAL | 664 | 47.038 | 15.181 | 17.376 | 1.00 | 36.92 |
| ATOM 5106 | CG1 | VAL | 664 | 47.885 | 16.408 | 17.160 | 1.00 | 37.55 |
| ATOM 5107 | CG2 | VAL | 664 | 46.091 | 14.989 | 16.186 | 1.00 | 38.28 |
| ATOM 5108 | C | VAL | 664 | 47.137 | 12.749 | 18.120 | 1.00 | 33.03 |
| ATOM 5109 | O | VAL | 664 | 46.908 | 12.641 | 19.318 | 1.00 | 34.62 |
| ATOM 5110 | N | LYS | 665 | 46.803 | 11.809 | 17.236 | 1.00 | 32.47 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5112 | CA | LYS | 665 | 46.040 | 10.631 | 17.614 | 1.00 | 30.71 |
| ATOM 5113 | CB | LYS | 665 | 45.456 | 9.958 | 16.370 | 1.00 | 29.59 |
| ATOM 5114 | CG | LYS | 665 | 44.324 | 10.774 | 15.760 | 1.00 | 29.64 |
| ATOM 5115 | CD | LYS | 665 | 43.927 | 10.334 | 14.367 | 1.00 | 31.86 |
| ATOM 5116 | CE | LYS | 665 | 42.664 | 11.056 | 13.899 | 1.00 | 30.42 |
| ATOM 5117 | NZ | LYS | 665 | 42.296 | 10.720 | 12.486 | 1.00 | 26.50 |
| ATOM 5121 | C | LYS | 665 | 46.801 | 9.644 | 18.498 | 1.00 | 32.23 |
| ATOM 5122 | O | LYS | 665 | 46.230 | 8.659 | 18.955 | 1.00 | 30.04 |
| ATOM 5123 | N | TRP | 666 | 48.080 | 9.915 | 18.748 | 1.00 | 31.38 |
| ATOM 5125 | CA | TRP | 666 | 48.886 | 9.068 | 19.619 | 1.00 | 32.32 |
| ATOM 5126 | CB | TRP | 666 | 50.204 | 5.682 | 18.945 | 1.00 | 31.07 |
| ATOM 5127 | CG | TRP | 666 | 50.078 | 7.530 | 18.006 | 1.00 | 28.26 |
| ATOM 5128 | CD2 | TRP | 666 | 49.531 | 7.559 | 16.684 | 1.00 | 27.07 |
| ATOM 5129 | CE2 | TRP | 666 | 49.630 | 6.257 | 16.163 | 1.00 | 26.71 |
| ATOM 5130 | CE3 | TRP | 666 | 48.982 | 8.569 | 15.882 | 1.00 | 26.56 |
| ATOM 5131 | CD1 | TRP | 666 | 50.473 | 6.238 | 18.234 | 1.00 | 24.97 |
| ATOM 5132 | NE1 | TRP | 666 | 50.206 | 5.469 | 17.132 | 1.00 | 27.38 |
| ATOM 5134 | CZ2 | TRP | 666 | 49.190 | 5.929 | 14.874 | 1.00 | 27.22 |
| ATOM 5135 | CZ3 | TRP | 666 | 48.548 | 8.248 | 14.599 | 1.00 | 30.14 |
| ATOM 5136 | CH2 | TRP | 666 | 48.658 | 6.934 | 14.107 | 1.00 | 26.64 |
| ATOM 5137 | C | TRP | 666 | 49.203 | 9.802 | 20.913 | 1.00 | 33.84 |
| ATOM 5138 | O | TRP | 666 | 49.688 | 9.202 | 21.873 | 1.00 | 32.82 |
| ATOM 5139 | N | MET | 667 | 48.905 | 11.099 | 20.929 | 1.00 | 35.75 |
| ATOM 5141 | CA | MET | 667 | 49.180 | 11.960 | 22.069 | 1.00 | 37.60 |
| ATOM 5142 | CB | MET | 667 | 49.150 | 13.423 | 21.641 | 1.00 | 41.95 |
| ATOM 5143 | CG | MET | 667 | 50.487 | 13.975 | 21.226 | 1.00 | 48.44 |
| ATOM 5144 | SD | MET | 667 | 50.384 | 15.728 | 20.919 | 1.00 | 55.33 |
| ATOM 5145 | CE | MET | 667 | 50.711 | 15.745 | 19.183 | 1.00 | 49.29 |
| ATOM 5146 | C | MET | 667 | 48.294 | 11.802 | 23.289 | 1.00 | 38.98 |
| ATOM 5147 | O | MET | 667 | 47.066 | 11.699 | 23.183 | 1.00 | 39.18 |
| ATOM 5148 | N | ALA | 668 | 48.933 | 11.824 | 24.456 | 1.00 | 38.72 |
| ATOM 5150 | CA | ALA | 668 | 48.231 | 11.728 | 25.727 | 1.00 | 37.82 |
| ATOM 5151 | CB | ALA | 668 | 49.224 | 11.527 | 26.857 | 1.00 | 38.49 |
| ATOM 5152 | C | ALA | 668 | 47.497 | 13.051 | 25.891 | 1.00 | 38.16 |
| ATOM 5153 | O | ALA | 668 | 47.937 | 14.072 | 25.363 | 1.00 | 37.21 |
| ATOM 5154 | N | PRO | 669 | 46.383 | 13.062 | 26.644 | 1.00 | 39.76 |
| ATOM 5155 | CD | PRO | 669 | 45.785 | 11.931 | 27.367 | 1.00 | 40.08 |
| ATOM 5156 | CA | PRO | 669 | 45.598 | 14.281 | 26.858 | 1.00 | 40.68 |
| ATOM 5157 | CB | PRO | 669 | 44.474 | 13.806 | 27.782 | 1.00 | 42.15 |
| ATOM 5158 | CG | PRO | 669 | 44.346 | 12.352 | 27.446 | 1.00 | 42.56 |
| ATOM 5159 | C | PRO | 669 | 46.396 | 15.432 | 27.484 | 1.00 | 42.69 |
| ATOM 5160 | O | PRO | 669 | 46.320 | 16.566 | 27.019 | 1.00 | 42.14 |
| ATOM 5161 | N | GLU | 670 | 47.168 | 15.153 | 28.532 | 1.00 | 43.21 |
| ATOM 5163 | CA | GLU | 670 | 47.956 | 16.211 | 29.160 | 1.00 | 44.62 |
| ATOM 5164 | CB | GLU | 670 | 48.651 | 15.719 | 30.429 | 1.00 | 44.95 |
| ATOM 5165 | CG | GLU | 670 | 49.824 | 14.782 | 30.197 | 1.00 | 45.54 |
| ATOM 5166 | CD | GLU | 670 | 49.422 | 13.332 | 30.079 | 1.00 | 42.72 |
| ATOM 5167 | OE1 | GLU | 670 | 50.332 | 12.481 | 30.066 | 1.00 | 41.43 |
| ATOM 5168 | OE2 | GLU | 670 | 48.212 | 13.036 | 30.015 | 1.00 | 44.44 |
| ATOM 5169 | C | GLU | 670 | 48.993 | 16.772 | 28.195 | 1.00 | 44.88 |
| ATOM 5170 | O | GLU | 670 | 49.248 | 17.968 | 28.194 | 1.00 | 45.08 |
| ATOM 5171 | N | ALA | 671 | 49.565 | 15.906 | 27.358 | 1.00 | 44.75 |
| ATOM 5173 | CA | ALA | 671 | 50.573 | 16.323 | 26.392 | 1.00 | 45.92 |
| ATOM 5174 | CB | ALA | 671 | 51.256 | 15.095 | 25.766 | 1.00 | 44.10 |
| ATOM 5175 | C | ALA | 671 | 49.944 | 17.193 | 25.314 | 1.00 | 47.96 |
| ATOM 5176 | O | ALA | 671 | 50.526 | 18.192 | 24.894 | 1.00 | 49.16 |
| ATOM 5177 | N | LEU | 672 | 48.729 | 16.836 | 24.917 | 1.00 | 49.84 |
| ATOM 5179 | CA | LEU | 672 | 47.989 | 17.554 | 23.861 | 1.00 | 50.74 |
| ATOM 5180 | CB | LEU | 672 | 46.926 | 16.619 | 23.289 | 1.00 | 53.20 |
| ATOM 5181 | CG | LEU | 672 | 46.184 | 16.989 | 22.004 | 1.00 | 55.26 |
| ATOM 5182 | CD1 | LEU | 672 | 47.153 | 17.155 | 20.656 | 1.00 | 57.12 |
| ATOM 5183 | CD2 | LEU | 672 | 45.203 | 15.895 | 21.680 | 1.00 | 52.86 |
| ATOM 5184 | C | LEU | 672 | 47.327 | 18.826 | 24.408 | 1.00 | 50.79 |
| ATOM 5165 | O | LEU | 672 | 47.302 | 19.855 | 23.736 | 1.00 | 50.95 |
| ATOM 5186 | N | PHE | 673 | 46.792 | 16.751 | 25.618 | 1.00 | 52.07 |
| ATOM 5166 | CA | PHE | 673 | 46.111 | 19.684 | 26.226 | 1.00 | 54.39 |
| ATOM 5189 | CB | PHE | 673 | 44.692 | 19.396 | 27.019 | 1.00 | 51.21 |
| ATOM 5190 | CG | PHE | 673 | 43.871 | 18.656 | 26.186 | 1.00 | 48.49 |
| ATOM 5191 | CD1 | PHE | 673 | 43.304 | 17.473 | 26.646 | 1.00 | 47.79 |
| ATOM 5192 | CD2 | PHE | 673 | 43.470 | 19.149 | 24.949 | 1.00 | 49.04 |
| ATOM 5193 | CE1 | PHE | 673 | 42.349 | 16.789 | 25.888 | 1.00 | 47.90 |
| ATOM 5194 | CE2 | PHE | 673 | 42.511 | 18.473 | 24.182 | 1.00 | 49.71 |
| ATOM 5195 | CZ | PHE | 673 | 41.952 | 17.288 | 24.655 | 1.00 | 46.86 |
| ATOM 5196 | C | PHE | 673 | 47.007 | 20.741 | 27.123 | 1.00 | 58.25 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5197 | O | PHE | 673 | 47.000 | 21.971 | 27.034 | 1.00 | 60.52 |
| ATOM 5198 | N | ASP | 674 | 47.784 | 20.094 | 27.983 | 1.00 | 59.63 |
| ATOM 5200 | CA | ASP | 674 | 48.652 | 20.815 | 28.905 | 1.00 | 62.11 |
| ATOM 5201 | CB | ASP | 674 | 48.568 | 20.196 | 30.307 | 1.00 | 63.61 |
| ATOM 5202 | CG | ASP | 674 | 47.143 | 20.015 | 30.791 | 1.00 | 66.46 |
| ATOM 5203 | OD1 | ASP | 674 | 46.815 | 18.901 | 31.247 | 1.00 | 66.70 |
| ATOM 5204 | OD2 | ASP | 674 | 46.354 | 20.981 | 30.722 | 1.00 | 68.77 |
| ATOM 5205 | C | ASP | 674 | 50.119 | 20.852 | 28.482 | 1.00 | 63.36 |
| ATOM 5206 | O | ASP | 674 | 50.979 | 21.175 | 29.310 | 1.00 | 64.11 |
| ATOM 5207 | N | ARG | 675 | 50.410 | 20.486 | 27.228 | 1.00 | 62.94 |
| ATOM 5209 | CA | ARG | 675 | 51.789 | 20.456 | 26.706 | 1.00 | 60.75 |
| ATOM 5210 | CB | ARG | 675 | 52.277 | 21.874 | 26.360 | 1.00 | 60.56 |
| ATOM 5211 | CG | ARG | 675 | 51.474 | 22.560 | 25.261 | 1.00 | 63.67 |
| ATOM 5212 | CD | ARG | 675 | 51.986 | 23.970 | 24.964 | 1.00 | 66.99 |
| ATOM 5213 | NE | ARG | 675 | 53.308 | 23.980 | 24.337 | 1.00 | 69.34 |
| ATOM 5215 | CZ | ARG | 675 | 54.063 | 25.068 | 24.173 | 1.00 | 68.48 |
| ATOM 5216 | NH1 | ARG | 675 | 53.637 | 26.254 | 24.590 | 1.00 | 65.81 |
| ATOM 5219 | NH2 | ARG | 675 | 55.254 | 24.965 | 23.593 | 1.00 | 68.76 |
| ATOM 5222 | C | ARG | 675 | 52.750 | 19.793 | 27.700 | 1.00 | 58.06 |
| ATOM 5223 | O | ARG | 675 | 53.933 | 20.130 | 27.766 | 1.00 | 59.30 |
| ATOM 5224 | N | ILE | 676 | 52.221 | 16.659 | 28.463 | 1.00 | 55.62 |
| ATOM 5226 | CA | ILE | 676 | 52.992 | 18.141 | 29.489 | 1.00 | 54.09 |
| ATOM 5227 | CB | ILE | 676 | 52.154 | 17.921 | 30.765 | 1.00 | 52.69 |
| ATOM 5228 | CG2 | ILE | 676 | 52.749 | 16.811 | 31.629 | 1.00 | 49.38 |
| ATOM 5229 | CG1 | ILE | 676 | 52.049 | 19.230 | 31.540 | 1.00 | 53.15 |
| ATOM 5230 | CD1 | ILE | 676 | 51.306 | 19.103 | 32.845 | 1.00 | 57.79 |
| ATOM 5231 | C | ILE | 676 | 53.468 | 16.796 | 28.953 | 1.00 | 53.83 |
| ATOM 5232 | O | ILE | 676 | 52.668 | 15.891 | 28.730 | 1.00 | 54.87 |
| ATOM 5233 | N | TYR | 677 | 54.773 | 16.671 | 28.745 | 1.00 | 51.76 |
| ATOM 5235 | CA | TYR | 677 | 55.343 | 15.436 | 28.236 | 1.00 | 49.42 |
| ATOM 5236 | CB | TYR | 677 | 56.232 | 15.722 | 27.031 | 1.00 | 51.33 |
| ATOM 5237 | CG | TYR | 677 | 55.466 | 16.181 | 25.809 | 1.00 | 56.22 |
| ATOM 5238 | CD1 | TYR | 677 | 55.158 | 17.529 | 25.619 | 1.00 | 56.12 |
| ATOM 5239 | CE1 | TYR | 677 | 54.491 | 17.960 | 24.479 | 1.00 | 56.18 |
| ATOM 5240 | CD2 | TYR | 677 | 55.078 | 15.269 | 24.823 | 1.00 | 58.13 |
| ATOM 5241 | CE2 | TYR | 677 | 54.411 | 15.689 | 23.679 | 1.00 | 57.65 |
| ATOM 5242 | CZ | TYR | 677 | 54.125 | 17.035 | 23.512 | 1.00 | 58.23 |
| ATOM 5243 | OH | TYR | 677 | 53.504 | 17.457 | 22.360 | 1.00 | 61.71 |
| ATOM 5245 | C | TYR | 677 | 56.136 | 14.730 | 29.316 | 1.00 | 46.46 |
| ATOM 5246 | O | TYR | 677 | 56.983 | 15.335 | 29.970 | 1.00 | 48.65 |
| ATOM 5247 | N | THR | 678 | 55.818 | 13.464 | 29.537 | 1.00 | 41.73 |
| ATOM 5249 | CA | THR | 678 | 56.498 | 12.664 | 30.535 | 1.00 | 39.83 |
| ATOM 5250 | CZ | THR | 678 | 55.660 | 12.593 | 31.861 | 1.00 | 41.78 |
| ATOM 5251 | CG1 | THR | 678 | 54.462 | 11.867 | 31.642 | 1.00 | 45.77 |
| ATOM 5253 | CG2 | THR | 678 | 55.342 | 13.988 | 32.383 | 1.00 | 41.84 |
| ATOM 5254 | C | THR | 678 | 56.661 | 11.242 | 30.011 | 1.00 | 37.46 |
| ATOM 5255 | O | THR | 678 | 56.258 | 10.917 | 28.897 | 1.00 | 37.51 |
| ATOM 5256 | N | HIS | 679 | 57.264 | 10.388 | 30.825 | 1.00 | 36.36 |
| ATOM 5258 | CA | HIS | 679 | 57.423 | 9.003 | 30.457 | 1.00 | 35.91 |
| ATOM 5259 | CB | HIS | 679 | 58.348 | 8.294 | 31.439 | 1.00 | 35.05 |
| ATOM 5260 | CG | HIS | 679 | 59.761 | 8.798 | 31.404 | 1.00 | 37.68 |
| ATOM 5261 | CD2 | HIS | 679 | 60.453 | 9.569 | 32.278 | 1.00 | 37.89 |
| ATOM 5262 | ND1 | HIS | 679 | 60.632 | 8.507 | 30.380 | 1.00 | 37.49 |
| ATOM 5264 | CE1 | HIS | 679 | 61.803 | 9.071 | 30.621 | 1.00 | 39.58 |
| ATOM 5265 | NE2 | HIS | 679 | 61.721 | 9.722 | 31.766 | 1.00 | 39.81 |
| ATOM 5267 | C | HIS | 679 | 56.032 | 8.376 | 30.441 | 1.00 | 36.76 |
| ATOM 5268 | O | HIS | 679 | 55.771 | 7.458 | 29.660 | 1.00 | 37.16 |
| ATOM 5269 | N | GLN | 680 | 55.126 | 8.908 | 31.264 | 1.00 | 36.27 |
| ATOM 5271 | CA | GLN | 680 | 53.754 | 8.407 | 31.332 | 1.00 | 37.71 |
| ATOM 5272 | CB | GLN | 680 | 53.069 | 8.815 | 32.640 | 1.00 | 40.95 |
| ATOM 5273 | CG | GLN | 680 | 53.645 | 8.128 | 33.884 | 1.00 | 45.23 |
| ATOM 5274 | CD | GLN | 680 | 53.676 | 6.595 | 33.780 | 1.00 | 44.44 |
| ATOM 5275 | OE1 | GLN | 680 | 52.669 | 5.925 | 33.996 | 1.00 | 42.76 |
| ATOM 5276 | NE2 | GLN | 680 | 54.846 | 6.043 | 33.464 | 1.00 | 40.57 |
| ATOM 5279 | C | GLN | 680 | 52.927 | 8.842 | 30.121 | 1.00 | 37.54 |
| ATOM 5280 | O | GLN | 680 | 51.950 | 8.185 | 29.765 | 1.00 | 37.93 |
| ATOM 5281 | N | SER | 681 | 53.282 | 9.961 | 29.504 | 1.00 | 36.38 |
| ATOM 5283 | CA | SER | 681 | 52.563 | 10.367 | 28.306 | 1.00 | 38.05 |
| ATOM 5284 | CB | SER | 681 | 52.857 | 11.819 | 27.940 | 1.00 | 41.41 |
| ATOM 5285 | CG | SER | 681 | 54.239 | 12.069 | 27.938 | 1.00 | 42.92 |
| ATOM 5287 | C | SER | 681 | 52.991 | 9.421 | 27.178 | 1.00 | 37.92 |
| ATOM 5288 | O | SER | 681 | 52.205 | 9.148 | 26.263 | 1.00 | 37.21 |
| ATOM 5289 | N | ASP | 682 | 54.237 | 8.932 | 27.248 | 1.00 | 34.77 |
| ATOM 5291 | CA | ASP | 682 | 54.750 | 7.972 | 26.267 | 1.00 | 31.99 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5292 | CB | ASP | 682 | 56.243 | 7.683 | 26.481 | 1.00 | 31.08 |
| ATOM 5293 | CG | ASP | 682 | 57.165 | 8.638 | 25.721 | 1.00 | 33.63 |
| ATOM 5294 | OD1 | ASP | 682 | 58.386 | 8.503 | 25.920 | 1.00 | 32.35 |
| ATOM 5295 | OD2 | ASP | 682 | 56.707 | 9.500 | 24.930 | 1.00 | 29.46 |
| ATOM 5296 | C | ASP | 682 | 53.969 | 6.672 | 26.457 | 1.00 | 31.54 |
| ATOM 5297 | O | ASP | 682 | 53.675 | 5.971 | 25.493 | 1.00 | 29.94 |
| ATOM 5298 | N | VAL | 683 | 53.677 | 6.334 | 27.712 | 1.00 | 30.48 |
| ATOM 5300 | CA | VAL | 683 | 52.913 | 5.126 | 28.023 | 1.00 | 32.94 |
| ATOM 5301 | CB | VAL | 683 | 52.731 | 4.939 | 29.572 | 1.00 | 33.94 |
| ATOM 5302 | CGZ | VAL | 683 | 51.635 | 3.905 | 29.872 | 1.00 | 32.71 |
| ATOM 5303 | CG2 | VAL | 683 | 54.042 | 4.474 | 30.209 | 1.00 | 27.41 |
| ATOM 5304 | C | VAL | 683 | 51.545 | 5.164 | 27.299 | 1.00 | 32.27 |
| ATOM 5305 | O | VAL | 683 | 51.106 | 4.158 | 26.733 | 1.00 | 30.54 |
| ATOM 5306 | N | TRP | 684 | 50.902 | 6.332 | 27.282 | 1.00 | 32.57 |
| ATOM 5308 | CA | TRP | 684 | 49.616 | 6.477 | 26.600 | 1.00 | 32.76 |
| ATOM 5309 | CB | TRP | 684 | 49.060 | 7.895 | 26.765 | 1.00 | 33.67 |
| ATOM 5310 | CG | TRP | 664 | 47.855 | 8.210 | 25.891 | 1.00 | 18.22 |
| ATOM 5311 | CD2 | TRP | 684 | 46.503 | 6.435 | 26.328 | 1.00 | 39.96 |
| ATOM 5312 | CE2 | TRP | 684 | 45.734 | 8.735 | 25.177 | 1.00 | 39.59 |
| ATOM 5313 | CE3 | TRP | 684 | 45.869 | 8.416 | 27.578 | 1.00 | 39.26 |
| ATOM 5314 | CD1 | TRP | 684 | 47.842 | 8.373 | 24.528 | 1.00 | 39.02 |
| ATOM 5315 | NE1 | TRP | 684 | 46.576 | 8.687 | 24.096 | 1.00 | 38.42 |
| ATOM 5317 | CZ2 | TRP | 684 | 44.362 | 9.011 | 25.240 | 1.00 | 36.62 |
| ATOM 5316 | CZ3 | TRP | 684 | 44.502 | 6.691 | 27.641 | 1.00 | 40.70 |
| ATOM 5319 | CH2 | TRP | 684 | 43.766 | 8.962 | 26.475 | 1.00 | 40.57 |
| ATOM 5320 | C | TRP | 684 | 49.819 | 6.158 | 25.125 | 1.00 | 31.98 |
| ATOM 5321 | O | TRP | 684 | 49.066 | 5.367 | 24.557 | 1.00 | 32.43 |
| ATOM 5322 | N | SER | 665 | 50.859 | 6.748 | 24.529 | 1.00 | 29.63 |
| ATOM 5324 | CA | SER | 685 | 51.195 | 6.531 | 23.119 | 1.00 | 28.62 |
| ATOM 5325 | CB | SER | 685 | 52.457 | 7.296 | 22.751 | 1.00 | 24.72 |
| ATOM 5326 | OG | SER | 685 | 52.323 | 8.664 | 23.072 | 1.00 | 30.04 |
| ATOM 5328 | C | SER | 685 | 51.414 | 5.055 | 22.825 | 1.00 | 27.91 |
| ATOM 5329 | O | SER | 685 | 51.022 | 4.555 | 21.767 | 1.00 | 28.60 |
| ATOM 5330 | N | PHE | 686 | 52.063 | 4.372 | 23.763 | 1.00 | 27.96 |
| ATOM 5332 | CA | PHE | 686 | 52.333 | 2.947 | 23.662 | 1.00 | 27.03 |
| ATOM 5333 | CB | PHE | 686 | 53.163 | 2.499 | 24.868 | 1.00 | 25.79 |
| ATOM 5334 | CG | PHE | 686 | 53.440 | 1.029 | 24.890 | 1.00 | 26.25 |
| ATOM 5335 | CD1 | PHE | 686 | 54.252 | 0.451 | 23.923 | 1.00 | 27.32 |
| ATOM 5336 | CD2 | PHE | 686 | 52.639 | 0.208 | 25.841 | 1.00 | 26.22 |
| ATOM 5337 | CE1 | PHE | 686 | 54.464 | −0.930 | 23.900 | 1.00 | 25.87 |
| ATOM 5338 | CE2 | PHE | 686 | 53.046 | −1.170 | 25.828 | 1.00 | 24.37 |
| ATOM 5339 | CZ | PHE | 686 | 53.856 | −1.740 | 24.854 | 1.00 | 26.42 |
| ATOM 5340 | C | PHE | 686 | 51.003 | 2.160 | 23.596 | 1.00 | 28.62 |
| ATOM 5341 | O | PHE | 686 | 50.912 | 1.129 | 22.914 | 1.00 | 26.74 |
| ATOM 5342 | N | GLY | 687 | 49.991 | 2.636 | 24.324 | 1.00 | 29.51 |
| ATOM 5344 | CA | GLY | 687 | 48.688 | 1.982 | 24.302 | 1.00 | 31.57 |
| ATOM 5345 | C | GLY | 687 | 46.095 | 2.036 | 22.896 | 1.00 | 30.73 |
| ATOM 5346 | O | GLY | 687 | 47.490 | 1.069 | 22.414 | 1.00 | 29.83 |
| ATOM 5347 | N | VAL | 688 | 48.269 | 3.179 | 22.238 | 1.00 | 29.06 |
| ATOM 5349 | CA | VAL | 688 | 47.777 | 3.350 | 20.679 | 1.00 | 28.93 |
| ATOM 5350 | CB | VAL | 688 | 47.800 | 4.831 | 20.424 | 1.00 | 27.24 |
| ATOM 5351 | CG1 | VAL | 688 | 47.211 | 4.963 | 19.020 | 1.00 | 28.29 |
| ATOM 5352 | CG2 | VAL | 688 | 46.990 | 5.691 | 21.404 | 1.00 | 26.96 |
| ATOM 5353 | C | VAL | 688 | 48.612 | 2.475 | 19.951 | 1.00 | 28.49 |
| ATOM 5354 | O | VAL | 688 | 48.080 | 1.866 | 19.024 | 1.00 | 28.84 |
| ATOM 5355 | N | LEU | 669 | 49.905 | 2.350 | 20.252 | 1.00 | 27.99 |
| ATOM 5357 | CA | LEU | 689 | 50.804 | 1.512 | 19.461 | 1.00 | 26.14 |
| ATOM 5358 | CB | LEU | 689 | 52.268 | 1.688 | 19.911 | 1.00 | 27.31 |
| ATOM 5359 | CG | LEU | 689 | 53.368 | 1.014 | 19.065 | 1.00 | 26.60 |
| ATOM 5360 | CD1 | LEU | 689 | 54.688 | 1.767 | 19.175 | 1.00 | 28.19 |
| ATOM 5361 | CD2 | LEU | 689 | 53.567 | −0.401 | 19.475 | 1.00 | 25.55 |
| ATOM 5362 | C | LEU | 689 | 50.362 | 0.053 | 19.605 | 1.00 | 26.48 |
| ATOM 5363 | O | LEU | 689 | 50.377 | −0.686 | 15.626 | 1.00 | 27.06 |
| ATOM 5364 | N | LEU | 690 | 49.953 | −0.344 | 20.816 | 1.00 | 28.55 |
| ATOM 5366 | CA | LEU | 690 | 49.465 | −1.708 | 21.065 | 1.00 | 29.16 |
| ATOM 5367 | CB | LEU | 690 | 49.070 | −1.888 | 22.560 | 1.00 | 31.40 |
| ATOM 5368 | CG | LEU | 690 | 50.114 | −2.085 | 23.667 | 1.00 | 31.49 |
| ATOM 5369 | CD1 | LEU | 690 | 49.427 | −2.028 | 25.026 | 1.00 | 34.09 |
| ATOM 5370 | CD2 | LEU | 690 | 50.821 | −3.410 | 23.491 | 1.00 | 30.84 |
| ATOM 5371 | C | LEU | 690 | 48.240 | −1.958 | 20.220 | 1.00 | 26.51 |
| ATOM 5372 | O | LEU | 690 | 48.088 | −3.023 | 19.631 | 1.00 | 25.15 |
| ATOM 5373 | N | TRP | 691 | 47.376 | −0.954 | 20.139 | 1.00 | 28.51 |
| ATOM 5375 | CA | TRP | 691 | 46.169 | −1.049 | 19.319 | 1.00 | 29.56 |
| ATOM 5376 | CB | TRP | 691 | 45.332 | 0.227 | 19.465 | 1.00 | 26.91 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5377 | CG | TRP | 691 | 43.992 | 0.169 | 18.759 | 1.00 | 30.95 |
| ATOM 5376 | CD2 | TRP | 691 | 43.718 | 0.556 | 17.406 | 1.00 | 29.87 |
| ATOM 5379 | CE2 | TRP | 691 | 42.337 | 0.367 | 17.189 | 1.00 | 31.97 |
| ATOM 5360 | CE3 | ThP | 691 | 44.505 | 1.049 | 16.358 | 1.00 | 27.72 |
| ATOM 5381 | CD1 | TRP | 691 | 42.796 | −0.231 | 19.292 | 1.00 | 30.68 |
| ATOM 5382 | NE1 | TRP | 691 | 41.797 | −0.111 | 18.355 | 1.00 | 33.68 |
| ATOM 5384 | CZ2 | TRP | 6.91 | 41.729 | 0.652 | 15.967 | 1.00 | 29.42 |
| ATOM 5385 | CZ3 | TRP | 691 | 43.906 | 1.327 | 15.154 | 1.00 | 27.13 |
| ATOM 5386 | CH2 | TRP | 691 | 42.523 | 1.129 | 14.965 | 1.00 | 29.18 |
| ATOM 5387 | C | TRP | 691 | 46.564 | −1.289 | 17.856 | 1.00 | 28.78 |
| ATOM 5388 | O | TRP | 691 | 45.996 | −2.156 | 17.194 | 1.00 | 27.64 |
| ATOM 5389 | N | GLU | 692 | 47.564 | −0.543 | 17.380 | 1.00 | 29.83 |
| ATOM 5391 | CA | GLU | 692 | 48.078 | −0.669 | 16.018 | 1.00 | 28.01 |
| ATOM 5392 | CB | GLU | 692 | 49.267 | 0.262 | 15.790 | 1.00 | 26.40 |
| ATOM 5393 | CG | GLU | 692 | 48.945 | 1.735 | 15.680 | 1.00 | 26.45 |
| ATOM 5394 | C1 | GLU | 692 | 50.183 | 2.561 | 15.369 | 1.00 | 29.47 |
| ATOM 5395 | OE1 | GLU | 692 | 50.938 | 2.886 | 16.320 | 1.00 | 29.66 |
| ATOM 5396 | OE2 | GLU | 692 | 50.413 | 2.875 | 14.182 | 1.00 | 29.44 |
| ATOM 5397 | C | GLU | 692 | 48.563 | −2.082 | 15.761 | 1.00 | 30.07 |
| ATOM 5398 | O | GLU | 692 | 48.385 | −2.612 | 14.665 | 1.00 | 30.18 |
| ATOM 5399 | N | ILE | 693 | 49.244 | −2.663 | 16.746 | 1.00 | 29.87 |
| ATOM 5401 | CA | ILE | 693 | 49.754 | −4.024 | 16.608 | 1.00 | 29.51 |
| ATOM 5402 | CB | ILE | 693 | 50.632 | −4.443 | 17.828 | 1.00 | 28.18 |
| ATOM 5403 | CG2 | ILE | 693 | 51.037 | −5.907 | 17.706 | 1.00 | 27.45 |
| ATOM 5404 | CG1 | ILE | 693 | 51.907 | −3.594 | 17.890 | 1.00 | 26.99 |
| ATOM 5405 | CD1 | ILE | 693 | 52.663 | −3.747 | 19.194 | 1.00 | 25.37 |
| ATOM 5406 | C | ILE | 693 | 48.603 | −5.023 | 16.452 | 1.00 | 29.21 |
| ATOM 5407 | O | ILE | 693 | 48.568 | −5.807 | 15.512 | 1.00 | 27.89 |
| ATOM 5408 | N | PHE | 694 | 47.623 | −4.942 | 17.336 | 1.00 | 31.33 |
| ATOM 5410 | CA | PHE | 694 | 46.523 | −5.888 | 17.279 | 1.00 | 34.41 |
| ATOM 5411 | CB | PHE | 694 | 45.958 | −6.114 | 18.687 | 1.00 | 35.37 |
| ATOM 5412 | CG | PHE | 694 | 46.978 | −6.717 | 19.621 | 1.00 | 35.60 |
| ATOM 5413 | CD1 | PHE | 694 | 47.606 | −5.942 | 20.586 | 1.00 | 37.23 |
| ATOM 5414 | CD2 | PHE | 694 | 47.424 | −8.024 | 19.426 | 1.00 | 35.59 |
| ATOM 5415 | CE1 | PHE | 694 | 48.669 | −6.460 | 21.333 | 1.00 | 36.39 |
| ATOM 5416 | CE2 | PHE | 694 | 48.484 | −8.546 | 20.170 | 1.00 | 35.34 |
| ATOM 5417 | CZ | PHE | 694 | 49.110 | −7.762 | 21.118 | 1.00 | 35.71 |
| ATOM 5418 | C | PHE | 694 | 45.481 | −5.715 | 16.176 | 1.00 | 34.41 |
| ATOM 5419 | O | PHE | 694 | 44.623 | −6.579 | 15.982 | 1.00 | 34.48 |
| ATOM 5420 | N | THR | 695 | 45.617 | −4.637 | 15.404 | 1.00 | 33.03 |
| ATOM 5422 | CA | THR | 695 | 44.742 | −4.379 | 14.263 | 1.00 | 31.81 |
| ATOM 5423 | CB | THR | 695 | 44.113 | −2.957 | 14.278 | 1.00 | 29.75 |
| ATOM 5424 | OG1 | THR | 695 | 45.142 | −1.961 | 14.218 | 1.00 | 30.72 |
| ATOM 5426 | CG2 | THR | 695 | 43.254 | −2.159 | 15.524 | 1.00 | 29.40 |
| ATOM 5427 | C | THR | 695 | 45.596 | −4.533 | 13.011 | 1.00 | 31.44 |
| ATOM 5428 | O | THR | 695 | 45.153 | −4.241 | 11.906 | 1.00 | 33.00 |
| ATOM 5429 | N | LEU | 696 | 46.832 | −4.987 | 11.209 | 1.00 | 31.24 |
| ATOM 5431 | CA | LEU | 696 | 47.799 | −5.199 | 12.134 | 1.00 | 31.36 |
| ATOM 5432 | CB | LEU | 696 | 47.421 | −6.418 | 11.291 | 1.00 | 33.53 |
| ATOM 5433 | CG | LEU | 696 | 47.270 | −7.741 | 12.042 | 1.00 | 33.00 |
| ATOM 5434 | CD1 | LEU | 696 | 47.010 | −8.838 | 11.052 | 1.00 | 35.50 |
| ATOM 5435 | CD2 | LEU | 696 | 48.515 | −8.061 | 12.830 | 1.00 | 36.09 |
| ATOM 5436 | C | LEU | 696 | 48.066 | −3.976 | 11.249 | 1.00 | 30.84 |
| ATOM 5437 | O | LEU | 696 | 48.135 | −4.067 | 10.024 | 1.00 | 28.23 |
| ATOM 5438 | N | GLY | 697 | 48.302 | −2.839 | 11.890 | 1.00 | 31.54 |
| ATOM 5440 | CA | GLY | 697 | 48.591 | −1.632 | 11.141 | 1.00 | 33.87 |
| ATOM 5441 | C | GLY | 697 | 47.375 | −0.765 | 10.924 | 1.00 | 32.77 |
| ATOM 5442 | O | GLY | 697 | 47.322 | 0.042 | 9.994 | 1.00 | 33.90 |
| ATOM 5443 | N | GLY | 698 | 46.392 | −0.921 | 11.797 | 1.00 | 33.29 |
| ATOM 5445 | CA | GLY | 698 | 45.187 | −0.122 | 11.681 | 1.00 | 32.66 |
| ATOM 5446 | C | GLY | 698 | 45.406 | 1.368 | 11.877 | 1.00 | 30.57 |
| ATOM 5447 | O | GLY | 698 | 46.336 | 1.803 | 12.553 | 1.00 | 27.36 |
| ATOM 5448 | N | SER | 699 | 44.517 | 2.148 | 11.285 | 1.00 | 30.92 |
| ATOM 5450 | CA | SER | 699 | 44.552 | 3.595 | 11.376 | 1.00 | 32.19 |
| ATOM 5451 | CB | SER | 699 | 44.062 | 4.202 | 10.058 | 1.00 | 34.24 |
| ATOM 5452 | OG | SER | 699 | 44.019 | 5.616 | 10.123 | 1.00 | 38.67 |
| ATOM 5454 | C | SER | 699 | 43.644 | 4.014 | 12.538 | 1.00 | 31.81 |
| ATOM 5455 | O | SER | 699 | 42.431 | 3.759 | 12.525 | 1.00 | 31.39 |
| ATOM 5456 | N | PRO | 700 | 44.228 | 4.597 | 13.594 | 1.00 | 31.82 |
| ATOM 5457 | CD | PRO | 700 | 45.645 | 4.842 | 13.919 | 1.00 | 28.82 |
| ATOM 5458 | CA | PRO | 700 | 43.353 | 4.992 | 14.697 | 1.00 | 31.31 |
| ATOM 5459 | CB | PRO | 700 | 44.345 | 5.341 | 15.809 | 1.00 | 31.31 |
| ATOM 5460 | CG | PRO | 700 | 45.552 | 5.800 | 15.061 | 1.00 | 30.41 |
| ATOM 5461 | C | PRO | 700 | 42.484 | 6.170 | 14.295 | 1.00 | 31.19 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5462 | O | PRO | 700 | 42.899 | 7.021 | 1.510 | 1.00 | 29.93 |
| ATOM 5463 | N | TYR | 701 | 41.235 | 6.144 | 14.736 | 1.00 | 32.69 |
| ATOM 5465 | CA | TYR | 701 | 40.291 | 7.223 | 14.445 | 1.00 | 32.54 |
| ATOM 5466 | CB | TYR | 701 | 40.650 | 8.416 | 15.323 | 1.00 | 34.47 |
| ATOM 5467 | CG | TYR | 701 | 40.512 | 8.141 | 16.794 | 1.00 | 39.16 |
| ATOM 5468 | CD1 | TYR | 701 | 41.542 | 8.433 | 17.683 | 1.00 | 44.31 |
| ATOM 5469 | CE1 | TYR | 701 | 41.372 | 8.241 | 19.080 | 1.00 | 46.85 |
| ATOM 5470 | CD2 | TYR | 701 | 39.321 | 7.642 | 17.07 | 1.00 | 41.21 |
| ATOM 5471 | CE2 | TYR | 701 | 39.147 | 7.447 | 18.657 | 1.00 | 45.05 |
| ATOM 5472 | CZ | TYR | 701 | 40.164 | 7.750 | 19.535 | 1.00 | 47.24 |
| ATOM 5473 | OM | TYR | 701 | 39.949 | 7.590 | 20.686 | 1.00 | 52.18 |
| ATOM 5475 | C | TYR | 701 | 40.215 | 7.655 | 12.972 | 1.00 | 30.56 |
| ATOM 5476 | O | TYR | 701 | 40.379 | 8.836 | 11.647 | 1.00 | 29.73 |
| ATOM 5477 | N | PRO | 702 | 39.928 | 6.712 | 11.018 | 1.00 | 30.38 |
| ATOM 5478 | CD | PRO | 702 | 39.659 | 5.278 | 12.261 | 1.00 | 30.22 |
| ATOM 5479 | CA | PRO | 702 | 39.847 | 7.071 | 10.642 | 1.00 | 28.87 |
| ATOM 5480 | CB | PRO | 702 | 39.693 | 5.722 | 9.948 | 1.00 | 29.63 |
| ATOM 5481 | CG | PRO | 702 | 39.007 | 4.889 | 10.959 | 1.00 | 30.99 |
| ATOM 5482 | C | PRO | 702 | 38.722 | 8.048 | 10.283 | 1.00 | 30.88 |
| ATOM 5483 | O | PRO | 702 | 37.557 | 7.843 | 10.636 | 1.00 | 33.98 |
| ATOM 5484 | N | GLY | 703 | 39.100 | 9.116 | 9.584 | 1.00 | 29.03 |
| ATOM 5486 | CA | GLY | 703 | 38.154 | 10.134 | 9.169 | 1.00 | 28.98 |
| ATOM 5487 | C | GLY | 703 | 37.893 | 11.169 | 10.244 | 1.00 | 29.69 |
| ATOM 5488 | O | GLY | 703 | 37.074 | 12.068 | 10.048 | 1.00 | 31.71 |
| ATOM 5489 | N | VAL | 704 | 38.579 | 11.040 | 11.378 | 1.00 | 30.74 |
| ATOM 5491 | CA | VAL | 704 | 38.416 | 11.951 | 12.509 | 1.00 | 32.06 |
| ATOM 5492 | CB | VAL | 704 | 38.582 | 11.208 | 13.860 | 1.00 | 31.70 |
| ATOM 5493 | CG1 | VAL | 704 | 38.322 | 12.197 | 15.044 | 1.00 | 30.29 |
| ATOM 5494 | CG2 | VAL | 704 | 37.506 | 10.144 | 14.005 | 1.00 | 31.56 |
| ATOM 5495 | C | VAL | 704 | 39.430 | 13.087 | 12.449 | 1.00 | 33.72 |
| ATOM 5496 | O | VAL | 704 | 40.634 | 12.867 | 12.548 | 1.00 | 35.31 |
| ATOM 5497 | N | PRO | 705 | 38.957 | 14.309 | 12.200 | 1.00 | 34.23 |
| ATOM 5498 | CD | PRO | 705 | 37.594 | 14.692 | 11.787 | 1.00 | 33.20 |
| ATOM 5499 | CA | PRO | 705 | 39.875 | 15.443 | 12.135 | 1.00 | 33.73 |
| ATOM 5500 | CS | PRO | 705 | 39.053 | 16.495 | 11.394 | 1.00 | 34.93 |
| ATOM 5501 | CG | PRO | 705 | 37.647 | 16.187 | 11.831 | 1.00 | 36.93 |
| ATOM 5502 | C | PRO | 705 | 40.280 | 15.879 | 13.543 | 1.00 | 33.25 |
| ATOM 5503 | O | PRO | 705 | 39.651 | 15.490 | 14.532 | 1.00 | 31.71 |
| ATOM 5504 | N | VAL | 706 | 41.322 | 16.697 | 13.623 | 1.00 | 34.46 |
| ATOM 5506 | CA | VAL | 706 | 41.852 | 17.176 | 14.900 | 1.00 | 36.99 |
| ATOM 5507 | CB | VAL | 706 | 42.923 | 18.261 | 14.687 | 1.00 | 39.01 |
| ATOM 5508 | CG1 | VAL | 706 | 43.577 | 18.618 | 16.017 | 1.00 | 40.33 |
| ATOM 5509 | CG2 | VAL | 706 | 43.961 | 17.786 | 13.673 | 1.00 | 38.61 |
| ATOM 5510 | C | VAL | 706 | 40.826 | 17.716 | 15.895 | 1.00 | 35.65 |
| ATOM 5511 | O | VAL | 706 | 40.823 | 17.319 | 17.065 | 1.00 | 33.55 |
| ATOM 5512 | N | GLU | 707 | 39.955 | 18.605 | 15.426 | 1.00 | 36.74 |
| ATOM 5514 | CA | GLU | 707 | 38.941 | 19.220 | 16.278 | 1.00 | 37.20 |
| ATOM 5515 | CS | GLU | 707 | 38.129 | 20.242 | 15.482 | 1.00 | 38.98 |
| ATOM 5516 | C | GLU | 707 | 38.014 | 18.188 | 16.900 | 1.00 | 38.46 |
| ATOM 5517 | O | GLU | 707 | 37.634 | 18.295 | 18.074 | 1.00 | 39.04 |
| ATOM 5518 | N | GLU | 708 | 37.681 | 17.170 | 16.115 | 1.00 | 37.81 |
| ATOM 5520 | CA | GLU | 708 | 36.802 | 16.105 | 16.571 | 1.00 | 17.70 |
| ATOM 5521 | CB | GLU | 708 | 36.316 | 15.289 | 15.378 | 1.00 | 40.73 |
| ATOM 5522 | CG | GLU | 708 | 35.459 | 16.091 | 14.413 | 1.00 | 43.44 |
| ATOM 5523 | CD | GLU | 708 | 34.235 | 16.677 | 15.084 | 1.00 | 51.52 |
| ATOM 5524 | OE1 | GLU | 708 | 33.629 | 16.007 | 15.961 | 1.00 | 50.14 |
| ATOM 5525 | OE2 | GLU | 708 | 33.882 | 17.824 | 14.732 | 1.00 | 59.46 |
| ATOM 5526 | C | GLU | 708 | 37.506 | 15.223 | 17.588 | 1.00 | 36.53 |
| ATOM 5527 | O | GLU | 708 | 36.897 | 14.782 | 18.567 | 1.00 | 36.80 |
| ATOM 5528 | N | LEU | 709 | 38.799 | 14.993 | 17.376 | 1.00 | 35.69 |
| ATOM 5530 | CA | LEU | 709 | 39.584 | 14.179 | 18.301 | 1.00 | 35.48 |
| ATOM 5531 | CS | LEU | 709 | 41.039 | 14.044 | 17.830 | 1.00 | 34.84 |
| ATOM 5532 | CG | LEU | 709 | 41.921 | 13.250 | 18.802 | 1.00 | 32.41 |
| ATOM 5533 | CD1 | LEU | 709 | 41.608 | 11.787 | 18.674 | 1.00 | 30.10 |
| ATOM 5534 | CD2 | LEU | 709 | 43.378 | 13.514 | 18.560 | 1.00 | 29.93 |
| ATOM 5535 | C | LEU | 709 | 39.568 | 14.842 | 19.673 | 1.00 | 35.58 |
| ATOM 5536 | O | LEU | 709 | 39.377 | 14.177 | 20.694 | 1.00 | 35.43 |
| ATOM 5537 | N | PHE | 710 | 39.792 | 16.150 | 19.686 | 1.00 | 36.79 |
| ATOM 5539 | CA | PHE | 710 | 39.800 | 16.918 | 20.927 | 1.00 | 40.58 |
| ATOM 5540 | CB | PHE | 710 | 39.944 | 18.413 | 20.637 | 1.00 | 42.55 |
| ATOM 5541 | CG | PHE | 710 | 41.308 | 18.808 | 20.162 | 1.00 | 46.38 |
| ATOM 5542 | CD1 | PHE | 710 | 42.392 | 17.942 | 20.313 | 1.00 | 47.29 |
| ATOM 5543 | CD2 | PHE | 710 | 41.515 | 20.050 | 19.580 | 1.00 | 47.93 |
| ATOM 5544 | CE1 | PHE | 710 | 43.659 | 18.312 | 19.892 | 1.00 | 51.21 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5545 | CE2 | PHE | 710 | 42.781 | 20.435 | 19.155 | 1.00 | 50.89 |
| ATOM 5546 | CZ | PHE | 710 | 43.859 | 19.562 | 19.312 | 1.00 | 53.31 |
| ATOM 5547 | C | PHE | 710 | 38.517 | 16.676 | 21.694 | 1.00 | 40.14 |
| ATOM 5548 | O | PHE | 710 | 38.543 | 16.446 | 22.898 | 1.00 | 39.86 |
| ATOM 5549 | N | LYS | 711 | 37.399 | 16.705 | 20.977 | 1.00 | 41.02 |
| ATOM 5551 | CA | LYS | 711 | 36.101 | 16.479 | 21.584 | 1.00 | 38.66 |
| ATOM 5552 | CB | LYS | 711 | 34.985 | 16.803 | 20.580 | 1.00 | 40.75 |
| ATOM 5553 | CG | LYS | 711 | 33.601 | 16.727 | 21.101 | 1.00 | 46.99 |
| ATOM 5554 | CD | LYS | 711 | 32.522 | 17.174 | 20.218 | 1.00 | 50.71 |
| ATOM 5555 | CE | LYS | 711 | 31.163 | 16.733 | 20.739 | 1.00 | 52.53 |
| ATOM 5556 | NZ | LYS | 711 | 30.041 | 17.194 | 19.884 | 1.00 | 57.76 |
| ATOM 5560 | C | LYS | 711 | 35.990 | 15.046 | 22.120 | 1.00 | 38.06 |
| ATOM 5561 | O | LYS | 711 | 35.535 | 14.831 | 23.250 | 1.00 | 36.29 |
| ATOM 5562 | N | LEU | 712 | 36.431 | 14.066 | 21.330 | 1.00 | 38.10 |
| ATOM 5564 | CA | LEU | 712 | 36.392 | 12.662 | 21.764 | 1.00 | 38.69 |
| ATOM 5565 | CB | LEU | 712 | 36.914 | 11.714 | 20.672 | 1.00 | 37.19 |
| ATOM 5566 | CG | LEU | 712 | 36.070 | 11.436 | 19.424 | 1.00 | 34.73 |
| ATOM 5567 | CD1 | LEU | 712 | 36.814 | 10.453 | 18.524 | 1.00 | 35.54 |
| ATOM 5568 | CD2 | LEU | 712 | 34.709 | 10.872 | 19.818 | 1.00 | 30.90 |
| ATOM 5569 | C | LEU | 712 | 37.230 | 12.472 | 23.021 | 1.00 | 39.62 |
| ATOM 5570 | O | LEU | 712 | 36.843 | 11.745 | 23.940 | 1.00 | 39.44 |
| ATOM 5571 | N | LEU | 713 | 38.398 | 13.101 | 23.044 | 1.00 | 40.10 |
| ATOM 5573 | CA | LEU | 713 | 39.279 | 12.999 | 24.199 | 1.00 | 42.81 |
| ATOM 5574 | CB | LEU | 713 | 40.606 | 13.736 | 23.924 | 1.00 | 41.70 |
| ATOM 5575 | CG | LEU | 713 | 41.495 | 13.040 | 22.868 | 1.00 | 41.86 |
| ATOM 5576 | CD1 | LEU | 713 | 42.742 | 13.862 | 22.607 | 1.00 | 37.19 |
| ATOM 5577 | CD2 | LEU | 713 | 41.873 | 11.647 | 23.340 | 1.00 | 41.17 |
| ATOM 5578 | C | LEU | 713 | 38.577 | 13.566 | 25.437 | 1.00 | 43.18 |
| ATOM 5579 | O | LEU | 713 | 38.479 | 12.889 | 26.457 | 1.00 | 44.79 |
| ATOM 5580 | N | LYS | 714 | 38.004 | 14.760 | 25.312 | 1.00 | 42.75 |
| ATOM 5582 | CA | LYS | 714 | 37.301 | 15.389 | 26.425 | 1.00 | 43.70 |
| ATOM 5583 | CB | LYS | 714 | 36.842 | 16.796 | 26.043 | 1.00 | 44.69 |
| ATOM 5584 | CG | LYS | 714 | 38.001 | 17.746 | 25.836 | 1.00 | 47.92 |
| ATOM 5585 | CD | LYS | 714 | 37.543 | 19.171 | 25.583 | 1.00 | 55.01 |
| ATOM 5586 | CE | LYS | 714 | 38.733 | 20.077 | 25.238 | 1.00 | 59.44 |
| ATOM 5587 | NZ | LYS | 714 | 39.773 | 20.132 | 26.320 | 1.00 | 60.10 |
| ATOM 5591 | C | LYS | 714 | 36.127 | 14.557 | 26.940 | 1.00 | 43.94 |
| ATOM 5592 | O | LYS | 714 | 35.843 | 14.551 | 28.140 | 1.00 | 44.20 |
| ATOM 5593 | N | GLU | 715 | 35.477 | 13.819 | 26.046 | 1.00 | 43.29 |
| ATOM 5595 | CA | GLU | 715 | 34.350 | 12.979 | 26.435 | 1.00 | 42.29 |
| ATOM 5596 | CB | GLU | 715 | 33.464 | 12.682 | 25.225 | 1.00 | 44.91 |
| ATOM 5597 | CG | GLU | 715 | 32.913 | 13.916 | 24.522 | 1.00 | 51.62 |
| ATOM 5598 | CD | GLU | 715 | 32.020 | 13.566 | 23.332 | 1.00 | 55.01 |
| ATOM 5599 | OE1 | GLU | 715 | 32.343 | 12.605 | 22.596 | 1.00 | 58.09 |
| ATOM 5600 | OE2 | GLU | 715 | 30.992 | 14.251 | 23.136 | 1.00 | 55.83 |
| ATOM 5601 | C | GLU | 715 | 34.806 | 11.665 | 27.064 | 1.00 | 41.07 |
| ATOM 5602 | O | GLU | 715 | 33.982 | 10.825 | 27.421 | 1.00 | 38.01 |
| ATOM 5603 | N | GLY | 716 | 36.118 | 11.476 | 27.182 | 1.00 | 41.11 |
| ATOM 5605 | CA | GLY | 716 | 36.642 | 10.252 | 27.770 | 1.00 | 39.69 |
| ATOM 5606 | c | GLY | 716 | 36.510 | 9.054 | 26.847 | 1.00 | 39.64 |
| ATOM 5607 | O | GLY | 716 | 36.562 | 7.904 | 27.290 | 1.00 | 36.71 |
| ATOM 5608 | N | HIS | 717 | 36.359 | 9.335 | 25.554 | 1.00 | 41.95 |
| ATOM 5610 | CA | HIS | 717 | 36.215 | 8.300 | 24.541 | 1.00 | 43.32 |
| ATOM 5611 | CB | HIS | 717 | 35.859 | 8.918 | 23.183 | 1.00 | 43.38 |
| ATOM 5612 | CG | HIS | 717 | 35.813 | 7.926 | 22.060 | 1.00 | 44.79 |
| ATOM 5613 | CD2 | HIS | 717 | 34.802 | 7.152 | 21.596 | 1.00 | 44.64 |
| ATOM 5614 | ND1 | HIS | 717 | 36.912 | 7.625 | 21.285 | 1.00 | 46.21 |
| ATOM 5616 | CE1 | HIS | 717 | 36.564 | 6.708 | 20.392 | 1.00 | 46.21 |
| ATOM 5617 | NE2 | HIS | 717 | 35.307 | 6.404 | 20.561 | 1.00 | 45.55 |
| ATOM 5619 | C | HIS | 717 | 37.485 | 7.481 | 24.403 | 1.00 | 43.90 |
| ATOM 5620 | O | HIS | 717 | 38.581 | 8.031 | 24.327 | 1.00 | 45.45 |
| ATOM 5621 | N | ARG | 718 | 37.304 | 6.169 | 24.289 | 1.00 | 43.44 |
| ATOM 5623 | CA | ARG | 718 | 38.387 | 5.207 | 24.139 | 1.00 | 42.68 |
| ATOM 5624 | CB | ARG | 718 | 38.500 | 4.361 | 25.412 | 1.00 | 41.00 |
| ATOM 5625 | CG | ARG | 718 | 38.844 | 5.165 | 26.658 | 1.00 | 40.09 |
| ATOM 5626 | CD | ARG | 718 | 40.214 | 5.825 | 26.495 | 1.00 | 41.06 |
| ATOM 5627 | NE | ARG | 718 | 40.658 | 6.549 | 27.685 | 1.00 | 39.51 |
| ATOM 5629 | CZ | ARG | 718 | 40.521 | 7.861 | 27.862 | 1.00 | 39.90 |
| ATOM 5630 | NH1 | ARG | 718 | 39.940 | 8.608 | 26.931 | 1.00 | 36.48 |
| ATOM 5633 | NH2 | ARG | 718 | 41.024 | 8.443 | 28.946 | 1.00 | 42.06 |
| ATOM 5636 | C | ARG | 718 | 38.080 | 4.308 | 22.927 | 1.00 | 43.91 |
| ATOM 5637 | O | ARG | 718 | 36.911 | 4.007 | 22.650 | 1.00 | 44.40 |
| ATOM 5638 | N | MET | 719 | 39.113 | 3.933 | 22.174 | 1.00 | 42.56 |
| ATOM 5640 | CA | MET | 719 | 38.928 | 3.079 | 21.004 | 1.00 | 42.82 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5641 | CB | MET | 719 | 40.219 | 2.964 | 20.181 | 1.00 | 42.59 |
| ATOM 5642 | CG | MET | 719 | 40.595 | 4.221 | 19.413 | 1.00 | 41.15 |
| ATOM 5643 | SD | MET | 719 | 42.093 | 4.079 | 18.400 | 1.00 | 44.11 |
| ATOM 5644 | CE | MET | 719 | 43.323 | 3.949 | 19.613 | 1.00 | 41.33 |
| ATOM 5645 | C | MET | 719 | 38.460 | 1.694 | 21.432 | 1.00 | 44.74 |
| ATOM 5646 | O | MET | 719 | 38.822 | 1.216 | 22.516 | 1.00 | 41.56 |
| ATOM 5647 | N | ASP | 720 | 37.635 | 1.075 | 20.582 | 1.00 | 45.50 |
| ATOM 5649 | CA | ASP | 720 | 37.090 | −0.265 | 20.824 | 1.00 | 45.51 |
| ATOM 5650 | CB | ASP | 720 | 36.077 | −0.660 | 19.733 | 1.00 | 48.60 |
| ATOM 5651 | CG | ASP | 720 | 34.811 | 0.181 | 19.749 | 1.00 | 53.03 |
| ATOM 5652 | OD1 | ASP | 720 | 34.678 | 1.082 | 20.612 | 1.00 | 59.61 |
| ATOM 5653 | OD2 | ASP | 720 | 33.943 | −0.067 | 18.880 | 1.00 | 50.58 |
| ATOM 5654 | C | ASP | 720 | 38.177 | −1.329 | 20.823 | 1.00 | 43.64 |
| ATOM 5655 | O | ASP | 720 | 39.235 | −1.172 | 20.199 | 1.00 | 43.66 |
| ATOM 5656 | N | LYS | 721 | 37.876 | −2.436 | 21.487 | 1.00 | 42.90 |
| ATOM 5658 | CA | LYS | 721 | 38.784 | −3.565 | 21.555 | 1.00 | 42.96 |
| ATOM 5659 | CB | LYS | 721 | 38.278 | −4.565 | 22.587 | 1.00 | 42.51 |
| ATOM 5660 | CG | LYS | 721 | 39.000 | −5.888 | 22.570 | 1.00 | 47.68 |
| ATOM 5661 | CD | LYS | 721 | 38.445 | −6.805 | 23.628 | 1.00 | 51.51 |
| ATOM 5662 | CE | LYS | 721 | 38.450 | −8.246 | 23.163 | 1.00 | 54.96 |
| ATOM 5663 | NZ | LYS | 721 | 38.165 | −9.190 | 24.282 | 1.00 | 59.67 |
| ATOM 5667 | C | LYS | 721 | 38.825 | −4.215 | 20.182 | 1.00 | 43.05 |
| ATOM 5668 | O | LYS | 721 | 37.779 | −4.577 | 19.625 | 1.00 | 46.08 |
| ATOM 5669 | N | PRO | 722 | 40.025 | −4.348 | 19.601 | 1.00 | 43.22 |
| ATOM 5670 | CD | PRO | 722 | 41.337 | −3.672 | 20.067 | 1.00 | 43.52 |
| ATOM 5671 | CA | PRO | 722 | 40.139 | −4.968 | 18.275 | 1.00 | 41.04 |
| ATOM 5672 | CB | PRO | 722 | 41.631 | −4.856 | 17.965 | 1.00 | 40.87 |
| ATOM 5673 | CG | PRO | 722 | 42.074 | −3.682 | 18.764 | 1.00 | 42.22 |
| ATOM 5674 | C | PRO | 722 | 39.726 | −6.427 | 18.346 | 1.00 | 39.64 |
| ATOM 5675 | O | PRO | 722 | 39.730 | −7.023 | 19.425 | 1.00 | 37.12 |
| ATOM 5676 | N | SER | 723 | 39.311 | −6.982 | 17.212 | 1.00 | 40.36 |
| ATOM 5678 | CA | SER | 723 | 38.947 | −8.389 | 17.158 | 1.00 | 41.41 |
| ATOM 5679 | CB | SER | 723 | 38.205 | −8.707 | 15.865 | 1.00 | 38.26 |
| ATOM 5680 | OG | SER | 723 | 39.049 | −8.520 | 14.749 | 1.00 | 43.87 |
| ATOM 5682 | C | SER | 723 | 40.294 | −9.102 | 17.191 | 1.00 | 41.54 |
| ATOM 5683 | O | SER | 723 | 41.284 | −8.575 | 16.703 | 1.00 | 40.90 |
| ATOM 5684 | N | ASN | 724 | 40.338 | −10.300 | 17.750 | 1.00 | 44.89 |
| ATOM 5686 | CA | ASN | 724 | 41.598 | −11.019 | 17.853 | 1.00 | 48.14 |
| ATOM 5687 | CB | ASN | 724 | 42.256 | −11.202 | 16.476 | 1.00 | 52.43 |
| ATOM 5688 | CG | ASN | 724 | 41.682 | −12.374 | 15.715 | 1.00 | 57.29 |
| ATOM 5689 | OD1 | ASN | 724 | 41.637 | −13.492 | 16.225 | 1.00 | 61.96 |
| ATOM 5690 | ND2 | ASN | 724 | 41.218 | −12.125 | 14.500 | 1.00 | 60.91 |
| ATOM 5693 | C | ASN | 724 | 42.509 | −10.255 | 18.811 | 1.00 | 48.17 |
| ATOM 5694 | O | ASN | 724 | 43.648 | −9.918 | 18.495 | 1.00 | 49.88 |
| ATOM 5695 | N | CYS | 725 | 41.960 | −9.935 | 19.973 | 1.00 | 47.12 |
| ATOM 5697 | CA | CYS | 725 | 42.686 | −9.238 | 21.010 | 1.00 | 46.17 |
| ATOM 5698 | CB | CYS | 725 | 42.569 | −7.717 | 20.862 | 1.00 | 44.83 |
| ATOM 5699 | SG | CYS | 725 | 43.459 | −6.813 | 22.159 | 1.00 | 42.51 |
| ATOM 5700 | C | CYS | 725 | 42.017 | −9.697 | 22.294 | 1.00 | 45.78 |
| ATOM 5701 | O | CYS | 725 | 40.803 | −9.642 | 22.423 | 1.00 | 44.83 |
| ATOM 5702 | N | TR | 726 | 42.810 | −10.224 | 23.212 | 1.00 | 45.63 |
| ATOM 5704 | CA | THR | 726 | 42.289 | −10.711 | 24.462 | 1.00 | 45.47 |
| ATOM 5705 | CB | THR | 726 | 43.351 | −11.545 | 25.217 | 1.00 | 45.93 |
| ATOM 5706 | OG1 | THR | 726 | 44.307 | −10.651 | 25.786 | 1.00 | 45.04 |
| ATOM 5708 | CG2 | THR | 726 | 44.061 | −12.495 | 24.233 | 1.00 | 42.99 |
| ATOM 5709 | C | THR | 726 | 41.858 | −9.545 | 25.359 | 1.00 | 45.73 |
| ATOM 5710 | O | THR | 726 | 42.368 | −8.445 | 25.216 | 1.00 | 46.91 |
| ATOM 5711 | N | ASN | 727 | 40.914 | −9.789 | 26.257 | 1.00 | 45.93 |
| ATOM 5713 | CA | ASN | 727 | 40.448 | −8.736 | 27.141 | 1.00 | 47.85 |
| ATOM 5714 | CB | ASN | 727 | 39.300 | −9.237 | 28.022 | 1.00 | 54.88 |
| ATOM 5715 | CG | ASN | 727 | 39.629 | −10.544 | 28.731 | 1.00 | 65.11 |
| ATOM 5716 | OD1 | ASN | 727 | 40.737 | −10.734 | 29.229 | 1.00 | 70.58 |
| ATOM 5717 | ND2 | ASN | 727 | 38.681 | −11.472 | 28.735 | 1.00 | 69.68 |
| ATOM 5720 | C | ASN | 727 | 41.591 | −8.212 | 27.999 | 1.00 | 44.18 |
| ATOM 5721 | O | ASN | 727 | 41.594 | −7.047 | 28.390 | 1.00 | 41.35 |
| ATOM 5722 | N | GLU | 728 | 42.572 | −9.073 | 28.260 | 1.00 | 42.82 |
| ATOM 5724 | CA | GLU | 728 | 43.725 | −8.713 | 29.071 | 1.00 | 42.37 |
| ATOM 5725 | CB | GLU | 728 | 44.573 | −9.952 | 29.379 | 1.00 | 43.09 |
| ATOM 5726 | CG | GLU | 728 | 45.806 | −9.654 | 30.245 | 1.00 | 46.30 |
| ATOM 5727 | CD | GLU | 728 | 46.643 | −10.889 | 39.568 | 1.00 | 50.11 |
| ATOM 5728 | OE1 | GLU | 728 | 46.867 | −11.732 | 29.668 | 1.00 | 47.98 |
| ATOM 5729 | OE2 | GLU | 728 | 47.085 | −11.010 | 31.733 | 1.00 | 51.69 |
| ATOM 5730 | C | GLU | 728 | 44.551 | −7.652 | 28.356 | 1.00 | 39.57 |
| ATOM 5731 | O | GLU | 728 | 44.852 | −6.605 | 28.933 | 1.00 | 39.30 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5732 | N | LEU | 729 | 44.872 | −7.907 | 27.089 | 1.00 | 37.38 |
| ATOM 5734 | CA | LEU | 729 | 45.655 | −6.977 | 26.274 | 1.00 | 36.74 |
| ATOM 5735 | CZ | LEU | 729 | 46.027 | −7.623 | 24.935 | 1.00 | 35.39 |
| ATOM 5736 | CG | LEU | 729 | 47.137 | −8.679 | 25.001 | 1.00 | 35.41 |
| ATOM 5737 | CD1 | LEU | 729 | 47.107 | −9.553 | 23.766 | 1.00 | 35.69 |
| ATOM 5738 | CD2 | LEU | 729 | 48.505 | −8.017 | 25.174 | 1.00 | 37.72 |
| ATOM 5739 | C | LEU | 729 | 44.885 | −5.679 | 26.050 | 1.00 | 35.52 |
| ATOM 5740 | O | LEU | 729 | 45.467 | −4.597 | 25.941 | 1.00 | 33.96 |
| ATOM 5741 | N | TYR | 730 | 43.565 | −5.779 | 26.000 | 1.00 | 32.90 |
| ATOM 5743 | CA | TYR | 730 | 42.760 | −4.598 | 25.812 | 1.00 | 32.41 |
| ATOM 5744 | CB | TYR | 730 | 41.335 | −4.981 | 25.398 | 1.00 | 32.16 |
| ATOM 5745 | CG | TYR | 730 | 40.445 | −3.787 | 25.172 | 1.00 | 34.93 |
| ATOM 5746 | CD1 | TYR | 730 | 40.769 | −2.827 | 24.203 | 1.00 | 32.49 |
| ATOM 5747 | CE1 | TYR | 730 | 39.962 | −1.716 | 23.994 | 1.00 | 32.80 |
| ATOM 5748 | CD2 | TYR | 730 | 39.282 | −3.605 | 25.931 | 1.00 | 33.45 |
| ATOM 5749 | CE2 | TYR | 730 | 38.465 | −2.496 | 25.728 | 1.00 | 34.81 |
| ATOM 5750 | CZ | TYR | 730 | 38.814 | −1.557 | 24.756 | 1.00 | 34.06 |
| ATOM 5751 | OH | TYR | 730 | 38.009 | −0.465 | 24.551 | 1.00 | 36.66 |
| ATOM 5753 | C | TYR | 730 | 42.767 | −3.788 | 27.107 | 1.00 | 33.48 |
| ATOM 5754 | O | TTh | 730 | 42.837 | −2.558 | 27.083 | 1.00 | 34.94 |
| ATOM 5755 | N | MET | 731 | 42.698 | −4.466 | 28.248 | 1.00 | 35.29 |
| ATOM 5757 | CA | MET | 731 | 42.724 | −3.755 | 29.525 | 1.00 | 38.38 |
| ATOM 5758 | CB | MET | 731 | 42.465 | −4.709 | 30.690 | 1.00 | 42.01 |
| ATOM 5759 | CG | MET | 731 | 41.048 | −5.264 | 30.702 | 1.00 | 53.67 |
| ATOM 5760 | SD | MET | 731 | 39.785 | −3.965 | 30.830 | 1.00 | 62.97 |
| ATOM 5761 | CE | MET | 731 | 39.828 | −3.688 | 32.641 | 1.00 | 61.83 |
| ATOM 5762 | C | MET | 731 | 44.073 | −3.049 | 29.670 | 1.00 | 34.52 |
| ATOM 5763 | O | MET | 731 | 44.160 | −1.958 | 30.232 | 1.00 | 33.23 |
| ATOM 5764 | N | MET | 732 | 45.118 | −3.669 | 29.134 | 1.00 | 33.93 |
| ATOM 5766 | CA | MET | 732 | 46.445 | −3.065 | 29.168 | 1.00 | 36.26 |
| ATOM 5767 | CB | MET | 732 | 47.506 | −3.995 | 28.565 | 1.00 | 35.56 |
| ATOM 5768 | CG | MET | 732 | 48.935 | −3.418 | 28.643 | 1.00 | 35.26 |
| ATOM 5769 | SD | MET | 732 | 50.186 | −4.522 | 28.001 | 1.00 | 30.46 |
| ATOM 5770 | CE | MET | 732 | 50.480 | −5.562 | 29.415 | 1.00 | 26.88 |
| ATOM 5771 | C | MET | 732 | 46.369 | −1.750 | 28.389 | 1.00 | 34.75 |
| ATOM 5772 | O | MET | 732 | 46.827 | −0.722 | 28.873 | 1.00 | 35.49 |
| ATOM 5773 | N | MET | 733 | 45.741 | −1.774 | 27.213 | 1.00 | 34.63 |
| ATOM 5775 | CA | MET | 733 | 45.571 | −0.566 | 26.413 | 1.00 | 32.79 |
| ATOM 5776 | CB | MET | 733 | 44.787 | −a.853 | 25.130 | 1.00 | 33.16 |
| ATOM 5777 | CG | MET | 733 | 45.544 | −1.601 | 24.047 | 1.00 | 32.32 |
| ATOM 5778 | SD | MET | 733 | 44.421 | −1.990 | 22.670 | 1.00 | 35.66 |
| ATOM 5779 | CE | MET | 733 | 45.155 | −3.496 | 22.068 | 1.00 | 29.47 |
| ATOM 5780 | C | MET | 733 | 44.789 | 0.452 | 27.229 | 1.00 | 33.94 |
| ATOM 5781 | O | MET | 733 | 45.176 | 1.619 | 27.318 | 1.00 | 35.72 |
| ATOM 5782 | N | ARG | 734 | 43.679 | 0.018 | 27.618 | 1.00 | 33.73 |
| ATOM 5784 | CA | ARG | 734 | 42.854 | 0.913 | 28.621 | 1.00 | 33.41 |
| ATOM 5765 | CB | ARG | 734 | 41.586 | 0.197 | 29.095 | 1.00 | 33.42 |
| ATOM 5786 | CG | ARG | 734 | 40.726 | −0.335 | 27.950 | 1.00 | 34.26 |
| ATOM 5787 | CD | ARG | 734 | 40.256 | 0.763 | 27.043 | 1.00 | 37.70 |
| ATOM 5786 | NE | ARG | 734 | 39.416 | 1.745 | 27.750 | 1.00 | 43.96 |
| ATOM 5790 | CZ | ARG | 734 | 38.092 | 1.661 | 27.844 | 1.00 | 46.43 |
| ATOM 5791 | NH1 | ARG | 734 | 37.439 | 0.660 | 27.266 | 1.00 | 48.63 |
| ATOM 5794 | NH2 | ARG | 734 | 37.420 | 2.571 | 28.530 | 1.00 | 44.65 |
| ATOM 5797 | C | ARG | 734 | 43.660 | 1.458 | 29.793 | 1.00 | 32.12 |
| ATOM 5798 | O | ARG | 734 | 43.492 | 2.610 | 30.180 | 1.00 | 35.37 |
| ATOM 5799 | N | ASP | 735 | 44.566 | 0.646 | 30.327 | 1.00 | 33.75 |
| ATOM 5801 | CA | ASP | 735 | 45.438 | 1.076 | 31.433 | 1.00 | 36.72 |
| ATOM 5802 | CB | ASP | 735 | 46.379 | −0.055 | 31.857 | 1.00 | 42.71 |
| ATOM 5803 | CG | ASP | 735 | 45.722 | −1.052 | 32.774 | 1.00 | 47.31 |
| ATOM 5804 | OD1 | ASP | 735 | 46.124 | −2.241 | 32.720 | 1.00 | 50.99 |
| ATOM 5805 | OD2 | ASP | 735 | 44.824 | −0.646 | 33.552 | 1.00 | 48.45 |
| ATOM 5806 | C | ASP | 735 | 46.291 | 2.251 | 30.972 | 1.00 | 34.25 |
| ATOM 5807 | O | ASP | 735 | 46.376 | 3.286 | 31.648 | 1.00 | 34.31 |
| ATOM 5806 | N | CYS | 736 | 46.927 | 2.064 | 29.816 | 1.00 | 31.65 |
| ATOM 5810 | CA | CYS | 736 | 47.780 | 3.077 | 29.204 | 1.00 | 29.93 |
| ATOM 5811 | CB | CYS | 736 | 48.413 | 2.545 | 27.921 | 1.00 | 24.97 |
| ATOM 5812 | SG | CYS | 736 | 49.504 | 1.159 | 28.180 | 1.00 | 31.35 |
| ATOM 5813 | C | CYS | 736 | 46.994 | 4.325 | 28.885 | 1.00 | 31.62 |
| ATOM 5814 | O | CYS | 736 | 47.562 | 5.416 | 28.823 | 1.00 | 30.73 |
| ATOM 5815 | N | TRP | 737 | 45.680 | 4.174 | 28.711 | 1.00 | 35.03 |
| ATOM 5817 | CA | TRP | 737 | 44.812 | 5.308 | 26.395 | 1.00 | 36.35 |
| ATOM 5816 | CB | TRP | 737 | 43.808 | 4.927 | 27.297 | 1.00 | 36.43 |
| ATOM 5819 | CG | TRP | 737 | 44.451 | 4.487 | 26.010 | 1.00 | 34.34 |
| ATOM 5820 | CD2 | TRP | 737 | 43.914 | 3.565 | 25.052 | 1.00 | 34.81 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5821 | CE2 | TRP | 737 | 44.852 | 3.461 | 23.999 | 1.00 | 33.92 |
| ATOM 5822 | CE3 | TRP | 737 | 42.730 | 2.816 | 24.980 | 1.00 | 33.06 |
| ATOM 5823 | CD1 | TRP | 737 | 45.659 | 4.890 | 25.514 | 1.00 | 35.19 |
| ATOM 5824 | NEi | TRP | 737 | 45.907 | 4.279 | 24.309 | 1.00 | 35.00 |
| ATOM 5826 | CZ2 | TRP | 737 | 44.644 | 2.633 | 22.886 | 1.00 | 33.45 |
| ATOM 5827 | CZ3 | TRP | 737 | 42.527 | 1.991 | 23.876 | 1.00 | 32.92 |
| ATOM 5828 | CH2 | TRP | 737 | 43.480 | 1.909 | 22.644 | 1.00 | 30.45 |
| ATOM 5829 | C | TRP | 737 | 44.080 | 5.895 | 29.609 | 1.00 | 37.23 |
| ATOM 5830 | O | TRP | 737 | 43.047 | 6.551 | 29.474 | 1.00 | 37.44 |
| ATOM 5831 | N | HIS | 738 | 44.624 | 5.681 | 30.798 | 1.00 | 41.45 |
| ATOM 5833 | CA | HIS | 738 | 44.006 | 6.208 | 32.008 | 1.00 | 41.52 |
| ATOM 5834 | CB | HIS | 738 | 44.675 | 5.635 | 33.258 | 1.00 | 41.23 |
| ATOM 5835 | CG | HIS | 738 | 43.925 | 5.924 | 34.522 | 1.00 | 43.31 |
| ATOM 5836 | CD2 | HIS | 738 | 43.618 | 7.096 | 35.126 | 1.00 | 41.58 |
| ATOM 5837 | ND1 | HIS | 738 | 43.338 | 4.935 | 35.279 | 1.00 | 44.22 |
| ATOM 5839 | CE1 | HIS | 738 | 42.693 | 5.487 | 36.294 | 1.00 | 46.62 |
| ATOM 5840 | NE2 | HIS | 738 | 42.848 | 6.798 | 36.223 | 1.00 | 43.99 |
| ATOM 5842 | C | HIS | 738 | 44.118 | 7.726 | 32.015 | 1.00 | 41.75 |
| ATOM 5843 | O | HIS | 738 | 45.179 | 8.268 | 31.731 | 1.00 | 40.84 |
| ATOM 5844 | N | ALA | 739 | 43.025 | 8.405 | 32.352 | 1.00 | 42.47 |
| ATOM 5846 | CA | ALA | 739 | 43.004 | 9.873 | 32.398 | 1.00 | 44.58 |
| ATOM 5847 | CB | ALA | 739 | 41.629 | 10.361 | 32.825 | 1.00 | 48.19 |
| ATOM 5848 | C | ALA | 739 | 44.081 | 10.467 | 33.317 | 1.00 | 45.12 |
| ATOM 5849 | O | ALA | 739 | 44.653 | 11.510 | 33.020 | 1.00 | 45.66 |
| ATOM 5650 | N | VAL | 740 | 44.262 | 9.852 | 34.481 | 1.00 | 46.64 |
| ATOM 5852 | CA | VAL | 740 | 45.278 | 10.273 | 35.453 | 1.00 | 46.78 |
| ATOM 5653 | CB | VAL | 740 | 44.667 | 9.893 | 36.688 | 1.00 | 47.74 |
| ATOM 5854 | CG1 | VAL | 740 | 45.919 | 10.372 | 37.890 | 1.00 | 49.35 |
| ATOM 5855 | CG2 | VAL | 740 | 43.515 | 10.495 | 37.211 | 1.00 | 47.89 |
| ATOM 5856 | C | VAL | 740 | 46.601 | 9.573 | 35.121 | 1.00 | 45.24 |
| ATOM 5857 | O | VAL | 740 | 46.754 | 8.362 | 35.347 | 1.00 | 45.01 |
| ATOM 5858 | N | PRO | 741 | 47.588 | 10.335 | 34.637 | 1.00 | 43.46 |
| ATOM 5859 | CD | PRO | 741 | 47.536 | 11.794 | 34.437 | 1.00 | 43.51 |
| ATOM 5860 | CA | PRO | 741 | 48.905 | 9.804 | 34.266 | 1.00 | 46.22 |
| ATOM 5861 | CB | PRO | 741 | 49.701 | 11.070 | 33.942 | 1.00 | 45.12 |
| ATOM 5862 | CG | PRO | 741 | 48.632 | 12.010 | 33.426 | 1.00 | 42.81 |
| ATOM 5863 | C | PRO | 741 | 49.588 | 8.936 | 35.328 | 1.00 | 47.45 |
| ATOM 5864 | O | PRO | 741 | 50.245 | 7.950 | 34.994 | 1.00 | 45.12 |
| ATOM 5865 | N | SER | 742 | 49.394 | 9.280 | 36.601 | 1.00 | 48.78 |
| ATOM 5867 | CA | SER | 742 | 49.994 | 8.532 | 37.703 | 1.00 | 48.76 |
| ATOM 5868 | CB | SER | 742 | 49.845 | 9.317 | 39.012 | 1.00 | 51.11 |
| ATOM 5869 | OG | SER | 742 | 48.482 | 9.488 | 39.373 | 1.00 | 53.50 |
| ATOM 5871 | C | SER | 742 | 49.376 | 7.150 | 37.867 | 1.00 | 47.77 |
| ATOM 5872 | O | SER | 742 | 49.932 | 6.283 | 38.539 | 1.00 | 47.31 |
| ATOM 5873 | N | GLN | 743 | 48.199 | 6.962 | 37.284 | 1.00 | 47.57 |
| ATOM 5875 | CA | GLN | 743 | 47.511 | 5.689 | 37.384 | 1.00 | 47.14 |
| ATOM 5876 | CB | GLN | 743 | 46.004 | 5.918 | 37.531 | 1.00 | 50.16 |
| ATOM 5877 | CG | GLN | 743 | 45.438 | 5.447 | 38.671 | 1.00 | 54.69 |
| ATOM 5878 | CD | GLN | 743 | 46.239 | 5.964 | 40.051 | 1.00 | 57.62 |
| ATOM 5879 | OE1 | GLN | 743 | 46.898 | 5.196 | 40.749 | 1.00 | 59.09 |
| ATOM 5880 | NE2 | GLN | 743 | 46.202 | 7.277 | 40.268 | 1.00 | 59.45 |
| ATOM 5883 | C | GLN | 743 | 47.816 | 4.774 | 36.212 | 1.00 | 44.41 |
| ATOM 5884 | O | GLN | 743 | 47.365 | 3.627 | 36.182 | 1.00 | 44.39 |
| ATOM 5885 | N | ARG | 744 | 48.515 | 5.305 | 35.212 | 1.00 | 42.87 |
| ATOM 5887 | CA | ARG | 744 | 48.902 | 4.506 | 34.046 | 1.00 | 41.45 |
| ATOM 5888 | CB | ARG | 744 | 49.350 | 5.397 | 32.883 | 1.00 | 37.34 |
| ATOM 5889 | CG | ARG | 744 | 48.316 | 6.380 | 32.412 | 1.00 | 32.30 |
| ATOM 5890 | CD | ARG | 744 | 48.854 | 7.207 | 31.270 | 1.00 | 31.37 |
| ATOM 5891 | NE | ARG | 744 | 47.921 | 8.276 | 30.946 | 1.00 | 36.76 |
| ATOM 5893 | CZ | ARG | 744 | 48.271 | 9.492 | 30.543 | 1.00 | 39.88 |
| ATOM 5894 | NH1 | ARG | 744 | 49.553 | 9.813 | 30.399 | 1.00 | 39.94 |
| ATOM 5897 | NH2 | ARG | 744 | 47.330 | 10.404 | 30.322 | 1.00 | 39.12 |
| ATOM 5900 | C | ARG | 744 | 50.068 | 3.616 | 34.471 | 1.00 | 41.40 |
| ATOM 5901 | O | ARG | 744 | 50.813 | 3.945 | 35.405 | 1.00 | 42.84 |
| ATOM 5902 | N | PRO | 745 | 50.203 | 2.441 | 33.849 | 1.00 | 40.11 |
| ATOM 5903 | CD | PRO | 745 | 49.345 | 1.739 | 32.876 | 1.00 | 19.91 |
| ATOM 5904 | CA | PRO | 745 | 51.332 | 1.607 | 34.266 | 1.00 | 38.58 |
| ATOM 5905 | CB | PRO | 745 | 51.019 | 0.261 | 33.605 | 1.00 | 37.46 |
| ATOM 5906 | CG | PRO | 745 | 50.250 | 0.645 | 32.377 | 1.00 | 37.41 |
| ATOM 5907 | C | PRO | 745 | 52.640 | 2.202 | 33.750 | 1.00 | 37.73 |
| ATOM 5908 | O | PRO | 745 | 52.634 | 3.027 | 32.835 | 1.00 | 37.71 |
| ATOM 5909 | N | ThR | 746 | 53.753 | 1.843 | 34.373 | 1.00 | 35.90 |
| ATOM 5911 | CA | THR | 746 | 55.050 | 2.328 | 33.913 | 1.00 | 34.77 |
| ATOM 5912 | CB | THR | 746 | 56.085 | 2.380 | 35.075 | 1.00 | 33.85 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 5913 | OG1 | THR | 746 | 56.296 | 1.059 | 35.602 | 1.00 | 33.92 |
| ATOM 5915 | CG2 | THR | 746 | 55.605 | 3.302 | 36.177 | 1.00 | 32.17 |
| ATOM 5916 | C | THR | 746 | 55.544 | 1.327 | 32.870 | 1.00 | 32.69 |
| ATOM 5917 | O | THR | 746 | 55.026 | 0.213 | 32.795 | 1.00 | 31.56 |
| ATOM 5918 | N | PHE | 747 | 56.538 | 1.708 | 32.066 | 1.00 | 34.04 |
| ATOM 5920 | CA | PHE | 747 | 57.093 | 0.782 | 31.083 | 1.00 | 31.74 |
| ATOM 5921 | CB | PHE | 747 | 58.121 | 1.472 | 30.193 | 1.00 | 30.55 |
| ATOM 5922 | CG | PHE | 747 | 57.504 | 2.287 | 29.096 | 1.00 | 29.40 |
| ATOM 5923 | CD1 | PHE | 747 | 56.772 | 1.666 | 28.092 | 1.00 | 28.24 |
| ATOM 5924 | CD2 | PHE | 747 | 57.609 | 3.667 | 29.091 | 1.00 | 27.50 |
| ATOM 5925 | CE1 | PHE | 747 | 56.170 | 2.407 | 27.100 | 1.00 | 24.35 |
| ATOM 5926 | CE2 | PHE | 747 | 57.001 | 4.413 | 28.091 | 1.00 | 29.27 |
| ATOM 5927 | CZ | PHE | 747 | 56.276 | 3.776 | 27.103 | 1.00 | 25.73 |
| ATOM 5928 | C | PHE | 747 | 57.714 | −0.413 | 31.782 | 1.00 | 31.92 |
| ATOM 5929 | O | PHE | 747 | 57.727 | −1.514 | 31.243 | 1.00 | 32.46 |
| ATOM 5930 | N | LYS | 748 | 58.233 | −0.199 | 32.986 | 1.00 | 33.47 |
| ATOM 5932 | CA | LYS | 748 | 58.816 | −1.302 | 33.733 | 1.00 | 35.57 |
| ATOM 5933 | CB | LYS | 748 | 59.468 | −0.800 | 35.826 | 1.00 | 39.42 |
| ATOM 5934 | CG | LYS | 748 | 60.083 | −1.923 | 35.861 | 1.00 | 46.49 |
| ATOM 5935 | CD | LYS | 748 | 60.817 | −1.407 | 37.103 | 1.00 | 50.69 |
| ATOM 5936 | CE | LYS | 748 | 61.253 | −2.574 | 37.999 | 1.00 | 52.57 |
| ATOM 5937 | NZ | LYS | 748 | 62.072 | −2.129 | 39.155 | 1.00 | 56.45 |
| ATOM 5941 | C | LYS | 748 | 57.700 | −2.318 | 34.028 | 1.00 | 35.58 |
| ATOM 5942 | O | LYS | 748 | 57.898 | −3.526 | 33.871 | 1.00 | 34.72 |
| ATOM 5943 | N | GLN | 749 | 56.522 | −1.818 | 34.411 | 1.00 | 35.59 |
| ATOM 5945 | CA | GLN | 749 | 55.369 | −2.684 | 34.692 | 1.00 | 38.20 |
| ATOM 5946 | CB | GLN | 749 | 54.154 | −1.872 | 35.162 | 1.00 | 42.73 |
| ATOM 5947 | CG | GLN | 749 | 54.264 | −1.171 | 36.499 | 1.00 | 49.30 |
| ATOM 5948 | CD | GLN | 749 | 53.060 | −0.282 | 36.761 | 1.00 | 53.13 |
| ATOM 5949 | OE1 | GLN | 749 | 53.194 | 0.915 | 37.023 | 1.00 | 52.71 |
| ATOM 5950 | NE2 | GLN | 749 | 51.873 | −0.856 | 36.644 | 1.00 | 58.54 |
| ATOM 5953 | C | GLN | 749 | 54.954 | −3.392 | 33.409 | 1.00 | 36.16 |
| ATOM 5954 | O | GLN | 749 | 54.745 | −4.605 | 33.393 | 1.00 | 36.67 |
| ATOM 5955 | N | LEU | 750 | 54.801 | −2.609 | 32.342 | 1.00 | 35.83 |
| ATOM 5957 | CA | LEU | 750 | 54.381 | −3.117 | 31.037 | 1.00 | 34.49 |
| ATOM 5958 | CB | LEU | 750 | 54.324 | −1.988 | 30.004 | 1.00 | 32.49 |
| ATOM 5959 | CG | LEU | 750 | 53.206 | −0.958 | 30.188 | 1.00 | 31.94 |
| ATOM 5960 | CD1 | LEU | 750 | 53.411 | 0.230 | 29.267 | 1.00 | 30.45 |
| ATOM 5961 | CD2 | LEU | 750 | 51.859 | −1.610 | 29.933 | 1.00 | 29.30 |
| ATOM 5962 | C | LEU | 750 | 55.294 | −4.214 | 30.559 | 1.00 | 33.87 |
| ATOM 5963 | O | LEU | 750 | 54.828 | −5.208 | 30.027 | 1.00 | 34.72 |
| ATOM 5964 | N | VAL | 751 | 56.598 | −4.038 | 30.759 | 1.00 | 36.12 |
| ATOM 5966 | CA | VAL | 751 | 57.585 | −5.045 | 30.363 | 1.00 | 34.50 |
| ATOM 5967 | CB | VAL | 751 | 59.054 | −4.532 | 30.559 | 1.00 | 31.96 |
| ATOM 5968 | CG1 | VAL | 751 | 60.052 | −5.646 | 30.308 | 1.00 | 30.24 |
| ATOM 5969 | CG2 | VAL | 751 | 59.342 | −3.386 | 29.604 | 1.00 | 28.02 |
| ATOM 5970 | C | VAL | 751 | 57.349 | −6.321 | 31.182 | 1.00 | 36.11 |
| ATOM 5971 | O | VAL | 751 | 57.333 | −7.422 | 30.638 | 1.00 | 36.45 |
| ATOM 5972 | N | GLU | 752 | 57.107 | −6.165 | 32.479 | 1.00 | 37.83 |
| ATOM 5914 | CA | GLU | 752 | 56.869 | −7.326 | 33.331 | 1.00 | 41.47 |
| ATOM 5975 | CB | GLU | 752 | 56.800 | −6.910 | 34.804 | 1.00 | 43.03 |
| ATOM 5976 | CG | GLU | 752 | 58.122 | −6.305 | 35.263 | 1.00 | 52.52 |
| ATOM 5977 | CD | GLU | 752 | 58.251 | −6.176 | 36.761 | 1.00 | 57.18 |
| ATOM 5978 | OE1 | GLU | 752 | 58.600 | −5.068 | 37.233 | 1.00 | 58.11 |
| ATOM 5979 | OE2 | GLU | 752 | 58.032 | −7.191 | 37.461 | 1.00 | 61.59 |
| ATOM 5980 | C | GLU | 752 | 55.623 | −8.097 | 32.890 | 1.00 | 40.16 |
| ATOM 5981 | O | GLU | 752 | 55.689 | −9.308 | 32.642 | 1.00 | 39.75 |
| ATOM 5982 | N | ASP | 753 | 54.524 | −7.376 | 32.696 | 1.00 | 40.06 |
| ATOM 5964 | CA | ASP | 753 | 53.275 | −7.982 | 32.264 | 1.00 | 39.73 |
| ATOM 5985 | CB | ASP | 7.53 | 52.157 | −6.947 | 32.247 | 1.00 | 41.00 |
| ATOM 5966 | CG | ASP | 753 | 51.668 | −6.591 | 33.640 | 1.00 | 45.17 |
| ATOM 5987 | OD1 | ASP | 753 | 51.753 | 7.468 | 34.543 | 1.00 | 49.78 |
| ATOM 5988 | OD2 | ASP | 753 | 51.210 | −5.439 | 33.829 | 1.00 | 45.51 |
| ATOM 5989 | C | ASP | 753 | 53.396 | −8.595 | 30.890 | 1.00 | 39.64 |
| ATOM 5990 | O | ASP | 753 | 52.955 | −9.720 | 30.674 | 1.00 | 41.84 |
| ATOM 5991 | N | LEU | 754 | 53.998 | −7.861 | 29.960 | 1.00 | 37.75 |
| ATOM 5993 | CA | LEU | 754 | 54.161 | −8.358 | 28.603 | 1.00 | 38.16 |
| ATOM 5994 | CB | LEU | 754 | 54.664 | −7.261 | 27.664 | 1.00 | 36.95 |
| ATOM 5995 | CG | LEU | 754 | 53.552 | −6.270 | 27.307 | 1.00 | 36.64 |
| ATOM 5996 | CD1 | LEU | 754 | 54.141 | −5.062 | 26.590 | 1.00 | 34.02 |
| ATOM 5997 | CD2 | LEU | 754 | 52.459 | −6.968 | 26.465 | 1.00 | 34.13 |
| ATOM 5998 | C | LEU | 754 | 55.070 | −9.561 | 28.571 | 1.00 | 38.46 |
| ATOM 5999 | O | LEU | 754 | 54.905 | −10.451 | 27.740 | 1.00 | 39.95 |
| ATOM 6000 | N | ASP | 755 | 56.014 | −9.602 | 29.502 | 1.00 | 39.19 |

TABLE 3-continued

Atomic Structure Coordinates of Unphosphorylated FLGK

| Atom No. | Atom Type | A.A. Type | A.A. No. | X | Y | Z | OCC | B | |
|---|---|---|---|---|---|---|---|---|---|
| ATOM 6002 | CA | ASP | 755 | 56.930 | −10.728 | 29.594 | 1.00 | 40.87 | |
| ATOM 6003 | CB | ASP | 755 | 57.956 | −10.462 | 30.696 | 1.00 | 45.11 | |
| ATOM 6004 | CG | ASP | 755 | 59.128 | −11.415 | 30.652 | 1.00 | 48.64 | |
| ATOM 6005 | OD1 | ASP | 755 | 59.759 | −11.612 | 31.711 | 1.00 | 54.27 | |
| ATOM 6006 | OD2 | ASP | 755 | 59.432 | −11.954 | 29.565 | 1.00 | 51.46 | |
| ATOM 6007 | C | ASP | 755 | 56.082 | −11.952 | 29.947 | 1.00 | 40.67 | |
| ATOM 6008 | O | ASP | 755 | 56.152 | −12.996 | 29.289 | 1.00 | 38.49 | |
| ATOM 6009 | N | ARG | 756 | 55.232 | −11.771 | 30.955 | 1.00 | 40.06 | |
| ATOM 6011 | CA | ARG | 756 | 54.340 | −12.817 | 31.437 | 1.00 | 40.07 | |
| ATOM 6012 | CB | ARG | 756 | 53.573 | −12.316 | 32.661 | 1.00 | 40.24 | |
| ATOM 6013 | CG | ARG | 756 | 52.435 | −13.217 | 33.138 | 1.00 | 42.12 | |
| ATOM 6014 | CD | ARG | 756 | 51.791 | −12.631 | 34.389 | 1.00 | 42.33 | |
| ATOM 6015 | NE | ARG | 756 | 51.353 | −11.247 | 34.186 | 1.00 | 46.68 | |
| ATOM 6017 | CZ | ARG | 756 | 50.295 | −10.891 | 33.460 | 1.00 | 48.17 | |
| ATOM 6018 | NH1 | ARG | 756 | 49.549 | −11.818 | 32.866 | 1.00 | 46.64 | |
| ATOM 6021 | NH2 | ARG | 756 | 49.998 | −9.605 | 33.305 | 1.00 | 46.92 | |
| ATOM 6024 | C | ARG | 756 | 53.362 | −13.275 | 30.364 | 1.00 | 40.19 | |
| ATOM 6025 | O | ARG | 756 | 53.247 | −14.469 | 30.110 | 1.00 | 42.24 | |
| ATOM 6026 | N | ILE | 757 | 52.688 | −12.27 | 29.717 | 1.00 | 18.18 | |
| ATOM 6028 | CA | ILE | 757 | 51.706 | −12.649 | 28.683 | 1.00 | 38.40 | |
| ATOM 6029 | CB | ILE | 757 | 50.952 | −11.382 | 28.187 | 1.00 | 36.55 | |
| ATOM 6030 | CG2 | IL1 | 757 | 49.952 | −11.758 | 27.105 | 1.00 | 34.67 | |
| ATOM 6031 | CG1 | ILE | 757 | 50.216 | −10.726 | 29.364 | 1.00 | 34.65 | |
| ATOM 6032 | CD1 | ILE | 757 | 49.554 | −9.423 | 29.048 | 1.00 | 36.49 | |
| ATOM 6033 | C | ILE | 757 | 52.301 | −13.400 | 27.500 | 1.00 | 39.19 | |
| ATOM 6034 | O | ILE | 757 | 51.709 | −14.360 | 27.025 | 1.00 | 39.66 | |
| ATOM 6035 | N | VAL | 758 | 53.492 | −12.996 | 27.061 | 1.00 | 42.36 | |
| ATOM 6037 | CA | VAL | 758 | 54.161 | −13.645 | 25.937 | 1.00 | 43.15 | |
| ATOM 6038 | CB | VAL | 758 | 55.582 | −13.052 | 25.682 | 1.00 | 41.72 | |
| ATOM 6039 | CG1 | VAL | 758 | 56.308 | −13.855 | 24.621 | 1.00 | 41.57 | |
| ATOM 6040 | CG2 | VAL | 758 | 55.491 | −11.619 | 25.229 | 1.00 | 40.06 | |
| ATOM 6041 | C | VAL | 758 | 54.299 | −15.133 | 26.231 | 1.00 | 47.11 | |
| ATOM 1042 | O | VAL | 758 | 54.045 | −15.971 | 25.369 | 1.00 | 48.62 | |
| ATOM 6043 | N | ALA | 759 | 54.695 | −15.446 | 27.464 | 1.00 | 49.64 | |
| ATOM 6045 | CA | ALA | 759 | 54.879 | −16.820 | 27.908 | 1.00 | 51.35 | |
| ATOM 6046 | CB | ALA | 759 | 55.423 | −16.830 | 29.317 | 1.00 | 50.11 | |
| ATOM 6047 | C | ALA | 759 | 53.568 | −17.598 | 27.850 | 1.00 | 54.72 | |
| ATOM 6048 | O | ALA | 759 | 53.520 | −18.717 | 27.348 | 1.00 | 58.64 | |
| ATOM 6049 | N | LEU | 760 | 52.496 | −16.983 | 28.329 | 1.00 | 54.84 | |
| ATOM 6051 | CA | LEU | 760 | 51.194 | −17.628 | 28.343 | 1.00 | 55.87 | |
| ATOM 6052 | CB | LEU | 760 | 50.330 | −17.034 | 29.459 | 1.00 | 56.85 | |
| ATOM 6053 | CG | LEU | 760 | 50.875 | −17.165 | 30.885 | 1.00 | 56.80 | |
| ATOM 6054 | CD1 | LEU | 760 | 49.991 | −16.392 | 31.849 | 1.00 | 56.78 | |
| ATOM 6055 | CD2 | LEU | 760 | 50.959 | −18.631 | 31.289 | 1.00 | 57.78 | |
| ATOM 6056 | C | LEU | 760 | 50.454 | −11.546 | 27.013 | 1.00 | 57.36 | |
| ATOM 6057 | O | LEU | 760 | 49.262 | −17.859 | 26.944 | 1.00 | 57.65 | |
| ATOM 6058 | N | THR | 761 | 51.151 | −17.134 | 25.956 | 1.00 | 58.71 | |
| ATOM 6060 | CA | THR | 761 | 50.541 | −17.025 | 24.630 | 1.00 | 59.04 | |
| ATOM 6061 | CB | THR | 761 | 50.839 | −15.657 | 23.971 | 1.00 | 56.72 | |
| ATOM 6062 | OGi | THR | 761 | 50.287 | −14.610 | 24.775 | 1.00 | 56.53 | |
| ATOM 6064 | CG2 | THR | 761 | 50.213 | −15.584 | 22.590 | 1.00 | 53.81 | |
| ATOM 6065 | C | THR | 761 | 51.049 | −15.138 | 23.721 | 1.00 | 60.44 | |
| ATOM 6066 | O | THR | 761 | 52.255 | −18.295 | 23.530 | 1.00 | 61.40 | |
| ATOM 6067 | SG | CYS | 1603 | 18.474 | −8.976 | 20.202 | 0.10 | 37.82 | PRT2 |
| ATOM 6068 | CG | MET | 534 | 69.311 | 12.109 | 23.281 | 0.50 | 36.25 | PRT2 |
| ATOM 6069 | SD | MET | 534 | 69.286 | 12.958 | 24.867 | 0.50 | 42.61 | PRT2 |
| ATOM 6070 | CE | MET | 534 | 70.539 | 12.083 | 25.804 | 0.50 | 43.27 | PRT2 |
| ATOM 6071 | SG | CYS | 603 | 56.046 | −7.949 | 16.446 | 0.50 | 36.47 | PRT2 |
| ATOM 2676 | OH2 | TIP3 | 1 | 71.794 | 25.061 | 2.660 | 1.00 | 24.53 | |
| ATOM 2679 | OH2 | TIP3 | 2 | 39.750 | 3.992 | 15.898 | 1.00 | 39.62 | |
| ATOM 2682 | OH2 | TIP3 | 3 | 83.809 | 19.717 | 10.596 | 1.00 | 28.26 | |
| ATOM 2685 | OH2 | TIP3 | 4 | 83.630 | 20.056 | 7.685 | 1.00 | 26.19 | |
| ATOM 2688 | OH2 | TIP3 | 5 | 75.073 | 16.616 | 6.785 | 1.00 | 26.48 | |
| ATOM 2691 | OH2 | TIP3 | 6 | 86.549 | 19.594 | 9.502 | 1.00 | 33.65 | |
| ATOM 2694 | OH2 | TIP3 | 7 | 51.913 | 11.060 | 24.263 | 1.00 | 35.55 | |
| ATOM 2697 | OH2 | TIP3 | 8 | 55.093 | 9.421 | 22.524 | 1.00 | 26.63 | |
| ATOM 2700 | OH2 | TIP3 | 9 | 57.161 | 4.614 | 32.443 | 1.00 | 29.69 | |
| ATOM 2703 | OH2 | TIP3 | 10 | 52.169 | 4.735 | 13.281 | 1.00 | 22.61 | |
| ATOM 2706 | OH2 | TIP3 | 11 | 41.110 | 5.543 | 22.764 | 1.00 | 41.60 | |
| ATOM 2709 | OH2 | TIP3 | 12 | 45.145 | 8.857 | 21.555 | 1.00 | 36.99 | |
| ATOM 2712 | OH2 | TIP3 | 13 | 64.465 | −2.607 | 28.883 | 1.00 | 30.17 | |
| ATOM 2715 | OH2 | TIP3 | 14 | 76.944 | 13.287 | 23.954 | 1.00 | 32.94 | |
| ATOM 2718 | OH2 | TIP3 | 15 | 79.062 | 17.048 | 18.200 | 1.00 | 51.65 | |
| ATOM 2721 | OH2 | TIP3 | 16 | 83.066 | 11.657 | 15.958 | 1.00 | 25.12 | |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2724 | OH2 | TIP3 | 17 | 13.957 | −9.951 | 0.095 | 1.00 | 26.02 |
| ATOM 2727 | OH2 | TIP3 | 18 | 38.359 | −0.001 | 5.000 | 1.00 | 37.43 |
| ATOM 2730 | OH2 | TIP3 | 19 | 5.442 | 2.705 | 19.077 | 1.00 | 29.46 |
| ATOM 2733 | OH2 | TIP3 | 20 | 27.008 | 6.166 | 4.885 | 1.00 | 25.05 |
| ATOM 2736 | OH2 | TIP3 | 21 | 34.242 | −1.725 | 16.911 | 1.00 | 52.12 |
| ATOM 2739 | OH2 | TIP3 | 22 | 20.167 | 2.428 | 27.681 | 1.00 | 42.69 |
| ATOM 2742 | OH2 | TIP3 | 23 | 50.794 | −11.834 | 38.045 | 1.00 | 60.16 |
| ATOM 2745 | OH2 | TIP3 | 24 | 17.261 | −5.993 | −1.757 | 1.00 | 25.88 |
| ATOM 2748 | OH2 | TIP3 | 25 | 27.516 | 7.803 | 15.070 | 1.00 | 39.33 |
| ATOM 2751 | OH2 | TIP3 | 26 | 31.574 | 0.146 | 6.684 | 1.00 | 35.78 |
| ATOM 2754 | OH2 | TIP3 | 27 | 27.119 | −12.972 | 27.844 | 1.00 | 43.66 |
| ATOM 2757 | OH2 | TIP3 | 28 | 28.439 | −17.074 | 13.203 | 1.00 | 36.44 |
| ATOM 2760 | OH2 | TIP3 | 29 | 88.706 | 14.393 | 7.969 | 1.00 | 32.49 |
| ATOM 2763 | OH2 | TIP3 | 30 | −2.338 | −3.424 | 11.295 | 1.00 | 49.20 |
| ATOM 2766 | OH2 | TIP3 | 31 | 35.086 | −4.130 | 18.836 | 1.00 | 37.83 |
| ATOM 2769 | OH2 | TIP3 | 32 | 80.455 | 17.922 | 9.507 | 1.00 | 23.69 |
| ATOM 2772 | OH2 | TIP3 | 33 | 5.538 | 3.619 | 10.835 | 1.00 | 29.13 |
| ATOM 2775 | OH2 | TIP3 | 34 | −10.685 | 5.290 | 11.288 | 1.00 | 24.40 |
| ATOM 2778 | OH2 | TIP3 | 35 | 29.210 | −8.799 | 20.241 | 1.00 | 46.52 |
| ATOM 2781 | OH2 | TIP3 | 36 | 6.195 | 3.150 | 13.803 | 1.00 | 31.39 |
| ATOM 2784 | OH2 | TIP3 | 37 | 31.898 | 2.830 | 0.154 | 1.00 | 40.17 |
| ATOM 2787 | OH2 | TIP3 | 38 | 19.915 | 2.023 | −3.939 | 1.00 | 1.34 |
| ATOM 2790 | OH2 | TIP3 | 39 | 62.242 | 2.604 | 32.859 | 1.00 | 39.67 |
| ATOM 2793 | OH2 | TIP3 | 40 | 21.231 | −7.063 | −3.900 | 1.00 | 23.55 |
| ATOM 2796 | OH2 | TIP3 | 41 | −15.809 | 8.838 | 22.610 | 1.00 | 36.02 |
| ATOM 2799 | OH2 | TIP3 | 42 | 40.120 | 2.154 | 8.433 | 1.00 | 60.62 |
| ATOM 2802 | OH2 | TIP3 | 43 | 19.583 | 11.128 | −0.045 | 1.00 | 37.85 |
| ATOM 2805 | OH2 | TIP3 | 44 | 67.056 | 9.030 | 17.389 | 1.00 | 29.79 |
| ATOM 2808 | OH2 | TIP3 | 45 | 87.772 | 18.919 | 18.595 | 1.00 | 48.44 |
| ATOM 2811 | OH2 | TIP3 | 46 | 74.584 | 17.123 | 4.200 | 1.00 | 39.18 |
| ATOM 2814 | OH2 | TIP3 | 47 | 29.365 | 16.707 | 10.560 | 1.00 | 34.11 |
| ATOM 2817 | OH2 | TIP3 | 48 | 66.486 | 6.826 | 15.051 | 1.00 | 32.28 |
| ATOM 2820 | OH2 | TIP3 | 49 | 85.008 | 21.441 | 5.731 | 1.00 | 23.97 |
| ATOM 2823 | OH2 | TIP3 | 50 | −4.572 | 2.912 | 3.173 | 1.00 | 28.05 |
| ATOM 2826 | OH2 | TIP3 | 51 | 19.496 | 5.141 | 4.881 | 1.00 | 28.88 |
| ATOM 2829 | OH2 | TIP3 | 52 | 67.492 | 3.490 | 10.902 | 1.00 | 33.57 |
| ATOM 2832 | OH2 | TIP3 | 53 | 34.791 | 5.413 | 24.797 | 1.00 | 40.16 |
| ATOM 2835 | OH2 | TIP3 | 54 | 34.787 | −16.910 | 13.756 | 1.00 | 39.46 |
| ATOM 2838 | OH2 | TIP3 | 55 | 59.972 | 7.450 | 27.870 | 1.00 | 31.56 |
| ATOM 2841 | OH2 | TIP3 | 56 | −7.139 | −1.696 | 6.345 | 1.00 | 42.01 |
| ATOM 2844 | OH2 | TIP3 | 57 | 54.998 | 11.953 | 25.360 | 1.00 | 42.05 |
| ATOM 2847 | OH2 | TIP3 | 58 | 68.697 | 6.686 | 16.740 | 1.00 | 46.12 |
| ATOM 2850 | OH2 | TIP3 | 59 | 73.750 | 20.885 | 19.041 | 1.00 | 32.26 |
| ATOM 2853 | OH2 | TIP3 | 60 | 3.431 | −8.270 | −8.218 | 1.00 | 31.27 |
| ATOM 2856 | OH2 | TIP3 | 61 | 37.904 | 10.790 | 5.612 | 1.00 | 33.72 |
| ATOM 2859 | OH2 | TIP3 | 62 | 29.982 | −9.545 | −1.303 | 1.00 | 39.11 |
| ATOM 2862 | OH2 | TIP3 | 63 | 66.918 | 1.757 | 8.678 | 1.00 | 34.68 |
| ATOM 2865 | OH2 | TIP3 | 64 | 49.117 | 1.310 | 12.227 | 1.00 | 34.31 |
| ATOM 2868 | OH2 | TIP3 | 65 | 41.246 | 3.987 | 29.033 | 1.00 | 34.55 |
| ATOM 2871 | OH2 | TIP3 | 66 | 10.755 | −12.957 | 1.167 | 1.00 | 42.14 |
| ATOM 2874 | OH2 | TIP3 | 67 | −1.184 | −4.327 | 21.439 | 1.00 | 37.90 |
| ATOM 2677 | OH2 | TIP3 | 68 | 30.349 | 16.267 | 13.265 | 1.00 | 55.23 |
| ATOM 2880 | OH2 | TIP3 | 69 | 8.111 | 4.362 | 3.445 | 1.00 | 23.88 |
| ATOM 2883 | OH2 | TIP3 | 70 | 73.131 | 18.780 | 22.628 | 1.00 | 40.20 |
| ATOM 2886 | OH2 | TIP3 | 71 | −7.949 | −3.409 | 24.953 | 1.00 | 35.49 |
| ATOM 2889 | OH2 | TIP3 | 72 | 66.379 | −4.621 | 28.423 | 1.00 | 45.46 |
| ATOM 2892 | OH2 | TIP3 | 73 | 21.506 | −20.711 | 4.815 | 1.00 | 52.46 |
| ATOM 2895 | OH2 | TIP3 | 74 | 59.539 | −6.865 | 4.928 | 1.00 | 48.87 |
| ATOM 2898 | OH2 | TIP3 | 75 | 16.565 | −13.297 | −3.008 | 1.00 | 51.80 |
| ATOM 2901 | OH2 | TIP3 | 76 | −15.235 | 7.385 | 4.428 | 1.00 | 29.13 |
| ATOM 2904 | OH2 | TIP3 | 77 | 32.926 | 2.785 | 13.213 | 1.00 | 37.62 |
| ATOM 2907 | OH2 | TIP3 | 78 | 0.246 | −2.768 | 10.996 | 1.00 | 28.25 |
| ATOM 2910 | OH2 | TIP3 | 79 | 17.495 | 2.354 | 5.447 | 1.00 | 23.63 |
| ATOM 2913 | OH2 | TIP3 | 80 | 6.336 | 2.434 | 21.950 | 1.00 | 29.56 |
| ATOM 2916 | OH2 | TIP3 | 81 | 27.374 | 3.628 | 6.163 | 1.00 | 34.06 |
| ATOM 2919 | OH2 | TIP3 | 82 | −8.708 | 6.263 | 9.522 | 1.00 | 30.34 |
| ATOM 2922 | OH2 | TIP3 | 83 | 1.500 | −1.935 | 8.721 | 1.00 | 27.61 |
| ATOM 2925 | OH2 | TIP3 | 84 | −4.825 | −3.133 | 6.984 | 1.00 | 33.50 |
| ATOM 2928 | OH2 | TIP3 | 85 | 17.513 | 2.839 | 1.966 | 1.00 | 24.27 |
| ATOM 2931 | OH2 | TIP3 | 86 | 20.298 | 3.414 | 2.920 | 1.00 | 26.15 |
| ATOM 2934 | OH2 | TIP3 | 87 | 0.488 | −2.158 | 22.213 | 1.00 | 25.95 |
| ATOM 2937 | OH2 | TIP3 | 88 | 19.939 | −6.185 | −1.553 | 1.00 | 19.14 |
| ATOM 2940 | OH2 | TIP3 | 89 | 10.670 | −15.654 | 6.839 | 1.00 | 33.36 |
| ATOM 2943 | OH2 | TIP3 | 90 | 4.107 | −12.003 | 11.805 | 1.00 | 33.92 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 2946 | OH2 | TIP3 | 91 | 6.238 | 0.927 | −3.342 | 1.00 | 23.31 |
| ATOM 2949 | OH2 | TIP3 | 92 | −13.563 | 1.438 | 5.472 | 1.00 | 27.86 |
| ATOM 2952 | OH2 | TIP3 | 93 | 15.707 | −7.454 | 0.106 | 1.00 | 26.69 |
| ATOM 2955 | OH2 | TIP3 | 94 | −1.856 | −5.393 | 3.795 | 1.00 | 39.91 |
| ATOM 2958 | OH2 | TIP3 | 95 | 12.654 | 4.928 | −4.474 | 1.00 | 31.32 |
| ATOM 2961 | OH2 | TIP3 | 96 | 69.774 | 27.363 | 2.127 | 1.00 | 35.86 |
| ATOM 2964 | OH2 | TIP3 | 97 | 24.636 | −13.192 | 0.040 | 1.00 | 48.53 |
| ATOM 2967 | OH2 | TIP3 | 98 | 60.453 | −4.625 | 33.829 | 1.00 | 31.97 |
| ATOM 2970 | OH2 | TIP3 | 99 | 10.513 | 5.719 | 3.487 | 1.00 | 38.90 |
| ATOM 2973 | OH2 | TIP3 | 100 | −9.499 | −4.011 | 4.342 | 1.00 | 30.61 |
| ATOM 2976 | OH2 | TIP3 | 101 | 73.056 | −1.608 | 10.514 | 1.00 | 36.08 |
| ATOM 2979 | OH2 | TIP3 | 102 | −3.152 | 5.709 | 30.608 | 1.00 | 29.38 |
| ATOM 2982 | OH2 | TIP3 | 103 | 36.630 | 0.702 | 11.792 | 1.00 | 47.80 |
| ATOM 2985 | OH2 | TIP3 | 104 | 21.475 | 6.325 | 16.924 | 1.00 | 24.03 |
| ATOM 2988 | OH2 | TIP3 | 105 | 31.272 | 0.656 | 19.432 | 1.00 | 53.74 |
| ATOM 2991 | OH2 | TIP3 | 106 | 5.620 | −6.417 | 22.266 | 1.00 | 51.90 |
| ATOM 2994 | OH2 | TIP3 | 107 | −13.144 | 8.294 | 17.464 | 1.00 | 35.23 |
| ATOM 2997 | OH2 | TIP3 | 108 | 26.680 | −10.556 | −1.042 | 1.00 | 27.83 |
| ATOM 3000 | OH2 | TIP3 | 109 | 24.149 | 1.846 | 18.172 | 1.00 | 30.90 |
| ATOM 3003 | OH2 | TIP3 | 110 | −1.943 | 12.643 | 3.558 | 1.00 | 33.82 |
| ATOM 3006 | OH2 | TIP3 | 111 | 59.560 | 13.617 | 33.196 | 1.00 | 54.79 |
| ATOM 3009 | OH2 | TIP3 | 112 | 4.351 | −10.740 | 1.991 | 1.00 | 37.96 |
| ATOM 3012 | OH2 | TIP3 | 113 | 8.396 | 2.913 | 0.958 | 1.00 | 29.64 |
| ATOM 3015 | OH2 | TIP3 | 114 | 75.905 | 1.753 | 25.812 | 1.00 | 38.73 |
| ATOM 3018 | OH2 | TIP3 | 115 | 48.783 | 15.535 | 14.189 | 1.00 | 35.24 |
| ATOM 3021 | OH2 | TIP3 | 116 | 2.419 | −11.312 | 9.146 | 1.00 | 32.85 |
| ATOM 3024 | OH2 | TIP3 | 117 | 83.014 | 26.360 | 12.964 | 1.00 | 41.83 |
| ATOM 3027 | OH2 | TIP3 | 118 | 8.761 | −6.579 | −3.252 | 1.00 | 42.78 |
| ATOM 3030 | OH2 | TIP3 | 119 | −8.417 | 4.493 | 4.305 | 1.00 | 28.32 |
| ATOM 3033 | OH2 | TIP3 | 120 | 7.908 | −13.090 | 8.639 | 1.00 | 33.73 |
| ATOM 3036 | OH2 | TIP3 | 121 | 51.437 | 6.329 | 10.373 | 1.00 | 31.72 |
| ATOM 3039 | OH2 | TIP3 | 122 | 20.660 | 3.686 | 15.591 | 1.00 | 32.37 |
| ATOM 3042 | OH2 | TIP3 | 123 | 73.039 | 3.790 | 20.450 | 1.00 | 35.80 |
| ATOM 3045 | OH2 | TIP3 | 124 | 5.155 | −11.467 | 22.590 | 1.00 | 45.12 |
| ATOM 3048 | OH2 | TIP3 | 125 | 34.172 | 2.412 | 16.576 | 1.00 | 41.90 |
| ATOM 3051 | OH2 | TIP3 | 126 | 9.597 | −11.905 | 7.083 | 1.00 | 24.83 |
| ATOM 3054 | OH2 | TIP3 | 127 | 8.276 | 3.860 | −1.622 | 1.00 | 35.46 |
| ATOM 3057 | OH2 | TIP3 | 128 | 66.282 | 5.755 | 12.352 | 1.00 | 35.43 |
| ATOM 3060 | OH2 | TIP3 | 129 | 7.377 | 6.932 | 2.982 | 1.00 | 40.68 |
| ATOM 3063 | OH2 | TIP3 | 130 | 35.832 | −1.778 | 0.201 | 1.00 | 34.99 |
| ATOM 3066 | OH2 | TIP3 | 131 | 44.781 | 10.362 | 11.064 | 1.00 | 42.31 |
| ATOM 3069 | OH2 | TiP3 | 132 | 27.790 | −12.638 | 18.958 | 1.00 | 58.71 |
| ATOM 3072 | OH2 | TIP3 | 133 | 45.221 | 11.540 | 21.428 | 1.00 | 36.75 |
| ATOM 3075 | OH2 | TIP3 | 134 | 57.560 | −10.846 | 14.099 | 1.00 | 52.90 |
| ATOM 3078 | OH2 | TIP3 | 135 | −3.354 | 15.001 | 16.515 | 1.00 | 37.81 |
| ATOM 3081 | OH2 | TIP3 | 136 | 85.717 | 11.251 | 9.062 | 1.00 | 35.18 |
| ATOM 3084 | OH2 | TIP3 | 137 | 12.951 | −2.469 | 2.075 | 1.00 | 22.07 |
| ATOM 3087 | OH2 | TIP3 | 138 | 75.645 | 3.486 | 29.527 | 1.00 | 38.01 |
| ATOM 3090 | OH2 | TIP3 | 139 | 13.237 | 7.412 | −2.649 | 1.00 | 33.50 |
| ATOM 3093 | OH2 | TIP3 | 140 | 11.262 | 9.970 | 0.974 | 1.00 | 26.14 |
| ATOM 3096 | OH2 | TIP3 | 141 | 59.480 | 10.772 | 14.098 | 1.00 | 52.08 |
| ATOM 3099 | OH2 | TIP3 | 142 | 13.869 | −16.121 | 3.919 | 1.00 | 40.06 |
| ATOM 3102 | OH2 | TIP3 | 143 | −6.407 | −3.413 | 16.641 | 1.00 | 44.38 |
| ATOM 3105 | OH2 | TIP3 | 144 | 25.667 | −12.645 | 3.411 | 1.00 | 48.28 |
| ATOM 3105 | OH2 | TIP3 | 145 | −16.282 | 10.641 | 6.423 | 1.00 | 40.94 |
| ATOM 3111 | OH2 | TIP3 | 146 | 86.637 | 12.861 | 7.005 | 1.00 | 39.45 |
| ATOM 3114 | OH2 | TIP3 | 147 | 32.082 | −4.569 | 1.892 | 1.00 | 27.35 |
| ATOM 3117 | OH2 | TIP3 | 148 | 44.809 | 7.627 | 11.670 | 1.00 | 35.65 |
| ATOM 3120 | OH2 | TIP3 | 149 | 80.693 | 12.459 | 16.523 | 1.00 | 37.21 |
| ATOM 3123 | OH2 | TIP3 | 150 | 2.941 | −7.111 | −1.805 | 1.00 | 38.43 |
| ATOM 3126 | OH2 | TIP3 | 151 | 31.794 | −6.066 | 20.704 | 1.00 | 42.80 |
| ATOM 3129 | OH2 | TIP3 | 152 | 74.770 | −2.683 | 12.398 | 1.00 | 40.40 |
| ATOM 3132 | OH2 | TIP3 | 153 | 7.731 | 6.640 | −1.037 | 1.00 | 35.61 |
| ATOM 3135 | OH2 | TIP3 | 154 | 71.617 | 5.599 | 21.835 | 1.00 | 40.14 |
| ATOM 3138 | OH2 | TIP3 | 155 | 68.113 | −4.968 | 8.886 | 1.00 | 34.38 |
| ATOM 3141 | OH2 | TIP3 | 156 | 0.042 | −9.364 | 7.055 | 1.00 | 33.08 |
| ATOM 3144 | OH2 | TIP3 | 157 | 68.020 | 18.352 | 10.995 | 1.00 | 34.76 |
| ATOM 3147 | OH2 | TIP3 | 158 | 3.795 | 8.550 | 4.533 | 1.00 | 34.69 |
| ATOM 3150 | OH2 | TIP3 | 159 | 52.106 | 11.746 | 10.410 | 1.00 | 40.06 |
| ATOM 3153 | OH2 | TIP3 | 160 | 6.414 | 3.927 | 16.889 | 1.00 | 37.07 |
| ATOM 3156 | OH2 | TIP3 | 161 | −10.282 | 6.603 | 4.715 | 1.00 | 38.48 |
| ATOM 3159 | OH2 | TIP3 | 162 | 76.410 | 1.681 | −0.781 | 1.00 | 42.87 |
| ATOM 3162 | OH2 | TIP3 | 163 | 9.910 | −12.046 | 17.157 | 1.00 | 32.79 |
| ATOM 3165 | OH2 | TIP3 | 164 | 33.983 | 14.219 | 18.191 | 1.00 | 37.35 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 3168 | OH2 | TIP3 | 165 | 2.330 | −7.952 | 16.978 | 1.00 | 44.25 |
| ATOM 3171 | OH2 | TIP3 | 166 | 29.701 | 1.780 | 5.987 | 1.00 | 39.86 |
| ATOM 3174 | OH2 | TIP3 | 167 | 32.494 | −17.319 | 11.798 | 1.00 | 38.46 |
| ATOM 3177 | OH2 | TIP3 | 168 | 42.107 | 17.932 | 10.978 | 1.00 | 44.83 |
| ATOM 3180 | OH2 | TIP3 | 169 | 87.822 | 10.537 | 5.568 | 1.00 | 54.30 |
| ATOM 3183 | OH2 | TIP3 | 170 | 70.261 | −4.143 | 25.064 | 1.00 | 44.75 |
| ATOM 3186 | OH2 | TIP3 | 171 | 77.519 | 5.882 | 1.891 | 1.00 | 42.67 |
| ATOM 3189 | OH2 | TIP3 | 172 | −0.921 | −8.166 | 4.521 | 1.00 | 45.91 |
| ATOM 3192 | OH2 | TIP3 | 173 | 34.213 | 15.329 | 1.478 | 1.00 | 40.10 |
| ATOM 3195 | OH2 | TIP3 | 174 | −9.647 | 7.731 | 7.383 | 1.00 | 35.63 |
| ATOM 3198 | OH2 | TIP3 | 175 | 11.619 | 5.799 | 7.440 | 1.00 | 36.36 |
| ATOM 3201 | OH2 | TTP3 | 176 | −8.709 | 13.964 | 13.507 | 1.00 | 51.97 |
| ATOM 3204 | OH2 | TIP3 | 177 | 31.770 | 3.376 | 18.354 | 1.00 | 46.26 |
| ATOM 3207 | OH2 | TIP3 | 178 | −8.494 | 9.789 | 24.269 | 1.00 | 50.98 |
| ATOM 3210 | OH2 | TIP3 | 179 | −1.234 | −6.253 | 15.622 | 1.00 | 38.47 |
| ATOM 3213 | OH2 | TIP3 | 180 | 80.252 | 0.887 | 15.691 | 1.00 | 39.48 |
| ATOM 3216 | OH2 | TIP3 | 181 | 67.248 | 20.272 | −1.555 | 1.00 | 48.22 |
| ATOM 3219 | OH2 | TIP3 | 182 | −0.566 | 4.367 | 1.362 | 1.00 | 39.84 |
| ATOM 3222 | OH2 | TIP3 | 183 | 0.120 | 6.523 | 2.615 | 1.00 | 33.11 |
| ATOM 3225 | OH2 | TIP3 | 184 | −1.496 | 8.789 | 1.237 | 1.00 | 41.03 |
| ATOM 3228 | OH2 | TIP3 | 185 | −5.143 | 9.130 | 2.236 | 1.00 | 40.47 |
| ATOM 3231 | OH2 | TIP3 | 186 | −7.275 | iC.106 | 3.833 | 1.00 | 40.55 |
| ATOM 3234 | OH2 | TIP3 | 187 | 2.717 | 7.275 | 0.769 | 1.00 | 44.67 |
| ATOM 3237 | OH2 | TIP3 | 188 | 5.176 | 10.645 | 8.459 | 1.00 | 34.48 |
| ATOM 3240 | OH2 | TIP3 | 189 | 63.822 | 12.690 | 22.883 | 1.00 | 41.88 |
| ATOM 3243 | OH2 | TIP3 | 190 | 79.109 | 1.028 | 18.201 | 1.00 | 46.40 |
| ATOM 3246 | OH2 | TIP3 | 191 | 59.332 | 11.681 | 7.236 | 1.00 | 63.45 |
| ATOM 3249 | OH2 | TIP3 | 192 | 13.967 | −1.218 | −4.268 | 1.00 | 34.79 |
| ATOM 3252 | OH2 | TIP3 | 193 | 59.444 | 2.867 | 33.368 | 1.00 | 41.00 |
| ATOM 3255 | OH2 | TIP3 | 194 | 32.024 | 13.487 | 19.852 | 1.00 | 53.61 |
| ATOM 3258 | OH2 | TIP3 | 195 | 72.101 | 16.218 | 22.802 | 1.00 | 44.03 |
| ATOM 3261 | OH2 | TIP3 | 196 | 0.987 | −8.546 | 14.474 | 1.00 | 41.38 |
| ATOM 3264 | OH2 | TIP3 | 197 | −0.491 | 5.461 | 30.372 | 1.00 | 38.51 |
| ATOM 3267 | OH2 | TIP3 | 198 | 61.179 | 6.795 | 11.905 | 1.00 | 41.77 |
| ATOM 3270 | OH2 | TIP3 | 199 | −1.365 | −4.128 | 27.656 | 1.00 | 50.98 |
| ATOM 3273 | OH2 | TIP3 | 200 | 81.440 | 15.558 | 17.262 | 1.00 | 44.47 |
| ATOM 3276 | OH2 | TIP3 | 201 | −17.491 | 4.116 | 23.873 | 1.00 | 50.58 |
| ATOM 3279 | OH2 | TIP3 | 202 | 27.546 | 10.513 | 14.499 | 1.00 | 39.06 |
| ATOM 3282 | OH2 | TIP3 | 203 | 34.992 | 4.513 | 27.719 | 1.00 | 49.89 |
| ATOM 3285 | OH2 | TIP3 | 204 | −3.486 | −4.591 | 9.171 | 1.00 | 49.53 |
| ATOM 3288 | OH2 | TIP3 | 205 | 42.799 | 7.848 | 22.320 | 1.00 | 43.50 |
| ATOM 3291 | OH2 | TIP3 | 206 | 52.728 | 11.884 | 21.811 | 1.00 | 39.98 |
| ATOM 3294 | OH2 | TIP3 | 207 | 26.706 | 14.069 | 19.833 | 1.00 | 46.68 |
| ATOM 3297 | OH2 | TIP3 | 208 | −7.154 | 8.907 | 6.444 | 1.00 | 42.83 |
| ATOM 3300 | OH2 | TIP3 | 209 | 86.648 | 5.606 | 16.034 | 1.00 | 51.15 |
| ATOM 3303 | OH2 | TIP3 | 210 | 54.879 | 15.840 | 20.379 | 1.00 | 50.23 |
| ATOM 3306 | OH2 | TIP3 | 211 | 51.417 | 19.473 | 22.691 | 1.00 | 48.35 |
| ATOM 3309 | OH2 | TIP3 | 212 | 20.102 | 6.924 | 7.085 | 1.00 | 38.15 |
| ATOM 3312 | OH2 | TIP3 | 213 | 28.991 | 1.941 | −3.570 | 1.00 | 47.39 |
| ATOM 3315 | OH2 | TIP3 | 214 | 26.505 | 2.386 | −4.633 | 1.00 | 46.48 |
| ATOM 3318 | OH2 | TIP3 | 215 | 36.482 | 2.810 | 18.521 | 1.00 | 46.26 |
| ATOM 3321 | OH2 | TIP3 | 216 | 16.941 | −20.504 | 14.128 | 1.00 | 49.74 |
| ATOM 3324 | OH2 | TIP3 | 217 | 28.572 | −14.448 | 6.157 | 1.00 | 49.13 |
| ATOM 3327 | OH2 | TIP3 | 218 | 31.380 | 1.471 | −1.998 | 1.00 | 43.02 |
| ATOM 3330 | OH2 | TIP3 | 219 | 10.065 | −16.338 | 15.455 | 1.00 | 42.75 |
| ATOM 3333 | OH2 | TIP3 | 220 | 7.350 | −11.974 | 5.652 | 1.00 | 55.35 |
| ATOM 3336 | OH2 | TIP3 | 221 | −12.328 | 14.547 | 10.986 | 1.00 | 51.29 |
| ATOM 3339 | OH2 | TIP3 | 222 | 11.186 | 91.609 | −1.388 | 1.00 | 37.68 |
| ATOM 3342 | OH2 | TIP3 | 223 | 11.389 | 12.276 | −1.400 | 1.00 | 46.93 |
| ATOM 3345 | OH2 | TIP3 | 224 | 34.202 | 13.069 | −1.161 | 1.00 | 41.79 |
| ATOM 3348 | OH2 | TIP3 | 225 | 31.303 | 17.822 | 7.853 | 1.00 | 48.21 |
| ATOM 3351 | OH2 | TIP3 | 226 | 36.875 | 11.804 | −2.106 | 1.00 | 59.03 |
| ATOM 3354 | OH2 | TIP3 | 227 | 35.134 | 3.048 | 12.020 | 1.00 | 50.41 |
| ATOM 3357 | OH2 | TIP3 | 228 | 63.950 | 13.409 | 26.627 | 1.00 | 43.40 |
| ATOM 3360 | OH2 | TIP3 | 229 | 36.367 | 6.116 | 15.221 | 1.00 | 57.79 |
| ATOM 3363 | OH2 | TIP3 | 230 | 90.606 | 4.355 | 6.342 | 1.00 | 47.53 |
| ATOM 3366 | OH2 | TIP3 | 231 | 50.038 | −11.673 | 10.767 | 1.00 | 56.90 |
| ATOM 3369 | OH2 | TIP3 | 232 | 60.196 | −10.144 | 16.590 | 1.00 | 51.61 |
| ATOM 3372 | OH2 | TIP3 | 233 | 18.021 | −21.179 | 7.008 | 1.00 | 49.93 |
| ATOM 3375 | OH2 | TIP3 | 234 | 66.236 | −1.218 | 30.583 | 1.00 | 39.55 |
| ATOM 3378 | OH2 | TIP3 | 235 | 74.959 | 18.928 | 20.659 | 1.00 | 38.04 |
| ATOM 3381 | OH2 | TIP3 | 236 | −2.816 | 10.082 | 3.187 | 1.00 | 49.31 |
| ATOM 3384 | OH2 | TIP3 | 237 | 5.894 | −3.410 | 25.289 | 1.00 | 35.55 |
| ATOM 3387 | OH2 | TIP3 | 238 | 35.784 | 6.047 | 12.543 | 1.00 | 41.96 |

TABLE 3-continued

Atomic Structure Coordinates of Unphosphorylated FLGK

| Atom No. | Atom Type | A.A. Type | A.A. No. | X | Y | Z | OCC | B |
|---|---|---|---|---|---|---|---|---|
| ATOM 3390 | OH2 | TIP3 | 239 | −5.400 | 16.537 | 14.180 | 1.00 | 43.13 |
| ATOM 3393 | OH2 | TIP3 | 240 | 46.589 | −11.622 | 26.970 | 1.00 | 43.71 |
| ATOM 3396 | OH2 | TIP3 | 241 | 6.199 | 6.592 | 13.797 | 1.00 | 46.51 |
| ATOM 3399 | OH2 | TIP3 | 242 | −3.777 | −5.158 | 20.907 | 1.00 | 42.08 |
| ATOM 3402 | OH2 | TIP3 | 243 | 1.969 | −3.711 | −0.282 | 1.00 | 37.38 |
| ATOM 3405 | OH2 | TIP3 | 244 | 86.200 | 11.629 | 22.877 | 1.00 | 56.51 |
| ATOM 3408 | OH2 | TIP3 | 245 | 10.557 | 7.565 | 5.514 | 1.00 | 47.58 |
| ATOM 3411 | OH2 | TIP3 | 246 | 4.802 | 8.149 | 2.136 | 1.00 | 50.70 |
| ATOM 3414 | OH2 | TIP3 | 247 | 64.590 | −8.128 | 20.596 | 1.00 | 43.65 |
| ATOM 3417 | OH2 | TIP3 | 248 | 11.346 | −17.840 | 13.283 | 1.00 | 47.64 |
| ATOM 3420 | OH2 | TIP3 | 249 | 42.116 | −6.808 | 14.953 | 1.00 | 53.79 |
| ATOM 3423 | OH2 | TIP3 | 250 | 2.745 | −4.054 | 22.128 | 1.00 | 60.88 |
| ATOM 3426 | OH2 | TIP3 | 251 | 71.999 | 1.177 | −2.124 | 1.00 | 47.90 |
| ATOM 3429 | OH2 | TIP3 | 252 | 50.326 | −3.210 | 33.068 | 1.00 | 57.01 |
| ATOM 3435 | OH2 | TIP3 | 253 | 57.838 | 9.337 | 11.631 | 1.00 | 52.55 |
| ATOM 3438 | OH2 | TIP3 | 254 | 43.373 | 20.489 | 30.490 | 1.00 | 51.97 |
| ATOM 3441 | OH2 | TIP3 | 255 | 67.145 | 16.529 | 15.793 | 1.00 | 49.02 |
| ATOM 3444 | OH2 | TIP3 | 256 | 87.509 | 21.566 | 5.114 | 1.00 | 54.21 |
| ATOM 3447 | OH2 | TIP3 | 257 | 21.060 | 10.052 | −9.215 | 1.00 | 60.32 |
| ATOM 3450 | OH2 | TIP3 | 258 | 11.827 | 2.450 | 27.951 | 1.00 | 54.26 |
| ATOM 3453 | OH2 | TIP3 | 259 | 64.788 | −0.418 | 3.563 | 1.00 | 50.94 |
| ATOM 3456 | OH2 | TIP3 | 260 | 71.859 | 28.473 | 7.950 | 1.00 | 62.81 |
| ATOM 3459 | OH2 | TIP3 | 261 | 25.605 | −8.106 | 27.287 | 1.00 | 52.81 |
| ATOM 3462 | OH2 | TIP3 | 262 | −18.804 | 10.886 | 12.628 | 1.00 | 55.25 |
| ATOM 3465 | OH2 | TIP3 | 263 | 30.652 | 11.349 | 16.201 | 1.00 | 50.40 |
| ATOM 3468 | OH2 | TIP3 | 264 | 22.350 | −16.098 | −2.742 | 1.00 | 53.27 |
| ATOM 3471 | OH2 | TIP3 | 265 | 29.720 | 9.106 | 18.465 | 1.00 | 57.23 |

TABLE 4

Atomic Structure Coordinates of Unphosphorylated FLGK:AMP-PCP Co-Complex

| Atom No. | Atom Type | A.A. Type | A.A. No. | X | Y | Z | OCC | B |
|---|---|---|---|---|---|---|---|---|
| ATOM 1 | N | GLU | 1464 | −13.425 | 16.769 | 8.973 | 1.00 | 61.21 |
| ATOM 3 | CA | GLU | 1464 | −12.536 | 16.852 | 7.821 | 1.00 | 59.70 |
| ATOM 4 | CB | GLU | 1464 | −11.383 | 17.829 | 8.085 | 1.00 | 60.05 |
| ATOM 5 | C | GLU | 1464 | −11.998 | 15.478 | 7.427 | 1.00 | 57.11 |
| ATOM 6 | O | GLU | 1464 | −12.134 | 15.076 | 6.274 | 1.00 | 59.75 |
| ATOM 7 | N | LEU | 1465 | −11.406 | 14.749 | 8.368 | 1.00 | 52.21 |
| ATOM 9 | CA | LEU | 1465 | −10.871 | 13.424 | 8.062 | 1.00 | 46.72 |
| ATOM 10 | CB | LEU | 1465 | −10.102 | 12.844 | 9.249 | 1.00 | 44.98 |
| ATOM 11 | CG | LEU | 1465 | −8.608 | 13.123 | 9.384 | 1.00 | 46.11 |
| ATOM 12 | CD1 | LEU | 1465 | −8.338 | 14.592 | 9.663 | 1.00 | 51.13 |
| ATOM 13 | CD2 | LEU | 1465 | −8.064 | 12.286 | 10.512 | 1.00 | 4.99 |
| ATOM 14 | C | LEU | 1465 | −12.000 | 12.475 | 7.700 | 1.00 | 44.16 |
| ATOM 15 | O | LEU | 1465 | −13.101 | 12.577 | 8.239 | 1.00 | 44.04 |
| ATOM 16 | N | PRO | 1466 | −11.760 | 11.580 | 6.732 | 1.00 | 42.53 |
| ATOM 17 | CD | PRO | 1466 | −10.535 | 11.534 | 5.913 | 1.00 | 41.30 |
| ATOM 18 | CA | PRO | 1466 | −12.740 | 10.591 | 6.269 | 1.00 | 41.16 |
| ATOM 19 | CB | PRO | 1466 | −12.134 | 10.111 | 4.959 | 1.00 | 41.48 |
| ATOM 20 | CG | PRO | 1466 | −10.658 | 10.213 | 5.220 | 1.00 | 41.30 |
| ATOM 21 | C | PRO | 1466 | −12.906 | 9.441 | 7.261 | 1.00 | 41.31 |
| ATOM 22 | O | PRO | 1466 | −11.929 | 8.936 | 7.816 | 1.00 | 41.05 |
| ATOM 23 | N | GLU | 1467 | −14.145 | 9.044 | 7.500 | 1.00 | 41.02 |
| ATOM 25 | CA | GLU | 1467 | −14.428 | 7.960 | 8.427 | 1.00 | 42.42 |
| ATOM 26 | CB | GLU | 1467 | −15.931 | 7.904 | 8.712 | 1.00 | 47.98 |
| ATOM 27 | CG | GLU | 1467 | −16.565 | 9.238 | 9.105 | 1.00 | 52.79 |
| ATOM 28 | CD | GLU | 1467 | −17.998 | 9.093 | 9.606 | 1.00 | 54.21 |
| ATOM 29 | OE1 | GLU | 1467 | −18.474 | 7.949 | 9.741 | 1.00 | 58.90 |
| ATOM 30 | OE2 | GLU | 1467 | −18.650 | 10.120 | 9.879 | 1.00 | 55.90 |
| ATOM 31 | C | GLU | 1467 | −13.972 | 6.628 | 7.837 | 1.00 | 40.93 |
| ATOM 32 | O | GLU | 1467 | −14.061 | 6.426 | 6.620 | 1.00 | 44.32 |
| ATOM 33 | N | ASP | 1468 | −13.473 | 5.731 | 8.689 | 1.00 | 35.10 |
| ATOM 35 | CA | ASP | 1468 | −13.024 | 4.404 | 8.256 | 1.00 | 31.82 |
| ATOM 36 | CB | ASP | 1468 | −11.507 | 4.358 | 7.992 | 1.00 | 30.65 |
| ATOM 37 | CG | ASP | 1468 | −11.025 | 3.002 | 7.440 | 1.00 | 29.93 |
| ATOM 38 | OD1 | ASP | 1468 | −11.689 | 1.958 | 7.603 | 1.00 | 29.63 |
| ATOM 39 | OD2 | ASP | 1468 | −9.945 | 2.974 | 6.835 | 1.00 | 33.63 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 40 | C | ASP | 1468 | −13.394 | 3.441 | 9.369 | 1.00 | 31.81 |
| ATOM 41 | O | ASP | 1468 | −12.618 | 3.209 | 10.302 | 1.00 | 31.91 |
| ATOM 42 | N | PRO | 1469 | −14.569 | 2.819 | 9.247 | 1.00 | 29.68 |
| ATOM 43 | CD | PRO | 1469 | −15.482 | 2.963 | 8.097 | 1.00 | 28.33 |
| ATOM 44 | CA | PRO | 1469 | −15.100 | 1.863 | 10.220 | 1.00 | 31.80 |
| ATOM 45 | CB | PRO | 1469 | −16.352 | 1.331 | 9.510 | 1.00 | 32.51 |
| ATOM 46 | CG | PRO | 1469 | −16.783 | 2.496 | 8.656 | 1.00 | 27.41 |
| ATOM 47 | C | PRO | 1469 | −14.146 | 0.731 | 10.590 | 1.00 | 30.44 |
| ATOM 48 | O | PRO | 1469 | −14.272 | 0.135 | 11.654 | 1.00 | 30.02 |
| ATOM 49 | N | ARG | 1470 | −13.198 | 0.442 | 9.704 | 1.00 | 31.06 |
| ATOM 51 | CA | ARG | 1470 | −12.240 | −0.636 | 9.917 | 1.00 | 31.86 |
| ATOM 52 | CB | ARG | 1470 | −11.386 | −0.860 | 8.660 | 1.00 | 31.36 |
| ATOM 53 | CG | ARG | 1470 | −12.107 | −1.437 | 7.448 | 1.00 | 33.08 |
| ATOM 54 | CD | ARG | 1470 | −11.148 | −1.588 | 6.248 | 1.00 | 31.08 |
| ATOM 55 | NE | ARG | 1470 | −10.540 | −0.310 | 5.891 | 1.00 | 34.36 |
| ATOM 57 | CZ | ARG | 1470 | −9.656 | −0.135 | 4.919 | 1.00 | 33.32 |
| ATOM 58 | NH1 | ARG | 1470 | −9.260 | −1.164 | 4.185 | 1.00 | 35.90 |
| ATOM 61 | NH2 | ARG | 1470 | −9.155 | 1.074 | 4.687 | 1.00 | 32.79 |
| ATOM 64 | C | ARG | 1470 | −11.290 | −0.436 | 11.095 | 1.00 | 32.68 |
| ATOM 65 | O | ARG | 1470 | −10.820 | −1.410 | 11.683 | 1.00 | 33.43 |
| ATOM 66 | N | TRP | 1471 | −11.031 | 0.814 | 11.456 | 1.00 | 31.84 |
| ATOM 68 | CA | TRP | 1471 | −10.063 | 1.090 | 12.505 | 1.00 | 31.17 |
| ATOM 69 | CB | TRP | 1471 | −8.816 | 1.677 | 11.850 | 1.00 | 30.15 |
| ATOM 70 | CG | TRP | 1471 | −8.173 | 0.725 | 10.941 | 1.00 | 29.54 |
| ATOM 71 | CD2 | TRP | 1471 | −7.288 | −0.329 | 11.315 | 1.00 | 31.07 |
| ATOM 72 | CE2 | TRP | 1471 | −6.913 | −0.992 | 10.132 | 1.00 | 34.41 |
| ATOM 73 | CE3 | TRP | 1471 | −6.762 | −0.768 | 12.536 | 1.00 | 29.46 |
| ATOM 74 | CD1 | TRP | 1471 | −8.309 | 0.660 | 9.587 | 1.00 | 30.20 |
| ATOM 75 | NE1 | TRP | 1471 | −7.557 | −0.371 | 9.089 | 1.00 | 33.09 |
| ATOM 77 | CZ2 | TRP | 1471 | −6.042 | −2.085 | 10.135 | 1.00 | 31.68 |
| ATOM 78 | CZ3 | TRP | 1471 | −5.897 | −1.853 | 12.540 | 1.00 | 29.65 |
| ATOM 79 | CH2 | TRP | 1471 | −5.541 | −2.494 | 11.347 | 1.00 | 30.18 |
| ATOM 80 | C | TRP | 1471 | −10.477 | 2.019 | 13.620 | 1.00 | 29.94 |
| ATOM 81 | O | TRP | 1471 | −9.782 | 2.108 | 14.631 | 1.00 | 30.00 |
| ATOM 82 | N | GLU | 1472 | −11.573 | 2.737 | 13.416 | 1.00 | 29.06 |
| ATOM 84 | CA | GLU | 1472 | −12.051 | 3.706 | 14.380 | 1.00 | 28.62 |
| ATOM 85 | CB | GLU | 1472 | −13.312 | 4.386 | 13.849 | 1.00 | 29.16 |
| ATOM 86 | CG | GLU | 1472 | −13.641 | 5.733 | 14.529 | 1.00 | 30.74 |
| ATOM 87 | CD | GLU | 1472 | −12.676 | 6.848 | 14.156 | 1.00 | 30.05 |
| ATOM 88 | OE1 | GLU | 1472 | −12.090 | 6.799 | 13.057 | 1.00 | 31.32 |
| ATOM 89 | OE2 | GLU | 1472 | −12.511 | 7.784 | 14.961 | 1.00 | 30.26 |
| ATOM 90 | C | GLU | 1472 | −12.327 | 3.159 | 15.767 | 1.00 | 28.70 |
| ATOM 91 | O | GLU | 1472 | −12.969 | 2.125 | 15.916 | 1.00 | 31.01 |
| ATOM 92 | N | LEU | 1473 | −11.810 | 3.842 | 16.781 | 1.00 | 27.38 |
| ATOM 94 | CA | LEU | 1473 | −12.054 | 3.451 | 18.161 | 1.00 | 29.61 |
| ATOM 95 | CB | LEU | 1473 | −10.763 | 3.073 | 18.899 | 1.00 | 28.56 |
| ATOM 96 | CG | LEU | 1473 | −10.923 | 2.756 | 20.403 | 1.00 | 30.06 |
| ATOM 97 | CD1 | LEU | 1473 | −11.485 | 1.354 | 20.639 | 1.00 | 28.42 |
| ATOM 98 | CD2 | LEU | 1473 | −9.595 | 2.876 | 21.115 | 1.00 | 28.15 |
| ATOM 99 | C | LEU | 1473 | −12.617 | 4.714 | 18.764 | 1.00 | 31.81 |
| ATOM 100 | O | LEU | 1473 | −12.179 | 5.814 | 18.407 | 1.00 | 33.00 |
| ATOM 101 | N | PRO | 1474 | −13.670 | 4.591 | 19.596 | 1.00 | 31.45 |
| ATOM 102 | CD | PRO | 1474 | −14.488 | 3.400 | 19.859 | 1.00 | 31.72 |
| ATOM 103 | CA | PRO | 1474 | −14.261 | 5.774 | 20.226 | 1.00 | 31.23 |
| ATOM 104 | CB | PRO | 1474 | −15.400 | 5.176 | 21.048 | 1.00 | 29.01 |
| ATOM 105 | CG | PRO | 1474 | −15.815 | 4.005 | 20.247 | 1.00 | 29.09 |
| ATOM 106 | C | PRO | 1474 | −13.217 | 6.444 | 21.120 | 1.00 | 33.36 |
| ATOM 107 | O | PRO | 1474 | −12.447 | 5.765 | 21.808 | 1.00 | 36.40 |
| ATOM 108 | N | ARG | 1475 | −13.188 | 7.770 | 21.112 | 1.00 | 33.67 |
| ATOM 110 | CA | ARG | 1475 | −12.228 | 8.498 | 21.924 | 1.00 | 33.96 |
| ATOM 111 | CB | ARG | 1475 | −12.433 | 9.991 | 21.735 | 1.00 | 35.31 |
| ATOM 112 | CG | ARG | 1475 | −12.134 | 10.405 | 20.333 | 1.00 | 40.10 |
| ATOM 113 | CD | ARG | 1475 | −12.060 | 11.906 | 20.145 | 1.00 | 42.98 |
| ATOM 114 | NE | ARG | 1475 | −11.785 | 12.194 | 18.737 | 1.00 | 42.91 |
| ATOM 116 | CZ | ARG | 1475 | −10.578 | 12.443 | 18.253 | 1.00 | 41.30 |
| ATOM 117 | NH1 | ARG | 1475 | −9.529 | 12.467 | 19.064 | 1.00 | 41.88 |
| ATOM 120 | NH2 | ARG | 1475 | −10.413 | 12.567 | 16.943 | 1.00 | 40.98 |
| ATOM 123 | C | ARG | 1475 | −12.278 | 8.142 | 23.404 | 1.00 | 35.88 |
| ATOM 124 | O | ARG | 1475 | −11.240 | 8.046 | 24.061 | 1.00 | 37.10 |
| ATOM 125 | N | ASP | 1476 | −13.479 | 7.920 | 23.928 | 1.00 | 36.47 |
| ATOM 127 | CA | ASP | 1476 | −13.632 | 7.581 | 25.335 | 1.00 | 37.24 |
| ATOM 128 | CB | ASP | 1476 | −15.112 | 7.629 | 25.741 | 1.00 | 39.66 |
| ATOM 129 | CG | ASP | 1476 | −15.930 | 6.480 | 25.163 | 1.00 | 42.38 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 130 | OD1 | ASP | 1476 | −15.438 | 5.706 | 24.322 | 1.00 | 47.52 |
| ATOM 131 | OD2 | ASP | 1476 | −17.098 | 6.349 | 25.568 | 1.00 | 48.06 |
| ATOM 132 | C | ASP | 1476 | −13.023 | 6.232 | 25.724 | 1.00 | 36.93 |
| ATOM 133 | O | ASP | 1476 | −13.034 | 5.856 | 26.898 | 1.00 | 40.09 |
| ATOM 134 | N | ARG | 1477 | −12.564 | 5.475 | 24.732 | 1.00 | 34.34 |
| ATOM 136 | CA | ARG | 1477 | −11.961 | 4.171 | 24.993 | 1.00 | 32.47 |
| ATOM 137 | CB | ARG | 1477 | −12.269 | 3.212 | 23.852 | 1.00 | 31.59 |
| ATOM 138 | CG | ARG | 1477 | −13.716 | 2.939 | 23.640 | 1.00 | 29.66 |
| ATOM 139 | CD | ARG | 1477 | −14.314 | 2.342 | 24.875 | 1.00 | 30.65 |
| ATOM 140 | NE | ARG | 1477 | −14.498 | 3.342 | 25.918 | 1.00 | 31.37 |
| ATOM 142 | CZ | ARG | 1477 | −14.822 | 3.055 | 27.174 | 1.00 | 32.81 |
| ATOM 143 | NH1 | ARG | 1477 | −15.002 | 1.794 | 27.549 | 1.00 | 33.92 |
| ATOM 146 | NH2 | ARG | 1477 | −14.950 | 4.025 | 28.062 | 1.00 | 31.74 |
| ATOM 149 | C | ARG | 1477 | −10.452 | 4.266 | 25.153 | 1.00 | 33.13 |
| ATOM 150 | O | ARG | 1477 | −9.777 | 3.281 | 25.445 | 1.00 | 33.55 |
| ATOM 151 | N | LEU | 1478 | −9.923 | 5.466 | 24.984 | 1.00 | 34.43 |
| ATOM 153 | CA | LEU | 1478 | −8.493 | 5.663 | 25.076 | 1.00 | 35.68 |
| ATOM 154 | CB | LEU | 1478 | −8.008 | 6.350 | 23.790 | 1.00 | 34.98 |
| ATOM 155 | CG | LEU | 1478 | −6.581 | 6.137 | 23.284 | 1.00 | 31.11 |
| ATOM 156 | CD1 | LEU | 1478 | −6.280 | 4.650 | 23.161 | 1.00 | 26.62 |
| ATOM 157 | CD2 | LEU | 1478 | −6.428 | 6.839 | 21.940 | 1.00 | 28.80 |
| ATOM 158 | C | LEU | 1478 | −8.158 | 6.505 | 26.295 | 1.00 | 36.21 |
| ATOM 159 | O | LEU | 1478 | −8.501 | 7.688 | 26.361 | 1.00 | 39.67 |
| ATOM 160 | N | VAL | 1479 | −7.558 | 5.878 | 27.293 | 1.00 | 35.42 |
| ATOM 162 | CA | VAL | 1479 | −7.156 | 6.599 | 28.491 | 1.00 | 35.80 |
| ATOM 163 | CB | VAL | 1479 | −7.269 | 5.707 | 29.742 | 1.00 | 36.29 |
| ATOM 164 | CG1 | VAL | 1479 | −7.017 | 6.527 | 30.983 | 1.00 | 37.23 |
| ATOM 165 | CG2 | VAL | 1479 | −8.650 | 5.059 | 29.812 | 1.00 | 34.41 |
| ATOM 166 | C | VAL | 1479 | −5.704 | 7.046 | 28.244 | 1.00 | 35.68 |
| ATOM 167 | O | VAL | 1479 | −4.764 | 6.246 | 28.319 | 1.00 | 33.45 |
| ATOM 168 | N | LEU | 1480 | −5.538 | 8.315 | 27.885 | 1.00 | 38.15 |
| ATOM 170 | CA | LEU | 1480 | −4.213 | 8.860 | 27.584 | 1.00 | 42.61 |
| ATOM 171 | CB | LEU | 1480 | −4.332 | 10.205 | 26.857 | 1.00 | 39.14 |
| ATOM 172 | CG | LEU | 1480 | −4.969 | 10.179 | 25.460 | 1.00 | 38.44 |
| ATOM 173 | CD1 | LEU | 1480 | −4.901 | 11.579 | 24.879 | 1.00 | 39.39 |
| ATOM 174 | CD2 | LEU | 1480 | −4.263 | 9.194 | 24.533 | 1.00 | 36.86 |
| ATOM 175 | C | LEU | 1480 | −3.274 | 8.970 | 28.783 | 1.00 | 46.37 |
| ATOM 176 | O | LEU | 1480 | −3.659 | 9.445 | 29.850 | 1.00 | 48.86 |
| ATOM 177 | N | GLY | 1481 | −2.033 | 8.537 | 28.594 | 1.00 | 47.13 |
| ATOM 179 | CA | GLY | 1481 | −1.081 | 8.573 | 29.678 | 1.00 | 48.19 |
| ATOM 180 | C | GLY | 1481 | 0.163 | 9.388 | 29.425 | 1.00 | 50.27 |
| ATOM 181 | O | GLY | 1481 | 0.152 | 10.367 | 28.675 | 1.00 | 51.19 |
| ATOM 182 | N | LYS | 1482 | 1.240 | 8.965 | 30.078 | 1.00 | 50.93 |
| ATOM 184 | CA | LYS | 1482 | 2.543 | 9.606 | 30.007 | 1.00 | 50.94 |
| ATOM 185 | CB | LYS | 1482 | 3.509 | 8.866 | 30.933 | 1.00 | 50.41 |
| ATOM 186 | CG | LYS | 1482 | 4.971 | 9.026 | 30.567 | 1.00 | 51.87 |
| ATOM 187 | CD | LYS | 1482 | 5.810 | 7.874 | 31.087 | 1.00 | 53.49 |
| ATOM 188 | CE | LYS | 1482 | 5.390 | 6.542 | 30.478 | 1.00 | 50.77 |
| ATOM 189 | NZ | LYS | 1482 | 6.251 | 5.433 | 30.986 | 1.00 | 49.92 |
| ATOM 193 | C | LYS | 1482 | 3.145 | 9.676 | 28.609 | 1.00 | 52.31 |
| ATOM 194 | O | LYS | 1482 | 3.115 | 8.700 | 27.851 | 1.00 | 52.30 |
| ATOM 195 | N | PRO | 1483 | 3.706 | 10.838 | 28.250 | 1.00 | 53.47 |
| ATOM 196 | CD | PRO | 1483 | 3.667 | 12.105 | 28.997 | 1.00 | 54.19 |
| ATOM 197 | CA | PRO | 1483 | 4.326 | 11.021 | 26.937 | 1.00 | 54.10 |
| ATOM 198 | CB | PRO | 1483 | 4.772 | 12.480 | 26.976 | 1.00 | 54.25 |
| ATOM 199 | CG | PRO | 1483 | 3.772 | 13.118 | 27.895 | 1.00 | 55.30 |
| ATOM 200 | C | PRO | 1483 | 5.535 | 10.096 | 26.827 | 1.00 | 54.72 |
| ATOM 201 | O | PRO | 1483 | 6.343 | 10.017 | 27.751 | 1.00 | 53.48 |
| ATOM 202 | N | LEU | 1484 | 5.619 | 9.351 | 25.731 | 1.00 | 57.05 |
| ATOM 204 | CA | LEU | 1484 | 6.739 | 8.447 | 25.503 | 1.00 | 59.26 |
| ATOM 205 | CB | LEU | 1484 | 6.307 | 7.241 | 24.669 | 1.00 | 59.35 |
| ATOM 206 | CG | LEU | 1484 | 5.391 | 6.216 | 25.343 | 1.00 | 60.87 |
| ATOM 207 | CD1 | LEU | 1484 | 4.975 | 5.161 | 24.329 | 1.00 | 57.14 |
| ATOM 208 | CD2 | LEU | 1484 | 6.081 | 5.571 | 26.551 | 1.00 | 59.79 |
| ATOM 209 | C | LEU | 1484 | 7.847 | 9.194 | 24.778 | 1.00 | 61.30 |
| ATOM 210 | O | LEU | 1484 | 8.980 | 8.720 | 24.701 | 1.00 | 62.17 |
| ATOM 211 | N | GLY | 1485 | 7.494 | 10.351 | 24.220 | 1.00 | 63.75 |
| ATOM 213 | CA | GLY | 1485 | 8.456 | 11.173 | 23.507 | 1.00 | 66.33 |
| ATOM 214 | C | GLY | 1485 | 8.081 | 11.412 | 22.054 | 1.00 | 67.79 |
| ATOM 215 | O | GLY | 1485 | 6.918 | 11.653 | 21.727 | 1.00 | 69.61 |
| ATOM 216 | N | GLN | 1491 | 4.615 | 13.762 | 18.385 | 1.00 | 58.26 |
| ATOM 218 | CA | GLN | 1491 | 4.353 | 13.353 | 19.762 | 1.00 | 57.98 |
| ATOM 219 | CB | GLN | 1491 | 3.476 | 14.379 | 20.468 | 1.00 | 61.80 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 220 | CG | GLN | 1491 | 3.134 | 14.034 | 21.920 | 1.00 | 70.31 |
| ATOM 221 | CD | GLN | 1491 | 2.019 | 14.911 | 22.482 | 1.00 | 75.91 |
| ATOM 222 | OE1 | GLN | 1491 | 1.355 | 15.636 | 21.748 | 1.00 | 77.85 |
| ATOM 223 | NE2 | GLN | 1491 | 1.820 | 14.832 | 23.788 | 1.00 | 78.30 |
| ATOM 226 | C | GLN | 1491 | 3.709 | 11.965 | 19.881 | 1.00 | 54.67 |
| ATOM 227 | O | GLN | 1491 | 2.701 | 11.669 | 19.222 | 1.00 | 54.91 |
| ATOM 228 | N | VAL | 1492 | 4.305 | 11.125 | 20.729 | 1.00 | 50.04 |
| ATOM 230 | CA | VAL | 1492 | 3.825 | 9.763 | 20.988 | 1.00 | 44.93 |
| ATOM 231 | CB | VAL | 1492 | 4.861 | 8.705 | 20.583 | 1.00 | 42.65 |
| ATOM 232 | CG1 | VAL | 1492 | 4.378 | 7.325 | 20.958 | 1.00 | 39.71 |
| ATOM 233 | CG2 | VAL | 1492 | 5.119 | 8.766 | 19.099 | 1.00 | 40.98 |
| ATOM 234 | C | VAL | 1492 | 3.584 | 9.661 | 22.490 | 1.00 | 43.43 |
| ATOM 235 | O | VAL | 1492 | 4.451 | 10.029 | 23.289 | 1.00 | 43.43 |
| ATOM 236 | N | VAL | 1493 | 2.400 | 9.212 | 22.888 | 1.00 | 41.13 |
| ATOM 238 | CA | VAL | 1493 | 2.107 | 9.080 | 24.304 | 1.00 | 38.77 |
| ATOM 239 | CB | VAL | 1493 | 1.052 | 10.133 | 24.782 | 1.00 | 36.35 |
| ATOM 240 | CG1 | VAL | 1493 | 1.410 | 11.508 | 24.287 | 1.00 | 36.06 |
| ATOM 241 | CG2 | VAL | 1493 | -0.329 | 9.755 | 24.339 | 1.00 | 37.64 |
| ATOM 242 | C | VAL | 1493 | 1.589 | 7.693 | 24.619 | 1.00 | 37.77 |
| ATOM 243 | O | VAL | 1493 | 0.948 | 7.058 | 23.783 | 1.00 | 38.88 |
| ATOM 244 | N | LEU | 1494 | 1.949 | 7.187 | 25.790 | 1.00 | 36.24 |
| ATOM 246 | CA | LEU | 1494 | 1.468 | 5.880 | 26.205 | 1.00 | 35.92 |
| ATOM 247 | CB | LEU | 1494 | 2.252 | 5.383 | 27.429 | 1.00 | 35.41 |
| ATOM 248 | CG | LEU | 1494 | 1.886 | 4.009 | 28.004 | 1.00 | 36.21 |
| ATOM 249 | CD1 | LEU | 1494 | 1.927 | 2.931 | 26.924 | 1.00 | 33.60 |
| ATOM 250 | CD2 | LEU | 1494 | 2.835 | 3.670 | 29.145 | 1.00 | 36.03 |
| ATOM 251 | C | LEU | 1494 | -0.010 | 6.095 | 26.564 | 1.00 | 35.27 |
| ATOM 252 | O | LEU | 1494 | -0.425 | 7.215 | 26.887 | 1.00 | 34.35 |
| ATOM 253 | N | ALA | 1495 | -0.807 | 5.043 | 26.468 | 1.00 | 34.93 |
| ATOM 255 | CA | ALA | 1495 | -2.220 | 5.145 | 26.768 | 1.00 | 34.44 |
| ATOM 256 | CB | ALA | 1495 | -2.955 | 5.794 | 25.616 | 1.00 | 35.29 |
| ATOM 257 | C | ALA | 1495 | -2.781 | 3.770 | 27.018 | 1.00 | 34.59 |
| ATOM 258 | O | ALA | 1495 | -2.128 | 2.766 | 26.748 | 1.00 | 35.52 |
| ATOM 259 | N | GLU | 1496 | -3.996 | 3.723 | 27.536 | 1.00 | 36.64 |
| ATOM 261 | CA | GLU | 1496 | -4.652 | 2.462 | 27.806 | 1.00 | 37.57 |
| ATOM 262 | CB | GLU | 1496 | -5.000 | 2.354 | 29.287 | 1.00 | 38.97 |
| ATOM 263 | CG | GLU | 1496 | -3.769 | 2.304 | 30.185 | 1.00 | 41.79 |
| ATOM 264 | CD | GLU | 1496 | -4.110 | 2.475 | 31.645 | 1.00 | 43.65 |
| ATOM 265 | OE1 | GLU | 1496 | -4.408 | 3.617 | 32.036 | 1.00 | 42.97 |
| ATOM 266 | OE2 | GLU | 1496 | -4.086 | 1.475 | 32.398 | 1.00 | 46.65 |
| ATOM 267 | C | GLU | 1496 | -5.896 | 2.404 | 26.943 | 1.00 | 38.50 |
| ATOM 268 | O | GLU | 1496 | -6.660 | 3.371 | 26.867 | 1.00 | 40.28 |
| ATOM 269 | N | ALA | 1497 | -6.051 | 1.301 | 26.223 | 1.00 | 37.34 |
| ATOM 271 | CA | ALA | 1497 | -7.194 | 1.131 | 25.352 | 1.00 | 37.42 |
| ATOM 272 | CB | ALA | 1497 | -6.743 | 0.625 | 23.985 | 1.00 | 35.92 |
| ATOM 273 | C | ALA | 1497 | -8.146 | 0.148 | 26.000 | 1.00 | 36.77 |
| ATOM 274 | O | ALA | 1497 | -7.759 | -0.977 | 26.323 | 1.00 | 35.74 |
| ATOM 275 | N | ILE | 1498 | -9.354 | 0.616 | 26.291 | 1.00 | 37.03 |
| ATOM 277 | CA | ILE | 1498 | -10.378 | -0.224 | 26.896 | 1.00 | 36.80 |
| ATOM 278 | CB | ILE | 1498 | -11.372 | 0.612 | 27.728 | 1.00 | 34.53 |
| ATOM 279 | CG2 | ILE | 1498 | -12.373 | -0.290 | 28.425 | 1.00 | 34.59 |
| ATOM 280 | CG1 | ILE | 1498 | -10.640 | 1.438 | 28.778 | 1.00 | 31.97 |
| ATOM 281 | CD1 | ILE | 1498 | -11.552 | 2.344 | 29.541 | 1.00 | 31.12 |
| ATOM 282 | C | ILE | 1498 | -11.126 | -0.807 | 25.709 | 1.00 | 38.72 |
| ATOM 283 | O | ILE | 1498 | -11.647 | -0.066 | 24.879 | 1.00 | 37.74 |
| ATOM 284 | N | GLY | 1499 | -11.137 | -2.126 | 25.590 | 1.00 | 40.98 |
| ATOM 286 | CA | GLY | 1499 | -11.839 | -2.728 | 24.482 | 1.00 | 44.64 |
| ATOM 287 | C | GLY | 1499 | -10.931 | -3.115 | 23.332 | 1.00 | 48.45 |
| ATOM 288 | O | GLY | 1499 | -10.260 | -4.147 | 23.401 | 1.00 | 51.92 |
| ATOM 289 | N | LEU | 1500 | -10.877 | -2.269 | 22.303 | 1.00 | 47.87 |
| ATOM 291 | CA | LEU | 1500 | -10.076 | -2.530 | 21.102 | 1.00 | 46.80 |
| ATOM 292 | CB | LEU | 1500 | -8.594 | -2.770 | 21.434 | 1.00 | 45.37 |
| ATOM 293 | CG | LEU | 1500 | -7.543 | -1.661 | 21.293 | 1.00 | 44.84 |
| ATOM 294 | CD1 | LEU | 1500 | -6.174 | -2.290 | 21.450 | 1.00 | 43.33 |
| ATOM 295 | CD2 | LEU | 1500 | -7.623 | -0.959 | 19.948 | 1.00 | 40.43 |
| ATOM 296 | C | LEU | 1500 | -10.631 | -3.737 | 20.349 | 1.00 | 45.63 |
| ATOM 297 | O | LEU | 1500 | -10.797 | -4.823 | 20.915 | 1.00 | 44.42 |
| ATOM 298 | N | PRO | 1505 | -13.569 | -5.910 | 25.549 | 1.00 | 52.13 |
| ATOM 299 | CD | PRO | 1505 | -14.316 | -7.170 | 25.398 | 1.00 | 54.09 |
| ATOM 300 | CA | PRO | 1505 | -14.451 | -4.828 | 25.999 | 1.00 | 50.46 |
| ATOM 301 | CB | PRO | 1505 | -15.841 | -5.455 | 25.891 | 1.00 | 49.86 |
| ATOM 302 | CG | PRO | 1505 | -15.586 | -6.898 | 26.193 | 1.00 | 52.17 |
| ATOM 303 | C | PRO | 1505 | -14.136 | -4.370 | 27.422 | 1.00 | 47.75 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 304 | O | PRO | 1505 | −14.148 | −3.180 | 27.710 | 1.00 | 47.93 |
| ATOM 305 | N | ASN | 1506 | −13.778 | −5.313 | 28.285 | 1.00 | 46.20 |
| ATOM 307 | CA | ASN | 1506 | −13.458 | −4.986 | 29.666 | 1.00 | 49.52 |
| ATOM 308 | CB | ASN | 1506 | −14.310 | −5.829 | 30.612 | 1.00 | 52.42 |
| ATOM 309 | CG | ASN | 1506 | −15.788 | −5.489 | 30.526 | 1.00 | 54.50 |
| ATOM 310 | OD1 | ASN | 1506 | −16.179 | −4.331 | 30.680 | 1.00 | 57.16 |
| ATOM 311 | ND2 | ASN | 1506 | −16.610 | −6.489 | 30.244 | 1.00 | 56.82 |
| ATOM 314 | C | ASN | 1506 | −11.973 | −5.124 | 30.003 | 1.00 | 50.65 |
| ATOM 315 | O | ASN | 1506 | −11.583 | −5.174 | 31.178 | 1.00 | 50.65 |
| ATOM 316 | N | ARG | 1507 | −11.142 | −5.145 | 28.968 | 1.00 | 50.90 |
| ATOM 318 | CA | ARG | 1507 | −9.700 | −5.276 | 29.127 | 1.00 | 49.77 |
| ATOM 319 | CB | ARG | 1507 | −9.192 | −6.483 | 28.339 | 1.00 | 55.81 |
| ATOM 320 | CG | ARG | 1507 | −9.450 | −7.833 | 28.988 | 1.00 | 61.63 |
| ATOM 321 | CD | ARG | 1507 | −8.408 | −8.149 | 30.041 | 1.00 | 66.01 |
| ATOM 322 | NE | ARG | 1507 | −8.600 | −9.490 | 30.583 | 1.00 | 72.55 |
| ATOM 324 | CZ | ARG | 1507 | −8.024 | −9.944 | 31.694 | 1.00 | 77.32 |
| ATOM 325 | NH1 | ARG | 1507 | −7.198 | −9.169 | 32.392 | 1.00 | 78.41 |
| ATOM 328 | NH2 | ARG | 1507 | −8.335 | −11.151 | 32.147 | 1.00 | 79.30 |
| ATOM 331 | C | ARG | 1507 | −9.015 | −4.036 | 28.595 | 1.00 | 45.60 |
| ATOM 332 | O | ARG | 1507 | −9.452 | −3.464 | 27.590 | 1.00 | 42.08 |
| ATOM 333 | N | VAL | 1508 | −7.977 | −3.597 | 29.297 | 1.00 | 42.86 |
| ATOM 335 | CA | VAL | 1508 | −7.216 | −2.443 | 28.858 | 1.00 | 40.75 |
| ATOM 336 | CB | VAL | 1508 | −6.903 | −1.428 | 30.010 | 1.00 | 38.75 |
| ATOM 337 | CG1 | VAL | 1508 | −8.184 | −1.015 | 30.702 | 1.00 | 43.29 |
| ATOM 338 | CG2 | VAL | 1508 | −5.919 | −2.005 | 31.012 | 1.00 | 37.56 |
| ATOM 339 | C | VAL | 1508 | −5.929 | −2.970 | 28.248 | 1.00 | 39.14 |
| ATOM 340 | O | VAL | 1508 | −5.369 | −3.972 | 28.708 | 1.00 | 39.16 |
| ATOM 341 | N | THR | 1509 | −5.517 | −2.345 | 27.157 | 1.00 | 37.26 |
| ATOM 343 | CA | THR | 1509 | −4.298 | −2.737 | 26.486 | 1.00 | 36.52 |
| ATOM 344 | CB | THR | 1509 | −4.571 | −3.187 | 25.019 | 1.00 | 37.83 |
| ATOM 345 | OG1 | THR | 1509 | −5.423 | −4.340 | 25.011 | 1.00 | 43.88 |
| ATOM 347 | CG2 | THR | 1509 | −3.267 | −3.540 | 24.310 | 1.00 | 34.51 |
| ATOM 348 | C | THR | 1509 | −3.434 | −1.495 | 26.473 | 1.00 | 35.82 |
| ATOM 349 | O | THR | 1509 | −3.927 | −0.408 | 26.174 | 1.00 | 34.37 |
| ATOM 350 | N | LYS | 1510 | −2.175 | −1.628 | 26.880 | 1.00 | 35.96 |
| ATOM 352 | CA | LYS | 1510 | −1.291 | −0.479 | 26.843 | 1.00 | 36.13 |
| ATOM 353 | CB | LYS | 1510 | −0.032 | −0.695 | 27.680 | 1.00 | 37.77 |
| ATOM 354 | CG | LYS | 1510 | −0.277 | −0.854 | 29.162 | 1.00 | 44.58 |
| ATOM 355 | CD | LYS | 1510 | 1.023 | −0.658 | 29.948 | 1.00 | 51.33 |
| ATOM 356 | CE | LYS | 1510 | 0.947 | −1.286 | 31.342 | 1.00 | 58.15 |
| ATOM 357 | NZ | LYS | 1510 | −0.149 | −0.728 | 32.187 | 1.00 | 64.94 |
| ATOM 361 | C | LYS | 1510 | −0.929 | −0.355 | 25.373 | 1.00 | 34.59 |
| ATOM 362 | O | LYS | 1510 | −0.574 | −1.345 | 24.734 | 1.00 | 31.43 |
| ATOM 363 | N | VAL | 1511 | −1.092 | 0.846 | 24.835 | 1.00 | 32.95 |
| ATOM 365 | CA | VAL | 1511 | −0.810 | 1.121 | 23.441 | 1.00 | 32.29 |
| ATOM 366 | CB | VAL | 1511 | −2.129 | 1.213 | 22.621 | 1.00 | 32.95 |
| ATOM 367 | CG1 | VAL | 1511 | −2.879 | −0.109 | 22.686 | 1.00 | 34.79 |
| ATOM 368 | CG2 | VAL | 1511 | −3.026 | 2.354 | 23.148 | 1.00 | 32.84 |
| ATOM 369 | C | VAL | 1511 | −0.058 | 2.446 | 23.353 | 1.00 | 32.65 |
| ATOM 370 | O | VAL | 1511 | 0.021 | 3.185 | 24.344 | 1.00 | 31.62 |
| ATOM 371 | N | ALA | 1512 | 0.521 | 2.721 | 22.186 | 1.00 | 30.24 |
| ATOM 373 | CA | ALA | 1512 | 1.244 | 3.969 | 21.954 | 1.00 | 28.18 |
| ATOM 374 | CB | ALA | 1512 | 2.599 | 3.700 | 21.316 | 1.00 | 25.62 |
| ATOM 375 | C | ALA | 1512 | 0.373 | 4.783 | 21.015 | 1.00 | 27.54 |
| ATOM 376 | O | ALA | 1512 | −0.151 | 4.264 | 20.040 | 1.00 | 27.17 |
| ATOM 377 | N | VAL | 1513 | 0.204 | 6.054 | 21.322 | 1.00 | 30.52 |
| ATOM 379 | CA | VAL | 1513 | −0.630 | 6.914 | 20.503 | 1.00 | 34.08 |
| ATOM 380 | CB | VAL | 1513 | −1.731 | 7.591 | 21.347 | 1.00 | 34.61 |
| ATOM 381 | CG1 | VAL | 1513 | −2.607 | 8.444 | 20.474 | 1.00 | 36.75 |
| ATOM 382 | CG2 | VAL | 1513 | −2.567 | 6.549 | 22.087 | 1.00 | 33.45 |
| ATOM 383 | C | VAL | 1513 | 0.203 | 8.008 | 19.837 | 1.00 | 36.38 |
| ATOM 384 | O | VAL | 1513 | 0.924 | 8.750 | 20.510 | 1.00 | 35.32 |
| ATOM 385 | N | LYS | 1514 | 0.105 | 8.093 | 18.513 | 1.00 | 38.19 |
| ATOM 387 | CA | LYS | 1514 | 0.818 | 9.104 | 17.746 | 1.00 | 40.12 |
| ATOM 388 | CB | LYS | 1514 | 1.339 | 8.513 | 16.439 | 1.00 | 40.93 |
| ATOM 389 | CG | LYS | 1514 | 2.452 | 7.488 | 16.632 | 1.00 | 42.52 |
| ATOM 390 | CD | LYS | 1514 | 2.861 | 6.803 | 15.338 | 1.00 | 46.25 |
| ATOM 391 | CE | LYS | 1514 | 3.268 | 7.796 | 14.261 | 1.00 | 49.76 |
| ATOM 392 | NZ | LYS | 1514 | 4.304 | 8.771 | 14.705 | 1.00 | 52.14 |
| ATOM 396 | C | LYS | 1514 | −0.166 | 10.215 | 17.458 | 1.00 | 40.69 |
| ATOM 397 | O | LYS | 1514 | −1.313 | 9.953 | 17.110 | 1.00 | 41.69 |
| ATOM 398 | N | MET | 1515 | 0.277 | 11.454 | 17.613 | 1.00 | 43.28 |
| ATOM 400 | CA | MET | 1515 | −0.569 | 12.610 | 17.379 | 1.00 | 46.21 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 401 | CB | MET | 1515 | −1.363 | 12.936 | 18.644 | 1.00 | 46.96 |
| ATOM 402 | CG | MET | 1515 | −0.488 | 13.293 | 19.837 | 1.00 | 47.61 |
| ATOM 403 | SD | MET | 1515 | −1.413 | 13.464 | 21.358 | 1.00 | 49.77 |
| ATOM 404 | CE | MET | 1515 | −1.593 | 11.761 | 21.814 | 1.00 | 47.84 |
| ATOM 405 | C | MET | 1515 | 0.299 | 13.805 | 17.000 | 1.00 | 49.90 |
| ATOM 406 | O | MET | 1515 | 1.519 | 13.788 | 17.194 | 1.00 | 49.83 |
| ATOM 407 | N | LEU | 1516 | −0.339 | 14.822 | 16.430 | 1.00 | 54.45 |
| ATOM 409 | CA | LEU | 1516 | 0.335 | 16.053 | 16.023 | 1.00 | 57.57 |
| ATOM 410 | CB | LEU | 1516 | −0.483 | 16.762 | 14.944 | 1.00 | 54.10 |
| ATOM 411 | CG | LEU | 1516 | −0.800 | 16.007 | 13.664 | 1.00 | 50.71 |
| ATOM 412 | CD1 | LEU | 1516 | −1.830 | 16.800 | 12.901 | 1.00 | 51.20 |
| ATOM 413 | CD2 | LEU | 1516 | 0.467 | 15.809 | 12.849 | 1.00 | 50.08 |
| ATOM 414 | C | LEU | 1516 | 0.487 | 17.010 | 17.202 | 1.00 | 61.88 |
| ATOM 415 | O | LEU | 1516 | −0.170 | 16.852 | 18.235 | 1.00 | 63.30 |
| ATOM 416 | N | LYS | 1517 | 1.335 | 18.018 | 17.021 | 1.00 | 66.83 |
| ATOM 418 | CA | LYS | 1517 | 1.568 | 19.036 | 18.037 | 1.00 | 71.46 |
| ATOM 419 | CB | LYS | 1517 | 2.985 | 19.593 | 17.911 | 1.00 | 76.28 |
| ATOM 420 | CG | LYS | 1517 | 4.084 | 18.626 | 18.349 | 1.00 | 82.19 |
| ATOM 421 | CD | LYS | 1517 | 5.450 | 19.085 | 17.846 | 1.00 | 86.93 |
| ATOM 422 | CE | LYS | 1517 | 6.579 | 18.228 | 18.411 | 1.00 | 90.46 |
| ATOM 423 | NZ | LYS | 1517 | 7.896 | 18.513 | 17.763 | 1.00 | 92.51 |
| ATOM 427 | C | LYS | 1517 | 0.549 | 20.156 | 17.837 | 1.00 | 72.44 |
| ATOM 428 | O | LYS | 1517 | −0.142 | 20.198 | 16.819 | 1.00 | 72.12 |
| ATOM 429 | N | SER | 1518 | 0.474 | 21.075 | 18.793 | 1.00 | 73.90 |
| ATOM 431 | CA | SER | 1518 | −0.470 | 22.185 | 18.697 | 1.00 | 74.96 |
| ATOM 432 | CB | SER | 1518 | −0.498 | 22.980 | 20.002 | 1.00 | 74.72 |
| ATOM 433 | C | SER | 1518 | −0.133 | 23.100 | 17.525 | 1.00 | 76.16 |
| ATOM 434 | O | SER | 1518 | −1.029 | 23.667 | 16.897 | 1.00 | 76.56 |
| ATOM 435 | N | ASP | 1519 | 1.158 | 23.245 | 17.232 | 1.00 | 77.24 |
| ATOM 437 | CA | ASP | 1519 | 1.601 | 24.094 | 16.125 | 1.00 | 78.51 |
| ATOM 438 | CB | ASP | 1519 | 2.849 | 24.888 | 16.535 | 1.00 | 79.70 |
| ATOM 439 | C | ASP | 1519 | 1.887 | 23.264 | 14.865 | 1.00 | 78.29 |
| ATOM 440 | O | ASP | 1519 | 2.797 | 23.580 | 14.088 | 1.00 | 78.52 |
| ATOM 441 | N | ALA | 1520 | 1.121 | 22.192 | 14.682 | 1.00 | 76.90 |
| ATOM 443 | CA | ALA | 1520 | 1.285 | 21.313 | 13.529 | 1.00 | 74.09 |
| ATOM 444 | CB | ALA | 1520 | 0.737 | 19.930 | 13.840 | 1.00 | 74.20 |
| ATOM 445 | C | ALA | 1520 | 0.580 | 21.895 | 12.318 | 1.00 | 71.82 |
| ATOM 446 | O | ALA | 1520 | −0.573 | 22.311 | 12.400 | 1.00 | 71.78 |
| ATOM 447 | N | THR | 1521 | 1.291 | 21.951 | 11.202 | 1.00 | 69.97 |
| ATOM 449 | CA | THR | 1521 | 0.734 | 22.480 | 9.970 | 1.00 | 68.86 |
| ATOM 450 | CB | THR | 1521 | 1.848 | 22.911 | 9.026 | 1.00 | 68.87 |
| ATOM 451 | OG1 | THR | 1521 | 2.621 | 21.762 | 8.651 | 1.00 | 70.03 |
| ATOM 453 | CG2 | THR | 1521 | 2.756 | 23.912 | 9.715 | 1.00 | 71.55 |
| ATOM 454 | C | THR | 1521 | −0.081 | 21.389 | 9.292 | 1.00 | 67.89 |
| ATOM 455 | O | THR | 1521 | 0.111 | 20.204 | 9.563 | 1.00 | 69.03 |
| ATOM 456 | N | GLU | 1522 | −0.964 | 21.783 | 8.382 | 1.00 | 66.59 |
| ATOM 458 | CA | GLU | 1522 | −1.785 | 20.821 | 7.657 | 1.00 | 65.71 |
| ATOM 459 | CB | GLU | 1522 | −2.737 | 21.532 | 6.692 | 1.00 | 65.61 |
| ATOM 460 | C | GLU | 1522 | −0.886 | 19.823 | 6.909 | 1.00 | 64.32 |
| ATOM 461 | O | GLU | 1522 | −1.324 | 18.729 | 6.549 | 1.00 | 66.29 |
| ATOM 462 | N | LYS | 1523 | 0.367 | 20.205 | 6.677 | 1.00 | 59.93 |
| ATOM 464 | CA | LYS | 1523 | 1.314 | 19.326 | 6.016 | 1.00 | 57.38 |
| ATOM 465 | CB | LYS | 1523 | 2.629 | 20.064 | 5.747 | 1.00 | 60.47 |
| ATOM 466 | CG | LYS | 1523 | 3.815 | 19.162 | 5.370 | 1.00 | 62.75 |
| ATOM 467 | CD | LYS | 1523 | 3.510 | 18.288 | 4.160 | 1.00 | 63.95 |
| ATOM 468 | CE | LYS | 1523 | 4.759 | 17.596 | 3.652 | 1.00 | 65.88 |
| ATOM 469 | NZ | LYS | 1523 | 4.429 | 16.721 | 2.494 | 1.00 | 70.37 |
| ATOM 473 | C | LYS | 1523 | 1.565 | 18.173 | 6.974 | 1.00 | 54.80 |
| ATOM 474 | O | LYS | 1523 | 1.548 | 17.003 | 6.581 | 1.00 | 54.44 |
| ATOM 475 | N | ASP | 1524 | 1.786 | 18.523 | 8.239 | 1.00 | 51.67 |
| ATOM 477 | CA | ASP | 1524 | 2.036 | 17.549 | 9.295 | 1.00 | 49.43 |
| ATOM 478 | CB | ASP | 1524 | 2.297 | 18.271 | 10.622 | 1.00 | 51.06 |
| ATOM 479 | CG | ASP | 1524 | 3.598 | 19.080 | 10.613 | 1.00 | 54.03 |
| ATOM 480 | OD1 | ASP | 1524 | 3.649 | 20.136 | 11.283 | 1.00 | 56.32 |
| ATOM 481 | OD2 | ASP | 1524 | 4.580 | 18.658 | 9.956 | 1.00 | 56.02 |
| ATOM 482 | C | ASP | 1524 | 0.847 | 16.596 | 9.413 | 1.00 | 47.73 |
| ATOM 483 | O | ASP | 1524 | 1.017 | 15.387 | 9.580 | 1.00 | 45.85 |
| ATOM 484 | N | LEU | 1525 | −0.354 | 17.155 | 9.300 | 1.00 | 47.62 |
| ATOM 486 | CA | LEU | 1525 | −1.585 | 16.380 | 9.354 | 1.00 | 45.95 |
| ATOM 487 | CB | LEU | 1525 | −2.801 | 17.307 | 9.271 | 1.00 | 43.61 |
| ATOM 488 | CG | LEU | 1525 | −4.193 | 16.665 | 9.234 | 1.00 | 44.56 |
| ATOM 489 | CD1 | LEU | 1525 | −4.364 | 15.543 | 10.268 | 1.00 | 46.02 |
| ATOM 490 | CD2 | LEU | 1525 | −5.215 | 17.740 | 9.468 | 1.00 | 43.80 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 491 | C | LEU | 1525 | −1.605 | 15.372 | 8.210 | 1.00 | 45.67 |
| ATOM 492 | O | LEU | 1525 | −1.921 | 14.204 | 8.416 | 1.00 | 46.78 |
| ATOM 493 | N | SER | 1526 | −1.245 | 15.822 | 7.014 | 1.00 | 45.44 |
| ATOM 495 | CA | SER | 1526 | −1.211 | 14.945 | 5.851 | 1.00 | 46.33 |
| ATOM 496 | CB | SER | 1526 | −0.903 | 15.744 | 4.584 | 1.00 | 48.48 |
| ATOM 497 | OG | SER | 1526 | −2.012 | 16.546 | 4.218 | 1.00 | 57.28 |
| ATOM 499 | C | SER | 1526 | −0.192 | 13.821 | 5.995 | 1.00 | 43.84 |
| ATOM 500 | O | SER | 1526 | −0.480 | 12.669 | 5.674 | 1.00 | 45.24 |
| ATOM 501 | N | ASP | 1527 | 0.994 | 14.144 | 6.489 | 1.00 | 40.88 |
| ATOM 503 | CA | ASP | 1527 | 2.024 | 13.128 | 6.646 | 1.00 | 39.70 |
| ATOM 504 | CB | ASP | 1527 | 3.376 | 13.767 | 6.960 | 1.00 | 37.62 |
| ATOM 505 | CG | ASP | 1527 | 3.934 | 14.555 | 5.786 | 1.00 | 37.01 |
| ATOM 506 | OD1 | ASP | 1527 | 3.399 | 14.434 | 4.657 | 1.00 | 35.78 |
| ATOM 507 | OD2 | ASP | 1527 | 4.916 | 15.295 | 5.992 | 1.00 | 40.23 |
| ATOM 508 | C | ASP | 1527 | 1.652 | 12.053 | 7.659 | 1.00 | 38.51 |
| ATOM 509 | O | ASP | 1527 | 1.951 | 10.872 | 7.461 | 1.00 | 37.68 |
| ATOM 510 | N | LEU | 1528 | 0.973 | 12.460 | 8.725 | 1.00 | 38.16 |
| ATOM 512 | CA | LEU | 1528 | 0.532 | 11.513 | 9.744 | 1.00 | 38.29 |
| ATOM 513 | CB | LEU | 1528 | 0.026 | 12.258 | 10.985 | 1.00 | 37.12 |
| ATOM 514 | CG | LEU | 1528 | −0.505 | 11.412 | 12.153 | 1.00 | 39.03 |
| ATOM 515 | CD1 | LEU | 1528 | 0.499 | 10.323 | 12.539 | 1.00 | 35.39 |
| ATOM 516 | CD2 | LEU | 1528 | −0.825 | 12.315 | 13.334 | 1.00 | 35.29 |
| ATOM 517 | C | LEU | 1528 | −0.568 | 10.611 | 9.155 | 1.00 | 38.10 |
| ATOM 518 | O | LEU | 1528 | −0.607 | 9.400 | 9.413 | 1.00 | 37.21 |
| ATOM 519 | N | ILE | 1529 | −1.450 | 11.210 | 8.355 | 1.00 | 36.71 |
| ATOM 521 | CA | ILE | 1529 | −2.531 | 10.472 | 7.718 | 1.00 | 35.93 |
| ATOM 522 | CB | ILE | 1529 | −3.486 | 11.419 | 6.931 | 1.00 | 35.67 |
| ATOM 523 | CG2 | ILE | 1529 | −4.492 | 10.619 | 6.119 | 1.00 | 34.04 |
| ATOM 524 | CG1 | ILE | 1529 | −4.259 | 12.295 | 7.916 | 1.00 | 33.81 |
| ATOM 525 | CD1 | ILE | 1529 | −5.177 | 13.288 | 7.276 | 1.00 | 33.58 |
| ATOM 526 | C | ILE | 1529 | −1.912 | 9.447 | 6.786 | 1.00 | 37.49 |
| ATOM 527 | O | ILE | 1529 | −2.274 | 8.269 | 6.829 | 1.00 | 37.11 |
| ATOM 528 | N | SER | 1530 | −0.926 | 9.893 | 6.003 | 1.00 | 38.20 |
| ATOM 530 | CA | SER | 1530 | −0.217 | 9.036 | 5.050 | 1.00 | 37.49 |
| ATOM 531 | CB | SER | 1530 | 0.911 | 9.822 | 4.370 | 1.00 | 43.32 |
| ATOM 532 | OG | SER | 1530 | 0.424 | 10.970 | 3.687 | 1.00 | 52.31 |
| ATOM 534 | C | SER | 1530 | 0.382 | 7.808 | 5.719 | 1.00 | 34.40 |
| ATOM 535 | O | SER | 1530 | 0.234 | 6.691 | 5.219 | 1.00 | 31.51 |
| ATOM 536 | N | GLU | 1531 | 1.048 | 8.028 | 6.851 | 1.00 | 32.08 |
| ATOM 538 | CA | GLU | 1531 | 1.690 | 6.952 | 7.594 | 1.00 | 30.60 |
| ATOM 539 | CB | GLU | 1531 | 2.506 | 7.515 | 8.759 | 1.00 | 29.70 |
| ATOM 540 | CG | GLU | 1531 | 3.094 | 6.428 | 9.657 | 1.00 | 30.53 |
| ATOM 541 | CD | GLU | 1531 | 3.871 | 6.962 | 10.839 | 1.00 | 33.17 |
| ATOM 542 | OE1 | GLU | 1531 | 4.473 | 6.134 | 11.552 | 1.00 | 33.38 |
| ATOM 543 | OE2 | GLU | 1531 | 3.883 | 8.193 | 11.062 | 1.00 | 37.52 |
| ATOM 544 | C | GLU | 1531 | 0.698 | 5.911 | 8.094 | 1.00 | 30.17 |
| ATOM 545 | O | GLU | 1531 | 0.991 | 4.714 | 8.100 | 1.00 | 29.76 |
| ATOM 546 | N | MET | 1532 | −0.464 | 6.379 | 8.530 | 1.00 | 31.34 |
| ATOM 548 | CA | MET | 1532 | −1.521 | 5.496 | 9.015 | 1.00 | 30.72 |
| ATOM 549 | CB | MET | 1532 | −2.666 | 6.336 | 9.591 | 1.00 | 29.99 |
| ATOM 550 | CG | MET | 1532 | −3.880 | 5.523 | 10.020 | 1.00 | 30.10 |
| ATOM 551 | SD | MET | 1532 | −5.173 | 6.510 | 10.727 | 1.00 | 29.46 |
| ATOM 552 | CE | MET | 1532 | −5.462 | 7.682 | 9.455 | 1.00 | 23.76 |
| ATOM 553 | C | MET | 1532 | −2.025 | 4.638 | 7.843 | 1.00 | 30.47 |
| ATOM 554 | O | MET | 1532 | −2.080 | 3.401 | 7.925 | 1.00 | 27.05 |
| ATOM 555 | N | GLU | 1533 | −2.387 | 5.319 | 6.756 | 1.00 | 30.56 |
| ATOM 557 | CA | GLU | 1533 | −2.863 | 4.674 | 5.542 | 1.00 | 30.56 |
| ATOM 558 | CB | GLU | 1533 | −3.090 | 5.725 | 4.458 | 1.00 | 28.60 |
| ATOM 559 | CG | GLU | 1533 | −4.226 | 6.677 | 4.761 | 1.00 | 29.08 |
| ATOM 560 | CD | GLU | 1533 | −5.531 | 5.954 | 5.014 | 1.00 | 31.28 |
| ATOM 561 | OE1 | GLU | 1533 | −6.006 | 5.230 | 4.117 | 1.00 | 33.09 |
| ATOM 562 | OE2 | GLU | 1533 | −6.086 | 6.104 | 6.121 | 1.00 | 34.97 |
| ATOM 563 | C | GLU | 1533 | −1.861 | 3.638 | 5.064 | 1.00 | 29.86 |
| ATOM 564 | O | GLU | 1533 | −2.232 | 2.541 | 4.677 | 1.00 | 32.28 |
| ATOM 565 | N | MET | 1534 | −0.590 | 4.014 | 5.107 | 1.00 | 32.54 |
| ATOM 567 | CA | MET | 1534 | 0.515 | 3.145 | 4.719 | 1.00 | 33.39 |
| ATOM 568 | CB | MET | 1534 | 1.826 | 3.894 | 4.885 | 1.00 | 34.70 |
| ATOM 569 | CG | MET | 1534 | 3.038 | 3.047 | 4.654 | 1.00 | 44.51 |
| ATOM 570 | SD | MET | 1534 | 3.479 | 3.063 | 2.943 | 1.00 | 52.81 |
| ATOM 571 | CE | MET | 1534 | 4.349 | 4.607 | 2.874 | 1.00 | 47.34 |
| ATOM 572 | C | MET | 1534 | 0.530 | 1.896 | 5.607 | 1.00 | 32.98 |
| ATOM 573 | O | MET | 1534 | 0.689 | 0.776 | 5.115 | 1.00 | 34.00 |
| ATOM 574 | N | MET | 1535 | 0.364 | 2.100 | 6.910 | 1.00 | 31.92 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 576 | CA | MET | 1535 | 0.336 | 0.986 | 7.848 | 1.00 | 30.80 |
| ATOM 577 | CB | MET | 1535 | 0.252 | 1.503 | 9.294 | 1.00 | 33.77 |
| ATOM 578 | CG | MET | 1535 | 1.509 | 2.216 | 9.810 | 1.00 | 32.26 |
| ATOM 579 | SD | MET | 1535 | 1.520 | 2.433 | 11.617 | 1.00 | 34.75 |
| ATOM 580 | CE | MET | 1535 | 1.183 | 4.173 | 11.723 | 1.00 | 37.86 |
| ATOM 581 | C | MET | 1535 | −0.837 | 0.052 | 7.521 | 1.00 | 30.80 |
| ATOM 582 | O | MET | 1535 | −0.704 | −1.175 | 7.589 | 1.00 | 32.03 |
| ATOM 583 | N | LYS | 1536 | −1.974 | 0.638 | 7.142 | 1.00 | 31.04 |
| ATOM 585 | CA | LYS | 1536 | −3.170 | −0.123 | 6.767 | 1.00 | 31.15 |
| ATOM 586 | CB | LYS | 1536 | −4.334 | 0.808 | 6.415 | 1.00 | 31.21 |
| ATOM 587 | CG | LYS | 1536 | −4.864 | 1.625 | 7.552 | 1.00 | 27.76 |
| ATOM 588 | CD | LYS | 1536 | −5.973 | 2.540 | 7.103 | 1.00 | 21.44 |
| ATOM 589 | CE | LYS | 1536 | −6.434 | 3.401 | 8.248 | 1.00 | 24.69 |
| ATOM 590 | NZ | LYS | 1536 | −7.578 | 4.241 | 7.868 | 1.00 | 25.84 |
| ATOM 594 | C | LYS | 1536 | −2.887 | −1.003 | 5.561 | 1.00 | 30.71 |
| ATOM 595 | O | LYS | 1536 | −3.238 | −2.175 | 5.560 | 1.00 | 34.73 |
| ATOM 596 | N | MET | 1537 | −2.309 | −0.412 | 4.523 | 1.00 | 31.18 |
| ATOM 598 | CA | MET | 1537 | −1.967 | −1.148 | 3.307 | 1.00 | 31.53 |
| ATOM 599 | CB | MET | 1537 | −1.370 | −0.200 | 2.267 | 1.00 | 35.11 |
| ATOM 600 | CG | MET | 1537 | −2.377 | 0.780 | 1.654 | 1.00 | 42.40 |
| ATOM 601 | SD | MET | 1537 | −3.657 | −0.051 | 0.685 | 1.00 | 50.10 |
| ATOM 602 | CE | MET | 1537 | −3.069 | 0.266 | −0.972 | 1.00 | 50.20 |
| ATOM 603 | C | MET | 1537 | −0.976 | −2.276 | 3.572 | 1.00 | 30.86 |
| ATOM 604 | O | MET | 1537 | −1.218 | −3.425 | 3.210 | 1.00 | 30.07 |
| ATOM 605 | N | ILE | 1538 | 0.119 | −1.950 | 4.259 | 1.00 | 30.92 |
| ATOM 607 | CA | ILE | 1538 | 1.173 | −2.923 | 4.563 | 1.00 | 28.12 |
| ATOM 608 | CB | ILE | 1538 | 2.359 | −2.254 | 5.313 | 1.00 | 28.71 |
| ATOM 609 | CG2 | ILE | 1538 | 3.310 | −3.303 | 5.865 | 1.00 | 29.72 |
| ATOM 610 | CG1 | ILE | 1538 | 3.126 | −1.343 | 4.350 | 1.00 | 30.79 |
| ATOM 611 | CD1 | ILE | 1538 | 4.375 | −0.745 | 4.945 | 1.00 | 32.46 |
| ATOM 612 | C | ILE | 1538 | 0.717 | −4.179 | 5.299 | 1.00 | 26.33 |
| ATOM 613 | O | ILE | 1538 | 1.178 | −5.276 | 4.996 | 1.00 | 24.20 |
| ATOM 614 | N | GLY | 1539 | −0.188 | −4.027 | 6.258 | 1.00 | 27.41 |
| ATOM 616 | CA | GLY | 1539 | −0.651 | −5.190 | 6.997 | 1.00 | 27.83 |
| ATOM 617 | C | GLY | 1539 | 0.240 | −5.533 | 8.179 | 1.00 | 29.10 |
| ATOM 618 | O | GLY | 1539 | 1.308 | −4.937 | 8.368 | 1.00 | 30.33 |
| ATOM 619 | N | LYS | 1540 | −0.157 | −6.561 | 8.916 | 1.00 | 29.46 |
| ATOM 621 | CA | LYS | 1540 | 0.539 | −6.976 | 10.120 | 1.00 | 29.27 |
| ATOM 622 | CB | LYS | 1540 | −0.470 | −7.520 | 11.139 | 1.00 | 27.01 |
| ATOM 623 | CG | LYS | 1540 | −1.438 | −6.483 | 11.638 | 1.00 | 29.58 |
| ATOM 624 | CD | LYS | 1540 | −2.496 | −7.103 | 12.530 | 1.00 | 39.41 |
| ATOM 625 | CE | LYS | 1540 | −3.548 | −6.069 | 12.952 | 1.00 | 44.14 |
| ATOM 626 | NZ | LYS | 1540 | −2.994 | −4.996 | 13.828 | 1.00 | 46.92 |
| ATOM 630 | C | LYS | 1540 | 1.679 | −7.962 | 10.020 | 1.00 | 27.17 |
| ATOM 631 | O | LYS | 1540 | 1.745 | −8.794 | 9.111 | 1.00 | 26.20 |
| ATOM 632 | N | HIS | 1541 | 2.565 | −7.856 | 11.006 | 1.00 | 26.96 |
| ATOM 634 | CA | HIS | 1541 | 3.690 | −8.761 | 11.144 | 1.00 | 27.30 |
| ATOM 635 | CB | HIS | 1541 | 4.787 | −8.506 | 10.120 | 1.00 | 22.20 |
| ATOM 636 | CG | HIS | 1541 | 5.849 | −9.555 | 10.125 | 1.00 | 21.32 |
| ATOM 637 | CD2 | HIS | 1541 | 5.886 | −10.789 | 9.555 | 1.00 | 23.29 |
| ATOM 638 | ND1 | HIS | 1541 | 7.052 | −9.413 | 10.791 | 1.00 | 19.41 |
| ATOM 640 | CE1 | HIS | 1541 | 7.775 | −10.509 | 10.633 | 1.00 | 23.61 |
| ATOM 641 | NE2 | HIS | 1541 | 7.097 | −11.355 | 9.889 | 1.00 | 21.81 |
| ATOM 643 | C | HIS | 1541 | 4.245 | −8.640 | 12.565 | 1.00 | 28.64 |
| ATOM 644 | O | HIS | 1541 | 4.290 | −7.549 | 13.132 | 1.00 | 30.64 |
| ATOM 645 | N | LYS | 1542 | 4.650 | −9.791 | 13.108 | 1.00 | 29.47 |
| ATOM 647 | CA | LYS | 1542 | 5.200 | −9.893 | 14.457 | 1.00 | 28.78 |
| ATOM 648 | CB | LYS | 1542 | 5.683 | −11.326 | 14.714 | 1.00 | 30.16 |
| ATOM 649 | CG | LYS | 1542 | 6.232 | −11.572 | 16.112 | 1.00 | 32.63 |
| ATOM 650 | CD | LYS | 1542 | 5.277 | −11.046 | 17.155 | 1.00 | 42.90 |
| ATOM 651 | CE | LYS | 1542 | 5.659 | −11.475 | 18.551 | 1.00 | 48.13 |
| ATOM 652 | NZ | LYS | 1542 | 4.726 | −10.930 | 19.564 | 1.00 | 54.87 |
| ATOM 656 | C | LYS | 1542 | 6.351 | −8.928 | 14.705 | 1.00 | 26.54 |
| ATOM 657 | O | LYS | 1542 | 6.440 | −8.321 | 15.773 | 1.00 | 26.19 |
| ATOM 658 | N | ASN | 1543 | 7.193 | −8.733 | 13.697 | 1.00 | 24.36 |
| ATOM 660 | CA | ASN | 1543 | 8.357 | −7.874 | 13.852 | 1.00 | 24.08 |
| ATOM 661 | CB | ASN | 1543 | 9.601 | −8.596 | 13.359 | 1.00 | 22.69 |
| ATOM 662 | CG | ASN | 1543 | 9.781 | −9.950 | 14.029 | 1.00 | 22.81 |
| ATOM 663 | OD1 | ASN | 1543 | 9.664 | −10.996 | 13.388 | 1.00 | 23.62 |
| ATOM 664 | ND2 | ASN | 1543 | 10.028 | −9.938 | 15.324 | 1.00 | 24.94 |
| ATOM 667 | C | ASN | 1543 | 8.318 | −6.429 | 13.377 | 1.00 | 23.48 |
| ATOM 668 | O | ASN | 1543 | 9.351 | −5.861 | 13.059 | 1.00 | 22.94 |
| ATOM 669 | N | ILE | 1544 | 7.130 | −5.821 | 13.380 | 1.00 | 24.15 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 671 | CA | ILE | 1544 | 6.976 | −4.407 | 13.012 | 1.00 | 24.60 |
| ATOM 672 | CB | ILE | 1544 | 6.516 | −4.191 | 11.531 | 1.00 | 24.90 |
| ATOM 673 | CG2 | ILE | 1544 | 7.495 | −4.852 | 10.571 | 1.00 | 21.57 |
| ATOM 674 | CG1 | ILE | 1544 | 5.081 | −4.688 | 11.316 | 1.00 | 26.66 |
| ATOM 675 | CD1 | ILE | 1544 | 4.481 | −4.321 | 9.945 | 1.00 | 23.98 |
| ATOM 676 | C | ILE | 1544 | 5.954 | −3.785 | 13.955 | 1.00 | 24.78 |
| ATOM 677 | O | ILE | 1544 | 5.160 | −4.503 | 14.558 | 1.00 | 27.87 |
| ATOM 678 | N | ILE | 1545 | 6.035 | −2.474 | 14.159 | 1.00 | 26.39 |
| ATOM 680 | CA | ILE | 1545 | 5.089 | −1.779 | 15.025 | 1.00 | 26.79 |
| ATOM 681 | CB | ILE | 1545 | 5.588 | −0.345 | 15.384 | 1.00 | 28.85 |
| ATOM 682 | CG2 | ILE | 1545 | 4.512 | 0.449 | 16.103 | 1.00 | 23.60 |
| ATOM 683 | CG1 | ILE | 1545 | 6.833 | −0.423 | 16.269 | 1.00 | 27.20 |
| ATOM 684 | CD1 | ILE | 1545 | 6.565 | −0.990 | 17.639 | 1.00 | 27.12 |
| ATOM 685 | C | ILE | 1545 | 3.792 | −1.708 | 14.224 | 1.00 | 26.99 |
| ATOM 686 | O | ILE | 1545 | 3.720 | −1.023 | 13.197 | 1.00 | 27.61 |
| ATOM 687 | N | ASN | 1546 | 2.809 | −2.495 | 14.654 | 1.00 | 26.70 |
| ATOM 689 | CA | ASN | 1546 | 1.514 | −2.565 | 13.983 | 1.00 | 26.53 |
| ATOM 690 | CB | ASN | 1546 | 0.871 | −3.953 | 14.169 | 1.00 | 26.23 |
| ATOM 691 | CG | ASN | 1546 | 1.695 | −5.072 | 13.551 | 1.00 | 24.96 |
| ATOM 692 | OD1 | ASN | 1546 | 1.773 | −5.206 | 12.330 | 1.00 | 28.08 |
| ATOM 693 | ND2 | ASN | 1546 | 2.319 | −5.872 | 14.387 | 1.00 | 22.38 |
| ATOM 696 | C | ASN | 1546 | 0.521 | −1.497 | 14.418 | 1.00 | 26.89 |
| ATOM 697 | O | ASN | 1546 | 0.610 | −0.952 | 15.523 | 1.00 | 27.40 |
| ATOM 698 | N | LEU | 1547 | −0.349 | −1.138 | 13.481 | 1.00 | 27.77 |
| ATOM 700 | CA | LEU | 1547 | −1.416 | −0.175 | 13.701 | 1.00 | 28.28 |
| ATOM 701 | CB | LEU | 1547 | −1.958 | 0.313 | 12.361 | 1.00 | 27.04 |
| ATOM 702 | CG | LEU | 1547 | −3.199 | 1.194 | 12.408 | 1.00 | 25.74 |
| ATOM 703 | CD1 | LEU | 1547 | −2.836 | 2.575 | 12.950 | 1.00 | 27.66 |
| ATOM 704 | CD2 | LEU | 1547 | −3.799 | 1.289 | 11.014 | 1.00 | 23.38 |
| ATOM 705 | C | LEU | 1547 | −2.498 | −0.972 | 14.435 | 1.00 | 29.80 |
| ATOM 706 | O | LEU | 1547 | −2.766 | −2.135 | 14.105 | 1.00 | 28.63 |
| ATOM 707 | N | LEU | 1548 | −3.088 | −0.351 | 15.448 | 1.00 | 29.91 |
| ATOM 709 | CA | LEU | 1548 | −4.114 | −0.997 | 16.256 | 1.00 | 28.46 |
| ATOM 710 | CB | LEU | 1548 | −3.735 | −0.956 | 17.749 | 1.00 | 26.76 |
| ATOM 711 | CG | LEU | 1548 | −2.460 | −1.701 | 18.162 | 1.00 | 22.44 |
| ATOM 712 | CD1 | LEU | 1548 | −2.277 | −1.554 | 19.653 | 1.00 | 21.91 |
| ATOM 713 | CD2 | LEU | 1548 | −2.551 | −3.179 | 17.778 | 1.00 | 20.79 |
| ATOM 714 | C | LEU | 1548 | −5.480 | −0.365 | 16.058 | 1.00 | 27.31 |
| ATOM 715 | O | LEU | 1548 | −6.489 | −1.043 | 16.193 | 1.00 | 28.25 |
| ATOM 716 | N | GLY | 1549 | −5.506 | 0.925 | 15.732 | 1.00 | 24.02 |
| ATOM 718 | CA | GLY | 1549 | −6.774 | 1.598 | 15.553 | 1.00 | 24.57 |
| ATOM 719 | C | GLY | 1549 | −6.548 | 3.077 | 15.395 | 1.00 | 25.19 |
| ATOM 720 | O | GLY | 1549 | −5.400 | 3.488 | 15.231 | 1.00 | 28.77 |
| ATOM 721 | N | ALA | 1550 | −7.617 | 3.875 | 15.427 | 1.00 | 24.66 |
| ATOM 723 | CA | ALA | 1550 | −7.487 | 5.319 | 15.282 | 1.00 | 24.17 |
| ATOM 724 | CB | ALA | 1550 | −7.206 | 5.680 | 13.824 | 1.00 | 24.29 |
| ATOM 725 | C | ALA | 1550 | −8.695 | 6.103 | 15.765 | 1.00 | 23.95 |
| ATOM 726 | O | ALA | 1550 | −9.810 | 5.590 | 15.780 | 1.00 | 24.95 |
| ATOM 727 | N | CYS | 1551 | −8.444 | 7.336 | 16.199 | 1.00 | 25.03 |
| ATOM 729 | CA | CYS | 1551 | −9.482 | 8.270 | 16.639 | 1.00 | 28.21 |
| ATOM 730 | CB | CYS | 1551 | −9.221 | 8.774 | 18.055 | 1.00 | 26.76 |
| ATOM 731 | SG | CYS | 1551 | −9.378 | 7.521 | 19.317 | 1.00 | 34.39 |
| ATOM 732 | C | CYS | 1551 | −9.359 | 9.426 | 15.656 | 1.00 | 29.98 |
| ATOM 733 | O | CYS | 1551 | −8.482 | 10.281 | 15.800 | 1.00 | 32.14 |
| ATOM 734 | N | THR | 1552 | −10.198 | 9.412 | 14.625 | 1.00 | 31.09 |
| ATOM 736 | CA | THR | 1552 | −10.135 | 10.435 | 13.595 | 1.00 | 32.91 |
| ATOM 737 | CB | THR | 1552 | −10.052 | 9.781 | 12.189 | 1.00 | 32.60 |
| ATOM 738 | OG1 | THR | 1552 | −11.276 | 9.097 | 11.890 | 1.00 | 32.12 |
| ATOM 740 | CG2 | THR | 1552 | −8.928 | 8.768 | 12.144 | 1.00 | 32.74 |
| ATOM 741 | C | THR | 1552 | −11.282 | 11.419 | 13.591 | 1.00 | 35.26 |
| ATOM 742 | O | THR | 1552 | −11.171 | 12.525 | 13.057 | 1.00 | 35.10 |
| ATOM 743 | N | GLN | 1553 | −12.397 | 11.014 | 14.179 | 1.00 | 39.01 |
| ATOM 745 | CA | GLN | 1553 | −13.585 | 11.846 | 14.180 | 1.00 | 41.97 |
| ATOM 746 | CB | GLN | 1553 | −14.832 | 10.968 | 14.020 | 1.00 | 41.17 |
| ATOM 747 | CG | GLN | 1553 | −14.915 | 10.238 | 12.672 | 1.00 | 39.06 |
| ATOM 748 | CD | GLN | 1553 | −14.900 | 11.200 | 11.496 | 1.00 | 41.84 |
| ATOM 749 | OE1 | GLN | 1553 | −15.785 | 12.045 | 11.359 | 1.00 | 41.92 |
| ATOM 750 | NE2 | GLN | 1553 | −13.876 | 11.090 | 10.652 | 1.00 | 42.33 |
| ATOM 753 | C | GLN | 1553 | −13.727 | 12.777 | 15.372 | 1.00 | 45.35 |
| ATOM 754 | O | GLN | 1553 | −13.358 | 12.423 | 16.489 | 1.00 | 47.02 |
| ATOM 755 | N | ASP | 1554 | −14.225 | 13.981 | 15.090 | 1.00 | 48.60 |
| ATOM 757 | CA | ASP | 1554 | −14.479 | 15.016 | 16.084 | 1.00 | 50.64 |
| ATOM 758 | CB | ASP | 1554 | −15.832 | 14.766 | 16.758 | 1.00 | 54.52 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 759 | CG | ASP | 1554 | −17.003 | 14.955 | 15.809 | 1.00 | 60.54 |
| ATOM 760 | OD1 | ASP | 1554 | −18.072 | 15.409 | 16.274 | 1.00 | 66.04 |
| ATOM 761 | OD2 | ASP | 1554 | −16.860 | 14.661 | 14.601 | 1.00 | 65.09 |
| ATOM 762 | C | ASP | 1554 | −13.395 | 15.173 | 17.133 | 1.00 | 49.89 |
| ATOM 763 | O | ASP | 1554 | −13.611 | 14.879 | 18.310 | 1.00 | 51.48 |
| ATOM 764 | N | GLY | 1555 | −12.232 | 15.643 | 16.699 | 1.00 | 48.40 |
| ATOM 766 | CA | GLY | 1555 | −11.131 | 15.834 | 17.617 | 1.00 | 46.16 |
| ATOM 767 | C | GLY | 1555 | −9.798 | 15.626 | 16.935 | 1.00 | 44.64 |
| ATOM 768 | O | GLY | 1555 | −9.737 | 15.581 | 15.716 | 1.00 | 45.22 |
| ATOM 769 | N | PRO | 1556 | −8.708 | 15.525 | 17.702 | 1.00 | 44.68 |
| ATOM 770 | CD | PRO | 1556 | −8.672 | 15.683 | 19.164 | 1.00 | 45.39 |
| ATOM 771 | CA | PRO | 1556 | −7.359 | 15.326 | 17.177 | 1.00 | 42.95 |
| ATOM 772 | CB | PRO | 1556 | −6.484 | 15.549 | 18.411 | 1.00 | 43.74 |
| ATOM 773 | CG | PRO | 1556 | −7.354 | 16.347 | 19.345 | 1.00 | 47.32 |
| ATOM 774 | C | PRO | 1556 | −7.164 | 13.912 | 16.665 | 1.00 | 42.34 |
| ATOM 775 | O | PRO | 1556 | −7.636 | 12.953 | 17.287 | 1.00 | 42.75 |
| ATOM 776 | N | LEU | 1557 | −6.451 | 13.788 | 15.547 | 1.00 | 39.83 |
| ATOM 778 | CA | LEU | 1557 | −6.169 | 12.490 | 14.954 | 1.00 | 36.64 |
| ATOM 779 | CB | LEU | 1557 | −5.496 | 12.669 | 13.587 | 1.00 | 34.49 |
| ATOM 780 | CG | LEU | 1557 | −5.009 | 11.404 | 12.870 | 1.00 | 31.29 |
| ATOM 781 | CD1 | LEU | 1557 | −6.169 | 10.436 | 12.628 | 1.00 | 27.86 |
| ATOM 782 | CD2 | LEU | 1557 | −4.314 | 11.775 | 11.570 | 1.00 | 25.40 |
| ATOM 783 | C | LEU | 1557 | −5.244 | 11.732 | 15.894 | 1.00 | 35.44 |
| ATOM 784 | O | LEU | 1557 | −4.210 | 12.264 | 16.316 | 1.00 | 36.12 |
| ATOM 785 | N | TYR | 1558 | −5.664 | 10.539 | 16.292 | 1.00 | 32.49 |
| ATOM 787 | CA | TYR | 1558 | −4.861 | 9.697 | 17.157 | 1.00 | 31.87 |
| ATOM 788 | CB | TYR | 1558 | −5.590 | 9.348 | 18.470 | 1.00 | 33.93 |
| ATOM 789 | CG | TYR | 1558 | −5.695 | 10.476 | 19.471 | 1.00 | 35.34 |
| ATOM 790 | CD1 | TYR | 1558 | −6.566 | 10.394 | 20.565 | 1.00 | 37.12 |
| ATOM 791 | CE1 | TYR | 1558 | −6.683 | 11.456 | 21.479 | 1.00 | 36.44 |
| ATOM 792 | CD2 | TYR | 1558 | −4.945 | 11.636 | 19.317 | 1.00 | 37.27 |
| ATOM 793 | CE2 | TYR | 1558 | −5.054 | 12.690 | 20.213 | 1.00 | 39.62 |
| ATOM 794 | CZ | TYR | 1558 | −5.921 | 12.598 | 21.289 | 1.00 | 40.05 |
| ATOM 795 | OH | TYR | 1558 | −6.008 | 13.668 | 22.155 | 1.00 | 44.98 |
| ATOM 797 | C | TYR | 1558 | −4.600 | 8.419 | 16.387 | 1.00 | 31.58 |
| ATOM 798 | O | TYR | 1558 | −5.532 | 7.750 | 15.936 | 1.00 | 30.22 |
| ATOM 799 | N | VAL | 1559 | −3.331 | 8.129 | 16.153 | 1.00 | 33.43 |
| ATOM 801 | CA | VAL | 1559 | −2.947 | 6.907 | 15.463 | 1.00 | 31.42 |
| ATOM 802 | CB | VAL | 1559 | −1.849 | 7.160 | 14.419 | 1.00 | 32.31 |
| ATOM 803 | CG1 | VAL | 1559 | −1.516 | 5.851 | 13.675 | 1.00 | 26.79 |
| ATOM 804 | CG2 | VAL | 1559 | −2.308 | 8.265 | 13.453 | 1.00 | 30.63 |
| ATOM 805 | C | VAL | 1559 | −2.438 | 5.979 | 16.556 | 1.00 | 28.67 |
| ATOM 806 | O | VAL | 1559 | −1.393 | 6.223 | 17.155 | 1.00 | 30.08 |
| ATOM 807 | N | ILE | 1560 | −3.230 | 4.960 | 16.852 | 1.00 | 25.80 |
| ATOM 809 | CA | ILE | 1560 | −2.915 | 3.998 | 17.894 | 1.00 | 25.33 |
| ATOM 810 | CB | ILE | 1560 | −4.219 | 3.443 | 18.506 | 1.00 | 22.34 |
| ATOM 811 | CG2 | ILE | 1560 | −3.931 | 2.695 | 19.784 | 1.00 | 20.36 |
| ATOM 812 | CG1 | ILE | 1560 | −5.172 | 4.603 | 18.809 | 1.00 | 21.34 |
| ATOM 813 | CD1 | ILE | 1560 | −6.583 | 4.190 | 19.093 | 1.00 | 20.68 |
| ATOM 814 | C | ILE | 1560 | −2.073 | 2.857 | 17.341 | 1.00 | 27.16 |
| ATOM 815 | O | ILE | 1560 | −2.520 | 2.116 | 16.455 | 1.00 | 29.67 |
| ATOM 816 | N | VAL | 1561 | −0.858 | 2.714 | 17.860 | 1.00 | 27.69 |
| ATOM 818 | CA | VAL | 1561 | 0.060 | 1.667 | 17.411 | 1.00 | 28.27 |
| ATOM 819 | CB | VAL | 1561 | 1.311 | 2.269 | 16.696 | 1.00 | 27.34 |
| ATOM 820 | CG1 | VAL | 1561 | 0.892 | 3.019 | 15.445 | 1.00 | 21.76 |
| ATOM 821 | CG2 | VAL | 1561 | 2.074 | 3.201 | 17.639 | 1.00 | 26.00 |
| ATOM 822 | C | VAL | 1561 | 0.509 | 0.809 | 18.588 | 1.00 | 28.70 |
| ATOM 823 | O | VAL | 1561 | 0.221 | 1.139 | 19.746 | 1.00 | 30.52 |
| ATOM 824 | N | GLU | 1562 | 1.166 | −0.311 | 18.286 | 1.00 | 28.64 |
| ATOM 826 | CA | GLU | 1562 | 1.658 | −1.220 | 19.318 | 1.00 | 27.77 |
| ATOM 827 | CB | GLU | 1562 | 2.278 | −2.465 | 18.693 | 1.00 | 24.57 |
| ATOM 828 | CG | GLU | 1562 | 1.251 | −3.452 | 18.208 | 1.00 | 24.76 |
| ATOM 829 | CD | GLU | 1562 | 1.864 | −4.641 | 17.501 | 1.00 | 27.27 |
| ATOM 830 | OE1 | GLU | 1562 | 1.272 | −5.739 | 17.580 | 1.00 | 28.27 |
| ATOM 831 | OE2 | GLU | 1562 | 2.920 | −4.487 | 16.849 | 1.00 | 29.25 |
| ATOM 832 | C | GLU | 1562 | 2.674 | −0.538 | 20.217 | 1.00 | 28.79 |
| ATOM 833 | O | GLU | 1562 | 3.453 | 0.292 | 19.760 | 1.00 | 29.38 |
| ATOM 834 | N | TYR | 1563 | 2.627 | −0.871 | 21.503 | 1.00 | 30.84 |
| ATOM 836 | CA | TYR | 1563 | 3.534 | −0.304 | 22.493 | 1.00 | 31.43 |
| ATOM 837 | CB | TYR | 1563 | 2.782 | −0.088 | 23.799 | 1.00 | 32.10 |
| ATOM 838 | CG | TYR | 1563 | 3.632 | 0.376 | 24.952 | 1.00 | 33.93 |
| ATOM 839 | CD1 | TYR | 1563 | 4.366 | 1.552 | 24.873 | 1.00 | 34.85 |
| ATOM 840 | CE1 | TYR | 1563 | 5.140 | 1.992 | 25.947 | 1.00 | 37.53 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 841 | CD2 | TYR | 1563 | 3.683 | −0.356 | 26.136 | 1.00 | 34.81 |
| ATOM 842 | CE2 | TYR | 1563 | 4.452 | 0.072 | 27.211 | 1.00 | 34.01 |
| ATOM 843 | CZ | TYR | 1563 | 5.173 | 1.245 | 27.113 | 1.00 | 35.79 |
| ATOM 844 | OH | TYR | 1563 | 5.920 | 1.677 | 28.184 | 1.00 | 39.10 |
| ATOM 846 | C | TYR | 1563 | 4.767 | −1.166 | 22.731 | 1.00 | 31.38 |
| ATOM 847 | O | TYR | 1563 | 4.672 | −2.385 | 22.905 | 1.00 | 30.73 |
| ATOM 848 | N | ALA | 1564 | 5.930 | −0.525 | 22.725 | 1.00 | 32.23 |
| ATOM 850 | CA | ALA | 1564 | 7.198 | −1.212 | 22.953 | 1.00 | 35.90 |
| ATOM 851 | CB | ALA | 1564 | 8.178 | −0.866 | 21.833 | 1.00 | 36.44 |
| ATOM 852 | C | ALA | 1564 | 7.711 | −0.719 | 24.307 | 1.00 | 36.52 |
| ATOM 853 | O | ALA | 1564 | 8.332 | 0.349 | 24.403 | 1.00 | 39.16 |
| ATOM 854 | N | SER | 1565 | 7.424 | −1.482 | 25.359 | 1.00 | 34.62 |
| ATOM 856 | CA | SER | 1565 | 7.801 | −1.071 | 26.700 | 1.00 | 34.91 |
| ATOM 857 | CB | SER | 1565 | 7.124 | −1.945 | 27.750 | 1.00 | 32.11 |
| ATOM 858 | OG | SER | 1565 | 7.606 | −3.271 | 27.696 | 1.00 | 32.92 |
| ATOM 860 | C | SER | 1565 | 9.288 | −0.968 | 26.996 | 1.00 | 35.56 |
| ATOM 861 | O | SER | 1565 | 9.674 | −0.219 | 27.886 | 1.00 | 38.69 |
| ATOM 862 | N | LYS | 1566 | 10.127 | −1.673 | 26.243 | 1.00 | 33.70 |
| ATOM 864 | CA | LYS | 1566 | 11.557 | −1.625 | 26.526 | 1.00 | 31.40 |
| ATOM 865 | CB | LYS | 1566 | 12.137 | −3.033 | 26.530 | 1.00 | 30.56 |
| ATOM 866 | CG | LYS | 1566 | 11.555 | −3.869 | 27.664 | 1.00 | 32.32 |
| ATOM 867 | CD | LYS | 1566 | 11.997 | −5.308 | 27.599 | 1.00 | 36.47 |
| ATOM 868 | CE | LYS | 1566 | 11.632 | −6.031 | 28.872 | 1.00 | 36.97 |
| ATOM 869 | NZ | LYS | 1566 | 12.104 | −7.436 | 28.804 | 1.00 | 41.62 |
| ATOM 873 | C | LYS | 1566 | 12.380 | −0.664 | 25.683 | 1.00 | 32.18 |
| ATOM 874 | O | LYS | 1566 | 13.616 | −0.691 | 25.715 | 1.00 | 32.57 |
| ATOM 875 | N | GLY | 1567 | 11.686 | 0.223 | 24.973 | 1.00 | 33.39 |
| ATOM 877 | CA | GLY | 1567 | 12.345 | 1.224 | 24.156 | 1.00 | 32.13 |
| ATOM 878 | C | GLY | 1567 | 13.074 | 0.719 | 22.928 | 1.00 | 31.70 |
| ATOM 879 | O | GLY | 1567 | 12.912 | −0.430 | 22.530 | 1.00 | 33.30 |
| ATOM 880 | N | ASN | 1568 | 13.883 | 1.589 | 22.331 | 1.00 | 31.08 |
| ATOM 882 | CA | ASN | 1568 | 14.632 | 1.230 | 21.139 | 1.00 | 31.00 |
| ATOM 883 | CB | ASN | 1568 | 15.066 | 2.478 | 20.365 | 1.00 | 31.30 |
| ATOM 884 | CG | ASN | 1568 | 16.127 | 3.271 | 21.074 | 1.00 | 30.47 |
| ATOM 885 | OD1 | ASN | 1568 | 17.130 | 2.733 | 21.508 | 1.00 | 32.19 |
| ATOM 886 | ND2 | ASN | 1568 | 15.934 | 4.580 | 21.144 | 1.00 | 32.13 |
| ATOM 889 | C | ASN | 1568 | 15.802 | 0.295 | 21.393 | 1.00 | 30.62 |
| ATOM 890 | O | ASN | 1568 | 16.357 | 0.256 | 22.483 | 1.00 | 32.91 |
| ATOM 891 | N | LEU | 1569 | 16.193 | −0.428 | 20.354 | 1.00 | 30.92 |
| ATOM 893 | CA | LEU | 1569 | 17.269 | −1.403 | 20.417 | 1.00 | 31.22 |
| ATOM 894 | CB | LEU | 1569 | 17.418 | −2.083 | 19.054 | 1.00 | 29.57 |
| ATOM 895 | CG | LEU | 1569 | 18.415 | −3.231 | 18.893 | 1.00 | 29.22 |
| ATOM 896 | CD1 | LEU | 1569 | 18.284 | −4.261 | 20.024 | 1.00 | 21.30 |
| ATOM 897 | CD2 | LEU | 1569 | 18.184 | −3.863 | 17.523 | 1.00 | 24.99 |
| ATOM 898 | C | LEU | 1569 | 18.609 | −0.838 | 20.878 | 1.00 | 32.44 |
| ATOM 899 | O | LEU | 1569 | 19.328 | −1.499 | 21.618 | 1.00 | 33.12 |
| ATOM 900 | N | ARG | 1570 | 18.954 | 0.370 | 20.432 | 1.00 | 33.24 |
| ATOM 902 | CA | ARG | 1570 | 20.218 | 0.983 | 20.834 | 1.00 | 33.01 |
| ATOM 903 | CB | ARG | 1570 | 20.348 | 2.394 | 20.256 | 1.00 | 32.36 |
| ATOM 904 | CG | ARG | 1570 | 21.586 | 3.129 | 20.758 | 1.00 | 38.28 |
| ATOM 905 | CD | ARG | 1570 | 21.672 | 4.538 | 20.221 | 1.00 | 41.93 |
| ATOM 906 | NE | ARG | 1570 | 20.428 | 5.278 | 20.412 | 1.00 | 49.82 |
| ATOM 908 | CZ | ARG | 1570 | 19.975 | 5.721 | 21.584 | 1.00 | 52.37 |
| ATOM 909 | NH1 | ARG | 1570 | 20.659 | 5.510 | 22.712 | 1.00 | 51.61 |
| ATOM 912 | NH2 | ARG | 1570 | 18.824 | 6.377 | 21.622 | 1.00 | 53.28 |
| ATOM 915 | C | ARG | 1570 | 20.308 | 1.023 | 22.371 | 1.00 | 33.90 |
| ATOM 916 | O | ARG | 1570 | 21.184 | 0.391 | 22.970 | 1.00 | 33.17 |
| ATOM 917 | N | GLU | 1571 | 19.359 | 1.730 | 22.981 | 1.00 | 33.45 |
| ATOM 919 | CA | GLU | 1571 | 19.284 | 1.861 | 24.432 | 1.00 | 34.87 |
| ATOM 920 | CB | GLU | 1571 | 18.052 | 2.688 | 24.794 | 1.00 | 35.83 |
| ATOM 921 | CG | GLU | 1571 | 18.158 | 4.145 | 24.354 | 1.00 | 41.61 |
| ATOM 922 | CD | GLU | 1571 | 16.814 | 4.870 | 24.318 | 1.00 | 47.33 |
| ATOM 923 | OE1 | GLU | 1571 | 15.759 | 4.199 | 24.362 | 1.00 | 50.68 |
| ATOM 924 | OE2 | GLU | 1571 | 16.812 | 6.120 | 24.218 | 1.00 | 48.07 |
| ATOM 925 | C | GLU | 1571 | 19.223 | 0.487 | 25.098 | 1.00 | 34.39 |
| ATOM 926 | O | GLU | 1571 | 19.968 | 0.202 | 26.041 | 1.00 | 34.04 |
| ATOM 927 | N | TYR | 1572 | 18.363 | −0.376 | 24.572 | 1.00 | 33.49 |
| ATOM 929 | CA | TYR | 1572 | 18.204 | −1.728 | 25.083 | 1.00 | 30.45 |
| ATOM 930 | CB | TYR | 1572 | 17.210 | −2.495 | 24.202 | 1.00 | 28.13 |
| ATOM 931 | CG | TYR | 1572 | 17.074 | −3.971 | 24.487 | 1.00 | 25.80 |
| ATOM 932 | CD1 | TYR | 1572 | 16.105 | −4.443 | 25.371 | 1.00 | 28.92 |
| ATOM 933 | CE1 | TYR | 1572 | 15.954 | −5.804 | 25.618 | 1.00 | 30.03 |
| ATOM 934 | CD2 | TYR | 1572 | 17.899 | −4.899 | 23.863 | 1.00 | 24.61 |

TABLE 4-continued

Atomic Structure Coordinates of Unphosphorylated FLGK:AMP-PCP Co-Complex

| Atom No. | Atom Type | A.A. Type | A.A. No. | X | Y | Z | OCC | B |
|---|---|---|---|---|---|---|---|---|
| ATOM 935 | CE2 | TYR | 1572 | 17.760 | −6.260 | 24.102 | 1.00 | 26.05 |
| ATOM 936 | CZ | TYR | 1572 | 16.790 | −6.705 | 24.982 | 1.00 | 29.23 |
| ATOM 937 | OH | TYR | 1572 | 16.651 | −8.052 | 25.227 | 1.00 | 33.74 |
| ATOM 939 | C | TYR | 1572 | 19.549 | −2.447 | 25.113 | 1.00 | 31.30 |
| ATOM 940 | O | TYR | 1572 | 19.880 | −3.126 | 26.090 | 1.00 | 32.43 |
| ATOM 941 | N | LEU | 1573 | 20.334 | −2.266 | 24.058 | 1.00 | 29.68 |
| ATOM 943 | CA | LEU | 1573 | 21.625 | −2.923 | 23.972 | 1.00 | 30.04 |
| ATOM 944 | CB | LEU | 1573 | 22.145 | −2.909 | 22.529 | 1.00 | 26.13 |
| ATOM 945 | CG | LEU | 1573 | 21.532 | −3.870 | 21.490 | 1.00 | 25.24 |
| ATOM 946 | CD1 | LEU | 1573 | 22.097 | −3.563 | 20.113 | 1.00 | 19.70 |
| ATOM 947 | CD2 | LEU | 1573 | 21.807 | −5.317 | 21.839 | 1.00 | 22.05 |
| ATOM 948 | C | LEU | 1573 | 22.645 | −2.308 | 24.927 | 1.00 | 34.47 |
| ATOM 949 | O | LEU | 1573 | 23.354 | −3.031 | 25.644 | 1.00 | 34.95 |
| ATOM 950 | N | GLN | 1574 | 22.691 | −0.980 | 24.978 | 1.00 | 35.47 |
| ATOM 952 | CA | GLN | 1574 | 23.639 | −0.293 | 25.850 | 1.00 | 37.09 |
| ATOM 953 | CB | GLN | 1574 | 23.601 | 1.206 | 25.579 | 1.00 | 36.70 |
| ATOM 954 | CG | GLN | 1574 | 24.033 | 1.559 | 24.171 | 1.00 | 39.77 |
| ATOM 955 | CD | GLN | 1574 | 23.960 | 3.045 | 23.884 | 1.00 | 41.51 |
| ATOM 956 | OE1 | GLN | 1574 | 23.592 | 3.837 | 24.751 | 1.00 | 42.57 |
| ATOM 957 | NE2 | GLN | 1574 | 24.288 | 3.431 | 22.652 | 1.00 | 41.34 |
| ATOM 960 | C | GLN | 1574 | 23.400 | −0.588 | 27.332 | 1.00 | 37.85 |
| ATOM 961 | O | GLN | 1574 | 24.343 | −0.801 | 28.090 | 1.00 | 38.87 |
| ATOM 962 | N | ALA | 1575 | 22.131 | −0.667 | 27.720 | 1.00 | 39.01 |
| ATOM 964 | CA | ALA | 1575 | 21.740 | −0.944 | 29.098 | 1.00 | 37.00 |
| ATOM 965 | CB | ALA | 1575 | 20.261 | −0.678 | 29.273 | 1.00 | 35.71 |
| ATOM 966 | C | ALA | 1575 | 22.061 | −2.359 | 29.559 | 1.00 | 39.14 |
| ATOM 967 | O | ALA | 1575 | 21.839 | −2.692 | 30.719 | 1.00 | 43.81 |
| ATOM 968 | N | ARG | 1576 | 22.563 | −3.201 | 28.665 | 1.00 | 38.39 |
| ATOM 970 | CA | ARG | 1576 | 22.897 | −4.568 | 29.032 | 1.00 | 37.71 |
| ATOM 971 | CB | ARG | 1576 | 21.994 | −5.544 | 28.290 | 1.00 | 38.26 |
| ATOM 972 | CG | ARG | 1576 | 20.555 | −5.383 | 28.700 | 1.00 | 38.00 |
| ATOM 973 | CD | ARG | 1576 | 19.653 | −6.282 | 27.920 | 1.00 | 34.74 |
| ATOM 974 | NE | ARG | 1576 | 18.279 | −6.190 | 28.388 | 1.00 | 32.88 |
| ATOM 976 | CZ | ARG | 1576 | 17.572 | −5.066 | 28.442 | 1.00 | 34.02 |
| ATOM 977 | NH1 | ARG | 1576 | 18.114 | −3.913 | 28.068 | 1.00 | 35.57 |
| ATOM 980 | NH2 | ARG | 1576 | 16.298 | −5.102 | 28.800 | 1.00 | 36.71 |
| ATOM 983 | C | ARG | 1576 | 24.365 | −4.927 | 28.828 | 1.00 | 39.59 |
| ATOM 984 | O | ARG | 1576 | 24.735 | −6.113 | 28.788 | 1.00 | 39.83 |
| ATOM 985 | N | ARG | 1577 | 25.200 | −3.900 | 28.687 | 1.00 | 38.82 |
| ATOM 987 | CA | ARG | 1577 | 26.631 | −4.101 | 28.520 | 1.00 | 39.07 |
| ATOM 988 | CB | ARG | 1577 | 27.310 | −2.797 | 28.090 | 1.00 | 34.91 |
| ATOM 989 | CG | ARG | 1577 | 27.033 | −2.323 | 26.681 | 1.00 | 33.87 |
| ATOM 990 | CD | ARG | 1577 | 27.730 | −0.981 | 26.428 | 1.00 | 33.06 |
| ATOM 991 | NE | ARG | 1577 | 27.722 | −0.612 | 25.015 | 1.00 | 38.87 |
| ATOM 993 | CZ | ARG | 1577 | 28.174 | 0.538 | 24.517 | 1.00 | 39.76 |
| ATOM 994 | NH1 | ARG | 1577 | 28.683 | 1.470 | 25.305 | 1.00 | 40.68 |
| ATOM 997 | NH2 | ARG | 1577 | 28.122 | 0.758 | 23.213 | 1.00 | 43.26 |
| ATOM 1000 | C | ARG | 1577 | 27.181 | −4.501 | 29.885 | 1.00 | 41.58 |
| ATOM 1001 | O | ARG | 1577 | 26.586 | −4.181 | 30.917 | 1.00 | 42.48 |
| ATOM 1002 | N | PRO | 1578 | 28.294 | −5.249 | 29.919 | 1.00 | 43.07 |
| ATOM 1003 | CD | PRO | 1578 | 29.110 | −5.812 | 28.823 | 1.00 | 43.36 |
| ATOM 1004 | CA | PRO | 1578 | 28.839 | −5.626 | 31.223 | 1.00 | 42.69 |
| ATOM 1005 | CB | PRO | 1578 | 29.966 | −6.595 | 30.857 | 1.00 | 42.22 |
| ATOM 1006 | CG | PRO | 1578 | 30.412 | −6.103 | 29.516 | 1.00 | 43.64 |
| ATOM 1007 | C | PRO | 1578 | 29.366 | −4.350 | 31.882 | 1.00 | 43.37 |
| ATOM 1008 | O | PRO | 1578 | 29.530 | −3.319 | 31.215 | 1.00 | 42.50 |
| ATOM 1009 | N | PRO | 1579 | 29.596 | −4.380 | 33.198 | 1.00 | 45.24 |
| ATOM 1010 | CD | PRO | 1579 | 29.279 | −5.435 | 34.174 | 1.00 | 44.69 |
| ATOM 1011 | CA | PRO | 1579 | 30.099 | −3.187 | 33.882 | 1.00 | 46.27 |
| ATOM 1012 | CB | PRO | 1579 | 29.979 | −3.567 | 35.353 | 1.00 | 45.78 |
| ATOM 1013 | CG | PRO | 1579 | 28.894 | −4.615 | 35.361 | 1.00 | 46.15 |
| ATOM 1014 | C | PRO | 1579 | 31.548 | −2.869 | 33.500 | 1.00 | 48.38 |
| ATOM 1015 | O | PRO | 1579 | 32.410 | −3.753 | 33.478 | 1.00 | 50.64 |
| ATOM 1016 | N | GLU | 1592 | 19.022 | −5.398 | 32.495 | 1.00 | 65.98 |
| ATOM 1018 | CA | GLU | 1592 | 20.442 | −5.048 | 32.492 | 1.00 | 64.80 |
| ATOM 1019 | CB | GLU | 1592 | 20.796 | −4.241 | 33.740 | 1.00 | 67.30 |
| ATOM 1020 | C | GLU | 1592 | 21.351 | −6.275 | 32.371 | 1.00 | 63.80 |
| ATOM 1021 | O | GLU | 1592 | 22.545 | −6.149 | 32.089 | 1.00 | 65.21 |
| ATOM 1022 | N | GLU | 1593 | 20.789 | −7.458 | 32.607 | 1.00 | 61.44 |
| ATOM 1024 | CA | GLU | 1593 | 21.560 | −8.691 | 32.495 | 1.00 | 60.82 |
| ATOM 1025 | CB | GLU | 1593 | 20.681 | −9.899 | 32.807 | 1.00 | 61.47 |
| ATOM 1026 | C | GLU | 1593 | 22.144 | −8.803 | 31.089 | 1.00 | 59.12 |
| ATOM 1027 | O | GLU | 1593 | 21.468 | −8.525 | 30.097 | 1.00 | 59.49 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B | |
|---|---|---|---|---|---|---|---|---|---|
| ATOM 1028 | N | GLN | 1594 | 23.408 | −9.201 | 31.017 | 1.00 | 57.33 | |
| ATOM 1030 | CA | GLN | 1594 | 24.103 | −9.334 | 29.744 | 1.00 | 55.30 | |
| ATOM 1031 | CB | GLN | 1594 | 25.523 | −9.880 | 29.957 | 1.00 | 54.87 | |
| ATOM 1032 | CG | GLN | 1594 | 26.438 | −8.959 | 30.757 | 1.00 | 53.34 | |
| ATOM 1033 | CD | GLN | 1594 | 27.704 | −9.660 | 31.248 | 1.00 | 55.27 | |
| ATOM 1034 | OE1 | GLN | 1594 | 28.256 | −10.536 | 30.572 | 1.00 | 56.47 | |
| ATOM 1035 | NE2 | GLN | 1594 | 28.166 | −9.275 | 32.434 | 1.00 | 51.46 | |
| ATOM 1038 | C | GLN | 1594 | 23.336 | −10.229 | 28.781 | 1.00 | 52.29 | |
| ATOM 1039 | O | GLN | 1594 | 22.648 | −11.166 | 29.190 | 1.00 | 52.56 | |
| ATOM 1040 | N | LEU | 1595 | 23.447 | −9.913 | 27.499 | 1.00 | 49.40 | |
| ATOM 1042 | CA | LEU | 1595 | 22.783 | −10.676 | 26.455 | 1.00 | 46.00 | |
| ATOM 1043 | CB | LEU | 1595 | 22.452 | −9.760 | 25.274 | 1.00 | 42.94 | |
| ATOM 1044 | CG | LEU | 1595 | 21.390 | −8.711 | 25.626 | 1.00 | 43.90 | |
| ATOM 1045 | CD1 | LEU | 1595 | 21.495 | −7.484 | 24.743 | 1.00 | 39.46 | |
| ATOM 1046 | CD2 | LEU | 1595 | 20.005 | −9.347 | 25.569 | 1.00 | 41.86 | |
| ATOM 1047 | C | LEU | 1595 | 23.741 | −11.762 | 26.029 | 1.00 | 43.96 | |
| ATOM 1048 | O | LEU | 1595 | 24.950 | −11.550 | 26.043 | 1.00 | 44.24 | |
| ATOM 1049 | N | SER | 1596 | 23.217 | −12.941 | 25.714 | 1.00 | 43.29 | |
| ATOM 1051 | CA | SER | 1596 | 24.076 | −14.027 | 25.275 | 1.00 | 42.40 | |
| ATOM 1052 | CB | SER | 1596 | 23.388 | −15.374 | 25.484 | 1.00 | 41.83 | |
| ATOM 1053 | OG | SER | 1596 | 22.218 | −15.483 | 24.697 | 1.00 | 44.25 | |
| ATOM 1055 | C | SER | 1596 | 24.392 | −13.817 | 23.800 | 1.00 | 42.64 | |
| ATOM 1056 | O | SER | 1596 | 23.857 | −12.900 | 23.171 | 1.00 | 43.14 | |
| ATOM 1057 | N | SER | 1597 | 25.277 | −14.645 | 23.255 | 1.00 | 42.59 | |
| ATOM 1059 | CA | SER | 1597 | 25.629 | −14.553 | 21.850 | 1.00 | 42.91 | |
| ATOM 1060 | CB | SER | 1597 | 26.739 | −15.547 | 21.516 | 1.00 | 45.26 | |
| ATOM 1061 | OG | SER | 1597 | 27.812 | −15.436 | 22.431 | 1.00 | 56.41 | |
| ATOM 1063 | C | SER | 1597 | 24.380 | −14.909 | 21.648 | 1.00 | 42.35 | |
| ATOM 1064 | O | SER | 1597 | 24.113 | −14.322 | 20.003 | 1.00 | 43.71 | |
| ATOM 1065 | N | LYS | 1598 | 23.621 | −15.881 | 21.544 | 1.00 | 40.61 | |
| ATOM 1067 | CA | LYS | 1598 | 22.405 | −16.298 | 20.867 | 1.00 | 38.61 | |
| ATOM 1068 | CB | LYS | 1598 | 21.848 | −17.575 | 21.483 | 1.00 | 36.33 | |
| ATOM 1069 | CG | LYS | 1598 | 21.135 | −18.439 | 20.468 | 1.00 | 40.09 | |
| ATOM 1070 | CD | LYS | 1598 | 20.213 | −19.434 | 21.118 | 1.00 | 43.39 | |
| ATOM 1071 | CE | LYS | 1598 | 19.766 | −20.494 | 20.122 | 1.00 | 48.25 | |
| ATOM 1072 | NZ | LYS | 1598 | 20.930 | −21.290 | 19.623 | 1.00 | 50.46 | |
| ATOM 1076 | C | LYS | 1598 | 21.348 | −15.194 | 20.895 | 1.00 | 38.17 | |
| ATOM 1077 | O | LYS | 1598 | 20.579 | −15.053 | 19.945 | 1.00 | 41.27 | |
| ATOM 1078 | N | ASP | 1599 | 21.321 | −14.408 | 21.969 | 1.00 | 35.90 | |
| ATOM 1080 | CA | ASP | 1599 | 20.366 | −13.307 | 22.099 | 1.00 | 34.08 | |
| ATOM 1081 | CB | ASP | 1599 | 20.450 | −12.661 | 23.477 | 1.00 | 37.83 | |
| ATOM 1082 | CG | ASP | 1599 | 19.822 | −13.505 | 24.562 | 1.00 | 39.93 | |
| ATOM 1083 | OD1 | ASP | 1599 | 20.089 | −13.217 | 25.742 | 1.00 | 45.85 | |
| ATOM 1084 | OD2 | ASP | 1599 | 19.060 | −14.444 | 24.240 | 1.00 | 41.06 | |
| ATOM 1085 | C | ASP | 1599 | 20.634 | −12.243 | 21.061 | 1.00 | 32.37 | |
| ATOM 1086 | O | ASP | 1599 | 19.704 | −11.701 | 20.466 | 1.00 | 32.58 | |
| ATOM 1087 | N | LEU | 1600 | 21.915 | −11.945 | 20.873 | 1.00 | 30.45 | |
| ATOM 1089 | CA | LEU | 1600 | 22.355 | −10.948 | 19.902 | 1.00 | 29.59 | |
| ATOM 1090 | CB | LEU | 1600 | 23.841 | −10.654 | 20.097 | 1.00 | 28.59 | |
| ATOM 1091 | CG | LEU | 1600 | 24.238 | −10.057 | 21.449 | 1.00 | 24.59 | |
| ATOM 1092 | CD1 | LEU | 1600 | 25.747 | −9.869 | 21.522 | 1.00 | 18.40 | |
| ATOM 1093 | CD2 | LEU | 1600 | 23.529 | −8.745 | 21.626 | 1.00 | 21.71 | |
| ATOM 1094 | C | LEU | 1600 | 22.073 | −11.393 | 18.458 | 1.00 | 28.54 | |
| ATOM 1095 | O | LEU | 1600 | 21.578 | −10.613 | 17.648 | 1.00 | 25.59 | |
| ATOM 1096 | N | VAL | 1601 | 22.377 | −12.645 | 18.134 | 1.00 | 29.13 | |
| ATOM 1098 | CA | VAL | 1601 | 22.111 | −13.154 | 16.793 | 1.00 | 29.74 | |
| ATOM 1099 | CB | VAL | 1601 | 22.780 | −14.513 | 16.551 | 1.00 | 29.63 | |
| ATOM 1100 | CG1 | VAL | 1601 | 22.615 | −14.922 | 15.105 | 1.00 | 29.30 | |
| ATOM 1101 | CG2 | VAL | 1601 | 24.259 | −14.422 | 16.873 | 1.00 | 28.52 | |
| ATOM 1102 | C | VAL | 1601 | 20.591 | −13.247 | 16.564 | 1.00 | 29.98 | |
| ATOM 1103 | O | VAL | 1601 | 20.106 | −13.040 | 15.452 | 1.00 | 29.73 | |
| ATOM 1104 | N | SER | 1602 | 19.855 | −13.493 | 17.645 | 1.00 | 30.97 | |
| ATOM 1106 | CA | SER | 1602 | 18.399 | −13.576 | 17.607 | 1.00 | 29.64 | |
| ATOM 1107 | CB | SER | 1602 | 17.894 | −14.141 | 18.925 | 1.00 | 30.45 | |
| ATOM 1108 | OG | SER | 1602 | 16.483 | −14.158 | 18.962 | 1.00 | 39.63 | |
| ATOM 1110 | C | SER | 1602 | 17.784 | −12.192 | 17.343 | 1.00 | 29.30 | |
| ATOM 1111 | O | SER | 1602 | 16.772 | −12.071 | 16.641 | 1.00 | 28.74 | |
| ATOM 1112 | N | CYS | 1603 | 18.385 | −11.157 | 17.925 | 1.00 | 27.68 | |
| ATOM 1114 | CA | CYS | 1603 | 17.931 | −9.783 | 17.717 | 1.00 | 27.32 | |
| ATOM 1115 | CB | CYS | 1603 | 16.791 | −8.790 | 16.516 | 1.00 | 25.40 | |
| ATOM 1116 | SG | CYS | 1603 | 18.472 | −7.039 | 18.177 | 0.50 | 20.76 | PRT1 |
| ATOM 1117 | C | CYS | 1603 | 18.057 | −9.468 | 16.225 | 1.00 | 28.34 | |
| ATOM 1118 | O | CYS | 1603 | 17.134 | −8.926 | 15.629 | 1.00 | 29.70 | |

TABLE 4-continued

Atomic Structure Coordinates of Unphosphorylated FLGK:AMP-PCP Co-Complex

| Atom No. | Atom Type | A.A. Type | A.A. No. | X | Y | Z | OCC | B |
|---|---|---|---|---|---|---|---|---|
| ATOM 1119 | N | ALA | 1604 | 19.192 | −9.837 | 15.627 | 1.00 | 29.36 |
| ATOM 1121 | CA | ALA | 1604 | 19.438 | −9.601 | 14.195 | 1.00 | 28.78 |
| ATOM 1122 | CB | ALA | 1604 | 20.861 | −10.066 | 13.808 | 1.00 | 22.61 |
| ATOM 1123 | C | ALA | 1604 | 18.386 | −10.304 | 13.324 | 1.00 | 30.14 |
| ATOM 1124 | O | ALA | 1604 | 17.792 | −9.690 | 12.426 | 1.00 | 31.64 |
| ATOM 1125 | N | TYR | 1605 | 18.156 | −11.587 | 13.605 | 1.00 | 29.84 |
| ATOM 1127 | CA | TYR | 1605 | 17.179 | −12.392 | 12.874 | 1.00 | 28.26 |
| ATOM 1128 | CB | TYR | 1605 | 17.107 | −13.789 | 13.488 | 1.00 | 28.74 |
| ATOM 1129 | CG | TYR | 1605 | 16.018 | −14.673 | 12.912 | 1.00 | 31.12 |
| ATOM 1130 | CD1 | TYR | 1605 | 16.152 | −15.256 | 11.650 | 1.00 | 32.53 |
| ATOM 1131 | CE1 | TYR | 1605 | 15.144 | −16.067 | 11.121 | 1.00 | 30.84 |
| ATOM 1132 | CD2 | TYR | 1605 | 14.853 | −14.926 | 13.634 | 1.00 | 31.21 |
| ATOM 1133 | CE2 | TYR | 1605 | 13.850 | −15.734 | 13.116 | 1.00 | 29.69 |
| ATOM 1134 | CZ | TYR | 1605 | 14.002 | −16.296 | 11.864 | 1.00 | 30.82 |
| ATOM 1135 | OH | TYR | 1605 | 12.990 | −17.069 | 11.359 | 1.00 | 33.77 |
| ATOM 1137 | C | TYR | 1605 | 15.788 | −11.758 | 12.853 | 1.00 | 27.33 |
| ATOM 1138 | O | TYR | 1605 | 15.152 | −11.691 | 11.805 | 1.00 | 27.94 |
| ATOM 1139 | N | GLN | 1606 | 15.323 | −11.292 | 14.007 | 1.00 | 27.93 |
| ATOM 1141 | CA | GLN | 1606 | 14.008 | −10.659 | 14.115 | 1.00 | 27.20 |
| ATOM 1142 | CB | GLN | 1606 | 13.686 | −10.335 | 15.570 | 1.00 | 26.40 |
| ATOM 1143 | CG | GLN | 1606 | 13.301 | −11.556 | 16.402 | 1.00 | 28.12 |
| ATOM 1144 | CD | GLN | 1606 | 13.114 | −11.215 | 17.865 | 1.00 | 30.41 |
| ATOM 1145 | OE1 | GLN | 1606 | 12.188 | −10.489 | 18.234 | 1.00 | 34.34 |
| ATOM 1146 | NE2 | GLN | 1606 | 14.008 | −11.701 | 18.700 | 1.00 | 31.44 |
| ATOM 1149 | C | GLN | 1606 | 13.906 | −9.397 | 13.275 | 1.00 | 29.67 |
| ATOM 1150 | O | GLN | 1606 | 12.884 | −9.148 | 12.622 | 1.00 | 30.74 |
| ATOM 1151 | N | VAL | 1607 | 14.970 | −8.602 | 13.281 | 1.00 | 29.59 |
| ATOM 1153 | CA | VAL | 1607 | 14.996 | −7.377 | 12.501 | 1.00 | 27.00 |
| ATOM 1154 | CB | VAL | 1607 | 16.235 | −6.544 | 12.842 | 1.00 | 27.20 |
| ATOM 1155 | CG1 | VAL | 1607 | 16.382 | −5.397 | 11.859 | 1.00 | 28.11 |
| ATOM 1156 | CG2 | VAL | 1607 | 16.113 | −5.996 | 14.266 | 1.00 | 24.79 |
| ATOM 1157 | C | VAL | 1607 | 14.966 | −7.725 | 11.014 | 1.00 | 28.02 |
| ATOM 1158 | O | VAL | 1607 | 14.229 | −7.108 | 10.241 | 1.00 | 28.28 |
| ATOM 1159 | N | ALA | 1608 | 15.736 | −8.741 | 10.626 | 1.00 | 27.56 |
| ATOM 1161 | CA | ALA | 1608 | 15.787 | −9.206 | 9.236 | 1.00 | 27.36 |
| ATOM 1162 | CB | ALA | 1608 | 16.801 | −10.339 | 9.095 | 1.00 | 26.25 |
| ATOM 1163 | C | ALA | 1608 | 14.402 | −9.674 | 8.779 | 1.00 | 28.58 |
| ATOM 1164 | O | ALA | 1608 | 14.013 | −9.446 | 7.624 | 1.00 | 29.11 |
| ATOM 1165 | N | ARG | 1609 | 13.660 | −10.326 | 9.680 | 1.00 | 28.88 |
| ATOM 1167 | CA | ARG | 1609 | 12.306 | −10.797 | 9.376 | 1.00 | 27.17 |
| ATOM 1168 | CB | ARG | 1609 | 11.797 | −11.731 | 10.464 | 1.00 | 29.68 |
| ATOM 1169 | CG | ARG | 1609 | 12.458 | −13.062 | 10.439 | 1.00 | 31.65 |
| ATOM 1170 | CD | ARG | 1609 | 11.612 | −14.049 | 11.177 | 1.00 | 38.21 |
| ATOM 1171 | NE | ARG | 1609 | 10.856 | −14.897 | 10.269 | 1.00 | 41.10 |
| ATOM 1173 | CZ | ARG | 1609 | 10.048 | −15.872 | 10.667 | 1.00 | 41.97 |
| ATOM 1174 | NH1 | ARG | 1609 | 9.886 | −16.125 | 11.959 | 1.00 | 40.69 |
| ATOM 1177 | NH2 | ARG | 1609 | 9.411 | −16.609 | 9.770 | 1.00 | 43.57 |
| ATOM 1180 | C | ARG | 1609 | 11.312 | −9.654 | 9.183 | 1.00 | 25.38 |
| ATOM 1181 | O | ARG | 1609 | 10.480 | −9.693 | 8.260 | 1.00 | 25.75 |
| ATOM 1182 | N | GLY | 1610 | 11.365 | −8.661 | 10.070 | 1.00 | 24.03 |
| ATOM 1184 | CA | GLY | 1610 | 10.480 | −7.517 | 9.939 | 1.00 | 21.74 |
| ATOM 1185 | C | GLY | 1610 | 10.734 | −6.864 | 8.592 | 1.00 | 23.32 |
| ATOM 1186 | O | GLY | 1610 | 9.805 | −6.540 | 7.850 | 1.00 | 23.39 |
| ATOM 1187 | N | MET | 1611 | 12.016 | −6.714 | 8.265 | 1.00 | 24.48 |
| ATOM 1189 | CA | MET | 1611 | 12.453 | −6.125 | 7.002 | 1.00 | 23.13 |
| ATOM 1190 | CB | MET | 1611 | 13.949 | −5.860 | 7.035 | 1.00 | 19.46 |
| ATOM 1191 | CG | MET | 1611 | 14.339 | −4.671 | 7.910 | 1.00 | 22.46 |
| ATOM 1192 | SD | MET | 1611 | 13.457 | −3.123 | 7.536 | 1.00 | 25.27 |
| ATOM 1193 | CE | MET | 1611 | 13.900 | −2.801 | 5.876 | 1.00 | 22.25 |
| ATOM 1194 | C | MET | 1611 | 12.100 | −7.005 | 5.811 | 1.00 | 24.87 |
| ATOM 1195 | O | MET | 1611 | 11.699 | −6.497 | 4.755 | 1.00 | 24.09 |
| ATOM 1196 | N | GLU | 1612 | 12.230 | −8.321 | 5.975 | 1.00 | 25.48 |
| ATOM 1198 | CA | GLU | 1612 | 11.894 | −9.232 | 4.890 | 1.00 | 25.42 |
| ATOM 1199 | CB | GLU | 1612 | 12.155 | −10.691 | 5.288 | 1.00 | 23.41 |
| ATOM 1200 | CG | GLU | 1612 | 11.664 | −11.679 | 4.232 | 1.00 | 25.14 |
| ATOM 1201 | CD | GLU | 1612 | 11.872 | −13.141 | 4.599 | 1.00 | 28.60 |
| ATOM 1202 | OE1 | GLU | 1612 | 11.637 | −13.514 | 5.777 | 1.00 | 30.10 |
| ATOM 1203 | OE2 | GLU | 1612 | 12.244 | −13.928 | 3.694 | 1.00 | 29.53 |
| ATOM 1204 | C | GLU | 1612 | 10.418 | −9.021 | 4.521 | 1.00 | 26.92 |
| ATOM 1205 | O | GLU | 1612 | 10.065 | −8.928 | 3.343 | 1.00 | 29.61 |
| ATOM 1206 | N | TYR | 1613 | 9.576 | −8.884 | 5.542 | 1.00 | 27.88 |
| ATOM 1208 | CA | TYR | 1613 | 8.154 | −8.675 | 5.337 | 1.00 | 23.82 |
| ATOM 1209 | CB | TYR | 1613 | 7.415 | −8.769 | 6.667 | 1.00 | 24.17 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1210 | CG | TYR | 1613 | 5.941 | −8.492 | 6.545 | 1.00 | 23.73 |
| ATOM 1211 | CD1 | TYR | 1613 | 5.064 | −9.483 | 6.096 | 1.00 | 22.17 |
| ATOM 1212 | CE1 | TYR | 1613 | 3.698 | −9.235 | 5.965 | 1.00 | 21.08 |
| ATOM 1213 | CD2 | TYR | 1613 | 5.419 | −7.237 | 6.865 | 1.00 | 23.16 |
| ATOM 1214 | CE2 | TYR | 1613 | 4.054 | −6.976 | 6.736 | 1.00 | 26.38 |
| ATOM 1215 | CZ | TYR | 1613 | 3.200 | −7.981 | 6.287 | 1.00 | 23.16 |
| ATOM 1216 | OH | TYR | 1613 | 1.855 | −7.725 | 6.149 | 1.00 | 25.50 |
| ATOM 1218 | C | TYR | 1613 | 7.885 | −7.327 | 4.670 | 1.00 | 23.17 |
| ATOM 1219 | O | TYR | 1613 | 7.147 | −7.246 | 3.689 | 1.00 | 24.21 |
| ATOM 1220 | N | LEU | 1614 | 8.481 | −6.266 | 5.206 | 1.00 | 23.04 |
| ATOM 1222 | CA | LEU | 1614 | 8.316 | −4.920 | 4.652 | 1.00 | 21.81 |
| ATOM 1223 | CB | LEU | 1614 | 9.107 | −3.906 | 5.484 | 1.00 | 19.94 |
| ATOM 1224 | CG | LEU | 1614 | 8.609 | −3.616 | 6.902 | 1.00 | 21.94 |
| ATOM 1225 | CD1 | LEU | 1614 | 9.580 | −2.719 | 7.654 | 1.00 | 14.28 |
| ATOM 1226 | CD2 | LEU | 1614 | 7.227 | −2.977 | 6.814 | 1.00 | 17.45 |
| ATOM 1227 | C | LEU | 1614 | 8.764 | −4.858 | 3.182 | 1.00 | 23.74 |
| ATOM 1228 | O | LEU | 1614 | 8.169 | −4.150 | 2.367 | 1.00 | 25.26 |
| ATOM 1229 | N | ALA | 1615 | 9.831 | −5.587 | 2.862 | 1.00 | 25.00 |
| ATOM 1231 | CA | ALA | 1615 | 10.357 | −5.644 | 1.502 | 1.00 | 23.04 |
| ATOM 1232 | CB | ALA | 1615 | 11.710 | −6.360 | 1.483 | 1.00 | 20.02 |
| ATOM 1233 | C | ALA | 1615 | 9.351 | −6.357 | 0.605 | 1.00 | 23.15 |
| ATOM 1234 | O | ALA | 1615 | 9.076 | −5.891 | −0.503 | 1.00 | 25.25 |
| ATOM 1235 | N | SER | 1616 | 8.754 | −7.441 | 1.104 | 1.00 | 23.64 |
| ATOM 1237 | CA | SER | 1616 | 7.758 | −8.199 | 0.337 | 1.00 | 23.60 |
| ATOM 1238 | CB | SER | 1616 | 7.346 | −9.453 | 1.107 | 1.00 | 22.46 |
| ATOM 1239 | OG | SER | 1616 | 6.531 | −9.131 | 2.224 | 1.00 | 26.66 |
| ATOM 1241 | C | SER | 1616 | 6.505 | −7.369 | 0.025 | 1.00 | 25.45 |
| ATOM 1242 | O | SER | 1616 | 5.813 | −7.607 | −0.967 | 1.00 | 26.67 |
| ATOM 1243 | N | LYS | 1617 | 6.193 | −6.436 | 0.916 | 1.00 | 25.47 |
| ATOM 1245 | CA | LYS | 1617 | 5.051 | −5.551 | 0.781 | 1.00 | 25.04 |
| ATOM 1246 | CB | LYS | 1617 | 4.513 | −5.183 | 2.163 | 1.00 | 26.30 |
| ATOM 1247 | CG | LYS | 1617 | 3.778 | −6.318 | 2.851 | 1.00 | 28.58 |
| ATOM 1248 | CD | LYS | 1617 | 2.438 | −6.530 | 2.169 | 1.00 | 33.00 |
| ATOM 1249 | CE | LYS | 1617 | 1.652 | −7.676 | 2.764 | 1.00 | 38.57 |
| ATOM 1250 | NZ | LYS | 1617 | 2.167 | −8.987 | 2.300 | 1.00 | 45.15 |
| ATOM 1254 | C | LYS | 1617 | 5.417 | −4.293 | 0.002 | 1.00 | 26.34 |
| ATOM 1255 | O | LYS | 1617 | 4.649 | −3.336 | −0.034 | 1.00 | 26.77 |
| ATOM 1256 | N | LYS | 1618 | 6.592 | −4.319 | −0.632 | 1.00 | 27.17 |
| ATOM 1258 | CA | LYS | 1618 | 7.084 | −3.197 | −1.447 | 1.00 | 28.20 |
| ATOM 1259 | CB | LYS | 1618 | 6.053 | −2.819 | −2.528 | 1.00 | 28.42 |
| ATOM 1260 | CG | LYS | 1618 | 5.971 | −3.749 | −3.730 | 1.00 | 26.63 |
| ATOM 1261 | CD | LYS | 1618 | 5.573 | −5.163 | −3.364 | 1.00 | 30.45 |
| ATOM 1262 | CE | LYS | 1618 | 5.636 | −6.087 | −4.570 | 1.00 | 32.50 |
| ATOM 1263 | NZ | LYS | 1618 | 4.621 | −5.729 | −5.600 | 1.00 | 34.89 |
| ATOM 1267 | C | LYS | 1618 | 7.466 | −1.951 | −0.643 | 1.00 | 28.78 |
| ATOM 1268 | O | LYS | 1618 | 7.556 | −0.848 | −1.199 | 1.00 | 28.78 |
| ATOM 1269 | N | CYS | 1619 | 7.753 | −2.130 | 0.646 | 1.00 | 29.26 |
| ATOM 1271 | CA | CYS | 1619 | 8.111 | −1.022 | 1.522 | 1.00 | 28.32 |
| ATOM 1272 | CB | CYS | 1619 | 7.391 | −1.173 | 2.873 | 1.00 | 26.33 |
| ATOM 1273 | SG | CYS | 1619 | 7.754 | 0.105 | 4.136 | 1.00 | 27.82 |
| ATOM 1274 | C | CYS | 1619 | 9.622 | −0.841 | 1.728 | 1.00 | 29.15 |
| ATOM 1275 | O | CYS | 1619 | 10.336 | −1.786 | 2.072 | 1.00 | 29.55 |
| ATOM 1276 | N | ILE | 1620 | 10.096 | 0.378 | 1.457 | 1.00 | 29.39 |
| ATOM 1278 | CA | ILE | 1620 | 11.502 | 0.761 | 1.625 | 1.00 | 27.44 |
| ATOM 1279 | CB | ILE | 1620 | 12.030 | 1.543 | 0.381 | 1.00 | 25.37 |
| ATOM 1280 | CG2 | ILE | 1620 | 13.521 | 1.806 | 0.506 | 1.00 | 19.80 |
| ATOM 1281 | CG1 | ILE | 1620 | 11.767 | 0.764 | −0.913 | 1.00 | 25.40 |
| ATOM 1282 | CD1 | ILE | 1620 | 12.100 | 1.557 | −2.164 | 1.00 | 27.51 |
| ATOM 1283 | C | ILE | 1620 | 11.553 | 1.686 | 2.855 | 1.00 | 26.56 |
| ATOM 1284 | O | ILE | 1620 | 11.011 | 2.792 | 2.833 | 1.00 | 26.68 |
| ATOM 1285 | N | HIS | 1621 | 12.193 | 1.210 | 3.916 | 1.00 | 26.31 |
| ATOM 1287 | CA | HIS | 1621 | 12.297 | 1.967 | 5.162 | 1.00 | 25.00 |
| ATOM 1288 | CB | HIS | 1621 | 13.081 | 1.174 | 6.210 | 1.00 | 23.08 |
| ATOM 1289 | CG | HIS | 1621 | 12.848 | 1.633 | 7.618 | 1.00 | 23.21 |
| ATOM 1290 | CD2 | HIS | 1621 | 12.224 | 1.027 | 8.656 | 1.00 | 22.69 |
| ATOM 1291 | ND1 | HIS | 1621 | 13.260 | 2.862 | 8.088 | 1.00 | 25.34 |
| ATOM 1293 | CE1 | HIS | 1621 | 12.909 | 2.993 | 9.356 | 1.00 | 24.18 |
| ATOM 1294 | NE2 | HIS | 1621 | 12.273 | 1.891 | 9.719 | 1.00 | 25.86 |
| ATOM 1296 | C | HIS | 1621 | 12.963 | 3.316 | 4.976 | 1.00 | 25.09 |
| ATOM 1297 | O | HIS | 1621 | 12.408 | 4.328 | 5.349 | 1.00 | 28.21 |
| ATOM 1298 | N | ARG | 1622 | 14.162 | 3.315 | 4.402 | 1.00 | 26.09 |
| ATOM 1300 | CA | ARG | 1622 | 14.976 | 4.520 | 4.183 | 1.00 | 26.50 |
| ATOM 1301 | CB | ARG | 1622 | 14.180 | 5.670 | 3.558 | 1.00 | 23.52 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1302 | CG | ARG | 1622 | 13.673 | 5.326 | 2.202 | 1.00 | 23.81 |
| ATOM 1303 | CD | ARG | 1622 | 12.995 | 6.494 | 1.551 | 1.00 | 28.42 |
| ATOM 1304 | NE | ARG | 1622 | 12.677 | 6.170 | 0.180 | 1.00 | 32.52 |
| ATOM 1306 | CZ | ARG | 1622 | 11.623 | 5.455 | −0.197 | 1.00 | 32.34 |
| ATOM 1307 | NH1 | ARG | 1622 | 10.774 | 4.994 | 0.711 | 1.00 | 30.07 |
| ATOM 1310 | NH2 | ARG | 1622 | 11.460 | 5.138 | −1.489 | 1.00 | 28.30 |
| ATOM 1313 | C | ARG | 1622 | 15.740 | 4.993 | 5.423 | 1.00 | 26.31 |
| ATOM 1314 | O | ARG | 1622 | 16.698 | 5.757 | 5.313 | 1.00 | 26.19 |
| ATOM 1315 | N | ASP | 1623 | 15.379 | 4.495 | 6.596 | 1.00 | 27.41 |
| ATOM 1317 | CA | ASP | 1623 | 16.114 | 4.879 | 7.788 | 1.00 | 29.94 |
| ATOM 1318 | CB | ASP | 1623 | 15.562 | 6.155 | 8.430 | 1.00 | 34.83 |
| ATOM 1319 | CG | ASP | 1623 | 16.481 | 6.689 | 9.533 | 1.00 | 38.84 |
| ATOM 1320 | OD1 | ASP | 1623 | 15.971 | 7.265 | 10.514 | 1.00 | 44.51 |
| ATOM 1321 | OD2 | ASP | 1623 | 17.721 | 6.514 | 9.423 | 1.00 | 37.59 |
| ATOM 1322 | C | ASP | 1623 | 16.203 | 3.763 | 8.812 | 1.00 | 28.71 |
| ATOM 1323 | O | ASP | 1623 | 15.845 | 3.927 | 9.990 | 1.00 | 26.21 |
| ATOM 1324 | N | LEU | 1624 | 16.735 | 2.633 | 8.357 | 1.00 | 26.82 |
| ATOM 1326 | CA | LEU | 1624 | 16.905 | 1.469 | 9.216 | 1.00 | 25.91 |
| ATOM 1327 | CB | LEU | 1624 | 17.025 | 0.209 | 8.367 | 1.00 | 23.35 |
| ATOM 1328 | CG | LEU | 1624 | 17.089 | −1.107 | 9.127 | 1.00 | 21.09 |
| ATOM 1329 | CD1 | LEU | 1624 | 15.824 | −1.303 | 10.009 | 1.00 | 14.44 |
| ATOM 1330 | CD2 | LEU | 1624 | 17.282 | −2.215 | 8.101 | 1.00 | 18.30 |
| ATOM 1331 | C | LEU | 1624 | 18.136 | 1.640 | 10.105 | 1.00 | 24.93 |
| ATOM 1332 | O | LEU | 1624 | 19.235 | 1.897 | 9.611 | 1.00 | 25.58 |
| ATOM 1333 | N | ALA | 1625 | 17.912 | 1.557 | 11.416 | 1.00 | 26.30 |
| ATOM 1335 | CA | ALA | 1625 | 18.945 | 1.702 | 12.445 | 1.00 | 23.59 |
| ATOM 1336 | CB | ALA | 1625 | 19.271 | 3.174 | 12.654 | 1.00 | 15.82 |
| ATOM 1337 | C | ALA | 1625 | 18.351 | 1.116 | 13.732 | 1.00 | 23.64 |
| ATOM 1338 | O | ALA | 1625 | 17.135 | 0.928 | 13.825 | 1.00 | 26.66 |
| ATOM 1339 | N | ALA | 1626 | 19.197 | 0.815 | 14.712 | 1.00 | 21.59 |
| ATOM 1341 | CA | ALA | 1626 | 18.708 | 0.266 | 15.974 | 1.00 | 21.66 |
| ATOM 1342 | CB | ALA | 1626 | 19.860 | −0.179 | 16.838 | 1.00 | 22.97 |
| ATOM 1343 | C | ALA | 1626 | 17.835 | 1.272 | 16.731 | 1.00 | 24.98 |
| ATOM 1344 | O | ALA | 1626 | 17.072 | 0.891 | 17.620 | 1.00 | 26.84 |
| ATOM 1345 | N | ARG | 1627 | 17.978 | 2.558 | 16.409 | 1.00 | 24.55 |
| ATOM 1347 | CA | ARG | 1627 | 17.178 | 3.598 | 17.042 | 1.00 | 25.29 |
| ATOM 1348 | CB | ARG | 1627 | 17.699 | 4.983 | 16.673 | 1.00 | 26.66 |
| ATOM 1349 | CG | ARG | 1627 | 17.675 | 5.276 | 15.179 | 1.00 | 30.56 |
| ATOM 1350 | CD | ARG | 1627 | 18.033 | 6.715 | 14.902 | 1.00 | 34.97 |
| ATOM 1351 | NE | ARG | 1627 | 18.177 | 6.980 | 13.470 | 1.00 | 40.03 |
| ATOM 1353 | CZ | ARG | 1627 | 19.322 | 6.864 | 12.809 | 1.00 | 40.62 |
| ATOM 1354 | NH1 | ARG | 1627 | 20.421 | 6.485 | 13.441 | 1.00 | 46.52 |
| ATOM 1357 | NH2 | ARG | 1627 | 19.377 | 7.159 | 11.523 | 1.00 | 43.25 |
| ATOM 1360 | C | ARG | 1627 | 15.739 | 3.472 | 16.542 | 1.00 | 27.33 |
| ATOM 1361 | O | ARG | 1627 | 14.804 | 3.895 | 17.210 | 1.00 | 28.14 |
| ATOM 1362 | N | ASN | 1628 | 15.576 | 2.894 | 15.353 | 1.00 | 27.46 |
| ATOM 1364 | CA | ASN | 1628 | 14.260 | 2.716 | 14.757 | 1.00 | 28.07 |
| ATOM 1365 | CB | ASN | 1628 | 14.254 | 3.178 | 13.304 | 1.00 | 31.54 |
| ATOM 1366 | CG | ASN | 1628 | 14.307 | 4.690 | 13.172 | 1.00 | 35.35 |
| ATOM 1367 | OD1 | ASN | 1628 | 13.538 | 5.405 | 13.824 | 1.00 | 37.63 |
| ATOM 1368 | ND2 | ASN | 1628 | 15.221 | 5.184 | 12.354 | 1.00 | 32.95 |
| ATOM 1371 | C | ASN | 1628 | 13.733 | 1.301 | 14.880 | 1.00 | 27.69 |
| ATOM 1372 | O | ASN | 1628 | 12.896 | 0.864 | 14.082 | 1.00 | 28.10 |
| ATOM 1373 | N | VAL | 1629 | 14.247 | 0.580 | 15.870 | 1.00 | 26.21 |
| ATOM 1375 | CA | VAL | 1629 | 13.817 | −0.775 | 16.169 | 1.00 | 25.90 |
| ATOM 1376 | CB | VAL | 1629 | 14.926 | −1.812 | 15.946 | 1.00 | 24.73 |
| ATOM 1377 | CG1 | VAL | 1629 | 14.480 | −3.151 | 16.499 | 1.00 | 19.90 |
| ATOM 1378 | CG2 | VAL | 1629 | 15.274 | −1.924 | 14.440 | 1.00 | 18.28 |
| ATOM 1379 | C | VAL | 1629 | 13.470 | −0.732 | 17.646 | 1.00 | 27.81 |
| ATOM 1380 | O | VAL | 1629 | 14.313 | −0.404 | 18.468 | 1.00 | 29.18 |
| ATOM 1381 | N | LEU | 1630 | 12.212 | −0.987 | 17.976 | 1.00 | 30.36 |
| ATOM 1383 | CA | LEU | 1630 | 11.776 | −0.950 | 19.365 | 1.00 | 31.04 |
| ATOM 1384 | CB | LEU | 1630 | 10.471 | −0.151 | 19.489 | 1.00 | 31.93 |
| ATOM 1385 | CG | LEU | 1630 | 10.441 | 1.211 | 18.784 | 1.00 | 27.43 |
| ATOM 1386 | CD1 | LEU | 1630 | 9.126 | 1.879 | 19.009 | 1.00 | 23.21 |
| ATOM 1387 | CD2 | LEU | 1630 | 11.564 | 2.093 | 19.271 | 1.00 | 28.21 |
| ATOM 1388 | C | LEU | 1630 | 11.625 | −2.356 | 19.935 | 1.00 | 31.58 |
| ATOM 1389 | O | LEU | 1630 | 11.415 | −3.321 | 19.195 | 1.00 | 33.03 |
| ATOM 1390 | N | VAL | 1631 | 11.752 | −2.467 | 21.253 | 1.00 | 31.30 |
| ATOM 1392 | CA | VAL | 1631 | 11.660 | −3.749 | 21.937 | 1.00 | 30.60 |
| ATOM 1393 | CB | VAL | 1631 | 12.964 | −4.027 | 22.745 | 1.00 | 29.35 |
| ATOM 1394 | CG1 | VAL | 1631 | 12.995 | −5.469 | 23.243 | 1.00 | 23.92 |
| ATOM 1395 | CG2 | VAL | 1631 | 14.197 | −3.714 | 21.895 | 1.00 | 24.26 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1396 | C | VAL | 1631 | 10.450 | −3.773 | 22.885 | 1.00 | 32.64 |
| ATOM 1397 | O | VAL | 1631 | 10.198 | −2.821 | 23.643 | 1.00 | 33.01 |
| ATOM 1398 | N | THR | 1632 | 9.697 | −4.863 | 22.827 | 1.00 | 34.45 |
| ATOM 1400 | CA | THR | 1632 | 8.516 | −5.035 | 23.660 | 1.00 | 34.29 |
| ATOM 1401 | CB | THR | 1632 | 7.466 | −5.941 | 22.962 | 1.00 | 34.62 |
| ATOM 1402 | OG1 | THR | 1632 | 7.965 | −7.288 | 22.881 | 1.00 | 34.40 |
| ATOM 1404 | CG2 | THR | 1632 | 7.154 | −5.414 | 21.551 | 1.00 | 31.61 |
| ATOM 1405 | C | THR | 1632 | 8.896 | −5.678 | 24.989 | 1.00 | 35.41 |
| ATOM 1406 | O | THR | 1632 | 10.002 | −6.189 | 25.146 | 1.00 | 34.79 |
| ATOM 1407 | N | GLU | 1633 | 7.939 | −5.706 | 25.913 | 1.00 | 36.86 |
| ATOM 1409 | CA | GLU | 1633 | 8.156 | −6.298 | 27.224 | 1.00 | 37.27 |
| ATOM 1410 | CB | GLU | 1633 | 6.893 | −6.182 | 28.079 | 1.00 | 37.66 |
| ATOM 1411 | CG | GLU | 1633 | 7.031 | −6.718 | 29.514 | 1.00 | 44.43 |
| ATOM 1412 | CD | GLU | 1633 | 8.048 | −5.959 | 30.378 | 1.00 | 46.68 |
| ATOM 1413 | OE1 | GLU | 1633 | 8.104 | −4.708 | 30.300 | 1.00 | 49.88 |
| ATOM 1414 | OE2 | GLU | 1633 | 8.783 | −6.612 | 31.156 | 1.00 | 48.53 |
| ATOM 1415 | C | GLU | 1633 | 8.561 | −7.753 | 27.088 | 1.00 | 37.15 |
| ATOM 1416 | O | GLU | 1633 | 9.227 | −8.292 | 27.954 | 1.00 | 38.60 |
| ATOM 1417 | N | ASP | 1634 | 8.167 | −8.384 | 25.990 | 1.00 | 38.41 |
| ATOM 1419 | CA | ASP | 1634 | 8.505 | −9.787 | 25.770 | 1.00 | 38.86 |
| ATOM 1420 | CB | ASP | 1634 | 7.381 | −10.499 | 25.013 | 1.00 | 44.27 |
| ATOM 1421 | CG | ASP | 1634 | 6.022 | −10.349 | 25.690 | 1.00 | 50.18 |
| ATOM 1422 | OD1 | ASP | 1634 | 5.726 | −11.141 | 26.617 | 1.00 | 52.07 |
| ATOM 1423 | OD2 | ASP | 1634 | 5.253 | −9.439 | 25.295 | 1.00 | 50.17 |
| ATOM 1424 | C | ASP | 1634 | 9.804 | −9.947 | 25.007 | 1.00 | 36.23 |
| ATOM 1425 | O | ASP | 1634 | 10.141 | −11.049 | 24.608 | 1.00 | 35.82 |
| ATOM 1426 | N | ASN | 1635 | 10.528 | −8.851 | 24.799 | 1.00 | 36.51 |
| ATOM 1428 | CA | ASN | 1635 | 11.795 | −8.864 | 24.052 | 1.00 | 37.41 |
| ATOM 1429 | CB | ASN | 1635 | 12.801 | −9.842 | 24.678 | 1.00 | 38.49 |
| ATOM 1430 | CG | ASN | 1635 | 13.343 | −9.359 | 26.003 | 1.00 | 37.71 |
| ATOM 1431 | OD1 | ASN | 1635 | 13.499 | −8.156 | 26.227 | 1.00 | 38.09 |
| ATOM 1432 | ND2 | ASN | 1635 | 13.679 | −10.300 | 26.874 | 1.00 | 39.63 |
| ATOM 1435 | C | ASN | 1635 | 11.655 | −9.162 | 22.552 | 1.00 | 36.37 |
| ATOM 1436 | O | ASN | 1635 | 12.522 | −9.811 | 21.944 | 1.00 | 36.41 |
| ATOM 1437 | N | VAL | 1636 | 10.547 | −8.721 | 21.966 | 1.00 | 33.79 |
| ATOM 1439 | CA | VAL | 1636 | 10.315 | −8.910 | 20.543 | 1.00 | 30.59 |
| ATOM 1440 | CB | VAL | 1636 | 8.820 | −9.139 | 20.218 | 1.00 | 28.83 |
| ATOM 1441 | CG1 | VAL | 1636 | 8.615 | −9.182 | 18.712 | 1.00 | 26.13 |
| ATOM 1442 | CG2 | VAL | 1636 | 8.339 | −10.431 | 20.838 | 1.00 | 25.67 |
| ATOM 1443 | C | VAL | 1636 | 10.782 | −7.630 | 19.863 | 1.00 | 30.18 |
| ATOM 1444 | O | VAL | 1636 | 10.436 | −6.527 | 20.301 | 1.00 | 27.86 |
| ATOM 1445 | N | MET | 1637 | 11.609 | −7.792 | 18.832 | 1.00 | 30.93 |
| ATOM 1447 | CA | MET | 1637 | 12.140 | −6.679 | 18.060 | 1.00 | 28.34 |
| ATOM 1448 | CB | MET | 1637 | 13.397 | −7.138 | 17.330 | 1.00 | 30.84 |
| ATOM 1449 | CG | MET | 1637 | 14.480 | −7.693 | 18.254 | 1.00 | 30.73 |
| ATOM 1450 | SD | MET | 1637 | 15.050 | −6.490 | 19.477 | 1.00 | 32.20 |
| ATOM 1451 | CE | MET | 1637 | 15.074 | −7.500 | 20.938 | 1.00 | 28.71 |
| ATOM 1452 | C | MET | 1637 | 11.082 | −6.264 | 17.051 | 1.00 | 27.29 |
| ATOM 1453 | O | MET | 1637 | 10.587 | −7.099 | 16.297 | 1.00 | 27.32 |
| ATOM 1454 | N | LYS | 1638 | 10.733 | −4.983 | 17.045 | 1.00 | 27.19 |
| ATOM 1456 | CA | LYS | 1638 | 9.716 | −4.450 | 16.143 | 1.00 | 26.38 |
| ATOM 1457 | CB | LYS | 1638 | 8.437 | −4.120 | 16.912 | 1.00 | 27.09 |
| ATOM 1458 | CG | LYS | 1638 | 7.702 | −5.351 | 17.407 | 1.00 | 29.71 |
| ATOM 1459 | CD | LYS | 1638 | 6.386 | −5.018 | 18.109 | 1.00 | 31.48 |
| ATOM 1460 | CE | LYS | 1638 | 5.485 | −6.263 | 18.202 | 1.00 | 27.09 |
| ATOM 1461 | NZ | LYS | 1638 | 4.888 | −6.561 | 16.869 | 1.00 | 26.68 |
| ATOM 1465 | C | LYS | 1638 | 10.196 | −3.208 | 15.416 | 1.00 | 26.56 |
| ATOM 1466 | O | LYS | 1638 | 10.514 | −2.194 | 16.040 | 1.00 | 27.40 |
| ATOM 1467 | N | ILE | 1639 | 10.211 | −3.271 | 14.092 | 1.00 | 24.31 |
| ATOM 1469 | CA | ILE | 1639 | 10.649 | −2.147 | 13.289 | 1.00 | 24.84 |
| ATOM 1470 | CB | ILE | 1639 | 10.924 | −2.588 | 11.836 | 1.00 | 25.81 |
| ATOM 1471 | CG2 | ILE | 1639 | 11.248 | −1.395 | 10.952 | 1.00 | 24.18 |
| ATOM 1472 | CG1 | ILE | 1639 | 12.094 | −3.566 | 11.826 | 1.00 | 25.01 |
| ATOM 1473 | CD1 | ILE | 1639 | 12.075 | −4.499 | 10.675 | 1.00 | 27.90 |
| ATOM 1474 | C | ILE | 1639 | 9.641 | −0.999 | 13.348 | 1.00 | 24.90 |
| ATOM 1475 | O | ILE | 1639 | 8.435 | −1.186 | 13.170 | 1.00 | 25.24 |
| ATOM 1476 | N | ALA | 1640 | 10.167 | 0.183 | 13.635 | 1.00 | 25.70 |
| ATOM 1478 | CA | ALA | 1640 | 9.378 | 1.392 | 13.744 | 1.00 | 27.61 |
| ATOM 1479 | CB | ALA | 1640 | 9.699 | 2.094 | 15.070 | 1.00 | 26.37 |
| ATOM 1480 | C | ALA | 1640 | 9.637 | 2.348 | 12.576 | 1.00 | 28.35 |
| ATOM 1481 | O | ALA | 1640 | 10.650 | 2.243 | 11.871 | 1.00 | 28.40 |
| ATOM 1482 | N | ASP | 1641 | 8.676 | 3.237 | 12.354 | 1.00 | 29.74 |
| ATOM 1484 | CA | ASP | 1641 | 8.760 | 4.272 | 11.325 | 1.00 | 32.13 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1485 | CB | ASP | 1641 | 9.873 | 5.273 | 11.688 | 1.00 | 34.31 |
| ATOM 1486 | CG | ASP | 1641 | 9.507 | 6.158 | 12.896 | 1.00 | 36.31 |
| ATOM 1487 | OD1 | ASP | 1641 | 10.299 | 7.056 | 13.258 | 1.00 | 42.18 |
| ATOM 1488 | OD2 | ASP | 1641 | 8.420 | 5.974 | 13.483 | 1.00 | 41.03 |
| ATOM 1489 | C | ASP | 1641 | 8.882 | 3.840 | 9.867 | 1.00 | 32.00 |
| ATOM 1490 | O | ASP | 1641 | 9.339 | 4.617 | 9.021 | 1.00 | 32.65 |
| ATOM 1491 | N | PHE | 1642 | 8.415 | 2.634 | 9.563 | 1.00 | 30.61 |
| ATOM 1493 | CA | PHE | 1642 | 8.473 | 2.119 | 8.200 | 1.00 | 30.06 |
| ATOM 1494 | CB | PHE | 1642 | 8.248 | 0.606 | 8.189 | 1.00 | 24.46 |
| ATOM 1495 | CG | PHE | 1642 | 6.981 | 0.176 | 8.854 | 1.00 | 23.26 |
| ATOM 1496 | CD1 | PHE | 1642 | 5.799 | 0.075 | 8.125 | 1.00 | 19.66 |
| ATOM 1497 | CD2 | PHE | 1642 | 6.966 | −0.134 | 10.209 | 1.00 | 22.88 |
| ATOM 1498 | CE1 | PHE | 1642 | 4.609 | −0.331 | 8.734 | 1.00 | 20.97 |
| ATOM 1499 | CE2 | PHE | 1642 | 5.785 | −0.540 | 10.830 | 1.00 | 26.61 |
| ATOM 1500 | CZ | PHE | 1642 | 4.599 | −0.639 | 10.083 | 1.00 | 24.82 |
| ATOM 1501 | C | PHE | 1642 | 7.512 | 2.830 | 7.225 | 1.00 | 33.14 |
| ATOM 1502 | O | PHE | 1642 | 7.791 | 2.922 | 6.029 | 1.00 | 36.48 |
| ATOM 1503 | N | GLY | 1643 | 6.411 | 3.372 | 7.741 | 1.00 | 32.65 |
| ATOM 1505 | CA | GLY | 1643 | 5.462 | 4.059 | 6.876 | 1.00 | 32.28 |
| ATOM 1506 | C | GLY | 1643 | 5.629 | 5.560 | 6.913 | 1.00 | 32.19 |
| ATOM 1507 | O | GLY | 1643 | 4.795 | 6.310 | 6.415 | 1.00 | 30.74 |
| ATOM 1508 | N | LEU | 1644 | 6.739 | 5.997 | 7.486 | 1.00 | 36.80 |
| ATOM 1510 | CA | LEU | 1644 | 7.052 | 7.406 | 7.630 | 1.00 | 41.95 |
| ATOM 1511 | CB | LEU | 1644 | 8.332 | 7.551 | 8.439 | 1.00 | 37.41 |
| ATOM 1512 | CG | LEU | 1644 | 8.377 | 8.746 | 9.369 | 1.00 | 38.98 |
| ATOM 1513 | CD1 | LEU | 1644 | 7.384 | 8.548 | 10.493 | 1.00 | 40.45 |
| ATOM 1514 | CD2 | LEU | 1644 | 9.775 | 8.904 | 9.929 | 1.00 | 41.94 |
| ATOM 1515 | C | LEU | 1644 | 7.189 | 8.150 | 6.296 | 1.00 | 47.55 |
| ATOM 1516 | O | LEU | 1644 | 7.787 | 7.648 | 5.341 | 1.00 | 50.55 |
| ATOM 1517 | N | ALA | 1645 | 6.637 | 9.356 | 6.247 | 1.00 | 52.59 |
| ATOM 1519 | CA | ALA | 1645 | 6.686 | 10.194 | 5.055 | 1.00 | 56.88 |
| ATOM 1520 | CB | ALA | 1645 | 5.391 | 10.999 | 4.942 | 1.00 | 58.01 |
| ATOM 1521 | C | ALA | 1645 | 7.880 | 11.135 | 5.178 | 1.00 | 58.95 |
| ATOM 1522 | O | ALA | 1645 | 8.064 | 11.770 | 6.224 | 1.00 | 59.37 |
| ATOM 1523 | N | ARG | 1646 | 8.700 | 11.211 | 4.133 | 1.00 | 60.26 |
| ATOM 1525 | CA | ARG | 1646 | 9.870 | 12.088 | 4.165 | 1.00 | 63.04 |
| ATOM 1526 | CB | ARG | 1646 | 10.995 | 11.444 | 4.976 | 1.00 | 64.92 |
| ATOM 1527 | C | ARG | 1646 | 10.377 | 12.461 | 2.782 | 1.00 | 63.84 |
| ATOM 1528 | O | ARG | 1646 | 10.361 | 11.641 | 1.864 | 1.00 | 63.55 |
| ATOM 1529 | N | ASP | 1647 | 10.801 | 13.714 | 2.633 | 1.00 | 65.18 |
| ATOM 1531 | CA | ASP | 1647 | 11.332 | 14.190 | 1.361 | 1.00 | 67.26 |
| ATOM 1532 | CB | ASP | 1647 | 10.989 | 15.670 | 1.150 | 1.00 | 68.92 |
| ATOM 1533 | CG | ASP | 1647 | 11.164 | 16.124 | −0.304 | 1.00 | 70.88 |
| ATOM 1534 | OD1 | ASP | 1647 | 12.196 | 15.811 | −0.943 | 1.00 | 70.33 |
| ATOM 1535 | OD2 | ASP | 1647 | 10.258 | 16.825 | −0.808 | 1.00 | 71.39 |
| ATOM 1536 | C | ASP | 1647 | 12.847 | 14.005 | 1.405 | 1.00 | 68.40 |
| ATOM 1537 | O | ASP | 1647 | 13.545 | 14.711 | 2.142 | 1.00 | 68.66 |
| ATOM 1538 | N | ILE | 1648 | 13.347 | 13.055 | 0.621 | 1.00 | 68.48 |
| ATOM 1540 | CA | ILE | 1648 | 14.777 | 12.773 | 0.570 | 1.00 | 69.00 |
| ATOM 1541 | CB | ILE | 1648 | 15.091 | 11.535 | −0.314 | 1.00 | 66.28 |
| ATOM 1542 | CG2 | ILE | 1648 | 14.231 | 10.352 | 0.131 | 1.00 | 65.14 |
| ATOM 1543 | CG1 | ILE | 1648 | 14.869 | 11.853 | −1.799 | 1.00 | 63.01 |
| ATOM 1544 | CD1 | ILE | 1648 | 15.274 | 10.746 | −2.738 | 1.00 | 60.11 |
| ATOM 1545 | C | ILE | 1648 | 15.542 | 13.990 | 0.046 | 1.00 | 71.12 |
| ATOM 1546 | O | ILE | 1648 | 16.628 | 14.310 | 0.525 | 1.00 | 72.41 |
| ATOM 1547 | N | HIS | 1649 | 14.923 | 14.710 | −0.883 | 1.00 | 73.09 |
| ATOM 1549 | CA | HIS | 1649 | 15.546 | 15.890 | −1.469 | 1.00 | 74.66 |
| ATOM 1550 | CB | HIS | 1649 | 14.921 | 16.191 | −2.835 | 1.00 | 76.00 |
| ATOM 1551 | CG | HIS | 1649 | 15.178 | 15.157 | −3.867 | 1.00 | 78.03 |
| ATOM 1552 | CD2 | HIS | 1649 | 16.314 | 14.425 | −4.151 | 1.00 | 78.85 |
| ATOM 1553 | ND1 | HIS | 1649 | 14.245 | 14.739 | −4.795 | 1.00 | 78.49 |
| ATOM 1555 | CE1 | HIS | 1649 | 14.765 | 13.835 | −5.584 | 1.00 | 78.94 |
| ATOM 1556 | NE2 | HIS | 1649 | 16.005 | 13.623 | −5.226 | 1.00 | 78.22 |
| ATOM 1558 | C | HIS | 1649 | 15.466 | 17.108 | −0.549 | 1.00 | 75.04 |
| ATOM 1559 | O | HIS | 1649 | 15.567 | 18.244 | −1.007 | 1.00 | 75.49 |
| ATOM 1560 | N | HIS | 1650 | 15.265 | 16.860 | 0.743 | 1.00 | 76.11 |
| ATOM 1562 | CA | HIS | 1650 | 15.181 | 17.918 | 1.748 | 1.00 | 77.63 |
| ATOM 1563 | CB | HIS | 1650 | 13.723 | 18.327 | 1.995 | 1.00 | 81.10 |
| ATOM 1564 | CG | HIS | 1650 | 13.206 | 19.352 | 1.033 | 1.00 | 86.06 |
| ATOM 1565 | CD2 | HIS | 1650 | 13.662 | 20.592 | 0.730 | 1.00 | 88.74 |
| ATOM 1566 | ND1 | HIS | 1650 | 12.099 | 19.146 | 0.239 | 1.00 | 88.83 |
| ATOM 1568 | CE1 | HIS | 1650 | 11.893 | 20.211 | −0.511 | 1.00 | 90.51 |
| ATOM 1569 | NE2 | HIS | 1650 | 12.823 | 21.103 | −0.238 | 1.00 | 90.75 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1571 | C | HIS | 1650 | 15.824 | 17.482 | 3.064 | 1.00 | 77.39 |
| ATOM 1572 | O | HIS | 1650 | 15.651 | 18.133 | 4.091 | 1.00 | 77.42 |
| ATOM 1573 | N | ILE | 1651 | 16.573 | 16.385 | 3.024 | 1.00 | 77.73 |
| ATOM 1575 | CA | ILE | 1651 | 17.241 | 15.864 | 4.212 | 1.00 | 77.02 |
| ATOM 1576 | CB | ILE | 1651 | 17.788 | 14.433 | 3.974 | 1.00 | 78.24 |
| ATOM 1577 | CG2 | ILE | 1651 | 18.647 | 13.963 | 5.153 | 1.00 | 77.92 |
| ATOM 1578 | CG1 | ILE | 1651 | 16.633 | 13.458 | 3.750 | 1.00 | 80.90 |
| ATOM 1579 | CD1 | ILE | 1651 | 17.094 | 12.032 | 3.483 | 1.00 | 82.41 |
| ATOM 1580 | C | ILE | 1651 | 18.411 | 16.748 | 4.620 | 1.00 | 76.15 |
| ATOM 1581 | O | ILE | 1651 | 19.269 | 17.078 | 3.803 | 1.00 | 76.52 |
| ATOM 1582 | N | ASP | 1652 | 18.432 | 17.150 | 5.882 | 1.00 | 75.13 |
| ATOM 1584 | CA | ASP | 1652 | 19.527 | 17.957 | 6.384 | 1.00 | 73.91 |
| ATOM 1585 | CB | ASP | 1652 | 19.068 | 18.781 | 7.592 | 1.00 | 76.30 |
| ATOM 1586 | CG | ASP | 1652 | 20.216 | 19.499 | 8.286 | 1.00 | 79.91 |
| ATOM 1587 | OD1 | ASP | 1652 | 21.247 | 19.786 | 7.636 | 1.00 | 82.38 |
| ATOM 1588 | OD2 | ASP | 1652 | 20.081 | 19.780 | 9.497 | 1.00 | 81.51 |
| ATOM 1589 | C | ASP | 1652 | 20.637 | 16.984 | 6.783 | 1.00 | 72.31 |
| ATOM 1590 | O | ASP | 1652 | 20.599 | 16.403 | 7.866 | 1.00 | 71.41 |
| ATOM 1591 | N | TYR | 1653 | 21.610 | 16.805 | 5.894 | 1.00 | 71.44 |
| ATOM 1593 | CA | TYR | 1653 | 22.736 | 15.900 | 6.143 | 1.00 | 70.07 |
| ATOM 1594 | CB | TYR | 1653 | 23.655 | 15.849 | 4.921 | 1.00 | 66.96 |
| ATOM 1595 | CG | TYR | 1653 | 23.153 | 14.932 | 3.834 | 1.00 | 66.43 |
| ATOM 1596 | CD1 | TYR | 1653 | 23.881 | 14.757 | 2.657 | 1.00 | 66.60 |
| ATOM 1597 | CE1 | TYR | 1653 | 23.434 | 13.898 | 1.653 | 1.00 | 68.33 |
| ATOM 1598 | CD2 | TYR | 1653 | 21.960 | 14.224 | 3.981 | 1.00 | 66.58 |
| ATOM 1599 | CE2 | TYR | 1653 | 21.500 | 13.363 | 2.990 | 1.00 | 68.84 |
| ATOM 1600 | CZ | TYR | 1653 | 22.241 | 13.205 | 1.823 | 1.00 | 69.34 |
| ATOM 1601 | OH | TYR | 1653 | 21.781 | 12.360 | 0.833 | 1.00 | 69.88 |
| ATOM 1603 | C | TYR | 1653 | 23.557 | 16.227 | 7.391 | 1.00 | 70.80 |
| ATOM 1604 | O | TYR | 1653 | 24.197 | 15.351 | 7.975 | 1.00 | 70.62 |
| ATOM 1605 | N | TYR | 1654 | 23.531 | 17.488 | 7.802 | 1.00 | 70.76 |
| ATOM 1607 | CA | TYR | 1654 | 24.280 | 17.902 | 8.972 | 1.00 | 70.97 |
| ATOM 1608 | CB | TYR | 1654 | 24.795 | 19.328 | 8.783 | 1.00 | 69.27 |
| ATOM 1609 | CG | TYR | 1654 | 25.935 | 19.401 | 7.787 | 1.00 | 69.68 |
| ATOM 1610 | CD1 | TYR | 1654 | 25.696 | 19.352 | 6.415 | 1.00 | 69.51 |
| ATOM 1611 | CE1 | TYR | 1654 | 26.750 | 19.380 | 5.498 | 1.00 | 70.15 |
| ATOM 1612 | CD2 | TYR | 1654 | 27.256 | 19.482 | 8.221 | 1.00 | 69.92 |
| ATOM 1613 | CE2 | TYR | 1654 | 28.314 | 19.513 | 7.316 | 1.00 | 70.26 |
| ATOM 1614 | CZ | TYR | 1654 | 28.057 | 19.462 | 5.958 | 1.00 | 70.22 |
| ATOM 1615 | OH | TYR | 1654 | 29.111 | 19.492 | 5.069 | 1.00 | 69.67 |
| ATOM 1617 | C | TYR | 1654 | 23.503 | 17.763 | 10.272 | 1.00 | 72.19 |
| ATOM 1618 | O | TYR | 1654 | 24.035 | 18.043 | 11.344 | 1.00 | 73.21 |
| ATOM 1619 | N | LYS | 1655 | 22.269 | 17.275 | 10.183 | 1.00 | 73.05 |
| ATOM 1621 | CA | LYS | 1655 | 21.424 | 17.108 | 11.363 | 1.00 | 74.81 |
| ATOM 1622 | CB | LYS | 1655 | 19.955 | 17.124 | 10.953 | 1.00 | 75.63 |
| ATOM 1623 | CG | LYS | 1655 | 18.978 | 17.239 | 12.102 | 1.00 | 79.16 |
| ATOM 1624 | CD | LYS | 1655 | 17.581 | 17.513 | 11.576 | 1.00 | 84.09 |
| ATOM 1625 | CE | LYS | 1655 | 16.517 | 17.244 | 12.634 | 1.00 | 87.56 |
| ATOM 1626 | NZ | LYS | 1655 | 15.139 | 17.478 | 12.097 | 1.00 | 89.36 |
| ATOM 1630 | C | LYS | 1655 | 21.738 | 15.834 | 12.156 | 1.00 | 75.72 |
| ATOM 1631 | O | LYS | 1655 | 21.900 | 14.751 | 11.586 | 1.00 | 77.14 |
| ATOM 1632 | N | LYS | 1656 | 21.815 | 15.977 | 13.477 | 1.00 | 75.08 |
| ATOM 1634 | CA | LYS | 1656 | 22.106 | 14.857 | 14.363 | 1.00 | 73.36 |
| ATOM 1635 | CB | LYS | 1656 | 23.062 | 15.296 | 15.477 | 1.00 | 72.88 |
| ATOM 1636 | CG | LYS | 1656 | 24.475 | 15.599 | 15.007 | 1.00 | 72.87 |
| ATOM 1637 | CD | LYS | 1656 | 25.346 | 16.048 | 16.167 | 1.00 | 74.66 |
| ATOM 1638 | CE | LYS | 1656 | 26.830 | 15.945 | 15.828 | 1.00 | 74.84 |
| ATOM 1639 | NZ | LYS | 1656 | 27.701 | 16.322 | 16.981 | 1.00 | 73.74 |
| ATOM 1643 | C | LYS | 1656 | 20.827 | 14.311 | 14.982 | 1.00 | 72.45 |
| ATOM 1644 | O | LYS | 1656 | 19.795 | 14.991 | 15.007 | 1.00 | 72.74 |
| ATOM 1645 | N | THR | 1657 | 20.900 | 13.075 | 15.469 | 1.00 | 71.26 |
| ATOM 1647 | CA | THR | 1657 | 19.763 | 12.426 | 16.107 | 1.00 | 70.05 |
| ATOM 1648 | CB | THR | 1657 | 19.969 | 10.886 | 16.206 | 1.00 | 68.30 |
| ATOM 1649 | OG1 | THR | 1657 | 21.084 | 10.598 | 17.060 | 1.00 | 69.34 |
| ATOM 1651 | CG2 | THR | 1657 | 20.244 | 10.292 | 14.839 | 1.00 | 66.16 |
| ATOM 1652 | C | THR | 1657 | 19.707 | 13.019 | 17.504 | 1.00 | 70.37 |
| ATOM 1653 | O | THR | 1657 | 20.608 | 13.761 | 17.892 | 1.00 | 71.47 |
| ATOM 1654 | N | THR | 1658 | 18.669 | 12.691 | 18.263 | 1.00 | 70.80 |
| ATOM 1656 | CA | THR | 1658 | 18.559 | 13.205 | 19.626 | 1.00 | 71.54 |
| ATOM 1657 | CB | THR | 1658 | 17.334 | 12.600 | 20.325 | 1.00 | 71.20 |
| ATOM 1658 | C | THR | 1658 | 19.844 | 12.865 | 20.394 | 1.00 | 70.91 |
| ATOM 1659 | O | THR | 1658 | 20.429 | 13.722 | 21.063 | 1.00 | 71.25 |
| ATOM 1660 | N | ASN | 1659 | 20.331 | 11.639 | 20.199 | 1.00 | 68.87 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1662 | CA | ASN | 1659 | 21.537 | 11.157 | 20.871 | 1.00 | 65.52 |
| ATOM 1663 | CB | ASN | 1659 | 21.602 | 9.635 | 20.796 | 1.00 | 67.39 |
| ATOM 1664 | CG | ASN | 1659 | 22.419 | 9.032 | 21.916 | 1.00 | 69.42 |
| ATOM 1665 | OD1 | ASN | 1659 | 22.261 | 9.410 | 23.076 | 1.00 | 71.70 |
| ATOM 1666 | ND2 | ASN | 1659 | 23.278 | 8.069 | 21.583 | 1.00 | 68.93 |
| ATOM 1669 | C | ASN | 1659 | 22.830 | 11.749 | 20.318 | 1.00 | 62.51 |
| ATOM 1670 | O | ASN | 1659 | 23.917 | 11.351 | 20.733 | 1.00 | 61.47 |
| ATOM 1671 | N | GLY | 1660 | 22.706 | 12.654 | 19.348 | 1.00 | 59.76 |
| ATOM 1673 | CA | GLY | 1660 | 23.859 | 13.307 | 18.750 | 1.00 | 57.70 |
| ATOM 1674 | C | GLY | 1660 | 24.553 | 12.593 | 17.597 | 1.00 | 56.98 |
| ATOM 1675 | O | GLY | 1660 | 25.659 | 12.979 | 17.199 | 1.00 | 57.55 |
| ATOM 1676 | N | ARG | 1661 | 23.909 | 11.573 | 17.037 | 1.00 | 55.34 |
| ATOM 1678 | CA | ARG | 1661 | 24.504 | 10.826 | 15.928 | 1.00 | 52.28 |
| ATOM 1679 | CB | ARG | 1661 | 24.255 | 9.334 | 16.092 | 1.00 | 50.68 |
| ATOM 1680 | CG | ARG | 1661 | 24.811 | 8.744 | 17.365 | 1.00 | 49.61 |
| ATOM 1681 | CD | ARG | 1661 | 24.542 | 7.267 | 17.361 | 1.00 | 52.30 |
| ATOM 1682 | NE | ARG | 1661 | 24.942 | 6.599 | 18.595 | 1.00 | 53.64 |
| ATOM 1684 | CZ | ARG | 1661 | 24.731 | 5.306 | 18.826 | 1.00 | 56.32 |
| ATOM 1685 | NH1 | ARG | 1661 | 24.124 | 4.559 | 17.901 | 1.00 | 54.04 |
| ATOM 1688 | NH2 | ARG | 1661 | 25.145 | 4.754 | 19.965 | 1.00 | 54.48 |
| ATOM 1691 | C | ARG | 1661 | 24.015 | 11.288 | 14.560 | 1.00 | 49.89 |
| ATOM 1692 | O | ARG | 1661 | 22.916 | 11.812 | 14.429 | 1.00 | 51.43 |
| ATOM 1693 | N | LEU | 1662 | 24.839 | 11.080 | 13.542 | 1.00 | 45.78 |
| ATOM 1695 | CA | LEU | 1662 | 24.503 | 11.481 | 12.186 | 1.00 | 43.05 |
| ATOM 1696 | CB | LEU | 1662 | 25.762 | 12.020 | 11.492 | 1.00 | 42.15 |
| ATOM 1697 | CG | LEU | 1662 | 26.351 | 13.306 | 12.088 | 1.00 | 40.60 |
| ATOM 1698 | CD1 | LEU | 1662 | 27.780 | 13.512 | 11.641 | 1.00 | 38.14 |
| ATOM 1699 | CD2 | LEU | 1662 | 25.484 | 14.499 | 11.705 | 1.00 | 42.00 |
| ATOM 1700 | C | LEU | 1662 | 23.867 | 10.346 | 11.370 | 1.00 | 41.81 |
| ATOM 1701 | O | LEU | 1662 | 24.548 | 9.406 | 10.957 | 1.00 | 40.46 |
| ATOM 1702 | N | PRO | 1663 | 22.546 | 10.428 | 11.118 | 1.00 | 40.49 |
| ATOM 1703 | CD | PRO | 1663 | 21.659 | 11.519 | 11.561 | 1.00 | 40.60 |
| ATOM 1704 | CA | PRO | 1663 | 21.794 | 9.423 | 10.351 | 1.00 | 38.17 |
| ATOM 1705 | CB | PRO | 1663 | 20.433 | 10.095 | 10.158 | 1.00 | 38.43 |
| ATOM 1706 | CG | PRO | 1663 | 20.282 | 10.901 | 11.414 | 1.00 | 40.65 |
| ATOM 1707 | C | PRO | 1663 | 22.445 | 9.059 | 9.012 | 1.00 | 35.40 |
| ATOM 1708 | O | PRO | 1663 | 22.265 | 7.949 | 8.521 | 1.00 | 33.01 |
| ATOM 1709 | N | VAL | 1664 | 23.200 | 9.989 | 8.426 | 1.00 | 34.56 |
| ATOM 1711 | CA | VAL | 1664 | 23.889 | 9.722 | 1.160 | 1.00 | 32.91 |
| ATOM 1712 | CB | VAL | 1664 | 24.757 | 10.916 | 6.659 | 1.00 | 33.13 |
| ATOM 1713 | CG1 | VAL | 1664 | 23.912 | 11.929 | 5.968 | 1.00 | 33.44 |
| ATOM 1714 | CG2 | VAL | 1664 | 25.521 | 11.554 | 7.792 | 1.00 | 33.68 |
| ATOM 1715 | C | VAL | 1664 | 24.812 | 8.511 | 7.266 | 1.00 | 30.58 |
| ATOM 1716 | O | VAL | 1664 | 25.157 | 7.903 | 6.257 | 1.00 | 29.20 |
| ATOM 1717 | N | LYS | 1665 | 25.211 | 8.171 | 8.489 | 1.00 | 28.02 |
| ATOM 1719 | CA | LYS | 1665 | 26.102 | 7.044 | 8.726 | 1.00 | 24.95 |
| ATOM 1720 | CB | LYS | 1665 | 26.749 | 7.153 | 10.098 | 1.00 | 24.39 |
| ATOM 1721 | CG | LYS | 1665 | 27.811 | 8.231 | 10.140 | 1.00 | 28.36 |
| ATOM 1722 | CD | LYS | 1665 | 28.189 | 8.628 | 11.548 | 1.00 | 29.24 |
| ATOM 1723 | CE | LYS | 1665 | 29.269 | 9.690 | 11.489 | 1.00 | 31.15 |
| ATOM 1724 | NZ | LYS | 1665 | 29.639 | 10.194 | 12.836 | 1.00 | 35.47 |
| ATOM 1728 | C | LYS | 1665 | 25.440 | 5.692 | 8.543 | 1.00 | 25.16 |
| ATOM 1729 | O | LYS | 1665 | 26.096 | 4.671 | 8.627 | 1.00 | 24.34 |
| ATOM 1730 | N | TRP | 1666 | 24.138 | 5.698 | 8.286 | 1.00 | 25.16 |
| ATOM 1732 | CA | TRP | 1666 | 23.414 | 4.461 | 8.053 | 1.00 | 26.61 |
| ATOM 1733 | CB | TRP | 1666 | 22.157 | 4.412 | 8.917 | 1.00 | 28.17 |
| ATOM 1734 | CG | TRP | 1666 | 22.428 | 3.931 | 10.330 | 1.00 | 30.26 |
| ATOM 1735 | CD2 | TRP | 1666 | 22.930 | 4.714 | 11.426 | 1.00 | 26.92 |
| ATOM 1736 | CE2 | TRP | 1666 | 23.063 | 3.837 | 12.537 | 1.00 | 26.34 |
| ATOM 1737 | CE3 | TRP | 1666 | 23.286 | 6.057 | 11.598 | 1.00 | 24.69 |
| ATOM 1738 | CD1 | TRP | 1666 | 22.276 | 2.656 | 10.800 | 1.00 | 26.44 |
| ATOM 1739 | NE1 | TRP | 1666 | 22.659 | 2.592 | 12.118 | 1.00 | 25.65 |
| ATOM 1741 | CZ2 | TRP | 1666 | 23.535 | 4.264 | 13.779 | 1.00 | 24.97 |
| ATOM 1742 | CZ3 | TRP | 1666 | 23.758 | 6.484 | 12.837 | 1.00 | 22.23 |
| ATOM 1743 | CH2 | TRP | 1666 | 23.877 | 5.587 | 13.908 | 1.00 | 24.97 |
| ATOM 1744 | C | TRP | 1666 | 23.048 | 4.345 | 6.572 | 1.00 | 27.24 |
| ATOM 1745 | O | TRP | 1666 | 22.573 | 3.301 | 6.116 | 1.00 | 29.16 |
| ATOM 1746 | N | MET | 1667 | 23.355 | 5.390 | 5.811 | 1.00 | 26.70 |
| ATOM 1748 | CA | MET | 1667 | 23.022 | 5.444 | 4.398 | 1.00 | 25.21 |
| ATOM 1749 | CB | MET | 1667 | 22.828 | 6.893 | 3.963 | 1.00 | 28.81 |
| ATOM 1750 | CG | MET | 1667 | 21.704 | 7.630 | 4.637 | 1.00 | 35.42 |
| ATOM 1751 | SD | MET | 1667 | 21.567 | 9.283 | 3.924 | 1.00 | 42.64 |
| ATOM 1752 | CE | MET | 1667 | 20.959 | 8.858 | 2.369 | 1.00 | 41.32 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1753 | C | MET | 1667 | 23.984 | 4.807 | 3.417 | 1.00 | 25.03 |
| ATOM 1754 | O | MET | 1667 | 25.182 | 5.047 | 3.446 | 1.00 | 24.24 |
| ATOM 1755 | N | ALA | 1668 | 23.420 | 4.034 | 2.501 | 1.00 | 26.70 |
| ATOM 1757 | CA | ALA | 1668 | 24.186 | 3.398 | 1.441 | 1.00 | 27.82 |
| ATOM 1758 | CB | ALA | 1668 | 23.272 | 2.509 | 0.601 | 1.00 | 25.36 |
| ATOM 1759 | C | ALA | 1668 | 24.738 | 4.528 | 0.575 | 1.00 | 28.42 |
| ATOM 1760 | O | ALA | 1668 | 24.044 | 5.521 | 0.321 | 1.00 | 27.52 |
| ATOM 1761 | N | PRO | 1669 | 25.972 | 4.374 | 0.065 | 1.00 | 28.95 |
| ATOM 1762 | CD | PRO | 1669 | 26.867 | 3.214 | 0.170 | 1.00 | 27.98 |
| ATOM 1763 | CA | PRO | 1669 | 26.571 | 5.418 | −0.775 | 1.00 | 28.76 |
| ATOM 1764 | CB | PRO | 1669 | 27.814 | 4.731 | −1.326 | 1.00 | 28.58 |
| ATOM 1765 | CG | PRO | 1669 | 28.193 | 3.809 | −0.209 | 1.00 | 30.22 |
| ATOM 1766 | C | PRO | 1669 | 25.647 | 5.909 | −1.893 | 1.00 | 27.08 |
| ATOM 1767 | O | PRO | 1669 | 25.496 | 7.107 | −2.093 | 1.00 | 28.31 |
| ATOM 1768 | N | GLU | 1670 | 24.993 | 4.997 | −2.595 | 1.00 | 25.42 |
| ATOM 1770 | CA | GLU | 1670 | 24.110 | 5.423 | −3.673 | 1.00 | 27.02 |
| ATOM 1771 | CB | GLU | 1670 | 23.680 | 4.233 | −4.542 | 1.00 | 27.18 |
| ATOM 1772 | CG | GLU | 1670 | 22.662 | 3.294 | −3.911 | 1.00 | 27.66 |
| ATOM 1773 | CD | GLU | 1670 | 23.280 | 2.162 | −3.112 | 1.00 | 27.75 |
| ATOM 1774 | OE1 | GLU | 1670 | 22.488 | 1.309 | −2.647 | 1.00 | 27.12 |
| ATOM 1775 | OE2 | GLU | 1670 | 24.526 | 2.114 | −2.944 | 1.00 | 21.64 |
| ATOM 1776 | C | GLU | 1670 | 22.896 | 6.229 | −3.189 | 1.00 | 26.88 |
| ATOM 1777 | O | GLU | 1670 | 22.348 | 7.037 | −3.929 | 1.00 | 24.52 |
| ATOM 1778 | N | ALA | 1671 | 22.477 | 6.009 | −1.948 | 1.00 | 29.43 |
| ATOM 1780 | CA | ALA | 1671 | 21.342 | 6.744 | −1.392 | 1.00 | 29.29 |
| ATOM 1781 | CB | ALA | 1671 | 20.751 | 5.989 | −0.217 | 1.00 | 26.98 |
| ATOM 1782 | C | ALA | 1671 | 21.826 | 8.124 | −0.939 | 1.00 | 31.14 |
| ATOM 1783 | O | ALA | 1671 | 21.159 | 9.135 | −1.143 | 1.00 | 31.67 |
| ATOM 1784 | N | LEU | 1672 | 23.013 | 8.139 | −0.343 | 1.00 | 32.31 |
| ATOM 1786 | CA | LEU | 1672 | 23.636 | 9.352 | 0.154 | 1.00 | 33.79 |
| ATOM 1787 | CB | LEU | 1672 | 24.841 | 8.986 | 1.008 | 1.00 | 34.49 |
| ATOM 1788 | CG | LEU | 1672 | 25.585 | 10.166 | 1.618 | 1.00 | 37.16 |
| ATOM 1789 | CD1 | LEU | 1672 | 24.713 | 10.840 | 2.666 | 1.00 | 42.22 |
| ATOM 1790 | CD2 | LEU | 1672 | 26.863 | 9.665 | 2.237 | 1.00 | 33.93 |
| ATOM 1791 | C | LEU | 1672 | 24.078 | 10.280 | −0.972 | 1.00 | 36.30 |
| ATOM 1792 | O | LEU | 1672 | 23.789 | 11.478 | −0.949 | 1.00 | 39.09 |
| ATOM 1793 | N | PHE | 1673 | 24.770 | 9.723 | −1.957 | 1.00 | 34.39 |
| ATOM 1795 | CA | PHE | 1673 | 25.266 | 10.504 | −3.075 | 1.00 | 33.81 |
| ATOM 1796 | CB | PHE | 1673 | 26.553 | 9.874 | −3.625 | 1.00 | 33.15 |
| ATOM 1797 | CG | PHE | 1673 | 27.661 | 9.761 | −2.617 | 1.00 | 33.44 |
| ATOM 1798 | CD1 | PHE | 1673 | 28.313 | 8.545 | −2.419 | 1.00 | 32.17 |
| ATOM 1799 | CD2 | PHE | 1673 | 28.055 | 10.867 | −1.861 | 1.00 | 34.87 |
| ATOM 1800 | CE1 | PHE | 1673 | 29.346 | 8.419 | −1.484 | 1.00 | 31.98 |
| ATOM 1801 | CE2 | PHE | 1673 | 29.090 | 10.757 | −0.919 | 1.00 | 36.31 |
| ATOM 1802 | CZ | PHE | 1673 | 29.736 | 9.525 | −0.732 | 1.00 | 34.55 |
| ATOM 1803 | C | PHE | 1673 | 24.273 | 10.670 | −4.217 | 1.00 | 34.79 |
| ATOM 1804 | O | PHE | 1673 | 24.135 | 11.754 | −4.765 | 1.00 | 35.74 |
| ATOM 1805 | N | ASP | 1674 | 23.584 | 9.588 | −4.572 | 1.00 | 37.31 |
| ATOM 1807 | CA | ASP | 1674 | 22.650 | 9.601 | −5.698 | 1.00 | 35.61 |
| ATOM 1808 | CB | ASP | 1674 | 22.917 | 8.392 | −6.600 | 1.00 | 37.01 |
| ATOM 1809 | CG | ASP | 1674 | 24.362 | 8.288 | −7.041 | 1.00 | 41.02 |
| ATOM 1810 | OD1 | ASP | 1674 | 25.030 | 9.340 | −7.194 | 1.00 | 43.07 |
| ATOM 1811 | OD2 | ASP | 1674 | 24.828 | 7.145 | −7.251 | 1.00 | 42.24 |
| ATOM 1812 | C | ASP | 1674 | 21.162 | 9.632 | −5.360 | 1.00 | 37.06 |
| ATOM 1813 | O | ASP | 1674 | 20.315 | 9.506 | −6.257 | 1.00 | 36.37 |
| ATOM 1814 | N | ARG | 1675 | 20.840 | 9.745 | −4.077 | 1.00 | 37.78 |
| ATOM 1816 | CA | ARG | 1675 | 19.445 | 9.791 | −3.650 | 1.00 | 39.41 |
| ATOM 1817 | CB | ARG | 1675 | 18.832 | 11.137 | −4.039 | 1.00 | 44.39 |
| ATOM 1818 | CG | ARG | 1675 | 19.413 | 12.299 | −3.269 | 1.00 | 54.30 |
| ATOM 1819 | CD | ARG | 1675 | 19.516 | 13.551 | −4.127 | 1.00 | 63.84 |
| ATOM 1820 | NE | ARG | 1675 | 20.060 | 14.664 | −3.349 | 1.00 | 73.69 |
| ATOM 1822 | CZ | ARG | 1675 | 19.652 | 15.925 | −3.453 | 1.00 | 77.10 |
| ATOM 1823 | NH1 | ARG | 1675 | 18.695 | 16.253 | −4.312 | 1.00 | 79.65 |
| ATOM 1826 | NH2 | ARG | 1675 | 20.177 | 16.855 | −2.665 | 1.00 | 79.31 |
| ATOM 1829 | C | ARG | 1675 | 18.617 | 8.639 | −4.221 | 1.00 | 37.46 |
| ATOM 1830 | O | ARG | 1675 | 17.447 | 8.808 | −4.557 | 1.00 | 38.57 |
| ATOM 1831 | N | ILE | 1676 | 19.235 | 7.475 | −4.351 | 1.00 | 34.37 |
| ATOM 1833 | CA | ILE | 1676 | 18.545 | 6.313 | −4.874 | 1.00 | 32.99 |
| ATOM 1834 | CB | ILE | 1676 | 19.358 | 5.644 | −5.976 | 1.00 | 33.98 |
| ATOM 1835 | CG2 | ILE | 1676 | 18.552 | 4.529 | −6.602 | 1.00 | 35.04 |
| ATOM 1836 | CG1 | ILE | 1676 | 19.708 | 6.663 | −7.050 | 1.00 | 34.92 |
| ATOM 1837 | CD1 | ILE | 1676 | 20.799 | 6.200 | −7.962 | 1.00 | 41.16 |
| ATOM 1838 | C | ILE | 1676 | 18.315 | 5.315 | −3.743 | 1.00 | 31.55 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1839 | O | ILE | 1676 | 19.245 | 4.632 | −3.300 | 1.00 | 30.65 |
| ATOM 1840 | N | TYR | 1677 | 17.082 | 5.279 | −3.246 | 1.00 | 30.88 |
| ATOM 1842 | CA | TYR | 1677 | 16.701 | 4.371 | −2.173 | 1.00 | 27.10 |
| ATOM 1843 | CB | TYR | 1677 | 15.771 | 5.074 | −1.208 | 1.00 | 28.30 |
| ATOM 1844 | CG | TYR | 1677 | 16.457 | 6.136 | −0.406 | 1.00 | 30.61 |
| ATOM 1845 | CD1 | TYR | 1677 | 16.598 | 7.432 | −0.905 | 1.00 | 30.82 |
| ATOM 1846 | CE1 | TYR | 1677 | 17.212 | 8.424 | −0.159 | 1.00 | 30.75 |
| ATOM 1847 | CD2 | TYR | 1677 | 16.952 | 5.857 | 0.863 | 1.00 | 29.75 |
| ATOM 1848 | CE2 | TYR | 1677 | 17.567 | 6.842 | 1.621 | 1.00 | 32.62 |
| ATOM 1849 | CZ | TYR | 1677 | 17.688 | 8.125 | 1.110 | 1.00 | 34.51 |
| ATOM 1850 | OH | TYR | 1677 | 18.238 | 9.118 | 1.888 | 1.00 | 38.89 |
| ATOM 1852 | C | TYR | 1677 | 16.029 | 3.149 | −2.743 | 1.00 | 25.47 |
| ATOM 1853 | O | TYR | 1677 | 15.132 | 3.264 | −3.578 | 1.00 | 26.00 |
| ATOM 1854 | N | THR | 1678 | 16.459 | 1.983 | −2.272 | 1.00 | 24.27 |
| ATOM 1856 | CA | THR | 1678 | 15.942 | 0.701 | −2.734 | 1.00 | 24.09 |
| ATOM 1857 | CB | THR | 1678 | 16.830 | 0.123 | −3.853 | 1.00 | 24.19 |
| ATOM 1858 | OG1 | THR | 1678 | 18.165 | −0.008 | −3.349 | 1.00 | 27.81 |
| ATOM 1860 | CG2 | THR | 1678 | 16.843 | 1.009 | −5.085 | 1.00 | 24.15 |
| ATOM 1861 | C | THR | 1678 | 15.979 | −0.297 | −1.577 | 1.00 | 25.02 |
| ATOM 1862 | O | THR | 1678 | 16.379 | 0.036 | −0.465 | 1.00 | 27.65 |
| ATOM 1863 | N | HIS | 1679 | 15.569 | −1.530 | −1.844 | 1.00 | 25.04 |
| ATOM 1865 | CA | HIS | 1679 | 15.591 | −2.560 | −0.818 | 1.00 | 24.35 |
| ATOM 1866 | CB | HIS | 1679 | 14.853 | −3.812 | −1.298 | 1.00 | 23.78 |
| ATOM 1867 | CG | HIS | 1679 | 13.390 | −3.592 | −1.536 | 1.00 | 27.24 |
| ATOM 1868 | CD2 | HIS | 1679 | 12.627 | −3.758 | −2.643 | 1.00 | 28.22 |
| ATOM 1869 | ND1 | HIS | 1679 | 12.532 | −3.137 | −0.551 | 1.00 | 30.64 |
| ATOM 1871 | CE1 | HIS | 1679 | 11.310 | −3.028 | −1.041 | 1.00 | 28.13 |
| ATOM 1872 | NE2 | HIS | 1679 | 11.339 | −3.400 | −2.307 | 1.00 | 28.52 |
| ATOM 1874 | C | HIS | 1679 | 17.056 | −2.846 | −0.514 | 1.00 | 22.52 |
| ATOM 1875 | O | HIS | 1679 | 17.419 | −3.179 | 0.613 | 1.00 | 22.58 |
| ATOM 1876 | N | GLN | 1680 | 17.898 | −2.604 | −1.516 | 1.00 | 24.34 |
| ATOM 1878 | CA | GLN | 1680 | 19.341 | −2.800 | −1.406 | 1.00 | 23.52 |
| ATOM 1879 | CB | GLN | 1680 | 19.998 | −2.781 | −2.782 | 1.00 | 25.36 |
| ATOM 1880 | CG | GLN | 1680 | 19.741 | −4.050 | −3.577 | 1.00 | 33.28 |
| ATOM 1881 | CD | GLN | 1680 | 19.212 | −3.763 | −4.949 | 1.00 | 34.68 |
| ATOM 1882 | OE1 | GLN | 1680 | 18.683 | −2.686 | −5.187 | 1.00 | 41.24 |
| ATOM 1883 | NE2 | GLN | 1680 | 19.357 | −4.713 | −5.867 | 1.00 | 32.10 |
| ATOM 1886 | C | GLN | 1680 | 19.998 | −1.767 | −0.514 | 1.00 | 23.38 |
| ATOM 1887 | O | GLN | 1680 | 20.925 | −2.094 | 0.224 | 1.00 | 25.12 |
| ATOM 1888 | N | SER | 1681 | 19.533 | −0.521 | −0.562 | 1.00 | 20.87 |
| ATOM 1890 | CA | SER | 1681 | 20.133 | 0.480 | 0.303 | 1.00 | 20.53 |
| ATOM 1891 | CB | SER | 1681 | 19.821 | 1.919 | −0.151 | 1.00 | 19.58 |
| ATOM 1892 | OG | SER | 1681 | 18.445 | 2.126 | −0.425 | 1.00 | 20.67 |
| ATOM 1894 | C | SER | 1681 | 19.696 | 0.189 | 1.741 | 1.00 | 22.22 |
| ATOM 1895 | O | SER | 1681 | 20.439 | 0.455 | 2.681 | 1.00 | 23.62 |
| ATOM 1896 | N | ASP | 1682 | 18.530 | −0.436 | 1.900 | 1.00 | 22.44 |
| ATOM 1898 | CA | ASP | 1682 | 18.054 | −0.816 | 3.231 | 1.00 | 22.70 |
| ATOM 1899 | CB | ASP | 1682 | 16.607 | −1.293 | 3.180 | 1.00 | 24.24 |
| ATOM 1900 | CG | ASP | 1682 | 15.603 | −0.165 | 3.352 | 1.00 | 28.23 |
| ATOM 1901 | OD1 | ASP | 1682 | 14.410 | −0.425 | 3.108 | 1.00 | 28.14 |
| ATOM 1902 | OD2 | ASP | 1682 | 15.976 | 0.960 | 3.757 | 1.00 | 25.23 |
| ATOM 1903 | C | ASP | 1682 | 18.926 | −1.941 | 3.777 | 1.00 | 23.92 |
| ATOM 1904 | O | ASP | 1682 | 19.121 | −2.057 | 4.990 | 1.00 | 26.24 |
| ATOM 1905 | N | VAL | 1683 | 19.433 | −2.788 | 2.884 | 1.00 | 23.67 |
| ATOM 1907 | CA | VAL | 1683 | 20.300 | −3.888 | 3.302 | 1.00 | 22.42 |
| ATOM 1908 | CB | VAL | 1683 | 20.562 | −4.881 | 2.141 | 1.00 | 23.70 |
| ATOM 1909 | CG1 | VAL | 1683 | 21.724 | −5.802 | 2.459 | 1.00 | 19.73 |
| ATOM 1910 | CG2 | VAL | 1683 | 19.292 | −5.713 | 1.889 | 1.00 | 19.85 |
| ATOM 1911 | C | VAL | 1683 | 21.584 | −3.298 | 3.860 | 1.00 | 21.94 |
| ATOM 1912 | O | VAL | 1683 | 22.030 | −3.688 | 4.938 | 1.00 | 22.69 |
| ATOM 1913 | N | TRP | 1684 | 22.141 | −2.320 | 3.154 | 1.00 | 20.51 |
| ATOM 1915 | CA | TRP | 1684 | 23.349 | −1.633 | 3.611 | 1.00 | 20.31 |
| ATOM 1916 | CB | TRP | 1684 | 23.659 | −0.446 | 2.680 | 1.00 | 19.01 |
| ATOM 1917 | CG | TRP | 1684 | 24.802 | 0.410 | 3.145 | 1.00 | 20.67 |
| ATOM 1918 | CD2 | TRP | 1684 | 26.114 | 0.468 | 2.587 | 1.00 | 22.26 |
| ATOM 1919 | CE2 | TRP | 1684 | 26.890 | 1.316 | 3.408 | 1.00 | 21.22 |
| ATOM 1920 | CE3 | TRP | 1684 | 26.718 | −0.127 | 1.463 | 1.00 | 22.51 |
| ATOM 1921 | CD1 | TRP | 1684 | 24.825 | 1.229 | 4.248 | 1.00 | 19.91 |
| ATOM 1922 | NE1 | TRP | 1684 | 26.079 | 1.763 | 4.414 | 1.00 | 18.59 |
| ATOM 1924 | CZ2 | TRP | 1684 | 28.236 | 1.586 | 3.148 | 1.00 | 20.81 |
| ATOM 1925 | CZ3 | TRP | 1684 | 28.059 | 0.141 | 1.204 | 1.00 | 22.01 |
| ATOM 1926 | CH2 | TRP | 1684 | 28.806 | 0.992 | 2.047 | 1.00 | 23.34 |
| ATOM 1927 | C | TRP | 1684 | 23.131 | −1.150 | 5.069 | 1.00 | 21.49 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 1928 | O | TRP | 1684 | 23.958 | −1.412 | 5.954 | 1.00 | 23.34 |
| ATOM 1929 | N | SER | 1685 | 22.015 | −0.463 | 5.308 | 1.00 | 21.84 |
| ATOM 1931 | CA | SER | 1685 | 21.652 | 0.042 | 6.634 | 1.00 | 20.02 |
| ATOM 1932 | CB | SER | 1685 | 20.310 | 0.773 | 6.559 | 1.00 | 19.12 |
| ATOM 1933 | OG | SER | 1685 | 20.335 | 1.791 | 5.578 | 1.00 | 21.62 |
| ATOM 1935 | C | SER | 1685 | 21.551 | −1.111 | 7.648 | 1.00 | 22.64 |
| ATOM 1936 | O | SER | 1685 | 21.908 | −0.946 | 8.829 | 1.00 | 22.09 |
| ATOM 1937 | N | PHE | 1686 | 21.043 | −2.266 | 7.202 | 1.00 | 22.44 |
| ATOM 1939 | CA | PHE | 1686 | 20.939 | −3.438 | 8.075 | 1.00 | 22.91 |
| ATOM 1940 | CB | PHE | 1686 | 20.196 | −4.588 | 7.380 | 1.00 | 23.75 |
| ATOM 1941 | CG | PHE | 1686 | 20.027 | −5.808 | 8.256 | 1.00 | 23.61 |
| ATOM 1942 | CD1 | PHE | 1686 | 19.220 | −5.757 | 9.388 | 1.00 | 21.21 |
| ATOM 1943 | CD2 | PHE | 1686 | 20.731 | −6.976 | 7.990 | 1.00 | 23.91 |
| ATOM 1944 | CE1 | PHE | 1686 | 19.118 | −6.836 | 10.240 | 1.00 | 20.66 |
| ATOM 1945 | CE2 | PHE | 1686 | 20.636 | −8.074 | 8.841 | 1.00 | 22.47 |
| ATOM 1946 | CZ | PHE | 1686 | 19.828 | −7.999 | 9.972 | 1.00 | 23.35 |
| ATOM 1947 | C | PHE | 1686 | 22.339 | −3.904 | 8.522 | 1.00 | 22.60 |
| ATOM 1948 | O | PHE | 1686 | 22.526 | −4.382 | 9.646 | 1.00 | 22.83 |
| ATOM 1949 | N | GLY | 1687 | 23.312 | −3.770 | 7.626 | 1.00 | 23.82 |
| ATOM 1951 | CA | GLY | 1687 | 24.682 | −4.140 | 7.941 | 1.00 | 22.58 |
| ATOM 1952 | C | GLY | 1687 | 25.175 | −3.262 | 9.071 | 1.00 | 21.49 |
| ATOM 1953 | O | GLY | 1687 | 25.832 | −3.749 | 9.990 | 1.00 | 21.62 |
| ATOM 1954 | N | VAL | 1688 | 24.849 | −1.968 | 9.008 | 1.00 | 21.15 |
| ATOM 1956 | CA | VAL | 1688 | 25.229 | −1.008 | 10.052 | 1.00 | 20.56 |
| ATOM 1957 | CB | VAL | 1688 | 24.894 | 0.479 | 9.647 | 1.00 | 17.69 |
| ATOM 1958 | CG1 | VAL | 1688 | 25.408 | 1.456 | 10.690 | 1.00 | 15.11 |
| ATOM 1959 | CG2 | VAL | 1688 | 25.518 | 0.821 | 8.314 | 1.00 | 11.54 |
| ATOM 1960 | C | VAL | 1688 | 24.494 | −1.398 | 11.346 | 1.00 | 22.60 |
| ATOM 1961 | O | VAL | 1688 | 25.083 | −1.407 | 12.428 | 1.00 | 25.23 |
| ATOM 1962 | N | LEU | 1689 | 23.215 | −1.755 | 11.229 | 1.00 | 26.09 |
| ATOM 1964 | CA | LEU | 1689 | 22.423 | −2.175 | 12.387 | 1.00 | 25.16 |
| ATOM 1965 | CB | LEU | 1689 | 20.976 | −2.455 | 11.965 | 1.00 | 25.91 |
| ATOM 1966 | CG | LEU | 1689 | 19.913 | −2.560 | 13.068 | 1.00 | 27.54 |
| ATOM 1967 | CD1 | LEU | 1689 | 18.557 | −2.241 | 12.496 | 1.00 | 28.11 |
| ATOM 1968 | CD2 | LEU | 1689 | 19.898 | −3.940 | 13.704 | 1.00 | 31.67 |
| ATOM 1969 | C | LEU | 1689 | 23.055 | −3.426 | 13.018 | 1.00 | 27.49 |
| ATOM 1970 | O | LEU | 1689 | 23.128 | −3.532 | 14.246 | 1.00 | 28.99 |
| ATOM 1971 | N | LEU | 1690 | 23.485 | −4.374 | 12.180 | 1.00 | 27.67 |
| ATOM 1973 | CA | LEU | 1690 | 24.149 | −5.596 | 12.643 | 1.00 | 26.76 |
| ATOM 1974 | CB | LEU | 1690 | 24.616 | −6.453 | 11.456 | 1.00 | 28.58 |
| ATOM 1975 | CG | LEU | 1690 | 23.651 | −7.406 | 10.733 | 1.00 | 29.46 |
| ATOM 1976 | CD1 | LEU | 1690 | 24.372 | −8.064 | 9.565 | 1.00 | 27.79 |
| ATOM 1977 | CD2 | LEU | 1690 | 23.130 | −8.488 | 11.691 | 1.00 | 28.15 |
| ATOM 1978 | C | LEU | 1690 | 25.362 | −5.176 | 13.476 | 1.00 | 26.19 |
| ATOM 1979 | O | LEU | 1690 | 25.565 | −5.670 | 14.597 | 1.00 | 25.29 |
| ATOM 1980 | N | TRP | 1691 | 26.124 | −4.217 | 12.946 | 1.00 | 25.89 |
| ATOM 1982 | CA | TRP | 1691 | 27.302 | −3.682 | 13.631 | 1.00 | 27.31 |
| ATOM 1983 | CB | TRP | 1691 | 27.979 | −2.628 | 12.755 | 1.00 | 25.21 |
| ATOM 1984 | CG | TRP | 1691 | 29.338 | −2.170 | 13.257 | 1.00 | 27.00 |
| ATOM 1985 | CD2 | TRP | 1691 | 29.606 | −1.060 | 14.134 | 1.00 | 24.28 |
| ATOM 1986 | CE2 | TRP | 1691 | 31.001 | −0.988 | 14.297 | 1.00 | 23.03 |
| ATOM 1987 | CE3 | TRP | 1691 | 28.792 | −0.118 | 14.778 | 1.00 | 22.80 |
| ATOM 1988 | CD1 | TRP | 1691 | 30.562 | −2.712 | 12.944 | 1.00 | 24.10 |
| ATOM 1989 | NE1 | TRP | 1691 | 31.557 | −2.010 | 13.567 | 1.00 | 23.41 |
| ATOM 1991 | CZ2 | TRP | 1691 | 31.617 | −0.011 | 15.097 | 1.00 | 25.00 |
| ATOM 1992 | CZ3 | TRP | 1691 | 29.398 | 0.851 | 15.573 | 1.00 | 26.78 |
| ATOM 1993 | CH2 | TRP | 1691 | 30.802 | 0.900 | 15.719 | 1.00 | 27.78 |
| ATOM 1994 | C | TRP | 1691 | 26.947 | −3.088 | 15.012 | 1.00 | 28.70 |
| ATOM 1995 | O | TRP | 1691 | 27.708 | −3.245 | 15.974 | 1.00 | 29.56 |
| ATOM 1996 | N | GLU | 1692 | 25.808 | −2.400 | 15.104 | 1.00 | 29.51 |
| ATOM 1998 | CA | GLU | 1692 | 25.349 | −1.817 | 16.371 | 1.00 | 27.55 |
| ATOM 1999 | CB | GLU | 1692 | 24.120 | −0.935 | 16.171 | 1.00 | 28.35 |
| ATOM 2000 | CG | GLU | 1692 | 24.273 | 0.221 | 15.219 | 1.00 | 24.70 |
| ATOM 2001 | CD | GLU | 1692 | 22.982 | 0.989 | 15.100 | 1.00 | 25.44 |
| ATOM 2002 | OE1 | GLU | 1692 | 22.224 | 0.744 | 14.148 | 1.00 | 24.34 |
| ATOM 2003 | OE2 | GLU | 1692 | 22.696 | 1.816 | 15.982 | 1.00 | 27.57 |
| ATOM 2004 | C | GLU | 1692 | 24.958 | −2.918 | 17.352 | 1.00 | 28.74 |
| ATOM 2005 | O | GLU | 1692 | 25.099 | −2.753 | 18.557 | 1.00 | 28.76 |
| ATOM 2006 | N | ILE | 1693 | 24.421 | −4.023 | 16.844 | 1.00 | 29.23 |
| ATOM 2008 | CA | ILE | 1693 | 24.027 | −5.125 | 17.712 | 1.00 | 27.48 |
| ATOM 2009 | CB | ILE | 1693 | 23.205 | −6.226 | 16.944 | 1.00 | 28.80 |
| ATOM 2010 | CG2 | ILE | 1693 | 22.983 | −7.469 | 17.842 | 1.00 | 22.98 |
| ATOM 2011 | CG1 | ILE | 1693 | 21.840 | −5.658 | 16.508 | 1.00 | 27.36 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2012 | CD1 | ILE | 1693 | 21.005 | −6.585 | 15.635 | 1.00 | 24.84 |
| ATOM 2013 | C | ILE | 1693 | 25.259 | −5.750 | 18.357 | 1.00 | 27.27 |
| ATOM 2014 | O | ILE | 1693 | 25.320 | −5.902 | 19.575 | 1.00 | 28.15 |
| ATOM 2015 | N | PHE | 1694 | 26.273 | −6.043 | 17.552 | 1.00 | 27.83 |
| ATOM 2017 | CA | PHE | 1694 | 27.473 | −6.677 | 18.095 | 1.00 | 29.88 |
| ATOM 2018 | CB | PHE | 1694 | 28.143 | −7.525 | 17.011 | 1.00 | 28.66 |
| ATOM 2019 | CG | PHE | 1694 | 27.223 | −8.574 | 16.463 | 1.00 | 29.92 |
| ATOM 2020 | CD1 | PHE | 1694 | 26.628 | −8.424 | 15.220 | 1.00 | 30.20 |
| ATOM 2021 | CD2 | PHE | 1694 | 26.809 | −9.630 | 17.269 | 1.00 | 30.81 |
| ATOM 2022 | CE1 | PHE | 1694 | 25.625 | −9.294 | 14.801 | 1.00 | 32.42 |
| ATOM 2023 | CE2 | PHE | 1694 | 25.805 | −10.508 | 16.857 | 1.00 | 32.30 |
| ATOM 2024 | CZ | PHE | 1694 | 25.210 | −10.337 | 15.628 | 1.00 | 31.13 |
| ATOM 2025 | C | PHE | 1694 | 28.429 | −5.784 | 18.890 | 1.00 | 31.07 |
| ATOM 2026 | O | PHE | 1694 | 29.376 | −6.273 | 19.509 | 1.00 | 33.16 |
| ATOM 2027 | N | THR | 1695 | 28.157 | −4.480 | 18.897 | 1.00 | 29.20 |
| ATOM 2029 | CA | THR | 1695 | 28.934 | −3.532 | 19.670 | 1.00 | 27.38 |
| ATOM 2030 | CB | THR | 1695 | 29.412 | −2.333 | 18.823 | 1.00 | 24.77 |
| ATOM 2031 | OG1 | THR | 1695 | 28.287 | −1.652 | 18.274 | 1.00 | 26.27 |
| ATOM 2033 | CG2 | THR | 1695 | 30.305 | −2.800 | 17.706 | 1.00 | 20.18 |
| ATOM 2034 | C | THR | 1695 | 28.053 | −3.034 | 20.822 | 1.00 | 29.84 |
| ATOM 2035 | O | THR | 1695 | 28.430 | −2.103 | 21.548 | 1.00 | 32.77 |
| ATOM 2036 | N | LEU | 1696 | 26.898 | −3.687 | 20.988 | 1.00 | 28.52 |
| ATOM 2038 | CA | LEU | 1696 | 25.915 | −3.364 | 22.029 | 1.00 | 28.82 |
| ATOM 2039 | CB | LEU | 1696 | 26.356 | −3.886 | 23.394 | 1.00 | 32.50 |
| ATOM 2040 | CG | LEU | 1696 | 26.658 | −5.379 | 23.476 | 1.00 | 33.24 |
| ATOM 2041 | CD1 | LEU | 1696 | 27.205 | −5.717 | 24.849 | 1.00 | 34.15 |
| ATOM 2042 | CD2 | LEU | 1696 | 25.398 | −6.150 | 23.191 | 1.00 | 37.24 |
| ATOM 2043 | C | LEU | 1696 | 25.553 | −1.888 | 22.131 | 1.00 | 26.98 |
| ATOM 2044 | O | LEU | 1696 | 25.579 | −1.297 | 23.207 | 1.00 | 27.59 |
| ATOM 2045 | N | GLY | 1697 | 25.148 | −1.317 | 21.007 | 1.00 | 27.86 |
| ATOM 2047 | CA | GLY | 1697 | 24.767 | 0.074 | 20.980 | 1.00 | 27.40 |
| ATOM 2048 | C | GLY | 1697 | 25.927 | 0.962 | 20.618 | 1.00 | 27.47 |
| ATOM 2049 | O | GLY | 1697 | 25.957 | 2.132 | 20.998 | 1.00 | 28.78 |
| ATOM 2050 | N | GLY | 1698 | 26.888 | 0.416 | 19.885 | 1.00 | 27.26 |
| ATOM 2052 | CA | GLY | 1698 | 28.031 | 1.212 | 19.482 | 1.00 | 29.54 |
| ATOM 2053 | C | GLY | 1698 | 27.651 | 2.301 | 18.492 | 1.00 | 31.17 |
| ATOM 2054 | O | GLY | 1698 | 26.669 | 2.177 | 17.755 | 1.00 | 33.73 |
| ATOM 2055 | N | SER | 1699 | 28.418 | 3.380 | 18.481 | 1.00 | 29.96 |
| ATOM 2057 | CA | SER | 1699 | 28.168 | 4.491 | 17.577 | 1.00 | 29.37 |
| ATOM 2058 | CB | SER | 1699 | 28.438 | 5.810 | 18.319 | 1.00 | 31.77 |
| ATOM 2059 | OG | SER | 1699 | 28.575 | 6.919 | 17.431 | 1.00 | 38.42 |
| ATOM 2061 | C | SER | 1699 | 29.093 | 4.350 | 16.369 | 1.00 | 27.98 |
| ATOM 2062 | O | SER | 1699 | 30.299 | 4.310 | 16.529 | 1.00 | 28.18 |
| ATOM 2063 | N | PRO | 1700 | 28.537 | 4.240 | 15.153 | 1.00 | 29.62 |
| ATOM 2064 | CD | PRO | 1700 | 27.104 | 4.259 | 14.794 | 1.00 | 31.22 |
| ATOM 2065 | CA | PRO | 1700 | 29.381 | 4.107 | 13.958 | 1.00 | 28.95 |
| ATOM 2066 | CB | PRO | 1700 | 28.356 | 4.003 | 12.807 | 1.00 | 27.21 |
| ATOM 2067 | CG | PRO | 1700 | 27.095 | 3.556 | 13.460 | 1.00 | 29.33 |
| ATOM 2068 | C | PRO | 1700 | 30.205 | 5.379 | 13.773 | 1.00 | 28.78 |
| ATOM 2069 | O | PRO | 1700 | 29.737 | 6.469 | 14.110 | 1.00 | 30.04 |
| ATOM 2070 | N | TYR | 1701 | 31.426 | 5.239 | 13.264 | 1.00 | 28.35 |
| ATOM 2072 | CA | TYR | 1701 | 32.296 | 6.390 | 12.987 | 1.00 | 30.77 |
| ATOM 2073 | CB | TYR | 1701 | 31.921 | 6.987 | 11.615 | 1.00 | 31.67 |
| ATOM 2074 | CG | TYR | 1701 | 32.060 | 6.037 | 10.454 | 1.00 | 34.61 |
| ATOM 2075 | CD1 | TYR | 1701 | 30.952 | 5.673 | 9.686 | 1.00 | 38.26 |
| ATOM 2076 | CE1 | TYR | 1701 | 31.083 | 4.806 | 8.587 | 1.00 | 40.99 |
| ATOM 2077 | CD2 | TYR | 1701 | 33.301 | 5.520 | 10.106 | 1.00 | 38.16 |
| ATOM 2078 | CE2 | TYR | 1701 | 33.449 | 4.662 | 9.020 | 1.00 | 41.04 |
| ATOM 2079 | CZ | TYR | 1701 | 32.343 | 4.312 | 8.263 | 1.00 | 43.11 |
| ATOM 2080 | OH | TYR | 1701 | 32.531 | 3.478 | 7.181 | 1.00 | 49.53 |
| ATOM 2082 | C | TYR | 1701 | 32.305 | 7.532 | 14.029 | 1.00 | 31.41 |
| ATOM 2083 | O | TYR | 1701 | 32.026 | 8.689 | 13.698 | 1.00 | 33.59 |
| ATOM 2084 | N | PRO | 1702 | 32.635 | 7.230 | 15.296 | 1.00 | 30.92 |
| ATOM 2085 | CD | PRO | 1702 | 32.998 | 5.938 | 15.888 | 1.00 | 32.30 |
| ATOM 2086 | CA | PRO | 1702 | 32.656 | 8.283 | 16.314 | 1.00 | 30.05 |
| ATOM 2087 | CB | PRO | 1702 | 33.123 | 7.548 | 17.561 | 1.00 | 27.77 |
| ATOM 2088 | CG | PRO | 1702 | 32.676 | 6.174 | 17.338 | 1.00 | 32.34 |
| ATOM 2089 | C | PRO | 1702 | 33.659 | 9.366 | 15.944 | 1.00 | 31.42 |
| ATOM 2090 | O | PRO | 1702 | 34.769 | 9.055 | 15.513 | 1.00 | 30.95 |
| ATOM 2091 | N | GLY | 1703 | 33.257 | 10.627 | 16.117 | 1.00 | 31.30 |
| ATOM 2093 | CA | GLY | 1703 | 34.122 | 11.751 | 15.817 | 1.00 | 29.66 |
| ATOM 2094 | C | GLY | 1703 | 34.172 | 12.138 | 14.351 | 1.00 | 31.00 |
| ATOM 2095 | O | GLY | 1703 | 34.752 | 13.165 | 13.999 | 1.00 | 30.69 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2096 | N | VAL | 1704 | 33.551 | 11.331 | 13.491 | 1.00 | 31.11 |
| ATOM 2098 | CA | VAL | 1704 | 33.553 | 11.610 | 12.059 | 1.00 | 29.88 |
| ATOM 2099 | CB | VAL | 1704 | 33.539 | 10.310 | 11.244 | 1.00 | 28.41 |
| ATOM 2100 | CG1 | VAL | 1704 | 33.585 | 10.624 | 9.750 | 1.00 | 26.24 |
| ATOM 2101 | CG2 | VAL | 1704 | 34.702 | 9.429 | 11.649 | 1.00 | 24.10 |
| ATOM 2102 | C | VAL | 1704 | 32.396 | 12.508 | 11.604 | 1.00 | 30.80 |
| ATOM 2103 | O | VAL | 1704 | 31.224 | 12.146 | 11.712 | 1.00 | 32.50 |
| ATOM 2104 | N | PRO | 1705 | 32.718 | 13.705 | 11.104 | 1.00 | 30.86 |
| ATOM 2105 | CD | PRO | 1705 | 34.039 | 14.350 | 11.077 | 1.00 | 30.59 |
| ATOM 2106 | CA | PRO | 1705 | 31.682 | 14.625 | 10.645 | 1.00 | 31.47 |
| ATOM 2107 | CB | PRO | 1705 | 32.400 | 15.971 | 10.680 | 1.00 | 32.75 |
| ATOM 2108 | CG | PRO | 1705 | 33.774 | 15.607 | 10.289 | 1.00 | 32.59 |
| ATOM 2109 | C | PRO | 1705 | 31.258 | 14.264 | 9.239 | 1.00 | 32.19 |
| ATOM 2110 | O | PRO | 1705 | 31.974 | 13.536 | 8.549 | 1.00 | 33.91 |
| ATOM 2111 | N | VAL | 1706 | 30.124 | 14.814 | 8.806 | 1.00 | 32.57 |
| ATOM 2113 | CA | VAL | 1706 | 29.560 | 14.576 | 7.474 | 1.00 | 31.80 |
| ATOM 2114 | CB | VAL | 1706 | 28.483 | 15.632 | 7.172 | 1.00 | 34.66 |
| ATOM 2115 | CG1 | VAL | 1706 | 28.022 | 15.538 | 5.738 | 1.00 | 39.06 |
| ATOM 2116 | CG2 | VAL | 1706 | 27.309 | 15.455 | 8.106 | 1.00 | 36.62 |
| ATOM 2117 | C | VAL | 1706 | 30.578 | 14.560 | 6.320 | 1.00 | 31.58 |
| ATOM 2118 | O | VAL | 1706 | 30.682 | 13.585 | 5.570 | 1.00 | 32.35 |
| ATOM 2119 | N | GLU | 1707 | 31.326 | 15.649 | 6.189 | 1.00 | 31.46 |
| ATOM 2121 | CA | GLU | 1707 | 32.329 | 15.788 | 5.139 | 1.00 | 31.68 |
| ATOM 2122 | CB | GLU | 1707 | 33.021 | 17.148 | 5.267 | 1.00 | 32.59 |
| ATOM 2123 | C | GLU | 1707 | 33.381 | 14.678 | 5.114 | 1.00 | 32.23 |
| ATOM 2124 | O | GLU | 1707 | 33.740 | 14.183 | 4.050 | 1.00 | 33.47 |
| ATOM 2125 | N | GLU | 1708 | 33.902 | 14.316 | 6.279 | 1.00 | 32.90 |
| ATOM 2127 | CA | GLU | 1708 | 34.909 | 13.268 | 6.352 | 1.00 | 33.86 |
| ATOM 2128 | CB | GLU | 1708 | 35.570 | 13.244 | 7.730 | 1.00 | 38.54 |
| ATOM 2129 | CG | GLU | 1708 | 36.190 | 14.575 | 8.165 | 1.00 | 47.63 |
| ATOM 2130 | CD | GLU | 1708 | 37.442 | 14.962 | 7.383 | 1.00 | 58.35 |
| ATOM 2131 | OE1 | GLU | 1708 | 38.117 | 14.067 | 6.816 | 1.00 | 62.88 |
| ATOM 2132 | OE2 | GLU | 1708 | 37.770 | 16.176 | 7.355 | 1.00 | 64.79 |
| ATOM 2133 | C | GLU | 1708 | 34.276 | 11.921 | 6.043 | 1.00 | 33.56 |
| ATOM 2134 | O | GLU | 1708 | 34.927 | 11.038 | 5.489 | 1.00 | 34.18 |
| ATOM 2135 | N | LEU | 1709 | 32.997 | 11.774 | 6.374 | 1.00 | 32.91 |
| ATOM 2137 | CA | LEU | 1709 | 32.285 | 10.532 | 6.108 | 1.00 | 33.83 |
| ATOM 2138 | CB | LEU | 1709 | 30.862 | 10.563 | 6.685 | 1.00 | 32.28 |
| ATOM 2139 | CG | LEU | 1709 | 30.015 | 9.363 | 6.231 | 1.00 | 32.92 |
| ATOM 2140 | CD1 | LEU | 1709 | 30.541 | 8.071 | 6.853 | 1.00 | 28.37 |
| ATOM 2141 | CD2 | LEU | 1709 | 28.563 | 9.580 | 6.568 | 1.00 | 31.90 |
| ATOM 2142 | C | LEU | 1709 | 32.222 | 10.283 | 4.606 | 1.00 | 34.15 |
| ATOM 2143 | O | LEU | 1709 | 32.412 | 9.152 | 4.156 | 1.00 | 34.75 |
| ATOM 2144 | N | PHE | 1710 | 31.918 | 11.332 | 3.844 | 1.00 | 33.83 |
| ATOM 2146 | CA | PHE | 1710 | 31.828 | 11.248 | 2.388 | 1.00 | 32.90 |
| ATOM 2147 | CB | PHE | 1710 | 31.531 | 12.622 | 1.787 | 1.00 | 34.85 |
| ATOM 2148 | CG | PHE | 1710 | 30.162 | 13.132 | 2.082 | 1.00 | 38.60 |
| ATOM 2149 | CD1 | PHE | 1710 | 29.150 | 12.268 | 2.469 | 1.00 | 43.69 |
| ATOM 2150 | CD2 | PHE | 1710 | 29.882 | 14.480 | 1.984 | 1.00 | 45.10 |
| ATOM 2151 | CE1 | PHE | 1710 | 27.873 | 12.742 | 2.764 | 1.00 | 46.23 |
| ATOM 2152 | CE2 | PHE | 1710 | 28.611 | 14.966 | 2.274 | 1.00 | 48.15 |
| ATOM 2153 | CZ | PHE | 1710 | 27.603 | 14.086 | 2.670 | 1.00 | 46.90 |
| ATOM 2154 | C | PHE | 1710 | 33.131 | 10.739 | 1.803 | 1.00 | 31.84 |
| ATOM 2155 | O | PHE | 1710 | 33.134 | 9.931 | 0.877 | 1.00 | 29.97 |
| ATOM 2156 | N | LYS | 1711 | 34.231 | 11.224 | 2.373 | 1.00 | 32.45 |
| ATOM 2158 | CA | LYS | 1711 | 35.582 | 10.860 | 1.947 | 1.00 | 34.53 |
| ATOM 2159 | CB | LYS | 1711 | 36.588 | 11.755 | 2.675 | 1.00 | 36.17 |
| ATOM 2160 | CG | LYS | 1711 | 38.008 | 11.669 | 2.182 | 1.00 | 41.07 |
| ATOM 2161 | CD | LYS | 1711 | 38.912 | 12.582 | 3.001 | 1.00 | 46.23 |
| ATOM 2162 | CE | LYS | 1711 | 40.311 | 12.648 | 2.418 | 1.00 | 51.79 |
| ATOM 2163 | NZ | LYS | 1711 | 41.036 | 11.360 | 2.556 | 1.00 | 57.27 |
| ATOM 2167 | C | LYS | 1711 | 35.867 | 9.375 | 2.215 | 1.00 | 33.82 |
| ATOM 2168 | O | LYS | 1711 | 36.451 | 8.688 | 1.376 | 1.00 | 33.20 |
| ATOM 2169 | N | LEU | 1712 | 35.439 | 8.885 | 3.382 | 1.00 | 34.52 |
| ATOM 2171 | CA | LEU | 1712 | 35.618 | 7.477 | 3.754 | 1.00 | 33.25 |
| ATOM 2172 | CB | LEU | 1712 | 35.094 | 7.211 | 5.189 | 1.00 | 30.99 |
| ATOM 2173 | CG | LEU | 1712 | 35.746 | 7.917 | 6.393 | 1.00 | 29.71 |
| ATOM 2174 | CD1 | LEU | 1712 | 35.047 | 7.552 | 7.678 | 1.00 | 24.11 |
| ATOM 2175 | CD2 | LEU | 1712 | 37.208 | 7.552 | 6.497 | 1.00 | 32.21 |
| ATOM 2176 | C | LEU | 1712 | 34.833 | 6.631 | 2.744 | 1.00 | 32.16 |
| ATOM 2177 | O | LEU | 1712 | 35.378 | 5.732 | 2.109 | 1.00 | 32.77 |
| ATOM 2178 | N | LEU | 1713 | 33.562 | 6.967 | 2.563 | 1.00 | 31.72 |
| ATOM 2180 | CA | LEU | 1713 | 32.700 | 6.259 | 1.637 | 1.00 | 33.60 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2181 | CB | LEU | 1713 | 31.299 | 6.879 | 1.619 | 1.00 | 36.57 |
| ATOM 2182 | CG | LEU | 1713 | 30.522 | 6.711 | 2.930 | 1.00 | 37.60 |
| ATOM 2183 | CD1 | LEU | 1713 | 29.284 | 7.575 | 2.927 | 1.00 | 35.03 |
| ATOM 2184 | CD2 | LEU | 1713 | 30.182 | 5.246 | 3.157 | 1.00 | 33.22 |
| ATOM 2185 | C | LEU | 1713 | 33.285 | 6.248 | 0.236 | 1.00 | 35.33 |
| ATOM 2186 | O | LEU | 1713 | 33.318 | 5.203 | −0.407 | 1.00 | 36.00 |
| ATOM 2187 | N | LYS | 1714 | 33.741 | 7.405 | −0.234 | 1.00 | 36.24 |
| ATOM 2189 | CA | LYS | 1714 | 34.331 | 7.501 | −1.566 | 1.00 | 36.35 |
| ATOM 2190 | CB | LYS | 1714 | 34.707 | 8.946 | −1.900 | 1.00 | 35.82 |
| ATOM 2191 | CG | LYS | 1714 | 33.520 | 9.837 | −2.168 | 1.00 | 37.23 |
| ATOM 2192 | CD | LYS | 1714 | 32.712 | 9.324 | −3.337 | 1.00 | 40.53 |
| ATOM 2193 | CE | LYS | 1714 | 31.506 | 10.198 | −3.600 | 1.00 | 44.51 |
| ATOM 2194 | NZ | LYS | 1714 | 30.747 | 9.724 | −4.804 | 1.00 | 50.76 |
| ATOM 2198 | C | LYS | 1714 | 35.559 | 6.613 | −1.701 | 1.00 | 37.60 |
| ATOM 2199 | O | LYS | 1714 | 35.808 | 6.039 | −2.764 | 1.00 | 40.82 |
| ATOM 2200 | N | GLU | 1715 | 36.299 | 6.452 | −0.615 | 1.00 | 35.61 |
| ATOM 2202 | CA | GLU | 1715 | 37.496 | 5.630 | −0.658 | 1.00 | 34.65 |
| ATOM 2203 | CB | GLU | 1715 | 38.517 | 6.188 | 0.320 | 1.00 | 37.83 |
| ATOM 2204 | CG | GLU | 1715 | 38.897 | 7.613 | −0.036 | 1.00 | 42.28 |
| ATOM 2205 | CD | GLU | 1715 | 39.634 | 8.342 | 1.061 | 1.00 | 45.64 |
| ATOM 2206 | OE1 | GLU | 1715 | 39.928 | 7.726 | 2.114 | 1.00 | 43.09 |
| ATOM 2207 | OE2 | GLU | 1715 | 39.918 | 9.544 | 0.853 | 1.00 | 47.56 |
| ATOM 2208 | C | GLU | 1715 | 37.244 | 4.145 | −0.419 | 1.00 | 32.94 |
| ATOM 2209 | O | GLU | 1715 | 38.177 | 3.348 | −0.419 | 1.00 | 33.31 |
| ATOM 2210 | N | GLY | 1716 | 35.983 | 3.779 | −0.213 | 1.00 | 29.12 |
| ATOM 2212 | CA | GLY | 1716 | 35.634 | 2.391 | 0.004 | 1.00 | 26.02 |
| ATOM 2213 | C | GLY | 1716 | 35.946 | 1.895 | 1.396 | 1.00 | 29.60 |
| ATOM 2214 | O | GLY | 1716 | 36.223 | 0.715 | 1.588 | 1.00 | 29.81 |
| ATOM 2215 | N | HIS | 1717 | 35.879 | 2.783 | 2.379 | 1.00 | 29.97 |
| ATOM 2217 | CA | HIS | 1717 | 36.158 | 2.409 | 3.763 | 1.00 | 30.78 |
| ATOM 2218 | CB | HIS | 1717 | 36.369 | 3.659 | 4.623 | 1.00 | 33.25 |
| ATOM 2219 | CG | HIS | 1717 | 36.653 | 3.360 | 6.067 | 1.00 | 34.70 |
| ATOM 2220 | CD2 | HIS | 1717 | 37.820 | 3.155 | 6.715 | 1.00 | 32.77 |
| ATOM 2221 | ND1 | HIS | 1717 | 35.656 | 3.219 | 7.010 | 1.00 | 36.90 |
| ATOM 2223 | CE1 | HIS | 1717 | 36.200 | 2.932 | 8.180 | 1.00 | 35.87 |
| ATOM 2224 | NE2 | HIS | 1717 | 37.513 | 2.887 | 8.027 | 1.00 | 31.93 |
| ATOM 2226 | C | HIS | 1717 | 35.035 | 1.577 | 4.375 | 1.00 | 29.63 |
| ATOM 2227 | O | HIS | 1717 | 33.861 | 1.847 | 4.133 | 1.00 | 30.82 |
| ATOM 2228 | N | ARG | 1718 | 35.406 | 0.600 | 5.201 | 1.00 | 27.92 |
| ATOM 2230 | CA | ARG | 1718 | 34.436 | −0.258 | 5.878 | 1.00 | 27.30 |
| ATOM 2231 | CB | ARG | 1718 | 34.379 | −1.641 | 5.236 | 1.00 | 24.10 |
| ATOM 2232 | CG | ARG | 1718 | 33.939 | −1.655 | 3.789 | 1.00 | 26.52 |
| ATOM 2233 | CD | ARG | 1718 | 32.469 | −1.288 | 3.627 | 1.00 | 26.96 |
| ATOM 2234 | NE | ARG | 1718 | 32.020 | −1.374 | 2.232 | 1.00 | 24.41 |
| ATOM 2236 | CZ | ARG | 1718 | 32.090 | −0.377 | 1.352 | 1.00 | 25.51 |
| ATOM 2237 | NH1 | ARG | 1718 | 32.611 | 0.801 | 1.706 | 1.00 | 23.61 |
| ATOM 2240 | NH2 | ARG | 1718 | 31.553 | −0.521 | 0.149 | 1.00 | 21.28 |
| ATOM 2243 | C | ARG | 1718 | 34.881 | −0.384 | 7.330 | 1.00 | 28.81 |
| ATOM 2244 | o | ARG | 1718 | 36.080 | −0.425 | 7.611 | 1.00 | 29.77 |
| ATOM 2245 | N | MET | 1719 | 33.920 | −0.377 | 8.250 | 1.00 | 30.40 |
| ATOM 2247 | CA | MET | 1719 | 34.215 | −0.485 | 9.673 | 1.00 | 30.62 |
| ATOM 2248 | CB | MET | 1719 | 32.942 | −0.339 | 10.497 | 1.00 | 28.91 |
| ATOM 2249 | CG | MET | 1719 | 32.235 | 1.003 | 10.316 | 1.00 | 30.85 |
| ATOM 2250 | SD | MET | 1719 | 30.829 | 1.237 | 11.432 | 1.00 | 33.27 |
| ATOM 2251 | CE | MET | 1719 | 29.521 | 0.416 | 10.561 | 1.00 | 31.81 |
| ATOM 2252 | C | MET | 1719 | 34.900 | −1.793 | 10.005 | 1.00 | 31.32 |
| ATOM 2253 | O | MET | 1719 | 34.755 | −2.769 | 9.278 | 1.00 | 31.47 |
| ATOM 2254 | N | ASP | 1720 | 35.651 | −1.799 | 11.103 | 1.00 | 33.78 |
| ATOM 2256 | CA | ASP | 1720 | 36.387 | −2.983 | 11.550 | 1.00 | 33.45 |
| ATOM 2257 | CB | ASP | 1720 | 37.478 | −2.580 | 12.546 | 1.00 | 36.99 |
| ATOM 2258 | CG | ASP | 1720 | 38.585 | −1.762 | 11.908 | 1.00 | 41.56 |
| ATOM 2259 | OD1 | ASP | 1720 | 38.403 | −1.339 | 10.742 | 1.00 | 48.43 |
| ATOM 2260 | OD2 | ASP | 1720 | 39.634 | −1.546 | 12.568 | 1.00 | 40.99 |
| ATOM 2261 | C | ASP | 1720 | 35.473 | −4.001 | 12.211 | 1.00 | 32.12 |
| ATOM 2262 | O | ASP | 1720 | 34.381 | −3.657 | 12.668 | 1.00 | 30.89 |
| ATOM 2263 | N | LYS | 1721 | 35.944 | −5.241 | 12.328 | 1.00 | 31.82 |
| ATOM 2265 | CA | LYS | 1721 | 35.127 | −6.270 | 12.953 | 1.00 | 31.71 |
| ATOM 2266 | CB | LYS | 1721 | 35.691 | −7.679 | 12.747 | 1.00 | 32.34 |
| ATOM 2267 | CG | LYS | 1721 | 34.762 | −8.738 | 13.344 | 1.00 | 34.85 |
| ATOM 2268 | CD | LYS | 1721 | 35.111 | −10.155 | 12.961 | 1.00 | 37.39 |
| ATOM 2269 | CE | LYS | 1721 | 36.266 | −10.674 | 13.765 | 1.00 | 41.42 |
| ATOM 2270 | NZ | LYS | 1721 | 36.348 | −12.154 | 13.635 | 1.00 | 46.55 |
| ATOM 2274 | C | LYS | 1721 | 35.007 | −6.018 | 14.430 | 1.00 | 33.40 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2275 | O | LYS | 1721 | 36.017 | −5.879 | 15.121 | 1.00 | 34.26 |
| ATOM 2276 | N | PRO | 1722 | 33.768 | −5.924 | 14.934 | 1.00 | 34.26 |
| ATOM 2277 | CD | PRO | 1722 | 32.494 | −6.002 | 14.203 | 1.00 | 32.16 |
| ATOM 2278 | CA | PRO | 1722 | 33.546 | −5.692 | 16.362 | 1.00 | 35.84 |
| ATOM 2279 | CB | PRO | 1722 | 32.027 | −5.682 | 16.473 | 1.00 | 35.35 |
| ATOM 2280 | CG | PRO | 1722 | 31.575 | −5.255 | 15.108 | 1.00 | 35.35 |
| ATOM 2281 | C | PRO | 1722 | 34.105 | −6.904 | 17.099 | 1.00 | 40.41 |
| ATOM 2282 | O | PRO | 1722 | 34.010 | −8.038 | 16.607 | 1.00 | 41.14 |
| ATOM 2283 | N | SER | 1723 | 34.739 | −6.680 | 18.240 | 1.00 | 43.60 |
| ATOM 2285 | CA | SER | 1723 | 35.260 | −7.808 | 18.999 | 1.00 | 45.51 |
| ATOM 2286 | CB | SER | 1723 | 36.078 | −7.324 | 20.191 | 1.00 | 45.30 |
| ATOM 2287 | OG | SER | 1723 | 35.384 | −6.300 | 20.879 | 1.00 | 49.62 |
| ATOM 2289 | C | SER | 1723 | 34.031 | −8.589 | 19.460 | 1.00 | 46.39 |
| ATOM 2290 | O | SER | 1723 | 32.939 | −8.028 | 19.614 | 1.00 | 45.16 |
| ATOM 2291 | N | ASN | 1724 | 34.199 | −9.891 | 19.631 | 1.00 | 48.53 |
| ATOM 2293 | CA | ASN | 1724 | 33.088 | −10.723 | 20.065 | 1.00 | 51.13 |
| ATOM 2294 | CB | ASN | 1724 | 32.509 | −10.194 | 21.390 | 1.00 | 56.87 |
| ATOM 2295 | CG | ASN | 1724 | 33.595 | −9.892 | 22.427 | 1.00 | 61.65 |
| ATOM 2296 | OD1 | ASN | 1724 | 34.503 | −10.702 | 22.649 | 1.00 | 63.73 |
| ATOM 2297 | ND2 | ASN | 1724 | 33.526 | −8.713 | 23.039 | 1.00 | 64.64 |
| ATOM 2300 | C | ASN | 1724 | 32.034 | −10.743 | 18.941 | 1.00 | 48.83 |
| ATOM 2301 | O | ASN | 1724 | 30.846 | −10.534 | 19.145 | 1.00 | 50.50 |
| ATOM 2302 | N | CYS | 1725 | 32.511 | −10.977 | 17.734 | 1.00 | 45.23 |
| ATOM 2304 | CA | CYS | 1725 | 31.654 | −11.056 | 16.570 | 1.00 | 42.33 |
| ATOM 2305 | CB | CYS | 1725 | 31.570 | −9.702 | 15.654 | 1.00 | 41.48 |
| ATOM 2306 | SG | CYS | 1725 | 30.711 | −9.751 | 14.275 | 1.00 | 40.38 |
| ATOM 2307 | C | CYS | 1725 | 32.383 | −12.077 | 15.725 | 1.00 | 39.64 |
| ATOM 2308 | O | CYS | 1725 | 33.601 | −12.004 | 15.579 | 1.00 | 42.00 |
| ATOM 2309 | N | THR | 1726 | 31.664 | −13.090 | 15.263 | 1.00 | 35.96 |
| ATOM 2311 | CA | THR | 1726 | 32.275 | −14.139 | 14.459 | 1.00 | 33.61 |
| ATOM 2312 | CB | THR | 1726 | 31.301 | −15.326 | 14.326 | 1.00 | 33.29 |
| ATOM 2313 | OG1 | THR | 1726 | 30.071 | −14.904 | 13.711 | 1.00 | 34.53 |
| ATOM 2315 | CG2 | THR | 1726 | 30.981 | −15.861 | 15.696 | 1.00 | 25.84 |
| ATOM 2316 | C | THR | 1726 | 32.720 | −13.629 | 13.092 | 1.00 | 32.27 |
| ATOM 2317 | O | THR | 1726 | 32.257 | −12.593 | 12.643 | 1.00 | 33.04 |
| ATOM 2318 | N | ASN | 1727 | 33.643 | −14.315 | 12.434 | 1.00 | 32.98 |
| ATOM 2320 | CA | ASN | 1727 | 34.050 | −13.850 | 11.114 | 1.00 | 34.97 |
| ATOM 2321 | CB | ASN | 1727 | 35.198 | −14.680 | 10.541 | 1.00 | 39.89 |
| ATOM 2322 | CG | ASN | 1727 | 36.540 | −14.271 | 11.103 | 1.00 | 45.37 |
| ATOM 2323 | OD1 | ASN | 1727 | 37.044 | −13.177 | 10.826 | 1.00 | 48.43 |
| ATOM 2324 | ND2 | ASN | 1727 | 37.125 | −15.141 | 11.909 | 1.00 | 45.88 |
| ATOM 2327 | C | ASN | 1727 | 32.846 | −13.947 | 10.192 | 1.00 | 33.97 |
| ATOM 2328 | O | ASN | 1727 | 32.646 | −13.088 | 9.341 | 1.00 | 35.07 |
| ATOM 2329 | N | GLU | 1728 | 32.024 | −14.973 | 10.414 | 1.00 | 31.69 |
| ATOM 2331 | CA | GLU | 1728 | 30.814 | −15.210 | 9.620 | 1.00 | 30.27 |
| ATOM 2332 | CB | GLU | 1728 | 30.141 | −16.493 | 10.083 | 1.00 | 32.53 |
| ATOM 2333 | CG | GLU | 1728 | 28.932 | −16.878 | 9.273 | 1.00 | 32.81 |
| ATOM 2334 | CD | GLU | 1728 | 28.353 | −18.190 | 9.711 | 1.00 | 36.43 |
| ATOM 2335 | OE1 | GLU | 1728 | 28.339 | −18.466 | 10.932 | 1.00 | 36.75 |
| ATOM 2336 | OE2 | GLU | 1728 | 27.908 | −18.945 | 8.829 | 1.00 | 41.92 |
| ATOM 2337 | C | GLU | 1728 | 29.814 | −14.049 | 9.681 | 1.00 | 28.70 |
| ATOM 2338 | o | GLU | 1728 | 29.234 | −13.655 | 8.660 | 1.00 | 28.51 |
| ATOM 2339 | N | LEU | 1729 | 29.594 | −13.517 | 10.880 | 1.00 | 26.77 |
| ATOM 2341 | CA | LEU | 1729 | 28.687 | −12.393 | 11.040 | 1.00 | 26.80 |
| ATOM 2342 | CB | LEU | 1729 | 28.228 | −12.274 | 12.490 | 1.00 | 27.91 |
| ATOM 2343 | CG | LEU | 1729 | 27.233 | −13.355 | 12.913 | 1.00 | 30.71 |
| ATOM 2344 | CD1 | LEU | 1729 | 27.095 | −13.345 | 14.428 | 1.00 | 35.79 |
| ATOM 2345 | CD2 | LEU | 1729 | 25.885 | −13.141 | 12.253 | 1.00 | 25.70 |
| ATOM 2346 | C | LEU | 1729 | 29.319 | −11.089 | 10.540 | 1.00 | 27.06 |
| ATOM 2347 | O | LEU | 1729 | 28.610 | −10.177 | 10.126 | 1.00 | 30.27 |
| ATOM 2348 | N | TYR | 1730 | 30.650 | −11.004 | 10.549 | 1.00 | 27.03 |
| ATOM 2350 | CA | TYR | 1730 | 31.328 | −9.812 | 10.039 | 1.00 | 26.21 |
| ATOM 2351 | CB | TYR | 1730 | 32.792 | −9.778 | 10.474 | 1.00 | 25.31 |
| ATOM 2352 | CG | TYR | 1730 | 33.538 | −8.553 | 9.982 | 1.00 | 24.89 |
| ATOM 2353 | CD1 | TYR | 1730 | 33.012 | −7.270 | 10.169 | 1.00 | 23.59 |
| ATOM 2354 | CE1 | TYR | 1730 | 33.655 | −6.148 | 9.665 | 1.00 | 24.74 |
| ATOM 2355 | CD2 | TYR | 1730 | 34.739 | −8.675 | 9.285 | 1.00 | 22.11 |
| ATOM 2356 | CE2 | TYR | 1730 | 35.399 | −7.560 | 8.775 | 1.00 | 22.32 |
| ATOM 2357 | CZ | TYR | 1730 | 34.853 | −6.295 | 8.962 | 1.00 | 26.07 |
| ATOM 2358 | OH | TYR | 1730 | 35.484 | −5.181 | 8.418 | 1.00 | 22.70 |
| ATOM 2360 | C | TYR | 1730 | 31.227 | −9.878 | 8.509 | 1.00 | 27.71 |
| ATOM 2361 | O | TYR | 1730 | 30.960 | −8.875 | 7.843 | 1.00 | 28.05 |
| ATOM 2362 | N | MET | 1731 | 31.409 | −11.081 | 7.977 | 1.00 | 27.92 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2364 | CA | MET | 1731 | 31.306 | −11.355 | 6.548 | 1.00 | 28.89 |
| ATOM 2365 | CB | MET | 1731 | 31.506 | −12.853 | 6.317 | 1.00 | 35.84 |
| ATOM 2366 | CG | MET | 1731 | 31.068 | −13.379 | 4.975 | 1.00 | 45.50 |
| ATOM 2367 | SD | MET | 1731 | 31.347 | −15.167 | 4.865 | 1.00 | 56.40 |
| ATOM 2368 | CE | MET | 1731 | 32.106 | −15.263 | 3.217 | 1.00 | 56.88 |
| ATOM 2369 | C | MET | 1731 | 29.916 | −10.928 | 6.102 | 1.00 | 27.79 |
| ATOM 2370 | O | MET | 1731 | 29.755 | −10.345 | 5.041 | 1.00 | 30.68 |
| ATOM 2371 | N | MET | 1732 | 28.915 | −11.203 | 6.932 | 1.00 | 28.02 |
| ATOM 2373 | CA | MET | 1732 | 27.546 | −10.804 | 6.639 | 1.00 | 25.74 |
| ATOM 2374 | CB | MET | 1732 | 26.598 | −11.317 | 7.718 | 1.00 | 24.94 |
| ATOM 2375 | CG | MET | 1732 | 25.153 | −10.911 | 7.492 | 1.00 | 22.96 |
| ATOM 2376 | SD | MET | 1732 | 24.008 | −11.593 | 8.684 | 1.00 | 24.39 |
| ATOM 2377 | CE | MET | 1732 | 23.798 | −13.272 | 8.002 | 1.00 | 18.04 |
| ATOM 2378 | C | MET | 1732 | 27.470 | −9.273 | 6.559 | 1.00 | 25.81 |
| ATOM 2379 | O | MET | 1732 | 26.889 | −8.729 | 5.620 | 1.00 | 26.85 |
| ATOM 2380 | N | MET | 1733 | 28.068 | −8.587 | 7.537 | 1.00 | 24.84 |
| ATOM 2382 | CA | MET | 1733 | 28.092 | −7.124 | 7.545 | 1.00 | 25.27 |
| ATOM 2383 | CB | MET | 1733 | 28.931 | −6.600 | 8.700 | 1.00 | 25.97 |
| ATOM 2384 | CG | MET | 1733 | 28.342 | −6.769 | 10.058 | 1.00 | 28.69 |
| ATOM 2385 | SD | MET | 1733 | 29.456 | −6.094 | 11.295 | 1.00 | 29.06 |
| ATOM 2386 | CE | MET | 1733 | 28.927 | −7.051 | 12.693 | 1.00 | 28.07 |
| ATOM 2387 | C | MET | 1733 | 28.741 | −6.628 | 6.270 | 1.00 | 26.97 |
| ATOM 2388 | O | MET | 1733 | 28.192 | −5.771 | 5.581 | 1.00 | 28.37 |
| ATOM 2389 | N | ARG | 1734 | 29.922 | −7.160 | 5.966 | 1.00 | 28.77 |
| ATOM 2391 | CA | ARG | 1734 | 30.664 | −6.775 | 4.762 | 1.00 | 29.66 |
| ATOM 2392 | CB | ARG | 1734 | 32.027 | −7.482 | 4.716 | 1.00 | 29.05 |
| ATOM 2393 | CG | ARG | 1734 | 32.968 | −7.109 | 5.866 | 1.00 | 25.00 |
| ATOM 2394 | CD | ARG | 1734 | 33.247 | −5.621 | 5.882 | 1.00 | 29.27 |
| ATOM 2395 | NE | ARG | 1734 | 33.911 | −5.210 | 4.647 | 1.00 | 35.43 |
| ATOM 2397 | CZ | ARG | 1734 | 35.233 | −5.220 | 4.466 | 1.00 | 38.24 |
| ATOM 2398 | NH1 | ARG | 1734 | 36.054 | −5.601 | 5.445 | 1.00 | 36.47 |
| ATOM 2401 | NH2 | ARG | 1734 | 35.732 | −4.907 | 3.277 | 1.00 | 38.57 |
| ATOM 2404 | C | ARG | 1734 | 29.859 | −7.034 | 3.478 | 1.00 | 29.57 |
| ATOM 2405 | O | ARG | 1734 | 29.920 | −6.242 | 2.538 | 1.00 | 29.55 |
| ATOM 2406 | N | ASP | 1735 | 29.095 | −8.124 | 3.448 | 1.00 | 28.07 |
| ATOM 2408 | CA | ASP | 1735 | 28.259 | −8.423 | 2.287 | 1.00 | 27.96 |
| ATOM 2409 | CB | ASP | 1735 | 27.634 | −9.813 | 2.408 | 1.00 | 28.60 |
| ATOM 2410 | CG | ASP | 1735 | 28.664 | −10.926 | 2.283 | 1.00 | 31.34 |
| ATOM 2411 | OD1 | ASP | 1735 | 29.785 | −10.660 | 1.798 | 1.00 | 31.12 |
| ATOM 2412 | OD2 | ASP | 1735 | 28.356 | −12.068 | 2.687 | 1.00 | 36.07 |
| ATOM 2413 | C | ASP | 1735 | 27.159 | −7.368 | 2.155 | 1.00 | 27.24 |
| ATOM 2414 | O | ASP | 1735 | 26.846 | −6.932 | 1.050 | 1.00 | 25.79 |
| ATOM 2415 | N | CYS | 1736 | 26.590 | −6.951 | 3.288 | 1.00 | 26.53 |
| ATOM 2417 | CA | CYS | 1736 | 25.547 | −5.930 | 3.314 | 1.00 | 24.35 |
| ATOM 2418 | CB | CYS | 1736 | 24.968 | −5.765 | 4.731 | 1.00 | 22.01 |
| ATOM 2419 | SG | CYS | 1736 | 23.885 | −7.101 | 5.281 | 1.00 | 21.52 |
| ATOM 2420 | C | CYS | 1736 | 26.119 | −4.595 | 2.847 | 1.00 | 24.26 |
| ATOM 2421 | O | CYS | 1736 | 25.386 | −3.725 | 2.368 | 1.00 | 24.19 |
| ATOM 2422 | N | TRP | 1737 | 27.432 | −4.437 | 3.002 | 1.00 | 22.94 |
| ATOM 2424 | CA | TRP | 1737 | 28.104 | −3.210 | 2.605 | 1.00 | 21.91 |
| ATOM 2425 | CB | TRP | 1737 | 29.146 | −2.820 | 3.640 | 1.00 | 19.26 |
| ATOM 2426 | CG | TRP | 1737 | 28.572 | −2.493 | 4.947 | 1.00 | 20.89 |
| ATOM 2427 | CD2 | TRP | 1737 | 29.226 | −2.602 | 6.212 | 1.00 | 23.33 |
| ATOM 2428 | CE2 | TRP | 1737 | 28.315 | −2.159 | 7.196 | 1.00 | 21.59 |
| ATOM 2429 | CE3 | TRP | 1737 | 30.506 | −3.026 | 6.614 | 1.00 | 25.00 |
| ATOM 2430 | CD1 | TRP | 1737 | 27.319 | −2.012 | 5.201 | 1.00 | 19.90 |
| ATOM 2431 | NE1 | TRP | 1737 | 27.158 | −1.807 | 6.551 | 1.00 | 20.77 |
| ATOM 2433 | CZ2 | TRP | 1737 | 28.641 | −2.127 | 8.563 | 1.00 | 19.89 |
| ATOM 2434 | CZ3 | TRP | 1737 | 30.825 | −2.993 | 7.971 | 1.00 | 21.23 |
| ATOM 2435 | CH2 | TRP | 1737 | 29.896 | −2.543 | 8.927 | 1.00 | 21.09 |
| ATOM 2436 | C | TRP | 1737 | 28.758 | −3.266 | 1.232 | 1.00 | 23.54 |
| ATOM 2437 | O | TRP | 1737 | 29.653 | −2.477 | 0.939 | 1.00 | 24.68 |
| ATOM 2438 | N | HIS | 1738 | 28.315 | −4.185 | 0.382 | 1.00 | 24.37 |
| ATOM 2440 | CA | HIS | 1738 | 28.877 | −4.287 | −0.947 | 1.00 | 24.42 |
| ATOM 2441 | CB | HIS | 1738 | 28.243 | −5.436 | −1.728 | 1.00 | 23.72 |
| ATOM 2442 | CG | HIS | 1738 | 29.131 | −5.985 | −2.801 | 1.00 | 27.20 |
| ATOM 2443 | CD2 | HIS | 1738 | 29.595 | −5.425 | −3.948 | 1.00 | 26.45 |
| ATOM 2444 | ND1 | HIS | 1738 | 29.681 | −7.255 | −2.751 | 1.00 | 29.26 |
| ATOM 2446 | CE1 | HIS | 1738 | 30.436 | −7.441 | −3.816 | 1.00 | 29.25 |
| ATOM 2447 | NE2 | HIS | 1738 | 30.409 | −6.358 | −4.556 | 1.00 | 27.32 |
| ATOM 2449 | C | HIS | 1738 | 28.716 | −2.970 | −1.713 | 1.00 | 25.82 |
| ATOM 2450 | O | HIS | 1738 | 27.675 | −2.314 | −1.660 | 1.00 | 23.96 |
| ATOM 2451 | N | ALA | 1739 | 29.802 | −2.564 | −2.362 | 1.00 | 26.27 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2453 | CA | ALA | 1739 | 29.825 | −1.346 | −3.158 | 1.00 | 25.46 |
| ATOM 2454 | CB | ALA | 1739 | 31.186 | −1.180 | −3.789 | 1.00 | 25.70 |
| ATOM 2455 | C | ALA | 1739 | 28.754 | −1.443 | −4.233 | 1.00 | 26.18 |
| ATOM 2456 | O | ALA | 1739 | 28.116 | −0.455 | −4.574 | 1.00 | 29.14 |
| ATOM 2457 | N | VAL | 1740 | 28.570 | −2.643 | −4.774 | 1.00 | 25.71 |
| ATOM 2459 | CA | VAL | 1740 | 27.560 | −2.875 | −5.802 | 1.00 | 26.12 |
| ATOM 2460 | CB | VAL | 1740 | 28.063 | −3.841 | −6.903 | 1.00 | 25.99 |
| ATOM 2461 | CG1 | VAL | 1740 | 27.102 | −3.832 | −8.090 | 1.00 | 23.37 |
| ATOM 2462 | CG2 | VAL | 1740 | 29.450 | −3.440 | −7.349 | 1.00 | 22.07 |
| ATOM 2463 | C | VAL | 1740 | 26.247 | −3.400 | −5.191 | 1.00 | 25.43 |
| ATOM 2464 | O | VAL | 1740 | 26.186 | −4.550 | −4.704 | 1.00 | 24.93 |
| ATOM 2465 | N | PRO | 1741 | 25.170 | −2.585 | −5.265 | 1.00 | 24.20 |
| ATOM 2466 | CD | PRO | 1741 | 25.151 | −1.277 | −5.953 | 1.00 | 18.88 |
| ATOM 2467 | CA | PRO | 1741 | 23.838 | −2.914 | −4.734 | 1.00 | 25.28 |
| ATOM 2468 | CB | PRO | 1741 | 22.953 | −1.788 | −5.294 | 1.00 | 22.75 |
| ATOM 2469 | CG | PRO | 1741 | 23.903 | −0.632 | −5.398 | 1.00 | 20.99 |
| ATOM 2470 | C | PRO | 1741 | 23.299 | −4.296 | −5.128 | 1.00 | 25.84 |
| ATOM 2471 | O | PRO | 1741 | 22.787 | −5.036 | −4.280 | 1.00 | 25.99 |
| ATOM 2472 | N | SER | 1742 | 23.425 | −4.642 | −6.407 | 1.00 | 26.48 |
| ATOM 2474 | CA | SER | 1742 | 22.942 | −5.919 | −6.930 | 1.00 | 25.19 |
| ATOM 2475 | CB | SER | 1742 | 23.151 | −5.992 | −8.440 | 1.00 | 25.68 |
| ATOM 2476 | OG | SER | 1742 | 24.530 | −5.943 | −8.769 | 1.00 | 27.46 |
| ATOM 2478 | C | SER | 1742 | 23.644 | −7.100 | −6.289 | 1.00 | 25.24 |
| ATOM 2479 | O | SER | 1742 | 23.124 | −8.218 | −6.300 | 1.00 | 26.09 |
| ATOM 2480 | N | GLN | 1743 | 24.826 | −6.851 | −5.731 | 1.00 | 23.88 |
| ATOM 2482 | CA | GLN | 1743 | 25.590 | −7.917 | −5.118 | 1.00 | 24.44 |
| ATOM 2483 | CB | GLN | 1743 | 27.069 | −7.733 | −5.437 | 1.00 | 27.26 |
| ATOM 2484 | CG | GLN | 1743 | 27.344 | −7.784 | −6.940 | 1.00 | 27.39 |
| ATOM 2485 | CD | GLN | 1743 | 26.803 | −9.047 | −7.581 | 1.00 | 26.46 |
| ATOM 2486 | OE1 | GLN | 1743 | 27.325 | −10.136 | −7.339 | 1.00 | 25.80 |
| ATOM 2487 | NE2 | GLN | 1743 | 25.760 | −8.914 | −8.393 | 1.00 | 27.42 |
| ATOM 2490 | C | GLN | 1743 | 25.348 | −8.151 | −3.633 | 1.00 | 23.20 |
| ATOM 2491 | O | GLN | 1743 | 25.810 | −9.147 | −3.083 | 1.00 | 22.90 |
| ATOM 2492 | N | ARG | 1744 | 24.628 | −7.243 | −2.984 | 1.00 | 22.15 |
| ATOM 2494 | CA | ARG | 1744 | 24.318 | −7.398 | −1.568 | 1.00 | 21.23 |
| ATOM 2495 | CB | ARG | 1744 | 23.767 | −6.088 | −0.998 | 1.00 | 19.01 |
| ATOM 2496 | CG | ARG | 1744 | 24.705 | −4.916 | −1.145 | 1.00 | 17.27 |
| ATOM 2497 | CD | ARG | 1744 | 24.091 | −3.605 | −0.679 | 1.00 | 14.79 |
| ATOM 2498 | NE | ARG | 1744 | 24.914 | −2.493 | −1.157 | 1.00 | 19.72 |
| ATOM 2500 | CZ | ARG | 1744 | 24.482 | −1.258 | −1.391 | 1.00 | 19.23 |
| ATOM 2501 | NH1 | ARG | 1744 | 23.201 | −0.931 | −1.201 | 1.00 | 15.90 |
| ATOM 2504 | NH2 | ARG | 1744 | 25.343 | −0.343 | −1.821 | 1.00 | 19.43 |
| ATOM 2507 | C | ARG | 1744 | 23.259 | −8.496 | −1.438 | 1.00 | 21.95 |
| ATOM 2508 | O | ARG | 1744 | 22.585 | −8.827 | −2.415 | 1.00 | 25.34 |
| ATOM 2509 | N | PRO | 1745 | 23.213 | −9.184 | −0.292 | 1.00 | 20.82 |
| ATOM 2510 | CD | PRO | 1745 | 24.191 | −9.219 | 0.804 | 1.00 | 21.25 |
| ATOM 2511 | CA | PRO | 1745 | 22.204 | −10.229 | −0.127 | 1.00 | 21.39 |
| ATOM 2512 | CB | PRO | 1745 | 22.687 | −10.980 | 1.117 | 1.00 | 21.69 |
| ATOM 2513 | CG | PRO | 1745 | 23.418 | −9.916 | 1.886 | 1.00 | 22.62 |
| ATOM 2514 | C | PRO | 1745 | 20.833 | −9.585 | 0.102 | 1.00 | 22.15 |
| ATOM 2515 | O | PRO | 1745 | 20.739 | −8.402 | 0.426 | 1.00 | 23.29 |
| ATOM 2516 | N | THR | 1746 | 19.771 | −10.349 | −0.109 | 1.00 | 20.93 |
| ATOM 2518 | CA | THR | 1746 | 18.440 | −9.827 | 0.107 | 1.00 | 19.90 |
| ATOM 2519 | CB | THR | 1746 | 17.391 | −10.554 | −0.783 | 1.00 | 20.21 |
| ATOM 2520 | OG1 | THR | 1746 | 17.484 | −11.974 | −0.584 | 1.00 | 22.03 |
| ATOM 2522 | CG2 | THR | 1746 | 17.609 | −10.242 | −2.255 | 1.00 | 20.82 |
| ATOM 2523 | C | THR | 1746 | 18.112 | −10.095 | 1.557 | 1.00 | 19.77 |
| ATOM 2524 | O | THR | 1746 | 18.842 | −10.823 | 2.228 | 1.00 | 19.19 |
| ATOM 2525 | N | PHE | 1747 | 17.010 | −9.526 | 2.045 | 1.00 | 23.46 |
| ATOM 2527 | CA | PHE | 1747 | 16.582 | −9.770 | 3.422 | 1.00 | 21.64 |
| ATOM 2528 | CB | PHE | 1747 | 15.473 | −8.794 | 3.827 | 1.00 | 18.89 |
| ATOM 2529 | CG | PHE | 1747 | 15.987 | −7.445 | 4.262 | 1.00 | 17.45 |
| ATOM 2530 | CD1 | PHE | 1747 | 16.757 | −7.317 | 5.417 | 1.00 | 17.65 |
| ATOM 2531 | CD2 | PHE | 1747 | 15.712 | −6.303 | 3.516 | 1.00 | 15.37 |
| ATOM 2532 | CE1 | PHE | 1747 | 17.242 | −6.073 | 5.819 | 1.00 | 16.17 |
| ATOM 2533 | CE2 | PHE | 1747 | 16.189 | −5.056 | 3.907 | 1.00 | 14.53 |
| ATOM 2534 | CZ | PHE | 1747 | 16.959 | −4.941 | 5.065 | 1.00 | 16.88 |
| ATOM 2535 | C | PHE | 1747 | 16.118 | −11.227 | 3.522 | 1.00 | 23.18 |
| ATOM 2536 | O | PHE | 1747 | 16.271 | −11.873 | 4.548 | 1.00 | 24.04 |
| ATOM 2537 | N | LYS | 1748 | 15.570 | −11.745 | 2.432 | 1.00 | 24.13 |
| ATOM 2539 | CA | LYS | 1748 | 15.137 | −13.132 | 2.385 | 1.00 | 26.35 |
| ATOM 2540 | CB | LYS | 1748 | 14.502 | −13.424 | 1.024 | 1.00 | 27.52 |
| ATOM 2541 | CG | LYS | 1748 | 14.034 | −14.849 | 0.836 | 1.00 | 33.88 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2542 | CD | LYS | 1748 | 13.598 | −15.062 | −0.600 | 1.00 | 41.83 |
| ATOM 2543 | CE | LYS | 1748 | 13.190 | −16.506 | −0.881 | 1.00 | 50.05 |
| ATOM 2544 | NZ | LYS | 1748 | 12.084 | −16.986 | 0.005 | 1.00 | 55.70 |
| ATOM 2548 | C | LYS | 1748 | 16.359 | −14.037 | 2.636 | 1.00 | 27.50 |
| ATOM 2549 | O | LYS | 1748 | 16.303 | −14.950 | 3.459 | 1.00 | 31.18 |
| ATOM 2550 | N | GLN | 1749 | 17.467 | −13.761 | 1.949 | 1.00 | 27.24 |
| ATOM 2552 | CA | GLN | 1749 | 18.699 | −14.529 | 2.122 | 1.00 | 27.03 |
| ATOM 2553 | CB | GLN | 1749 | 19.797 | −14.039 | 1.169 | 1.00 | 31.80 |
| ATOM 2554 | CG | GLN | 1749 | 19.501 | −14.196 | −0.323 | 1.00 | 38.57 |
| ATOM 2555 | CD | GLN | 1749 | 20.460 | −13.385 | −1.209 | 1.00 | 39.93 |
| ATOM 2556 | OE1 | GLN | 1749 | 20.025 | −12.535 | −1.974 | 1.00 | 39.90 |
| ATOM 2557 | NE2 | GLN | 1749 | 21.768 | −13.620 | −1.068 | 1.00 | 40.23 |
| ATOM 2560 | C | GLN | 1749 | 19.205 | −14.380 | 3.552 | 1.00 | 25.98 |
| ATOM 2561 | O | GLN | 1749 | 19.533 | −15.371 | 4.198 | 1.00 | 27.18 |
| ATOM 2562 | N | LEU | 1750 | 19.293 | −13.133 | 4.018 | 1.00 | 25.20 |
| ATOM 2564 | CA | LEU | 1750 | 19.774 | −12.823 | 5.369 | 1.00 | 25.74 |
| ATOM 2565 | CB | LEU | 1750 | 19.722 | −11.317 | 5.631 | 1.00 | 20.99 |
| ATOM 2566 | CG | LEU | 1750 | 20.708 | −10.468 | 4.831 | 1.00 | 20.90 |
| ATOM 2567 | CD1 | LEU | 1750 | 20.302 | −8.987 | 4.822 | 1.00 | 19.88 |
| ATOM 2568 | CD2 | LEU | 1750 | 22.071 | −10.643 | 5.426 | 1.00 | 17.26 |
| ATOM 2569 | C | LEU | 1750 | 18.985 | −13.555 | 6.441 | 1.00 | 27.10 |
| ATOM 2570 | O | LEU | 1750 | 19.553 | −14.094 | 7.392 | 1.00 | 27.89 |
| ATOM 2571 | N | VAL | 1751 | 17.672 | −13.598 | 6.265 | 1.00 | 29.40 |
| ATOM 2573 | CA | VAL | 1751 | 16.798 | −14.262 | 7.210 | 1.00 | 26.80 |
| ATOM 2574 | CB | VAL | 1751 | 15.324 | −14.030 | 6.843 | 1.00 | 26.94 |
| ATOM 2575 | CG1 | VAL | 1751 | 14.429 | −14.941 | 7.657 | 1.00 | 29.93 |
| ATOM 2576 | CG2 | VAL | 1751 | 14.941 | −12.575 | 7.117 | 1.00 | 24.10 |
| ATOM 2577 | C | VAL | 1751 | 17.136 | −15.745 | 7.228 | 1.00 | 27.80 |
| ATOM 2578 | O | VAL | 1751 | 17.223 | −16.359 | 8.285 | 1.00 | 26.77 |
| ATOM 2579 | N | GLU | 1752 | 17.408 | −16.300 | 6.056 | 1.00 | 32.26 |
| ATOM 2581 | CA | GLU | 1752 | 17.749 | −17.717 | 5.966 | 1.00 | 35.72 |
| ATOM 2582 | CB | GLU | 1752 | 17.721 | −18.173 | 4.504 | 1.00 | 39.33 |
| ATOM 2583 | CG | GLU | 1752 | 16.306 | −18.078 | 3.911 | 1.00 | 49.41 |
| ATOM 2584 | CD | GLU | 1752 | 16.209 | −18.421 | 2.429 | 1.00 | 55.88 |
| ATOM 2585 | OE1 | GLU | 1752 | 15.141 | −18.138 | 1.835 | 1.00 | 58.00 |
| ATOM 2586 | OE2 | GLU | 1752 | 17.180 | −18.978 | 1.863 | 1.00 | 61.03 |
| ATOM 2587 | C | GLU | 1752 | 19.093 | −18.002 | 6.635 | 1.00 | 34.59 |
| ATOM 2588 | O | GLU | 1752 | 19.230 | −18.975 | 7.393 | 1.00 | 33.95 |
| ATOM 2589 | N | ASP | 1753 | 20.057 | −17.114 | 6.401 | 1.00 | 34.38 |
| ATOM 2591 | CA | ASP | 1753 | 21.393 | −17.235 | 6.977 | 1.00 | 32.81 |
| ATOM 2592 | CB | ASP | 1753 | 22.338 | −16.227 | 6.334 | 1.00 | 31.57 |
| ATOM 2593 | CG | ASP | 1753 | 22.628 | −16.556 | 4.888 | 1.00 | 33.68 |
| ATOM 2594 | OD1 | ASP | 1753 | 22.573 | −17.755 | 4.536 | 1.00 | 35.14 |
| ATOM 2595 | OD2 | ASP | 1753 | 22.914 | −15.624 | 4.104 | 1.00 | 34.44 |
| ATOM 2596 | C | ASP | 1753 | 21.378 | −17.058 | 8.489 | 1.00 | 32.04 |
| ATOM 2597 | O | ASP | 1753 | 21.997 | −17.837 | 9.214 | 1.00 | 31.21 |
| ATOM 2598 | N | LEU | 1754 | 20.648 | −16.045 | 8.955 | 1.00 | 31.00 |
| ATOM 2600 | CA | LEU | 1754 | 20.528 | −15.754 | 10.382 | 1.00 | 29.46 |
| ATOM 2601 | CB | LEU | 1754 | 19.822 | −14.426 | 10.598 | 1.00 | 23.47 |
| ATOM 2602 | CG | LEU | 1754 | 20.816 | −13.309 | 10.318 | 1.00 | 23.58 |
| ATOM 2603 | CD1 | LEU | 1754 | 20.114 | −11.963 | 10.128 | 1.00 | 20.46 |
| ATOM 2604 | CD2 | LEU | 1754 | 21.828 | −13.282 | 11.462 | 1.00 | 19.18 |
| ATOM 2605 | C | LEU | 1754 | 19.806 | −16.866 | 11.110 | 1.00 | 31.84 |
| ATOM 2606 | O | LEU | 1754 | 20.125 | −17.178 | 12.254 | 1.00 | 30.78 |
| ATOM 2607 | N | ASP | 1755 | 18.832 | −17.471 | 10.445 | 1.00 | 34.03 |
| ATOM 2609 | CA | ASP | 1755 | 18.116 | −18.578 | 11.044 | 1.00 | 35.22 |
| ATOM 2610 | CB | ASP | 1755 | 16.973 | −19.027 | 10.148 | 1.00 | 38.40 |
| ATOM 2611 | CG | ASP | 1755 | 16.159 | −20.119 | 10.779 | 1.00 | 41.85 |
| ATOM 2612 | OD1 | ASP | 1755 | 15.560 | −19.866 | 11.841 | 1.00 | 47.90 |
| ATOM 2613 | OD2 | ASP | 1755 | 16.142 | −21.241 | 10.238 | 1.00 | 46.67 |
| ATOM 2614 | C | ASP | 1755 | 19.114 | −19.724 | 11.222 | 1.00 | 36.79 |
| ATOM 2615 | O | ASP | 1755 | 19.114 | −20.411 | 12.250 | 1.00 | 38.33 |
| ATOM 2616 | N | ARG | 1756 | 19.973 | −19.920 | 10.226 | 1.00 | 34.81 |
| ATOM 2618 | CA | ARG | 1756 | 20.982 | −20.969 | 10.302 | 1.00 | 34.68 |
| ATOM 2619 | CB | ARG | 1756 | 21.688 | −21.100 | 8.959 | 1.00 | 34.78 |
| ATOM 2620 | CG | ARG | 1756 | 22.746 | −22.179 | 8.910 | 1.00 | 35.93 |
| ATOM 2621 | CD | ARG | 1756 | 23.297 | −22.306 | 7.511 | 1.00 | 41.60 |
| ATOM 2622 | NE | ARG | 1756 | 23.786 | −21.025 | 6.999 | 1.00 | 46.42 |
| ATOM 2624 | CZ | ARG | 1756 | 24.889 | −20.419 | 7.427 | 1.00 | 48.38 |
| ATOM 2625 | NH1 | ARG | 1756 | 25.637 | −20.976 | 8.381 | 1.00 | 48.10 |
| ATOM 2628 | NH2 | ARG | 1756 | 25.236 | −19.242 | 6.909 | 1.00 | 46.62 |
| ATOM 2631 | C | ARG | 1756 | 22.002 | −20.666 | 11.399 | 1.00 | 36.17 |
| ATOM 2632 | O | ARG | 1756 | 22.372 | −21.541 | 12.177 | 1.00 | 38.33 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2633 | N | ILE | 1757 | 22.433 | −19.413 | 11.478 | 1.00 | 37.00 |
| ATOM 2635 | CA | ILE | 1757 | 23.416 | −18.998 | 12.468 | 1.00 | 35.60 |
| ATOM 2636 | CB | ILE | 1757 | 23.964 | −17.588 | 12.141 | 1.00 | 35.54 |
| ATOM 2637 | CG2 | ILE | 1757 | 24.921 | −17.131 | 13.217 | 1.00 | 32.41 |
| ATOM 2638 | CG1 | ILE | 1757 | 24.693 | −17.612 | 10.794 | 1.00 | 33.77 |
| ATOM 2639 | CD1 | ILE | 1757 | 25.097 | −16.253 | 10.287 | 1.00 | 33.49 |
| ATOM 2640 | C | ILE | 1757 | 22.866 | −19.048 | 13.891 | 1.00 | 37.28 |
| ATOM 2641 | O | ILE | 1757 | 23.531 | −19.556 | 14.779 | 1.00 | 38.42 |
| ATOM 2642 | N | VAL | 1758 | 21.634 | −18.585 | 14.088 | 1.00 | 39.19 |
| ATOM 2644 | CA | VAL | 1758 | 21.016 | −18.584 | 15.421 | 1.00 | 39.84 |
| ATOM 2645 | CB | VAL | 1758 | 19.560 | −18.017 | 15.403 | 1.00 | 37.62 |
| ATOM 2646 | CG1 | VAL | 1758 | 18.918 | −18.144 | 16.773 | 1.00 | 38.30 |
| ATOM 2647 | CG2 | VAL | 1758 | 19.560 | −16.560 | 15.009 | 1.00 | 39.62 |
| ATOM 2648 | C | VAL | 1758 | 20.983 | −19.997 | 15.988 | 1.00 | 41.98 |
| ATOM 2649 | O | VAL | 1758 | 21.380 | −20.229 | 17.128 | 1.00 | 43.36 |
| ATOM 2650 | N | ALA | 1759 | 20.501 | −20.932 | 15.182 | 1.00 | 43.31 |
| ATOM 2652 | CA | ALA | 1759 | 20.418 | −22.325 | 15.589 | 1.00 | 44.00 |
| ATOM 2653 | CB | ALA | 1759 | 19.836 | −23.150 | 14.459 | 1.00 | 44.52 |
| ATOM 2654 | C | ALA | 1759 | 21.784 | −22.867 | 15.976 | 1.00 | 45.98 |
| ATOM 2655 | O | ALA | 1759 | 21.894 | −23.725 | 16.841 | 1.00 | 48.78 |
| ATOM 2656 | N | LEU | 1760 | 22.823 | −22.375 | 15.319 | 1.00 | 48.93 |
| ATOM 2658 | CA | LEU | 1760 | 24.175 | −22.831 | 15.592 | 1.00 | 51.47 |
| ATOM 2659 | CB | LEU | 1760 | 24.954 | −22.900 | 14.280 | 1.00 | 53.63 |
| ATOM 2660 | CG | LEU | 1760 | 24.284 | −23.864 | 13.295 | 1.00 | 57.84 |
| ATOM 2661 | CD1 | LEU | 1760 | 24.993 | −23.847 | 11.948 | 1.00 | 61.83 |
| ATOM 2662 | CD2 | LEU | 1760 | 24.260 | −25.277 | 13.886 | 1.00 | 58.57 |
| ATOM 2663 | C | LEU | 1760 | 24.911 | −21.965 | 16.607 | 1.00 | 53.60 |
| ATOM 2664 | O | LEU | 1760 | 26.078 | −22.214 | 16.919 | 1.00 | 54.00 |
| ATOM 2665 | N | THR | 1761 | 24.222 | −20.963 | 17.141 | 1.00 | 55.77 |
| ATOM 2667 | CA | THR | 1761 | 24.820 | −20.060 | 18.111 | 1.00 | 56.64 |
| ATOM 2668 | CB | THR | 1761 | 24.250 | −18.627 | 17.979 | 1.00 | 55.76 |
| ATOM 2669 | OG1 | THR | 1761 | 24.444 | −18.154 | 16.644 | 1.00 | 56.20 |
| ATOM 2671 | CG2 | THR | 1761 | 24.962 | −17.680 | 18.917 | 1.00 | 55.25 |
| ATOM 2672 | C | THR | 1761 | 24.636 | −20.548 | 19.539 | 1.00 | 58.16 |
| ATOM 2673 | O | THR | 1761 | 23.566 | −21.021 | 19.919 | 1.00 | 56.85 |
| ATOM 2674 | N | SER | 1762 | 25.706 | −20.436 | 20.318 | 1.00 | 61.74 |
| ATOM 2676 | CA | SER | 1762 | 25.706 | −20.833 | 21.717 | 1.00 | 64.50 |
| ATOM 2677 | CB | SER | 1762 | 27.155 | −20.979 | 22.205 | 1.00 | 68.82 |
| ATOM 2678 | OG | SER | 1762 | 27.232 | −21.544 | 23.508 | 1.00 | 73.15 |
| ATOM 2680 | C | SER | 1762 | 24.965 | −19.775 | 22.547 | 1.00 | 63.87 |
| ATOM 2681 | O | SER | 1762 | 25.080 | −18.563 | 22.296 | 1.00 | 63.22 |
| ATOM 3420 | PA | PCP | 400 | 62.748 | 10.301 | 7.817 | 1.00 | 90.90 |
| ATOM 3421 | O1A | PCP | 400 | 62.509 | 10.036 | 9.280 | 1.00 | 92.35 |
| ATOM 3422 | O2A | PCP | 400 | 61.832 | 11.180 | 7.038 | 1.00 | 90.49 |
| ATOM 3423 | O5* | PCP | 400 | 62.744 | 8.904 | 7.142 | 1.00 | 83.57 |
| ATOM 3424 | PB | PCP | 400 | 65.226 | 11.946 | 8.294 | 1.00 | 101.51 |
| ATOM 3425 | O1B | PCP | 400 | 65.246 | 13.015 | 7.264 | 1.00 | 102.85 |
| ATOM 3426 | O2B | PCP | 400 | 66.527 | 11.458 | 8.830 | 1.00 | 99.88 |
| ATOM 3427 | O3A | PCP | 400 | 64.334 | 10.725 | 7.584 | 1.00 | 96.64 |
| ATOM 3428 | C3B | PCP | 400 | 64.345 | 12.502 | 9.635 | 1.00 | 102.94 |
| ATOM 3429 | C5* | PCP | 400 | 62.337 | 8.684 | 5.839 | 1.00 | 71.21 |
| ATOM 3430 | C4* | PCP | 400 | 62.479 | 7.204 | 5.587 | 1.00 | 64.48 |
| ATOM 3431 | O4* | PCP | 400 | 63.713 | 6.745 | 6.169 | 1.00 | 60.91 |
| ATOM 3432 | C1* | PCP | 400 | 63.394 | 5.459 | 6.680 | 1.00 | 54.96 |
| ATOM 3433 | N9 | PCP | 400 | 64.326 | 5.101 | 7.712 | 1.00 | 47.26 |
| ATOM 3434 | C4 | PCP | 400 | 65.017 | 3.903 | 7.840 | 1.00 | 46.24 |
| ATOM 3435 | N3 | PCP | 400 | 64.926 | 2.770 | 7.062 | 1.00 | 41.02 |
| ATOM 3436 | C2 | PCP | 400 | 65.802 | 1.878 | 7.531 | 1.00 | 40.72 |
| ATOM 3437 | N1 | PCP | 400 | 66.674 | 1.917 | 8.558 | 1.00 | 37.37 |
| ATOM 3438 | C6 | PCP | 400 | 66.735 | 3.028 | 9.305 | 1.00 | 40.23 |
| ATOM 3439 | N6 | PCP | 400 | 67.573 | 3.134 | 10.333 | 1.00 | 33.92 |
| ATOM 3442 | C5 | PCP | 400 | 65.862 | 4.091 | 8.937 | 1.00 | 44.12 |
| ATOM 3443 | N7 | PCP | 400 | 65.674 | 5.361 | 9.472 | 1.00 | 45.15 |
| ATOM 3444 | C8 | PCP | 400 | 64.761 | 5.894 | 8.702 | 1.00 | 44.83 |
| ATOM 3445 | C2* | PCP | 400 | 61.986 | 5.500 | 7.254 | 1.00 | 57.63 |
| ATOM 3446 | O2* | PCP | 400 | 61.454 | 4.153 | 7.211 | 1.00 | 56.45 |
| ATOM 3448 | C3* | PCP | 400 | 61.328 | 6.402 | 6.245 | 1.00 | 61.31 |
| ATOM 3449 | O3* | PCP | 400 | 60.689 | 5.644 | 5.206 | 1.00 | 64.65 |
| ATOM 3451 | PA | PCP | 401 | 9.366 | 9.801 | 17.743 | 0.50 | 74.43 |
| ATOM 3452 | O1A | PCP | 401 | 9.463 | 8.736 | 16.709 | 0.50 | 75.37 |
| ATOM 3453 | O2A | PCP | 401 | 10.330 | 10.926 | 17.699 | 0.50 | 75.86 |
| ATOM 3454 | O5* | PCP | 401 | 9.427 | 9.108 | 19.186 | 0.50 | 67.44 |
| ATOM 3455 | PB | PCP | 401 | 6.878 | 10.679 | 16.547 | 0.50 | 82.27 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3456 | O1B | PCP | 401 | 6.223 | 11.982 | 16.778 | 0.50 | 82.91 |
| ATOM 3457 | O2B | PCP | 401 | 6.020 | 9.486 | 16.408 | 0.50 | 82.70 |
| ATOM 3458 | O3A | PCP | 401 | 7.868 | 10.423 | 17.814 | 0.50 | 78.30 |
| ATOM 3459 | C3B | PCP | 401 | 7.790 | 10.845 | 15.159 | 0.50 | 82.50 |
| ATOM 3460 | C5* | PCP | 401 | 10.184 | 9.593 | 20.275 | 0.50 | 54.44 |
| ATOM 3461 | C4* | PCP | 401 | 10.228 | 8.637 | 21.442 | 0.50 | 45.38 |
| ATOM 3462 | O4* | PCP | 401 | 9.032 | 7.855 | 21.412 | 0.50 | 39.40 |
| ATOM 3463 | C1* | PCP | 401 | 9.397 | 6.509 | 21.641 | 0.50 | 35.00 |
| ATOM 3464 | N9 | PCP | 401 | 8.386 | 5.627 | 21.044 | 0.50 | 27.91 |
| ATOM 3465 | C4 | PCP | 401 | 7.790 | 4.469 | 21.564 | 0.50 | 23.36 |
| ATOM 3466 | N3 | PCP | 401 | 7.982 | 3.849 | 22.732 | 0.50 | 22.33 |
| ATOM 3467 | C2 | PCP | 401 | 7.239 | 2.768 | 22.838 | 0.50 | 20.26 |
| ATOM 3468 | N1 | PCP | 401 | 6.382 | 2.251 | 22.003 | 0.50 | 17.29 |
| ATOM 3469 | C6 | PCP | 401 | 6.202 | 2.877 | 20.856 | 0.50 | 19.35 |
| ATOM 3470 | N6 | PCP | 401 | 5.327 | 2.415 | 19.975 | 0.50 | 16.87 |
| ATOM 3473 | CS | PCP | 401 | 6.932 | 4.038 | 20.603 | 0.50 | 21.72 |
| ATOM 3474 | N7 | PCP | 401 | 6.983 | 4.880 | 19.507 | 0.50 | 24.59 |
| ATOM 3475 | C8 | PCP | 401 | 7.847 | 5.786 | 19.832 | 0.50 | 24.26 |
| ATOM 3476 | C2* | PCP | 401 | 10.762 | 6.409 | 20.931 | 0.50 | 39.01 |
| ATOM 3477 | O2* | PCP | 401 | 11.609 | 5.326 | 21.412 | 0.50 | 43.88 |
| ATOM 3479 | C3* | PCP | 401 | 11.396 | 7.674 | 21.373 | 0.50 | 42.14 |
| ATOM 3480 | O3* | PCP | 401 | 11.918 | 7.515 | 22.681 | 0.50 | 44.21 |
| ATOM 3482 | N | SER | 461 | 78.844 | 26.057 | 14.057 | 1.00 | 43.87 |
| ATOM 3484 | CA | SER | 461 | 79.399 | 24.884 | 13.385 | 1.00 | 43.50 |
| ATOM 3485 | CB | SER | 461 | 78.488 | 23.655 | 13.616 | 1.00 | 39.99 |
| ATOM 3486 | C | SER | 461 | 79.572 | 25.181 | 11.888 | 1.00 | 42.14 |
| ATOM 3487 | O | SER | 461 | 79.473 | 24.292 | 11.038 | 1.00 | 40.29 |
| ATOM 3488 | N | GLU | 462 | 79.883 | 26.441 | 11.594 | 1.00 | 43.19 |
| ATOM 3490 | CA | GLU | 462 | 80.061 | 26.951 | 10.233 | 1.00 | 42.77 |
| ATOM 3491 | CB | GLU | 462 | 80.303 | 28.446 | 10.250 | 1.00 | 47.75 |
| ATOM 3492 | CG | GLU | 462 | 79.209 | 29.301 | 10.860 | 1.00 | 60.57 |
| ATOM 3493 | CD | GLU | 462 | 79.647 | 30.752 | 11.061 | 1.00 | 67.56 |
| ATOM 3494 | OE1 | GLU | 462 | 80.866 | 31.016 | 10.994 | 1.00 | 67.47 |
| ATOM 3495 | OE2 | GLU | 462 | 78.764 | 31.611 | 11.296 | 1.00 | 72.32 |
| ATOM 3496 | C | GLU | 462 | 81.207 | 26.357 | 9.457 | 1.00 | 39.55 |
| ATOM 3497 | O | GLU | 462 | 81.051 | 26.032 | 8.292 | 1.00 | 38.74 |
| ATOM 3498 | N | TYR | 463 | 82.375 | 26.299 | 10.091 | 1.00 | 36.47 |
| ATOM 3500 | CA | TYR | 463 | 83.567 | 25.806 | 9.420 | 1.00 | 34.19 |
| ATOM 3501 | CB | TYR | 463 | 84.702 | 26.828 | 9.505 | 1.00 | 35.55 |
| ATOM 3502 | CG | TYR | 463 | 84.393 | 28.059 | 8.675 | 1.00 | 42.11 |
| ATOM 3503 | CD1 | TYR | 463 | 84.004 | 29.264 | 9.283 | 1.00 | 43.15 |
| ATOM 3504 | CE1 | TYR | 463 | 83.619 | 30.361 | 8.513 | 1.00 | 42.40 |
| ATOM 3505 | CD2 | TYR | 463 | 84.395 | 27.990 | 7.280 | 1.00 | 39.78 |
| ATOM 3506 | CE2 | TYR | 463 | 84.012 | 29.078 | 6.509 | 1.00 | 39.04 |
| ATOM 3507 | CZ | TYR | 463 | 83.625 | 30.256 | 7.129 | 1.00 | 39.86 |
| ATOM 3508 | OH | TYR | 463 | 83.260 | 31.330 | 6.366 | 1.00 | 42.58 |
| ATOM 3510 | C | TYR | 463 | 84.055 | 24.434 | 9.800 | 1.00 | 33.28 |
| ATOM 3511 | O | TYR | 463 | 84.739 | 23.781 | 9.005 | 1.00 | 33.47 |
| ATOM 3512 | N | GLU | 464 | 83.695 | 23.976 | 10.993 | 1.00 | 34.42 |
| ATOM 3514 | CA | GLU | 464 | 84.117 | 22.660 | 11.444 | 1.00 | 36.38 |
| ATOM 3515 | CB | GLU | 464 | 85.618 | 22.663 | 11.750 | 1.00 | 40.92 |
| ATOM 3516 | CG | GLU | 464 | 86.041 | 23.755 | 12.729 | 1.00 | 46.29 |
| ATOM 3517 | CD | GLU | 464 | 87.548 | 23.810 | 12.943 | 1.00 | 51.33 |
| ATOM 3518 | OE1 | GLU | 464 | 87.970 | 24.247 | 14.038 | 1.00 | 54.49 |
| ATOM 3519 | OE2 | GLU | 464 | 88.312 | 23.430 | 12.025 | 1.00 | 53.18 |
| ATOM 3520 | C | GLU | 464 | 83.374 | 22.224 | 12.678 | 1.00 | 35.64 |
| ATOM 3521 | O | GLU | 464 | 83.111 | 23.052 | 13.555 | 1.00 | 37.40 |
| ATOM 3522 | N | LEU | 465 | 82.962 | 20.955 | 12.711 | 1.00 | 34.21 |
| ATOM 3524 | CA | LEU | 465 | 82.267 | 20.429 | 13.887 | 1.00 | 34.92 |
| ATOM 3525 | CB | LEU | 465 | 81.285 | 19.300 | 13.542 | 1.00 | 31.30 |
| ATOM 3526 | CG | LEU | 465 | 80.272 | 19.381 | 12.405 | 1.00 | 32.22 |
| ATOM 3527 | CD1 | LEU | 465 | 79.152 | 18.407 | 12.720 | 1.00 | 21.95 |
| ATOM 3528 | CD2 | LEU | 465 | 79.738 | 20.802 | 12.212 | 1.00 | 29.75 |
| ATOM 3529 | C | LEU | 465 | 83.326 | 19.855 | 14.814 | 1.00 | 36.17 |
| ATOM 3530 | O | LEU | 465 | 84.473 | 19.621 | 14.400 | 1.00 | 35.80 |
| ATOM 3531 | N | PRO | 466 | 82.970 | 19.629 | 16.083 | 1.00 | 36.20 |
| ATOM 3532 | CD | PRO | 466 | 81.722 | 20.018 | 16.758 | 1.00 | 38.17 |
| ATOM 3533 | CA | PRO | 466 | 83.925 | 19.072 | 17.037 | 1.00 | 36.06 |
| ATOM 3534 | CB | PRO | 466 | 83.132 | 19.035 | 18.333 | 1.00 | 35.57 |
| ATOM 3535 | CG | PRO | 466 | 82.185 | 20.194 | 18.171 | 1.00 | 38.67 |
| ATOM 3536 | C | PRO | 466 | 84.294 | 17.666 | 16.605 | 1.00 | 37.06 |
| ATOM 3537 | O | PRO | 466 | 83.498 | 16.959 | 15.979 | 1.00 | 34.50 |
| ATOM 3538 | N | GLU | 467 | 85.504 | 17.258 | 16.936 | 1.00 | 39.97 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3540 | CA | GLU | 467 | 85.951 | 15.932 | 16.587 | 1.00 | 44.69 |
| ATOM 3541 | CB | GLU | 467 | 87.412 | 15.985 | 16.151 | 1.00 | 50.43 |
| ATOM 3542 | CG | GLU | 467 | 87.902 | 14.695 | 15.518 | 1.00 | 60.27 |
| ATOM 3543 | CD | GLU | 467 | 89.321 | 14.796 | 14.986 | 1.00 | 65.75 |
| ATOM 3544 | OE1 | GLU | 467 | 90.024 | 15.804 | 15.269 | 1.00 | 64.40 |
| ATOM 3545 | OE2 | GLU | 467 | 89.726 | 13.850 | 14.275 | 1.00 | 71.13 |
| ATOM 3546 | C | GLU | 467 | 85.775 | 15.002 | 17.783 | 1.00 | 43.30 |
| ATOM 3547 | O | GLU | 467 | 85.888 | 15.428 | 18.936 | 1.00 | 43.26 |
| ATOM 3548 | N | ASP | 468 | 85.433 | 13.750 | 17.504 | 1.00 | 43.09 |
| ATOM 3550 | CA | ASP | 468 | 85.254 | 12.739 | 18.545 | 1.00 | 44.15 |
| ATOM 3551 | CB | ASP | 468 | 83.785 | 12.614 | 18.979 | 1.00 | 44.54 |
| ATOM 3552 | CG | ASP | 468 | 83.574 | 11.562 | 20.072 | 1.00 | 41.84 |
| ATOM 3553 | OD1 | ASP | 468 | 82.405 | 11.244 | 20.368 | 1.00 | 39.81 |
| ATOM 3554 | OD2 | ASP | 468 | 84.570 | 11.057 | 20.636 | 1.00 | 42.92 |
| ATOM 3555 | C | ASP | 468 | 85.746 | 11.422 | 17.970 | 1.00 | 44.66 |
| ATOM 3556 | O | ASP | 468 | 84.982 | 10.663 | 17.368 | 1.00 | 44.56 |
| ATOM 3557 | N | PRO | 469 | 87.034 | 11.126 | 18.176 | 1.00 | 44.56 |
| ATOM 3558 | CD | PRO | 469 | 87.953 | 11.959 | 18.971 | 1.00 | 45.43 |
| ATOM 3559 | CA | PRO | 469 | 87.707 | 9.916 | 17.707 | 1.00 | 43.90 |
| ATOM 3560 | CB | PRO | 469 | 89.024 | 9.959 | 18.476 | 1.00 | 45.66 |
| ATOM 3561 | CG | PRO | 469 | 89.300 | 11.438 | 18.547 | 1.00 | 44.89 |
| ATOM 3562 | C | PRO | 469 | 86.934 | 8.627 | 17.971 | 1.00 | 42.60 |
| ATOM 3563 | O | PRO | 469 | 86.935 | 7.730 | 17.139 | 1.00 | 41.35 |
| ATOM 3564 | N | ARG | 470 | 86.229 | 8.569 | 19.096 | 1.00 | 43.25 |
| ATOM 3566 | CA | ARG | 470 | 85.460 | 7.380 | 19.470 | 1.00 | 44.81 |
| ATOM 3567 | CB | ARG | 470 | 84.722 | 7.612 | 20.789 | 1.00 | 48.36 |
| ATOM 3568 | CG | ARG | 470 | 85.579 | 8.201 | 21.889 | 1.00 | 53.41 |
| ATOM 3569 | CD | ARG | 470 | 84.764 | 8.458 | 23.138 | 1.00 | 55.42 |
| ATOM 3570 | NE | ARG | 470 | 83.581 | 9.261 | 22.861 | 1.00 | 58.57 |
| ATOM 3572 | CZ | ARG | 470 | 82.748 | 9.712 | 23.791 | 1.00 | 62.24 |
| ATOM 3573 | NH1 | ARG | 470 | 82.972 | 9.445 | 25.077 | 1.00 | 64.57 |
| ATOM 3576 | NH2 | ARG | 470 | 81.670 | 10.398 | 23.436 | 1.00 | 63.66 |
| ATOM 3579 | C | ARG | 470 | 84.439 | 6.924 | 18.437 | 1.00 | 43.69 |
| ATOM 3580 | O | ARG | 470 | 84.166 | 5.735 | 18.313 | 1.00 | 45.68 |
| ATOM 3581 | N | TRP | 471 | 83.879 | 7.866 | 17.693 | 1.00 | 42.41 |
| ATOM 3583 | CA | TRP | 471 | 82.851 | 7.534 | 16.720 | 1.00 | 38.92 |
| ATOM 3584 | CB | TRP | 471 | 81.577 | 8.268 | 17.095 | 100 | 35.80 |
| ATOM 3585 | CG | TRP | 471 | 80.967 | 7.741 | 18.335 | 1.00 | 37.13 |
| ATOM 3586 | CD2 | TRP | 471 | 80.158 | 6.569 | 18.443 | 1.00 | 37.26 |
| ATOM 3587 | CE2 | TRP | 471 | 79.723 | 6.483 | 19.785 | 1.00 | 38.20 |
| ATOM 3588 | CE3 | TRP | 471 | 79.748 | 5.582 | 17.530 | 1.00 | 35.59 |
| ATOM 3589 | CD1 | TRP | 471 | 81.010 | 8.300 | 19.584 | 1.00 | 36.42 |
| ATOM 3590 | NE1 | TRP | 471 | 80.260 | 7.553 | 20.462 | 1.00 | 35.89 |
| ATOM 3592 | CZ2 | TRP | 471 | 78.896 | 5.454 | 20.239 | 1.00 | 36.18 |
| ATOM 3593 | CZ3 | TRP | 471 | 78.934 | 4.561 | 17.978 | 1.00 | 32.81 |
| ATOM 3594 | CH2 | TRP | 471 | 78.514 | 4.505 | 19.321 | 1.00 | 34.82 |
| ATOM 3595 | C | TRP | 471 | 83.175 | 7.845 | 15.277 | 1.00 | 39.77 |
| ATOM 3596 | O | TRP | 471 | 82.478 | 7.391 | 14.362 | 1.00 | 39.56 |
| ATOM 3597 | N | GLU | 472 | 84.224 | 8.628 | 15.075 | 1.00 | 39.37 |
| ATOM 3599 | CA | GLU | 472 | 84.605 | 9.043 | 13.739 | 1.00 | 38.42 |
| ATOM 3600 | CB | GLU | 472 | 85.794 | 9.994 | 13.812 | 1.00 | 37.11 |
| ATOM 3601 | CG | GLU | 472 | 85.958 | 10.849 | 12.582 | 1.00 | 34.11 |
| ATOM 3602 | CD | GLU | 472 | 84.772 | 11.757 | 12.338 | 1.00 | 34.03 |
| ATOM 3603 | OE1 | GLU | 472 | 84.260 | 12.348 | 13.317 | 1.00 | 31.87 |
| ATOM 3604 | OE2 | GLU | 472 | 84.367 | 11.885 | 11.163 | 1.00 | 32.11 |
| ATOM 3605 | C | GLU | 472 | 84.910 | 7.901 | 12.791 | 1.00 | 39.78 |
| ATOM 3606 | O | GLU | 472 | 85.656 | 6.975 | 13.128 | 1.00 | 41.64 |
| ATOM 3607 | N | LEU | 473 | 84.303 | 7.958 | 11.610 | 1.00 | 37.71 |
| ATOM 3609 | CA | LEU | 473 | 84.538 | 6.957 | 10.590 | 1.00 | 36.94 |
| ATOM 3610 | CB | LEU | 473 | 83.258 | 6.196 | 10.265 | 1.00 | 35.38 |
| ATOM 3611 | CG | LEU | 473 | 83.438 | 5.065 | 9.236 | 1.00 | 37.67 |
| ATOM 3612 | CD1 | LEU | 473 | 84.070 | 3.845 | 9.903 | 1.00 | 37.28 |
| ATOM 3613 | CD2 | LEU | 473 | 82.106 | 4.687 | 8.598 | 1.00 | 37.87 |
| ATOM 3614 | C | LEU | 473 | 85.035 | 7.664 | 9.330 | 1.00 | 39.31 |
| ATOM 3615 | O | LEU | 473 | 84.484 | 8.697 | 8.938 | 1.00 | 40.55 |
| ATOM 3616 | N | PRO | 474 | 86.140 | 7.164 | 8.732 | 1.00 | 39.20 |
| ATOM 3617 | CD | PRO | 474 | 87.052 | 6.170 | 9.327 | 1.00 | 37.83 |
| ATOM 3618 | CA | PRO | 474 | 86.735 | 7.716 | 7.513 | 1.00 | 38.53 |
| ATOM 3619 | CB | PRO | 474 | 87.914 | 6.777 | 7.282 | 1.00 | 37.16 |
| ATOM 3620 | CG | PRO | 474 | 88.355 | 6.488 | 8.644 | 1.00 | 34.42 |
| ATOM 3621 | C | PRO | 474 | 85.733 | 7.607 | 6.370 | 1.00 | 40.25 |
| ATOM 3622 | O | PRO | 474 | 85.220 | 6.523 | 6.098 | 1.00 | 40.70 |
| ATOM 3623 | N | ARG | 475 | 85.492 | 8.723 | 5.685 | 1.00 | 41.09 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3625 | CA | ARG | 475 | 84.534 | 8.746 | 4.590 | 1.00 | 42.26 |
| ATOM 3626 | CB | ARG | 475 | 84.487 | 10.132 | 3.948 | 1.00 | 39.19 |
| ATOM 3627 | CG | ARG | 475 | 83.957 | 11.199 | 4.876 | 1.00 | 35.19 |
| ATOM 3628 | CD | ARG | 475 | 84.074 | 12.593 | 4.301 | 1.00 | 30.76 |
| ATOM 3629 | NE | ARG | 475 | 83.796 | 13.567 | 5.345 | 1.00 | 22.86 |
| ATOM 3631 | CZ | ARG | 475 | 82.581 | 13.898 | 5.748 | 1.00 | 21.99 |
| ATOM 3632 | NH1 | ARG | 475 | 81.529 | 13.350 | 5.165 | 1.00 | 23.39 |
| ATOM 3635 | NH2 | ARG | 475 | 82.412 | 14.662 | 6.813 | 1.00 | 22.55 |
| ATOM 3638 | C | ARG | 475 | 84.838 | 7.692 | 3.538 | 1.00 | 45.38 |
| ATOM 3639 | O | ARG | 475 | 83.927 | 7.182 | 2.892 | 1.00 | 47.15 |
| ATOM 3640 | N | ASP | 476 | 86.106 | 7.319 | 3.390 | 1.00 | 47.13 |
| ATOM 3642 | CA | ASP | 476 | 86.461 | 6.325 | 2.387 | 1.00 | 51.33 |
| ATOM 3643 | CB | ASP | 476 | 87.973 | 6.294 | 2.134 | 1.00 | 55.23 |
| ATOM 3644 | CG | ASP | 476 | 88.768 | 5.841 | 3.340 | 1.00 | 61.16 |
| ATOM 3645 | OD1 | ASP | 476 | 88.863 | 4.617 | 3.573 | 1.00 | 65.55 |
| ATOM 3646 | OD2 | ASP | 476 | 89.331 | 6.713 | 4.036 | 1.00 | 65.78 |
| ATOM 3647 | C | ASP | 476 | 85.932 | 4.940 | 2.746 | 1.00 | 52.35 |
| ATOM 3648 | O | ASP | 476 | 85.815 | 4.063 | 1.885 | 1.00 | 55.49 |
| ATOM 3649 | N | ARG | 477 | 85.609 | 4.752 | 4.021 | 1.00 | 50.77 |
| ATOM 3651 | CA | ARG | 477 | 85.080 | 3.482 | 4.508 | 1.00 | 48.65 |
| ATOM 3652 | CB | ARG | 477 | 85.612 | 3.208 | 5.908 | 1.00 | 50.02 |
| ATOM 3653 | CG | ARG | 477 | 87.067 | 2.799 | 5.881 | 1.00 | 55.33 |
| ATOM 3654 | CD | ARG | 477 | 87.760 | 3.030 | 7.201 | 1.00 | 60.38 |
| ATOM 3655 | NE | ARG | 477 | 87.238 | 2.207 | 8.285 | 1.00 | 64.36 |
| ATOM 3657 | CZ | ARG | 477 | 87.748 | 2.203 | 9.513 | 1.00 | 69.16 |
| ATOM 3658 | NH1 | ARG | 477 | 88.794 | 2.968 | 9.814 | 1.00 | 70.73 |
| ATOM 3661 | NH2 | ARG | 477 | 87.190 | 1.459 | 10.459 | 1.00 | 71.59 |
| ATOM 3664 | C | ARG | 477 | 83.546 | 3.414 | 4.484 | 1.00 | 46.25 |
| ATOM 3665 | O | ARG | 477 | 82.957 | 2.481 | 5.013 | 1.00 | 46.36 |
| ATOM 3666 | N | LEU | 478 | 82.913 | 4.372 | 3.815 | 1.00 | 42.23 |
| ATOM 3668 | CA | LEU | 478 | 81.464 | 4.418 | 3.743 | 1.00 | 38.89 |
| ATOM 3669 | CB | LEU | 478 | 80.938 | 5.537 | 4.657 | 1.00 | 37.17 |
| ATOM 3670 | CG | LEU | 478 | 79.418 | 5.733 | 4.678 | 1.00 | 34.13 |
| ATOM 3671 | CD1 | LEU | 478 | 78.777 | 4.723 | 5.609 | 1.00 | 32.24 |
| ATOM 3672 | CD2 | LEU | 478 | 79.074 | 7.133 | 5.101 | 1.00 | 33.15 |
| ATOM 3673 | C | LEU | 478 | 81.059 | 4.697 | 2.303 | 1.00 | 38.34 |
| ATOM 3674 | O | LEU | 478 | 81.515 | 5.671 | 1.711 | 1.00 | 40.88 |
| ATOM 3675 | N | VAL | 479 | 80.208 | 3.850 | 1.738 | 1.00 | 37.34 |
| ATOM 3677 | CA | VAL | 479 | 79.763 | 4.042 | 0.364 | 1.00 | 37.61 |
| ATOM 3678 | CB | VAL | 479 | 80.105 | 2.829 | −0.563 | 1.00 | 36.57 |
| ATOM 3679 | CG1 | VAL | 479 | 79.647 | 3.105 | −1.994 | 1.00 | 31.59 |
| ATOM 3680 | CG2 | VAL | 479 | 81.608 | 2.567 | −0.561 | 1.00 | 36.11 |
| ATOM 3681 | C | VAL | 479 | 78.267 | 4.277 | 0.375 | 1.00 | 39.24 |
| ATOM 3682 | O | VAL | 479 | 77.484 | 3.358 | 0.619 | 1.00 | 39.16 |
| ATOM 3683 | N | LEU | 480 | 77.894 | 5.528 | 0.142 | 1.00 | 41.32 |
| ATOM 3685 | CA | LEU | 480 | 76.505 | 5.960 | 0.123 | 1.00 | 41.60 |
| ATOM 3686 | CB | LEU | 480 | 76.446 | 7.480 | −0.008 | 1.00 | 41.31 |
| ATOM 3687 | CG | LEU | 480 | 77.129 | 8.257 | 1.118 | 1.00 | 39.82 |
| ATOM 3688 | CD1 | LEU | 480 | 76.985 | 9.737 | 0.856 | 1.00 | 37.96 |
| ATOM 3689 | CD2 | LEU | 480 | 76.512 | 7.887 | 2.458 | 1.00 | 37.70 |
| ATOM 3690 | C | LEU | 480 | 75.733 | 5.312 | −1.015 | 1.00 | 41.85 |
| ATOM 3691 | O | LEU | 480 | 76.235 | 5.224 | −2.131 | 1.00 | 45.02 |
| ATOM 3692 | N | GLY | 481 | 74.501 | 4.897 | −0.727 | 1.00 | 40.86 |
| ATOM 3694 | CA | GLY | 481 | 73.673 | 4.247 | −1.727 | 1.00 | 40.21 |
| ATOM 3695 | C | GLY | 481 | 72.270 | 4.806 | −1.873 | 1.00 | 39.78 |
| ATOM 3696 | O | GLY | 481 | 72.058 | 6.015 | −1.810 | 1.00 | 41.68 |
| ATOM 3697 | N | LYS | 482 | 71.306 | 3.914 | −2.063 | 1.00 | 39.98 |
| ATOM 3699 | CA | LYS | 482 | 69.910 | 4.297 | −2.249 | 1.00 | 42.13 |
| ATOM 3700 | CB | LYS | 482 | 69.061 | 3.056 | −2.566 | 1.00 | 42.73 |
| ATOM 3701 | C | LYS | 482 | 69.284 | 5.050 | −1.084 | 1.00 | 43.13 |
| ATOM 3702 | O | LYS | 482 | 69.373 | 4.625 | 0.060 | 1.00 | 44.49 |
| ATOM 3703 | N | PRO | 483 | 68.676 | 6.204 | −1.358 | 1.00 | 43.22 |
| ATOM 3704 | CD | PRO | 483 | 68.708 | 6.969 | −2.613 | 1.00 | 44.40 |
| ATOM 3705 | CA | PRO | 483 | 68.044 | 6.973 | −0.290 | 1.00 | 45.44 |
| ATOM 3706 | CB | PRO | 483 | 67.701 | 8.295 | −0.980 | 1.00 | 45.01 |
| ATOM 3707 | CG | PRO | 483 | 67.573 | 7.923 | −2.414 | 1.00 | 43.95 |
| ATOM 3708 | C | PRO | 483 | 66.801 | 6.261 | 0.232 | 1.00 | 47.67 |
| ATOM 3709 | O | PRO | 483 | 66.012 | 5.725 | −0.547 | 1.00 | 46.76 |
| ATOM 3710 | N | LEU | 484 | 66.650 | 6.242 | 1.552 | 1.00 | 49.68 |
| ATOM 3712 | CA | LEU | 484 | 65.514 | 5.598 | 2.196 | 1.00 | 54.51 |
| ATOM 3713 | CB | LEU | 484 | 65.935 | 5.026 | 3.555 | 1.00 | 52.70 |
| ATOM 3714 | CG | LEU | 484 | 67.132 | 4.066 | 3.530 | 1.00 | 51.83 |
| ATOM 3715 | CD1 | LEU | 484 | 67.620 | 3.766 | 4.933 | 1.00 | 50.19 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3716 | CD2 | LEU | 484 | 66.755 | 2.788 | 2.825 | 1.00 | 52.22 |
| ATOM 3717 | C | LEU | 484 | 64.317 | 6.554 | 2.357 | 1.00 | 58.82 |
| ATOM 3718 | O | LEU | 484 | 63.158 | 6.138 | 2.244 | 1.00 | 60.07 |
| ATOM 3719 | N | GLY | 485 | 64.599 | 7.831 | 2.609 | 1.00 | 61.91 |
| ATOM 3721 | CA | GLY | 485 | 63.538 | 8.810 | 2.778 | 1.00 | 65.89 |
| ATOM 3722 | C | GLY | 485 | 64.057 | 10.167 | 3.227 | 1.00 | 69.46 |
| ATOM 3723 | O | GLY | 485 | 65.230 | 10.301 | 3.597 | 1.00 | 70.65 |
| ATOM 3724 | N | GLU | 486 | 63.178 | 11.165 | 3.241 | 1.00 | 70.72 |
| ATOM 3726 | CA | GLU | 486 | 63.563 | 12.521 | 3.624 | 1.00 | 71.32 |
| ATOM 3727 | CB | GLU | 486 | 64.015 | 13.298 | 2.389 | 1.00 | 73.69 |
| ATOM 3728 | C | GLU | 486 | 62.435 | 13.269 | 4.312 | 1.00 | 70.93 |
| ATOM 3729 | O | GLU | 486 | 61.281 | 12.846 | 4.275 | 1.00 | 71.58 |
| ATOM 3730 | N | GLY | 487 | 62.781 | 14.404 | 4.909 | 1.00 | 70.10 |
| ATOM 3732 | CA | GLY | 487 | 61.798 | 15.211 | 5.603 | 1.00 | 68.11 |
| ATOM 3733 | C | GLY | 487 | 62.218 | 16.669 | 5.598 | 1.00 | 67.97 |
| ATOM 3734 | O | GLY | 487 | 62.938 | 17.109 | 4.696 | 1.00 | 67.68 |
| ATOM 3735 | N | ALA | 488 | 61.780 | 17.409 | 6.615 | 1.00 | 67.26 |
| ATOM 3737 | CA | ALA | 488 | 62.106 | 18.826 | 6.737 | 1.00 | 66.90 |
| ATOM 3738 | CB | ALA | 488 | 61.362 | 19.428 | 7.909 | 1.00 | 68.72 |
| ATOM 3739 | C | ALA | 488 | 63.607 | 19.004 | 6.921 | 1.00 | 67.08 |
| ATOM 3740 | O | ALA | 488 | 64.124 | 18.867 | 8.037 | 1.00 | 65.97 |
| ATOM 3741 | N | PHE | 489 | 64.297 | 19.248 | 5.806 | 1.00 | 66.76 |
| ATOM 3743 | CA | PHE | 489 | 65.754 | 19.439 | 5.773 | 1.00 | 65.91 |
| ATOM 3744 | CB | PHE | 489 | 66.134 | 20.794 | 6.379 | 1.00 | 66.45 |
| ATOM 3745 | C | PHE | 489 | 66.563 | 18.288 | 6.414 | 1.00 | 63.92 |
| ATOM 3746 | O | PHE | 489 | 67.622 | 18.503 | 7.031 | 1.00 | 63.16 |
| ATOM 3747 | N | GLY | 490 | 66.067 | 17.069 | 6.209 | 1.00 | 59.03 |
| ATOM 3749 | CA | GLY | 490 | 66.710 | 15.878 | 6.720 | 1.00 | 51.12 |
| ATOM 3750 | C | GLY | 490 | 66.619 | 14.823 | 5.638 | 1.00 | 48.59 |
| ATOM 3751 | O | GLY | 490 | 65.608 | 14.736 | 4.938 | 1.00 | 45.25 |
| ATOM 3752 | N | GLN | 491 | 67.659 | 14.003 | 5.525 | 1.00 | 48.77 |
| ATOM 3754 | CA | GLN | 491 | 67.732 | 12.951 | 4.519 | 1.00 | 47.40 |
| ATOM 3755 | CB | GLN | 491 | 68.529 | 13.474 | 3.319 | 1.00 | 49.92 |
| ATOM 3756 | CG | GLN | 491 | 68.653 | 12.514 | 2.155 | 1.00 | 56.31 |
| ATOM 3757 | CD | GLN | 491 | 69.604 | 13.020 | 1.088 | 1.00 | 58.79 |
| ATOM 3758 | OE1 | GLN | 491 | 70.043 | 14.171 | 1.130 | 1.00 | 59.63 |
| ATOM 3759 | NE2 | GLN | 491 | 69.929 | 12.161 | 0.122 | 1.00 | 59.05 |
| ATOM 3762 | C | GLN | 491 | 68.407 | 11.693 | 5.086 | 1.00 | 44.46 |
| ATOM 3763 | O | GLN | 491 | 69.396 | 11.782 | 5.806 | 1.00 | 44.15 |
| ATOM 3764 | N | VAL | 492 | 67.867 | 10.527 | 4.752 | 1.00 | 42.55 |
| ATOM 3766 | CA | VAL | 492 | 68.416 | 9.247 | 5.205 | 1.00 | 39.22 |
| ATOM 3767 | CB | VAL | 492 | 67.375 | 8.458 | 6.042 | 1.00 | 39.40 |
| ATOM 3768 | CG1 | VAL | 492 | 67.947 | 7.127 | 6.524 | 1.00 | 40.17 |
| ATOM 3769 | CG2 | VAL | 492 | 66.922 | 9.267 | 7.210 | 1.00 | 36.12 |
| ATOM 3770 | C | VAL | 492 | 68.746 | 8.396 | 3.975 | 1.00 | 37.57 |
| ATOM 3771 | O | VAL | 492 | 67.888 | 8.178 | 3.115 | 1.00 | 35.70 |
| ATOM 3772 | N | VAL | 493 | 69.990 | 7.961 | 3.845 | 1.00 | 36.27 |
| ATOM 3774 | CA | VAL | 493 | 70.333 | 7.127 | 2.711 | 1.00 | 37.61 |
| ATOM 3775 | CB | VAL | 493 | 71.237 | 7.863 | 1.643 | 1.00 | 37.45 |
| ATOM 3776 | CG1 | VAL | 493 | 70.836 | 9.319 | 1.524 | 1.00 | 38.29 |
| ATOM 3777 | CG2 | VAL | 493 | 72.717 | 7.713 | 1.943 | 1.00 | 36.53 |
| ATOM 3778 | C | VAL | 493 | 70.952 | 5.806 | 3.156 | 1.00 | 37.54 |
| ATOM 3779 | O | VAL | 493 | 71.542 | 5.711 | 4.233 | 1.00 | 37.32 |
| ATOM 3780 | N | LEU | 494 | 70.691 | 4.763 | 2.380 | 1.00 | 37.67 |
| ATOM 3782 | CA | LEU | 494 | 71.236 | 3.450 | 2.656 | 1.00 | 38.41 |
| ATOM 3783 | CB | LEU | 494 | 70.482 | 2.387 | 1.851 | 1.00 | 39.16 |
| ATOM 3784 | CG | LEU | 494 | 70.834 | 0.908 | 2.021 | 1.00 | 36.43 |
| ATOM 3785 | CD1 | LEU | 494 | 70.809 | 0.508 | 3.479 | 1.00 | 34.69 |
| ATOM 3786 | CD2 | LEU | 494 | 69.840 | 0.086 | 1.229 | 1.00 | 37.48 |
| ATOM 3787 | C | LEU | 494 | 72.683 | 3.541 | 2.202 | 1.00 | 39.30 |
| ATOM 3788 | O | LEU | 494 | 72.976 | 4.201 | 1.207 | 1.00 | 39.21 |
| ATOM 3789 | N | ALA | 495 | 73.584 | 2.922 | 2.954 | 1.00 | 40.08 |
| ATOM 3791 | CA | ALA | 495 | 74.996 | 2.954 | 2.619 | 1.00 | 41.70 |
| ATOM 3792 | CB | ALA | 495 | 75.654 | 4.162 | 3.283 | 1.00 | 41.63 |
| ATOM 3793 | C | ALA | 495 | 75.670 | 1.669 | 3.080 | 1.00 | 43.92 |
| ATOM 3794 | O | ALA | 495 | 75.033 | 0.818 | 3.711 | 1.00 | 45.20 |
| ATOM 3795 | N | GLU | 496 | 76.946 | 1.515 | 2.731 | 1.00 | 44.21 |
| ATOM 3797 | CA | GLU | 496 | 77.712 | 0.347 | 3.137 | 1.00 | 43.44 |
| ATOM 3798 | CB | GLU | 496 | 78.046 | −0.538 | 1.943 | 1.00 | 45.87 |
| ATOM 3799 | CG | GLU | 496 | 76.816 | −1.142 | 1.301 | 1.00 | 53.11 |
| ATOM 3800 | CD | GLU | 496 | 77.145 | −2.262 | 0.339 | 1.00 | 56.68 |
| ATOM 3801 | OE1 | GLU | 496 | 76.473 | −3.316 | 0.410 | 1.00 | 61.87 |
| ATOM 3802 | OE2 | GLU | 496 | 78.068 | −2.091 | −0.482 | 1.00 | 58.18 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3803 | C | GLU | 496 | 78.973 | 0.773 | 3.860 | 1.00 | 40.97 |
| ATOM 3804 | O | GLU | 496 | 79.835 | 1.437 | 3.302 | 1.00 | 40.91 |
| ATOM 3805 | N | ALA | 497 | 79.036 | 0.439 | 5.136 | 1.00 | 42.07 |
| ATOM 3807 | CA | ALA | 497 | 80.173 | 0.786 | 5.959 | 1.00 | 43.69 |
| ATOM 3808 | CB | ALA | 497 | 79.709 | 1.104 | 7.366 | 1.00 | 40.90 |
| ATOM 3809 | C | ALA | 497 | 81.160 | −0.372 | 5.962 | 1.00 | 46.16 |
| ATOM 3810 | O | ALA | 497 | 80.764 | −1.525 | 5.814 | 1.00 | 46.90 |
| ATOM 3811 | N | ILE | 498 | 82.446 | −0.059 | 6.090 | 1.00 | 48.78 |
| ATOM 3813 | CA | ILE | 498 | 83.494 | −1.068 | 6.114 | 1.00 | 49.59 |
| ATOM 3814 | CB | ILE | 498 | 84.395 | −0.993 | 4.858 | 1.00 | 49.46 |
| ATOM 3815 | CG2 | ILE | 498 | 85.524 | −2.006 | 4.954 | 1.00 | 51.16 |
| ATOM 3816 | CG1 | ILE | 498 | 83.577 | −1.244 | 3.591 | 1.00 | 48.96 |
| ATOM 3817 | CD1 | ILE | 498 | 82.924 | 0.009 | 2.998 | 1.00 | 52.50 |
| ATOM 3818 | C | ILE | 498 | 84.352 | −0.877 | 7.355 | 1.00 | 51.33 |
| ATOM 3819 | O | ILE | 498 | 84.818 | 0.230 | 7.641 | 1.00 | 50.42 |
| ATOM 3820 | N | GLY | 499 | 84.506 | −1.952 | 8.119 | 1.00 | 53.87 |
| ATOM 3822 | CA | GLY | 499 | 85.314 | −1.909 | 9.324 | 1.00 | 58.16 |
| ATOM 3823 | C | GLY | 499 | 84.759 | −1.094 | 10.483 | 1.00 | 62.44 |
| ATOM 3824 | O | GLY | 499 | 85.510 | −0.400 | 11.175 | 1.00 | 65.17 |
| ATOM 3825 | N | LEU | 500 | 83.454 | −1.187 | 10.720 | 1.00 | 62.92 |
| ATOM 3827 | CA | LEU | 500 | 82.839 | −0.453 | 11.822 | 1.00 | 61.93 |
| ATOM 3828 | CB | LEU | 500 | 81.339 | −0.752 | 11.888 | 1.00 | 58.77 |
| ATOM 3829 | CG | LEU | 500 | 80.501 | −0.207 | 10.736 | 1.00 | 56.68 |
| ATOM 3830 | CD1 | LEU | 500 | 79.047 | −0.547 | 10.964 | 1.00 | 55.05 |
| ATOM 3831 | CD2 | LEU | 500 | 80.682 | 1.298 | 10.635 | 1.00 | 56.30 |
| ATOM 3832 | C | LEU | 500 | 83.501 | −0.820 | 13.149 | 1.00 | 63.28 |
| ATOM 3833 | O | LEU | 500 | 83.623 | −2.002 | 13.487 | 1.00 | 64.91 |
| ATOM 3834 | N | PRO | 505 | 87.387 | −6.451 | 10.091 | 1.00 | 82.92 |
| ATOM 3835 | CD | PRO | 505 | 88.522 | −6.966 | 10.874 | 1.00 | 83.74 |
| ATOM 3836 | CA | PRO | 505 | 87.618 | −5.052 | 9.705 | 1.00 | 80.73 |
| ATOM 3837 | CB | PRO | 505 | 89.027 | −4.770 | 10.247 | 1.00 | 81.95 |
| ATOM 3838 | CG | PRO | 505 | 89.655 | −6.133 | 10.342 | 1.00 | 83.54 |
| ATOM 3839 | C | PRO | 505 | 87.514 | −4.794 | 8.205 | 1.00 | 77.60 |
| ATOM 3840 | O | PRO | 505 | 87.445 | −3.651 | 7.761 | 1.00 | 77.24 |
| ATOM 3841 | N | ASN | 506 | 87.488 | −5.863 | 7.424 | 1.00 | 75.24 |
| ATOM 3843 | CA | ASN | 506 | 87.380 | −5.727 | 5.981 | 1.00 | 72.92 |
| ATOM 3844 | CB | ASN | 506 | 88.435 | −6.589 | 5.283 | 1.00 | 73.87 |
| ATOM 3845 | C | ASN | 506 | 85.978 | −6.122 | 5.529 | 1.00 | 70.43 |
| ATOM 3846 | O | ASN | 506 | 85.719 | −6.281 | 4.340 | 1.00 | 70.01 |
| ATOM 3847 | N | ARG | 507 | 85.075 | −6.273 | 6.491 | 1.00 | 68.31 |
| ATOM 3849 | CA | ARG | 507 | 83.697 | −6.647 | 6.200 | 1.00 | 65.59 |
| ATOM 3850 | CB | ARG | 507 | 83.112 | −7.429 | 7.378 | 1.00 | 66.34 |
| ATOM 3851 | C | ARG | 507 | 82.846 | −5.413 | 5.941 | 1.00 | 62.97 |
| ATOM 3852 | O | ARG | 507 | 83.191 | −4.313 | 6.375 | 1.00 | 63.16 |
| ATOM 3853 | N | VAL | 508 | 81.740 | −5.599 | 5.231 | 1.00 | 60.02 |
| ATOM 3855 | CA | VAL | 508 | 80.840 | −4.495 | 4.947 | 1.00 | 58.59 |
| ATOM 3856 | CB | VAL | 508 | 80.532 | −4.357 | 3.439 | 1.00 | 58.40 |
| ATOM 3857 | CG1 | VAL | 508 | 81.813 | −4.196 | 2.658 | 1.00 | 61.14 |
| ATOM 3858 | CG2 | VAL | 508 | 79.751 | −5.553 | 2.938 | 1.00 | 61.01 |
| ATOM 3859 | C | VAL | 508 | 79.537 | −4.682 | 5.707 | 1.00 | 57.24 |
| ATOM 3860 | O | VAL | 508 | 79.031 | −5.803 | 5.836 | 1.00 | 58.42 |
| ATOM 3861 | N | THR | 509 | 79.020 | −3.579 | 6.237 | 1.00 | 54.22 |
| ATOM 3863 | CA | THR | 509 | 77.769 | −3.572 | 6.973 | 1.00 | 48.99 |
| ATOM 3864 | CB | THR | 509 | 77.971 | −3.100 | 8.428 | 1.00 | 49.59 |
| ATOM 3865 | OG1 | THR | 509 | 78.932 | −3.935 | 9.082 | 1.00 | 51.71 |
| ATOM 3867 | CG2 | THR | 509 | 76.665 | −3.166 | 9.198 | 1.00 | 50.69 |
| ATOM 3868 | C | THR | 509 | 76.837 | −2.606 | 6.253 | 1.00 | 46.51 |
| ATOM 3869 | O | THR | 509 | 77.231 | −1.503 | 5.886 | 1.00 | 44.91 |
| ATOM 3870 | N | LYS | 510 | 75.628 | −3.059 | 5.966 | 1.00 | 45.65 |
| ATOM 3872 | CA | LYS | 510 | 74.658 | −2.208 | 5.314 | 1.00 | 43.61 |
| ATOM 3873 | CB | LYS | 510 | 73.598 | −3.058 | 4.632 | 1.00 | 45.46 |
| ATOM 3874 | CG | LYS | 510 | 72.845 | −2.306 | 3.568 | 1.00 | 54.00 |
| ATOM 3875 | CD | LYS | 510 | 73.022 | −2.912 | 2.183 | 1.00 | 58.74 |
| ATOM 3876 | CE | LYS | 510 | 72.194 | −4.184 | 2.007 | 1.00 | 59.63 |
| ATOM 3877 | NZ | LYS | 510 | 72.711 | −5.323 | 2.815 | 1.00 | 61.62 |
| ATOM 3881 | C | LYS | 510 | 74.065 | −1.359 | 6.450 | 1.00 | 42.05 |
| ATOM 3882 | O | LYS | 510 | 73.566 | −1.898 | 7.439 | 1.00 | 41.29 |
| ATOM 3883 | N | VAL | 511 | 74.185 | −0.038 | 6.333 | 1.00 | 40.14 |
| ATOM 3885 | CA | VAL | 511 | 73.719 | 0.894 | 7.359 | 1.00 | 35.38 |
| ATOM 3886 | CB | VAL | 511 | 74.932 | 1.554 | 8.074 | 1.00 | 33.16 |
| ATOM 3887 | CG1 | VAL | 511 | 75.761 | 0.501 | 8.795 | 1.00 | 29.24 |
| ATOM 3888 | CG2 | VAL | 511 | 75.804 | 2.295 | 7.054 | 1.00 | 30.37 |
| ATOM 3889 | C | VAL | 511 | 72.856 | 2.005 | 6.776 | 1.00 | 33.90 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3890 | O | VAL | 511 | 72.722 | 2.110 | 5.558 | 1.00 | 32.53 |
| ATOM 3891 | N | ALA | 512 | 72.261 | 2.813 | 7.655 | 1.00 | 31.97 |
| ATOM 3893 | CA | ALA | 512 | 71.434 | 3.956 | 7.248 | 1.00 | 31.10 |
| ATOM 3894 | CB | ALA | 512 | 70.088 | 3.945 | 7.952 | 1.00 | 27.38 |
| ATOM 3895 | C | ALA | 512 | 72.225 | 5.186 | 7.660 | 1.00 | 30.49 |
| ATOM 3896 | O | ALA | 512 | 72.775 | 5.235 | 8.766 | 1.00 | 30.10 |
| ATOM 3897 | N | VAL | 513 | 72.312 | 6.162 | 6.765 | 1.00 | 30.50 |
| ATOM 3899 | CA | VAL | 513 | 73.064 | 7.382 | 7.041 | 1.00 | 29.68 |
| ATOM 3900 | CB | VAL | 513 | 74.204 | 7.593 | 6.015 | 1.00 | 28.89 |
| ATOM 3901 | CG1 | VAL | 513 | 74.966 | 8.856 | 6.334 | 1.00 | 26.30 |
| ATOM 3902 | CG2 | VAL | 513 | 75.134 | 6.389 | 5.987 | 1.00 | 26.66 |
| ATOM 3903 | C | VAL | 513 | 72.171 | 8.607 | 7.012 | 1.00 | 28.50 |
| ATOM 3904 | O | VAL | 513 | 71.536 | 8.893 | 5.994 | 1.00 | 26.27 |
| ATOM 3905 | N | LYS | 514 | 72.091 | 9.282 | 8.154 | 1.00 | 29.18 |
| ATOM 3907 | CA | LYS | 514 | 71.307 | 10.508 | 8.295 | 1.00 | 31.52 |
| ATOM 3908 | CB | LYS | 514 | 70.797 | 10.659 | 9.728 | 1.00 | 33.52 |
| ATOM 3909 | CG | LYS | 514 | 69.890 | 9.540 | 10.198 | 1.00 | 35.67 |
| ATOM 3910 | CD | LYS | 514 | 69.439 | 9.831 | 11.618 | 1.00 | 44.89 |
| ATOM 3911 | CE | LYS | 514 | 68.313 | 8.909 | 12.060 | 1.00 | 51.12 |
| ATOM 3912 | NZ | LYS | 514 | 67.029 | 9.137 | 11.307 | 1.00 | 57.11 |
| ATOM 3916 | C | LYS | 514 | 72.233 | 11.681 | 7.956 | 1.00 | 30.75 |
| ATOM 3917 | O | LYS | 514 | 73.390 | 11.698 | 8.379 | 1.00 | 30.08 |
| ATOM 3918 | N | MET | 515 | 71.724 | 12.651 | 7.201 | 1.00 | 29.45 |
| ATOM 3920 | CA | MET | 515 | 72.511 | 13.814 | 6.786 | 1.00 | 28.74 |
| ATOM 3921 | CB | MET | 515 | 73.342 | 13.466 | 5.552 | 1.00 | 27.72 |
| ATOM 3922 | CG | MET | 515 | 72.487 | 13.034 | 4.378 | 1.00 | 31.56 |
| ATOM 3923 | SD | MET | 515 | 73.442 | 12.549 | 2.945 | 1.00 | 34.98 |
| ATOM 3924 | CE | MET | 515 | 73.730 | 10.878 | 3.330 | 1.00 | 31.23 |
| ATOM 3925 | C | MET | 515 | 71.585 | 14.966 | 6.444 | 1.00 | 27.75 |
| ATOM 3926 | O | MET | 515 | 70.369 | 14.794 | 6.359 | 1.00 | 29.07 |
| ATOM 3927 | N | LEU | 516 | 72.152 | 16.145 | 6.247 | 1.00 | 28.33 |
| ATOM 3929 | CA | LEU | 516 | 71.348 | 17.313 | 5.912 | 1.00 | 31.16 |
| ATOM 3930 | CB | LEU | 516 | 72.052 | 18.605 | 6.339 | 1.00 | 28.70 |
| ATOM 3931 | CG | LEU | 516 | 72.312 | 18.866 | 7.826 | 1.00 | 28.33 |
| ATOM 3932 | CD1 | LEU | 516 | 73.098 | 20.156 | 7.949 | 1.00 | 28.45 |
| ATOM 3933 | CD2 | LEU | 516 | 71.020 | 18.959 | 8.604 | 1.00 | 21.64 |
| ATOM 3934 | C | LEU | 516 | 71.069 | 17.378 | 4.421 | 1.00 | 33.22 |
| ATOM 3935 | O | LEU | 516 | 71.762 | 16.760 | 3.619 | 1.00 | 35.00 |
| ATOM 3936 | N | LYS | 517 | 70.022 | 18.100 | 4.061 | 1.00 | 34.69 |
| ATOM 3938 | CA | LYS | 517 | 69.696 | 18.286 | 2.665 | 1.00 | 34.20 |
| ATOM 3939 | CB | LYS | 517 | 68.194 | 18.475 | 2.496 | 1.00 | 37.45 |
| ATOM 3940 | CG | LYS | 517 | 67.403 | 17.264 | 2.950 | 1.00 | 43.71 |
| ATOM 3941 | CD | LYS | 517 | 66.157 | 17.072 | 2.126 | 1.00 | 51.25 |
| ATOM 3942 | CE | LYS | 517 | 65.123 | 18.135 | 2.419 | 1.00 | 58.56 |
| ATOM 3943 | NZ | LYS | 517 | 64.010 | 18.049 | 1.438 | 1.00 | 63.12 |
| ATOM 3947 | C | LYS | 517 | 70.482 | 19.533 | 2.259 | 1.00 | 33.81 |
| ATOM 3948 | O | LYS | 517 | 70.991 | 20.244 | 3.130 | 1.00 | 33.17 |
| ATOM 3949 | N | SER | 518 | 70.603 | 19.788 | 0.959 | 1.00 | 33.42 |
| ATOM 3951 | CA | SER | 518 | 71.369 | 20.938 | 0.472 | 1.00 | 33.33 |
| ATOM 3952 | CB | SER | 518 | 71.550 | 20.842 | −1.042 | 1.00 | 33.23 |
| ATOM 3953 | OG | SER | 518 | 70.306 | 20.624 | −1.678 | 1.00 | 38.84 |
| ATOM 3955 | C | SER | 518 | 70.794 | 22.298 | 0.846 | 1.00 | 33.23 |
| ATOM 3956 | O | SER | 518 | 71.509 | 23.305 | 0.865 | 1.00 | 34.14 |
| ATOM 3957 | N | ASP | 519 | 69.510 | 22.313 | 1.178 | 1.00 | 32.77 |
| ATOM 3959 | CA | ASP | 519 | 68.825 | 23.541 | 1.570 | 1.00 | 33.26 |
| ATOM 3960 | CB | ASP | 519 | 67.401 | 23.563 | 0.995 | 1.00 | 35.10 |
| ATOM 3961 | CG | ASP | 519 | 66.484 | 22.503 | 1.617 | 1.00 | 38.98 |
| ATOM 3962 | OD1 | ASP | 519 | 66.958 | 21.430 | 2.042 | 1.00 | 37.30 |
| ATOM 3963 | OD2 | ASP | 519 | 65.261 | 22.754 | 1.674 | 1.00 | 43.65 |
| ATOM 3964 | C | ASP | 519 | 68.793 | 23.747 | 3.091 | 1.00 | 33.05 |
| ATOM 3965 | O | ASP | 519 | 68.114 | 24.648 | 3.580 | 1.00 | 35.19 |
| ATOM 3966 | N | ALA | 520 | 69.538 | 22.931 | 3.833 | 1.00 | 31.38 |
| ATOM 3968 | CA | ALA | 520 | 69.570 | 23.032 | 5.293 | 1.00 | 29.47 |
| ATOM 3969 | CB | ALA | 520 | 70.264 | 21.830 | 5.870 | 1.00 | 29.74 |
| ATOM 3970 | C | ALA | 520 | 70.229 | 24.301 | 5.812 | 1.00 | 29.83 |
| ATOM 3971 | O | ALA | 520 | 71.004 | 24.952 | 5.106 | 1.00 | 30.23 |
| ATOM 3972 | N | THR | 521 | 69.938 | 24.616 | 7.071 | 1.00 | 31.57 |
| ATOM 3974 | CA | THR | 521 | 70.487 | 25.793 | 7.742 | 1.00 | 34.56 |
| ATOM 3975 | CB | THR | 521 | 69.361 | 26.736 | 8.302 | 1.00 | 38.37 |
| ATOM 3976 | OG1 | THR | 521 | 68.670 | 26.082 | 9.376 | 1.00 | 41.75 |
| ATOM 3978 | CG2 | THR | 521 | 68.357 | 27.117 | 7.209 | 1.00 | 38.30 |
| ATOM 3979 | C | THR | 521 | 71.353 | 25.363 | 8.916 | 1.00 | 33.22 |
| ATOM 3980 | O | THR | 521 | 71.320 | 24.207 | 9.327 | 1.00 | 32.31 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3981 | N | GLU | 522 | 72.092 | 26.310 | 9.479 | 1.00 | 34.43 |
| ATOM 3983 | CA | GLU | 522 | 72.951 | 26.042 | 10.619 | 1.00 | 39.53 |
| ATOM 3984 | CB | GLU | 522 | 73.634 | 27.340 | 11.068 | 1.00 | 46.35 |
| ATOM 3985 | CG | GLU | 522 | 74.398 | 27.271 | 12.402 | 1.00 | 58.03 |
| ATOM 3986 | CD | GLU | 522 | 75.772 | 26.603 | 12.301 | 1.00 | 63.14 |
| ATOM 3987 | OE1 | GLU | 522 | 76.800 | 27.321 | 12.404 | 1.00 | 61.75 |
| ATOM 3988 | OE2 | GLU | 522 | 75.824 | 25.359 | 12.158 | 1.00 | 66.35 |
| ATOM 3989 | C | GLU | 522 | 72.130 | 25.428 | 11.765 | 1.00 | 38.40 |
| ATOM 3990 | O | GLU | 522 | 72.642 | 24.622 | 12.543 | 1.00 | 37.92 |
| ATOM 3991 | N | LYS | 523 | 70.853 | 25.792 | 11.849 | 1.00 | 36.43 |
| ATOM 3993 | CA | LYS | 523 | 69.995 | 25.261 | 12.893 | 1.00 | 36.83 |
| ATOM 3994 | CB | LYS | 523 | 68.703 | 26.065 | 13.008 | 1.00 | 40.88 |
| ATOM 3995 | CG | LYS | 523 | 67.793 | 25.636 | 14.152 | 1.00 | 44.55 |
| ATOM 3996 | CD | LYS | 523 | 66.584 | 24.898 | 13.607 | 1.00 | 52.68 |
| ATOM 3997 | CE | LYS | 523 | 65.629 | 24.483 | 14.708 | 1.00 | 56.04 |
| ATOM 3998 | NZ | LYS | 523 | 64.537 | 23.646 | 14.123 | 1.00 | 58.13 |
| ATOM 4002 | C | LYS | 523 | 69.689 | 23.804 | 12.601 | 1.00 | 35.27 |
| ATOM 4003 | O | LYS | 523 | 69.645 | 22.985 | 13.513 | 1.00 | 36.58 |
| ATOM 4004 | N | ASP | 524 | 69.496 | 23.473 | 11.326 | 1.00 | 32.27 |
| ATOM 4006 | CA | ASP | 524 | 69.235 | 22.089 | 10.963 | 1.00 | 27.18 |
| ATOM 4007 | CB | ASP | 524 | 68.952 | 21.953 | 9.480 | 1.00 | 26.32 |
| ATOM 4008 | CG | ASP | 524 | 67.635 | 22.555 | 9.089 | 1.00 | 25.22 |
| ATOM 4009 | OD1 | ASP | 524 | 66.662 | 22.394 | 9.848 | 1.00 | 31.78 |
| ATOM 4010 | OD2 | ASP | 524 | 67.568 | 23.190 | 8.028 | 1.00 | 24.00 |
| ATOM 4011 | C | ASP | 524 | 70.445 | 21.268 | 11.342 | 1.00 | 26.83 |
| ATOM 4012 | O | ASP | 524 | 70.312 | 20.165 | 11.851 | 1.00 | 28.65 |
| ATOM 4013 | N | LEU | 525 | 71.633 | 21.827 | 11.129 | 1.00 | 28.69 |
| ATOM 4015 | CA | LEU | 525 | 72.872 | 21.148 | 11.473 | 1.00 | 26.96 |
| ATOM 4016 | CB | LEU | 525 | 74.077 | 21.981 | 11.049 | 1.00 | 22.80 |
| ATOM 4017 | CG | LEU | 525 | 75.445 | 21.355 | 11.341 | 1.00 | 22.32 |
| ATOM 4018 | CD1 | LEU | 525 | 75.522 | 19.883 | 10.858 | 1.00 | 18.89 |
| ATOM 4019 | CD2 | LEU | 525 | 76.504 | 22.212 | 10.704 | 1.00 | 17.44 |
| ATOM 4020 | C | LEU | 525 | 72.886 | 20.926 | 12.980 | 1.00 | 28.00 |
| ATOM 4021 | O | LEU | 525 | 73.160 | 19.816 | 13.462 | 1.00 | 28.82 |
| ATOM 4022 | N | SER | 526 | 72.567 | 21.992 | 13.707 | 1.00 | 27.98 |
| ATOM 4024 | CA | SER | 526 | 72.496 | 21.994 | 15.168 | 1.00 | 30.78 |
| ATOM 4025 | CB | SER | 526 | 71.939 | 23.345 | 15.627 | 1.00 | 33.18 |
| ATOM 4026 | OG | SER | 526 | 71.624 | 23.347 | 17.009 | 1.00 | 42.73 |
| ATOM 4028 | C | SER | 526 | 71.599 | 20.865 | 15.704 | 1.00 | 30.56 |
| ATOM 4029 | O | SER | 526 | 71.906 | 20.206 | 16.716 | 1.00 | 31.92 |
| ATOM 4030 | N | ASP | 527 | 70.484 | 20.665 | 15.018 | 1.00 | 28.19 |
| ATOM 4032 | CA | ASP | 527 | 69.516 | 19.651 | 15.366 | 1.00 | 27.41 |
| ATOM 4033 | CB | ASP | 527 | 68.207 | 19.932 | 14.632 | 1.00 | 27.63 |
| ATOM 4034 | CG | ASP | 527 | 67.492 | 21.172 | 15.149 | 1.00 | 27.37 |
| ATOM 4035 | OD1 | ASP | 527 | 67.870 | 21.728 | 16.211 | 1.00 | 26.70 |
| ATOM 4036 | OD2 | ASP | 527 | 66.525 | 21.579 | 14.487 | 1.00 | 33.80 |
| ATOM 4037 | C | ASP | 527 | 70.007 | 18.241 | 15.063 | 1.00 | 27.36 |
| ATOM 4038 | O | ASP | 527 | 69.722 | 17.309 | 15.816 | 1.00 | 30.13 |
| ATOM 4039 | N | LEU | 528 | 70.716 | 18.077 | 13.952 | 1.00 | 25.76 |
| ATOM 4041 | CA | LEU | 528 | 71.245 | 16.765 | 13.588 | 1.00 | 25.29 |
| ATOM 4042 | CB | LEU | 528 | 71.777 | 16.771 | 12.143 | 1.00 | 23.65 |
| ATOM 4043 | CG | LEU | 528 | 72.283 | 15.432 | 11.574 | 1.00 | 25.86 |
| ATOM 4044 | CD1 | LEU | 528 | 71.234 | 14.341 | 11.770 | 1.00 | 23.35 |
| ATOM 4045 | CD2 | LEU | 528 | 72.652 | 15.566 | 10.102 | 1.00 | 17.46 |
| ATOM 4046 | C | LEU | 528 | 72.351 | 16.368 | 14.578 | 1.00 | 25.66 |
| ATOM 4047 | O | LEU | 528 | 72.418 | 15.210 | 15.015 | 1.00 | 24.02 |
| ATOM 4048 | N | ILE | 529 | 73.200 | 17.338 | 14.934 | 1.00 | 26.36 |
| ATOM 4050 | CA | ILE | 529 | 74.304 | 17.130 | 15.886 | 1.00 | 26.17 |
| ATOM 4051 | CB | ILE | 529 | 75.192 | 18.381 | 16.003 | 1.00 | 22.77 |
| ATOM 4052 | CG2 | ILE | 529 | 76.250 | 18.180 | 17.057 | 1.00 | 21.32 |
| ATOM 4053 | CG1 | ILE | 529 | 75.876 | 18.666 | 14.685 | 1.00 | 20.71 |
| ATOM 4054 | CD1 | ILE | 529 | 76.621 | 19.965 | 14.675 | 1.00 | 25.60 |
| ATOM 4055 | C | ILE | 529 | 73.756 | 16.835 | 17.283 | 1.00 | 29.87 |
| ATOM 4056 | O | ILE | 529 | 74.253 | 15.948 | 17.977 | 1.00 | 32.20 |
| ATOM 4057 | N | SER | 530 | 72.741 | 17.591 | 17.693 | 1.00 | 28.63 |
| ATOM 4059 | CA | SER | 530 | 72.143 | 17.381 | 18.991 | 1.00 | 32.21 |
| ATOM 4060 | CB | SER | 530 | 71.031 | 18.399 | 19.231 | 1.00 | 37.45 |
| ATOM 4061 | OG | SER | 530 | 70.065 | 18.342 | 18.195 | 1.00 | 49.52 |
| ATOM 4063 | C | SER | 530 | 71.598 | 15.956 | 19.075 | 1.00 | 30.96 |
| ATOM 4064 | O | SER | 530 | 71.728 | 15.301 | 20.105 | 1.00 | 33.05 |
| ATOM 4065 | N | GLU | 531 | 70.996 | 15.476 | 17.996 | 1.00 | 29.13 |
| ATOM 4067 | CA | GLU | 531 | 70.468 | 14.117 | 17.987 | 1.00 | 29.84 |
| ATOM 4068 | CB | GLU | 531 | 69.672 | 13.847 | 16.709 | 1.00 | 30.29 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B | |
|---|---|---|---|---|---|---|---|---|---|
| ATOM 4069 | CG | GLU | 531 | 69.093 | 12.445 | 16.666 | 1.00 | 27.39 | |
| ATOM 4070 | CD | GLU | 531 | 68.521 | 12.074 | 15.331 | 1.00 | 31.34 | |
| ATOM 4071 | OE1 | GLU | 531 | 67.929 | 10.981 | 15.228 | 1.00 | 35.90 | |
| ATOM 4072 | OE2 | GLU | 531 | 68.660 | 12.860 | 14.376 | 1.00 | 38.37 | |
| ATOM 4073 | C | GLU | 531 | 71.600 | 13.081 | 18.109 | 1.00 | 28.48 | |
| ATOM 4074 | O | GLU | 531 | 71.468 | 12.094 | 18.822 | 1.00 | 28.17 | |
| ATOM 4075 | N | MET | 532 | 72.682 | 13.281 | 17.364 | 1.00 | 28.12 | |
| ATOM 4077 | CA | MET | 532 | 73.832 | 12.376 | 17.409 | 1.00 | 27.64 | |
| ATOM 4078 | CB | MET | 532 | 74.953 | 12.899 | 16.499 | 1.00 | 26.47 | |
| ATOM 4079 | CG | MET | 532 | 76.267 | 12.125 | 16.601 | 1.00 | 22.25 | |
| ATOM 4080 | SD | MET | 532 | 77.406 | 12.610 | 15.286 | 1.00 | 30.32 | |
| ATOM 4081 | CE | MET | 532 | 77.613 | 14.366 | 15.661 | 1.00 | 20.92 | |
| ATOM 4082 | C | MET | 532 | 74.339 | 12.328 | 18.832 | 1.00 | 27.87 | |
| ATOM 4083 | O | MET | 532 | 74.640 | 11.267 | 19.364 | 1.00 | 30.31 | |
| ATOM 4084 | N | GLU | 533 | 74.439 | 13.497 | 19.442 | 1.00 | 27.08 | |
| ATOM 4086 | CA | GLU | 533 | 74.906 | 13.594 | 20.802 | 1.00 | 28.50 | |
| ATOM 4087 | CB | GLU | 533 | 75.071 | 15.064 | 21.177 | 1.00 | 29.09 | |
| ATOM 4088 | CG | GLU | 533 | 76.216 | 15.745 | 20.433 | 1.00 | 28.90 | |
| ATOM 4089 | CD | GLU | 533 | 77.564 | 15.070 | 20.661 | 1.00 | 31.08 | |
| ATOM 4090 | OE1 | GLU | 533 | 78.001 | 14.969 | 21.823 | 1.00 | 34.15 | |
| ATOM 4091 | OE2 | GLU | 533 | 78.202 | 14.643 | 19.678 | 1.00 | 33.60 | |
| ATOM 4092 | C | GLU | 533 | 73.981 | 12.850 | 21.774 | 1.00 | 29.91 | |
| ATOM 4093 | O | GLU | 533 | 74.455 | 12.093 | 22.637 | 1.00 | 29.73 | |
| ATOM 4094 | N | MET | 534 | 72.670 | 13.014 | 21.588 | 1.00 | 29.70 | |
| ATOM 4096 | CA | MET | 534 | 71.692 | 12.346 | 22.444 | 1.00 | 27.97 | |
| ATOM 4097 | CB | MET | 534 | 70.258 | 12.751 | 22.082 | 1.00 | 28.95 | |
| ATOM 4098 | CG | MET | 534 | 69.311 | 12.594 | 23.278 | 0.50 | 29.62 | PRT1 |
| ATOM 4099 | SD | MET | 534 | 67.538 | 12.682 | 22.961 | 0.50 | 29.87 | PRT1 |
| ATOM 4100 | CE | MET | 534 | 67.269 | 14.452 | 22.795 | 0.50 | 31.07 | PRT1 |
| ATOM 4101 | C | MET | 534 | 71.855 | 10.821 | 22.362 | 1.00 | 28.36 | |
| ATOM 4102 | O | MET | 534 | 71.833 | 10.143 | 23.386 | 1.00 | 27.02 | |
| ATOM 4103 | N | MET | 535 | 72.048 | 10.297 | 21.151 | 1.00 | 26.96 | |
| ATOM 4105 | CA | MET | 535 | 72.239 | 8.861 | 20.947 | 1.00 | 26.63 | |
| ATOM 4106 | CB | MET | 535 | 72.347 | 8.521 | 19.456 | 1.00 | 24.67 | |
| ATOM 4107 | CG | MET | 535 | 71.089 | 8.778 | 18.659 | 1.00 | 23.15 | |
| ATOM 4108 | SD | MET | 535 | 71.160 | 8.062 | 17.011 | 1.00 | 24.57 | |
| ATOM 4109 | CE | MET | 535 | 71.251 | 9.486 | 16.023 | 1.00 | 24.79 | |
| ATOM 4110 | C | MET | 535 | 73.498 | 8.390 | 21.669 | 1.00 | 27.66 | |
| ATOM 4111 | O | MET | 535 | 73.564 | 7.259 | 22.164 | 1.00 | 28.83 | |
| ATOM 4112 | N | LYS | 536 | 74.515 | 9.246 | 21.698 | 1.00 | 29.13 | |
| ATOM 4114 | CA | LYS | 536 | 75.757 | 8.918 | 22.392 | 1.00 | 30.50 | |
| ATOM 4115 | CB | LYS | 536 | 76.812 | 9.985 | 22.131 | 1.00 | 29.15 | |
| ATOM 4116 | CG | LYS | 536 | 77.499 | 9.883 | 20.802 | 1.00 | 27.71 | |
| ATOM 4117 | CD | LYS | 536 | 78.377 | 11.100 | 20.615 | 1.00 | 28.12 | |
| ATOM 4118 | CE | LYS | 536 | 79.085 | 11.096 | 19.279 | 1.00 | 26.89 | |
| ATOM 4119 | NZ | LYS | 536 | 79.688 | 12.436 | 19.077 | 1.00 | 27.54 | |
| ATOM 4123 | C | LYS | 536 | 75.480 | 8.836 | 23.892 | 1.00 | 31.92 | |
| ATOM 4124 | O | LYS | 536 | 75.921 | 7.908 | 24.559 | 1.00 | 31.19 | |
| ATOM 4125 | N | MET | 537 | 74.742 | 9.814 | 24.409 | 1.00 | 34.02 | |
| ATOM 4127 | CA | MET | 537 | 74.384 | 9.881 | 25.822 | 1.00 | 36.35 | |
| ATOM 4128 | CB | MET | 537 | 73.648 | 11.197 | 26.083 | 1.00 | 43.33 | |
| ATOM 4129 | CG | MET | 537 | 73.096 | 11.376 | 27.507 | 1.00 | 54.60 | |
| ATOM 4130 | SD | MET | 537 | 71.426 | 10.674 | 27.856 | 1.00 | 67.38 | |
| ATOM 4131 | CE | MET | 537 | 71.684 | 9.813 | 29.440 | 1.00 | 62.03 | |
| ATOM 4132 | C | MET | 537 | 73.507 | 8.705 | 26.253 | 1.00 | 34.53 | |
| ATOM 4133 | O | MET | 537 | 73.744 | 8.069 | 27.275 | 1.00 | 36.76 | |
| ATOM 4134 | N | ILE | 538 | 72.496 | 8.425 | 25.454 | 1.00 | 32.24 | |
| ATOM 4136 | CA | ILE | 538 | 71.568 | 7.367 | 25.757 | 1.00 | 29.88 | |
| ATOM 4137 | CB | ILE | 538 | 70.396 | 7.384 | 24.757 | 1.00 | 26.98 | |
| ATOM 4138 | CG2 | ILE | 538 | 69.582 | 6.096 | 24.842 | 1.00 | 27.93 | |
| ATOM 4139 | CG1 | ILE | 538 | 69.527 | 8.614 | 25.036 | 1.00 | 22.58 | |
| ATOM 4140 | CD1 | ILE | 538 | 68.399 | 8.787 | 24.058 | 1.00 | 24.58 | |
| ATOM 4141 | C | ILE | 538 | 72.236 | 6.006 | 25.804 | 1.00 | 31.83 | |
| ATOM 4142 | O | ILE | 538 | 71.983 | 5.227 | 26.713 | 1.00 | 36.32 | |
| ATOM 4143 | N | GLY | 539 | 73.102 | 5.716 | 24.848 | 1.00 | 32.45 | |
| ATOM 4145 | CA | GLY | 539 | 73.744 | 4.422 | 24.850 | 1.00 | 32.13 | |
| ATOM 4146 | C | GLY | 539 | 72.974 | 3.380 | 24.056 | 1.00 | 33.83 | |
| ATOM 4147 | O | GLY | 539 | 71.876 | 3.654 | 23.530 | 1.00 | 33.75 | |
| ATOM 4148 | N | LYS | 540 | 73.539 | 2.173 | 24.010 | 1.00 | 33.36 | |
| ATOM 4150 | CA | LYS | 540 | 72.980 | 1.054 | 23.256 | 1.00 | 37.04 | |
| ATOM 4151 | CB | LYS | 540 | 74.110 | 0.181 | 22.709 | 1.00 | 39.21 | |
| ATOM 4152 | CG | LYS | 540 | 74.865 | 0.893 | 21.623 | 1.00 | 48.72 | |
| ATOM 4153 | CD | LYS | 540 | 75.818 | 0.009 | 20.850 | 1.00 | 56.84 | |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4154 | CE | LYS | 540 | 76.225 | 0.693 | 19.516 | 1.00 | 62.14 |
| ATOM 4155 | NZ | LYS | 540 | 77.252 | −0.102 | 18.805 | 1.00 | 71.02 |
| ATOM 4159 | C | LYS | 540 | 71.938 | 0.162 | 23.901 | 1.00 | 36.51 |
| ATOM 4160 | O | LYS | 540 | 71.963 | −0.096 | 25.113 | 1.00 | 38.52 |
| ATOM 4161 | N | HIS | 541 | 71.017 | −0.295 | 23.058 | 1.00 | 32.98 |
| ATOM 4163 | CA | HIS | 541 | 69.963 | −1.230 | 23.424 | 1.00 | 31.20 |
| ATOM 4164 | CB | HIS | 541 | 68.779 | −0.561 | 24.095 | 1.00 | 30.35 |
| ATOM 4165 | CG | HIS | 541 | 67.815 | −1.540 | 24.694 | 1.00 | 32.56 |
| ATOM 4166 | CD2 | HIS | 541 | 67.737 | −2.058 | 25.941 | 1.00 | 32.45 |
| ATOM 4167 | ND1 | HIS | 541 | 66.795 | −2.124 | 23.974 | 1.00 | 29.22 |
| ATOM 4169 | CE1 | HIS | 541 | 66.134 | −2.965 | 24.753 | 1.00 | 31.56 |
| ATOM 4170 | NE2 | HIS | 541 | 66.679 | −2.932 | 25.957 | 1.00 | 32.22 |
| ATOM 4172 | C | HIS | 541 | 69.509 | −1.937 | 22.152 | 1.00 | 32.00 |
| ATOM 4173 | O | HIS | 541 | 69.409 | −1.324 | 21.095 | 1.00 | 32.84 |
| ATOM 4174 | N | LYS | 542 | 69.187 | −3.222 | 22.273 | 1.00 | 33.61 |
| ATOM 4176 | CA | LYS | 542 | 68.786 | −4.061 | 21.154 | 1.00 | 31.54 |
| ATOM 4177 | CB | LYS | 542 | 68.653 | −5.516 | 21.596 | 1.00 | 33.94 |
| ATOM 4178 | CG | LYS | 542 | 68.322 | −6.451 | 20.437 | 1.00 | 42.34 |
| ATOM 4179 | CD | LYS | 542 | 68.083 | −7.885 | 20.856 | 1.00 | 47.57 |
| ATOM 4180 | CE | LYS | 542 | 67.634 | −8.726 | 19.658 | 1.00 | 52.70 |
| ATOM 4181 | NZ | LYS | 542 | 67.402 | −10.146 | 20.023 | 1.00 | 59.51 |
| ATOM 4185 | C | LYS | 542 | 67.495 | −3.611 | 20.487 | 1.00 | 29.57 |
| ATOM 4186 | O | LYS | 542 | 67.268 | −3.884 | 19.305 | 1.00 | 27.99 |
| ATOM 4187 | N | ASN | 543 | 66.649 | −2.931 | 21.253 | 1.00 | 28.32 |
| ATOM 4189 | CA | ASN | 543 | 65.378 | −2.476 | 20.714 | 1.00 | 28.86 |
| ATOM 4190 | CB | ASN | 543 | 64.231 | −2.947 | 21.601 | 1.00 | 29.33 |
| ATOM 4191 | CG | ASN | 543 | 64.247 | −4.452 | 21.811 | 1.00 | 29.64 |
| ATOM 4192 | OD1 | ASN | 543 | 64.437 | −4.926 | 22.930 | 1.00 | 33.86 |
| ATOM 4193 | ND2 | ASN | 543 | 64.106 | −5.206 | 20.732 | 1.00 | 28.02 |
| ATOM 4196 | C | ASN | 543 | 65.252 | −0.983 | 20.378 | 1.00 | 29.69 |
| ATOM 4197 | O | ASN | 543 | 64.159 | −0.413 | 20.457 | 1.00 | 30.02 |
| ATOM 4198 | N | ILE | 544 | 66.372 | −0.357 | 20.011 | 1.00 | 27.35 |
| ATOM 4200 | CA | ILE | 544 | 66.382 | 1.046 | 19.593 | 1.00 | 25.95 |
| ATOM 4201 | CB | ILE | 544 | 66.898 | 2.030 | 20.706 | 1.00 | 25.56 |
| ATOM 4202 | CG2 | ILE | 544 | 66.146 | 1.819 | 22.037 | 1.00 | 21.06 |
| ATOM 4203 | CG1 | ILE | 544 | 68.406 | 1.901 | 20.902 | 1.00 | 25.61 |
| ATOM 4204 | CD1 | ILE | 544 | 68.952 | 2.818 | 21.976 | 1.00 | 25.89 |
| ATOM 4205 | C | ILE | 544 | 67.341 | 1.083 | 18.399 | 1.00 | 25.97 |
| ATOM 4206 | O | ILE | 544 | 68.126 | 0.152 | 18.227 | 1.00 | 25.69 |
| ATOM 4207 | N | ILE | 545 | 67.226 | 2.095 | 17.537 | 1.00 | 27.27 |
| ATOM 4209 | CA | ILE | 545 | 68.129 | 2.243 | 16.384 | 1.00 | 27.02 |
| ATOM 4210 | CB | ILE | 545 | 67.541 | 3.194 | 15.307 | 1.00 | 27.30 |
| ATOM 4211 | CG2 | ILE | 545 | 68.592 | 3.553 | 14.269 | 1.00 | 26.52 |
| ATOM 4212 | CG1 | ILE | 545 | 66.309 | 2.570 | 14.638 | 1.00 | 22.63 |
| ATOM 4213 | CD1 | ILE | 545 | 66.605 | 1.447 | 13.665 | 1.00 | 17.57 |
| ATOM 4214 | C | ILE | 545 | 69.383 | 2.873 | 16.979 | 1.00 | 28.55 |
| ATOM 4215 | O | ILE | 545 | 69.346 | 4.014 | 17.451 | 1.00 | 29.47 |
| ATOM 4216 | N | ASN | 546 | 70.482 | 2.123 | 16.965 | 1.00 | 30.90 |
| ATOM 4218 | CA | ASN | 546 | 71.748 | 2.564 | 17.560 | 1.00 | 29.56 |
| ATOM 4219 | CB | ASN | 546 | 72.497 | 1.365 | 18.159 | 1.00 | 26.32 |
| ATOM 4220 | CG | ASN | 546 | 71.732 | 0.695 | 19.281 | 1.00 | 23.81 |
| ATOM 4221 | OD1 | ASN | 546 | 71.580 | 1.252 | 20.362 | 1.00 | 27.34 |
| ATOM 4222 | ND2 | ASN | 546 | 71.267 | −0.515 | 19.039 | 1.00 | 23.49 |
| ATOM 4225 | C | ASN | 546 | 72.700 | 3.330 | 16.653 | 1.00 | 30.99 |
| ATOM 4226 | O | ASN | 546 | 72.679 | 3.169 | 15.430 | 1.00 | 30.98 |
| ATOM 4227 | N | LEU | 547 | 73.543 | 4.148 | 17.286 | 1.00 | 32.29 |
| ATOM 4229 | CA | LEU | 547 | 74.570 | 4.948 | 16.610 | 1.00 | 30.93 |
| ATOM 4230 | CB | LEU | 547 | 75.043 | 6.076 | 17.542 | 1.00 | 25.97 |
| ATOM 4231 | CG | LEU | 547 | 76.075 | 7.088 | 17.021 | 1.00 | 22.12 |
| ATOM 4232 | CD1 | LEU | 547 | 75.553 | 7.815 | 15.765 | 1.00 | 22.10 |
| ATOM 4233 | CD2 | LEU | 547 | 76.415 | 8.089 | 18.112 | 1.00 | 18.67 |
| ATOM 4234 | C | LEU | 547 | 75.756 | 4.039 | 16.264 | 1.00 | 30.70 |
| ATOM 4235 | O | LEU | 547 | 76.284 | 3.361 | 17.137 | 1.00 | 34.46 |
| ATOM 4236 | N | LEU | 548 | 76.141 | 3.993 | 14.992 | 1.00 | 30.97 |
| ATOM 4238 | CA | LEU | 548 | 77.262 | 3.165 | 14.562 | 1.00 | 30.73 |
| ATOM 4239 | CB | LEU | 548 | 76.929 | 2.406 | 13.281 | 1.00 | 29.24 |
| ATOM 4240 | CG | LEU | 548 | 75.788 | 1.394 | 13.371 | 1.00 | 28.77 |
| ATOM 4241 | CD1 | LEU | 548 | 75.924 | 0.460 | 12.209 | 1.00 | 26.55 |
| ATOM 4242 | CD2 | LEU | 548 | 75.839 | 0.616 | 14.683 | 1.00 | 23.48 |
| ATOM 4243 | C | LEU | 548 | 78.522 | 3.982 | 14.347 | 1.00 | 33.00 |
| ATOM 4244 | O | LEU | 548 | 79.640 | 3.500 | 14.558 | 1.00 | 35.92 |
| ATOM 4245 | N | GLY | 549 | 78.351 | 5.215 | 13.901 | 1.00 | 32.52 |
| ATOM 4247 | CA | GLY | 549 | 79.503 | 6.051 | 13.673 | 1.00 | 32.76 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4248 | C | GLY | 549 | 79.092 | 7.411 | 13.180 | 1.00 | 33.72 |
| ATOM 4249 | O | GLY | 549 | 77.895 | 7.707 | 13.092 | 1.00 | 35.01 |
| ATOM 4250 | N | ALA | 550 | 80.089 | 8.226 | 12.840 | 1.00 | 33.47 |
| ATOM 4252 | CA | ALA | 550 | 79.848 | 9.566 | 12.337 | 1.00 | 30.69 |
| ATOM 4253 | CB | ALA | 550 | 79.555 | 10.509 | 13.497 | 1.00 | 28.66 |
| ATOM 4254 | C | ALA | 550 | 81.022 | 10.099 | 11.523 | 1.00 | 30.41 |
| ATOM 4255 | O | ALA | 550 | 82.181 | 9.780 | 11.808 | 1.00 | 29.13 |
| ATOM 4256 | N | CYS | 551 | 80.695 | 10.817 | 10.446 | 1.00 | 30.29 |
| ATOM 4258 | CA | CYS | 551 | 81.675 | 11.490 | 9.584 | 1.00 | 28.44 |
| ATOM 4259 | CB | CYS | 551 | 81.432 | 11.214 | 8.096 | 1.00 | 27.25 |
| ATOM 4260 | SG | CYS | 551 | 81.639 | 9.508 | 7.566 | 1.00 | 28.89 |
| ATOM 4261 | C | CYS | 551 | 81.337 | 12.950 | 9.883 | 1.00 | 27.07 |
| ATOM 4262 | O | CYS | 551 | 80.293 | 13.441 | 9.467 | 1.00 | 29.86 |
| ATOM 4263 | N | THR | 552 | 82.184 | 13.616 | 10.658 | 1.00 | 25.10 |
| ATOM 4265 | CA | THR | 552 | 81.952 | 14.997 | 11.047 | 1.00 | 24.37 |
| ATOM 4266 | CB | THR | 552 | 81.959 | 15.091 | 12.569 | 1.00 | 27.67 |
| ATOM 4267 | OG1 | THR | 552 | 83.271 | 14.760 | 13.052 | 1.00 | 26.11 |
| ATOM 4269 | CG2 | THR | 552 | 80.951 | 14.120 | 13.164 | 1.00 | 30.41 |
| ATOM 4270 | C | THR | 552 | 83.003 | 15.980 | 10.557 | 1.00 | 24.51 |
| ATOM 4271 | O | THR | 552 | 82.804 | 17.194 | 10.604 | 1.00 | 21.56 |
| ATOM 4272 | N | GLN | 553 | 84.151 | 15.441 | 10.162 | 1.00 | 27.13 |
| ATOM 4274 | CA | GLN | 553 | 85.284 | 16.243 | 9.710 | 1.00 | 26.64 |
| ATOM 4275 | CB | GLN | 553 | 86.592 | 15.679 | 10.283 | 1.00 | 25.24 |
| ATOM 4276 | CG | GLN | 553 | 86.641 | 15.561 | 11.809 | 1.00 | 22.38 |
| ATOM 4277 | CD | GLN | 553 | 86.464 | 16.897 | 12.515 | 1.00 | 24.04 |
| ATOM 4278 | OE1 | GLN | 553 | 87.267 | 17.815 | 12.344 | 1.00 | 31.50 |
| ATOM 4279 | NE2 | GLN | 553 | 85.403 | 17.017 | 13.304 | 1.00 | 21.59 |
| ATOM 4282 | C | GLN | 553 | 85.384 | 16.276 | 8.206 | 1.00 | 28.02 |
| ATOM 4283 | O | GLN | 553 | 85.069 | 15.293 | 7.537 | 1.00 | 30.20 |
| ATOM 4284 | N | ASP | 554 | 85.794 | 17.430 | 7.695 | 1.00 | 28.08 |
| ATOM 4286 | CA | ASP | 554 | 86.000 | 17.652 | 6.263 | 1.00 | 30.14 |
| ATOM 4287 | CB | ASP | 554 | 87.330 | 17.034 | 5.833 | 1.00 | 29.82 |
| ATOM 4288 | CG | ASP | 554 | 88.451 | 17.470 | 6.707 | 1.00 | 31.79 |
| ATOM 4289 | OD1 | ASP | 554 | 88.699 | 18.666 | 6.767 | 1.00 | 36.45 |
| ATOM 4290 | OD2 | ASP | 554 | 89.066 | 16.623 | 7.364 | 1.00 | 33.06 |
| ATOM 4291 | C | ASP | 554 | 84.895 | 17.217 | 5.317 | 1.00 | 29.52 |
| ATOM 4292 | O | ASP | 554 | 85.128 | 16.411 | 4.424 | 1.00 | 33.67 |
| ATOM 4293 | N | GLY | 555 | 83.709 | 17.793 | 5.488 | 1.00 | 29.02 |
| ATOM 4295 | CA | GLY | 555 | 82.586 | 17.476 | 4.621 | 1.00 | 26.05 |
| ATOM 4296 | C | GLY | 555 | 81.286 | 17.447 | 5.405 | 1.00 | 23.80 |
| ATOM 4297 | O | GLY | 555 | 81.269 | 17.751 | 6.597 | 1.00 | 24.09 |
| ATOM 4298 | N | PRO | 556 | 80.175 | 17.117 | 4.740 | 1.00 | 23.29 |
| ATOM 4299 | CD | PRO | 556 | 80.094 | 16.804 | 3.304 | 1.00 | 18.93 |
| ATOM 4300 | CA | PRO | 556 | 78.860 | 17.045 | 5.378 | 1.00 | 23.45 |
| ATOM 4301 | CB | PRO | 556 | 77.943 | 16.643 | 4.226 | 1.00 | 22.35 |
| ATOM 4302 | CG | PRO | 556 | 78.889 | 15.931 | 3.261 | 1.00 | 24.94 |
| ATOM 4303 | C | PRO | 556 | 78.806 | 16.019 | 6.503 | 1.00 | 26.66 |
| ATOM 4304 | O | PRO | 556 | 79.488 | 14.984 | 6.464 | 1.00 | 27.76 |
| ATOM 4305 | N | LEU | 557 | 78.006 | 16.324 | 7.522 | 1.00 | 29.14 |
| ATOM 4307 | CA | LEU | 557 | 77.842 | 15.440 | 8.676 | 1.00 | 30.83 |
| ATOM 4308 | CB | LEU | 557 | 77.173 | 16.181 | 9.842 | 1.00 | 28.40 |
| ATOM 4309 | CG | LEU | 557 | 76.775 | 15.393 | 11.097 | 1.00 | 22.93 |
| ATOM 4310 | CD1 | LEU | 557 | 77.989 | 14.897 | 11.835 | 1.00 | 23.02 |
| ATOM 4311 | CD2 | LEU | 557 | 75.970 | 16.285 | 11.984 | 1.00 | 23.53 |
| ATOM 4312 | C | LEU | 557 | 77.028 | 14.200 | 8.321 | 1.00 | 31.04 |
| ATOM 4313 | O | LEU | 557 | 75.968 | 14.293 | 7.694 | 1.00 | 31.89 |
| ATOM 4314 | N | TYR | 558 | 77.552 | 13.041 | 8.700 | 1.00 | 29.88 |
| ATOM 4316 | CA | TYR | 558 | 76.891 | 11.773 | 8.460 | 1.00 | 27.80 |
| ATOM 4317 | CB | TYR | 558 | 77.741 | 10.878 | 7.562 | 1.00 | 28.04 |
| ATOM 4318 | CG | TYR | 558 | 77.895 | 11.339 | 6.122 | 1.00 | 29.98 |
| ATOM 4319 | CD1 | TYR | 558 | 78.843 | 10.751 | 5.289 | 1.00 | 31.81 |
| ATOM 4320 | CE1 | TYR | 558 | 78.980 | 11.140 | 3.956 | 1.00 | 32.22 |
| ATOM 4321 | CD2 | TYR | 558 | 77.086 | 12.335 | 5.584 | 1.00 | 31.50 |
| ATOM 4322 | CE2 | TYR | 558 | 77.214 | 12.729 | 4.256 | 1.00 | 31.57 |
| ATOM 4323 | CZ | TYR | 558 | 78.166 | 12.125 | 3.449 | 1.00 | 32.04 |
| ATOM 4324 | OH | TYR | 558 | 78.317 | 12.511 | 2.134 | 1.00 | 33.34 |
| ATOM 4326 | C | TYR | 558 | 76.715 | 11.099 | 9.809 | 1.00 | 27.34 |
| ATOM 4327 | O | TYR | 558 | 77.678 | 10.937 | 10.558 | 1.00 | 25.80 |
| ATOM 4328 | N | VAL | 559 | 75.464 | 10.798 | 10.147 | 1.00 | 28.06 |
| ATOM 4330 | CA | VAL | 559 | 75.118 | 10.118 | 11.394 | 1.00 | 26.67 |
| ATOM 4331 | CB | VAL | 559 | 73.930 | 10.816 | 12.129 | 1.00 | 26.22 |
| ATOM 4332 | CG1 | VAL | 559 | 73.590 | 10.079 | 13.425 | 1.00 | 22.58 |
| ATOM 4333 | CG2 | VAL | 559 | 74.298 | 12.278 | 12.440 | 1.00 | 23.09 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4334 | C | VAL | 559 | 74.745 | 8.715 | 10.943 | 1.00 | 24.32 |
| ATOM 4335 | O | VAL | 559 | 73.665 | 8.464 | 10.412 | 1.00 | 26.37 |
| ATOM 4336 | N | ILE | 560 | 75.689 | 7.815 | 11.095 | 1.00 | 23.63 |
| ATOM 4338 | CA | ILE | 560 | 75.514 | 6.448 | 10.664 | 1.00 | 24.67 |
| ATOM 4339 | CB | ILE | 560 | 76.901 | 5.859 | 10.299 | 1.00 | 24.62 |
| ATOM 4340 | CG2 | ILE | 560 | 76.753 | 4.507 | 9.646 | 1.00 | 30.13 |
| ATOM 4341 | CG1 | ILE | 560 | 77.627 | 6.810 | 9.326 | 1.00 | 21.87 |
| ATOM 4342 | CD1 | ILE | 560 | 79.114 | 6.538 | 9.162 | 1.00 | 22.25 |
| ATOM 4343 | C | ILE | 560 | 74.814 | 5.621 | 11.737 | 1.00 | 27.30 |
| ATOM 4344 | O | ILE | 560 | 75.306 | 5.505 | 12.865 | 1.00 | 28.80 |
| ATOM 4345 | N | VAL | 561 | 73.641 | 5.090 | 11.406 | 1.00 | 26.80 |
| ATOM 4347 | CA | VAL | 561 | 72.894 | 4.272 | 12.352 | 1.00 | 26.16 |
| ATOM 4348 | CB | VAL | 561 | 71.572 | 4.953 | 12.810 | 1.00 | 24.10 |
| ATOM 4349 | CG1 | VAL | 561 | 71.866 | 6.208 | 13.599 | 1.00 | 24.11 |
| ATOM 4350 | CG2 | VAL | 561 | 70.676 | 5.254 | 11.625 | 1.00 | 21.97 |
| ATOM 4351 | C | VAL | 561 | 72.572 | 2.901 | 11.761 | 1.00 | 27.98 |
| ATOM 4352 | O | VAL | 561 | 72.853 | 2.632 | 10.584 | 1.00 | 26.49 |
| ATOM 4353 | N | GLU | 562 | 71.998 | 2.039 | 12.599 | 1.00 | 28.86 |
| ATOM 4355 | CA | GLU | 562 | 71.605 | 0.685 | 12.219 | 1.00 | 28.23 |
| ATOM 4356 | CB | GLU | 562 | 71.090 | −0.068 | 13.440 | 1.00 | 25.86 |
| ATOM 4357 | CG | GLU | 562 | 72.170 | −0.392 | 14.424 | 1.00 | 27.04 |
| ATOM 4358 | CD | GLU | 562 | 71.641 | −0.969 | 15.714 | 1.00 | 28.37 |
| ATOM 4359 | OE1 | GLU | 562 | 72.389 | −1.714 | 16.372 | 1.00 | 33.36 |
| ATOM 4360 | OE2 | GLU | 562 | 70.491 | −0.665 | 16.092 | 1.00 | 31.60 |
| ATOM 4361 | C | GLU | 562 | 70.529 | 0.720 | 11.171 | 1.00 | 29.67 |
| ATOM 4362 | O | GLU | 562 | 69.581 | 1.489 | 11.287 | 1.00 | 32.53 |
| ATOM 4363 | N | TYR | 563 | 70.666 | −0.126 | 10.162 | 1.00 | 30.70 |
| ATOM 4365 | CA | TYR | 563 | 69.699 | −0.209 | 9.083 | 1.00 | 30.65 |
| ATOM 4366 | CB | TYR | 563 | 70.419 | −0.621 | 7.801 | 1.00 | 30.83 |
| ATOM 4367 | CG | TYR | 563 | 69.510 | −0.905 | 6.633 | 1.00 | 32.10 |
| ATOM 4368 | CD1 | TYR | 563 | 68.545 | 0.018 | 6.236 | 1.00 | 33.24 |
| ATOM 4369 | CE1 | TYR | 563 | 67.715 | −0.227 | 5.160 | 1.00 | 34.65 |
| ATOM 4370 | CD2 | TYR | 563 | 69.609 | −2.098 | 5.922 | 1.00 | 31.04 |
| ATOM 4371 | CE2 | TYR | 563 | 68.779 | −2.353 | 4.838 | 1.00 | 33.12 |
| ATOM 4372 | CZ | TYR | 563 | 67.831 | −1.413 | 4.470 | 1.00 | 34.22 |
| ATOM 4373 | OH | TYR | 563 | 67.002 | −1.650 | 3.400 | 1.00 | 34.76 |
| ATOM 4375 | C | TYR | 563 | 68.592 | −1.223 | 9.406 | 1.00 | 34.39 |
| ATOM 4376 | O | TYR | 563 | 68.855 | −2.325 | 9.884 | 1.00 | 34.87 |
| ATOM 4377 | N | ALA | 564 | 67.356 | −0.861 | 9.091 | 1.00 | 35.49 |
| ATOM 4379 | CA | ALA | 564 | 66.212 | −1.726 | 9.324 | 1.00 | 35.41 |
| ATOM 4380 | CB | ALA | 564 | 65.213 | −1.000 | 10.210 | 1.00 | 35.93 |
| ATOM 4381 | C | ALA | 564 | 65.585 | −2.056 | 7.962 | 1.00 | 37.19 |
| ATOM 4382 | O | ALA | 564 | 64.789 | −1.276 | 7.434 | 1.00 | 38.08 |
| ATOM 4383 | N | SER | 565 | 65.931 | −3.211 | 7.401 | 1.00 | 37.14 |
| ATOM 4385 | CA | SER | 565 | 65.433 | −3.616 | 6.080 | 1.00 | 36.83 |
| ATOM 4386 | CB | SER | 565 | 66.151 | −4.881 | 5.614 | 1.00 | 35.24 |
| ATOM 4387 | OG | SER | 565 | 66.105 | −5.873 | 6.619 | 1.00 | 34.96 |
| ATOM 4389 | C | SER | 565 | 63.932 | −3.782 | 5.886 | 1.00 | 38.65 |
| ATOM 4390 | O | SER | 565 | 63.428 | −3.617 | 4.760 | 1.00 | 37.80 |
| ATOM 4391 | N | LYS | 566 | 63.212 | −4.077 | 6.964 | 1.00 | 38.96 |
| ATOM 4393 | CA | LYS | 566 | 61.772 | −4.271 | 6.851 | 1.00 | 37.83 |
| ATOM 4394 | CB | LYS | 566 | 61.357 | −5.495 | 7.655 | 1.00 | 39.07 |
| ATOM 4395 | CG | LYS | 566 | 61.954 | −6.765 | 7.078 | 1.00 | 43.73 |
| ATOM 4396 | CD | LYS | 566 | 61.813 | −7.950 | 7.996 | 1.00 | 47.07 |
| ATOM 4397 | CE | LYS | 566 | 62.258 | −9.216 | 7.299 | 1.00 | 47.77 |
| ATOM 4398 | NZ | LYS | 566 | 62.361 | −10.326 | 8.278 | 1.00 | 51.48 |
| ATOM 4402 | C | LYS | 566 | 60.899 | −3.050 | 7.165 | 1.00 | 37.53 |
| ATOM 4403 | O | LYS | 566 | 59.702 | −3.180 | 7.442 | 1.00 | 38.55 |
| ATOM 4404 | N | GLY | 567 | 61.496 | −1.866 | 7.066 | 1.00 | 35.23 |
| ATOM 4406 | CA | GLY | 567 | 60.788 | −0.627 | 7.305 | 1.00 | 33.64 |
| ATOM 4407 | C | GLY | 567 | 60.120 | −0.485 | 8.656 | 1.00 | 33.24 |
| ATOM 4408 | O | GLY | 567 | 60.518 | −1.133 | 9.627 | 1.00 | 33.80 |
| ATOM 4409 | N | ASN | 568 | 59.120 | 0.389 | 8.716 | 1.00 | 31.65 |
| ATOM 4411 | CA | ASN | 568 | 58.407 | 0.623 | 9.952 | 1.00 | 33.38 |
| ATOM 4412 | CB | ASN | 568 | 57.831 | 2.055 | 10.025 | 1.00 | 37.10 |
| ATOM 4413 | CG | ASN | 568 | 56.624 | 2.272 | 9.116 | 1.00 | 37.78 |
| ATOM 4414 | OD1 | ASN | 568 | 55.552 | 1.708 | 9.337 | 1.00 | 41.15 |
| ATOM 4415 | ND2 | ASN | 568 | 56.780 | 3.147 | 8.124 | 1.00 | 35.74 |
| ATOM 4418 | C | ASN | 568 | 57.357 | −0.435 | 10.263 | 1.00 | 33.33 |
| ATOM 4419 | O | ASN | 568 | 56.917 | −1.178 | 9.384 | 1.00 | 32.54 |
| ATOM 4420 | N | LEU | 569 | 56.971 | −0.490 | 11.532 | 1.00 | 33.35 |
| ATOM 4422 | CA | LEU | 569 | 56.004 | −1.455 | 12.040 | 1.00 | 32.38 |
| ATOM 4423 | CB | LEU | 569 | 55.838 | −1.263 | 13.552 | 1.00 | 27.50 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4424 | CG | LEU | 569 | 54.954 | −2.259 | 14.291 | 1.00 | 26.34 |
| ATOM 4425 | CD1 | LEU | 569 | 55.452 | −3.671 | 14.007 | 1.00 | 24.19 |
| ATOM 4426 | CD2 | LEU | 569 | 54.968 | −1.951 | 15.787 | 1.00 | 21.44 |
| ATOM 4427 | C | LEU | 569 | 54.641 | −1.433 | 11.355 | 1.00 | 33.35 |
| ATOM 4428 | O | LEU | 569 | 54.060 | −2.484 | 11.095 | 1.00 | 34.99 |
| ATOM 4429 | N | ARG | 570 | 54.130 | −0.239 | 11.083 | 1.00 | 34.36 |
| ATOM 4431 | CA | ARG | 570 | 52.827 | −0.091 | 10.445 | 1.00 | 36.82 |
| ATOM 4432 | CB | ARG | 570 | 52.548 | 1.393 | 10.188 | 1.00 | 37.28 |
| ATOM 4433 | CG | ARG | 570 | 51.210 | 1.689 | 9.539 | 1.00 | 43.90 |
| ATOM 4434 | CD | ARG | 570 | 51.212 | 3.099 | 8.967 | 1.00 | 50.39 |
| ATOM 4435 | NE | ARG | 570 | 52.273 | 3.268 | 7.973 | 1.00 | 54.99 |
| ATOM 4437 | CZ | ARG | 570 | 53.075 | 4.328 | 7.887 | 1.00 | 54.96 |
| ATOM 4438 | NH1 | ARG | 570 | 52.947 | 5.343 | 8.735 | 1.00 | 54.71 |
| ATOM 4441 | NH2 | ARG | 570 | 54.030 | 4.357 | 6.966 | 1.00 | 56.12 |
| ATOM 4444 | C | ARG | 570 | 52.818 | −0.877 | 9.133 | 1.00 | 36.53 |
| ATOM 4445 | O | ARG | 570 | 51.968 | −1.737 | 8.909 | 1.00 | 34.68 |
| ATOM 4446 | N | GLU | 571 | 53.830 | −0.611 | 8.320 | 1.00 | 37.14 |
| ATOM 4448 | CA | GLU | 571 | 53.994 | −1.253 | 7.031 | 1.00 | 37.94 |
| ATOM 4449 | CB | GLU | 571 | 55.126 | −0.558 | 6.274 | 1.00 | 39.71 |
| ATOM 4450 | CG | GLU | 571 | 54.834 | 0.916 | 6.062 | 1.00 | 44.69 |
| ATOM 4451 | CD | GLU | 571 | 55.934 | 1.665 | 5.346 | 1.00 | 52.22 |
| ATOM 4452 | OE1 | GLU | 571 | 57.098 | 1.196 | 5.358 | 1.00 | 54.87 |
| ATOM 4453 | OE2 | GLU | 571 | 55.629 | 2.743 | 4.777 | 1.00 | 56.37 |
| ATOM 4454 | C | GLU | 571 | 54.258 | −2.744 | 7.164 | 1.00 | 36.53 |
| ATOM 4455 | O | GLU | 571 | 53.692 | −3.550 | 6.426 | 1.00 | 36.35 |
| ATOM 4456 | N | TYR | 572 | 55.105 | −3.105 | 8.120 | 1.00 | 35.77 |
| ATOM 4458 | CA | TYR | 572 | 55.456 | −4.499 | 8.371 | 1.00 | 36.28 |
| ATOM 4459 | CB | TYR | 572 | 56.446 | −4.555 | 9.534 | 1.00 | 30.27 |
| ATOM 4460 | CG | TYR | 572 | 56.859 | −5.925 | 10.006 | 1.00 | 31.65 |
| ATOM 4461 | CD1 | TYR | 572 | 57.889 | −6.626 | 9.371 | 1.00 | 29.40 |
| ATOM 4462 | CE1 | TYR | 572 | 58.354 | −7.839 | 9.883 | 1.00 | 29.32 |
| ATOM 4463 | CD2 | TYR | 572 | 56.292 | −6.480 | 11.161 | 1.00 | 35.17 |
| ATOM 4464 | CE2 | TYR | 572 | 56.749 | −7.696 | 11.680 | 1.00 | 33.08 |
| ATOM 4465 | CZ | TYR | 572 | 57.780 | −8.366 | 11.038 | 1.00 | 35.15 |
| ATOM 4466 | OH | TYR | 572 | 58.234 | −9.559 | 11.558 | 1.00 | 36.91 |
| ATOM 4468 | C | TYR | 572 | 54.189 | −5.321 | 8.672 | 1.00 | 37.70 |
| ATOM 4469 | O | TYR | 572 | 53.942 | −6.369 | 8.068 | 1.00 | 36.82 |
| ATOM 4470 | N | LEU | 573 | 53.368 | −4.799 | 9.576 | 1.00 | 37.64 |
| ATOM 4472 | CA | LEU | 573 | 52.126 | −5.442 | 9.970 | 1.00 | 36.03 |
| ATOM 4473 | CB | LEU | 573 | 51.497 | −4.659 | 11.122 | 1.00 | 36.17 |
| ATOM 4474 | CG | LEU | 573 | 52.257 | −4.641 | 12.445 | 1.00 | 36.39 |
| ATOM 4475 | CD1 | LEU | 573 | 51.590 | −3.665 | 13.412 | 1.00 | 36.17 |
| ATOM 4476 | CD2 | LEU | 573 | 52.311 | −6.042 | 13.032 | 1.00 | 32.13 |
| ATOM 4477 | C | LEU | 573 | 51.117 | −5.562 | 8.822 | 1.00 | 36.33 |
| ATOM 4478 | O | LEU | 573 | 50.477 | −6.596 | 8.649 | 1.00 | 35.19 |
| ATOM 4479 | N | GLN | 574 | 50.975 | −4.502 | 8.038 | 1.00 | 37.66 |
| ATOM 4481 | CA | GLN | 574 | 50.024 | −4.514 | 6.936 | 1.00 | 41.78 |
| ATOM 4482 | CB | GLN | 574 | 49.798 | −3.103 | 6.413 | 1.00 | 43.82 |
| ATOM 4483 | CG | GLN | 574 | 48.898 | −2.273 | 7.264 | 1.00 | 45.42 |
| ATOM 4484 | CD | GLN | 574 | 48.871 | −0.850 | 6.801 | 1.00 | 49.56 |
| ATOM 4485 | OE1 | GLN | 574 | 49.456 | −0.506 | 5.772 | 1.00 | 52.22 |
| ATOM 4486 | NE2 | GLN | 574 | 48.207 | 0.001 | 7.565 | 1.00 | 54.86 |
| ATOM 4489 | C | GLN | 574 | 50.401 | −5.427 | 5.783 | 1.00 | 42.89 |
| ATOM 4490 | O | GLN | 574 | 49.532 | −5.898 | 5.042 | 1.00 | 46.15 |
| ATOM 4491 | N | ALA | 575 | 51.695 | −5.646 | 5.599 | 1.00 | 42.39 |
| ATOM 4493 | CA | ALA | 575 | 52.165 | −6.516 | 4.532 | 1.00 | 40.19 |
| ATOM 4494 | CB | ALA | 575 | 53.597 | −6.165 | 4.170 | 1.00 | 40.68 |
| ATOM 4495 | C | ALA | 575 | 52.088 | −7.970 | 4.971 | 1.00 | 40.49 |
| ATOM 4496 | O | ALA | 575 | 52.437 | −8.867 | 4.210 | 1.00 | 43.34 |
| ATOM 4497 | N | ARG | 576 | 51.630 | −8.197 | 6.202 | 1.00 | 38.76 |
| ATOM 4499 | CA | ARG | 576 | 51.538 | −9.542 | 6.761 | 1.00 | 38.44 |
| ATOM 4500 | CB | ARG | 576 | 52.600 | −9.708 | 7.846 | 1.00 | 34.26 |
| ATOM 4501 | CG | ARG | 576 | 53.991 | −9.609 | 7.284 | 1.00 | 37.16 |
| ATOM 4502 | CD | ARG | 576 | 55.052 | −9.625 | 8.356 | 1.00 | 36.38 |
| ATOM 4503 | NE | ARG | 576 | 56.384 | −9.663 | 7.760 | 1.00 | 36.98 |
| ATOM 4505 | CZ | ARG | 576 | 56.897 | −8.714 | 6.983 | 1.00 | 38.62 |
| ATOM 4506 | NH1 | ARG | 576 | 56.204 | −7.618 | 6.689 | 1.00 | 41.41 |
| ATOM 4509 | NH2 | ARG | 576 | 58.112 | −8.863 | 6.491 | 1.00 | 37.48 |
| ATOM 4512 | C | ARG | 576 | 50.165 | −9.860 | 7.321 | 1.00 | 40.55 |
| ATOM 4513 | O | ARG | 576 | 50.013 | −10.746 | 8.169 | 1.00 | 43.20 |
| ATOM 4514 | N | ARG | 577 | 49.156 | −9.146 | 6.844 | 1.00 | 41.98 |
| ATOM 4516 | CA | ARG | 577 | 47.794 | −9.372 | 7.309 | 1.00 | 43.12 |
| ATOM 4517 | CB | ARG | 577 | 46.896 | −8.226 | 6.851 | 1.00 | 44.21 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4518 | CG | ARG | 577 | 47.206 | −6.910 | 7.525 | 1.00 | 45.21 |
| ATOM 4519 | CD | ARG | 577 | 46.402 | −5.766 | 6.941 | 1.00 | 47.50 |
| ATOM 4520 | NE | ARG | 577 | 46.172 | −4.734 | 7.948 | 1.00 | 47.58 |
| ATOM 4522 | CZ | ARG | 577 | 45.447 | −3.641 | 7.752 | 1.00 | 47.63 |
| ATOM 4523 | NH1 | ARG | 577 | 44.882 | −3.421 | 6.574 | 1.00 | 49.05 |
| ATOM 4526 | NH2 | ARG | 577 | 45.256 | −2.789 | 8.747 | 1.00 | 49.88 |
| ATOM 4529 | C | ARG | 577 | 47.241 | −10.715 | 6.821 | 1.00 | 43.10 |
| ATOM 4530 | O | ARG | 577 | 47.297 | −11.015 | 5.627 | 1.00 | 43.86 |
| ATOM 4531 | N | GLN | 594 | 53.448 | −13.666 | 7.976 | 1.00 | 64.97 |
| ATOM 4533 | CA | GLN | 594 | 52.231 | −13.872 | 8.759 | 1.00 | 66.30 |
| ATOM 4534 | CB | GLN | 594 | 51.419 | −15.042 | 8.200 | 1.00 | 67.44 |
| ATOM 4535 | C | GLN | 594 | 52.582 | −14.116 | 10.224 | 1.00 | 66.02 |
| ATOM 4536 | O | GLN | 594 | 53.162 | −15.145 | 10.583 | 1.00 | 67.47 |
| ATOM 4537 | N | LEU | 595 | 52.218 | −13.151 | 11.058 | 1.00 | 62.86 |
| ATOM 4539 | CA | LEU | 595 | 52.499 | −13.187 | 12.480 | 1.00 | 59.77 |
| ATOM 4540 | CB | LEU | 595 | 52.597 | −11.751 | 12.987 | 1.00 | 59.35 |
| ATOM 4541 | CG | LEU | 595 | 53.471 | −10.905 | 12.051 | 1.00 | 61.70 |
| ATOM 4542 | CD1 | LEU | 595 | 53.307 | −9.427 | 12.322 | 1.00 | 64.61 |
| ATOM 4543 | CD2 | LEU | 595 | 54.923 | −11.324 | 12.175 | 1.00 | 62.38 |
| ATOM 4544 | C | LEU | 595 | 51.482 | −13.985 | 13.290 | 1.00 | 57.49 |
| ATOM 4545 | O | LEU | 595 | 50.302 | −14.026 | 12.951 | 1.00 | 56.36 |
| ATOM 4546 | N | SER | 596 | 51.969 | −14.647 | 14.338 | 1.00 | 55.62 |
| ATOM 4548 | CA | SER | 596 | 51.134 | −15.447 | 15.222 | 1.00 | 54.72 |
| ATOM 4549 | CB | SER | 596 | 51.905 | −16.669 | 15.721 | 1.00 | 55.13 |
| ATOM 4550 | OG | SER | 596 | 52.871 | −16.309 | 16.698 | 1.00 | 54.98 |
| ATOM 4552 | C | SER | 596 | 50.723 | −14.597 | 16.415 | 1.00 | 54.73 |
| ATOM 4553 | O | SER | 596 | 51.348 | −13.579 | 16.704 | 1.00 | 53.29 |
| ATOM 4554 | N | SER | 597 | 49.704 | −15.051 | 17.137 | 1.00 | 55.09 |
| ATOM 4556 | CA | SER | 597 | 49.215 | −14.337 | 18.307 | 1.00 | 56.44 |
| ATOM 4557 | CB | SER | 597 | 48.178 | −15.185 | 19.044 | 1.00 | 59.14 |
| ATOM 4558 | OG | SER | 597 | 47.455 | −16.009 | 18.138 | 1.00 | 65.57 |
| ATOM 4560 | C | SER | 597 | 50.387 | −14.026 | 19.238 | 1.00 | 55.64 |
| ATOM 4561 | O | SER | 597 | 50.430 | −12.966 | 19.856 | 1.00 | 56.04 |
| ATOM 4562 | N | LYS | 598 | 51.345 | −14.948 | 19.315 | 1.00 | 54.91 |
| ATOM 4564 | CA | LYS | 598 | 52.528 | −14.773 | 20.161 | 1.00 | 54.25 |
| ATOM 4565 | CB | LYS | 598 | 53.287 | −16.096 | 20.311 | 1.00 | 54.23 |
| ATOM 4566 | CG | LYS | 598 | 54.236 | −16.138 | 21.494 | 1.00 | 55.12 |
| ATOM 4567 | CD | LYS | 598 | 55.009 | −17.448 | 21.523 | 1.00 | 59.41 |
| ATOM 4568 | CE | LYS | 598 | 55.711 | −17.679 | 22.858 | 1.00 | 58.10 |
| ATOM 4569 | NZ | LYS | 598 | 54.750 | −17.983 | 23.959 | 1.00 | 56.10 |
| ATOM 4573 | C | LYS | 598 | 53.439 | −13.716 | 19.536 | 1.00 | 52.32 |
| ATOM 4574 | O | LYS | 598 | 53.986 | −12.869 | 20.249 | 1.00 | 52.23 |
| ATOM 4575 | N | ASP | 599 | 53.573 | −13.768 | 18.208 | 1.00 | 47.57 |
| ATOM 4577 | CA | ASP | 599 | 54.389 | −12.818 | 17.466 | 1.00 | 45.47 |
| ATOM 4578 | CB | ASP | 599 | 54.324 | −13.101 | 15.959 | 1.00 | 49.05 |
| ATOM 4579 | CG | ASP | 599 | 55.245 | −14.238 | 15.525 | 1.00 | 54.16 |
| ATOM 4580 | OD1 | ASP | 599 | 56.242 | −14.503 | 16.223 | 1.00 | 61.34 |
| ATOM 4581 | OD2 | ASP | 599 | 54.992 | −14.863 | 14.471 | 1.00 | 55.80 |
| ATOM 4582 | C | ASP | 599 | 53.933 | −11.383 | 17.721 | 1.00 | 43.55 |
| ATOM 4583 | O | ASP | 599 | 54.762 | −10.491 | 17.895 | 1.00 | 44.34 |
| ATOM 4584 | N | LEU | 600 | 52.622 | −11.160 | 17.751 | 1.00 | 39.73 |
| ATOM 4586 | CA | LEU | 600 | 52.104 | −9.821 | 17.989 | 1.00 | 37.64 |
| ATOM 4587 | CB | LEU | 600 | 50.597 | −9.743 | 17.719 | 1.00 | 35.42 |
| ATOM 4588 | CG | LEU | 600 | 50.075 | −9.951 | 16.287 | 1.00 | 33.95 |
| ATOM 4589 | CD1 | LEU | 600 | 48.621 | −9.552 | 16.262 | 1.00 | 36.59 |
| ATOM 4590 | CD2 | LEU | 600 | 50.841 | −9.139 | 15.265 | 1.00 | 28.40 |
| ATOM 4591 | C | LEU | 600 | 52.429 | −9.347 | 19.402 | 1.00 | 38.24 |
| ATOM 4592 | O | LEU | 600 | 52.817 | −8.193 | 19.590 | 1.00 | 38.28 |
| ATOM 4593 | N | VAL | 601 | 52.305 | −10.235 | 20.391 | 1.00 | 38.77 |
| ATOM 4595 | CA | VAL | 601 | 52.610 | −9.855 | 21.772 | 1.00 | 38.87 |
| ATOM 4596 | CB | VAL | 601 | 52.121 | −10.906 | 22.812 | 1.00 | 38.03 |
| ATOM 4597 | CG1 | VAL | 601 | 52.150 | −10.303 | 24.223 | 1.00 | 36.21 |
| ATOM 4598 | CG2 | VAL | 601 | 50.710 | −11.332 | 22.504 | 1.00 | 39.07 |
| ATOM 4599 | C | VAL | 601 | 54.123 | −9.662 | 21.887 | 1.00 | 38.98 |
| ATOM 4600 | O | VAL | 601 | 54.601 | −8.757 | 22.580 | 1.00 | 39.93 |
| ATOM 4601 | N | SER | 602 | 54.861 | −10.488 | 21.155 | 1.00 | 37.35 |
| ATOM 4603 | CA | SER | 602 | 56.311 | −10.422 | 21.126 | 1.00 | 37.11 |
| ATOM 4604 | CB | SER | 602 | 56.853 | −11.469 | 20.154 | 1.00 | 39.38 |
| ATOM 4605 | OG | SER | 602 | 58.265 | −11.413 | 20.061 | 1.00 | 46.76 |
| ATOM 4607 | C | SER | 602 | 56.695 | −9.020 | 20.664 | 1.00 | 35.43 |
| ATOM 4608 | O | SER | 602 | 57.493 | −8.339 | 21.315 | 1.00 | 35.01 |
| ATOM 4609 | N | CYS | 603 | 56.091 | −8.586 | 19.561 | 1.00 | 33.42 |
| ATOM 4611 | CA | CYS | 603 | 56.329 | −7.254 | 19.015 | 1.00 | 32.18 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B | |
|---|---|---|---|---|---|---|---|---|---|
| ATOM 4612 | CB | CYS | 603 | 55.449 | −7.035 | 17.790 | 1.00 | 32.38 | |
| ATOM 4613 | SG | CYS | 603 | 55.440 | −5.365 | 17.123 | 0.50 | 35.11 | PRT1 |
| ATOM 4614 | C | CYS | 603 | 56.074 | −6.167 | 20.059 | 1.00 | 31.20 | |
| ATOM 4615 | O | CYS | 603 | 56.862 | −5.234 | 20.185 | 1.00 | 32.44 | |
| ATOM 4616 | N | ALA | 604 | 55.001 | −6.321 | 20.828 | 1.00 | 29.74 | |
| ATOM 4618 | CA | ALA | 604 | 54.640 | −5.363 | 21.872 | 1.00 | 32.26 | |
| ATOM 4619 | CB | ALA | 604 | 53.232 | −5.675 | 22.412 | 1.00 | 31.75 | |
| ATOM 4620 | C | ALA | 604 | 55.656 | −5.365 | 23.019 | 1.00 | 33.71 | |
| ATOM 4621 | O | ALA | 604 | 55.933 | −4.326 | 23.621 | 1.00 | 33.49 | |
| ATOM 4622 | N | TYR | 605 | 56.186 | −6.544 | 23.326 | 1.00 | 35.56 | |
| ATOM 4624 | CA | TYR | 605 | 57.176 | −6.709 | 24.388 | 1.00 | 35.49 | |
| ATOM 4625 | CB | TYR | 605 | 57.447 | −8.206 | 24.617 | 1.00 | 36.12 | |
| ATOM 4626 | CG | TYR | 605 | 58.562 | −8.495 | 25.591 | 1.00 | 34.75 | |
| ATOM 4627 | CD1 | TYR | 605 | 58.415 | −8.237 | 26.954 | 1.00 | 34.30 | |
| ATOM 4628 | CE1 | TYR | 605 | 59.444 | −8.499 | 27.853 | 1.00 | 36.26 | |
| ATOM 4629 | CD2 | TYR | 605 | 59.773 | −9.021 | 25.150 | 1.00 | 37.39 | |
| ATOM 4630 | CE2 | TYR | 605 | 60.812 | −9.288 | 26.040 | 1.00 | 37.81 | |
| ATOM 4631 | CZ | TYR | 605 | 60.641 | −9.027 | 27.388 | 1.00 | 38.34 | |
| ATOM 4632 | OH | TYR | 605 | 61.662 | −9.324 | 28.265 | 1.00 | 42.09 | |
| ATOM 4634 | C | TYR | 605 | 58.475 | −5.972 | 24.027 | 1.00 | 34.98 | |
| ATOM 4635 | O | TYR | 605 | 58.981 | −5.171 | 24.822 | 1.00 | 35.83 | |
| ATOM 4636 | N | GLN | 606 | 58.996 | −6.247 | 22.828 | 1.00 | 33.99 | |
| ATOM 4638 | CA | GLN | 606 | 60.218 | −5.620 | 22.315 | 1.00 | 33.60 | |
| ATOM 4639 | CB | GLN | 606 | 60.506 | −6.111 | 20.894 | 1.00 | 31.37 | |
| ATOM 4640 | CG | GLN | 606 | 60.858 | −7.584 | 20.786 | 1.00 | 32.05 | |
| ATOM 4641 | CD | GLN | 606 | 61.175 | −8.015 | 19.354 | 1.00 | 30.33 | |
| ATOM 4642 | OE1 | GLN | 606 | 62.145 | −7.558 | 18.754 | 1.00 | 30.84 | |
| ATOM 4643 | NE2 | GLN | 606 | 60.353 | −8.895 | 18.810 | 1.00 | 33.75 | |
| ATOM 4646 | C | GLN | 606 | 60.123 | −4.079 | 22.321 | 1.00 | 34.86 | |
| ATOM 4647 | O | GLN | 606 | 61.070 | −3.390 | 22.702 | 1.00 | 37.54 | |
| ATOM 4648 | N | VAL | 607 | 58.975 | −3.555 | 21.904 | 1.00 | 32.89 | |
| ATOM 4650 | CA | VAL | 607 | 58.748 | −2.114 | 21.883 | 1.00 | 30.80 | |
| ATOM 4651 | CB | VAL | 607 | 57.426 | −1.777 | 21.120 | 1.00 | 28.82 | |
| ATOM 4652 | CG1 | VAL | 607 | 57.121 | −0.299 | 21.191 | 1.00 | 25.36 | |
| ATOM 4653 | CG2 | VAL | 607 | 57.541 | −2.204 | 19.661 | 1.00 | 23.37 | |
| ATOM 4654 | C | VAL | 607 | 58.747 | −1.532 | 23.312 | 1.00 | 30.48 | |
| ATOM 4655 | O | VAL | 607 | 59.359 | −0.486 | 23.563 | 1.00 | 29.42 | |
| ATOM 4656 | N | ALA | 608 | 58.106 | −2.225 | 24.255 | 1.00 | 30.07 | |
| ATOM 4658 | CA | ALA | 608 | 58.064 | −1.761 | 25.646 | 1.00 | 30.14 | |
| ATOM 4659 | CB | ALA | 608 | 57.027 | −2.548 | 26.452 | 1.00 | 28.49 | |
| ATOM 4660 | C | ALA | 608 | 59.455 | −1.849 | 26.305 | 1.00 | 31.25 | |
| ATOM 4661 | O | ALA | 608 | 59.791 | −1.054 | 27.198 | 1.00 | 28.90 | |
| ATOM 4662 | N | ARG | 609 | 60.257 | −2.819 | 25.870 | 1.00 | 31.61 | |
| ATOM 4664 | CA | ARG | 609 | 61.608 | −2.979 | 26.393 | 1.00 | 31.99 | |
| ATOM 4665 | CB | ARG | 609 | 62.253 | −4.245 | 25.856 | 1.00 | 34.93 | |
| ATOM 4666 | CG | ARG | 609 | 61.606 | −5.507 | 26.317 | 1.00 | 40.82 | |
| ATOM 4667 | CD | ARG | 609 | 62.633 | −6.606 | 26.397 | 1.00 | 42.68 | |
| ATOM 4668 | NE | ARG | 609 | 63.275 | −6.621 | 27.705 | 1.00 | 43.85 | |
| ATOM 4670 | CZ | ARG | 609 | 64.332 | −7.364 | 28.019 | 1.00 | 44.73 | |
| ATOM 4671 | NH1 | ARG | 609 | 64.889 | −8.162 | 27.108 | 1.00 | 41.40 | |
| ATOM 4674 | NH2 | ARG | 609 | 64.803 | −7.341 | 29.260 | 1.00 | 44.85 | |
| ATOM 4677 | C | ARG | 609 | 62.459 | −1.796 | 25.966 | 1.00 | 33.70 | |
| ATOM 4678 | O | ARG | 609 | 63.130 | −1.174 | 26.793 | 1.00 | 35.94 | |
| ATOM 4679 | N | GLY | 610 | 62.459 | −1.511 | 24.663 | 1.00 | 31.22 | |
| ATOM 4681 | CA | GLY | 610 | 63.232 | −0.391 | 24.157 | 1.00 | 27.21 | |
| ATOM 4682 | C | GLY | 610 | 62.819 | 0.875 | 24.865 | 1.00 | 25.81 | |
| ATOM 4683 | O | GLY | 610 | 63.665 | 1.652 | 25.300 | 1.00 | 26.21 | |
| ATOM 4684 | N | MET | 611 | 61.511 | 1.056 | 25.015 | 1.00 | 27.12 | |
| ATOM 4686 | CA | MET | 611 | 60.969 | 2.222 | 25.695 | 1.00 | 28.82 | |
| ATOM 4687 | CB | MET | 611 | 59.457 | 2.288 | 25.524 | 1.00 | 29.29 | |
| ATOM 4688 | CG | MET | 611 | 59.004 | 2.706 | 24.135 | 1.00 | 31.07 | |
| ATOM 4689 | SD | MET | 611 | 59.732 | 4.286 | 23.617 | 1.00 | 28.38 | |
| ATOM 4690 | CE | MET | 611 | 59.155 | 5.431 | 24.922 | 1.00 | 28.34 | |
| ATOM 4691 | C | MET | 611 | 61.341 | 2.261 | 27.178 | 1.00 | 30.34 | |
| ATOM 4692 | O | MET | 611 | 61.596 | 3.334 | 27.730 | 1.00 | 31.73 | |
| ATOM 4693 | N | GLU | 612 | 61.347 | 1.109 | 27.837 | 1.00 | 32.72 | |
| ATOM 4695 | CA | GLU | 612 | 61.723 | 1.057 | 29.253 | 1.00 | 35.46 | |
| ATOM 4696 | CB | GLU | 612 | 61.603 | −0.370 | 29.792 | 1.00 | 34.70 | |
| ATOM 4697 | CG | GLU | 612 | 62.029 | −0.516 | 31.237 | 1.00 | 32.31 | |
| ATOM 4698 | CD | GLU | 612 | 62.135 | −1.968 | 31.688 | 1.00 | 33.14 | |
| ATOM 4699 | OE1 | GLU | 612 | 62.546 | −2.834 | 30.883 | 1.00 | 30.79 | |
| ATOM 4700 | OE2 | GLU | 612 | 61.826 | −2.240 | 32.867 | 1.00 | 36.13 | |
| ATOM 4701 | C | GLU | 612 | 63.178 | 1.544 | 29.353 | 1.00 | 36.43 | |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4702 | O | GLU | 612 | 63.534 | 2.319 | 30.261 | 1.00 | 35.38 |
| ATOM 4703 | N | TYR | 613 | 63.999 | 1.107 | 28.391 | 1.00 | 35.47 |
| ATOM 4705 | CA | TYR | 613 | 65.403 | 1.507 | 28.334 | 1.00 | 33.16 |
| ATOM 4706 | CB | TYR | 613 | 66.156 | 0.743 | 27.241 | 1.00 | 31.33 |
| ATOM 4707 | CG | TYR | 613 | 67.612 | 1.146 | 27.132 | 1.00 | 33.03 |
| ATOM 4708 | CD1 | TYR | 613 | 68.584 | 0.544 | 27.931 | 1.00 | 36.69 |
| ATOM 4709 | CE1 | TYR | 613 | 69.930 | 0.927 | 27.851 | 1.00 | 36.82 |
| ATOM 4710 | CD2 | TYR | 613 | 68.021 | 2.148 | 26.247 | 1.00 | 33.49 |
| ATOM 4711 | CE2 | TYR | 613 | 69.352 | 2.540 | 26.157 | 1.00 | 34.73 |
| ATOM 4712 | CZ | TYR | 613 | 70.307 | 1.927 | 26.963 | 1.00 | 37.07 |
| ATOM 4713 | OH | TYR | 613 | 71.632 | 2.318 | 26.896 | 1.00 | 36.77 |
| ATOM 4715 | C | TYR | 613 | 65.539 | 3.005 | 28.088 | 1.00 | 31.82 |
| ATOM 4716 | O | TYR | 613 | 66.256 | 3.682 | 28.814 | 1.00 | 34.76 |
| ATOM 4717 | N | LEU | 614 | 64.836 | 3.536 | 27.090 | 1.00 | 28.44 |
| ATOM 4719 | CA | LEU | 614 | 64.931 | 4.956 | 26.793 | 1.00 | 25.67 |
| ATOM 4720 | CB | LEU | 614 | 64.089 | 5.319 | 25.569 | 1.00 | 24.75 |
| ATOM 4721 | CG | LEU | 614 | 64.545 | 4.778 | 24.208 | 1.00 | 23.73 |
| ATOM 4722 | CD1 | LEU | 614 | 63.594 | 5.257 | 23.125 | 1.00 | 20.54 |
| ATOM 4723 | CD2 | LEU | 614 | 65.983 | 5.213 | 23.894 | 1.00 | 23.21 |
| ATOM 4724 | C | LEU | 614 | 64.499 | 5.761 | 28.001 | 1.00 | 28.30 |
| ATOM 4725 | O | LEU | 614 | 65.110 | 6.770 | 28.345 | 1.00 | 27.09 |
| ATOM 4726 | N | ALA | 615 | 63.470 | 5.272 | 28.683 | 1.00 | 32.73 |
| ATOM 4728 | CA | ALA | 615 | 62.955 | 5.945 | 29.871 | 1.00 | 34.10 |
| ATOM 4729 | CB | ALA | 615 | 61.625 | 5.314 | 30.314 | 1.00 | 33.68 |
| ATOM 4730 | C | ALA | 615 | 63.986 | 5.913 | 31.007 | 1.00 | 33.84 |
| ATOM 4731 | O | ALA | 615 | 64.112 | 6.885 | 31.753 | 1.00 | 34.95 |
| ATOM 4732 | N | SER | 616 | 64.722 | 4.809 | 31.134 | 1.00 | 32.69 |
| ATOM 4734 | CA | SER | 616 | 65.738 | 4.703 | 32.175 | 1.00 | 33.50 |
| ATOM 4735 | CB | SER | 616 | 66.287 | 3.277 | 32.285 | 1.00 | 28.27 |
| ATOM 4736 | OG | SER | 616 | 67.076 | 2.935 | 31.165 | 1.00 | 25.54 |
| ATOM 4738 | C | SER | 616 | 66.870 | 5.678 | 31.865 | 1.00 | 35.43 |
| ATOM 4739 | O | SER | 616 | 67.637 | 6.061 | 32.755 | 1.00 | 37.32 |
| ATOM 4740 | N | LYS | 617 | 66.971 | 6.060 | 30.592 | 1.00 | 34.80 |
| ATOM 4742 | CA | LYS | 617 | 67.975 | 7.010 | 30.143 | 1.00 | 33.01 |
| ATOM 4743 | CB | LYS | 617 | 68.508 | 6.620 | 28.776 | 1.00 | 33.18 |
| ATOM 4744 | CG | LYS | 617 | 69.224 | 5.302 | 28.797 | 1.00 | 35.64 |
| ATOM 4745 | CD | LYS | 617 | 70.423 | 5.380 | 29.710 | 1.00 | 40.31 |
| ATOM 4746 | CE | LYS | 617 | 71.075 | 4.025 | 29.863 | 1.00 | 43.03 |
| ATOM 4747 | NZ | LYS | 617 | 72.426 | 4.152 | 30.449 | 1.00 | 45.54 |
| ATOM 4751 | C | LYS | 617 | 67.360 | 8.397 | 30.102 | 1.00 | 32.87 |
| ATOM 4752 | O | LYS | 617 | 67.892 | 9.308 | 29.470 | 1.00 | 34.06 |
| ATOM 4753 | N | LYS | 618 | 66.221 | 8.542 | 30.772 | 1.00 | 33.53 |
| ATOM 4755 | CA | LYS | 618 | 65.500 | 9.808 | 30.872 | 1.00 | 33.28 |
| ATOM 4756 | CB | LYS | 618 | 66.384 | 10.842 | 31.558 | 1.00 | 37.22 |
| ATOM 4757 | CG | LYS | 618 | 66.968 | 10.367 | 32.869 | 1.00 | 43.11 |
| ATOM 4758 | CD | LYS | 618 | 65.927 | 10.278 | 33.957 | 1.00 | 49.82 |
| ATOM 4759 | CE | LYS | 618 | 66.520 | 9.636 | 35.199 | 1.00 | 55.20 |
| ATOM 4760 | NZ | LYS | 618 | 65.669 | 9.853 | 36.415 | 1.00 | 61.31 |
| ATOM 4764 | C | LYS | 618 | 65.012 | 10.359 | 29.542 | 1.00 | 31.57 |
| ATOM 4765 | O | LYS | 618 | 64.651 | 11.530 | 29.455 | 1.00 | 31.10 |
| ATOM 4766 | N | CYS | 619 | 64.953 | 9.506 | 28.524 | 1.00 | 31.04 |
| ATOM 4768 | CA | CYS | 619 | 64.519 | 9.922 | 27.196 | 1.00 | 29.21 |
| ATOM 4769 | CB | CYS | 619 | 65.213 | 9.065 | 26.125 | 1.00 | 28.55 |
| ATOM 4770 | SG | CYS | 619 | 64.782 | 9.400 | 24.392 | 1.00 | 26.31 |
| ATOM 4771 | C | CYS | 619 | 62.999 | 9.849 | 27.051 | 1.00 | 30.91 |
| ATOM 4772 | O | CYS | 619 | 62.376 | 8.827 | 27.364 | 1.00 | 31.18 |
| ATOM 4773 | N | ILE | 620 | 62.411 | 10.967 | 26.632 | 1.00 | 29.48 |
| ATOM 4775 | CA | ILE | 620 | 60.981 | 11.073 | 26.416 | 1.00 | 29.34 |
| ATOM 4776 | CB | ILE | 620 | 60.402 | 12.344 | 27.060 | 1.00 | 28.12 |
| ATOM 4777 | CG2 | ILE | 620 | 58.944 | 12.535 | 26.645 | 1.00 | 28.76 |
| ATOM 4778 | CG1 | ILE | 620 | 60.521 | 12.267 | 28.581 | 1.00 | 28.36 |
| ATOM 4779 | CD1 | ILE | 620 | 60.062 | 13.522 | 29.270 | 1.00 | 25.55 |
| ATOM 4780 | C | ILE | 620 | 60.852 | 11.188 | 24.908 | 1.00 | 30.97 |
| ATOM 4781 | O | ILE | 620 | 61.254 | 12.193 | 24.336 | 1.00 | 33.88 |
| ATOM 4782 | N | HIS | 621 | 60.307 | 10.147 | 24.284 | 1.00 | 31.55 |
| ATOM 4784 | CA | HIS | 621 | 60.148 | 10.080 | 22.831 | 1.00 | 31.85 |
| ATOM 4785 | CB | HIS | 621 | 59.721 | 8.668 | 22.425 | 1.00 | 28.27 |
| ATOM 4786 | CG | HIS | 621 | 59.913 | 8.373 | 20.979 | 1.00 | 24.68 |
| ATOM 4787 | CD2 | HIS | 621 | 60.608 | 7.383 | 20.356 | 1.00 | 24.39 |
| ATOM 4788 | ND1 | HIS | 621 | 59.354 | 9.130 | 19.973 | 1.00 | 25.87 |
| ATOM 4790 | CE1 | HIS | 621 | 59.691 | 8.623 | 18.798 | 1.00 | 27.65 |
| ATOM 4791 | NE2 | HIS | 621 | 60.444 | 7.571 | 19.007 | 1.00 | 25.80 |
| ATOM 4793 | C | HIS | 621 | 59.187 | 11.096 | 22.224 | 1.00 | 34.38 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4794 | O | HIS | 621 | 59.387 | 11.539 | 21.104 | 1.00 | 38.74 |
| ATOM 4795 | N | ARG | 622 | 58.080 | 11.374 | 22.898 | 1.00 | 37.17 |
| ATOM 4797 | CA | ARG | 622 | 57.093 | 12.346 | 22.425 | 1.00 | 37.27 |
| ATOM 4798 | CB | ARG | 622 | 57.718 | 13.746 | 22.298 | 1.00 | 38.63 |
| ATOM 4799 | CG | ARG | 622 | 58.261 | 14.271 | 23.601 | 1.00 | 40.47 |
| ATOM 4800 | CD | ARG | 622 | 58.661 | 15.739 | 23.530 | 1.00 | 44.76 |
| ATOM 4801 | NE | ARG | 622 | 59.129 | 16.174 | 24.842 | 1.00 | 52.09 |
| ATOM 4803 | CZ | ARG | 622 | 60.299 | 15.821 | 25.375 | 1.00 | 56.86 |
| ATOM 4804 | NH1 | ARG | 622 | 61.132 | 15.041 | 24.699 | 1.00 | 61.20 |
| ATOM 4807 | NH2 | ARG | 622 | 60.606 | 16.167 | 26.624 | 1.00 | 58.19 |
| ATOM 4810 | C | ARG | 622 | 56.324 | 11.994 | 21.151 | 1.00 | 37.23 |
| ATOM 4811 | O | ARG | 622 | 55.300 | 12.614 | 20.867 | 1.00 | 38.45 |
| ATOM 4812 | N | ASP | 623 | 56.805 | 11.035 | 20.364 | 1.00 | 36.55 |
| ATOM 4814 | CA | ASP | 623 | 56.075 | 10.652 | 19.160 | 1.00 | 36.52 |
| ATOM 4815 | CB | ASP | 623 | 56.581 | 11.403 | 17.910 | 1.00 | 39.68 |
| ATOM 4816 | CG | ASP | 623 | 55.635 | 11.247 | 16.687 | 1.00 | 48.75 |
| ATOM 4817 | OD1 | ASP | 623 | 56.077 | 11.491 | 15.538 | 1.00 | 49.98 |
| ATOM 4818 | OD2 | ASP | 623 | 54.445 | 10.879 | 16.872 | 1.00 | 49.65 |
| ATOM 4819 | C | ASP | 623 | 56.126 | 9.143 | 18.967 | 1.00 | 33.37 |
| ATOM 4820 | O | ASP | 623 | 56.325 | 8.650 | 17.864 | 1.00 | 31.77 |
| ATOM 4821 | N | LEU | 624 | 55.999 | 8.404 | 20.059 | 1.00 | 30.45 |
| ATOM 4823 | CA | LEU | 624 | 56.014 | 6.954 | 19.950 | 1.00 | 30.77 |
| ATOM 4824 | CB | LEU | 624 | 55.983 | 6.307 | 21.342 | 1.00 | 27.43 |
| ATOM 4825 | CG | LEU | 624 | 55.949 | 4.778 | 21.441 | 1.00 | 28.69 |
| ATOM 4826 | CD1 | LEU | 624 | 57.139 | 4.132 | 20.731 | 1.00 | 24.75 |
| ATOM 4827 | CD2 | LEU | 624 | 55.927 | 4.389 | 22.894 | 1.00 | 27.39 |
| ATOM 4828 | C | LEU | 624 | 54.803 | 6.532 | 19.109 | 1.00 | 31.22 |
| ATOM 4829 | O | LEU | 624 | 53.680 | 6.952 | 19.380 | 1.00 | 33.44 |
| ATOM 4830 | N | ALA | 625 | 55.053 | 5.763 | 18.054 | 1.00 | 28.85 |
| ATOM 4832 | CA | ALA | 625 | 54.009 | 5.286 | 17.159 | 1.00 | 26.93 |
| ATOM 4833 | CB | ALA | 625 | 53.559 | 6.400 | 16.227 | 1.00 | 25.03 |
| ATOM 4834 | C | ALA | 625 | 54.642 | 4.162 | 16.356 | 1.00 | 28.44 |
| ATOM 4835 | O | ALA | 625 | 55.863 | 4.065 | 16.317 | 1.00 | 31.32 |
| ATOM 4836 | N | ALA | 626 | 53.828 | 3.329 | 15.705 | 1.00 | 29.14 |
| ATOM 4838 | CA | ALA | 626 | 54.344 | 2.205 | 14.905 | 1.00 | 28.42 |
| ATOM 4839 | CB | ALA | 626 | 53.192 | 1.357 | 14.353 | 1.00 | 27.37 |
| ATOM 4840 | C | ALA | 626 | 55.231 | 2.698 | 13.771 | 1.00 | 26.38 |
| ATOM 4841 | O | ALA | 626 | 56.195 | 2.041 | 13.395 | 1.00 | 26.12 |
| ATOM 4842 | N | ARG | 627 | 54.890 | 3.861 | 13.230 | 1.00 | 27.16 |
| ATOM 4844 | CA | ARG | 627 | 55.669 | 4.474 | 12.158 | 1.00 | 28.44 |
| ATOM 4845 | CB | ARG | 627 | 55.022 | 5.794 | 11.733 | 1.00 | 28.19 |
| ATOM 4846 | CG | ARG | 627 | 54.889 | 6.793 | 12.867 | 1.00 | 30.34 |
| ATOM 4847 | CD | ARG | 627 | 54.456 | 8.155 | 12.361 | 1.00 | 34.08 |
| ATOM 4848 | NE | ARG | 627 | 54.081 | 9.024 | 13.471 | 1.00 | 35.58 |
| ATOM 4850 | CZ | ARG | 627 | 52.849 | 9.123 | 13.950 | 1.00 | 35.55 |
| ATOM 4851 | NH1 | ARG | 627 | 51.860 | 8.422 | 13.420 | 1.00 | 35.67 |
| ATOM 4854 | NH2 | ARG | 627 | 52.618 | 9.898 | 14.993 | 1.00 | 40.81 |
| ATOM 4857 | C | ARG | 627 | 57.108 | 4.733 | 12.630 | 1.00 | 28.06 |
| ATOM 4858 | O | ARG | 627 | 58.044 | 4.737 | 11.825 | 1.00 | 29.80 |
| ATOM 4859 | N | ASN | 628 | 57.272 | 4.935 | 13.940 | 1.00 | 28.50 |
| ATOM 4861 | CA | ASN | 628 | 58.582 | 5.195 | 14.544 | 1.00 | 26.14 |
| ATOM 4862 | CB | ASN | 628 | 58.494 | 6.340 | 15.551 | 1.00 | 23.55 |
| ATOM 4863 | CG | ASN | 628 | 58.319 | 7.681 | 14.874 | 1.00 | 27.48 |
| ATOM 4864 | OD1 | ASN | 628 | 58.874 | 7.919 | 13.800 | 1.00 | 34.12 |
| ATOM 4865 | ND2 | ASN | 628 | 57.543 | 8.556 | 15.479 | 1.00 | 23.21 |
| ATOM 4868 | C | ASN | 628 | 59.263 | 3.965 | 15.153 | 1.00 | 26.76 |
| ATOM 4869 | O | ASN | 628 | 60.202 | 4.078 | 15.948 | 1.00 | 26.90 |
| ATOM 4870 | N | VAL | 629 | 58.774 | 2.794 | 14.767 | 1.00 | 27.02 |
| ATOM 4872 | CA | VAL | 629 | 59.344 | 1.523 | 15.186 | 1.00 | 27.81 |
| ATOM 4873 | CB | VAL | 629 | 58.298 | 0.622 | 15.864 | 1.00 | 26.83 |
| ATOM 4874 | CG1 | VAL | 629 | 58.876 | −0.766 | 16.115 | 1.00 | 20.74 |
| ATOM 4875 | CG2 | VAL | 629 | 57.836 | 1.259 | 17.165 | 1.00 | 22.49 |
| ATOM 4876 | C | VAL | 629 | 59.781 | 0.895 | 13.861 | 1.00 | 28.61 |
| ATOM 4877 | O | VAL | 629 | 58.983 | 0.809 | 12.924 | 1.00 | 28.76 |
| ATOM 4878 | N | LEU | 630 | 61.059 | 0.557 | 13.746 | 1.00 | 30.35 |
| ATOM 4880 | CA | LEU | 630 | 61.576 | −0.033 | 12.514 | 1.00 | 32.42 |
| ATOM 4881 | CB | LEU | 630 | 62.824 | 0.725 | 12.040 | 1.00 | 32.28 |
| ATOM 4882 | CG | LEU | 630 | 62.697 | 2.249 | 11.880 | 1.00 | 27.75 |
| ATOM 4883 | CD1 | LEU | 630 | 64.019 | 2.860 | 11.469 | 1.00 | 24.71 |
| ATOM 4884 | CD2 | LEU | 630 | 61.611 | 2.582 | 10.872 | 1.00 | 27.70 |
| ATOM 4885 | C | LEU | 630 | 61.895 | −1.488 | 12.799 | 1.00 | 32.89 |
| ATOM 4886 | O | LEU | 630 | 62.167 | −1.838 | 13.943 | 1.00 | 32.32 |
| ATOM 4887 | N | VAL | 631 | 61.831 | −2.336 | 11.774 | 1.00 | 34.81 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4889 | CA | VAL | 631 | 62.087 | −3.772 | 11.943 | 1.00 | 33.87 |
| ATOM 4890 | CB | VAL | 631 | 60.818 | −4.616 | 11.597 | 1.00 | 31.60 |
| ATOM 4891 | CG1 | VAL | 631 | 60.929 | −6.004 | 12.197 | 1.00 | 30.84 |
| ATOM 4892 | CG2 | VAL | 631 | 59.545 | −3.916 | 12.089 | 1.00 | 25.53 |
| ATOM 4893 | C | VAL | 631 | 63.286 | −4.256 | 11.109 | 1.00 | 34.95 |
| ATOM 4894 | O | VAL | 631 | 63.365 | −4.009 | 9.892 | 1.00 | 37.01 |
| ATOM 4895 | N | THR | 632 | 64.215 | −4.942 | 11.770 | 1.00 | 35.08 |
| ATOM 4897 | CA | THR | 632 | 65.418 | −5.444 | 11.104 | 1.00 | 35.96 |
| ATOM 4898 | CB | THR | 632 | 66.541 | −5.711 | 12.116 | 1.00 | 34.29 |
| ATOM 4899 | OG1 | THR | 632 | 66.187 | −6.818 | 12.953 | 1.00 | 32.35 |
| ATOM 4901 | CG2 | THR | 632 | 66.750 | −4.488 | 12.985 | 1.00 | 33.42 |
| ATOM 4902 | C | THR | 632 | 65.162 | −6.712 | 10.300 | 1.00 | 39.32 |
| ATOM 4903 | O | THR | 632 | 64.078 | −7.302 | 10.382 | 1.00 | 41.24 |
| ATOM 4904 | N | GLU | 633 | 66.153 | −7.123 | 9.511 | 1.00 | 42.32 |
| ATOM 4906 | CA | GLU | 633 | 66.030 | −8.335 | 8.703 | 1.00 | 44.34 |
| ATOM 4907 | CB | GLU | 633 | 67.314 | −8.609 | 7.912 | 1.00 | 46.06 |
| ATOM 4908 | CG | GLU | 633 | 67.205 | −9.767 | 6.898 | 1.00 | 49.87 |
| ATOM 4909 | CD | GLU | 633 | 66.380 | −9.445 | 5.629 | 1.00 | 53.04 |
| ATOM 4910 | OE1 | GLU | 633 | 65.637 | −8.430 | 5.570 | 1.00 | 51.31 |
| ATOM 4911 | OE2 | GLU | 633 | 66.479 | −10.226 | 4.667 | 1.00 | 55.48 |
| ATOM 4912 | C | GLU | 633 | 65.708 | −9.526 | 9.600 | 1.00 | 44.58 |
| ATOM 4913 | O | GLU | 633 | 64.974 | −10.423 | 9.207 | 1.00 | 46.56 |
| ATOM 4914 | N | ASP | 634 | 66.201 | −9.493 | 10.833 | 1.00 | 44.12 |
| ATOM 4916 | CA | ASP | 634 | 65.961 | −10.583 | 11.759 | 1.00 | 44.23 |
| ATOM 4917 | CB | ASP | 634 | 67.221 | −10.867 | 12.580 | 1.00 | 50.17 |
| ATOM 4918 | CG | ASP | 634 | 68.443 | −11.181 | 11.697 | 1.00 | 56.79 |
| ATOM 4919 | OD1 | ASP | 634 | 68.363 | −12.113 | 10.857 | 1.00 | 59.62 |
| ATOM 4920 | OD2 | ASP | 634 | 69.482 | −10.490 | 11.837 | 1.00 | 58.62 |
| ATOM 4921 | C | ASP | 634 | 64.756 | −10.331 | 12.644 | 1.00 | 43.26 |
| ATOM 4922 | O | ASP | 634 | 64.652 | −10.879 | 13.733 | 1.00 | 43.58 |
| ATOM 4923 | N | ASN | 635 | 63.858 | −9.475 | 12.166 | 1.00 | 43.97 |
| ATOM 4925 | CA | ASN | 635 | 62.612 | −9.126 | 12.847 | 1.00 | 43.66 |
| ATOM 4926 | CB | ASN | 635 | 61.698 | −10.355 | 12.930 | 1.00 | 46.94 |
| ATOM 4927 | CG | ASN | 635 | 61.413 | −10.958 | 11.572 | 1.00 | 48.19 |
| ATOM 4928 | OD1 | ASN | 635 | 60.831 | −10.314 | 10.702 | 1.00 | 51.42 |
| ATOM 4929 | ND2 | ASN | 635 | 61.832 | −12.198 | 11.380 | 1.00 | 49.44 |
| ATOM 4932 | C | ASN | 635 | 62.694 | −8.463 | 14.216 | 1.00 | 43.03 |
| ATOM 4933 | O | ASN | 635 | 61.774 | −8.596 | 15.031 | 1.00 | 43.03 |
| ATOM 4934 | N | VAL | 636 | 63.763 | −7.712 | 14.467 | 1.00 | 42.69 |
| ATOM 4936 | CA | VAL | 636 | 63.915 | −7.034 | 15.756 | 1.00 | 38.30 |
| ATOM 4937 | CB | VAL | 636 | 65.406 | −6.861 | 16.134 | 1.00 | 37.92 |
| ATOM 4938 | CG1 | VAL | 636 | 65.555 | −6.040 | 17.421 | 1.00 | 37.14 |
| ATOM 4939 | CG2 | VAL | 636 | 66.052 | −8.226 | 16.306 | 1.00 | 37.55 |
| ATOM 4940 | C | VAL | 636 | 63.251 | −5.673 | 15.688 | 1.00 | 35.75 |
| ATOM 4941 | O | VAL | 636 | 63.486 | −4.926 | 14.746 | 1.00 | 36.28 |
| ATOM 4942 | N | MET | 637 | 62.355 | −5.396 | 16.628 | 1.00 | 34.73 |
| ATOM 4944 | CA | MET | 637 | 61.672 | −4.103 | 16.680 | 1.00 | 33.22 |
| ATOM 4945 | CB | MET | 637 | 60.456 | −4.152 | 17.608 | 1.00 | 34.83 |
| ATOM 4946 | CG | MET | 637 | 59.364 | −5.148 | 17.231 | 1.00 | 34.41 |
| ATOM 4947 | SD | MET | 637 | 58.661 | −4.926 | 15.589 | 1.00 | 33.19 |
| ATOM 4948 | CE | MET | 637 | 58.869 | −6.584 | 14.913 | 1.00 | 29.73 |
| ATOM 4949 | C | MET | 637 | 62.677 | −3.107 | 17.250 | 1.00 | 33.75 |
| ATOM 4950 | O | MET | 637 | 63.281 | −3.357 | 18.308 | 1.00 | 31.79 |
| ATOM 4951 | N | LYS | 638 | 62.839 | −1.980 | 16.558 | 1.00 | 31.83 |
| ATOM 4953 | CA | LYS | 638 | 63.774 | −0.939 | 16.965 | 1.00 | 28.17 |
| ATOM 4954 | CB | LYS | 638 | 64.986 | −0.930 | 16.038 | 1.00 | 24.98 |
| ATOM 4955 | CG | LYS | 638 | 66.006 | −1.967 | 16.400 | 1.00 | 23.17 |
| ATOM 4956 | CD | LYS | 638 | 67.193 | −1.916 | 15.470 | 1.00 | 25.04 |
| ATOM 4957 | CE | LYS | 638 | 68.212 | −2.969 | 15.847 | 1.00 | 24.79 |
| ATOM 4958 | NZ | LYS | 638 | 68.747 | −2.765 | 17.220 | 1.00 | 24.91 |
| ATOM 4962 | C | LYS | 638 | 63.165 | 0.445 | 16.986 | 1.00 | 26.04 |
| ATOM 4963 | O | LYS | 638 | 62.803 | 0.958 | 15.936 | 1.00 | 24.44 |
| ATOM 4964 | N | ILE | 639 | 63.052 | 1.031 | 18.181 | 1.00 | 25.14 |
| ATOM 4966 | CA | ILE | 639 | 62.508 | 2.376 | 18.351 | 1.00 | 25.68 |
| ATOM 4967 | CB | ILE | 639 | 62.589 | 2.863 | 19.839 | 1.00 | 27.40 |
| ATOM 4968 | CG2 | ILE | 639 | 61.875 | 4.189 | 19.984 | 1.00 | 18.94 |
| ATOM 4969 | CG1 | ILE | 639 | 62.019 | 1.827 | 20.826 | 1.00 | 26.05 |
| ATOM 4970 | CD1 | ILE | 639 | 60.517 | 1.667 | 20.792 | 1.00 | 25.07 |
| ATOM 4971 | C | ILE | 639 | 63.387 | 3.338 | 17.543 | 1.00 | 25.82 |
| ATOM 4972 | O | ILE | 639 | 64.619 | 3.283 | 17.642 | 1.00 | 25.76 |
| ATOM 4973 | N | ALA | 640 | 62.758 | 4.231 | 16.783 | 1.00 | 25.92 |
| ATOM 4975 | CA | ALA | 640 | 63.477 | 5.218 | 15.976 | 1.00 | 26.12 |
| ATOM 4976 | CB | ALA | 640 | 63.222 | 4.964 | 14.506 | 1.00 | 26.54 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 4977 | C | ALA | 640 | 63.042 | 6.643 | 16.344 | 1.00 | 26.33 |
| ATOM 4978 | O | ALA | 640 | 61.996 | 6.828 | 16.974 | 1.00 | 26.20 |
| ATOM 4979 | N | ASP | 641 | 63.863 | 7.637 | 15.993 | 1.00 | 26.59 |
| ATOM 4981 | CA | ASP | 641 | 63.545 | 9.052 | 16.245 | 1.00 | 28.09 |
| ATOM 4982 | CB | ASP | 641 | 62.217 | 9.443 | 15.593 | 1.00 | 31.43 |
| ATOM 4983 | CG | ASP | 641 | 62.346 | 9.762 | 14.107 | 1.00 | 36.81 |
| ATOM 4984 | OD1 | ASP | 641 | 63.409 | 9.478 | 13.500 | 1.00 | 40.24 |
| ATOM 4985 | OD2 | ASP | 641 | 61.356 | 10.299 | 13.548 | 1.00 | 40.49 |
| ATOM 4986 | C | ASP | 641 | 63.455 | 9.442 | 17.700 | 1.00 | 28.40 |
| ATOM 4987 | O | ASP | 641 | 62.825 | 10.446 | 18.041 | 1.00 | 29.30 |
| ATOM 4988 | N | PHE | 642 | 64.080 | 8.658 | 18.564 | 1.00 | 30.27 |
| ATOM 4990 | CA | PHE | 642 | 64.044 | 8.943 | 19.992 | 1.00 | 30.97 |
| ATOM 4991 | CB | PHE | 642 | 64.327 | 7.664 | 20.787 | 1.00 | 24.64 |
| ATOM 4992 | CG | PHE | 642 | 65.673 | 7.063 | 20.505 | 1.00 | 20.96 |
| ATOM 4993 | CD1 | PHE | 642 | 66.812 | 7.539 | 21.163 | 1.00 | 16.89 |
| ATOM 4994 | CD2 | PHE | 642 | 65.806 | 6.026 | 19.576 | 1.00 | 16.23 |
| ATOM 4995 | CE1 | PHE | 642 | 68.072 | 6.990 | 20.900 | 1.00 | 18.35 |
| ATOM 4996 | CE2 | PHE | 642 | 67.051 | 5.471 | 19.305 | 1.00 | 18.76 |
| ATOM 4997 | CZ | PHE | 642 | 68.195 | 5.954 | 19.970 | 1.00 | 17.91 |
| ATOM 4998 | C | PHE | 642 | 65.024 | 10.045 | 20.414 | 1.00 | 34.53 |
| ATOM 4999 | O | PHE | 642 | 64.990 | 10.503 | 21.563 | 1.00 | 35.23 |
| ATOM 5000 | N | GLY | 643 | 65.910 | 10.433 | 19.500 | 1.00 | 36.40 |
| ATOM 5002 | CA | GLY | 643 | 66.888 | 11.455 | 19.799 | 1.00 | 38.28 |
| ATOM 5003 | C | GLY | 643 | 66.634 | 12.768 | 19.093 | 1.00 | 41.44 |
| ATOM 5004 | O | GLY | 643 | 67.482 | 13.652 | 19.132 | 1.00 | 44.10 |
| ATOM 5005 | N | LEU | 644 | 65.461 | 12.921 | 18.484 | 1.00 | 45.44 |
| ATOM 5007 | CA | LEU | 644 | 65.131 | 14.144 | 17.748 | 1.00 | 49.14 |
| ATOM 5008 | CB | LEU | 644 | 63.832 | 13.975 | 16.969 | 1.00 | 46.26 |
| ATOM 5009 | CG | LEU | 644 | 63.823 | 12.967 | 15.836 | 1.00 | 42.90 |
| ATOM 5010 | CD1 | LEU | 644 | 62.527 | 13.134 | 15.070 | 1.00 | 42.68 |
| ATOM 5011 | CD2 | LEU | 644 | 65.004 | 13.228 | 14.934 | 1.00 | 45.15 |
| ATOM 5012 | C | LEU | 644 | 65.027 | 15.396 | 18.605 | 1.00 | 53.90 |
| ATOM 5013 | O | LEU | 644 | 64.488 | 15.356 | 19.715 | 1.00 | 56.54 |
| ATOM 5014 | N | ALA | 645 | 65.534 | 16.505 | 18.068 | 1.00 | 57.59 |
| ATOM 5016 | CA | ALA | 645 | 65.505 | 17.794 | 18.759 | 1.00 | 60.15 |
| ATOM 5017 | CB | ALA | 645 | 66.539 | 18.741 | 18.156 | 1.00 | 59.55 |
| ATOM 5018 | C | ALA | 645 | 64.112 | 18.407 | 18.667 | 1.00 | 61.90 |
| ATOM 5019 | O | ALA | 645 | 63.393 | 18.500 | 19.663 | 1.00 | 63.83 |
| ATOM 5020 | N | ASP | 652 | 52.090 | 22.191 | 14.865 | 1.00 | 89.91 |
| ATOM 5022 | CA | ASP | 652 | 50.913 | 22.199 | 14.007 | 1.00 | 89.75 |
| ATOM 5023 | CB | ASP | 652 | 51.314 | 22.428 | 12.537 | 1.00 | 88.08 |
| ATOM 5024 | CG | ASP | 652 | 50.109 | 22.557 | 11.607 | 1.00 | 87.09 |
| ATOM 5025 | OD1 | ASP | 652 | 49.028 | 22.996 | 12.052 | 1.00 | 86.85 |
| ATOM 5026 | OD2 | ASP | 652 | 50.252 | 22.222 | 10.411 | 1.00 | 86.69 |
| ATOM 5027 | C | ASP | 652 | 50.145 | 20.890 | 14.156 | 1.00 | 89.98 |
| ATOM 5028 | O | ASP | 652 | 50.434 | 19.899 | 13.483 | 1.00 | 90.19 |
| ATOM 5029 | N | TYR | 653 | 49.145 | 20.905 | 15.027 | 1.00 | 90.26 |
| ATOM 5031 | CA | TYR | 653 | 48.318 | 19.730 | 15.277 | 1.00 | 90.78 |
| ATOM 5032 | CB | TYR | 653 | 47.272 | 20.048 | 16.344 | 1.00 | 91.65 |
| ATOM 5033 | CG | TYR | 653 | 47.804 | 20.185 | 17.755 | 1.00 | 93.43 |
| ATOM 5034 | CD1 | TYR | 653 | 47.017 | 20.757 | 18.752 | 1.00 | 94.60 |
| ATOM 5035 | CE1 | TYR | 653 | 47.477 | 20.885 | 20.058 | 1.00 | 95.35 |
| ATOM 5036 | CD2 | TYR | 653 | 49.083 | 19.738 | 18.101 | 1.00 | 93.46 |
| ATOM 5037 | CE2 | TYR | 653 | 49.558 | 19.860 | 19.406 | 1.00 | 94.36 |
| ATOM 5038 | CZ | TYR | 653 | 48.748 | 20.435 | 20.378 | 1.00 | 95.26 |
| ATOM 5039 | OH | TYR | 653 | 49.220 | 20.554 | 21.669 | 1.00 | 95.00 |
| ATOM 5041 | C | TYR | 653 | 47.602 | 19.231 | 14.021 | 1.00 | 90.47 |
| ATOM 5042 | O | TYR | 653 | 47.045 | 18.131 | 14.012 | 1.00 | 91.33 |
| ATOM 5043 | N | TYR | 654 | 47.632 | 20.031 | 12.962 | 1.00 | 89.21 |
| ATOM 5045 | CA | TYR | 654 | 46.954 | 19.673 | 11.727 | 1.00 | 89.09 |
| ATOM 5046 | CB | TYR | 654 | 46.205 | 20.893 | 11.188 | 1.00 | 88.23 |
| ATOM 5047 | CG | TYR | 654 | 45.275 | 21.499 | 12.209 | 1.00 | 87.65 |
| ATOM 5048 | CD1 | TYR | 654 | 45.776 | 22.140 | 13.343 | 1.00 | 86.76 |
| ATOM 5049 | CE1 | TYR | 654 | 44.929 | 22.655 | 14.312 | 1.00 | 87.17 |
| ATOM 5050 | CD2 | TYR | 654 | 43.895 | 21.396 | 12.067 | 1.00 | 88.61 |
| ATOM 5051 | CE2 | TYR | 654 | 43.032 | 21.912 | 13.033 | 1.00 | 89.32 |
| ATOM 5052 | CZ | TYR | 654 | 43.557 | 22.538 | 14.153 | 1.00 | 88.66 |
| ATOM 5053 | OH | TYR | 654 | 42.710 | 23.034 | 15.117 | 1.00 | 89.39 |
| ATOM 5055 | C | TYR | 654 | 47.857 | 19.080 | 10.651 | 1.00 | 89.49 |
| ATOM 5056 | O | TYR | 654 | 47.396 | 18.772 | 9.552 | 1.00 | 88.37 |
| ATOM 5057 | N | LYS | 655 | 49.139 | 18.919 | 10.959 | 1.00 | 90.80 |
| ATOM 5059 | CA | LYS | 655 | 50.056 | 18.356 | 9.982 | 1.00 | 93.18 |
| ATOM 5060 | CB | LYS | 655 | 51.508 | 18.713 | 10.311 | 1.00 | 95.66 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5061 | CG | LYS | 655 | 52.504 | 18.133 | 9.315 | 1.00 | 99.82 |
| ATOM 5062 | CD | LYS | 655 | 53.932 | 18.585 | 9.562 | 1.00 | 103.58 |
| ATOM 5063 | CE | LYS | 655 | 54.898 | 17.833 | 8.637 | 1.00 | 106.15 |
| ATOM 5064 | NZ | LYS | 655 | 56.325 | 18.246 | 8.821 | 1.00 | 108.43 |
| ATOM 5068 | C | LYS | 655 | 49.884 | 16.847 | 9.935 | 1.00 | 93.56 |
| ATOM 5069 | O | LYS | 655 | 49.904 | 16.182 | 10.972 | 1.00 | 93.72 |
| ATOM 5070 | N | LYS | 656 | 49.670 | 16.320 | 8.735 | 1.00 | 94.19 |
| ATOM 5072 | CA | LYS | 656 | 49.500 | 14.886 | 8.545 | 1.00 | 94.84 |
| ATOM 5073 | CB | LYS | 656 | 48.628 | 14.620 | 7.320 | 1.00 | 94.64 |
| ATOM 5074 | CG | LYS | 656 | 47.155 | 14.874 | 7.542 | 1.00 | 95.54 |
| ATOM 5075 | CD | LYS | 656 | 46.402 | 14.709 | 6.241 | 1.00 | 99.56 |
| ATOM 5076 | CE | LYS | 656 | 44.926 | 14.449 | 6.473 | 1.00 | 101.77 |
| ATOM 5077 | NZ | LYS | 656 | 44.202 | 14.327 | 5.173 | 1.00 | 103.77 |
| ATOM 5081 | C | LYS | 656 | 50.859 | 14.225 | 8.368 | 1.00 | 95.18 |
| ATOM 5082 | O | LYS | 656 | 51.823 | 14.878 | 7.956 | 1.00 | 95.74 |
| ATOM 5083 | N | GLY | 660 | 48.651 | 9.665 | 5.782 | 1.00 | 58.76 |
| ATOM 5085 | CA | GLY | 660 | 47.932 | 10.910 | 6.012 | 1.00 | 56.04 |
| ATOM 5086 | C | GLY | 660 | 47.241 | 10.937 | 7.364 | 1.00 | 53.90 |
| ATOM 5087 | O | GLY | 660 | 46.183 | 11.552 | 7.525 | 1.00 | 53.92 |
| ATOM 5088 | N | ARG | 661 | 47.838 | 10.243 | 8.328 | 1.00 | 51.87 |
| ATOM 5090 | CA | ARG | 661 | 47.297 | 10.177 | 9.679 | 1.00 | 48.23 |
| ATOM 5091 | CB | ARG | 661 | 47.755 | 8.891 | 10.377 | 1.00 | 49.74 |
| ATOM 5092 | CG | ARG | 661 | 47.506 | 7.620 | 9.566 | 1.00 | 47.59 |
| ATOM 5093 | CD | ARG | 661 | 47.561 | 6.390 | 10.446 | 1.00 | 51.85 |
| ATOM 5094 | NE | ARG | 661 | 47.584 | 5.155 | 9.663 | 1.00 | 52.94 |
| ATOM 5096 | CZ | ARG | 661 | 48.035 | 3.988 | 10.117 | 1.00 | 52.19 |
| ATOM 5097 | NH1 | ARG | 661 | 48.503 | 3.884 | 11.356 | 1.00 | 52.10 |
| ATOM 5100 | NH2 | ARG | 661 | 48.036 | 2.926 | 9.327 | 1.00 | 54.43 |
| ATOM 5103 | C | ARG | 661 | 47.722 | 11.401 | 10.483 | 1.00 | 43.67 |
| ATOM 5104 | O | ARG | 661 | 48.658 | 12.103 | 10.104 | 1.00 | 41.45 |
| ATOM 5105 | N | LEU | 662 | 47.019 | 11.656 | 11.579 | 1.00 | 40.27 |
| ATOM 5107 | CA | LEU | 662 | 47.310 | 12.799 | 12.437 | 1.00 | 37.15 |
| ATOM 5108 | CB | LEU | 662 | 46.021 | 13.533 | 12.783 | 1.00 | 37.39 |
| ATOM 5109 | CG | LEU | 662 | 45.301 | 14.149 | 11.588 | 1.00 | 37.67 |
| ATOM 5110 | CD1 | LEU | 662 | 43.852 | 14.428 | 11.937 | 1.00 | 35.38 |
| ATOM 5111 | CD2 | LEU | 662 | 46.041 | 15.407 | 11.163 | 1.00 | 39.79 |
| ATOM 5112 | C | LEU | 662 | 47.973 | 12.330 | 13.716 | 1.00 | 34.68 |
| ATOM 5113 | O | LEU | 662 | 47.327 | 11.718 | 14.568 | 1.00 | 33.33 |
| ATOM 5114 | N | PRO | 663 | 49.260 | 12.655 | 13.892 | 1.00 | 34.11 |
| ATOM 5115 | CD | PRO | 663 | 50.086 | 13.389 | 12.924 | 1.00 | 33.67 |
| ATOM 5116 | CA | PRO | 663 | 50.052 | 12.281 | 15.068 | 1.00 | 33.55 |
| ATOM 5117 | CB | PRO | 663 | 51.367 | 13.003 | 14.833 | 1.00 | 32.99 |
| ATOM 5118 | CG | PRO | 663 | 51.479 | 12.966 | 13.328 | 1.00 | 36.09 |
| ATOM 5119 | C | PRO | 663 | 49.412 | 12.665 | 16.399 | 1.00 | 33.55 |
| ATOM 5120 | O | PRO | 663 | 49.683 | 12.036 | 17.426 | 1.00 | 34.11 |
| ATOM 5121 | N | VAL | 664 | 48.566 | 13.697 | 16.387 | 1.00 | 32.63 |
| ATOM 5123 | CA | VAL | 664 | 47.874 | 14.092 | 17.613 | 1.00 | 32.24 |
| ATOM 5124 | CB | VAL | 664 | 46.953 | 15.327 | 17.396 | 1.00 | 33.24 |
| ATOM 5125 | CG1 | VAL | 664 | 47.779 | 16.583 | 17.252 | 1.00 | 35.01 |
| ATOM 5126 | CG2 | VAL | 664 | 46.089 | 15.154 | 16.155 | 1.00 | 35.44 |
| ATOM 5127 | C | VAL | 664 | 47.072 | 12.896 | 18.150 | 1.00 | 31.08 |
| ATOM 5128 | O | VAL | 664 | 46.866 | 12.760 | 19.360 | 1.00 | 31.49 |
| ATOM 5129 | N | LYS | 665 | 46.710 | 11.978 | 17.255 | 1.00 | 29.75 |
| ATOM 5131 | CA | LYS | 665 | 45.956 | 10.788 | 17.638 | 1.00 | 28.83 |
| ATOM 5132 | CB | LYS | 665 | 45.411 | 10.083 | 16.397 | 1.00 | 29.52 |
| ATOM 5133 | CG | LYS | 665 | 44.242 | 10.835 | 15.797 | 1.00 | 27.21 |
| ATOM 5134 | CD | LYS | 665 | 43.905 | 10.431 | 14.397 | 1.00 | 27.25 |
| ATOM 5135 | CE | LYS | 665 | 42.684 | 11.228 | 13.931 | 1.00 | 28.63 |
| ATOM 5136 | NZ | LYS | 665 | 42.266 | 10.902 | 12.545 | 1.00 | 25.33 |
| ATOM 5140 | C | LYS | 665 | 46.718 | 9.830 | 18.537 | 1.00 | 29.03 |
| ATOM 5141 | O | LYS | 665 | 46.152 | 8.869 | 19.046 | 1.00 | 28.37 |
| ATOM 5142 | N | TRP | 666 | 47.994 | 10.123 | 18.765 | 1.00 | 30.40 |
| ATOM 5144 | CA | TRP | 666 | 48.825 | 9.296 | 19.628 | 1.00 | 31.10 |
| ATOM 5145 | CB | TRP | 666 | 50.123 | 8.906 | 18.917 | 1.00 | 29.53 |
| ATOM 5146 | CG | TRP | 666 | 49.946 | 7.781 | 17.966 | 1.00 | 27.03 |
| ATOM 5147 | CD2 | TRP | 666 | 49.407 | 7.853 | 16.638 | 1.00 | 25.06 |
| ATOM 5148 | CE2 | TRP | 666 | 49.418 | 6.546 | 16.116 | 1.00 | 23.83 |
| ATOM 5149 | CE3 | TRP | 666 | 48.924 | 8.899 | 15.835 | 1.00 | 26.08 |
| ATOM 5150 | CD1 | TRP | 666 | 50.257 | 6.475 | 18.186 | 1.00 | 20.75 |
| ATOM 5151 | NE1 | TRP | 666 | 49.937 | 5.729 | 17.086 | 1.00 | 24.92 |
| ATOM 5153 | CZ2 | TRP | 666 | 48.962 | 6.245 | 14.832 | 1.00 | 23.95 |
| ATOM 5154 | CZ3 | TRP | 666 | 48.466 | 8.604 | 14.548 | 1.00 | 29.09 |
| ATOM 5155 | CH2 | TRP | 666 | 48.491 | 7.282 | 14.060 | 1.00 | 29.22 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5156 | C | TRP | 666 | 49.174 | 10.049 | 20.896 | 1.00 | 33.20 |
| ATOM 5157 | O | TRP | 666 | 49.701 | 9.469 | 21.849 | 1.00 | 34.39 |
| ATOM 5158 | N | MET | 667 | 48.862 | 11.340 | 20.910 | 1.00 | 34.82 |
| ATOM 5160 | CA | MET | 667 | 49.169 | 12.175 | 22.056 | 1.00 | 36.31 |
| ATOM 5161 | CB | MET | 667 | 49.205 | 13.645 | 21.651 | 1.00 | 40.08 |
| ATOM 5162 | CG | MET | 667 | 50.475 | 14.047 | 20.931 | 1.00 | 42.41 |
| ATOM 5163 | SD | MET | 667 | 50.555 | 15.818 | 20.713 | 1.00 | 51.31 |
| ATOM 5164 | CE | MET | 667 | 50.957 | 15.928 | 18.949 | 1.00 | 45.44 |
| ATOM 5165 | C | MET | 667 | 48.299 | 12.003 | 23.287 | 1.00 | 37.81 |
| ATOM 5166 | O | MET | 667 | 47.081 | 11.871 | 23.195 | 1.00 | 38.91 |
| ATOM 5167 | N | ALA | 668 | 48.958 | 11.964 | 24.442 | 1.00 | 36.47 |
| ATOM 5169 | CA | ALA | 668 | 48.286 | 11.846 | 25.718 | 1.00 | 37.06 |
| ATOM 5170 | CB | ALA | 668 | 49.308 | 11.654 | 26.835 | 1.00 | 35.76 |
| ATOM 5171 | C | ALA | 668 | 47.548 | 13.161 | 25.893 | 1.00 | 38.76 |
| ATOM 5172 | O | ALA | 668 | 48.000 | 14.201 | 25.414 | 1.00 | 38.04 |
| ATOM 5173 | N | PRO | 669 | 46.416 | 13.142 | 26.608 | 1.00 | 41.60 |
| ATOM 5174 | CD | PRO | 669 | 45.819 | 11.981 | 27.282 | 1.00 | 41.64 |
| ATOM 5175 | CA | PRO | 669 | 45.614 | 14.347 | 26.841 | 1.00 | 43.25 |
| ATOM 5176 | CB | PRO | 669 | 44.478 | 13.827 | 27.718 | 1.00 | 45.08 |
| ATOM 5177 | CG | PRO | 669 | 44.383 | 12.368 | 27.325 | 1.00 | 44.04 |
| ATOM 5178 | C | PRO | 669 | 46.390 | 15.486 | 27.526 | 1.00 | 44.68 |
| ATOM 5179 | O | PRO | 669 | 46.304 | 16.644 | 27.111 | 1.00 | 43.79 |
| ATOM 5180 | N | GLU | 670 | 47.135 | 15.164 | 28.580 | 1.00 | 44.29 |
| ATOM 5182 | CA | GLU | 670 | 47.905 | 16.195 | 29.266 | 1.00 | 45.36 |
| ATOM 5183 | CB | GLU | 670 | 48.596 | 15.637 | 30.509 | 1.00 | 46.97 |
| ATOM 5184 | CG | GLU | 670 | 49.858 | 14.819 | 30.243 | 1.00 | 50.04 |
| ATOM 5185 | CD | GLU | 670 | 49.588 | 13.345 | 30.070 | 1.00 | 51.35 |
| ATOM 5186 | OE1 | GLU | 670 | 50.512 | 12.552 | 30.327 | 1.00 | 50.99 |
| ATOM 5187 | OE2 | GLU | 670 | 48.458 | 12.975 | 29.700 | 1.00 | 52.70 |
| ATOM 5188 | C | GLU | 670 | 48.942 | 16.802 | 28.320 | 1.00 | 45.63 |
| ATOM 5189 | O | GLU | 670 | 49.174 | 18.006 | 28.340 | 1.00 | 44.75 |
| ATOM 5190 | N | ALA | 671 | 49.546 | 15.962 | 27.482 | 1.00 | 46.18 |
| ATOM 5192 | CA | ALA | 671 | 50.555 | 16.406 | 26.531 | 1.00 | 46.44 |
| ATOM 5193 | CB | ALA | 671 | 51.218 | 15.203 | 25.860 | 1.00 | 43.27 |
| ATOM 5194 | C | ALA | 671 | 49.931 | 17.313 | 25.483 | 1.00 | 47.85 |
| ATOM 5195 | O | ALA | 671 | 50.485 | 18.355 | 25.150 | 1.00 | 47.61 |
| ATOM 5196 | N | LEU | 672 | 48.748 | 16.928 | 25.018 | 1.00 | 51.40 |
| ATOM 5198 | CA | LEU | 672 | 48.010 | 17.657 | 23.990 | 1.00 | 54.25 |
| ATOM 5199 | CB | LEU | 672 | 46.996 | 16.705 | 23.346 | 1.00 | 55.60 |
| ATOM 5200 | CG | LEU | 672 | 46.202 | 17.113 | 22.105 | 1.00 | 58.92 |
| ATOM 5201 | CD1 | LEU | 672 | 47.114 | 17.425 | 20.932 | 1.00 | 58.60 |
| ATOM 5202 | CD2 | LEU | 672 | 45.269 | 15.977 | 21.753 | 1.00 | 60.32 |
| ATOM 5203 | C | LEU | 672 | 47.315 | 18.925 | 24.514 | 1.00 | 55.91 |
| ATOM 5204 | O | LEU | 672 | 47.289 | 19.958 | 23.837 | 1.00 | 55.72 |
| ATOM 5205 | N | PHE | 673 | 46.782 | 18.846 | 25.730 | 1.00 | 57.88 |
| ATOM 5207 | CA | PHE | 673 | 46.089 | 19.977 | 26.342 | 1.00 | 60.07 |
| ATOM 5208 | CB | PHE | 673 | 44.873 | 19.484 | 27.127 | 1.00 | 57.08 |
| ATOM 5209 | CG | PHE | 673 | 43.876 | 18.742 | 26.290 | 1.00 | 56.39 |
| ATOM 5210 | CD1 | PHE | 673 | 43.191 | 17.653 | 26.813 | 1.00 | 57.67 |
| ATOM 5211 | CD2 | PHE | 673 | 43.633 | 19.116 | 24.970 | 1.00 | 55.36 |
| ATOM 5212 | CE1 | PHE | 673 | 42.281 | 16.939 | 26.036 | 1.00 | 57.42 |
| ATOM 5213 | CE2 | PHE | 673 | 42.724 | 18.410 | 24.183 | 1.00 | 55.91 |
| ATOM 5214 | CZ | PHE | 673 | 42.049 | 17.317 | 24.720 | 1.00 | 56.42 |
| ATOM 5215 | C | PHE | 673 | 46.974 | 20.854 | 27.238 | 1.00 | 63.00 |
| ATOM 5216 | O | PHE | 673 | 46.926 | 22.085 | 27.155 | 1.00 | 65.31 |
| ATOM 5217 | N | ASP | 674 | 47.786 | 20.223 | 28.081 | 1.00 | 64.08 |
| ATOM 5219 | CA | ASP | 674 | 48.656 | 20.954 | 28.999 | 1.00 | 64.97 |
| ATOM 5220 | CB | ASP | 674 | 48.545 | 20.375 | 30.409 | 1.00 | 65.13 |
| ATOM 5221 | CG | ASP | 674 | 47.128 | 20.358 | 30.923 | 1.00 | 67.33 |
| ATOM 5222 | OD1 | ASP | 674 | 46.684 | 19.283 | 31.372 | 1.00 | 66.68 |
| ATOM 5223 | OD2 | ASP | 674 | 46.462 | 21.416 | 30.869 | 1.00 | 69.20 |
| ATOM 5224 | C | ASP | 674 | 50.132 | 20.971 | 28.603 | 1.00 | 66.38 |
| ATOM 5225 | O | ASP | 674 | 50.984 | 21.304 | 29.434 | 1.00 | 68.44 |
| ATOM 5226 | N | ARG | 675 | 50.441 | 20.585 | 27.365 | 1.00 | 65.68 |
| ATOM 5228 | CA | ARG | 675 | 51.829 | 20.550 | 26.883 | 1.00 | 63.71 |
| ATOM 5229 | CB | ARG | 675 | 52.321 | 21.970 | 26.576 | 1.00 | 63.67 |
| ATOM 5230 | CG | ARG | 675 | 51.491 | 22.685 | 25.531 | 1.00 | 67.65 |
| ATOM 5231 | CD | ARG | 675 | 52.094 | 24.034 | 25.146 | 1.00 | 73.20 |
| ATOM 5232 | NE | ARG | 675 | 53.382 | 23.911 | 24.457 | 1.00 | 74.09 |
| ATOM 5234 | CZ | ARG | 675 | 54.159 | 24.939 | 24.122 | 1.00 | 73.41 |
| ATOM 5235 | NH1 | ARG | 675 | 53.788 | 26.182 | 24.408 | 1.00 | 72.90 |
| ATOM 5238 | NH2 | ARG | 675 | 55.324 | 24.720 | 23.524 | 1.00 | 71.96 |
| ATOM 5241 | C | ARG | 675 | 52.780 | 19.864 | 27.876 | 1.00 | 61.41 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5242 | O | ARG | 675 | 53.960 | 20.208 | 27.966 | 1.00 | 62.62 |
| ATOM 5243 | N | ILE | 676 | 52.248 | 18.903 | 28.627 | 1.00 | 59.15 |
| ATOM 5245 | CA | ILE | 676 | 53.016 | 18.162 | 29.623 | 1.00 | 56.88 |
| ATOM 5246 | CB | ILE | 676 | 52.175 | 17.904 | 30.891 | 1.00 | 56.26 |
| ATOM 5247 | CG2 | ILE | 676 | 52.871 | 16.904 | 31.807 | 1.00 | 53.11 |
| ATOM 5248 | CG1 | ILE | 676 | 51.920 | 19.224 | 31.614 | 1.00 | 57.86 |
| ATOM 5249 | CD1 | ILE | 676 | 51.038 | 19.096 | 32.835 | 1.00 | 61.05 |
| ATOM 5250 | C | ILE | 676 | 53.494 | 16.828 | 29.070 | 1.00 | 56.58 |
| ATOM 5251 | O | ILE | 676 | 52.727 | 15.869 | 28.985 | 1.00 | 58.12 |
| ATOM 5252 | N | TYR | 677 | 54.760 | 16.773 | 28.680 | 1.00 | 54.34 |
| ATOM 5254 | CA | TYR | 677 | 55.340 | 15.556 | 28.143 | 1.00 | 51.14 |
| ATOM 5255 | CB | TYR | 677 | 56.240 | 15.868 | 26.954 | 1.00 | 52.37 |
| ATOM 5256 | CG | TYR | 677 | 55.488 | 16.315 | 25.719 | 1.00 | 56.21 |
| ATOM 5257 | CD1 | TYR | 677 | 55.187 | 17.660 | 25.512 | 1.00 | 56.78 |
| ATOM 5258 | CE1 | TYR | 677 | 54.534 | 18.086 | 24.353 | 1.00 | 57.54 |
| ATOM 5259 | CD2 | TYR | 677 | 55.113 | 15.395 | 24.738 | 1.00 | 57.82 |
| ATOM 5260 | CE2 | TYR | 677 | 54.458 | 15.809 | 23.571 | 1.00 | 59.32 |
| ATOM 5261 | CZ | TYR | 677 | 54.177 | 17.159 | 23.385 | 1.00 | 59.59 |
| ATOM 5262 | OH | TYR | 677 | 53.557 | 17.589 | 22.230 | 1.00 | 60.15 |
| ATOM 5264 | C | TYR | 677 | 56.124 | 14.854 | 29.224 | 1.00 | 48.64 |
| ATOM 5265 | O | TYR | 677 | 57.040 | 15.430 | 29.812 | 1.00 | 50.45 |
| ATOM 5266 | N | THR | 678 | 55.733 | 13.621 | 29.510 | 1.00 | 44.59 |
| ATOM 5268 | CA | THR | 678 | 56.397 | 12.834 | 30.524 | 1.00 | 42.21 |
| ATOM 5269 | CB | THR | 678 | 55.524 | 12.726 | 31.791 | 1.00 | 43.55 |
| ATOM 5270 | OG1 | THR | 678 | 54.302 | 12.045 | 31.475 | 1.00 | 47.42 |
| ATOM 5272 | CG2 | THR | 678 | 55.190 | 14.105 | 32.327 | 1.00 | 48.74 |
| ATOM 5273 | C | THR | 678 | 56.634 | 11.432 | 29.992 | 1.00 | 39.94 |
| ATOM 5274 | O | THR | 678 | 56.207 | 11.085 | 28.892 | 1.00 | 39.34 |
| ATOM 5275 | N | HIS | 679 | 57.312 | 10.616 | 30.784 | 1.00 | 38.54 |
| ATOM 5277 | CA | HIS | 679 | 57.532 | 9.248 | 30.390 | 1.00 | 38.29 |
| ATOM 5278 | CB | HIS | 679 | 58.441 | 8.546 | 31.391 | 1.00 | 39.51 |
| ATOM 5279 | CG | HIS | 679 | 59.869 | 8.997 | 31.331 | 1.00 | 43.13 |
| ATOM 5280 | CD2 | HIS | 679 | 60.630 | 9.668 | 32.233 | 1.00 | 43.49 |
| ATOM 5281 | ND1 | HIS | 679 | 60.694 | 8.726 | 30.263 | 1.00 | 43.00 |
| ATOM 5283 | CE1 | HIS | 679 | 61.903 | 9.201 | 30.510 | 1.00 | 43.62 |
| ATOM 5284 | NE2 | HIS | 679 | 61.889 | 9.778 | 31.695 | 1.00 | 44.68 |
| ATOM 5286 | C | HIS | 679 | 56.147 | 8.599 | 30.359 | 1.00 | 39.42 |
| ATOM 5287 | O | HIS | 679 | 55.898 | 7.667 | 29.593 | 1.00 | 40.00 |
| ATOM 5288 | N | GLN | 680 | 55.228 | 9.156 | 31.142 | 1.00 | 38.96 |
| ATOM 5290 | CA | GLN | 680 | 53.867 | 8.649 | 31.209 | 1.00 | 38.84 |
| ATOM 5291 | CB | GLN | 680 | 53.214 | 9.010 | 32.543 | 1.00 | 40.90 |
| ATOM 5292 | CG | GLN | 680 | 53.835 | 8.278 | 33.732 | 1.00 | 44.42 |
| ATOM 5293 | CD | GLN | 680 | 53.677 | 6.756 | 33.660 | 1.00 | 44.47 |
| ATOM 5294 | OE1 | GLN | 680 | 52.595 | 6.225 | 33.908 | 1.00 | 45.52 |
| ATOM 5295 | NE2 | GLN | 680 | 54.767 | 6.050 | 33.348 | 1.00 | 42.06 |
| ATOM 5298 | C | GLN | 680 | 53.013 | 9.099 | 30.036 | 1.00 | 38.25 |
| ATOM 5299 | O | GLN | 680 | 51.968 | 8.505 | 29.758 | 1.00 | 39.27 |
| ATOM 5300 | N | SER | 681 | 53.427 | 10.155 | 29.349 | 1.00 | 37.00 |
| ATOM 5302 | CA | SER | 681 | 52.665 | 10.571 | 28.182 | 1.00 | 38.02 |
| ATOM 5303 | CB | SER | 681 | 52.929 | 12.034 | 27.813 | 1.00 | 40.29 |
| ATOM 5304 | OG | SER | 681 | 54.307 | 12.286 | 27.620 | 1.00 | 47.29 |
| ATOM 5306 | C | SER | 681 | 53.066 | 9.620 | 27.051 | 1.00 | 37.43 |
| ATOM 5307 | O | SER | 681 | 52.289 | 9.366 | 26.136 | 1.00 | 37.86 |
| ATOM 5308 | N | ASP | 682 | 54.281 | 9.077 | 27.162 | 1.00 | 35.23 |
| ATOM 5310 | CA | ASP | 682 | 54.800 | 8.106 | 26.205 | 1.00 | 33.24 |
| ATOM 5311 | CB | ASP | 682 | 56.284 | 7.820 | 26.464 | 1.00 | 31.85 |
| ATOM 5312 | CG | ASP | 682 | 57.224 | 8.732 | 25.677 | 1.00 | 34.18 |
| ATOM 5313 | OD1 | ASP | 682 | 58.445 | 8.537 | 25.826 | 1.00 | 31.79 |
| ATOM 5314 | OD2 | ASP | 682 | 56.763 | 9.620 | 24.908 | 1.00 | 29.15 |
| ATOM 5315 | C | ASP | 682 | 54.015 | 6.810 | 26.374 | 1.00 | 31.52 |
| ATOM 5316 | O | ASP | 682 | 53.788 | 6.087 | 25.411 | 1.00 | 31.93 |
| ATOM 5317 | N | VAL | 683 | 53.653 | 6.499 | 27.617 | 1.00 | 33.14 |
| ATOM 5319 | CA | VAL | 683 | 52.879 | 5.293 | 27.935 | 1.00 | 32.79 |
| ATOM 5320 | CB | VAL | 683 | 52.725 | 5.095 | 29.478 | 1.00 | 34.56 |
| ATOM 5321 | CG1 | VAL | 683 | 51.653 | 4.059 | 29.790 | 1.00 | 32.39 |
| ATOM 5322 | CG2 | VAL | 683 | 54.050 | 4.649 | 30.088 | 1.00 | 28.08 |
| ATOM 5323 | C | VAL | 683 | 51.506 | 5.338 | 27.245 | 1.00 | 31.45 |
| ATOM 5324 | O | VAL | 683 | 51.008 | 4.311 | 26.779 | 1.00 | 30.37 |
| ATOM 5325 | N | TRP | 684 | 50.919 | 6.531 | 27.147 | 1.00 | 31.04 |
| ATOM 5327 | CA | TRP | 684 | 49.638 | 6.686 | 26.464 | 1.00 | 31.23 |
| ATOM 5328 | CB | TRP | 684 | 49.158 | 8.137 | 26.525 | 1.00 | 34.14 |
| ATOM 5329 | CG | TRP | 684 | 47.913 | 8.423 | 25.694 | 1.00 | 37.17 |
| ATOM 5330 | CD2 | TRP | 684 | 46.573 | 8.593 | 26.187 | 1.00 | 38.61 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5331 | CE2 | TRP | 684 | 45.755 | 8.888 | 25.064 | 1.00 | 37.91 |
| ATOM 5332 | CE3 | TRP | 684 | 45.978 | 8.528 | 27.452 | 1.00 | 37.63 |
| ATOM 5333 | CD1 | TRP | 684 | 47.850 | 8.612 | 24.337 | 1.00 | 37.39 |
| ATOM 5334 | NE1 | TRP | 684 | 46.560 | 8.894 | 23.956 | 1.00 | 34.76 |
| ATOM 5336 | CZ2 | TRP | 684 | 44.380 | 9.118 | 25.181 | 1.00 | 34.79 |
| ATOM 5337 | CZ3 | TRP | 684 | 44.611 | 8.759 | 27.563 | 1.00 | 38.53 |
| ATOM 5338 | CH2 | TRP | 684 | 43.830 | 9.048 | 26.428 | 1.00 | 37.59 |
| ATOM 5339 | C | TRP | 684 | 49.876 | 6.294 | 25.013 | 1.00 | 29.99 |
| ATOM 5340 | O | TRP | 684 | 49.254 | 5.356 | 24.503 | 1.00 | 30.82 |
| ATOM 5341 | N | SER | 685 | 50.815 | 6.992 | 24.380 | 1.00 | 28.28 |
| ATOM 5343 | CA | SER | 685 | 51.174 | 6.738 | 22.986 | 1.00 | 27.54 |
| ATOM 5344 | CB | SER | 685 | 52.444 | 7.504 | 22.631 | 1.00 | 26.69 |
| ATOM 5345 | OG | SER | 685 | 52.355 | 8.874 | 22.986 | 1.00 | 32.15 |
| ATOM 5347 | C | SER | 685 | 51.399 | 5.249 | 22.737 | 1.00 | 26.41 |
| ATOM 5348 | O | SER | 685 | 50.968 | 4.709 | 21.713 | 1.00 | 29.52 |
| ATOM 5349 | N | PHE | 686 | 52.065 | 4.582 | 23.676 | 1.00 | 26.47 |
| ATOM 5351 | CA | PHE | 686 | 52.325 | 3.151 | 23.563 | 1.00 | 26.35 |
| ATOM 5352 | CB | PHE | 686 | 53.167 | 2.668 | 24.754 | 1.00 | 25.01 |
| ATOM 5353 | CG | PHE | 686 | 53.447 | 1.182 | 24.742 | 1.00 | 27.24 |
| ATOM 5354 | CD1 | PHE | 686 | 54.187 | 0.600 | 23.712 | 1.00 | 24.88 |
| ATOM 5355 | CD2 | PHE | 686 | 52.915 | 0.351 | 25.729 | 1.00 | 24.99 |
| ATOM 5356 | CE1 | PHE | 686 | 54.389 | −0.783 | 23.655 | 1.00 | 22.77 |
| ATOM 5357 | CE2 | PHE | 686 | 53.113 | −1.036 | 25.679 | 1.00 | 28.39 |
| ATOM 5358 | CZ | PHE | 686 | 53.853 | −1.601 | 24.631 | 1.00 | 22.71 |
| ATOM 5359 | C | PHE | 686 | 50.997 | 2.366 | 23.466 | 1.00 | 28.82 |
| ATOM 5360 | O | PHE | 686 | 50.892 | 1.398 | 22.696 | 1.00 | 26.41 |
| ATOM 5361 | N | GLY | 687 | 49.988 | 2.797 | 24.229 | 1.00 | 29.65 |
| ATOM 5363 | CA | GLY | 687 | 48.692 | 2.134 | 24.194 | 1.00 | 29.88 |
| ATOM 5364 | C | GLY | 687 | 48.099 | 2.158 | 22.794 | 1.00 | 29.57 |
| ATOM 5365 | O | GLY | 687 | 47.560 | 1.165 | 22.300 | 1.00 | 30.38 |
| ATOM 5366 | N | VAL | 688 | 48.222 | 3.310 | 22.147 | 1.00 | 29.19 |
| ATOM 5368 | CA | VAL | 688 | 47.718 | 3.478 | 20.795 | 1.00 | 25.09 |
| ATOM 5369 | CB | VAL | 688 | 47.747 | 4.956 | 20.359 | 1.00 | 22.52 |
| ATOM 5370 | CG1 | VAL | 688 | 47.106 | 5.115 | 18.985 | 1.00 | 21.13 |
| ATOM 5371 | CG2 | VAL | 688 | 47.001 | 5.810 | 21.366 | 1.00 | 22.50 |
| ATOM 5372 | C | VAL | 688 | 48.574 | 2.636 | 19.865 | 1.00 | 23.82 |
| ATOM 5373 | O | VAL | 688 | 48.080 | 2.132 | 18.871 | 1.00 | 25.39 |
| ATOM 5374 | N | LEU | 689 | 49.849 | 2.463 | 20.208 | 1.00 | 24.46 |
| ATOM 5376 | CA | LEU | 689 | 50.764 | 1.655 | 19.401 | 1.00 | 25.68 |
| ATOM 5377 | CB | LEU | 689 | 52.222 | 1.893 | 19.834 | 1.00 | 25.93 |
| ATOM 5378 | CG | LEU | 689 | 53.374 | 1.307 | 19.004 | 1.00 | 25.01 |
| ATOM 5379 | CD1 | LEU | 689 | 54.655 | 2.080 | 19.257 | 1.00 | 25.86 |
| ATOM 5380 | CD2 | LEU | 689 | 53.593 | −0.145 | 19.318 | 1.00 | 24.90 |
| ATOM 5381 | C | LEU | 689 | 50.374 | 0.171 | 19.531 | 1.00 | 26.50 |
| ATOM 5382 | O | LEU | 689 | 50.464 | −0.578 | 18.558 | 1.00 | 27.13 |
| ATOM 5383 | N | LEU | 690 | 49.927 | −0.234 | 20.724 | 1.00 | 27.76 |
| ATOM 5385 | CA | LEU | 690 | 49.481 | −1.610 | 20.980 | 1.00 | 28.59 |
| ATOM 5386 | CB | LEU | 690 | 49.087 | −1.800 | 22.447 | 1.00 | 30.38 |
| ATOM 5387 | CG | LEU | 690 | 50.121 | −2.065 | 23.545 | 1.00 | 29.57 |
| ATOM 5388 | CD1 | LEU | 690 | 49.435 | −1.966 | 24.907 | 1.00 | 27.40 |
| ATOM 5389 | CD2 | LEU | 690 | 50.744 | −3.431 | 23.360 | 1.00 | 28.79 |
| ATOM 5390 | C | LEU | 690 | 48.242 | −1.849 | 20.134 | 1.00 | 28.77 |
| ATOM 5391 | O | LEU | 690 | 48.055 | −2.922 | 19.573 | 1.00 | 28.07 |
| ATOM 5392 | N | TRP | 691 | 47.383 | −0.838 | 20.075 | 1.00 | 29.58 |
| ATOM 5394 | CA | TRP | 691 | 46.166 | −0.921 | 19.275 | 1.00 | 30.53 |
| ATOM 5395 | CB | TRP | 691 | 45.327 | 0.349 | 19.451 | 1.00 | 28.28 |
| ATOM 5396 | CG | TRP | 691 | 43.985 | 0.300 | 18.769 | 1.00 | 25.86 |
| ATOM 5397 | CD2 | TRP | 691 | 43.702 | 0.689 | 17.421 | 1.00 | 23.99 |
| ATOM 5398 | CE2 | TRP | 691 | 42.321 | 0.498 | 17.215 | 1.00 | 25.08 |
| ATOM 5399 | CE3 | TRP | 691 | 44.487 | 1.165 | 16.367 | 1.00 | 20.88 |
| ATOM 5400 | CD1 | TRP | 691 | 42.791 | −0.090 | 19.314 | 1.00 | 23.72 |
| ATOM 5401 | NE1 | TRP | 691 | 41.786 | 0.031 | 18.389 | 1.00 | 26.15 |
| ATOM 5403 | CZ2 | TRP | 691 | 41.704 | 0.788 | 15.997 | 1.00 | 25.07 |
| ATOM 5404 | CZ3 | TRP | 691 | 43.883 | 1.448 | 15.163 | 1.00 | 22.80 |
| ATOM 5405 | CH2 | TRP | 691 | 42.501 | 1.251 | 14.982 | 1.00 | 24.95 |
| ATOM 5406 | C | TRP | 691 | 46.566 | −1.116 | 17.811 | 1.00 | 30.63 |
| ATOM 5407 | O | TRP | 691 | 45.943 | −1.892 | 17.093 | 1.00 | 33.02 |
| ATOM 5408 | N | GLU | 692 | 47.625 | −0.431 | 17.386 | 1.00 | 31.00 |
| ATOM 5410 | CA | GLU | 692 | 48.130 | −0.545 | 16.018 | 1.00 | 29.00 |
| ATOM 5411 | CB | GLU | 692 | 49.285 | 0.426 | 15.778 | 1.00 | 26.55 |
| ATOM 5412 | CG | GLU | 692 | 48.873 | 1.876 | 15.651 | 1.00 | 29.90 |
| ATOM 5413 | CD | GLU | 692 | 50.040 | 2.781 | 15.316 | 1.00 | 29.83 |
| ATOM 5414 | OE1 | GLU | 692 | 50.770 | 3.174 | 16.247 | 1.00 | 32.18 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5415 | OE2 | GLU | 692 | 50.227 | 3.110 | 14.124 | 1.00 | 31.57 |
| ATOM 5416 | C | GLU | 692 | 48.622 | −1.959 | 15.735 | 1.00 | 29.02 |
| ATOM 5417 | O | GLU | 692 | 48.474 | −2.467 | 14.627 | 1.00 | 29.22 |
| ATOM 5418 | N | ILE | 693 | 49.258 | −2.573 | 16.724 | 1.00 | 29.54 |
| ATOM 5420 | CA | ILE | 693 | 49.766 | −3.933 | 16.555 | 1.00 | 31.01 |
| ATOM 5421 | CB | ILE | 693 | 50.634 | −4.360 | 17.757 | 1.00 | 32.36 |
| ATOM 5422 | CG2 | ILE | 693 | 51.006 | −5.845 | 17.641 | 1.00 | 34.39 |
| ATOM 5423 | CG1 | ILE | 693 | 51.909 | −3.506 | 17.815 | 1.00 | 30.30 |
| ATOM 5424 | CD1 | ILE | 693 | 52.696 | −3.693 | 19.082 | 1.00 | 25.66 |
| ATOM 5425 | C | ILE | 693 | 48.638 | −4.939 | 16.381 | 1.00 | 30.63 |
| ATOM 5426 | O | ILE | 693 | 48.633 | −5.738 | 15.451 | 1.00 | 31.10 |
| ATOM 5427 | N | PHE | 694 | 47.644 | −4.858 | 17.248 | 1.00 | 32.60 |
| ATOM 5429 | CA | PHE | 694 | 46.543 | −5.793 | 17.172 | 1.00 | 33.86 |
| ATOM 5430 | CB | PHE | 694 | 45.938 | −5.970 | 18.563 | 1.00 | 35.66 |
| ATOM 5431 | CG | PHE | 694 | 46.941 | −6.499 | 19.559 | 1.00 | 35.70 |
| ATOM 5432 | CD1 | PHE | 694 | 47.460 | −5.684 | 20.556 | 1.00 | 37.18 |
| ATOM 5433 | CD2 | PHE | 694 | 47.449 | −7.794 | 19.426 | 1.00 | 34.37 |
| ATOM 5434 | CE1 | PHE | 694 | 48.473 | −6.150 | 21.392 | 1.00 | 36.90 |
| ATOM 5435 | CE2 | PHE | 694 | 48.456 | −8.265 | 20.255 | 1.00 | 31.89 |
| ATOM 5436 | CZ | PHE | 694 | 48.970 | −7.446 | 21.234 | 1.00 | 34.95 |
| ATOM 5437 | C | PHE | 694 | 45.532 | −5.576 | 16.049 | 1.00 | 34.26 |
| ATOM 5438 | O | PHE | 694 | 44.702 | −6.442 | 15.787 | 1.00 | 37.52 |
| ATOM 5439 | N | THR | 695 | 45.636 | −4.441 | 15.359 | 1.00 | 32.23 |
| ATOM 5441 | CA | THR | 695 | 44.775 | −4.160 | 14.215 | 1.00 | 28.08 |
| ATOM 5442 | CB | THR | 695 | 44.186 | −2.728 | 14.241 | 1.00 | 25.71 |
| ATOM 5443 | OG1 | THR | 695 | 45.237 | −1.762 | 14.228 | 1.00 | 24.94 |
| ATOM 5445 | CG2 | THR | 695 | 43.353 | −2.528 | 15.468 | 1.00 | 23.07 |
| ATOM 5446 | C | THR | 695 | 45.615 | −4.348 | 12.955 | 1.00 | 27.53 |
| ATOM 5447 | O | THR | 695 | 45.166 | −4.066 | 11.845 | 1.00 | 30.89 |
| ATOM 5448 | N | LEU | 696 | 46.833 | −4.848 | 13.145 | 1.00 | 27.73 |
| ATOM 5450 | CA | LEU | 696 | 47.781 | −5.081 | 12.061 | 1.00 | 28.99 |
| ATOM 5451 | CB | LEU | 696 | 47.370 | −6.297 | 11.226 | 1.00 | 27.78 |
| ATOM 5452 | CG | LEU | 696 | 47.379 | −7.591 | 12.047 | 1.00 | 29.89 |
| ATOM 5453 | CD1 | LEU | 696 | 47.251 | −8.823 | 11.164 | 1.00 | 29.96 |
| ATOM 5454 | CD2 | LEU | 696 | 48.668 | −7.656 | 12.803 | 1.00 | 30.20 |
| ATOM 5455 | C | LEU | 696 | 48.044 | −3.853 | 11.179 | 1.00 | 30.33 |
| ATOM 5456 | O | LEU | 696 | 48.006 | −3.926 | 9.948 | 1.00 | 29.41 |
| ATOM 5457 | N | GLY | 697 | 48.374 | −2.738 | 11.831 | 1.00 | 30.92 |
| ATOM 5459 | CA | GLY | 697 | 48.655 | −1.503 | 11.113 | 1.00 | 30.35 |
| ATOM 5460 | C | GLY | 697 | 47.420 | −0.650 | 10.912 | 1.00 | 30.65 |
| ATOM 5461 | O | GLY | 697 | 47.359 | 0.178 | 10.000 | 1.00 | 30.01 |
| ATOM 5462 | N | GLY | 698 | 46.428 | −0.836 | 11.772 | 1.00 | 30.50 |
| ATOM 5464 | CA | GLY | 698 | 45.209 | −0.063 | 11.656 | 1.00 | 30.36 |
| ATOM 5465 | C | GLY | 698 | 45.416 | 1.415 | 11.930 | 1.00 | 30.07 |
| ATOM 5466 | O | GLY | 698 | 46.320 | 1.809 | 12.666 | 1.00 | 30.56 |
| ATOM 5467 | N | SER | 699 | 44.554 | 2.228 | 11.338 | 1.00 | 29.65 |
| ATOM 5469 | CA | SER | 699 | 44.597 | 3.674 | 11.485 | 1.00 | 28.42 |
| ATOM 5470 | CB | SER | 699 | 44.263 | 4.324 | 10.145 | 1.00 | 24.61 |
| ATOM 5471 | OG | SER | 699 | 43.960 | 5.693 | 10.280 | 1.00 | 31.25 |
| ATOM 5473 | C | SER | 699 | 43.621 | 4.137 | 12.574 | 1.00 | 28.27 |
| ATOM 5474 | O | SER | 699 | 42.406 | 3.930 | 12.474 | 1.00 | 27.14 |
| ATOM 5475 | N | PRO | 700 | 44.160 | 4.682 | 13.675 | 1.00 | 29.29 |
| ATOM 5476 | CD | PRO | 700 | 45.587 | 4.867 | 13.999 | 1.00 | 26.09 |
| ATOM 5477 | CA | PRO | 700 | 43.303 | 5.155 | 14.764 | 1.00 | 29.30 |
| ATOM 5478 | CB | PRO | 700 | 44.319 | 5.624 | 15.812 | 1.00 | 27.68 |
| ATOM 5479 | CG | PRO | 700 | 45.531 | 5.982 | 14.985 | 1.00 | 27.85 |
| ATOM 5480 | C | PRO | 700 | 42.413 | 6.305 | 14.306 | 1.00 | 29.71 |
| ATOM 5481 | O | PRO | 700 | 42.800 | 7.096 | 13.446 | 1.00 | 31.38 |
| ATOM 5482 | N | TYR | 701 | 41.204 | 6.357 | 14.854 | 1.00 | 29.51 |
| ATOM 5484 | CA | TYR | 701 | 40.246 | 7.419 | 14.548 | 1.00 | 30.25 |
| ATOM 5485 | CB | TYR | 701 | 40.559 | 8.647 | 15.405 | 1.00 | 33.50 |
| ATOM 5486 | CG | TYR | 701 | 40.321 | 8.413 | 16.866 | 1.00 | 37.84 |
| ATOM 5487 | CD1 | TYR | 701 | 41.323 | 8.638 | 17.803 | 1.00 | 40.05 |
| ATOM 5488 | CE1 | TYR | 701 | 41.092 | 8.412 | 19.158 | 1.00 | 42.28 |
| ATOM 5489 | CD2 | TYR | 701 | 39.084 | 7.965 | 17.310 | 1.00 | 41.54 |
| ATOM 5490 | CE2 | TYR | 701 | 38.845 | 7.738 | 18.653 | 1.00 | 43.70 |
| ATOM 5491 | CZ | TYR | 701 | 39.845 | 7.963 | 19.574 | 1.00 | 42.63 |
| ATOM 5492 | OH | TYR | 701 | 39.584 | 7.716 | 20.907 | 1.00 | 45.31 |
| ATOM 5494 | C | TYR | 701 | 40.173 | 7.829 | 13.088 | 1.00 | 28.45 |
| ATOM 5495 | O | TYR | 701 | 40.356 | 9.001 | 12.760 | 1.00 | 29.03 |
| ATOM 5496 | N | PRO | 702 | 39.901 | 6.867 | 12.191 | 1.00 | 28.05 |
| ATOM 5497 | CD | PRO | 702 | 39.671 | 5.430 | 12.417 | 1.00 | 26.90 |
| ATOM 5498 | CA | PRO | 702 | 39.815 | 7.181 | 10.764 | 1.00 | 27.48 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5499 | CB | PRO | 702 | 39.610 | 5.807 | 10.119 | 1.00 | 27.06 |
| ATOM 5500 | CG | PRO | 702 | 38.923 | 5.036 | 11.169 | 1.00 | 28.28 |
| ATOM 5501 | C | PRO | 702 | 38.689 | 8.145 | 10.440 | 1.00 | 26.81 |
| ATOM 5502 | O | PRO | 702 | 37.554 | 7.953 | 10.865 | 1.00 | 26.26 |
| ATOM 5503 | N | GLY | 703 | 39.035 | 9.192 | 9.693 | 1.00 | 28.48 |
| ATOM 5505 | CA | GLY | 703 | 38.085 | 10.217 | 9.295 | 1.00 | 26.54 |
| ATOM 5506 | C | GLY | 703 | 37.862 | 11.285 | 10.351 | 1.00 | 28.03 |
| ATOM 5507 | O | GLY | 703 | 37.110 | 12.231 | 10.108 | 1.00 | 28.93 |
| ATOM 5508 | N | VAL | 704 | 38.518 | 11.149 | 11.505 | 1.00 | 28.16 |
| ATOM 5510 | CA | VAL | 704 | 38.369 | 12.081 | 12.619 | 1.00 | 29.55 |
| ATOM 5511 | CB | VAL | 704 | 38.473 | 11.360 | 13.984 | 1.00 | 28.50 |
| ATOM 5512 | CG1 | VAL | 704 | 38.330 | 12.350 | 15.135 | 1.00 | 28.07 |
| ATOM 5513 | CG2 | VAL | 704 | 37.403 | 10.295 | 14.091 | 1.00 | 29.78 |
| ATOM 5514 | C | VAL | 704 | 39.375 | 13.227 | 12.588 | 1.00 | 32.00 |
| ATOM 5515 | O | VAL | 704 | 40.578 | 13.028 | 12.758 | 1.00 | 33.85 |
| ATOM 5516 | N | PRO | 705 | 38.888 | 14.446 | 12.336 | 1.00 | 33.56 |
| ATOM 5517 | CD | PRO | 705 | 37.512 | 14.763 | 11.906 | 1.00 | 33.69 |
| ATOM 5518 | CA | PRO | 705 | 39.745 | 15.628 | 12.280 | 1.00 | 32.65 |
| ATOM 5519 | CB | PRO | 705 | 38.863 | 16.647 | 11.569 | 1.00 | 34.10 |
| ATOM 5520 | CG | PRO | 705 | 37.478 | 16.256 | 12.021 | 1.00 | 36.38 |
| ATOM 5521 | C | PRO | 705 | 40.164 | 16.081 | 13.668 | 1.00 | 33.22 |
| ATOM 5522 | O | PRO | 705 | 39.549 | 15.708 | 14.668 | 1.00 | 33.26 |
| ATOM 5523 | N | VAL | 706 | 41.198 | 16.912 | 13.710 | 1.00 | 34.61 |
| ATOM 5525 | CA | VAL | 706 | 41.764 | 17.417 | 14.954 | 1.00 | 37.72 |
| ATOM 5526 | CB | VAL | 706 | 42.803 | 18.527 | 14.673 | 1.00 | 39.14 |
| ATOM 5527 | CG1 | VAL | 706 | 43.483 | 18.941 | 15.957 | 1.00 | 39.12 |
| ATOM 5528 | CG2 | VAL | 706 | 43.836 | 18.038 | 13.670 | 1.00 | 41.07 |
| ATOM 5529 | C | VAL | 706 | 40.740 | 17.934 | 15.969 | 1.00 | 38.70 |
| ATOM 5530 | O | VAL | 706 | 40.761 | 17.536 | 17.136 | 1.00 | 38.42 |
| ATOM 5531 | N | GLU | 707 | 39.834 | 18.796 | 15.517 | 1.00 | 40.43 |
| ATOM 5533 | CA | GLU | 707 | 38.823 | 19.375 | 16.395 | 1.00 | 40.66 |
| ATOM 5534 | CB | GLU | 707 | 37.973 | 20.379 | 15.621 | 1.00 | 43.40 |
| ATOM 5535 | C | GLU | 707 | 37.940 | 18.316 | 17.028 | 1.00 | 41.03 |
| ATOM 5536 | O | GLU | 707 | 37.642 | 18.370 | 18.231 | 1.00 | 41.52 |
| ATOM 5537 | N | GLU | 708 | 37.560 | 17.327 | 16.224 | 1.00 | 41.62 |
| ATOM 5539 | CA | GLU | 708 | 36.708 | 16.243 | 16.700 | 1.00 | 41.06 |
| ATOM 5540 | CB | GLU | 708 | 36.179 | 15.425 | 15.523 | 1.00 | 45.19 |
| ATOM 5541 | CG | GLU | 708 | 35.281 | 16.221 | 14.571 | 1.00 | 48.74 |
| ATOM 5542 | CD | GLU | 708 | 34.063 | 16.825 | 15.258 | 1.00 | 57.18 |
| ATOM 5543 | OE1 | GLU | 708 | 33.523 | 16.203 | 16.207 | 1.00 | 54.30 |
| ATOM 5544 | OE2 | GLU | 708 | 33.646 | 17.934 | 14.837 | 1.00 | 61.76 |
| ATOM 5545 | C | GLU | 708 | 37.443 | 15.363 | 17.694 | 1.00 | 38.39 |
| ATOM 5546 | O | GLU | 708 | 36.867 | 14.927 | 18.696 | 1.00 | 36.76 |
| ATOM 5547 | N | LEU | 709 | 38.725 | 15.131 | 17.434 | 1.00 | 37.78 |
| ATOM 5549 | CA | LEU | 709 | 39.555 | 14.327 | 18.324 | 1.00 | 38.13 |
| ATOM 5550 | CB | LEU | 709 | 41.007 | 14.255 | 17.820 | 1.00 | 35.45 |
| ATOM 5551 | CG | LEU | 709 | 41.984 | 13.560 | 18.786 | 1.00 | 35.57 |
| ATOM 5552 | CD1 | LEU | 709 | 41.825 | 12.049 | 18.729 | 1.00 | 32.33 |
| ATOM 5553 | CD2 | LEU | 709 | 43.407 | 13.965 | 18.484 | 1.00 | 31.98 |
| ATOM 5554 | C | LEU | 709 | 39.550 | 14.946 | 19.716 | 1.00 | 38.31 |
| ATOM 5555 | O | LEU | 709 | 39.362 | 14.250 | 20.717 | 1.00 | 38.16 |
| ATOM 5556 | N | PHE | 710 | 39.776 | 16.254 | 19.770 | 1.00 | 40.09 |
| ATOM 5558 | CA | PHE | 710 | 39.807 | 16.973 | 21.036 | 1.00 | 43.61 |
| ATOM 5559 | CB | PHE | 710 | 39.997 | 18.475 | 20.797 | 1.00 | 48.22 |
| ATOM 5560 | CG | PHE | 710 | 41.328 | 18.834 | 20.192 | 1.00 | 51.77 |
| ATOM 5561 | CD1 | PHE | 710 | 42.395 | 17.939 | 20.231 | 1.00 | 52.94 |
| ATOM 5562 | CD2 | PHE | 710 | 41.513 | 20.072 | 19.579 | 1.00 | 53.99 |
| ATOM 5563 | CE1 | PHE | 710 | 43.632 | 18.275 | 19.679 | 1.00 | 56.48 |
| ATOM 5564 | CE2 | PHE | 710 | 42.746 | 20.422 | 19.021 | 1.00 | 55.72 |
| ATOM 5565 | CZ | PHE | 710 | 43.807 | 19.517 | 19.069 | 1.00 | 57.84 |
| ATOM 5566 | C | PHE | 710 | 38.519 | 16.726 | 21.796 | 1.00 | 43.35 |
| ATOM 5567 | O | PHE | 710 | 38.539 | 16.424 | 22.989 | 1.00 | 43.22 |
| ATOM 5568 | N | LYS | 711 | 37.399 | 16.804 | 21.083 | 1.00 | 44.68 |
| ATOM 5570 | CA | LYS | 711 | 36.095 | 16.587 | 21.690 | 1.00 | 43.47 |
| ATOM 5571 | CB | LYS | 711 | 34.977 | 16.878 | 20.687 | 1.00 | 44.33 |
| ATOM 5572 | CG | LYS | 711 | 33.601 | 16.765 | 21.299 | 1.00 | 47.63 |
| ATOM 5573 | CD | LYS | 711 | 32.510 | 17.206 | 20.362 | 1.00 | 49.97 |
| ATOM 5574 | CE | LYS | 711 | 31.158 | 16.873 | 20.960 | 1.00 | 51.70 |
| ATOM 5575 | NZ | LYS | 711 | 30.038 | 17.412 | 20.150 | 1.00 | 57.55 |
| ATOM 5579 | C | LYS | 711 | 35.986 | 15.173 | 22.261 | 1.00 | 42.72 |
| ATOM 5580 | O | LYS | 711 | 35.589 | 14.999 | 23.420 | 1.00 | 41.16 |
| ATOM 5581 | N | LEU | 712 | 36.392 | 14.176 | 21.471 | 1.00 | 42.52 |
| ATOM 5583 | CA | LEU | 712 | 36.361 | 12.770 | 21.898 | 1.00 | 42.52 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5584 | CB | LEU | 712 | 36.922 | 11.843 | 20.809 | 1.00 | 41.56 |
| ATOM 5585 | CG | LEU | 712 | 36.090 | 11.528 | 19.560 | 1.00 | 41.87 |
| ATOM 5586 | CD1 | LEU | 712 | 36.902 | 10.620 | 18.636 | 1.00 | 36.28 |
| ATOM 5587 | CD2 | LEU | 712 | 34.760 | 10.868 | 19.951 | 1.00 | 37.19 |
| ATOM 5588 | C | LEU | 712 | 37.158 | 12.564 | 23.180 | 1.00 | 42.34 |
| ATOM 5589 | O | LEU | 712 | 36.697 | 11.886 | 24.107 | 1.00 | 40.77 |
| ATOM 5590 | N | LEU | 713 | 38.366 | 13.121 | 23.208 | 1.00 | 42.68 |
| ATOM 5592 | CA | LEU | 713 | 39.240 | 13.025 | 24.371 | 1.00 | 44.05 |
| ATOM 5593 | CB | LEU | 713 | 40.581 | 13.710 | 24.100 | 1.00 | 45.45 |
| ATOM 5594 | CG | LEU | 713 | 41.418 | 13.114 | 22.963 | 1.00 | 44.78 |
| ATOM 5595 | CD1 | LEU | 713 | 42.676 | 13.945 | 22.750 | 1.00 | 41.89 |
| ATOM 5596 | CD2 | LEU | 713 | 41.757 | 11.660 | 23.282 | 1.00 | 43.21 |
| ATOM 5597 | C | LEU | 713 | 38.571 | 13.654 | 25.591 | 1.00 | 44.66 |
| ATOM 5598 | O | LEU | 713 | 38.562 | 13.051 | 26.662 | 1.00 | 45.70 |
| ATOM 5599 | N | LYS | 714 | 37.980 | 14.839 | 25.418 | 1.00 | 43.05 |
| ATOM 5601 | CA | LYS | 714 | 37.300 | 15.510 | 26.524 | 1.00 | 42.19 |
| ATOM 5602 | CB | LYS | 714 | 36.884 | 16.921 | 26.127 | 1.00 | 42.41 |
| ATOM 5603 | CG | LYS | 714 | 38.076 | 17.828 | 25.918 | 1.00 | 46.10 |
| ATOM 5604 | CD | LYS | 714 | 37.684 | 19.259 | 25.589 | 1.00 | 49.86 |
| ATOM 5605 | CE | LYS | 714 | 38.939 | 20.097 | 25.292 | 1.00 | 52.55 |
| ATOM 5606 | NZ | LYS | 714 | 39.889 | 20.148 | 26.459 | 1.00 | 50.17 |
| ATOM 5610 | C | LYS | 714 | 36.104 | 14.728 | 27.054 | 1.00 | 42.39 |
| ATOM 5611 | O | LYS | 714 | 35.767 | 14.824 | 28.237 | 1.00 | 43.44 |
| ATOM 5612 | N | GLU | 715 | 35.480 | 13.934 | 26.192 | 1.00 | 40.44 |
| ATOM 5614 | CA | GLU | 715 | 34.342 | 13.118 | 26.593 | 1.00 | 37.90 |
| ATOM 5615 | CB | GLU | 715 | 33.408 | 12.893 | 25.411 | 1.00 | 39.54 |
| ATOM 5616 | CG | GLU | 715 | 32.800 | 14.174 | 24.846 | 1.00 | 45.20 |
| ATOM 5617 | CD | GLU | 715 | 32.032 | 13.936 | 23.563 | 1.00 | 47.85 |
| ATOM 5618 | OE1 | GLU | 715 | 32.409 | 13.008 | 22.810 | 1.00 | 50.00 |
| ATOM 5619 | OE2 | GLU | 715 | 31.061 | 14.677 | 23.304 | 1.00 | 50.41 |
| ATOM 5620 | C | GLU | 715 | 34.793 | 11.773 | 27.157 | 1.00 | 37.31 |
| ATOM 5621 | O | GLU | 715 | 33.970 | 10.907 | 27.450 | 1.00 | 36.79 |
| ATOM 5622 | N | GLY | 716 | 36.102 | 11.585 | 27.286 | 1.00 | 36.60 |
| ATOM 5624 | CA | GLY | 716 | 36.623 | 10.336 | 27.819 | 1.00 | 37.11 |
| ATOM 5625 | C | GLY | 716 | 36.503 | 9.140 | 26.887 | 1.00 | 38.30 |
| ATOM 5626 | O | GLY | 716 | 36.603 | 7.994 | 27.340 | 1.00 | 36.84 |
| ATOM 5627 | N | HIS | 717 | 36.307 | 9.404 | 25.592 | 1.00 | 40.24 |
| ATOM 5629 | CA | HIS | 717 | 36.167 | 8.353 | 24.579 | 1.00 | 42.63 |
| ATOM 5630 | CB | HIS | 717 | 35.800 | 8.951 | 23.217 | 1.00 | 43.11 |
| ATOM 5631 | CG | HIS | 717 | 35.745 | 7.941 | 22.112 | 1.00 | 44.69 |
| ATOM 5632 | CD2 | HIS | 717 | 34.756 | 7.101 | 21.717 | 1.00 | 45.13 |
| ATOM 5633 | ND1 | HIS | 717 | 36.818 | 7.683 | 21.263 | 1.00 | 47.31 |
| ATOM 5635 | CE1 | HIS | 717 | 36.494 | 6.728 | 20.426 | 1.00 | 47.61 |
| ATOM 5636 | NE2 | HIS | 717 | 35.250 | 6.357 | 20.670 | 1.00 | 44.95 |
| ATOM 5638 | C | HIS | 717 | 37.451 | 7.567 | 24.413 | 1.00 | 44.84 |
| ATOM 5639 | O | HIS | 717 | 38.528 | 8.152 | 24.295 | 1.00 | 46.79 |
| ATOM 5640 | N | ARG | 718 | 37.313 | 6.247 | 24.337 | 1.00 | 45.44 |
| ATOM 5642 | CA | ARG | 718 | 38.440 | 5.345 | 24.170 | 1.00 | 45.36 |
| ATOM 5643 | CB | ARG | 718 | 38.614 | 4.496 | 25.434 | 1.00 | 43.82 |
| ATOM 5644 | CG | ARG | 718 | 38.976 | 5.308 | 26.687 | 1.00 | 44.52 |
| ATOM 5645 | CD | ARG | 718 | 46.284 | 6.065 | 26.476 | 1.00 | 45.02 |
| ATOM 5646 | NE | ARG | 718 | 40.718 | 6.856 | 27.630 | 1.00 | 43.12 |
| ATOM 5648 | CZ | ARG | 718 | 40.550 | 8.173 | 27.744 | 1.00 | 44.77 |
| ATOM 5649 | NH1 | ARG | 718 | 39.940 | 8.859 | 26.784 | 1.00 | 44.67 |
| ATOM 5652 | NH2 | ARG | 718 | 41.067 | 8.826 | 28.777 | 1.00 | 46.39 |
| ATOM 5655 | C | ARG | 718 | 38.124 | 4.474 | 22.952 | 1.00 | 45.94 |
| ATOM 5656 | O | ARG | 718 | 36.953 | 4.243 | 22.645 | 1.00 | 47.59 |
| ATOM 5657 | N | MET | 719 | 39.145 | 4.077 | 22.204 | 1.00 | 45.34 |
| ATOM 5659 | CA | MET | 719 | 38.925 | 3.253 | 21.029 | 1.00 | 44.28 |
| ATOM 5660 | CB | MET | 719 | 40.198 | 3.125 | 20.185 | 1.00 | 42.30 |
| ATOM 5661 | CG | MET | 719 | 40.575 | 4.399 | 19.441 | 1.00 | 38.44 |
| ATOM 5662 | SD | MET | 719 | 42.000 | 4.225 | 18.368 | 1.00 | 36.97 |
| ATOM 5663 | CE | MET | 719 | 43.317 | 4.219 | 19.511 | 1.00 | 36.09 |
| ATOM 5664 | C | MET | 719 | 38.415 | 1.877 | 21.418 | 1.00 | 46.21 |
| ATOM 5665 | O | MET | 719 | 38.708 | 1.393 | 22.517 | 1.00 | 43.29 |
| ATOM 5666 | N | ASP | 720 | 37.659 | 1.267 | 20.498 | 1.00 | 48.79 |
| ATOM 5668 | CA | ASP | 720 | 37.069 | −0.063 | 20.666 | 1.00 | 48.87 |
| ATOM 5669 | CB | ASP | 720 | 36.099 | −0.369 | 19.513 | 1.00 | 54.01 |
| ATOM 5670 | CG | ASP | 720 | 34.766 | 0.374 | 19.632 | 1.00 | 59.30 |
| ATOM 5671 | OD1 | ASP | 720 | 34.762 | 1.583 | 19.981 | 1.00 | 62.96 |
| ATOM 5672 | OD2 | ASP | 720 | 33.716 | −0.259 | 19.354 | 1.00 | 58.64 |
| ATOM 5673 | C | ASP | 720 | 38.126 | −1.154 | 20.688 | 1.00 | 46.10 |
| ATOM 5674 | O | ASP | 720 | 39.213 | −0.992 | 20.125 | 1.00 | 44.13 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5675 | N | LYS | 721 | 37.788 | −2.272 | 21.322 | 1.00 | 45.27 |
| ATOM 5677 | CA | LYS | 721 | 38.689 | −3.413 | 21.404 | 1.00 | 43.25 |
| ATOM 5678 | CB | LYS | 721 | 38.172 | −4.436 | 22.416 | 1.00 | 42.02 |
| ATOM 5679 | CG | LYS | 721 | 39.072 | −5.651 | 22.557 | 1.00 | 46.57 |
| ATOM 5680 | CD | LYS | 721 | 38.602 | −6.576 | 23.666 | 1.00 | 49.96 |
| ATOM 5681 | CE | LYS | 721 | 38.300 | −7.971 | 23.141 | 1.00 | 51.80 |
| ATOM 5682 | NZ | LYS | 721 | 37.937 | −8.920 | 24.240 | 1.00 | 56.08 |
| ATOM 5686 | C | LYS | 721 | 38.769 | −4.055 | 20.031 | 1.00 | 43.67 |
| ATOM 5687 | O | LYS | 721 | 37.736 | −4.313 | 19.394 | 1.00 | 44.02 |
| ATOM 5688 | N | PRO | 722 | 39.995 | −4.233 | 19.513 | 1.00 | 43.94 |
| ATOM 5689 | CD | PRO | 722 | 41.281 | −3.711 | 20.001 | 1.00 | 45.90 |
| ATOM 5690 | CA | PRO | 722 | 40.159 | −4.853 | 18.198 | 1.00 | 43.96 |
| ATOM 5691 | CB | PRO | 722 | 41.665 | −4.720 | 17.941 | 1.00 | 43.11 |
| ATOM 5692 | CG | PRO | 722 | 42.046 | −3.509 | 18.715 | 1.00 | 45.16 |
| ATOM 5693 | C | PRO | 722 | 39.772 | −6.317 | 18.295 | 1.00 | 43.09 |
| ATOM 5694 | O | PRO | 722 | 39.764 | −6.888 | 19.385 | 1.00 | 41.32 |
| ATOM 5695 | N | SER | 723 | 39.382 | −6.902 | 17.170 | 1.00 | 45.79 |
| ATOM 5697 | CA | SER | 723 | 39.044 | −8.316 | 17.144 | 1.00 | 46.67 |
| ATOM 5698 | CB | SER | 723 | 38.303 | −8.664 | 15.857 | 1.00 | 44.69 |
| ATOM 5699 | OG | SER | 723 | 39.131 | −8.414 | 14.736 | 1.00 | 49.79 |
| ATOM 5701 | C | SER | 723 | 40.422 | −8.961 | 17.148 | 1.00 | 46.90 |
| ATOM 5702 | O | SER | 723 | 41.360 | −8.411 | 16.581 | 1.00 | 48.81 |
| ATOM 5703 | N | ASN | 724 | 40.540 | −10.131 | 17.760 | 1.00 | 49.28 |
| ATOM 5705 | CA | ASN | 724 | 41.826 | −10.804 | 17.849 | 1.00 | 52.10 |
| ATOM 5706 | CB | ASN | 724 | 42.480 | −10.947 | 16.469 | 1.00 | 55.86 |
| ATOM 5707 | CG | ASN | 724 | 41.774 | −11.957 | 15.592 | 1.00 | 58.72 |
| ATOM 5708 | OD1 | ASN | 724 | 41.686 | −13.140 | 15.941 | 1.00 | 62.28 |
| ATOM 5709 | ND2 | ASN | 724 | 41.258 | −11.503 | 14.449 | 1.00 | 59.56 |
| ATOM 5712 | C | ASN | 724 | 42.665 | −9.931 | 16.770 | 1.00 | 51.97 |
| ATOM 5713 | O | ASN | 724 | 43.621 | −9.274 | 18.369 | 1.00 | 53.85 |
| ATOM 5714 | N | CYS | 725 | 42.202 | −9.859 | 20.004 | 1.00 | 51.02 |
| ATOM 5716 | CA | CYS | 725 | 42.853 | −9.094 | 21.049 | 1.00 | 50.18 |
| ATOM 5717 | CB | CYS | 725 | 42.708 | −7.583 | 20.811 | 1.00 | 47.75 |
| ATOM 5718 | SG | CYS | 725 | 43.424 | −6.577 | 22.130 | 1.00 | 44.37 |
| ATOM 5719 | C | CYS | 725 | 42.131 | −9.507 | 22.315 | 1.00 | 49.31 |
| ATOM 5720 | O | CYS | 725 | 40.916 | −9.371 | 22.417 | 1.00 | 49.90 |
| ATOM 5721 | N | THR | 726 | 42.866 | −10.088 | 23.249 | 1.00 | 48.52 |
| ATOM 5723 | CA | THR | 726 | 42.262 | −10.541 | 24.490 | 1.00 | 49.58 |
| ATOM 5724 | CB | THR | 726 | 43.251 | −11.444 | 25.291 | 1.00 | 49.84 |
| ATOM 5725 | OG1 | THR | 726 | 44.236 | −10.648 | 25.976 | 1.00 | 49.05 |
| ATOM 5727 | CG2 | THR | 726 | 43.982 | −12.363 | 24.352 | 1.00 | 47.96 |
| ATOM 5728 | C | THR | 726 | 41.788 | −9.369 | 25.356 | 1.00 | 49.93 |
| ATOM 5729 | O | THR | 726 | 42.305 | −8.256 | 25.244 | 1.00 | 51.55 |
| ATOM 5730 | N | ASN | 727 | 40.829 | −9.622 | 26.242 | 1.00 | 50.48 |
| ATOM 5732 | CA | ASN | 727 | 40.335 | −8.577 | 27.144 | 1.00 | 52.17 |
| ATOM 5733 | CB | ASN | 727 | 39.190 | −9.099 | 28.016 | 1.00 | 57.57 |
| ATOM 5734 | CG | ASN | 727 | 39.533 | −10.409 | 28.714 | 1.00 | 66.49 |
| ATOM 5735 | OD1 | ASN | 727 | 40.709 | −10.786 | 28.833 | 1.00 | 70.43 |
| ATOM 5736 | ND2 | ASN | 727 | 38.500 | −11.122 | 29.175 | 1.00 | 68.43 |
| ATOM 5739 | C | ASN | 727 | 41.491 | −8.091 | 28.023 | 1.00 | 50.29 |
| ATOM 5740 | O | ASN | 727 | 41.467 | −6.976 | 28.540 | 1.00 | 49.88 |
| ATOM 5741 | N | GLU | 728 | 42.518 | −8.927 | 28.163 | 1.00 | 50.60 |
| ATOM 5743 | CA | GLU | 728 | 43.700 | −8.597 | 28.956 | 1.00 | 49.33 |
| ATOM 5744 | CB | GLU | 728 | 44.529 | −9.859 | 29.220 | 1.00 | 50.44 |
| ATOM 5745 | CG | GLU | 728 | 45.802 | −9.600 | 30.008 | 1.00 | 55.30 |
| ATOM 5746 | CD | GLU | 728 | 46.577 | −10.862 | 30.354 | 1.00 | 57.40 |
| ATOM 5747 | OE1 | GLU | 728 | 46.716 | −11.754 | 29.489 | 1.00 | 56.75 |
| ATOM 5748 | OE2 | GLU | 728 | 47.062 | −10.950 | 31.502 | 1.00 | 59.85 |
| ATOM 5749 | C | GLU | 728 | 44.539 | −7.552 | 28.212 | 1.00 | 47.08 |
| ATOM 5750 | O | GLU | 728 | 44.888 | −6.512 | 28.776 | 1.00 | 48.02 |
| ATOM 5751 | N | LEU | 729 | 44.846 | −7.821 | 26.945 | 1.00 | 43.34 |
| ATOM 5753 | CA | LEU | 729 | 45.630 | −6.891 | 26.129 | 1.00 | 42.01 |
| ATOM 5754 | CB | LEU | 729 | 45.899 | −7.500 | 24.751 | 1.00 | 39.46 |
| ATOM 5755 | CG | LEU | 729 | 46.911 | −8.639 | 24.772 | 1.00 | 40.31 |
| ATOM 5756 | CD1 | LEU | 729 | 46.782 | −9.482 | 23.531 | 1.00 | 42.21 |
| ATOM 5757 | CD2 | LEU | 729 | 48.314 | −8.068 | 24.900 | 1.00 | 42.49 |
| ATOM 5758 | C | LEU | 729 | 44.901 | −5.557 | 25.980 | 1.00 | 40.61 |
| ATOM 5759 | O | LEU | 729 | 45.510 | −4.481 | 25.953 | 1.00 | 38.33 |
| ATOM 5760 | N | TYR | 730 | 43.580 | −5.637 | 25.909 | 1.00 | 39.07 |
| ATOM 5762 | CA | TYR | 730 | 42.761 | −4.455 | 25.773 | 1.00 | 38.61 |
| ATOM 5763 | CB | TYR | 730 | 41.341 | −4.837 | 25.369 | 1.00 | 36.79 |
| ATOM 5764 | CG | TYR | 730 | 40.454 | −3.646 | 25.125 | 1.00 | 37.08 |
| ATOM 5765 | CD1 | TYR | 730 | 40.760 | −2.721 | 24.127 | 1.00 | 32.86 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5766 | CE1 | TYR | 730 | 39.961 | −1.616 | 23.912 | 1.00 | 29.79 |
| ATOM 5767 | CD2 | TYR | 730 | 39.328 | −3.420 | 25.916 | 1.00 | 36.99 |
| ATOM 5768 | CE2 | TYR | 730 | 38.522 | −2.312 | 25.704 | 1.00 | 36.69 |
| ATOM 5769 | CZ | TYR | 730 | 38.853 | −1.412 | 24.706 | 1.00 | 32.69 |
| ATOM 5770 | OH | TYR | 730 | 38.044 | −0.320 | 24.492 | 1.00 | 38.80 |
| ATOM 5772 | C | TYR | 730 | 42.767 | −3.662 | 27.080 | 1.00 | 39.75 |
| ATOM 5773 | O | TYR | 730 | 42.781 | −2.430 | 27.065 | 1.00 | 40.53 |
| ATOM 5774 | N | MET | 731 | 42.738 | −4.360 | 28.210 | 1.00 | 41.88 |
| ATOM 5776 | CA | MET | 731 | 42.778 | −3.684 | 29.509 | 1.00 | 45.34 |
| ATOM 5777 | CB | MET | 731 | 42.658 | −4.697 | 30.646 | 1.00 | 53.46 |
| ATOM 5778 | CG | MET | 731 | 41.253 | −5.248 | 30.836 | 1.00 | 64.30 |
| ATOM 5779 | SD | MET | 731 | 40.134 | −4.095 | 31.653 | 1.00 | 75.78 |
| ATOM 5780 | CE | MET | 731 | 40.657 | −4.338 | 33.370 | 1.00 | 69.70 |
| ATOM 5781 | C | MET | 731 | 44.099 | −2.927 | 29.614 | 1.00 | 41.53 |
| ATOM 5782 | O | MET | 731 | 44.157 | −1.814 | 30.138 | 1.00 | 37.91 |
| ATOM 5783 | N | MET | 732 | 45.156 | −3.545 | 29.098 | 1.00 | 40.48 |
| ATOM 5785 | CA | MET | 732 | 46.478 | −2.937 | 29.091 | 1.00 | 40.23 |
| ATOM 5786 | CB | MET | 732 | 47.508 | −3.872 | 28.436 | 1.00 | 40.29 |
| ATOM 5787 | CG | MET | 732 | 48.929 | −3.307 | 28.390 | 1.00 | 38.07 |
| ATOM 5788 | SD | MET | 732 | 50.171 | −4.522 | 27.908 | 1.00 | 37.65 |
| ATOM 5789 | CE | MET | 732 | 50.407 | −5.343 | 29.431 | 1.00 | 37.90 |
| ATOM 5790 | C | MET | 732 | 46.378 | −1.623 | 28.317 | 1.00 | 38.96 |
| ATOM 5791 | O | MET | 732 | 46.843 | −0.591 | 28.790 | 1.00 | 41.36 |
| ATOM 5792 | N | MET | 733 | 45.744 | −1.663 | 27.148 | 1.00 | 36.94 |
| ATOM 5794 | CA | MET | 733 | 45.574 | −0.463 | 26.340 | 1.00 | 35.19 |
| ATOM 5795 | CB | MET | 733 | 44.796 | −0.769 | 25.070 | 1.00 | 36.07 |
| ATOM 5796 | CG | MET | 733 | 45.549 | −1.577 | 24.048 | 1.00 | 35.99 |
| ATOM 5797 | SD | MET | 733 | 44.471 | −1.851 | 22.641 | 1.00 | 40.05 |
| ATOM 5798 | CE | MET | 733 | 45.244 | −3.351 | 21.909 | 1.00 | 33.13 |
| ATOM 5799 | C | MET | 733 | 44.800 | 0.560 | 27.141 | 1.00 | 37.29 |
| ATOM 5800 | O | MET | 733 | 45.207 | 1.719 | 27.245 | 1.00 | 39.14 |
| ATOM 5801 | N | ARG | 734 | 43.690 | 0.125 | 27.735 | 1.00 | 38.76 |
| ATOM 5803 | CA | ARG | 734 | 42.849 | 1.014 | 28.532 | 1.00 | 39.49 |
| ATOM 5804 | CB | ARG | 734 | 41.577 | 0.297 | 28.993 | 1.00 | 40.33 |
| ATOM 5805 | CG | ARG | 734 | 40.699 | −0.225 | 27.856 | 1.00 | 38.02 |
| ATOM 5806 | CD | ARG | 734 | 40.256 | 0.877 | 26.909 | 1.00 | 42.72 |
| ATOM 5807 | NE | ARG | 734 | 39.443 | 1.898 | 27.567 | 1.00 | 48.85 |
| ATOM 5809 | CZ | ARG | 734 | 38.120 | 1.838 | 27.700 | 1.00 | 52.35 |
| ATOM 5810 | NH1 | ARG | 734 | 37.435 | 0.811 | 27.222 | 1.00 | 54.79 |
| ATOM 5813 | NH2 | ARG | 734 | 37.477 | 2.804 | 28.338 | 1.00 | 54.69 |
| ATOM 5816 | C | ARG | 734 | 43.627 | 1.587 | 29.715 | 1.00 | 38.70 |
| ATOM 5817 | O | ARG | 734 | 43.445 | 2.757 | 30.068 | 1.00 | 40.92 |
| ATOM 5818 | N | ASP | 735 | 44.530 | 0.782 | 30.276 | 1.00 | 38.76 |
| ATOM 5820 | CA | ASP | 735 | 45.379 | 1.208 | 31.399 | 1.00 | 38.60 |
| ATOM 5821 | CB | ASP | 735 | 46.325 | 0.087 | 31.825 | 1.00 | 41.34 |
| ATOM 5822 | CG | ASP | 735 | 45.622 | −1.022 | 32.574 | 1.00 | 44.66 |
| ATOM 5823 | OD1 | ASP | 735 | 46.048 | −2.194 | 32.428 | 1.00 | 43.15 |
| ATOM 5824 | OD2 | ASP | 735 | 44.657 | −0.713 | 33.313 | 1.00 | 44.46 |
| ATOM 5825 | C | ASP | 735 | 46.215 | 2.385 | 30.938 | 1.00 | 37.76 |
| ATOM 5826 | O | ASP | 735 | 46.235 | 3.446 | 31.585 | 1.00 | 36.35 |
| ATOM 5827 | N | CYS | 736 | 46.890 | 2.182 | 29.805 | 1.00 | 35.39 |
| ATOM 5829 | CA | CYS | 736 | 47.730 | 3.196 | 29.181 | 1.00 | 34.77 |
| ATOM 5830 | CB | CYS | 736 | 48.379 | 2.652 | 27.916 | 1.00 | 30.62 |
| ATOM 5831 | SG | CYS | 736 | 49.453 | 1.261 | 28.198 | 1.00 | 30.96 |
| ATOM 5832 | C | CYS | 736 | 46.938 | 4.429 | 28.814 | 1.00 | 35.98 |
| ATOM 5833 | O | CYS | 736 | 47.516 | 5.491 | 28.606 | 1.00 | 37.38 |
| ATOM 5834 | N | TRP | 737 | 45.620 | 4.290 | 28.713 | 1.00 | 38.50 |
| ATOM 5836 | CA | TRP | 737 | 44.772 | 5.423 | 28.370 | 1.00 | 40.16 |
| ATOM 5837 | CB | TRP | 737 | 43.791 | 5.028 | 27.271 | 1.00 | 38.41 |
| ATOM 5838 | CG | TRP | 737 | 44.453 | 4.586 | 26.011 | 1.00 | 39.33 |
| ATOM 5839 | CD2 | TRP | 737 | 43.893 | 3.718 | 25.020 | 1.00 | 39.64 |
| ATOM 5840 | CE2 | TRP | 737 | 44.852 | 3.583 | 23.992 | 1.00 | 39.97 |
| ATOM 5841 | CE3 | TRP | 737 | 42.672 | 3.040 | 24.900 | 1.00 | 37.06 |
| ATOM 5842 | CD1 | TRP | 737 | 45.695 | 4.932 | 25.556 | 1.00 | 39.56 |
| ATOM 5843 | NE1 | TRP | 737 | 45.941 | 4.336 | 24.343 | 1.00 | 38.61 |
| ATOM 5845 | CZ2 | TRP | 737 | 44.627 | 2.795 | 22.859 | 1.00 | 38.78 |
| ATOM 5846 | CZ3 | TRP | 737 | 42.452 | 2.261 | 23.778 | 1.00 | 38.90 |
| ATOM 5847 | CH2 | TRP | 737 | 43.426 | 2.145 | 22.772 | 1.00 | 38.18 |
| ATOM 5848 | C | TRP | 737 | 44.028 | 6.029 | 29.563 | 1.00 | 41.30 |
| ATOM 5849 | O | TRP | 737 | 42.979 | 6.658 | 29.398 | 1.00 | 41.45 |
| ATOM 5850 | N | HIS | 738 | 44.575 | 5.873 | 30.763 | 1.00 | 43.01 |
| ATOM 5852 | CA | HIS | 738 | 43.932 | 6.423 | 31.948 | 1.00 | 44.64 |
| ATOM 5853 | CB | HIS | 738 | 44.454 | 5.735 | 33.205 | 1.00 | 46.20 |

TABLE 4-continued

Atomic Structure Coordinates of Unphosphorylated FLGK:AMP-PCP Co-Complex

| Atom No. | Atom Type | A.A. Type | A.A. No. | X | Y | Z | OCC | B |
|---|---|---|---|---|---|---|---|---|
| ATOM 5854 | CG | HIS | 738 | 43.742 | 6.154 | 34.458 | 1.00 | 50.35 |
| ATOM 5855 | CD2 | HIS | 738 | 43.473 | 7.379 | 34.963 | 1.00 | 49.09 |
| ATOM 5856 | ND1 | HIS | 738 | 43.220 | 5.244 | 35.355 | 1.00 | 49.94 |
| ATOM 5858 | CE1 | HIS | 738 | 42.659 | 5.899 | 36.357 | 1.00 | 52.92 |
| ATOM 5859 | NE2 | HIS | 738 | 42.798 | 7.194 | 36.146 | 1.00 | 46.91 |
| ATOM 5861 | C | HIS | 738 | 44.174 | 7.921 | 32.037 | 1.00 | 45.26 |
| ATOM 5862 | O | HIS | 738 | 45.314 | 8.356 | 32.021 | 1.00 | 45.31 |
| ATOM 5863 | N | ALA | 739 | 43.099 | 8.686 | 32.224 | 1.00 | 46.61 |
| ATOM 5865 | CA | ALA | 739 | 43.155 | 10.150 | 32.322 | 1.00 | 48.49 |
| ATOM 5866 | CB | ALA | 739 | 41.823 | 10.681 | 32.790 | 1.00 | 49.69 |
| ATOM 5867 | C | ALA | 739 | 44.272 | 10.682 | 33.224 | 1.00 | 50.77 |
| ATOM 5868 | O | ALA | 739 | 45.004 | 11.601 | 32.846 | 1.00 | 51.77 |
| ATOM 5869 | N | VAL | 740 | 44.336 | 10.138 | 34.439 | 1.00 | 51.47 |
| ATOM 5871 | CA | VAL | 740 | 45.352 | 10.485 | 35.439 | 1.00 | 51.09 |
| ATOM 5872 | CB | VAL | 740 | 44.897 | 10.075 | 36.850 | 1.00 | 52.40 |
| ATOM 5873 | CG1 | VAL | 740 | 45.847 | 10.624 | 37.878 | 1.00 | 53.38 |
| ATOM 5874 | CG2 | VAL | 740 | 43.485 | 10.544 | 37.105 | 1.00 | 55.18 |
| ATOM 5875 | C | VAL | 740 | 46.649 | 9.727 | 35.130 | 1.00 | 48.99 |
| ATOM 5876 | O | VAL | 740 | 46.773 | 8.534 | 35.440 | 1.00 | 47.72 |
| ATOM 5877 | N | PRO | 741 | 47.646 | 10.421 | 34.565 | 1.00 | 48.31 |
| ATOM 5878 | CD | PRO | 741 | 47.603 | 11.861 | 34.253 | 1.00 | 47.84 |
| ATOM 5879 | CA | PRO | 741 | 48.949 | 9.852 | 34.197 | 1.00 | 48.51 |
| ATOM 5880 | CB | PRO | 741 | 49.762 | 11.087 | 33.828 | 1.00 | 46.83 |
| ATOM 5881 | CG | PRO | 741 | 48.714 | 12.000 | 33.255 | 1.00 | 46.21 |
| ATOM 5882 | C | PRO | 741 | 49.641 | 9.016 | 35.275 | 1.00 | 49.12 |
| ATOM 5883 | O | PRO | 741 | 50.449 | 8.139 | 34.955 | 1.00 | 46.57 |
| ATOM 5884 | N | SER | 742 | 49.327 | 9.290 | 36.541 | 1.00 | 49.47 |
| ATOM 5886 | CA | SER | 742 | 49.928 | 8.557 | 37.651 | 1.00 | 49.50 |
| ATOM 5887 | CB | SER | 742 | 49.760 | 9.326 | 38.963 | 1.00 | 51.06 |
| ATOM 5888 | OG | SER | 742 | 48.403 | 9.638 | 39.209 | 1.00 | 53.81 |
| ATOM 5890 | C | SER | 742 | 49.339 | 7.159 | 37.787 | 1.00 | 48.81 |
| ATOM 5891 | O | SER | 742 | 49.926 | 6.284 | 38.427 | 1.00 | 49.45 |
| ATOM 5892 | N | GLN | 743 | 48.164 | 6.959 | 37.203 | 1.00 | 47.82 |
| ATOM 5894 | CA | GLN | 743 | 47.529 | 5.658 | 37.273 | 1.00 | 46.34 |
| ATOM 5895 | CB | GLN | 743 | 46.022 | 5.791 | 37.432 | 1.00 | 49.74 |
| ATOM 5896 | CG | GLN | 743 | 45.519 | 5.305 | 38.784 | 1.00 | 55.41 |
| ATOM 5897 | CD | GLN | 743 | 46.178 | 6.030 | 39.947 | 1.00 | 59.15 |
| ATOM 5898 | OE1 | GLN | 743 | 46.905 | 5.425 | 40.748 | 1.00 | 59.02 |
| ATOM 5899 | NE2 | GLN | 743 | 45.922 | 7.338 | 40.052 | 1.00 | 60.03 |
| ATOM 5902 | C | GLN | 743 | 47.874 | 4.768 | 36.095 | 1.00 | 44.34 |
| ATOM 5903 | O | GLN | 743 | 47.548 | 3.578 | 36.114 | 1.00 | 44.64 |
| ATOM 5904 | N | ARG | 744 | 48.497 | 5.339 | 35.059 | 1.00 | 42.83 |
| ATOM 5906 | CA | ARG | 744 | 48.914 | 4.559 | 33.880 | 1.00 | 40.34 |
| ATOM 5907 | CB | ARG | 744 | 49.349 | 5.469 | 32.724 | 1.00 | 35.84 |
| ATOM 5908 | CG | ARG | 744 | 48.296 | 6.406 | 32.190 | 1.00 | 28.25 |
| ATOM 5909 | CD | ARG | 744 | 48.906 | 7.383 | 31.216 | 1.00 | 22.56 |
| ATOM 5910 | NE | ARG | 744 | 47.948 | 8.437 | 30.922 | 1.00 | 28.09 |
| ATOM 5912 | CZ | ARG | 744 | 48.258 | 9.658 | 30.493 | 1.00 | 32.83 |
| ATOM 5913 | NH1 | ARG | 744 | 49.524 | 10.001 | 30.278 | 1.00 | 34.44 |
| ATOM 5916 | NH2 | ARG | 744 | 47.307 | 10.569 | 30.360 | 1.00 | 32.00 |
| ATOM 5919 | C | ARG | 744 | 50.110 | 3.712 | 34.295 | 1.00 | 41.58 |
| ATOM 5920 | O | ARG | 744 | 50.906 | 4.124 | 35.145 | 1.00 | 45.48 |
| ATOM 5921 | N | PRO | 745 | 50.223 | 2.489 | 33.754 | 1.00 | 40.97 |
| ATOM 5922 | CD | PRO | 745 | 49.345 | 1.749 | 32.831 | 1.00 | 39.90 |
| ATOM 5923 | CA | PRO | 745 | 51.381 | 1.685 | 34.157 | 1.00 | 39.77 |
| ATOM 5924 | CB | PRO | 745 | 51.063 | 0.311 | 33.558 | 1.00 | 39.31 |
| ATOM 5925 | CG | PRO | 745 | 50.255 | 0.642 | 32.344 | 1.00 | 40.98 |
| ATOM 5926 | C | PRO | 745 | 52.664 | 2.269 | 33.573 | 1.00 | 38.44 |
| ATOM 5927 | O | PRO | 745 | 52.631 | 3.009 | 32.595 | 1.00 | 39.64 |
| ATOM 5928 | N | THR | 746 | 53.783 | 2.001 | 34.224 | 1.00 | 37.50 |
| ATOM 5930 | CA | THR | 746 | 55.066 | 2.462 | 33.728 | 1.00 | 37.56 |
| ATOM 5931 | CB | THR | 746 | 56.108 | 2.571 | 34.869 | 1.00 | 38.58 |
| ATOM 5932 | OG1 | THR | 746 | 56.286 | 1.285 | 35.487 | 1.00 | 43.28 |
| ATOM 5934 | CG2 | THR | 746 | 55.666 | 3.567 | 35.899 | 1.00 | 34.64 |
| ATOM 5935 | C | THR | 746 | 55.546 | 1.393 | 32.739 | 1.00 | 36.49 |
| ATOM 5936 | O | THR | 746 | 55.118 | 0.234 | 32.817 | 1.00 | 34.18 |
| ATOM 5937 | N | PHE | 747 | 56.453 | 1.768 | 31.839 | 1.00 | 35.27 |
| ATOM 5939 | CA | PHE | 747 | 56.995 | 0.814 | 30.880 | 1.00 | 33.48 |
| ATOM 5940 | CB | PHE | 747 | 58.025 | 1.475 | 29.970 | 1.00 | 34.35 |
| ATOM 5941 | CG | PHE | 747 | 57.419 | 2.369 | 28.920 | 1.00 | 32.49 |
| ATOM 5942 | CD1 | PHE | 747 | 56.715 | 1.825 | 27.856 | 1.00 | 30.69 |
| ATOM 5943 | CD2 | PHE | 747 | 57.519 | 3.749 | 29.018 | 1.00 | 32.81 |
| ATOM 5944 | CE1 | PHE | 747 | 56.122 | 2.639 | 26.907 | 1.00 | 29.41 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 5945 | CE2 | PHE | 747 | 56.926 | 4.573 | 28.072 | 1.00 | 32.93 |
| ATOM 5946 | CZ | PHE | 747 | 56.223 | 4.014 | 27.015 | 1.00 | 31.50 |
| ATOM 5947 | C | PHE | 747 | 57.621 | −0.363 | 31.606 | 1.00 | 34.65 |
| ATOM 5948 | O | PHE | 747 | 57.616 | −1.474 | 31.099 | 1.00 | 36.34 |
| ATOM 5949 | N | LYS | 748 | 58.142 | −0.128 | 32.808 | 1.00 | 37.75 |
| ATOM 5951 | CA | LYS | 748 | 58.748 | −1.205 | 33.583 | 1.00 | 39.67 |
| ATOM 5952 | CB | LYS | 748 | 59.382 | −0.664 | 34.873 | 1.00 | 43.06 |
| ATOM 5953 | CG | LYS | 748 | 59.958 | −1.757 | 35.774 | 1.00 | 48.96 |
| ATOM 5954 | CD | LYS | 748 | 60.750 | −1.207 | 36.966 | 1.00 | 52.20 |
| ATOM 5955 | CE | LYS | 748 | 61.183 | −2.344 | 37.907 | 1.00 | 53.62 |
| ATOM 5956 | NZ | LYS | 748 | 62.057 | −1.893 | 39.031 | 1.00 | 54.82 |
| ATOM 5960 | C | LYS | 748 | 57.680 | −2.263 | 33.882 | 1.00 | 39.65 |
| ATOM 5961 | O | LYS | 748 | 57.902 | −3.454 | 33.652 | 1.00 | 38.91 |
| ATOM 5962 | N | GLN | 749 | 56.503 | −1.818 | 34.331 | 1.00 | 39.39 |
| ATOM 5964 | CA | GLN | 749 | 55.402 | −2.742 | 34.623 | 1.00 | 40.70 |
| ATOM 5965 | CB | GLN | 749 | 54.177 | −1.991 | 35.140 | 1.00 | 43.82 |
| ATOM 5966 | CG | GLN | 749 | 54.395 | −1.149 | 36.373 | 1.00 | 50.97 |
| ATOM 5967 | CD | GLN | 749 | 53.175 | −0.304 | 36.715 | 1.00 | 55.53 |
| ATOM 5968 | OE1 | GLN | 749 | 53.272 | 0.914 | 36.895 | 1.00 | 55.80 |
| ATOM 5969 | NE2 | GLN | 749 | 52.012 | −0.940 | 36.773 | 1.00 | 60.05 |
| ATOM 5972 | C | GLN | 749 | 55.009 | −3.455 | 33.334 | 1.00 | 40.03 |
| ATOM 5973 | O | GLN | 749 | 54.903 | −4.679 | 33.298 | 1.00 | 40.26 |
| ATOM 5974 | N | LEU | 750 | 54.802 | −2.666 | 32.278 | 1.00 | 39.18 |
| ATOM 5976 | CA | LEU | 750 | 54.400 | −3.171 | 30.964 | 1.00 | 36.65 |
| ATOM 5977 | CB | LEU | 750 | 54.369 | −2.039 | 29.927 | 1.00 | 34.58 |
| ATOM 5978 | CG | LEU | 750 | 53.355 | −0.910 | 30.116 | 1.00 | 32.52 |
| ATOM 5979 | CD1 | LEU | 750 | 53.644 | 0.210 | 29.125 | 1.00 | 31.67 |
| ATOM 5980 | CD2 | LEU | 750 | 51.947 | −1.435 | 29.935 | 1.00 | 31.37 |
| ATOM 5981 | C | LEU | 750 | 55.321 | −4.255 | 30.477 | 1.00 | 35.81 |
| ATOM 5982 | O | LEU | 750 | 54.856 | −5.267 | 29.963 | 1.00 | 35.81 |
| ATOM 5983 | N | VAL | 751 | 56.626 | −4.035 | 30.620 | 1.00 | 37.38 |
| ATOM 5985 | CA | VAL | 751 | 57.607 | −5.029 | 30.193 | 1.00 | 38.66 |
| ATOM 5986 | CB | VAL | 751 | 59.077 | −4.545 | 30.411 | 1.00 | 35.42 |
| ATOM 5987 | CG1 | VAL | 751 | 60.075 | −5.646 | 30.041 | 1.00 | 29.83 |
| ATOM 5988 | CG2 | VAL | 751 | 59.342 | −3.324 | 29.559 | 1.00 | 29.95 |
| ATOM 5989 | C | VAL | 751 | 57.337 | −6.314 | 30.974 | 1.00 | 41.63 |
| ATOM 5990 | O | VAL | 751 | 57.312 | −7.401 | 30.396 | 1.00 | 42.43 |
| ATOM 5991 | N | GLU | 752 | 57.051 | −6.174 | 32.267 | 1.00 | 43.35 |
| ATOM 5993 | CA | GLU | 752 | 56.766 | −7.329 | 33.111 | 1.00 | 47.39 |
| ATOM 5994 | CB | GLU | 752 | 56.674 | −6.914 | 34.587 | 1.00 | 50.66 |
| ATOM 5995 | CG | GLU | 752 | 57.950 | −6.243 | 35.101 | 1.00 | 54.77 |
| ATOM 5996 | CD | GLU | 752 | 58.006 | −6.101 | 36.612 | 1.00 | 55.14 |
| ATOM 5997 | OE1 | GLU | 752 | 58.246 | −4.972 | 37.102 | 1.00 | 54.14 |
| ATOM 5998 | OE2 | GLU | 752 | 57.844 | −7.131 | 37.308 | 1.00 | 57.73 |
| ATOM 5999 | C | GLU | 752 | 55.496 | −8.068 | 32.655 | 1.00 | 46.00 |
| ATOM 6000 | O | GLU | 752 | 55.548 | −9.261 | 32.328 | 1.00 | 46.25 |
| ATOM 6001 | N | ASP | 753 | 54.380 | −7.346 | 32.601 | 1.00 | 44.35 |
| ATOM 6003 | CA | ASP | 753 | 53.099 | −7.912 | 32.180 | 1.00 | 44.19 |
| ATOM 6004 | CB | ASP | 753 | 52.059 | −6.814 | 31.985 | 1.00 | 46.22 |
| ATOM 6005 | CG | ASP | 753 | 51.512 | −6.279 | 33.278 | 1.00 | 50.48 |
| ATOM 6006 | OD1 | ASP | 753 | 51.396 | −7.062 | 34.248 | 1.00 | 52.15 |
| ATOM 6007 | OD2 | ASP | 753 | 51.170 | −5.069 | 33.306 | 1.00 | 52.20 |
| ATOM 6008 | C | ASP | 753 | 53.244 | −8.608 | 30.849 | 1.00 | 44.54 |
| ATOM 6009 | O | ASP | 753 | 52.770 | −9.724 | 30.674 | 1.00 | 46.03 |
| ATOM 6010 | N | LEU | 754 | 53.880 | −7.918 | 29.906 | 1.00 | 44.43 |
| ATOM 6012 | CA | LEU | 754 | 54.079 | −8.438 | 28.563 | 1.00 | 43.70 |
| ATOM 6013 | CB | LEU | 754 | 54.576 | −7.339 | 27.618 | 1.00 | 43.48 |
| ATOM 6014 | CG | LEU | 754 | 53.481 | −6.350 | 27.201 | 1.00 | 44.67 |
| ATOM 6015 | CD1 | LEU | 754 | 54.095 | −5.218 | 26.399 | 1.00 | 44.51 |
| ATOM 6016 | CD2 | LEU | 754 | 52.384 | −7.069 | 26.408 | 1.00 | 42.07 |
| ATOM 6017 | C | LEU | 754 | 54.993 | −9.642 | 28.512 | 1.00 | 43.14 |
| ATOM 6018 | O | LEU | 754 | 54.795 | −10.536 | 27.697 | 1.00 | 41.32 |
| ATOM 6019 | N | ASP | 755 | 55.990 | −9.671 | 29.383 | 1.00 | 44.74 |
| ATOM 6021 | CA | ASP | 755 | 56.897 | −10.800 | 29.426 | 1.00 | 47.24 |
| ATOM 6022 | CB | ASP | 755 | 57.942 | −10.575 | 30.517 | 1.00 | 51.26 |
| ATOM 6023 | CG | ASP | 755 | 59.121 | −11.518 | 30.407 | 1.00 | 55.39 |
| ATOM 6024 | OD1 | ASP | 755 | 59.739 | −11.793 | 31.455 | 1.00 | 60.61 |
| ATOM 6025 | OD2 | ASP | 755 | 59.443 | −11.970 | 29.283 | 1.00 | 57.16 |
| ATOM 6026 | C | ASP | 755 | 56.023 | −12.005 | 29.771 | 1.00 | 47.67 |
| ATOM 6027 | O | ASP | 755 | 56.041 | −13.032 | 29.081 | 1.00 | 45.99 |
| ATOM 6028 | N | ARG | 756 | 55.186 | −11.816 | 30.789 | 1.00 | 46.72 |
| ATOM 6030 | CA | ARG | 756 | 54.272 | −12.851 | 31.256 | 1.00 | 46.25 |
| ATOM 6031 | CB | ARG | 756 | 53.519 | −12.368 | 32.499 | 1.00 | 46.31 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B | |
|---|---|---|---|---|---|---|---|---|---|
| ATOM 6032 | CG | ARG | 756 | 52.391 | −13.287 | 32.953 | 1.00 | 46.99 | |
| ATOM 6033 | CD | ARG | 756 | 51.733 | −12.776 | 34.227 | 1.00 | 48.10 | |
| ATOM 6034 | NE | ARG | 756 | 51.320 | −11.379 | 34.118 | 1.00 | 53.67 | |
| ATOM 6036 | CZ | ARG | 756 | 50.294 | −10.951 | 33.385 | 1.00 | 55.35 | |
| ATOM 6037 | NH1 | ARG | 756 | 49.562 | −11.812 | 32.684 | 1.00 | 54.10 | |
| ATOM 6040 | NH2 | ARG | 756 | 50.008 | −9.654 | 33.344 | 1.00 | 56.02 | |
| ATOM 6043 | C | ARG | 756 | 53.282 | −13.261 | 30.175 | 1.00 | 45.05 | |
| ATOM 6044 | O | ARG | 756 | 53.213 | −14.429 | 29.806 | 1.00 | 47.19 | |
| ATOM 6045 | N | ILE | 757 | 52.550 | −12.289 | 29.647 | 1.00 | 43.47 | |
| ATOM 6047 | CA | ILE | 757 | 51.552 | −12.553 | 28.617 | 1.00 | 43.80 | |
| ATOM 6048 | CB | ILE | 757 | 50.842 | −11.241 | 28.161 | 1.00 | 42.02 | |
| ATOM 6049 | CG2 | ILE | 757 | 49.811 | −11.536 | 27.086 | 1.00 | 39.63 | |
| ATOM 6050 | CG1 | ILE | 757 | 50.154 | −10.578 | 29.361 | 1.00 | 40.00 | |
| ATOM 6051 | CD1 | ILE | 757 | 49.600 | −9.212 | 29.086 | 1.00 | 42.68 | |
| ATOM 6052 | C | ILE | 757 | 52.148 | −13.296 | 27.428 | 1.00 | 46.03 | |
| ATOM 6053 | O | ILE | 757 | 51.549 | −14.250 | 26.947 | 1.00 | 47.78 | |
| ATOM 6054 | N | VAL | 758 | 53.359 | −12.925 | 27.015 | 1.00 | 49.03 | |
| ATOM 6056 | CA | VAL | 758 | 54.015 | −13.584 | 25.884 | 1.00 | 51.51 | |
| ATOM 6057 | CB | VAL | 758 | 55.412 | −12.971 | 25.556 | 1.00 | 50.75 | |
| ATOM 6058 | CG1 | VAL | 758 | 56.105 | −13.780 | 24.470 | 1.00 | 50.31 | |
| ATOM 6059 | CG2 | VAL | 758 | 55.269 | −11.541 | 25.081 | 1.00 | 52.52 | |
| ATOM 6060 | C | VAL | 758 | 54.209 | −15.050 | 26.212 | 1.00 | 54.30 | |
| ATOM 6061 | O | VAL | 758 | 53.991 | −15.915 | 25.369 | 1.00 | 54.80 | |
| ATOM 6062 | N | ALA | 759 | 54.617 | −15.311 | 27.450 | 1.00 | 57.65 | |
| ATOM 6064 | CA | ALA | 759 | 54.858 | −16.667 | 27.919 | 1.00 | 60.62 | |
| ATOM 6065 | CB | ALA | 759 | 55.423 | −16.637 | 29.327 | 1.00 | 60.32 | |
| ATOM 6066 | C | ALA | 759 | 53.571 | −17.478 | 27.889 | 1.00 | 63.25 | |
| ATOM 6067 | O | ALA | 759 | 53.568 | −18.638 | 27.478 | 1.00 | 65.81 | |
| ATOM 6068 | N | LEU | 760 | 52.475 | −16.856 | 28.305 | 1.00 | 63.56 | |
| ATOM 6070 | CA | LEU | 760 | 51.191 | −17.533 | 28.333 | 1.00 | 64.25 | |
| ATOM 6071 | CB | LEU | 760 | 50.302 | −16.912 | 29.407 | 1.00 | 65.66 | |
| ATOM 6072 | CG | LEU | 760 | 50.894 | −16.962 | 30.820 | 1.00 | 65.62 | |
| ATOM 6073 | CD1 | LEU | 760 | 49.988 | −16.246 | 31.809 | 1.00 | 64.75 | |
| ATOM 6074 | CD2 | LEU | 760 | 51.109 | −18.410 | 31.227 | 1.00 | 66.65 | |
| ATOM 6075 | C | LEU | 760 | 50.483 | −17.535 | 26.984 | 1.00 | 64.89 | |
| ATOM 6076 | O | LEU | 760 | 49.390 | −18.088 | 26.860 | 1.00 | 66.37 | |
| ATOM 6077 | N | THR | 761 | 51.103 | −16.933 | 25.973 | 1.00 | 65.24 | |
| ATOM 6079 | CA | THR | 761 | 50.516 | −16.882 | 24.634 | 1.00 | 64.44 | |
| ATOM 6080 | CB | THR | 761 | 50.829 | −15.539 | 23.925 | 1.00 | 62.95 | |
| ATOM 6081 | OG1 | THR | 761 | 50.247 | −14.463 | 24.669 | 1.00 | 62.70 | |
| ATOM 6083 | CG2 | THR | 761 | 50.249 | −15.525 | 22.521 | 1.00 | 60.59 | |
| ATOM 6084 | C | THR | 761 | 51.003 | −18.044 | 23.769 | 1.00 | 64.71 | |
| ATOM 6085 | O | THR | 761 | 52.202 | −18.201 | 23.533 | 1.00 | 64.70 | |
| ATOM 6086 | SG | CYS | 1603 | 18.536 | −8.818 | 20.295 | 0.50 | 33.97 | PRT2 |
| ATOM 6087 | CG | MET | 534 | 69.178 | 12.159 | 22.968 | 0.50 | 31.30 | PRT2 |
| ATOM 6088 | SD | MET | 534 | 68.892 | 13.138 | 24.442 | 0.50 | 33.06 | PRT2 |
| ATOM 6089 | CE | MET | 534 | 70.060 | 12.456 | 25.568 | 0.50 | 34.22 | PRT2 |
| ATOM 6090 | SG | CYS | 603 | 56.041 | −7.885 | 16.319 | 0.50 | 37.82 | PRT2 |
| ATOM 2682 | OH2 | TIP3 | 1 | 71.788 | 25.340 | 2.479 | 1.00 | 24.18 | |
| ATOM 2685 | OH2 | TIP3 | 2 | 40.022 | 4.089 | 16.127 | 1.00 | 43.09 | |
| ATOM 2688 | OH2 | TIP3 | 3 | 83.745 | 19.577 | 10.510 | 1.00 | 27.38 | |
| ATOM 2691 | OH2 | TIP3 | 4 | 83.420 | 20.163 | 7.482 | 1.00 | 30.85 | |
| ATOM 2694 | OH2 | TIP3 | 5 | 75.022 | 16.439 | 6.505 | 1.00 | 33.15 | |
| ATOM 2697 | OH2 | TIP3 | 6 | 86.308 | 19.567 | 9.284 | 1.00 | 33.55 | |
| ATOM 2700 | OH2 | TIP3 | 7 | 51.888 | 11.346 | 24.141 | 1.00 | 34.30 | |
| ATOM 2703 | OH2 | TIP3 | 8 | 55.125 | 9.616 | 22.499 | 1.00 | 21.44 | |
| ATOM 2706 | OH2 | TIP3 | 9 | 57.087 | 4.825 | 32.412 | 1.00 | 28.79 | |
| ATOM 2709 | OH2 | TIP3 | 10 | 52.142 | 4.824 | 13.180 | 1.00 | 21.14 | |
| ATOM 2712 | OH2 | TIP3 | 11 | 41.312 | 5.600 | 22.910 | 1.00 | 49.23 | |
| ATOM 2715 | OH2 | TIP3 | 12 | 45.083 | 9.130 | 21.671 | 1.00 | 37.09 | |
| ATOM 2718 | OH2 | TIP3 | 13 | 64.608 | −2.335 | 28.803 | 1.00 | 44.31 | |
| ATOM 2721 | OH2 | TIP3 | 14 | 77.192 | 13.199 | 23.753 | 1.00 | 32.96 | |
| ATOM 2724 | OH2 | TIP3 | 15 | 79.201 | 17.296 | 17.997 | 1.00 | 38.51 | |
| ATOM 2727 | OH2 | TIP3 | 16 | 82.988 | 11.608 | 15.745 | 1.00 | 27.56 | |
| ATOM 2730 | OH2 | TIP3 | 17 | 14.096 | −9.819 | 0.333 | 1.00 | 23.53 | |
| ATOM 2733 | OH2 | TIP3 | 18 | 38.325 | 0.249 | 5.313 | 1.00 | 43.17 | |
| ATOM 2736 | OH2 | TIP3 | 19 | 26.939 | 6.001 | 5.100 | 1.00 | 30.00 | |
| ATOM 2739 | OH2 | TIP3 | 20 | 34.305 | −1.615 | 16.992 | 1.00 | 44.82 | |
| ATOM 2742 | OH2 | TIP3 | 21 | 20.300 | 2.328 | 27.798 | 1.00 | 45.23 | |
| ATOM 2745 | OH2 | TIP3 | 22 | 50.996 | −11.607 | 38.052 | 1.00 | 43.49 | |
| ATOM 2748 | OH2 | TIP3 | 23 | 17.261 | −6.167 | −1.444 | 1.00 | 27.13 | |
| ATOM 2751 | OH2 | TIP3 | 24 | 27.724 | 8.124 | 14.996 | 1.00 | 31.20 | |
| ATOM 2754 | OH2 | TIP3 | 25 | 31.558 | 0.294 | 6.872 | 1.00 | 34.54 | |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 2757 | OH2 | TIP3 | 26 | 26.907 | −12.815 | 28.161 | 1.00 | 49.20 |
| ATOM 2760 | OH2 | TIP3 | 27 | 28.705 | −17.192 | 13.269 | 1.00 | 30.16 |
| ATOM 2763 | OH2 | TIP3 | 28 | 88.639 | 13.953 | 7.692 | 1.00 | 41.04 |
| ATOM 2766 | OH2 | TIP3 | 29 | −2.328 | −3.576 | 11.086 | 1.00 | 44.89 |
| ATOM 2769 | OH2 | TIP3 | 30 | 34.919 | −4.069 | 19.070 | 1.00 | 53.72 |
| ATOM 2772 | OH2 | TIP3 | 31 | 80.124 | 17.865 | 9.324 | 1.00 | 28.96 |
| ATOM 2775 | OH2 | TIP3 | 32 | 5.417 | 3.492 | 10.771 | 1.00 | 34.07 |
| ATOM 2778 | OH2 | TIP3 | 33 | −10.718 | 4.889 | 11.542 | 1.00 | 30.81 |
| ATOM 2781 | OH2 | TIP3 | 34 | 29.486 | −8.823 | 20.599 | 1.00 | 51.35 |
| ATOM 2784 | OH2 | TIP3 | 35 | 6.151 | 3.065 | 13.821 | 1.00 | 34.56 |
| ATOM 2787 | OH2 | TIP3 | 36 | 31.907 | 2.919 | 0.361 | 1.00 | 48.13 |
| ATOM 2790 | OH2 | TIP3 | 37 | 19.974 | 1.928 | −3.873 | 1.00 | 30.12 |
| ATOM 2793 | OH2 | TIP3 | 38 | 61.976 | 2.660 | 32.604 | 1.00 | 36.01 |
| ATOM 2796 | OH2 | TIP3 | 39 | 21.084 | −7.119 | −3.759 | 1.00 | 20.12 |
| ATOM 2799 | OH2 | TIP3 | 40 | −15.729 | 8.693 | 22.468 | 1.00 | 54.88 |
| ATOM 2802 | OH2 | TIP3 | 41 | 40.160 | 2.461 | 8.734 | 1.00 | 37.95 |
| ATOM 2805 | OH2 | TIP3 | 42 | 19.248 | 11.349 | 0.190 | 1.00 | 37.63 |
| ATOM 2808 | OH2 | TIP3 | 43 | 66.856 | 9.143 | 17.185 | 1.00 | 27.91 |
| ATOM 2811 | OH2 | TIP3 | 44 | 87.262 | 19.150 | 18.734 | 1.00 | 57.83 |
| ATOM 2814 | OH2 | TIP3 | 45 | 74.597 | 17.144 | 3.987 | 1.00 | 42.19 |
| ATOM 2817 | OH2 | TIP3 | 46 | 29.192 | 16.988 | 10.582 | 1.00 | 37.28 |
| ATOM 2820 | OH2 | TIP3 | 47 | 66.415 | 7.073 | 14.829 | 1.00 | 34.86 |
| ATOM 2823 | OH2 | TIP3 | 48 | 85.063 | 21.453 | 5.510 | 1.00 | 27.42 |
| ATOM 2826 | OH2 | TIP3 | 49 | −4.716 | 2.835 | 2.998 | 1.00 | 40.54 |
| ATOM 2829 | OH2 | TIP3 | 50 | 19.369 | 5.069 | 4.888 | 1.00 | 38.40 |
| ATOM 2832 | OH2 | TIP3 | 51 | 34.750 | 5.517 | 24.999 | 1.00 | 29.11 |
| ATOM 2835 | OH2 | TIP3 | 52 | 34.740 | −16.765 | 14.093 | 1.00 | 32.68 |
| ATOM 2838 | OH2 | TIP3 | 53 | 59.994 | 7.555 | 27.844 | 1.00 | 32.60 |
| ATOM 2841 | OH2 | TIP3 | 54 | −7.401 | −1.595 | 6.080 | 1.00 | 43.73 |
| ATOM 2844 | OH2 | TIP3 | 55 | 55.257 | 12.084 | 25.108 | 1.00 | 44.32 |
| ATOM 2847 | OH2 | TIP3 | 56 | 68.239 | 6.953 | 16.647 | 1.00 | 44.46 |
| ATOM 2850 | OH2 | TIP3 | 57 | 73.621 | 20.852 | 18.820 | 1.00 | 29.47 |
| ATOM 2853 | OH2 | TIP3 | 58 | 3.399 | −8.294 | −8.210 | 1.00 | 22.31 |
| ATOM 2856 | OH2 | TIP3 | 59 | 37.999 | 10.824 | 5.505 | 1.00 | 31.62 |
| ATOM 2859 | OH2 | TIP3 | 60 | 29.779 | −9.515 | −1.395 | 1.00 | 40.76 |
| ATOM 2862 | OH2 | TIP3 | 61 | 49.114 | 1.432 | 12.261 | 1.00 | 29.92 |
| ATOM 2865 | OH2 | TIP3 | 62 | 41.257 | 4.012 | 29.005 | 1.00 | 39.24 |
| ATOM 2868 | OH2 | TIP3 | 63 | 11.113 | −12.848 | 1.296 | 1.00 | 34.36 |
| ATOM 2871 | OH2 | TIP3 | 64 | −1.221 | −4.593 | 21.504 | 1.00 | 34.24 |
| ATOM 2874 | OH2 | TIP3 | 65 | 30.002 | 16.453 | 13.258 | 1.00 | 49.66 |
| ATOM 2877 | OH2 | TIP3 | 66 | 8.212 | 4.106 | 3.434 | 1.00 | 36.54 |
| ATOM 2880 | OH2 | TIP3 | 67 | 72.868 | 18.807 | 22.589 | 1.00 | 38.26 |
| ATOM 2883 | OH2 | TIP3 | 68 | −8.056 | −3.666 | 25.021 | 1.00 | 39.81 |
| ATOM 2886 | OH2 | TIP3 | 69 | 66.436 | −4.683 | 28.008 | 1.00 | 60.97 |
| ATOM 2889 | OH2 | TIP3 | 70 | 22.063 | −20.641 | 4.804 | 1.00 | 42.25 |
| ATOM 2892 | OH2 | TIP3 | 71 | 59.860 | −7.407 | 4.859 | 1.00 | 56.78 |
| ATOM 2895 | OH2 | TIP3 | 72 | 16.887 | −13.832 | −2.611 | 1.00 | 59.32 |
| ATOM 2898 | OH2 | TIP3 | 73 | −15.108 | 7.351 | 4.303 | 1.00 | 31.87 |
| ATOM 2901 | OH2 | TIP3 | 74 | 32.901 | 2.922 | 13.663 | 1.00 | 37.89 |
| ATOM 2904 | OH2 | TIP3 | 75 | 0.173 | −2.666 | 11.035 | 1.00 | 39.12 |
| ATOM 2907 | OH2 | TIP3 | 76 | 17.533 | 2.317 | 5.808 | 1.00 | 18.66 |
| ATOM 2910 | OH2 | TIP3 | 77 | 27.183 | 3.730 | 6.349 | 1.00 | 29.04 |
| ATOM 2913 | OH2 | TIP3 | 78 | −8.812 | 5.887 | 9.703 | 1.00 | 30.53 |
| ATOM 2916 | OH2 | TIP3 | 79 | 1.614 | −2.195 | 8.694 | 1.00 | 30.79 |
| ATOM 2919 | OH2 | TIP3 | 80 | −5.304 | −3.157 | 6.846 | 1.00 | 47.38 |
| ATOM 2922 | OH2 | TIP3 | 81 | 17.401 | 2.918 | 1.973 | 1.00 | 20.47 |
| ATOM 2925 | OH2 | TIP3 | 82 | 20.333 | 3.188 | 3.159 | 1.00 | 24.44 |
| ATOM 2928 | OH2 | TIP3 | 83 | 0.408 | −2.516 | 22.276 | 1.00 | 31.11 |
| ATOM 2931 | OH2 | TIP3 | 84 | 20.095 | −6.123 | −1.372 | 1.00 | 17.62 |
| ATOM 2934 | OH2 | TIP3 | 85 | 11.018 | −15.627 | 7.421 | 1.00 | 60.29 |
| ATOM 2937 | OH2 | TIP3 | 86 | 4.089 | −12.037 | 11.797 | 1.00 | 39.47 |
| ATOM 2940 | OH2 | TIP3 | 87 | 6.459 | 0.908 | −3.278 | 1.00 | 30.31 |
| ATOM 2943 | OH2 | TIP3 | 88 | −13.493 | 1.004 | 5.319 | 1.00 | 41.13 |
| ATOM 2946 | OH2 | TIP3 | 89 | 15.418 | −7.532 | 0.022 | 1.00 | 21.29 |
| ATOM 2949 | OH2 | TIP3 | 90 | −2.128 | −5.834 | 4.052 | 1.00 | 57.55 |
| ATOM 2952 | OH2 | TIP3 | 91 | 12.731 | 4.833 | −4.212 | 1.00 | 44.52 |
| ATOM 2955 | OH2 | TIP3 | 92 | 69.320 | 27.812 | 2.191 | 1.00 | 37.47 |
| ATOM 2958 | OH2 | TIP3 | 93 | 24.851 | −12.871 | 0.285 | 1.00 | 44.73 |
| ATOM 2961 | OH2 | TIP3 | 94 | 60.301 | −4.459 | 33.927 | 1.00 | 40.13 |
| ATOM 2964 | OH2 | TIP3 | 95 | 10.488 | 5.951 | 3.205 | 1.00 | 41.53 |
| ATOM 2967 | OH2 | TIP3 | 96 | −9.708 | −4.233 | 4.439 | 1.00 | 29.77 |
| ATOM 2970 | OH2 | TIP3 | 97 | 72.950 | −1.768 | 10.144 | 1.00 | 39.69 |
| ATOM 2973 | OH2 | TIP3 | 98 | −3.287 | 5.612 | 30.618 | 1.00 | 34.65 |

TABLE 4-continued

Atomic Structure Coordinates of Unphosphorylated FLGK:AMP-PCP Co-Complex

| Atom No. | Atom Type | A.A. Type | A.A. No. | X | Y | Z | OCC | B |
|---|---|---|---|---|---|---|---|---|
| ATOM 2976 | OH2 | TIP3 | 99 | 36.658 | 1.007 | 11.717 | 1.00 | 35.43 |
| ATOM 2979 | OH2 | TIP3 | 100 | 21.221 | 6.459 | 16.863 | 1.00 | 20.70 |
| ATOM 2982 | OH2 | TIP3 | 101 | 5.833 | −8.726 | 22.274 | 1.00 | 47.13 |
| ATOM 2985 | OH2 | TIP3 | 102 | −13.529 | 7.868 | 17.445 | 1.00 | 31.95 |
| ATOM 2988 | OH2 | TIP3 | 103 | 26.795 | −10.682 | −0.807 | 1.00 | 28.65 |
| ATOM 2991 | OH2 | TIP3 | 104 | 23.711 | 1.909 | 18.309 | 1.00 | 28.29 |
| ATOM 2994 | OH2 | TIP3 | 105 | −2.187 | 12.232 | 3.920 | 1.00 | 44.98 |
| ATOM 2997 | OH2 | TIP3 | 106 | 59.483 | 12.398 | 33.535 | 1.00 | 39.58 |
| ATOM 3000 | OH2 | TIP3 | 107 | 4.439 | −10.915 | 1.996 | 1.00 | 43.77 |
| ATOM 3003 | OH2 | TIP3 | 108 | 8.041 | 2.687 | 0.648 | 1.00 | 45.32 |
| ATOM 3006 | OH2 | TIP3 | 109 | 75.836 | 1.477 | 25.476 | 1.00 | 41.65 |
| ATOM 3009 | OH2 | TIP3 | 110 | 48.604 | 15.594 | 14.349 | 1.00 | 36.36 |
| ATOM 3012 | OH2 | TIP3 | 111 | 2.396 | −11.387 | 9.259 | 1.00 | 34.21 |
| ATOM 3015 | OH2 | TIP3 | 112 | 82.927 | 26.453 | 12.807 | 1.00 | 36.54 |
| ATOM 3018 | OH2 | TIP3 | 113 | 8.983 | −6.631 | −3.299 | 1.00 | 47.01 |
| ATOM 3021 | OH2 | TIP3 | 114 | −8.690 | 4.367 | 4.504 | 1.00 | 41.25 |
| ATOM 3024 | OH2 | TIP3 | 115 | 7.941 | −13.921 | 8.777 | 1.00 | 36.12 |
| ATOM 3027 | OH2 | TIP3 | 116 | 51.295 | 6.440 | 10.632 | 1.00 | 28.37 |
| ATOM 3030 | OH2 | TIP3 | 117 | 20.432 | 3.771 | 15.637 | 1.00 | 31.22 |
| ATOM 3033 | OH2 | TIP3 | 118 | 72.882 | 3.887 | 20.227 | 1.00 | 30.22 |
| ATOM 3036 | OH2 | TIP3 | 119 | 5.187 | −11.863 | 22.711 | 1.00 | 47.49 |
| ATOM 3039 | OH2 | TIP3 | 120 | 33.889 | 2.571 | 16.293 | 1.00 | 40.04 |
| ATOM 3042 | OH2 | TIP3 | 121 | 9.504 | −12.183 | 7.160 | 1.00 | 31.48 |
| ATOM 3045 | OH2 | TIP3 | 122 | 8.397 | 3.827 | −1.647 | 1.00 | 46.92 |
| ATOM 3048 | OH2 | TIP3 | 123 | 7.281 | 7.321 | 2.391 | 1.00 | 62.46 |
| ATOM 3051 | OH2 | TIP3 | 124 | 35.682 | −1.725 | 0.534 | 1.00 | 36.75 |
| ATOM 3054 | OH2 | TIP3 | 125 | 44.465 | 10.095 | 11.089 | 1.00 | 44.72 |
| ATOM 3057 | OH2 | TIP3 | 126 | 45.247 | 11.893 | 21.405 | 1.00 | 33.51 |
| ATOM 3060 | OH2 | TIP3 | 127 | 57.386 | −10.506 | 14.020 | 1.00 | 45.72 |
| ATOM 3063 | OH2 | TIP3 | 128 | −3.033 | 15.103 | 16.644 | 1.00 | 38.48 |
| ATOM 3066 | OH2 | TIP3 | 129 | 85.621 | 11.111 | 8.814 | 1.00 | 38.13 |
| ATOM 3069 | OH2 | TIP3 | 130 | 13.040 | −2.760 | 2.176 | 1.00 | 31.26 |
| ATOM 3072 | OH2 | TIP3 | 131 | 75.607 | 3.932 | 20.836 | 1.00 | 55.09 |
| ATOM 3075 | OH2 | TIP3 | 132 | 13.080 | 7.467 | −2.358 | 1.00 | 35.05 |
| ATOM 3078 | OH2 | TIP3 | 133 | 11.308 | −9.967 | 0.995 | 1.00 | 28.96 |
| ATOM 3081 | OH2 | TIP3 | 134 | 13.716 | −16.170 | 3.848 | 1.00 | 44.64 |
| ATOM 3084 | OH2 | TIP3 | 135 | −6.498 | −3.706 | 16.178 | 1.00 | 43.17 |
| ATOM 3087 | OH2 | TIP3 | 136 | 25.841 | −12.949 | 3.950 | 1.00 | 41.14 |
| ATOM 3090 | OH2 | TIP3 | 137 | −16.285 | 10.803 | 6.585 | 1.00 | 45.75 |
| ATOM 3093 | OH2 | TIP3 | 138 | 86.457 | 12.585 | 6.477 | 1.00 | 36.37 |
| ATOM 3096 | OH2 | TIP3 | 139 | 32.097 | −4.644 | 2.224 | 1.00 | 28.35 |
| ATOM 3099 | OH2 | TIP3 | 140 | 44.936 | 7.528 | 11.961 | 1.00 | 46.60 |
| ATOM 3102 | OH2 | TIP3 | 141 | 80.781 | 12.162 | 16.353 | 1.00 | 41.46 |
| ATOM 3105 | OH2 | TIP3 | 142 | 2.547 | −7.532 | −1.453 | 1.00 | 41.42 |
| ATOM 3108 | OH2 | TIP3 | 143 | 31.850 | −5.907 | 21.194 | 1.00 | 54.70 |
| ATOM 3111 | OH2 | TIP3 | 144 | 74.524 | −2.663 | 12.264 | 1.00 | 40.35 |
| ATOM 3114 | OH2 | TIP3 | 145 | 7.592 | 6.769 | −0.931 | 1.00 | 58.34 |
| ATOM 3117 | OH2 | TIP3 | 146 | 71.168 | 5.735 | 21.648 | 1.00 | 27.86 |
| ATOM 3120 | OH2 | TIP3 | 147 | 67.876 | −4.900 | 8.725 | 1.00 | 33.58 |
| ATOM 3123 | OH2 | TIP3 | 148 | 0.554 | −10.181 | 6.605 | 1.00 | 75.65 |
| ATOM 3126 | OH2 | TIP3 | 149 | 67.965 | 18.266 | 10.874 | 1.00 | 30.42 |
| ATOM 3129 | OH2 | TIP3 | 150 | 3.509 | 8.125 | 4.021 | 1.00 | 40.77 |
| ATOM 3132 | OH2 | TIP3 | 151 | 52.216 | 12.175 | 18.131 | 1.00 | 47.63 |
| ATOM 3135 | OH2 | TIP3 | 152 | −10.336 | 6.394 | 5.014 | 1.00 | 48.53 |
| ATOM 3138 | OH2 | TIP3 | 153 | 76.427 | 1.384 | −1.196 | 1.00 | 47.21 |
| ATOM 3141 | OH2 | TIP3 | 154 | 10.116 | −12.199 | 17.089 | 1.00 | 70.16 |
| ATOM 3144 | OH2 | TIP3 | 155 | 34.043 | 14.595 | 18.314 | 1.00 | 40.56 |
| ATOM 3147 | OH2 | TIP3 | 156 | 2.488 | −8.304 | 16.835 | 1.00 | 64.47 |
| ATOM 3150 | OH2 | TIP3 | 157 | 29.610 | 1.954 | 6.685 | 1.00 | 48.74 |
| ATOM 3153 | OH2 | TIP3 | 158 | 32.578 | −17.270 | 12.109 | 1.00 | 37.35 |
| ATOM 3156 | OH2 | TIP3 | 159 | 42.013 | 18.106 | 11.196 | 1.00 | 68.33 |
| ATOM 3159 | OH2 | TIP3 | 160 | 87.646 | 10.346 | 5.465 | 1.00 | 75.39 |
| ATOM 3162 | OH2 | TIP3 | 161 | 69.931 | −3.739 | 24.921 | 1.00 | 70.42 |
| ATOM 3165 | OH2 | TIP3 | 162 | 77.277 | 5.700 | 23.531 | 1.00 | 53.26 |
| ATOM 3168 | OH2 | TIP3 | 163 | 34.172 | 15.704 | 1.865 | 1.00 | 44.88 |
| ATOM 3171 | OH2 | TIP3 | 164 | −9.871 | 7.514 | 7.751 | 1.00 | 39.18 |
| ATOM 3174 | OH2 | TIP3 | 165 | 11.814 | 5.604 | 7.443 | 1.00 | 46.70 |
| ATOM 3177 | OH2 | TIP3 | 166 | −8.801 | 13.912 | 13.532 | 1.00 | 52.89 |
| ATOM 3180 | OH2 | TIP3 | 167 | 32.195 | 3.409 | 18.336 | 1.00 | 32.33 |
| ATOM 3183 | OH2 | TIP3 | 168 | −8.858 | 9.696 | 24.279 | 1.00 | 38.90 |
| ATOM 3186 | OH2 | TIP3 | 169 | −1.135 | −6.924 | 15.691 | 1.00 | 43.05 |
| ATOM 3189 | OH2 | TIP3 | 170 | 79.806 | 0.323 | 15.371 | 1.00 | 36.91 |
| ATOM 3192 | OH2 | TIP3 | 171 | 67.181 | 20.622 | −1.545 | 1.00 | 44.72 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3195 | OH2 | TIP3 | 172 | −0.823 | 3.732 | 1.065 | 1.00 | 52.11 |
| ATOM 3198 | OH2 | TIP3 | 173 | −0.130 | 6.021 | 2.491 | 1.00 | 40.87 |
| ATOM 3201 | OH2 | TIP3 | 174 | −1.027 | 8.941 | 1.064 | 1.00 | 60.72 |
| ATOM 3204 | OH2 | TIP3 | 175 | −5.566 | 8.867 | 2.163 | 1.00 | 47.25 |
| ATOM 3207 | OH2 | TIP3 | 176 | −7.259 | 10.294 | 4.033 | 1.00 | 53.61 |
| ATOM 3210 | OH2 | TIP3 | 177 | 2.664 | 7.247 | 1.058 | 1.00 | 46.41 |
| ATOM 3213 | OH2 | TIP3 | 178 | 5.295 | 10.728 | 8.257 | 1.00 | 39.84 |
| ATOM 3216 | OH2 | TIP3 | 179 | 63.743 | 12.726 | 22.713 | 1.00 | 49.55 |
| ATOM 3219 | OH2 | TIP3 | 180 | 79.165 | 1.016 | 17.948 | 1.00 | 51.41 |
| ATOM 3222 | OH2 | TIP3 | 181 | 13.823 | −1.538 | −3.942 | 1.00 | 39.85 |
| ATOM 3225 | OH2 | TIP3 | 182 | 59.255 | 3.213 | 32.873 | 1.00 | 76.77 |
| ATOM 3228 | OH2 | TIP3 | 183 | 32.210 | 13.612 | 20.027 | 1.00 | 60.41 |
| ATOM 3231 | OH2 | TIP3 | 184 | 72.606 | 16.267 | 22.574 | 1.00 | 60.78 |
| ATOM 3234 | OH2 | TIP3 | 185 | −0.147 | 5.713 | 30.877 | 1.00 | 50.19 |
| ATOM 3237 | OH2 | TIP3 | 186 | −1.207 | −4.507 | 27.969 | 1.00 | 65.19 |
| ATOM 3240 | OH2 | TIP3 | 187 | 81.340 | 15.584 | 16.808 | 1.00 | 64.48 |
| ATOM 3243 | OH2 | TIP3 | 188 | −17.535 | 3.884 | 23.785 | 1.00 | 57.17 |
| ATOM 3246 | OH2 | TIP3 | 189 | 27.503 | 10.697 | 14.669 | 1.00 | 36.11 |
| ATOM 3249 | OH2 | TIP3 | 190 | 34.585 | 4.535 | 27.618 | 1.00 | 61.68 |
| ATOM 3252 | OH2 | TIP3 | 191 | −3.701 | −4.982 | 9.069 | 1.00 | 43.66 |
| ATOM 3255 | OH2 | TIP3 | 192 | 42.524 | 7.811 | 22.390 | 1.00 | 34.53 |
| ATOM 3258 | OH2 | TIP3 | 193 | 52.937 | 11.764 | 21.790 | 1.00 | 36.19 |
| ATOM 3261 | OH2 | TIP3 | 194 | −7.665 | 8.600 | 6.358 | 1.00 | 59.08 |
| ATOM 3264 | OH2 | TIP3 | 195 | 86.880 | 5.187 | 16.579 | 1.00 | 55.88 |
| ATOM 3267 | OH2 | TIP3 | 196 | 55.377 | 16.147 | 20.540 | 1.00 | 48.25 |
| ATOM 3270 | OH2 | TIP3 | 197 | 51.394 | 19.664 | 22.988 | 1.00 | 46.81 |
| ATOM 3273 | OH2 | TIP3 | 198 | 20.021 | 7.087 | 7.226 | 1.00 | 52.98 |
| ATOM 3276 | OH2 | TIP3 | 199 | 28.959 | 1.819 | −3.219 | 1.00 | 40.50 |
| ATOM 3279 | OH2 | TIP3 | 200 | 26.533 | 2.812 | −4.295 | 1.00 | 54.24 |
| ATOM 3282 | OH2 | TIP3 | 201 | 36.739 | 3.003 | 18.397 | 1.00 | 42.13 |
| ATOM 3285 | OH2 | TIP3 | 202 | 16.968 | −20.752 | 14.318 | 1.00 | 54.54 |
| ATOM 3288 | OH2 | TIP3 | 203 | 28.177 | −14.418 | 6.134 | 1.00 | 61.36 |
| ATOM 3291 | OH2 | TIP3 | 204 | 31.488 | 1.501 | −1.796 | 1.00 | 47.49 |
| ATOM 3294 | OH2 | TIP3 | 205 | 10.665 | −16.494 | 15.731 | 1.00 | 41.42 |
| ATOM 3297 | OH2 | TIP3 | 206 | 6.916 | −12.200 | 6.160 | 1.00 | 61.94 |
| ATOM 3300 | OH2 | TIP3 | 207 | −12.659 | 14.357 | 10.908 | 1.00 | 52.96 |
| ATOM 3303 | OH2 | TIP3 | 208 | 11.274 | 9.662 | −1.588 | 1.00 | 48.45 |
| ATOM 3306 | OH2 | TIP3 | 209 | 11.491 | 12.484 | −1.531 | 1.00 | 44.51 |
| ATOM 3309 | OH2 | TIP3 | 210 | 34.037 | 13.520 | −1.011 | 1.00 | 48.43 |
| ATOM 3312 | OH2 | TIP3 | 211 | 31.162 | 18.259 | 7.980 | 1.00 | 44.86 |
| ATOM 3315 | OH2 | TIP3 | 212 | 36.937 | 11.633 | −1.971 | 1.00 | 49.85 |
| ATOM 3318 | OH2 | TIP3 | 213 | 64.024 | 13.599 | 26.505 | 1.00 | 37.53 |
| ATOM 3321 | OH2 | TIP3 | 214 | 36.528 | 5.933 | 14.857 | 1.00 | 57.04 |
| ATOM 3324 | OH2 | TIP3 | 215 | 90.599 | 4.042 | 6.342 | 1.00 | 54.08 |
| ATOM 3327 | OH2 | TIP3 | 216 | 50.139 | −11.645 | 10.526 | 1.00 | 54.64 |
| ATOM 3330 | OH2 | TIP3 | 217 | 66.523 | −1.024 | 30.536 | 1.00 | 39.41 |
| ATOM 3333 | OH2 | TIP3 | 218 | 74.880 | 18.976 | 20.591 | 1.00 | 41.84 |
| ATOM 3336 | OH2 | TIP3 | 219 | −3.095 | 9.744 | 3.142 | 1.00 | 52.35 |
| ATOM 3339 | OH2 | TIP3 | 220 | 5.601 | −3.682 | 25.022 | 1.00 | 29.30 |
| ATOM 3342 | OH2 | TIP3 | 221 | 35.616 | 6.407 | 12.455 | 1.00 | 44.48 |
| ATOM 3345 | OH2 | TIP3 | 222 | −5.381 | 16.006 | 14.081 | 1.00 | 44.23 |
| ATOM 3348 | OH2 | TIP3 | 223 | 46.509 | −11.503 | 26.814 | 1.00 | 53.82 |
| ATOM 3351 | OH2 | TIP3 | 224 | −3.791 | −5.481 | 20.929 | 1.00 | 61.42 |
| ATOM 3354 | OH2 | TIP3 | 225 | 1.622 | −3.876 | −0.402 | 1.00 | 58.60 |
| ATOM 3357 | OH2 | TIP3 | 226 | 86.244 | 11.220 | 23.133 | 1.00 | 59.84 |
| ATOM 3360 | OH2 | TIP3 | 227 | 11.011 | 7.959 | 5.659 | 1.00 | 63.07 |
| ATOM 3363 | OH2 | TIP3 | 228 | 64.610 | −8.031 | 20.406 | 1.00 | 48.11 |
| ATOM 3366 | OH2 | TIP3 | 229 | 11.446 | −17.829 | 13.438 | 1.00 | 51.35 |
| ATOM 3369 | OH2 | TIP3 | 230 | 72.056 | 1.258 | −1.830 | 1.00 | 43.88 |
| ATOM 3372 | OH2 | TIP3 | 231 | 57.359 | 9.732 | 11.744 | 1.00 | 65.45 |
| ATOM 3375 | OH2 | TIP3 | 232 | 43.344 | 20.728 | 30.066 | 1.00 | 61.52 |
| ATOM 3378 | OH2 | TIP3 | 233 | 66.723 | 16.772 | 15.661 | 1.00 | 43.79 |
| ATOM 3381 | OH2 | TIP3 | 234 | 88.036 | 22.036 | 4.257 | 1.00 | 61.83 |
| ATOM 3384 | OH2 | TIP3 | 235 | 12.085 | 2.346 | 27.862 | 1.00 | 46.29 |
| ATOM 3387 | OH2 | TIP3 | 236 | 64.898 | −0.425 | 3.209 | 1.00 | 50.06 |
| ATOM 3390 | OH2 | TIP3 | 237 | 72.114 | 28.348 | 7.731 | 1.00 | 53.01 |
| ATOM 3393 | OH2 | TIP3 | 238 | 25.792 | −8.081 | 27.181 | 1.00 | 55.19 |
| ATOM 3396 | OH2 | TIP3 | 239 | −18.262 | 10.614 | 12.607 | 1.00 | 51.54 |
| ATOM 3399 | OH2 | TIP3 | 240 | 30.336 | 11.280 | 16.201 | 1.00 | 46.53 |
| ATOM 3402 | OH2 | TIP3 | 241 | 22.712 | −15.818 | −2.226 | 1.00 | 47.29 |
| ATOM 3405 | OH2 | TIP3 | 242 | 29.700 | 9.496 | 18.074 | 1.00 | 40.10 |
| ATOM 3408 | OH2 | TIP3 | 243 | 63.297 | −0.480 | 5.497 | 1.00 | 49.90 |
| ATOM 3411 | OH2 | TIP3 | 244 | 61.458 | 7.093 | 11.497 | 1.00 | 45.71 |

TABLE 4-continued

Atomic Structure Coordinates of Unphosphorylated
FLGK:AMP-PCP Co-Complex

| Atom No. | Atom Type | A.A. Type | A.A. No. | X | Y | Z | OCC | B |
|---|---|---|---|---|---|---|---|---|
| ATOM 3414 | OH2 | TIP3 | 245 | −0.217 | 2.232 | 32.172 | 1.00 | 46.12 |
| ATOM 3417 | OH2 | TIP3 | 246 | 66.196 | 6.250 | 12.159 | 1.00 | 34.47 |

The following abbreviations are used in Tables 3 and 4:

"Atom Type" refers to the element whose coordinates are provided. The first letter in the column defines the element.

"A.A." refers to amino acid.

"X, Y and Z" provide the Cartesian coordinates of the element.

"B" is a thermal factor that measures movement of the atom around its atomic center.

"OCC" refers to occupancy, and represents the percentage of time the atom type occupies the particular coordinate. OCC values range from 0 to 1, with 1 being 100%.

"PRT1" or "PRT2" relate to occupancy, with PRT1 designating the coordinates of the atom when in the first conformation and PRT2 designating the coordinates of the atom when in the second or alternate conformation.

Structures coordinates for FLGK according to Tables 3 and 4 may be modified by mathematical manipulation. Such manipulations include, but are not limited to, crystallographic permutations of the raw structure coordinates, fractionalization of the raw structure coordinates, integer additions or subtractions to sets of the raw structure coordinates, inversion of the raw structure coordinates and any combination of the above.

The present invention is not to be limited in scope by the exemplified embodiments, which are intended as illustrations of single aspects of the invention. Indeed, various modifications of the invention in addition to those described herein will become apparent to those having skill in the art from the foregoing description and accompanying drawings. Such modifications are intended to fall with in the scope of the appended claims.

REFERENCES

The following references, which are cited herein, are hereby incorporated by reference in their entireties:

Ausubel et al.; 1989, *Current Protocols in Molecular Biolocy*, Greene Publishing Associates and Wiley Interscience, NY.

Basilico and Moscatelli, 1992, "The FGF family of growth factors and oncogenes," *Advances in Cancer Research* 59:116–65.

Bellot et al., 1991, "Ligand-induced transphosphorylation between different FGF receptors," *EMBO J.* 10:2849–2854.

Bellus et al., 1995, "A recurrent mutation in the tyrosine kinase domain of fibroblast growth factor receptor 3 causes hypochondroplasia," *Nature Genetics* 10:357–359.

Blaikie et al., 1994, "A region distinct from the SH2 domain can bind tyrosine-phosphorylated growth factor receptors," *J. Biol. Chem.* 269:32031–32034.

Blundel et al., 1976, *Protein Crystallography*, Academic Press.

Bossemeyer et al., 2993, "Phosphotransferase and substrate binding mechanism of the cAMP-dependent protein kinase catalytic subunit from porcine heart as deduced from the 2.0 Å structure of the complex with $Mn^{2+}$adenylyl imidodiphosphate and inhibitor peptide PKI (5–24)," *EMBO J.* 12:849–859.

Brünger, 1992, *X-PLOR (Version 3.1) Manual* (New Haven, Conn.: The Howard Hughes Medical Institute and Department of Molecular Biophysics and Biochemistry, Yale University).

Brünger, 1992, "Free R value: a novel statistical quantity for assessing the accuracy of crystal structures," *Nature* 355:472–475.

Burgess and Winkles, 1994, *In regulation of the proliferation of neoplastic cells*, Pusztai et al., eds, Oxford University Press, Oxford.

Burgess and Maciag, 1989, "Heparin binding (fibroblast) growth factor family of proteins," *Ann. Rev. Biochem.* 58:575–606.

Cantley et al., 1991, "Oncogenes and signal transduction," *Cell* 64:281–302.

Chan et al., 1995, "Activation of ZAP-70 kinase activity by phosphorylation of tyrosine 493 is required for lymphocyte antigen receptor function," *EMBO J.* 14(11):2499–2508.

Clark et al., 1988, "Loss of three major auto phosphorylation sites in the EGF receptor does not block the mitogenic action of EGF. J.," *Cell. Physiol.* 134(3):421–428.

Cowtan, 1994, "Protein Crystallography," CCP4 and ESF-EACBM Newsletter (joint) 31:34–38.

Creighton, 1983, *Proteins: Structures and Molecular Principles*, W. H. Freeman & Co., NY.

DeBondt et al., 1993, "Crystal structure of cyclin-dependent kinase 2," *Nature* 363:595–602.

DeVore et al., 1995, "An FGF receptor signaling pathway is required for the normal cell migrations of the sex myoblasts in C. elegans hermaphrodites," *Cell* 83:611–620.

Ducruix and Giege, 1992, *Crystallization of Nucleic Acids and Proteins: A Practical Approach*, IRL Press, Oxford, England.

Ellis et al., 1986, "Replacement of insulin receptor tyrosine residues 1162 and 1163 compromises insulin-stimulated kinase activity and uptake of 2-deoxyglucose," *Cell* 45:721–732.

Friesel and Dawid, 1991, "cDNA cloning and development expression of fibroblast growth factors from Xenopus laevis," *Mol. Cell. Biol.* 11(5):2481–2488.

Friesel and Brown, 1992, "Spatially restricted expression of fibroblast growth factor receptor-2 during Xenopus development," *Development* 116(4):1051–1058.

Flores-Riveros et al., 1989, "Substrate phosphorylation catalyzed by the insulin receptor tyrosine kinase. Kinetic correlation to autophosphorylation of specific sites in the beta subunit," *J. Biol. Chem.* 264:21557–21572.

Givol and Yayon, 1992, "Complexity of FGF receptors: genetic basis for structural diversity and functional specificity," *FASEB J.* 6(15):3362–3369.

Goldsmith and Cobb, 1994, "Protein kinases," *Current Opinion in Structural Biology* 4(6):833–840.

Gotoh et al., 1992, "A highly conserved tyrosine residue at codon 845 within the kinase domain is not required for the transforming activity of human epidermal growth factor receptor," *Biochem. Biophys. Res. Commun.* 186(2):768–774.

Hendrickson, 1979, "Transformations to optimize the superposition of similar structures," *Acta Crystallogr.* A35:158–163.

Honegger et al., 1988, "Biological activities of EGF-receptor mutants with individually altered autophosphorylation sites," *EMBO J.* 7(10):3045–3052.

Honegger et al., 1988, "Kinetic parameters of the protein tyrosine kinase activity of EGF-receptor mutants ithin individually altered autophosphorylation sites," *EMBO J.* 7(10):3053–3060.

Hu et al., 1994, "Insights into autoregulation from the crystal structure of twitching kinase," *Nature* 369:581–584.

Hubbard et al., 1994, "Crystal structure of tyrosine inase domain of the human insulin receptor," *Nature* 372:746–754.

Hunter, 1991, "Protein kinase classification," *Methods Enzymol.* 200:3–37.

Jaye et al., 1992, "Fibroblast growth factor receptor tyrosine kinases: molecular analysis and signal transduction," *Biochem. Biophys. Acta* 1135:185–199.

Jeffrey et al., 1995, "Mechanism of CDK activation revealed by the structure of a cyclinA-CDK2 complex," *Nature* 376(6538):313–320.

Johnson and Williams, 1993, "Structural and functional diversity in the FGF receptor multigene family," *Adv. Cancer Res.* 60:1–41.

Johnson et al., 1996, "Active and inactive protein kinases."

Jones, 1985, "Diffraction methods for biological macromolecules. Interactive computer graphics: FRODO," *Methods in Enzymoloay* 115:157–171.

Kabsch and Sander, 1983, "Dictionary of protein secondary structure: pattern recognition of hydrogen-bonded and geometrical features," *Biopolymers* 22:2577–2637.

Klagsbrun and Baird, 1991, "A dual receptor system is required for basic fibroblast growth factor activity," *Cell* 67(2):229–231.

Klambt et al., 1992, "Breathless, a Drosophila FGF receptor homolog, is essential for migration of tracheal and specific midline glial cells," *Genes & Development* 6:1668–1678.

Kmiecik and Shalloway, 1987, "Activation and suppression of pp60c-src transforming ability by mutation of its primary sites of tyrosine phosphorylation," *Cell* 49:65–73.

Knighton et al., 1991, "Crystal structure of the catalytic subunit of cyclic adenosine monophosphate-dependent protein kinase," *Science* 253:407–414.

Komada and Kitamura, 1994, "Regulatory role of major tyrosine autophosphorylation site of kinase domain of c-Met receptor (scatter factor/hepatocyte growth factor receptor)," *J. Biol. Chem.* 269:16131–16136.

Kusari et al., 1991, "Insulin resistance and diabetes due to different mutations in the tyrosine kinase domain of both insulin receptor gene alleles," *J. Biol. Chem.* 266:5260–5267.

Laskowski et al., 1993, "PROCHECK: a program to check the stereochemical quality of protein structures," *J. Appl. Cryst.* 26:283–291.

Lattman, 1985, *Methods in Enzymology* 115:55–77.

Levitzki and Gazit, 1995, "Tyrosine Kinase Inhibition: An Approach to Drug Development," *Science* 267:1782–1788.

Longati et al., 1994, "Tyrosines 1234–1235 are critical for activation of the tyrosine kinase encoded by the MET roto-oncogene (HGF receptor)," *Oncogene* 9:49–57.

Maniatis et al., 1989, *Molecular Cloning: A Laboratory Manual*, Cold Spring Harbor Laboratory, NY.

McPherson, *Preparation and Analysis of Protein Crystals*, 1982, John Wiley, New York.

McPherson, 1990, *Eur. J. Biochem.* 189:1–23.

Middlemas et al., 1994, "Identification of TrkB autophosphorylation sites and evidence that phospholipase C-gamma 1 is a substrate of the TrkB receptor," *J. Biol. Chem.* 269:5458–5466.

Mohammadi et al., 1996, "Identification of six novel autophosphorylation sites on fibroblast growth factor receptor 1 and elucidation of their importance in receptor activation and signal transduction," *Mol. Cell. Biol.* 16:977–989.

Mohammadi et al., 1992, "Point mutation in FGF receptor eliminates phosphatidylinositol hydrolysis without affecting mitogenesis," *Nature* 358:681–684.

Mohammadi et al., 1991, "A tyrosine-phosphorylated carboxy-terminal peptide of the fibroblast growth factor receptor (flg) is a binding site for the SH2 domain of phospholipase C-γ1," *Mol. Cell. Biol.* 11:5068–5078.

Naski, 1996, "Graded activation of fibroblast growth factor receptor 3 by mutations causing achondroplasia and thanatophoric dysplasia," *Nature Genetics*, in press.

Navaza, 1994, "AMoRe: an automated package for molecular replacement," *Acta Crystalloqr.* A50:157–163.

Nicholls et al., 1991, "Protein folding and association: insights from the interfacial and thermodynamic properties of hydrocarbons," *Proteins* 11:281–296.

Ornitz et al., 1992, "Heparin is required for cell-free binding of basic fibroblast growth factor to a soluble receptor and for mitogenesis in whole cells," *Mol. Cell. Biol.* 12(1):240–247.

Otwinowski, 1991, "Maximum likelihood refinement of heavy atom parameters," *Isomorphous Replacement and Anomalous Scattering*, Evans and Leslie eds. (Daresbury, United Kingdom: Daresbury Laboratory), 80–86.

Otwinowski, 1993, "Oscillation data reduction program," Proceedings of the CCP4 Study Weekend, Sawyer et al., eds. (Daresbury, United Kingdom: SERC Daresbury Laboratory), 56–62.

Pawson and Schlessinger, 1993, "SH2 and SH3 domains," *Current Biology* 3:434–442.

Peters et al., 1992, "Point mutation of an FGF receptor abolishes phospatidylinositol turnover and Ca2+ flux but not mitogenesis," *Nature* 358:678–781.

Piwnica-Worms et al., 1987, "Tyrosine phosphorylation regulates the biochemical and biological properties of pp60c-src.," *Cell* 49:75–82.

Rodrigues and Park, 1994, "Autophosphorylation modulates the kinase activity and oncogenic potential of the Met receptor tyrosine kinase," *Oncogene* 9:2019–2027.

Rossmann, 1972, "The Molecular Replacement Method," *Int. Sci. Rev. Ser.* No. 13, Gordon & Breach, New York.

Schlessinger and Lemmon, 1995, "Regulation of growth factor activation by proteoglycans: what is the role of the low affinity receptors?," *Cell* 83(3):357–360.

Shishido et al., 1993, "Two FGF-receptor homologues or Drosophila: one is expressed in mesodermal primordium in early embryos," *Development* 117:751–761.

Spivak-Kroizman et al., 1994, "Heparin-induced oligomerization of FGF molecules is-responsible for FGF receptor dimerization, activation, and cell proliferation," Cell 79:1015–1024.

Stephens et al., 1994, "Trk receptors use redundant signal transduction pathways involving Shc and PLC-gamma 1 to mediate NGF responses," Neuron 12:691–705.

Tavormina et al., 1995, "Thanatophoric dysplasia (types I and II) caused by distinct mutations in fibroblast growth factor receptor 3," Nature Genetics 9(3):321–328.

Taylor et al., 1995, "How do protein kinases discriminate between serine/threonine and tyrosine? Structural insights from the insulin receptor protein-tyrosine kinase," FASEB Journal 9(13):1255–66.

Taylor and Radzio-Andzelm, 1994, "Three protein kinase structures define a common motif," Structure 2(5):345–355.

Ueno et al., 1992, "A Truncated form of fibroblast growth factor receptor 1 inhibits signal transduction by multiple types of fibroblast growth factor receptor," J. Biol. Chem. 267:1470–1476.

Ullrich and Schlessinger, 1990, "Signal transduction by receptors with tyrosine kinase activity," Cell 61:203–212.

van der Geer et al., 1994, "Receptor protein-tyrosine kinases and their signal transduction pathways," Annu. Rev. Cell Biol. 10:251–337.

Venkataraman et al., 1996, "Preferential self-association of basic fibroblast growth factor is stabilized by heparin during receptor dimerization and activation," Proceedings of the National Academy of Sciences of the United States of America 93(2):845–850.

Wange et al., 1995, "Activating and inhibitory mutations in adjacent tyrosines in the kinase domain of ZAP-70," J. Am. Chem. Soc. 270(32):18730–18733.

Weber, 1991, Adv. Protein Chem. 41:1–36.

Wei et al., 1994, "Protein kinase superfamily—comparisons of sequence data with three-dimensional structures," Curr. Olin. Struct. Biol. 4:450–455.

Zhang et al., 1994, "Atomic structure of the MAP kinase ERK2 at 2.3 A resolution," Nature 367:704–711.

Zheng et al., 1993, "Crystal structure of the catalytic subunit of cAMP-dependent protein kinase complexed with MgATP and peptide inhibitor," Biochem. J. 32:2154–2161.

Zhang et al., 1991, "The regulatory role of known tyrosine autophosphorylation sites of the insulin receptor kinase domain. An assessment by replacement with neutral and negatively charged amino acids," J. Biol. Chem. 266:990–996.

What is claimed is:

1. An isolated nucleic acid sequence encoding an FGF receptor tyrosine kinase domain protein, wherein a coding strand of the isolated nucleic acid sequence has the nucleotide sequence of SEQ ID NO: 5.

2. An expression vector comprising the nucleotide sequence of SEQ ID NO: 5.

3. A host cell comprising the expression vector of claim 2.

4. A method of making a protein comprising culturig the host cell of claim 3 so that a protein encoded by SEQ ID NO: 5 is expressed by said cell and isolating said protein.

* * * * *

UNITED STATES PATENT AND TRADEMARK OFFICE
CERTIFICATE OF CORRECTION

| | | |
|---|---|---|
| PATENT NO. | : 6,682,921 B1 | Page 1 of 1 |
| APPLICATION NO. | : 09/664526 | |
| DATED | : January 27, 2004 | |
| INVENTOR(S) | : Mohammadi et al. | |

It is certified that error appears in the above-identified patent and that said Letters Patent is hereby corrected as shown below:

On the title page (*) Notice, delete "442 days" and insert therefor --221 days--.

Signed and Sealed this

Seventh Day of August, 2007

JON W. DUDAS
*Director of the United States Patent and Trademark Office*

SEQUENCE LISTING

```
<160> NUMBER OF SEQ ID NOS: 41

<210> SEQ ID NO 1
<211> LENGTH: 310
<212> TYPE: PRT
<213> ORGANISM: Homo sapiens

<400> SEQUENCE: 1

Met Leu Ala Gly Val Ser Glu Tyr Glu Leu Pro Glu Asp Pro Arg Trp
  1               5                  10                  15

Glu Leu Pro Arg Asp Arg Leu Val Leu Gly Lys Pro Leu Gly Glu Gly
             20                  25                  30

Cys Phe Gly Gln Val Val Leu Ala Glu Ala Ile Gly Leu Asp Lys Asp
         35                  40                  45

Lys Pro Asn Arg Val Thr Lys Val Ala Val Lys Met Leu Lys Ser Asp
     50                  55                  60

Ala Thr Glu Lys Asp Leu Ser Asp Leu Ile Ser Glu Met Glu Met Met
 65                  70                  75                  80

Lys Met Ile Gly Lys His Lys Asn Ile Ile Asn Leu Leu Gly Ala Cys
                 85                  90                  95

Thr Gln Asp Gly Pro Leu Tyr Val Ile Val Glu Tyr Ala Ser Lys Gly
                100                 105                 110

Asn Leu Arg Glu Tyr Leu Gln Ala Arg Arg Pro Pro Gly Leu Glu Tyr
            115                 120                 125

Cys Tyr Asn Pro Ser His Asn Pro Glu Glu Gln Leu Ser Ser Lys Asp
        130                 135                 140

Leu Val Ser Cys Ala Tyr Gln Val Ala Arg Gly Met Glu Tyr Leu Ala
145                 150                 155                 160

Ser Lys Lys Cys Ile His Arg Asp Leu Ala Ala Arg Asn Val Leu Val
                165                 170                 175
```

```
Thr Glu Asp Asn Val Met Lys Ile Ala Asp Phe Gly Leu Ala Arg Asp
            180                 185                 190
Ile His His Ile Asp Tyr Tyr Lys Lys Thr Thr Asn Gly Arg Leu Pro
            195                 200                 205
Val Lys Trp Met Ala Pro Glu Ala Leu Phe Asp Arg Ile Tyr Thr His
    210                 215                 220
Gln Ser Asp Val Trp Ser Phe Gly Val Leu Leu Trp Glu Ile Phe Thr
225                 230                 235                 240
Leu Gly Gly Ser Pro Tyr Pro Gly Val Pro Val Glu Glu Leu Phe Lys
                245                 250                 255
Leu Leu Lys Glu Gly His Arg Met Asp Lys Pro Ser Asn Cys Thr Asn
            260                 265                 270
Glu Leu Tyr Met Met Met Arg Asp Cys Trp His Ala Val Pro Ser Gln
            275                 280                 285
Arg Pro Thr Phe Lys Gln Leu Val Glu Asp Leu Asp Arg Ile Val Ala
        290                 295                 300
Leu Thr Ser Asn Gln Glu
305                 310

<210> SEQ ID NO 2
<211> LENGTH: 315
<212> TYPE: PRT
<213> ORGANISM: Homo sapiens

<400> SEQUENCE: 2

Ser Ala Ala Gly Thr Met Val Ala Gly Val Ser Glu Tyr Glu Leu Pro
  1               5                  10                  15
Glu Asp Pro Arg Trp Glu Leu Pro Arg Asp Arg Leu Val Leu Gly Lys
             20                  25                  30
Pro Leu Gly Glu Gly Ala Phe Gly Gln Val Val Leu Ala Glu Ala Ile
         35                  40                  45
Gly Leu Asp Lys Asp Lys Pro Asn Arg Val Thr Lys Val Ala Val Lys
     50                  55                  60
Met Leu Lys Ser Asp Ala Thr Glu Lys Asp Leu Ser Asp Leu Ile Ser
 65                  70                  75                  80
Glu Met Glu Met Met Lys Met Ile Gly Lys His Lys Asn Ile Ile Asn
                 85                  90                  95
Leu Leu Gly Ala Cys Thr Gln Asp Gly Pro Leu Tyr Val Ile Val Glu
            100                 105                 110
Tyr Ala Ser Lys Gly Asn Leu Arg Glu Tyr Leu Gln Ala Arg Arg Pro
        115                 120                 125
Pro Gly Leu Glu Tyr Ser Tyr Asn Pro Ser His Asn Pro Glu Glu Gln
    130                 135                 140
Leu Ser Ser Lys Asp Leu Val Ser Cys Ala Tyr Gln Val Ala Arg Gly
145                 150                 155                 160
Met Glu Tyr Leu Ala Ser Lys Lys Cys Ile His Arg Asp Leu Ala Ala
                165                 170                 175
Arg Asn Val Leu Val Thr Glu Asp Asn Val Met Lys Ile Ala Asp Phe
            180                 185                 190
Gly Leu Ala Arg Asp Ile His His Ile Asp Tyr Tyr Lys Lys Thr Thr
        195                 200                 205
Asn Gly Arg Leu Pro Val Lys Trp Met Ala Pro Glu Ala Leu Phe Asp
    210                 215                 220
Arg Ile Tyr Thr His Gln Ser Asp Val Trp Ser Phe Gly Val Leu Leu
225                 230                 235                 240
```

```
Trp Glu Ile Phe Thr Leu Gly Gly Ser Pro Tyr Pro Gly Val Pro Val
                245                 250                 255

Glu Glu Leu Phe Lys Leu Leu Lys Glu Gly His Arg Met Asp Lys Pro
            260                 265                 270

Ser Asn Cys Thr Asn Glu Leu Tyr Met Met Met Arg Asp Cys Trp His
        275                 280                 285

Ala Val Pro Ser Gln Arg Pro Thr Phe Lys Gln Leu Val Glu Asp Leu
    290                 295                 300

Asp Arg Ile Val Ala Leu Thr Ser Asn Gln Glu
305                 310                 315

<210> SEQ ID NO 3
<211> LENGTH: 351
<212> TYPE: PRT
<213> ORGANISM: Artificial Sequence
<220> FEATURE:
<223> OTHER INFORMATION: Description of Artificial Sequence: Synthetic
      protein encoded by recombinant baculovirus

<400> SEQUENCE: 3

Met Arg Gly Ser His His His His His His Gly Met Ala Ser Met Thr
  1               5                  10                  15

Gly Gly Gln Gln Met Gly Arg Asp Leu Tyr Asp Asp Asp Lys Asp
                 20                  25                  30

Pro Ser Ser Arg Ser Ala Ala Gly Thr Met Val Ala Gly Val Ser Glu
             35                  40                  45

Tyr Glu Leu Pro Glu Asp Pro Arg Trp Glu Leu Pro Arg Asp Arg Leu
         50                  55                  60

Val Leu Gly Lys Pro Leu Gly Glu Gly Ala Phe Gly Gln Val Val Leu
 65                  70                  75                  80

Ala Glu Ala Ile Gly Leu Asp Lys Asp Lys Pro Asn Arg Val Thr Lys
                 85                  90                  95

Val Ala Val Lys Met Leu Lys Ser Asp Ala Thr Glu Lys Asp Leu Ser
            100                 105                 110

Asp Leu Ile Ser Glu Met Glu Met Met Lys Met Ile Gly Lys His Lys
        115                 120                 125

Asn Ile Ile Asn Leu Leu Gly Ala Cys Thr Gln Asp Gly Pro Leu Tyr
    130                 135                 140

Val Ile Val Glu Tyr Ala Ser Lys Gly Asn Leu Arg Glu Tyr Leu Gln
145                 150                 155                 160

Ala Arg Arg Pro Pro Gly Leu Glu Tyr Ser Tyr Asn Pro Ser His Asn
                165                 170                 175

Pro Glu Glu Gln Leu Ser Ser Lys Asp Leu Val Ser Cys Ala Tyr Gln
            180                 185                 190

Val Ala Arg Gly Met Glu Tyr Leu Ala Ser Lys Lys Cys Ile His Arg
        195                 200                 205

Asp Leu Ala Ala Arg Asn Val Leu Val Thr Glu Asp Asn Val Met Lys
    210                 215                 220

Ile Ala Asp Phe Gly Leu Ala Arg Asp Ile His His Ile Asp Tyr Tyr
225                 230                 235                 240

Lys Lys Thr Thr Asn Gly Arg Leu Pro Val Lys Trp Met Ala Pro Glu
                245                 250                 255

Ala Leu Phe Asp Arg Ile Tyr Thr His Gln Ser Asp Val Trp Ser Phe
            260                 265                 270
```

```
Gly Val Leu Leu Trp Glu Ile Phe Thr Leu Gly Ser Pro Tyr Pro
            275                 280                 285
Gly Val Pro Val Glu Glu Leu Phe Lys Leu Leu Lys Glu Gly His Arg
            290                 295                 300
Met Asp Lys Pro Ser Asn Cys Thr Asn Glu Leu Tyr Met Met Met Arg
305                 310                 315                 320
Asp Cys Trp His Ala Val Pro Ser Gln Arg Pro Thr Phe Lys Gln Leu
                325                 330                 335
Val Glu Asp Leu Asp Arg Ile Val Ala Leu Thr Ser Asn Gln Glu
            340                 345                 350

<210> SEQ ID NO 4
<211> LENGTH: 933
<212> TYPE: DNA
<213> ORGANISM: Homo sapiens

<400> SEQUENCE: 4
atgctagcag gggtctctga gtatgagctt cccgaagacc ctcgctggga gctgcctcgg      60
gacagactgg tcttaggcaa acccctggga gagggctgct tgggcaggt ggtgttggca     120 gaggctatcg gctggacaa ggacaaaccc aaccgtgtga ccaaagtggc tgtgaagatg     180
ttgaagtcgg acgcaacaga gaaagacttg tcagacctga tctcagaaat ggagatgatg     240
aagatgatcg ggaagcataa gaatatcatc aacctgctgg gggcctgcac gcaggatggt     300
cccttgtatg tcatcgtgga gtatgcctcc aagggcaacc tgcgggagta cctgcaggcc     360
cggaggcccc cagggctgga atactgctac aaccccagcc acaacccaga ggagcagctc     420
tcctccaagg acctggtgtc ctgcgcctac caggtggccc gaggcatgga gtatctggcc     480
tccaagaagt gcatacaccg agacctggca gccaggaatg tcctggtgac agaggacaat     540
gtgatgaaga tagcagactt tggcctcgca cgggacattc accatcga ctactataaa      600 aagacaacca acggccgact gcctgtgaag tggatggcac ccgaggcatt atttgaccgg     660
atctacaccc accagagtga tgtgtggtct ttcggggtgc tcctgtggga gatcttcact     720
ctgggcggct ccccataccc cggtgtgcct gtggaggaac ttttcaagct gctgaaggag     780
ggtcaccgca tggacaagcc cagtaactgc accaacgagc tgtacatgat gatgcgggac     840
tgctggcatg cagtgccctc acagagaccc accttcaagc agctggtgga agacctggac     900
cgcatcgtgg ccttgacctc caaccaggag tag                                933

<210> SEQ ID NO 5
<211> LENGTH: 1056
<212> TYPE: DNA
<213> ORGANISM: Homo sapiens

<400> SEQUENCE: 5
atgcggggtt ctcatcatca tcatcatcat ggtatggcta gcatgactgg tggacagcaa      60
atgggtcggg atctgtacga cgatgacgat aaggatccga gctcgagatc tgcagctggt     120
accatggtag cagggtctc tgagtatgag cttcccgaag accctcgctg ggagctgcct     180
cgggacagac tggtcttagg caaacccctg ggagagggcg cctttgggca ggtggtgttg     240
gcagaggcta tcgggctgga caaggacaaa cccaaccgtg tgaccaaagt ggctgtgaag     300
atgttgaagt cggacgcaac agagaaagac ttgtcagacc tgatctcaga aatggagatg     360
atgaagatga tcgggaagca taagaatatc atcaacctgc tggggcctg cacgcaggat     420 ggtcccttgt atgtcatcgt ggagtatgcc tccaagggca acctgcggga gtacctgcag     480
```

```
gcccggaggc cccaggggct ggaatactcc tacaacccca gccacaaccc agaggagcag    540
ctctcctcca aggacctggt gtcctgcgcc taccaggtgg cccgaggcat ggagtatctg    600
gcctccaaga agtgcataca ccgagacctg gcagccagga atgtcctggt gacagaggac    660
aatgtgatga agatagcaga ctttggcctc gcacgggaca ttcaccacat cgactactat    720
aaaaagacaa ccaacggccg actgcctgtg aagtggatgg cacccgaggc attatttgac    780
cggatctaca cccaccagag tgatgtgtgg tctttcgggg tgctcctgtg ggagatcttc    840
actctgggcg gctccccata ccccggtgtg cctgtggagg aacttttcaa gctgctgaag    900
gagggtcacc gcatggacaa gcccagtaac tgcaccaacg agctgtacat gatgatgcgg    960
gactgctggc atgcagtgcc ctcacagaga cccaccttca agcagctggt ggaagacctg   1020
gaccgcatcg tggccttgac ctccaaccag gagtag                             1056

<210> SEQ ID NO 6
<211> LENGTH: 310
<212> TYPE: PRT
<213> ORGANISM: Homo sapiens

<400> SEQUENCE: 6

Met Leu Ala Gly Val Ser Glu Tyr Glu Leu Pro Glu Asp Pro Arg Trp
  1               5                  10                  15

Glu Leu Pro Arg Asp Arg Leu Val Leu Gly Lys Pro Leu Gly Glu Gly
                 20                  25                  30

Cys Phe Gly Gln Val Val Leu Ala Glu Ala Ile Gly Leu Asp Lys Asp
             35                  40                  45

Lys Pro Asn Arg Val Thr Lys Val Ala Val Lys Met Leu Lys Ser Asp
         50                  55                  60

Ala Thr Glu Lys Asp Leu Ser Asp Leu Ile Ser Glu Met Glu Met Met
 65                  70                  75                  80

Lys Met Ile Gly Lys His Lys Asn Ile Ile Asn Leu Leu Gly Ala Cys
                 85                  90                  95

Thr Gln Asp Gly Pro Leu Tyr Val Ile Val Glu Tyr Ala Ser Lys Gly
            100                 105                 110

Asn Leu Arg Glu Tyr Leu Gln Ala Arg Arg Pro Pro Gly Leu Glu Tyr
        115                 120                 125

Cys Tyr Asn Pro Ser His Asn Pro Glu Glu Gln Leu Ser Ser Lys Asp
    130                 135                 140

Leu Val Ser Cys Ala Tyr Gln Val Ala Arg Gly Met Glu Tyr Leu Ala
145                 150                 155                 160

Ser Lys Lys Cys Ile His Arg Asp Leu Ala Ala Arg Asn Val Leu Val
                165                 170                 175

Thr Glu Asp Asn Val Met Lys Ile Ala Asp Phe Gly Leu Ala Arg Asp
            180                 185                 190

Ile His His Ile Asp Tyr Tyr Lys Lys Thr Thr Asn Gly Arg Leu Pro
        195                 200                 205

Val Lys Trp Met Ala Pro Glu Ala Leu Phe Asp Arg Ile Tyr Thr His
    210                 215                 220

Gln Ser Asp Val Trp Ser Phe Gly Val Leu Leu Trp Glu Ile Phe Thr
225                 230                 235                 240

Leu Gly Gly Ser Pro Tyr Pro Gly Val Pro Val Glu Glu Leu Phe Lys
                245                 250                 255

Leu Leu Lys Glu Gly His Arg Met Asp Lys Pro Ser Asn Cys Thr Asn
            260                 265                 270
```

```
Glu Leu Tyr Met Met Met Arg Asp Cys Trp His Ala Val Pro Ser Gln
        275                 280                 285

Arg Pro Thr Phe Lys Gln Leu Val Glu Asp Leu Asp Arg Ile Val Ala
    290                 295                 300

Leu Thr Ser Asn Gln Glu
305                 310

<210> SEQ ID NO 7
<211> LENGTH: 310
<212> TYPE: PRT
<213> ORGANISM: Homo sapiens

<400> SEQUENCE: 7

Met Leu Ala Gly Val Ser Glu Tyr Glu Leu Pro Glu Asp Pro Lys Trp
  1               5                  10                  15

Glu Phe Pro Arg Asp Lys Leu Thr Leu Gly Lys Pro Leu Gly Glu Gly
             20                  25                  30

Cys Phe Gly Gln Val Val Met Ala Glu Ala Val Gly Ile Asp Lys Asp
         35                  40                  45

Lys Pro Lys Glu Ala Val Thr Val Ala Val Lys Met Leu Lys Asp Asp
     50                  55                  60

Ala Thr Glu Lys Asp Leu Ser Asp Leu Val Ser Glu Met Glu Met Met
 65                  70                  75                  80

Lys Met Ile Gly Lys His Lys Asn Ile Ile Asn Leu Leu Gly Ala Cys
                 85                  90                  95

Thr Gln Asp Gly Pro Leu Tyr Val Ile Val Glu Tyr Ala Ser Lys Gly
            100                 105                 110

Asn Leu Arg Glu Tyr Leu Arg Ala Arg Arg Pro Pro Gly Met Glu Tyr
        115                 120                 125

Ser Tyr Asp Ile Asn Arg Val Pro Glu Glu Gln Met Thr Phe Lys Asp
    130                 135                 140

Leu Val Ser Cys Thr Tyr Gln Leu Ala Arg Gly Met Glu Tyr Leu Ala
145                 150                 155                 160

Ser Gln Lys Cys Ile His Arg Asp Leu Ala Ala Arg Asn Val Leu Val
                165                 170                 175

Thr Glu Asn Asn Val Met Lys Ile Ala Asp Phe Gly Leu Ala Arg Asp
            180                 185                 190

Ile Asn Asn Ile Asp Tyr Tyr Lys Lys Thr Thr Asn Gly Arg Leu Pro
        195                 200                 205

Val Lys Trp Met Ala Pro Glu Ala Leu Phe Asp Arg Val Tyr Thr His
    210                 215                 220

Gln Ser Asp Val Trp Ser Phe Gly Val Leu Met Trp Glu Ile Phe Thr
225                 230                 235                 240

Leu Gly Gly Ser Pro Tyr Pro Gly Ile Pro Val Glu Glu Leu Phe Lys
                245                 250                 255

Leu Leu Lys Glu Gly His Arg Met Asp Lys Pro Ala Asn Cys Thr Asn
            260                 265                 270

Glu Leu Tyr Met Met Met Arg Asp Cys Trp His Ala Val Pro Ser Gln
        275                 280                 285

Arg Pro Thr Phe Lys Gln Leu Val Glu Asp Leu Asp Arg Ile Val Ala
    290                 295                 300

Leu Thr Ser Asn Gln Glu
305                 310
```

```
<210> SEQ ID NO 8
<211> LENGTH: 310
<212> TYPE: PRT
<213> ORGANISM: Homo sapiens

<400> SEQUENCE: 8

Met Leu Ala Asn Val Ser Glu Leu Glu Leu Pro Ala Asp Pro Lys Trp
 1               5                  10                  15

Glu Leu Ser Arg Ala Arg Leu Thr Leu Gly Lys Pro Leu Gly Glu Gly
            20                  25                  30

Cys Phe Gly Gln Val Val Met Ala Glu Ala Ile Gly Ile Asp Lys Asp
        35                  40                  45

Arg Ala Ala Lys Pro Val Thr Val Ala Val Lys Met Leu Lys Asp Asp
    50                  55                  60

Ala Thr Asp Lys Asp Leu Ser Asp Leu Val Ser Glu Met Glu Met Met
65                  70                  75                  80

Lys Met Ile Gly Lys His Lys Asn Ile Ile Asn Leu Leu Gly Ala Cys
                85                  90                  95

Thr Gln Gly Gly Pro Leu Tyr Val Leu Val Glu Tyr Ala Ala Lys Gly
            100                 105                 110

Asn Leu Arg Glu Phe Leu Arg Ala Arg Arg Pro Pro Gly Leu Asp Tyr
        115                 120                 125

Ser Phe Asp Thr Cys Lys Pro Pro Glu Glu Gln Leu Thr Phe Lys Asp
    130                 135                 140

Leu Val Ser Cys Ala Tyr Gln Val Ala Arg Gly Met Glu Tyr Leu Ala
145                 150                 155                 160

Ser Gln Lys Cys Ile His Arg Asp Leu Ala Ala Arg Asn Val Leu Val
                165                 170                 175

Thr Glu Asp Asn Val Met Lys Ile Ala Asp Phe Gly Leu Ala Arg Asp
            180                 185                 190

Val His Asn Leu Asp Tyr Tyr Lys Lys Thr Thr Asn Gly Arg Leu Pro
        195                 200                 205

Val Lys Trp Met Ala Pro Glu Ala Leu Phe Asp Arg Val Tyr Thr His
    210                 215                 220

Gln Ser Asp Val Trp Ser Phe Gly Val Leu Leu Trp Glu Ile Phe Thr
225                 230                 235                 240

Leu Gly Gly Ser Pro Tyr Pro Gly Ile Pro Val Glu Glu Leu Phe Lys
                245                 250                 255

Leu Leu Lys Glu Gly His Arg Met Asp Lys Pro Ala Asn Cys Thr His
            260                 265                 270

Asp Leu Tyr Met Ile Met Arg Glu Cys Trp His Ala Ala Pro Ser Gln
        275                 280                 285

Arg Pro Thr Phe Lys Gln Leu Val Glu Asp Leu Asp Arg Val Leu Thr
    290                 295                 300

Val Thr Ser Thr Asp Glu
305                 310

<210> SEQ ID NO 9
<211> LENGTH: 309
<212> TYPE: PRT
<213> ORGANISM: Homo sapiens

<400> SEQUENCE: 9

Leu Leu Ala Gly Leu Val Ser Leu Asp Leu Pro Leu Asp Pro Leu Trp
 1               5                  10                  15

Glu Phe Pro Arg Asp Arg Leu Val Leu Gly Lys Pro Leu Gly Glu Gly
```

```
                        20                  25                  30
Cys Phe Gly Gln Val Val Arg Ala Glu Ala Phe Gly Met Asp Pro Ala
                35                  40                  45
Arg Pro Asp Gln Ala Ser Thr Val Ala Val Lys Met Leu Lys Asp Asn
         50                  55                  60
Ala Ser Asp Lys Asp Leu Ala Asp Leu Val Ser Glu Met Glu Val Met
 65                  70                  75                  80
Lys Leu Ile Gly Arg His Lys Asn Ile Ile Asn Leu Leu Gly Val Cys
                 85                  90                  95
Thr Gln Glu Gly Pro Leu Tyr Val Ile Val Glu Cys Ala Ala Lys Gly
                100                 105                 110
Asn Leu Arg Glu Phe Leu Arg Ala Arg Arg Pro Gly Pro Asp Leu
             115                 120                 125
Ser Pro Asp Gly Pro Arg Ser Ser Glu Gly Pro Leu Ser Phe Pro Val
            130                 135                 140
Leu Val Ser Cys Ala Tyr Gln Val Ala Arg Gly Met Gln Tyr Leu Glu
145                 150                 155                 160
Ser Arg Lys Cys Ile His Arg Asp Leu Ala Ala Arg Asn Val Leu Val
                165                 170                 175
Thr Glu Asp Asn Val Met Lys Ile Ala Asp Phe Gly Leu Ala Arg Gly
            180                 185                 190
Val His His Ile Asp Tyr Tyr Lys Lys Thr Ser Asn Gly Arg Leu Pro
            195                 200                 205
Val Lys Trp Met Ala Pro Glu Ala Leu Phe Asp Arg Val Tyr Thr His
        210                 215                 220
Gln Ser Asp Val Trp Ser Phe Gly Ile Leu Leu Trp Glu Ile Phe Thr
225                 230                 235                 240
Leu Gly Gly Ser Pro Tyr Pro Gly Ile Pro Val Glu Glu Leu Phe Ser
                245                 250                 255
Leu Leu Arg Glu Gly His Arg Met Asp Arg Pro Pro His Cys Pro Pro
                260                 265                 270
Glu Leu Tyr Gly Leu Met Arg Glu Cys Trp His Ala Ala Pro Ser Gln
                275                 280                 285
Arg Pro Thr Phe Lys Gln Leu Val Glu Ala Leu Asp Lys Val Leu Leu
            290                 295                 300
Ala Val Ser Glu Glu
305

<210> SEQ ID NO 10
<211> LENGTH: 318
<212> TYPE: PRT
<213> ORGANISM: Drosophila melanogaster

<400> SEQUENCE: 10

Pro Ala Gln Gly Phe Asn Glu Tyr Glu Phe Pro Leu Asp Ser Asn Trp
 1                5                  10                  15
Glu Ile Pro Arg Gln Gln Leu Ser Leu Gly Ser Ile Leu Gly Glu Gly
             20                  25                  30
Ala Phe Gly Arg Val Val Met Ala Glu Ala Glu Gly Leu Pro Arg Ser
         35                  40                  45
Pro Gln Leu Ala Glu Thr Ile Val Ala Val Lys Met Val Lys Glu Glu
     50                  55                  60
His Thr Asp Thr Asp Met Ala Ser Leu Val Arg Glu Met Glu Val Met
 65                  70                  75                  80
```

```
Lys Met Ile Gly Lys His Ile Asn Ile Ile Asn Leu Leu Gly Cys Cys
                 85                  90                  95

Ser Gln Gly Gly Pro Leu Trp Val Ile Val Glu Tyr Ala Pro His Gly
            100                 105                 110

Asn Leu Lys Asp Phe Leu Lys Gln Asn Arg Pro Gly Ala Pro Gln Arg
        115                 120                 125

Arg Ser Asp Ser Asp Gly Tyr Leu Asp Asp Lys Pro Leu Ile Ser Thr
    130                 135                 140

Gln His Leu Gly Glu Lys Glu Leu Thr Lys Phe Ala Phe Gln Ile Ala
145                 150                 155                 160

Arg Gly Met Glu Tyr Leu Ala Ser Arg Arg Cys Ile His Arg Asp Leu
                165                 170                 175

Ala Ala Arg Asn Val Leu Val Ser Asp Gly Tyr Val Met Lys Ile Ala
            180                 185                 190

Asp Phe Gly Leu Ala Arg Asp Ile Gln Asp Thr Glu Tyr Tyr Arg Lys
        195                 200                 205

Asn Thr Asn Gly Arg Leu Pro Ile Lys Trp Met Ala Pro Glu Ser Leu
    210                 215                 220

Gln Glu Lys Lys Tyr Asp Ser Gln Ser Asp Val Trp Ser Tyr Gly Val
225                 230                 235                 240

Leu Leu Trp Glu Ile Met Thr Tyr Gly Asp Gln Pro Tyr Pro His Ile
                245                 250                 255

Leu Ser Ala Glu Glu Leu Tyr Ser Tyr Leu Ile Thr Gly Gln Arg Met
            260                 265                 270

Glu Lys Pro Ala Lys Cys Ser Leu Asn Ile Tyr Val Val Met Arg Gln
        275                 280                 285

Cys Trp His Phe Gln Ser Cys Ala Arg Pro Thr Phe Ala Glu Leu Val
    290                 295                 300

Glu Ser Phe Asp Gly Ile Leu Gln Gln Ala Ser Ser Asn Pro
305                 310                 315

<210> SEQ ID NO 11
<211> LENGTH: 322
<212> TYPE: PRT
<213> ORGANISM: Caenorhabditis elegans

<400> SEQUENCE: 11

Glu Asn Thr Val Leu Ser Glu Tyr Glu Val Asp Ser Asp Pro Val Trp
  1               5                  10                  15

Glu Val Glu Arg Ser Lys Leu Ser Leu Val His Met Leu Gly Glu Gly
             20                  25                  30

Ala Phe Gly Glu Val Trp Lys Ala Thr Tyr Lys Glu Thr Glu Asn Asn
         35                  40                  45

Glu Ile Ala Val Ala Val Lys Lys Leu Lys Met Ser Ala His Glu Lys
     50                  55                  60

Glu Leu Ile Asp Leu Val Ser Glu Met Glu Thr Phe Lys Val Ile Gly
 65                  70                  75                  80

Glu His Glu Asn Val Leu Arg Leu Ile Gly Cys Cys Thr Gly Ala Gly
                 85                  90                  95

Pro Leu Tyr Val Val Val Glu Leu Cys Lys His Gly Asn Leu Arg Asp
            100                 105                 110

Phe Leu Arg Ala His Arg Pro Lys Glu Glu Lys Ala Lys Lys Ser Ser
        115                 120                 125

Gln Glu Leu Thr Asp Tyr Leu Glu Pro Arg Lys Ala Ser Asp Lys Asp
    130                 135                 140
```

-continued

```
Asp Ile Glu Leu Ile Pro Asn Leu Thr Gln Arg His Leu Val Gln Phe
145                 150                 155                 160

Ala Trp Gln Val Ala Gln Gly Met Asn Phe Leu Ala Ser Lys Lys Ile
                165                 170                 175

Ile His Arg Asp Leu Ala Ala Arg Asn Val Leu Val Gly Asp Gly His
            180                 185                 190

Val Leu Lys Ile Ser Asp Phe Gly Leu Ser Arg Asp Val His Cys Asn
        195                 200                 205

Asp Tyr Tyr Arg Lys Arg Gly Asn Gly Arg Leu Pro Ile Lys Trp Met
    210                 215                 220

Ala Leu Glu Ala Leu Asp Ser Asn Val Tyr Thr Val Glu Ser Asp Val
225                 230                 235                 240

Trp Ser Tyr Gly Val Leu Leu Trp Glu Ile Met Thr Leu Gly Gly Thr
                245                 250                 255

Pro Tyr Pro Thr Ile Ala Met Pro Glu Leu Tyr Ala Asn Leu Lys Glu
            260                 265                 270

Gly Tyr Arg Met Glu Pro Pro His Leu Cys Pro Gln Glu Val Tyr His
        275                 280                 285

Leu Met Cys Ser Cys Trp Arg Glu Lys Leu Glu Glu Arg Pro Ser Phe
    290                 295                 300

Lys Thr Ile Val Asp Tyr Leu Asp Trp Met Leu Thr Met Thr Asn Glu
305                 310                 315                 320

Thr Ile

<210> SEQ ID NO 12
<211> LENGTH: 306
<212> TYPE: PRT
<213> ORGANISM: Unknown Organism
<220> FEATURE:
<223> OTHER INFORMATION: Description of Unknown Organism: Insulin
      receptor tyrosine kinase

<400> SEQUENCE: 12

Val Phe Pro Cys Ser Val Tyr Val Pro Asp Glu Trp Glu Val Ser Arg
  1               5                  10                  15

Glu Lys Ile Thr Leu Leu Arg Glu Leu Gly Gln Gly Ser Phe Gly Met
                20                  25                  30

Val Tyr Glu Gly Asn Ala Arg Asp Ile Ile Lys Gly Glu Ala Glu Thr
            35                  40                  45

Arg Val Ala Val Lys Thr Val Asn Glu Ser Ala Ser Leu Arg Glu Arg
        50                  55                  60

Ile Glu Phe Leu Asn Glu Ala Ser Val Met Lys Gly Phe Thr Cys His
65                  70                  75                  80

His Val Val Arg Leu Leu Gly Val Val Ser Lys Gly Gln Pro Thr Leu
                85                  90                  95

Val Val Met Glu Leu Met Ala His Gly Asp Leu Lys Ser Tyr Leu Arg
            100                 105                 110

Ser Leu Arg Pro Glu Ala Glu Asn Asn Pro Gly Arg Pro Pro Pro Thr
        115                 120                 125

Leu Gln Glu Met Ile Gln Met Ala Ala Glu Ile Ala Asp Gly Met Ala
    130                 135                 140

Tyr Leu Asn Ala Lys Lys Phe Val His Arg Asp Leu Ala Ala Arg Asn
145                 150                 155                 160

Cys Met Val Ala His Asp Phe Thr Val Lys Ile Gly Asp Phe Gly Met
                165                 170                 175
```

```
Thr Arg Asp Ile Tyr Glu Thr Asp Tyr Tyr Arg Lys Gly Gly Lys Gly
            180                 185                 190

Leu Leu Pro Val Arg Trp Met Ala Pro Glu Ser Leu Lys Asp Gly Val
        195                 200                 205

Phe Thr Thr Ser Ser Asp Met Trp Ser Phe Gly Val Val Leu Trp Glu
        210                 215                 220

Ile Thr Ser Leu Ala Glu Gln Pro Tyr Gln Gly Leu Ser Asn Glu Gln
225                 230                 235                 240

Val Leu Lys Phe Val Met Asp Gly Gly Tyr Leu Asp Gln Pro Asp Asn
                245                 250                 255

Cys Pro Glu Arg Val Thr Asp Leu Met Arg Met Cys Trp Gln Phe Asn
            260                 265                 270

Pro Lys Met Arg Pro Thr Phe Leu Glu Ile Val Asn Leu Leu Lys Asp
        275                 280                 285

Asp Leu His Pro Ser Phe Pro Glu Val Ser Phe Phe His Ser Glu Glu
        290                 295                 300

Asn Lys
305

<210> SEQ ID NO 13
<211> LENGTH: 299
<212> TYPE: PRT
<213> ORGANISM: Homo sapiens

<400> SEQUENCE: 13

Leu Pro Glu Asp Pro Arg Trp Glu Leu Pro Arg Asp Arg Leu Val Leu
  1               5                  10                  15

Gly Lys Pro Leu Gly Glu Gly Cys Phe Gly Gln Val Val Leu Ala Glu
                20                  25                  30

Ala Ile Gly Leu Asp Lys Asp Lys Pro Asn Arg Val Thr Lys Val Ala
            35                  40                  45

Val Lys Met Leu Lys Ser Asp Ala Thr Glu Lys Asp Leu Ser Asp Leu
    50                  55                  60

Ile Ser Glu Met Glu Met Met Lys Met Ile Gly Lys His Lys Asn Ile
 65                  70                  75                  80

Ile Asn Leu Leu Gly Ala Cys Thr Gln Asp Gly Pro Leu Tyr Val Ile
                85                  90                  95

Val Glu Tyr Ala Ser Lys Gly Asn Leu Arg Glu Tyr Leu Gln Ala Arg
                100                 105                 110

Arg Pro Pro Gly Leu Glu Tyr Cys Tyr Asn Pro Ser His Asn Pro Glu
            115                 120                 125

Glu Gln Leu Ser Ser Lys Asp Leu Val Ser Cys Ala Tyr Gln Val Ala
130                 135                 140

Arg Gly Met Glu Tyr Leu Ala Ser Lys Lys Cys Ile His Arg Asp Leu
145                 150                 155                 160

Ala Ala Arg Asn Val Leu Val Thr Glu Asp Asn Val Met Lys Ile Ala
                165                 170                 175

Asp Phe Gly Leu Ala Arg Asp Ile His His Ile Asp Tyr Tyr Lys Lys
            180                 185                 190

Thr Thr Asn Gly Arg Leu Pro Val Lys Trp Met Ala Pro Glu Ala Leu
        195                 200                 205

Phe Asp Arg Ile Tyr Thr His Gln Ser Asp Val Trp Ser Phe Gly Val
        210                 215                 220

Leu Leu Trp Glu Ile Phe Thr Leu Gly Gly Ser Pro Tyr Pro Gly Val
```

```
                225                 230                 235                 240
Pro Val Glu Glu Leu Phe Lys Leu Leu Lys Glu Gly His Arg Met Asp
                    245                 250                 255

Lys Pro Ser Asn Cys Thr Asn Glu Leu Tyr Met Met Arg Asp Cys
                260                 265                 270

Trp His Ala Val Pro Ser Gln Arg Pro Thr Phe Lys Gln Leu Val Glu
            275                 280                 285

Asp Leu Asp Arg Ile Val Ala Leu Thr Ser Asn
        290                 295

<210> SEQ ID NO 14
<211> LENGTH: 279
<212> TYPE: PRT
<213> ORGANISM: Homo sapiens

<400> SEQUENCE: 14

Pro Asn Gln Ala Leu Leu Arg Ile Leu Lys Glu Thr Glu Phe Lys Lys
 1               5                   10                  15

Ile Lys Val Leu Gly Ser Gly Ala Phe Gly Thr Val Tyr Lys Gly Leu
                20                  25                  30

Trp Ile Pro Glu Gly Glu Lys Val Lys Ile Pro Val Ala Ile Lys Glu
            35                  40                  45

Leu Arg Glu Ala Thr Ser Pro Lys Ala Asn Lys Glu Ile Leu Asp Glu
    50                  55                  60

Ala Tyr Val Met Ala Ser Val Asp Asn Pro His Val Cys Arg Leu Leu
65                  70                  75                  80

Gly Ile Cys Leu Thr Ser Thr Val Gln Leu Ile Thr Gln Leu Met Pro
                85                  90                  95

Phe Gly Cys Leu Leu Asp Tyr Val Arg Glu His Lys Asp Asn Ile Gly
            100                 105                 110

Ser Gln Tyr Leu Leu Asn Trp Cys Val Gln Ile Ala Lys Gly Met Asn
        115                 120                 125

Tyr Leu Glu Asp Arg Arg Leu Val His Arg Asp Leu Ala Ala Arg Asn
130                 135                 140

Val Leu Val Lys Thr Pro Gln His Val Lys Ile Thr Asp Phe Gly Leu
145                 150                 155                 160

Ala Lys Leu Leu Gly Ala Glu Glu Lys Glu Tyr His Ala Glu Gly Gly
                165                 170                 175

Lys Val Pro Ile Lys Trp Met Ala Leu Glu Ser Ile Leu His Arg Ile
            180                 185                 190

Tyr Thr His Gln Ser Asp Val Trp Ser Tyr Gly Val Thr Val Trp Glu
        195                 200                 205

Leu Met Thr Phe Gly Ser Lys Pro Tyr Asp Gly Ile Pro Ala Ser Glu
    210                 215                 220

Ile Ser Ser Ile Leu Glu Lys Gly Glu Arg Leu Pro Gln Pro Pro Ile
225                 230                 235                 240

Cys Thr Ile Asp Val Tyr Met Ile Met Val Lys Cys Trp Met Ile Asp
                245                 250                 255

Ala Asp Ser Arg Pro Lys Phe Arg Glu Leu Ile Ile Glu Phe Ser Lys
            260                 265                 270

Met Ala Arg Asp Pro Gln Arg
        275

<210> SEQ ID NO 15
<211> LENGTH: 290
```

```
<212> TYPE: PRT
<213> ORGANISM: Homo sapiens

<400> SEQUENCE: 15

Val Tyr Val Pro Asp Glu Trp Glu Val Ser Arg Glu Lys Ile Thr Leu
  1               5                  10                  15

Leu Arg Glu Leu Gly Gln Gly Ser Phe Gly Met Val Tyr Glu Gly Asn
             20                  25                  30

Ala Arg Asp Ile Ile Lys Gly Glu Ala Glu Thr Arg Val Ala Val Lys
         35                  40                  45

Thr Val Asn Glu Ser Ala Ser Leu Arg Glu Arg Ile Glu Phe Leu Asn
     50                  55                  60

Glu Ala Ser Val Met Lys Gly Phe Thr Cys His His Val Arg Leu
 65                  70                  75                  80

Leu Gly Val Val Ser Lys Gly Gln Pro Thr Leu Val Val Met Glu Leu
                 85                  90                  95

Met Ala His Gly Asp Leu Lys Ser Tyr Leu Arg Ser Leu Arg Pro Glu
            100                 105                 110

Ala Glu Asn Asn Pro Gly Arg Pro Pro Thr Leu Gln Glu Met Ile
        115                 120                 125

Gln Met Ala Ala Glu Ile Ala Asp Gly Met Ala Tyr Leu Asn Ala Lys
    130                 135                 140

Lys Phe Val His Arg Asp Leu Ala Ala Arg Asn Cys Met Val Ala His
145                 150                 155                 160

Asp Phe Thr Val Lys Ile Gly Asp Phe Gly Met Thr Arg Asp Ile Tyr
                165                 170                 175

Glu Thr Asp Tyr Tyr Arg Lys Gly Gly Lys Gly Leu Leu Pro Val Arg
            180                 185                 190

Trp Met Ala Pro Glu Gly Leu Lys Asp Gly Val Phe Thr Thr Ser Ser
        195                 200                 205

Asp Met Trp Ser Phe Gly Val Val Leu Trp Glu Ile Thr Ser Leu Ala
    210                 215                 220

Glu Gln Pro Tyr Gln Gly Leu Ser Asn Glu Gln Val Leu Lys Phe Val
225                 230                 235                 240

Met Asp Gly Gly Tyr Leu Asp Gln Pro Asp Asn Cys Pro Glu Arg Val
                245                 250                 255

Thr Asp Leu Met Arg Met Cys Trp Gln Phe Asn Pro Lys Met Arg Pro
            260                 265                 270

Thr Phe Leu Glu Ile Val Asn Leu Leu Lys Asp Asp Leu His Pro Ser
        275                 280                 285

Phe Pro
    290

<210> SEQ ID NO 16
<211> LENGTH: 293
<212> TYPE: PRT
<213> ORGANISM: Homo sapiens

<400> SEQUENCE: 16

Leu Pro Tyr Asp Ser Arg Trp Glu Phe Pro Arg Asp Gly Leu Val Leu
  1               5                  10                  15

Gly Arg Val Leu Gly Ser Gly Ala Phe Gly Lys Val Val Glu Gly Thr
             20                  25                  30

Ala Tyr Gly Leu Ser Arg Ser Gln Pro Val Met Lys Val Ala Val Lys
         35                  40                  45
```

-continued

Met Leu Lys Pro Thr Ala Arg Ser Ser Glu Lys Gln Ala Leu Met Ser
 50                  55                  60

Glu Leu Lys Ile Met Thr His Leu Gly Pro His Leu Asn Ile Val Asn
 65                      70                  75                  80

Leu Leu Gly Ala Cys Thr Lys Ser Gly Pro Ile Tyr Ile Ile Thr Glu
                     85                  90                  95

Tyr Cys Phe Tyr Gly Asp Leu Val Asn Tyr Leu His Lys Asn Arg Asp
                100                 105                 110

Ser Phe Leu Ser His His Pro Glu Ser Glu Gly Leu Thr Leu Leu Asp
            115                 120                 125

Leu Leu Ser Phe Thr Tyr Gln Val Ala Arg Gly Met Glu Phe Leu Ala
130                 135                 140

Ser Lys Asn Cys Val His Arg Asp Leu Ala Ala Arg Asn Val Leu Leu
145                 150                 155                 160

Ala Gln Gly Lys Ile Val Lys Ile Cys Asp Phe Gly Leu Ala Arg Asp
                165                 170                 175

Ile Met His Asp Ser Asn Tyr Val Ser Lys Gly Ser Thr Phe Leu Pro
            180                 185                 190

Val Lys Trp Met Ala Pro Glu Ser Ile Phe Asp Asn Leu Tyr Thr Thr
        195                 200                 205

Leu Ser Asp Val Trp Ser Tyr Gly Ile Leu Leu Trp Glu Ile Phe Ser
210                 215                 220

Leu Gly Gly Thr Pro Tyr Pro Gly Met Met Val Asp Ser Thr Phe Tyr
225                 230                 235                 240

Asn Lys Ile Lys Ser Gly Tyr Arg Met Ala Lys Pro Asp His Ala Thr
                245                 250                 255

Ser Glu Val Tyr Glu Ile Met Val Lys Cys Trp Asn Ser Glu Pro Glu
            260                 265                 270

Lys Arg Pro Ser Phe Tyr His Leu Ser Glu Ile Val Glu Asn Leu Leu
        275                 280                 285

Pro Gly Gln Tyr Lys
    290

<210> SEQ ID NO 17
<211> LENGTH: 294
<212> TYPE: PRT
<213> ORGANISM: Homo sapiens

<400> SEQUENCE: 17

Pro Tyr Asp Ala Ser Lys Trp Glu Phe Pro Arg Asp Arg Leu Asn Leu
  1               5                  10                  15

Gly Lys Pro Leu Gly Arg Gly Ala Phe Gly Gln Glu Ile Glu Ala Asp
             20                  25                  30

Ala Phe Gly Ile Asp Lys Thr Ala Thr Cys Arg Thr Val Ala Val Lys
         35                  40                  45

Met Leu Lys Glu Gly Ala Thr His Ser Glu His Arg Ala Leu Met Ser
 50                  55                  60

Glu Leu Lys Ile Leu Ile His Ile Gly His His Leu Asn Val Val Asn
 65                      70                  75                  80

Leu Leu Gly Ala Cys Thr Lys Pro Gly Gly Pro Leu Met Val Ile Val
                     85                  90                  95

Glu Phe Cys Lys Phe Gly Asn Leu Ser Thr Tyr Leu Arg Ser Lys Arg
                100                 105                 110

Asn Glu Phe Val Pro Tyr Lys Thr Lys Asp Phe Leu Thr Leu Glu
            115                 120                 125

```
His Leu Ile Cys Tyr Ser Phe Gln Val Ala Lys Gly Met Glu Phe Leu
    130                 135                 140

Ala Ser Arg Lys Cys Ile His Arg Asp Leu Ala Ala Arg Asn Ile Leu
145                 150                 155                 160

Leu Ser Glu Lys Asn Val Val Lys Ile Cys Asp Phe Gly Leu Ala Arg
                165                 170                 175

Asp Ile Tyr Lys Asp Pro Asp Tyr Val Arg Lys Gly Asp Ala Arg Leu
            180                 185                 190

Pro Leu Lys Trp Met Ala Pro Glu Thr Ile Phe Asp Arg Val Tyr Thr
        195                 200                 205

Ile Gln Ser Asp Val Trp Ser Phe Gly Val Leu Leu Trp Glu Ile Phe
    210                 215                 220

Ser Leu Gly Ala Ser Pro Tyr Pro Gly Val Lys Ile Asp Glu Glu Phe
225                 230                 235                 240

Cys Arg Arg Leu Lys Glu Gly Thr Arg Met Arg Ala Pro Asp Tyr Thr
                245                 250                 255

Thr Pro Glu Met Tyr Gln Thr Met Leu Asp Cys Trp His Gly Glu Pro
            260                 265                 270

Ser Gln Arg Pro Thr Phe Ser Glu Leu Val Glu His Leu Gly Asn Leu
        275                 280                 285

Leu Gln Ala Asn Ala Gln
    290

<210> SEQ ID NO 18
<211> LENGTH: 288
<212> TYPE: PRT
<213> ORGANISM: Homo sapiens

<400> SEQUENCE: 18

His Ser Thr Ser Asp Lys Met His Phe Pro Arg Ser Ser Leu Gln Pro
1               5                   10                  15

Ile Thr Thr Leu Gly Lys Ser Glu Phe Gly Glu Val Phe Leu Ala Lys
            20                  25                  30

Ala Gln Gly Leu Glu Glu Gly Val Ala Glu Thr Leu Val Leu Val Lys
        35                  40                  45

Ser Leu Gln Ser Lys Asp Glu Gln Gln Leu Asp Phe Arg Arg Glu
    50                  55                  60

Leu Glu Met Phe Gly Lys Leu Asn His Ala Asn Val Val Arg Leu Leu
65                  70                  75                  80

Gly Leu Cys Arg Glu Ala Glu Pro His Tyr Met Val Leu Glu Tyr Val
                85                  90                  95

Asp Leu Gly Asp Leu Lys Gln Phe Leu Arg Ile Ser Lys Ser Lys Asp
            100                 105                 110

Glu Lys Leu Lys Ser Gln Pro Leu Ser Thr Lys Gln Lys Val Ala Leu
        115                 120                 125

Cys Thr Gln Val Ala Leu Gly Met Glu His Leu Ser Asn Asn Arg Phe
130                 135                 140

Val His Lys Asp Leu Ala Ala Arg Asn Cys Leu Val Ser Ala Gln Arg
145                 150                 155                 160

Gln Val Lys Val Ser Ala Leu Gly Leu Ser Lys Asp Val Tyr Asn Ser
                165                 170                 175

Glu Tyr Tyr His Phe Arg Gln Ala Trp Val Pro Leu Arg Trp Met Ser
            180                 185                 190

Pro Glu Ala Ile Leu Glu Gly Asp Phe Ser Thr Lys Ser Asp Val Trp
```

```
                 195                 200                 205
Ala Phe Gly Val Leu Met Trp Glu Val Phe Thr His Gly Glu Met Pro
            210                 215                 220

His Gly Gly Gln Ala Asp Asp Glu Val Leu Ala Asp Leu Gln Ala Gly
225                 230                 235                 240

Lys Ala Arg Leu Pro Gln Pro Glu Gly Cys Pro Ser Lys Leu Tyr Arg
                245                 250                 255

Leu Met Gln Arg Cys Trp Ala Leu Ser Pro Lys Asp Arg Pro Ser Phe
                260                 265                 270

Ser Glu Ile Ala Ser Ala Leu Gly Asp Ser Thr Val Asp Ser Lys Pro
                275                 280                 285
```

<210> SEQ ID NO 19
<211> LENGTH: 282
<212> TYPE: PRT
<213> ORGANISM: Homo sapiens

<400> SEQUENCE: 19

```
Ala Val Gln His Val Val Ile Gly Pro Ser Ser Leu Ile Val His Phe
  1               5                  10                  15

Asn Glu Val Ile Gly Arg Gly His Phe Gly Cys Val Tyr His Gly Thr
                 20                  25                  30

Leu Leu Asp Asn Asp Gly Lys Lys Ile His Cys Ala Val Lys Ser Leu
             35                  40                  45

Asn Arg Ile Thr Asp Ile Gly Glu Val Ser Gln Phe Leu Thr Glu Gly
         50                  55                  60

Ile Ile Met Lys Asp Phe Ser His Pro Asn Val Leu Ser Leu Leu Gly
 65                  70                  75                  80

Ile Cys Leu Arg Ser Glu Gly Ser Pro Leu Val Val Leu Pro Tyr Met
                 85                  90                  95

Lys His Gly Asp Leu Arg Asn Phe Ile Arg Asn Glu Thr His Asn Pro
                100                 105                 110

Thr Val Lys Asp Leu Ile Gly Phe Gly Leu Gln Val Ala Lys Gly Met
            115                 120                 125

Lys Tyr Leu Ala Ser Lys Lys Phe Val His Arg Asp Leu Ala Ala Arg
        130                 135                 140

Asn Cys Met Leu Asp Glu Lys Phe Thr Val Lys Val Ala Asp Phe Gly
145                 150                 155                 160

Leu Ala Arg Asp Met Tyr Asp Lys Glu Tyr Tyr Ser Val His Asn Lys
                165                 170                 175

Thr Gly Ala Lys Leu Pro Val Lys Trp Met Ala Leu Glu Ser Leu Gln
            180                 185                 190

Thr Gln Lys Phe Thr Thr Lys Ser Asp Val Trp Ser Phe Gly Val Val
        195                 200                 205

Leu Trp Glu Leu Met Thr Arg Gly Ala Pro Pro Tyr Pro Asp Val Asn
    210                 215                 220

Thr Phe Asp Ile Thr Val Tyr Leu Leu Gln Gly Arg Arg Leu Leu Gln
225                 230                 235                 240

Pro Glu Tyr Cys Pro Asp Pro Leu Tyr Glu Val Met Leu Lys Cys Trp
                245                 250                 255

His Pro Lys Ala Glu Met Arg Pro Ser Phe Ser Glu Leu Val Ser Arg
            260                 265                 270

Ile Ser Ala Ile Phe Ser Thr Phe Ile Gly
        275                 280
```

```
<210> SEQ ID NO 20
<211> LENGTH: 294
<212> TYPE: PRT
<213> ORGANISM: Homo sapiens

<400> SEQUENCE: 20

Phe Ser Asp Ala Cys Val His His Ile Lys Arg Arg Asp Ile Val Leu
 1               5                  10                  15

Lys Trp Glu Leu Gly Glu Gly Ala Phe Gly Lys Val Phe Leu Ala Glu
             20                  25                  30

Cys His Asn Leu Leu Pro Glu Gln Asp Lys Met Leu Val Ala Val Lys
         35                  40                  45

Ala Leu Lys Glu Ala Ser Glu Ser Ala Arg Gln Asp Phe Gln Arg Glu
     50                  55                  60

Ala Glu Leu Leu Thr Met Leu Gln His Gln His Ile Val Arg Phe Phe
 65                  70                  75                  80

Gly Val Cys Thr Glu Gly Arg Pro Leu Leu Met Val Phe Glu Tyr Met
                 85                  90                  95

Arg His Gly Asp Leu Asn Arg Phe Leu Arg Ser His Gly Pro Asp Ala
            100                 105                 110

Lys Leu Leu Ala Gly Gly Glu Asp Val Ala Pro Gly Pro Leu Gly Leu
        115                 120                 125

Gly Gln Leu Leu Ala Val Ala Ser Gln Val Ala Ala Gly Met Val Tyr
    130                 135                 140

Leu Ala Gly Leu His Phe Val His Arg Asp Leu Ala Thr Arg Asn Cys
145                 150                 155                 160

Leu Val Gly Gln Gly Leu Val Val Lys Ile Gly Asp Phe Gly Met Ser
                165                 170                 175

Arg Asp Ile Tyr Ser Thr Asp Tyr Tyr Arg Val Gly Gly Arg Thr Met
            180                 185                 190

Leu Pro Ile Arg Trp Met Pro Pro Glu Ser Ile Leu Tyr Arg Lys Phe
        195                 200                 205

Thr Thr Glu Ser Asp Val Trp Ser Phe Gly Val Val Leu Trp Glu Ile
    210                 215                 220

Phe Thr Tyr Gly Lys Gln Pro Trp Tyr Gln Leu Ser Asn Thr Glu Ala
225                 230                 235                 240

Ile Asp Cys Ile Thr Gln Gly Arg Glu Leu Glu Arg Pro Arg Ala Cys
                245                 250                 255

Pro Pro Glu Val Tyr Ala Ile Met Arg Gly Cys Trp Gln Arg Glu Pro
            260                 265                 270

Gln Gln Arg His Ser Ile Lys Asp Val His Ala Arg Leu Gln Ala Leu
        275                 280                 285

Ala Gln Ala Pro Pro Val
    290

<210> SEQ ID NO 21
<211> LENGTH: 290
<212> TYPE: PRT
<213> ORGANISM: Homo sapiens

<400> SEQUENCE: 21

Lys Glu Lys Leu Arg Asp Val Met Val Asp Arg His Lys Val Ala Leu
 1               5                  10                  15

Gly Lys Thr Leu Gly Glu Gly Glu Phe Gly Ala Val Met Glu Gly Gln
             20                  25                  30
```

-continued

```
Leu Asn Gln Asp Asp Ser Ile Leu Lys Val Ala Val Lys Thr Met Lys
             35                  40                  45

Ile Ala Ile Cys Thr Arg Ser Glu Leu Glu Asp Phe Leu Ser Glu Ala
 50                  55                  60

Val Cys Met Lys Glu Phe Asp His Pro Asn Val Met Arg Leu Ile Gly
 65                  70                  75                  80

Val Cys Phe Gln Gly Ser Glu Arg Glu Ser Phe Pro Ala Pro Val Val
                 85                  90                  95

Ile Leu Pro Phe Met Lys His Gly Asp Leu His Ser Phe Leu Leu Tyr
                100                 105                 110

Ser Arg Leu Gly Asp Gln Pro Val Tyr Leu Pro Thr Gln Met Leu Val
            115                 120                 125

Lys Phe Met Ala Asp Ile Ala Ser Gly Met Glu Tyr Leu Ser Thr Lys
130                 135                 140

Arg Phe Ile His Arg Asp Leu Ala Ala Arg Asn Cys Met Leu Asn Glu
145                 150                 155                 160

Asn Met Ser Val Cys Val Ala Asp Phe Gly Leu Ser Lys Lys Ile Tyr
                165                 170                 175

Asn Gly Asp Tyr Tyr Arg Gln Gly Arg Ile Ala Lys Met Pro Val Lys
            180                 185                 190

Trp Ile Ala Ile Glu Ser Leu Ala Asp Arg Val Tyr Thr Ser Lys Ser
        195                 200                 205

Asp Val Trp Ser Phe Gly Val Thr Met Trp Glu Ile Ala Thr Arg Gly
210                 215                 220

Gln Thr Pro Tyr Pro Gly Val Glu Asn Ser Glu Ile Tyr Asp Tyr Leu
225                 230                 235                 240

Arg Gln Gly Asn Arg Leu Lys Gln Pro Ala Asp Cys Leu Asp Gly Leu
                245                 250                 255

Tyr Ala Leu Met Ser Arg Cys Trp Glu Leu Asn Pro Gln Asp Arg Pro
            260                 265                 270

Ser Phe Thr Glu Leu Arg Glu Asp Leu Glu Asn Thr Leu Lys Ala Leu
        275                 280                 285

Pro Pro
    290
```

<210> SEQ ID NO 22
<211> LENGTH: 291
<212> TYPE: PRT
<213> ORGANISM: Homo sapiens

<400> SEQUENCE: 22

```
Pro Glu Pro Leu Ser Tyr Pro Val Leu Glu Trp Glu Asp Ile Thr Phe
 1               5                  10                  15

Glu Asp Leu Ile Gly Glu Gly Asn Phe Gly Gln Val Ile Arg Ala Met
             20                  25                  30

Ile Lys Lys Asp Gly Leu Lys Met Asn Ala Ala Ile Lys Met Leu Lys
         35                  40                  45

Glu Tyr Ala Ser Glu Asn Asp His Arg Asp Phe Ala Gly Glu Leu Glu
 50                  55                  60

Val Leu Cys Lys Leu Gly His His Pro Asn Ile Ile Asn Leu Leu Gly
 65                  70                  75                  80

Ala Cys Lys Asn Arg Gly Tyr Leu Tyr Ile Ala Ile Glu Tyr Ala Pro
                 85                  90                  95

Tyr Gly Asn Leu Leu Asp Phe Leu Arg Lys Ser Arg Val Leu Glu Thr
                100                 105                 110
```

-continued

```
Asp Pro Ala Phe Ala Arg Glu His Gly Thr Ala Ser Thr Leu Ser Ser
        115                 120                 125
Arg Gln Leu Leu Arg Phe Ala Ser Asp Ala Ala Asn Gly Met Gln Tyr
    130                 135                 140
Leu Ser Glu Lys Gln Phe Ile His Arg Asp Leu Ala Ala Arg Asn Val
145                 150                 155                 160
Leu Val Gly Glu Asn Leu Ala Ser Lys Ile Ala Asp Phe Gly Leu Ser
                165                 170                 175
Arg Gly Glu Glu Val Tyr Val Lys Lys Thr Met Gly Arg Leu Pro Val
            180                 185                 190
Arg Trp Met Ala Ile Glu Ser Leu Asn Tyr Ser Val Tyr Thr Thr Lys
        195                 200                 205
Ser Asp Val Trp Ser Phe Gly Val Leu Leu Trp Glu Ile Val Ser Leu
210                 215                 220
Gly Gly Thr Pro Tyr Cys Gly Met Thr Cys Ala Glu Leu Tyr Glu Lys
225                 230                 235                 240
Leu Pro Gln Gly Tyr Arg Met Glu Gln Pro Arg Asn Cys Asp Asp Glu
                245                 250                 255
Val Tyr Glu Leu Met Arg Gln Cys Trp Arg Asp Arg Pro Tyr Glu Arg
            260                 265                 270
Pro Pro Phe Ala Gln Ile Ala Leu Gln Leu Gly Arg Met Leu Glu Ala
        275                 280                 285
Arg Lys Ala
    290

<210> SEQ ID NO 23
<211> LENGTH: 279
<212> TYPE: PRT
<213> ORGANISM: Homo sapiens

<400> SEQUENCE: 23

Trp Ser Asn Phe Pro Ser Arg Glu Leu Asp Pro Ala Trp Leu Met Val
 1               5                  10                  15
Asp Thr Val Ile Gly Glu Gly Glu Phe Gly Glu Val Tyr Arg Gly Thr
                20                  25                  30
Leu Arg Leu Pro Ser Gln Asp Cys Lys Thr Val Ala Ile Lys Thr Leu
            35                  40                  45
Lys Asp Thr Ser Pro Gly Gly Gln Trp Trp Asn Phe Leu Arg Glu Ala
        50                  55                  60
Thr Ile Met Gly Gln Phe Ser His Pro His Ile Leu His Leu Glu Gly
65                  70                  75                  80
Val Val Thr Lys Arg Lys Pro Ile Met Ile Ile Thr Glu Phe Met Glu
                85                  90                  95
Asn Gly Ala Leu Asp Ala Phe Leu Arg Glu Arg Glu Asp Gln Leu Val
            100                 105                 110
Pro Gly Gln Leu Val Ala Met Leu Gln Gly Ile Ala Ser Gly Met Asn
        115                 120                 125
Tyr Leu Ser Asn His Asn Tyr Val His Arg Asp Leu Ala Ala Arg Asn
    130                 135                 140
Ile Leu Val Asn Gln Asn Leu Cys Cys Lys Val Ser Asp Phe Gly Leu
145                 150                 155                 160
Thr Arg Leu Leu Asp Asp Phe Asp Gly Thr Tyr Glu Thr Gln Gly Gly
                165                 170                 175
Lys Ile Pro Ile Arg Trp Thr Ala Pro Glu Ala Ile Ala His Arg Ile
```

```
                    180                 185                 190
Phe Thr Thr Ala Ser Asp Val Trp Ser Phe Gly Ile Val Met Trp Glu
            195                 200                 205

Val Leu Ser Phe Gly Asp Lys Pro Tyr Gly Glu Met Ser Asn Gln Glu
    210                 215                 220

Val Met Lys Ser Ile Glu Asp Gly Tyr Arg Leu Pro Pro Val Asp
225                 230                 235                 240

Cys Pro Ala Pro Leu Tyr Glu Leu Met Lys Asn Cys Trp Ala Tyr Asp
                245                 250                 255

Arg Ala Arg Arg Pro His Phe Gln Lys Leu Gln Ala His Leu Glu Gln
            260                 265                 270

Leu Leu Ala Asn Pro His Ser
            275

<210> SEQ ID NO 24
<211> LENGTH: 291
<212> TYPE: PRT
<213> ORGANISM: Homo sapiens

<400> SEQUENCE: 24

Lys Gly Lys Val Lys Asp Ile Ala Ile Ser Arg Glu Arg Ile Thr Leu
1               5                   10                  15

Lys Asp Val Leu Gln Glu Gly Thr Phe Gly Arg Ile Phe His Gly Ile
            20                  25                  30

Leu Ile Asp Glu Lys Asp Pro Asn Lys Glu Lys Gln Ala Phe Val Lys
        35                  40                  45

Thr Val Lys Asp Gln Ala Ser Glu Ile Gln Val Thr Met Met Leu Thr
    50                  55                  60

Glu Ser Cys Lys Leu Arg Gly Leu His His Arg Asn Leu Leu Pro Ile
65                  70                  75                  80

Thr His Val Cys Ile Glu Glu Gly Glu Lys Pro Met Val Ile Leu Pro
                85                  90                  95

Tyr Met Asn Trp Gly Asn Leu Lys Leu Phe Leu Arg Gln Cys Lys Leu
            100                 105                 110

Val Glu Ala Asn Asn Pro Gln Ala Ile Ser Gln Gln Asp Leu Val His
        115                 120                 125

Met Ala Ile Gln Ile Ala Cys Gly Met Ser Tyr Leu Ala Arg Arg Glu
    130                 135                 140

Val Ile His Lys Asp Leu Ala Ala Arg Asn Cys Val Ile Asp Asp Thr
145                 150                 155                 160

Leu Gln Val Lys Ile Thr Asp Asn Ala Leu Ser Arg Asp Leu Phe Pro
                165                 170                 175

Met Asp Tyr His Cys Leu Gly Asp Asn Glu Asn Arg Pro Val Arg Trp
            180                 185                 190

Met Ala Leu Glu Ser Leu Val Asn Asn Glu Phe Ser Ser Ala Ser Asp
        195                 200                 205

Val Trp Ala Phe Gly Val Asn Ser Leu Trp Glu Leu Met Thr Leu Gly
    210                 215                 220

Gln Thr Pro Tyr Thr Leu Asp Ile Asp Pro Phe Glu Met Ala Ala Tyr
225                 230                 235                 240

Leu Lys Asp Gly Tyr Arg Ile Ala Gln Pro Ile Thr Cys Pro Asp Glu
                245                 250                 255

Leu Phe Ala Val Met Ala Cys Cys Trp Ala Leu Asp Pro Glu Glu Arg
            260                 265                 270
```

```
Pro Arg Phe Gln Gln Leu Val Gln Cys Leu Thr Glu Phe His Ala Ala
        275                 280                 285

Leu Gly Ala
    290

<210> SEQ ID NO 25
<211> LENGTH: 317
<212> TYPE: PRT
<213> ORGANISM: Homo sapiens

<400> SEQUENCE: 25

Gly Asp Gly Pro Pro Arg Val Asp Phe Pro Arg Ser Arg Leu Arg Phe
  1               5                  10                  15

Lys Glu Lys Leu Gly Phe Gly Gln Phe Gly Glu Val His Leu Cys Glu
             20                  25                  30

Val Asp Ser Pro Gln Asp Leu Val Ser Leu Asp Phe Pro Leu Asn Val
         35                  40                  45

Arg Lys Gly His Pro Leu Leu Val Ala Val Lys Ile Leu Arg Pro Asp
     50                  55                  60

Ala Thr Lys Asn Ala Arg Asn Asp Phe Leu Lys Glu Val Lys Ile Met
 65                  70                  75                  80

Ser Arg Leu Lys Asp Pro Asn Ile Ile Arg Leu Leu Gly Val Cys Val
                 85                  90                  95

Gln Asp Asp Pro Leu Cys Met Ile Thr Asp Tyr Met Glu Asn Gly Asp
            100                 105                 110

Leu Asn Gln Phe Leu Ser Ala His Gln Leu Glu Asp Lys Ala Ala Glu
        115                 120                 125

Gly Ala Pro Gly Asp Gly Gln Ala Ala Gln Gly Pro Thr Ile Ser Tyr
    130                 135                 140

Pro Met Leu Leu His Val Ala Ala Gln Ile Ala Ser Gly Met Arg Tyr
145                 150                 155                 160

Leu Ala Thr Leu Asn Phe Val His Arg Asp Leu Ala Thr Arg Asn Cys
                165                 170                 175

Leu Val Gly Glu Asn Phe Thr Ile Lys Ile Ala Asp Phe Gly Met Ser
            180                 185                 190

Arg Asn Leu Tyr Ala Gly Asp Tyr Tyr Arg Val Gln Gly Arg Ala Val
        195                 200                 205

Leu Pro Ile Arg Trp Met Ala Trp Glu Cys Ile Leu Met Gly Lys Phe
    210                 215                 220

Thr Thr Ala Ser Asp Val Trp Ala Phe Gly Val Thr Val Trp Glu Val
225                 230                 235                 240

Leu Met Leu Cys Arg Ala Gln Pro Phe Gly Gln Leu Thr Asp Glu Gln
                245                 250                 255

Val Ile Glu Asn Ala Gly Glu Phe Phe Arg Asp Gln Gly Arg Gln Val
            260                 265                 270

Tyr Leu Ser Arg Pro Pro Ala Cys Pro Gln Gly Leu Tyr Glu Leu Met
        275                 280                 285

Leu Arg Cys Trp Gly Arg Glu Ser Glu Gln Arg Pro Pro Phe Ser Gln
    290                 295                 300

Leu His Arg Phe Leu Ala Glu Asp Ala Leu Asn Thr Val
305                 310                 315

<210> SEQ ID NO 26
<211> LENGTH: 293
<212> TYPE: PRT
<213> ORGANISM: Homo sapiens
```

<400> SEQUENCE: 26

```
Glu Glu Ile Glu Asn Leu Pro Ala Phe Pro Arg Glu Lys Leu Thr Leu
 1               5                  10                  15

Arg Leu Leu Leu Gly Ser Gly Ala Phe Gly Glu Val Tyr Glu Gly Thr
            20                  25                  30

Ala Val Asp Ile Leu Gly Val Gly Ser Gly Glu Ile Lys Val Ala Val
        35                  40                  45

Lys Thr Leu Lys Lys Gly Ser Thr Asp Gln Glu Lys Ile Glu Phe Leu
 50                  55                  60

Lys Glu Ala His Leu Met Ser Lys Phe Asn His Pro Asn Ile Leu Lys
 65                  70                  75                  80

Gln Leu Gly Val Cys Leu Leu Asn Glu Pro Gln Tyr Ile Ile Leu Glu
                85                  90                  95

Leu Met Glu Gly Gly Asp Leu Leu Thr Tyr Leu Arg Lys Ala Arg Met
            100                 105                 110

Ala Thr Phe Tyr Gly Pro Leu Leu Thr Leu Val Asp Leu Val Asp Leu
        115                 120                 125

Cys Val Asp Ile Ser Lys Gly Cys Val Tyr Leu Glu Arg Met His Phe
130                 135                 140

Ile His Arg Asp Leu Ala Ala Arg Asn Cys Leu Val Ser Val Lys Asp
145                 150                 155                 160

Tyr Thr Ser Pro Arg Ile Val Lys Ile Gly Asp Phe Gly Leu Ala Arg
                165                 170                 175

Asp Ile Tyr Lys Asn Asp Tyr Tyr Arg Lys Arg Gly Glu Gly Leu Leu
            180                 185                 190

Pro Val Arg Trp Met Ala Pro Glu Ser Leu Met Asp Gly Ile Phe Thr
        195                 200                 205

Thr Gln Ser Asp Val Trp Ser Phe Gly Ile Leu Ile Trp Glu Ile Leu
    210                 215                 220

Thr Leu Gly His Gln Pro Tyr Pro Ala His Ser Asn Leu Asp Val Leu
225                 230                 235                 240

Asn Tyr Val Gln Thr Gly Gly Arg Leu Glu Pro Pro Arg Asn Cys Pro
                245                 250                 255

Asp Asp Leu Trp Asn Leu Met Thr Gln Cys Trp Ala Gln Glu Pro Asp
            260                 265                 270

Gln Arg Pro Thr Phe His Arg Ile Gln Asn Gln Leu Gln Leu Phe Arg
        275                 280                 285

Asn Phe Phe Leu Asn
        290

<210> SEQ ID NO 27
<211> LENGTH: 304
<212> TYPE: PRT
<213> ORGANISM: Homo sapiens

<400> SEQUENCE: 27

Ile Leu Glu Asp Pro Lys Trp Glu Phe Pro Arg Lys Asn Leu Val Leu
 1               5                  10                  15

Gly Lys Thr Leu Gly Glu Gly Glu Phe Gly Lys Val Val Lys Ala Thr
            20                  25                  30

Ala Phe His Leu Lys Gly Arg Ala Gly Tyr Thr Thr Val Ala Val Lys
        35                  40                  45

Met Leu Lys Glu Asn Ala Ser Pro Ser Glu Leu Arg Asp Leu Leu Ser
 50                  55                  60
```

```
Glu Phe Asn Val Leu Lys Gln Val Asn His Pro His Val Ile Lys Leu
 65                  70                  75                  80

Tyr Gly Ala Cys Ser Gln Asp Gly Pro Leu Leu Ile Val Glu Tyr
                 85                  90                  95

Ala Lys Tyr Gly Ser Leu Arg Gly Phe Leu Arg Glu Ser Arg Lys Val
                100                 105                 110

Gly Pro Gly Tyr Leu Gly Ser Gly Gly Ser Arg Asn Ser Ser Ser Leu
                115                 120                 125

Asp His Pro Asp Glu Arg Ala Leu Thr Met Gly Asp Leu Ile Ser Phe
        130                 135                 140

Ala Trp Gln Ile Ser Gln Gly Met Gln Tyr Leu Ala Glu Met Lys Leu
145                 150                 155                 160

Val His Arg Asp Leu Ala Ala Arg Asn Ile Leu Val Ala Glu Gly Arg
                165                 170                 175

Lys Met Lys Ile Ser Asp Phe Gly Leu Ser Arg Asp Val Tyr Glu Glu
                180                 185                 190

Asp Ser Tyr Val Lys Arg Ser Gln Gly Arg Ile Pro Val Lys Trp Met
        195                 200                 205

Ala Ile Glu Ser Leu Phe Asp His Ile Tyr Thr Thr Gln Ser Asp Val
210                 215                 220

Trp Ser Phe Gly Val Leu Leu Trp Glu Ile Val Thr Leu Gly Gly Asn
225                 230                 235                 240

Pro Tyr Pro Gly Ile Pro Pro Glu Arg Leu Phe Asn Leu Leu Lys Thr
                245                 250                 255

Gly His Arg Met Glu Arg Pro Asp Asn Cys Ser Glu Glu Met Tyr Arg
                260                 265                 270

Leu Met Leu Gln Cys Trp Lys Gln Glu Pro Asp Lys Arg Pro Val Phe
        275                 280                 285

Ala Asp Ile Ser Lys Asp Leu Glu Lys Met Met Val Lys Arg Arg Asp
290                 295                 300

<210> SEQ ID NO 28
<211> LENGTH: 290
<212> TYPE: PRT
<213> ORGANISM: Homo sapiens

<400> SEQUENCE: 28

Pro Leu Pro Pro Gly Val Thr Glu Val Ser Pro Ala Asn Val Thr Leu
  1               5                  10                  15

Leu Arg Ala Leu Gly His Gly Ala Phe Gly Glu Val Tyr Glu Gly Leu
                 20                  25                  30

Val Ile Gly Leu Pro Gly Asp Ser Ser Pro Leu Gln Val Ala Ile Lys
                 35                  40                  45

Thr Leu Pro Glu Leu Cys Ser Pro Gln Asp Glu Leu Asp Phe Leu Met
         50                  55                  60

Glu Ala Leu Ile Ile Ser Lys Phe Arg His Gln Asn Ile Val Arg Cys
 65                  70                  75                  80

Val Gly Leu Ser Leu Arg Ala Thr Pro Arg Leu Ile Leu Leu Glu Leu
                 85                  90                  95

Met Ser Gly Gly Asp Met Lys Ser Phe Leu Arg His Ser Arg Pro His
                100                 105                 110

Leu Gly Gln Pro Ser Pro Leu Val Met Arg Asp Leu Leu Gln Leu Ala
                115                 120                 125

Gln Asp Ile Ala Gln Gly Cys His Tyr Leu Glu Glu Asn His Phe Ile
```

```
            130                 135                 140
His Arg Asp Ile Ala Ala Arg Asn Cys Leu Leu Ser Cys Ala Gly Pro
145                 150                 155                 160

Ser Arg Val Ala Lys Ile Gly Asp Phe Gly Met Ala Arg Asp Ile Tyr
                165                 170                 175

Arg Ala Ser Tyr Tyr Arg Arg Gly Asp Arg Ala Leu Leu Pro Val Lys
            180                 185                 190

Trp Met Pro Pro Glu Ala Phe Leu Glu Gly Ile Phe Thr Ser Lys Thr
        195                 200                 205

Asp Ser Trp Ser Phe Gly Val Leu Leu Trp Glu Ile Phe Ser Leu Gly
    210                 215                 220

Tyr Met Pro Tyr Pro Gly Arg Thr Asn Gln Glu Val Leu Asp Phe Val
225                 230                 235                 240

Val Gly Gly Gly Arg Met Asp Pro Pro Arg Gly Cys Pro Gly Pro Val
                245                 250                 255

Tyr Arg Ile Met Thr Gln Cys Trp Gln His Glu Pro Glu Leu Arg Pro
            260                 265                 270

Ser Phe Ala Ser Ile Leu Glu Arg Leu Gln Tyr Cys Thr Gln Asp Pro
        275                 280                 285

Asp Val
    290

<210> SEQ ID NO 29
<211> LENGTH: 296
<212> TYPE: PRT
<213> ORGANISM: Homo sapiens

<400> SEQUENCE: 29

Lys Pro Lys Ser Lys Ala Lys Glu Leu Pro Leu Ser Ala Val Arg Phe
  1               5                  10                  15

Met Glu Glu Leu Gly Glu Cys Ala Phe Gly Lys Ile Tyr Lys Gly His
                 20                  25                  30

Leu Tyr Leu Pro Gly Met Asp His Ala Gln Leu Val Ala Ile Lys Thr
             35                  40                  45

Leu Lys Asp Tyr Asn Asn Pro Gln Gln Trp Met Glu Phe Gln Gln Glu
 50                  55                  60

Ala Ser Leu Met Ala Glu Leu His His Pro Asn Ile Val Cys Leu Leu
 65                  70                  75                  80

Gly Ala Val Thr Gln Glu Gln Pro Val Cys Met Leu Phe Glu Tyr Ile
                 85                  90                  95

Asn Gln Gly Asp Leu His Glu Phe Leu Ile Met Arg Ser Pro His Ser
            100                 105                 110

Asp Val Gly Cys Ser Ser Asp Glu Asp Gly Thr Val Lys Ser Ser Leu
        115                 120                 125

Asp His Gly Asp Phe Leu His Ile Ala Ile Gln Ile Ala Ala Gly Met
    130                 135                 140

Glu Tyr Leu Ser Ser His Phe Phe Val His Lys Asp Leu Ala Ala Arg
145                 150                 155                 160

Asn Ile Leu Ile Gly Glu Gln Leu His Val Lys Ile Ser Asp Leu Gly
                165                 170                 175

Leu Ser Arg Glu Ile Tyr Ser Ala Asp Tyr Tyr Arg Val Gln Ser Lys
            180                 185                 190

Ser Leu Leu Pro Ile Arg Trp Met Pro Pro Glu Ala Ile Met Tyr Gly
        195                 200                 205
```

-continued

```
Lys Phe Ser Asp Ser Asp Ile Trp Ser Phe Gly Val Leu Trp
    210                 215                 220

Glu Ile Phe Ser Phe Gly Leu Gln Pro Tyr Tyr Gly Phe Ser Asn Gln
225                 230                 235                 240

Glu Val Ile Glu Met Val Arg Lys Arg Gln Leu Leu Pro Cys Ser Glu
                245                 250                 255

Asp Cys Pro Pro Arg Met Tyr Ser Leu Met Thr Glu Cys Trp Asn Glu
            260                 265                 270

Ile Pro Ser Arg Arg Pro Arg Phe Lys Asp Ile His Val Arg Leu Arg
            275                 280                 285

Ser Trp Glu Gly Leu Ser Ser His
            290                 295

<210> SEQ ID NO 30
<211> LENGTH: 304
<212> TYPE: PRT
<213> ORGANISM: Mus sp.

<400> SEQUENCE: 30

Asn Pro Lys Leu Leu Ser Leu Glu Tyr Pro Arg Asn Asn Ile Glu Tyr
  1               5                  10                  15

Val Arg Asp Ile Gly Glu Gly Ala Phe Gly Arg Val Phe Gln Ala Arg
                20                  25                  30

Ala Pro Gly Leu Leu Pro Tyr Glu Pro Phe Thr Met Val Ala Val Lys
            35                  40                  45

Met Leu Lys Glu Glu Ala Ser Ala Asp Met Gln Ala Asp Phe Gln Arg
        50                  55                  60

Glu Ala Ala Leu Met Ala Glu Phe Asp Asn Pro Asn Ile Val Lys Leu
65                  70                  75                  80

Leu Gly Val Cys Ala Val Gly Lys Pro Met Cys Leu Leu Phe Glu Tyr
                85                  90                  95

Met Ala Tyr Gly Asp Leu Asn Glu Phe Leu Arg Ser Met Ser Pro His
                100                 105                 110

Thr Val Cys Ser Leu Ser His Ser Asp Leu Ser Thr Arg Ala Arg Val
            115                 120                 125

Ser Ser Pro Gly Pro Pro Leu Ser Cys Ala Glu Gln Leu Cys Ile
130                 135                 140

Ala Arg Gln Val Ala Ala Gly Met Ala Tyr Leu Ser Glu Arg Lys Phe
145                 150                 155                 160

Val His Arg Asp Leu Ala Thr Arg Asn Cys Leu Val Gly Glu Thr Met
                165                 170                 175

Val Val Lys Ile Ala Asp Phe Gly Leu Ser Arg Asn Ile Tyr Ser Ala
                180                 185                 190

Asp Tyr Tyr Lys Ala Asp Gly Asn Asp Ala Ile Pro Ile Arg Trp Met
            195                 200                 205

Pro Pro Glu Ser Ile Phe Tyr Asn Arg Tyr Thr Thr Glu Ser Asp Val
210                 215                 220

Trp Ala Tyr Gly Val Val Leu Trp Glu Ile Phe Ser Tyr Gly Leu Gln
225                 230                 235                 240

Pro Tyr Tyr Gly Met Ala His Glu Glu Val Ile Tyr Tyr Val Arg Asp
                245                 250                 255

Gly Asn Ile Leu Ala Cys Pro Glu Asn Cys Pro Leu Glu Leu Tyr Asn
            260                 265                 270

Leu Met Arg Leu Cys Trp Ser Lys Leu Pro Ala Asp Arg Pro Ser Phe
            275                 280                 285
```

```
Cys Ser Ile His Arg Ile Leu Gln Arg Met Cys Glu Arg Ala Glu Gly
        290                 295                 300

<210> SEQ ID NO 31
<211> LENGTH: 300
<212> TYPE: PRT
<213> ORGANISM: Homo sapiens

<400> SEQUENCE: 31

Leu Pro Glu Asp Pro Arg Trp Glu Leu Pro Arg Asp Arg Leu Val Leu
  1               5                  10                  15

Gly Lys Pro Leu Gly Glu Gly Cys Phe Gly Gln Val Val Leu Ala Glu
             20                  25                  30

Ala Ile Gly Leu Asp Lys Asp Lys Pro Asn Arg Val Thr Lys Val Ala
         35                  40                  45

Val Lys Met Leu Lys Ser Asp Ala Thr Glu Lys Asp Leu Ser Asp Leu
     50                  55                  60

Ile Ser Glu Met Glu Met Met Lys Met Ile Gly Lys His Lys Asn Ile
 65                  70                  75                  80

Ile Asn Leu Leu Gly Ala Cys Thr Gln Asp Gly Pro Leu Tyr Val Ile
                 85                  90                  95

Val Glu Tyr Ala Ser Lys Gly Asn Leu Arg Glu Tyr Leu Gln Ala Arg
            100                 105                 110

Arg Pro Pro Gly Leu Glu Tyr Cys Tyr Asn Pro Ser His Asn Pro Glu
        115                 120                 125

Glu Gln Leu Ser Ser Lys Asp Leu Val Ser Cys Ala Tyr Gln Val Ala
    130                 135                 140

Arg Gly Met Glu Tyr Leu Ala Ser Lys Lys Cys Ile His Arg Asp Leu
145                 150                 155                 160

Ala Ala Arg Asn Val Leu Val Thr Glu Asp Asn Val Met Lys Ile Ala
                165                 170                 175

Asp Phe Gly Leu Ala Arg Asp Ile His His Ile Asp Tyr Tyr Lys Lys
            180                 185                 190

Thr Thr Asn Gly Arg Leu Pro Val Lys Trp Met Ala Pro Glu Ala Leu
        195                 200                 205

Phe Asp Arg Ile Tyr Thr His Gln Ser Asp Val Trp Ser Phe Gly Val
    210                 215                 220

Leu Leu Trp Glu Ile Phe Thr Leu Gly Gly Ser Pro Tyr Pro Gly Val
225                 230                 235                 240

Pro Val Glu Glu Leu Phe Lys Leu Leu Lys Glu Gly His Arg Met Asp
                245                 250                 255

Lys Pro Ser Asn Cys Thr Asn Glu Leu Tyr Met Met Arg Asp Cys
            260                 265                 270

Trp His Ala Val Pro Ser Gln Arg Pro Thr Phe Lys Gln Leu Val Glu
        275                 280                 285

Asp Leu Asp Arg Ile Val Ala Leu Thr Ser Asn Gln
    290                 295                 300

<210> SEQ ID NO 32
<211> LENGTH: 273
<212> TYPE: PRT
<213> ORGANISM: Homo sapiens

<400> SEQUENCE: 32

Gly Leu Ala Lys Asp Ala Trp Glu Ile Pro Arg Glu Ser Leu Arg Leu
  1               5                  10                  15
```

```
Glu Val Lys Leu Gly Gln Gly Cys Phe Gly Glu Val Trp Met Gly Thr
             20                  25                  30

Trp Asn Gly Thr Thr Arg Val Ala Ile Lys Thr Leu Lys Pro Gly Thr
         35                  40                  45

Met Ser Pro Glu Ala Phe Leu Gln Glu Ala Gln Val Met Lys Lys Leu
     50                  55                  60

Arg His Glu Lys Leu Val Gln Leu Tyr Ala Val Val Ser Glu Glu Pro
 65                  70                  75                  80

Ile Tyr Ile Val Thr Glu Tyr Met Ser Lys Gly Ser Leu Leu Asp Phe
                 85                  90                  95

Leu Lys Gly Glu Thr Gly Lys Tyr Leu Arg Leu Pro Gln Leu Val Asp
             100                 105                 110

Met Ala Ala Gln Ile Ala Ser Gly Met Ala Tyr Val Glu Arg Met Asn
         115                 120                 125

Tyr Val His Arg Asp Leu Arg Ala Ala Asn Ile Leu Val Gly Glu Asn
     130                 135                 140

Leu Val Cys Lys Val Ala Asp Phe Gly Leu Ala Arg Leu Ile Glu Asp
145                 150                 155                 160

Asn Glu Tyr Thr Ala Arg Gln Gly Ala Lys Phe Pro Ile Lys Trp Thr
                 165                 170                 175

Ala Pro Glu Ala Ala Leu Tyr Gly Arg Phe Thr Ile Lys Ser Asp Val
             180                 185                 190

Trp Ser Phe Gly Ile Leu Leu Thr Glu Leu Thr Thr Lys Gly Arg Val
         195                 200                 205

Pro Tyr Pro Gly Met Val Asn Arg Glu Val Leu Asp Gln Val Glu Arg
     210                 215                 220

Gly Tyr Arg Met Pro Cys Pro Pro Glu Cys Pro Glu Ser Leu His Asp
225                 230                 235                 240

Leu Met Cys Gln Cys Trp Arg Lys Glu Pro Glu Glu Arg Pro Thr Phe
                 245                 250                 255

Glu Tyr Leu Gln Ala Phe Leu Glu Asp Tyr Phe Thr Ser Thr Glu Pro
             260                 265                 270

Gln

<210> SEQ ID NO 33
<211> LENGTH: 274
<212> TYPE: PRT
<213> ORGANISM: Homo sapiens

<400> SEQUENCE: 33

Leu Pro His Trp Asp Asp Trp Glu Arg Pro Arg Glu Glu Phe Thr Leu
 1               5                  10                  15

Cys Arg Lys Leu Gly Ser Gly Tyr Phe Gly Glu Val Phe Glu Gly Leu
             20                  25                  30

Trp Lys Asp Arg Val Gln Val Ala Ile Lys Val Ile Ser Arg Asp Asn
         35                  40                  45

Leu Leu His Gln Gln Met Leu Gln Ser Glu Ile Gln Ala Met Lys Lys
     50                  55                  60

Leu Arg His Lys His Ile Leu Ala Leu Tyr Ala Val Val Ser Val Gly
 65                  70                  75                  80

Asp Pro Val Tyr Ile Ile Thr Glu Leu Met Ala Lys Gly Ser Leu Leu
                 85                  90                  95

Glu Leu Leu Arg Asp Ser Asp Glu Lys Val Leu Pro Val Ser Glu Leu
             100                 105                 110
```

```
Leu Asp Ile Ala Trp Gln Val Ala Glu Gly Met Cys Tyr Leu Glu Ser
            115                 120                 125

Gln Asn Tyr Ile His Arg Asp Leu Ala Arg Asn Ile Leu Val Gly
        130                 135                 140

Glu Asn Thr Leu Cys Lys Val Gly Asp Phe Gly Leu Ala Arg Leu Ile
145                 150                 155                 160

Lys Glu Asp Val Tyr Leu Ser His Asp His Asn Ile Pro Tyr Lys Trp
                165                 170                 175

Thr Ala Pro Glu Ala Leu Ser Arg Gly His Tyr Ser Thr Lys Ser Asp
            180                 185                 190

Val Trp Ser Phe Gly Ile Leu Leu His Glu Met Phe Ser Arg Gly Gln
        195                 200                 205

Val Pro Tyr Pro Gly Met Ser Asn His Glu Ala Phe Leu Arg Val Asp
210                 215                 220

Ala Gly Tyr Arg Met Pro Cys Pro Leu Glu Cys Pro Pro Ser Val His
225                 230                 235                 240

Lys Leu Met Leu Thr Cys Trp Cys Arg Asp Pro Glu Gln Arg Pro Cys
                245                 250                 255

Phe Lys Ala Leu Arg Glu Arg Leu Ser Ser Phe Thr Ser Tyr Glu Asn
            260                 265                 270

Pro Thr

<210> SEQ ID NO 34
<211> LENGTH: 271
<212> TYPE: PRT
<213> ORGANISM: Homo sapiens

<400> SEQUENCE: 34

Gly Leu Gly Tyr Gly Ser Trp Glu Ile Asp Pro Lys Asp Leu Thr Phe
1               5                   10                  15

Leu Lys Glu Leu Gly Thr Gly Gln Phe Gly Val Val Lys Tyr Gly Lys
            20                  25                  30

Trp Arg Gly Gln Tyr Asp Val Ala Ile Lys Met Ile Lys Glu Gly Ser
        35                  40                  45

Met Ser Glu Asp Glu Phe Ile Glu Glu Ala Lys Val Met Met Asn Leu
    50                  55                  60

Ser His Glu Lys Leu Val Gln Leu Tyr Gly Val Cys Thr Lys Gln Arg
65                  70                  75                  80

Pro Ile Phe Ile Ile Thr Glu Tyr Met Ala Asn Gly Cys Leu Leu Asn
                85                  90                  95

Tyr Leu Arg Glu Met Arg His Arg Phe Gln Thr Gln Leu Leu Glu
            100                 105                 110

Met Cys Lys Asp Val Cys Glu Ala Met Glu Tyr Leu Glu Ser Lys Gln
        115                 120                 125

Phe Leu His Arg Asp Leu Ala Ala Arg Asn Cys Leu Val Asn Asp Gln
    130                 135                 140

Gly Val Val Lys Val Ser Asp Phe Gly Leu Ser Arg Tyr Val Leu Asp
145                 150                 155                 160

Asp Glu Tyr Thr Ser Ser Val Gly Ser Lys Phe Pro Val Arg Trp Ser
                165                 170                 175

Pro Pro Glu Val Leu Met Tyr Ser Lys Phe Ser Ser Lys Ser Asp Ile
            180                 185                 190

Trp Ala Phe Gly Val Leu Met Trp Glu Ile Tyr Ser Leu Gly Lys Met
        195                 200                 205
```

```
Pro Tyr Glu Arg Phe Thr Asn Ser Glu Thr Ala Glu His Ile Ala Gln
    210                 215                 220

Gly Leu Arg Leu Tyr Arg Pro His Leu Ala Ser Glu Lys Val Tyr Thr
225                 230                 235                 240

Ile Met Tyr Ser Cys Trp His Glu Lys Ala Asp Glu Arg Pro Thr Phe
                245                 250                 255

Lys Ile Leu Leu Ser Asn Ile Leu Asp Val Met Asp Glu Glu Ser
                260                 265                 270

<210> SEQ ID NO 35
<211> LENGTH: 269
<212> TYPE: PRT
<213> ORGANISM: Homo sapiens

<400> SEQUENCE: 35

Glu Phe Tyr Arg Ser Gly Trp Ala Leu Asn Met Lys Glu Leu Lys Leu
  1               5                  10                  15

Leu Gln Thr Ile Gly Lys Gly Glu Phe Gly Asp Val Met Leu Gly Asp
                 20                  25                  30

Tyr Arg Gly Asn Lys Val Ala Val Lys Cys Ile Lys Asn Asp Ala Thr
             35                  40                  45

Ala Gln Ala Phe Leu Ala Glu Ala Ser Val Met Thr Gln Leu Arg His
         50                  55                  60

Ser Asn Leu Val Gln Leu Leu Gly Val Ile Val Glu Glu Lys Gly Gly
 65                  70                  75                  80

Leu Tyr Ile Val Thr Glu Tyr Met Ala Lys Gly Ser Leu Val Asp Tyr
                 85                  90                  95

Leu Arg Ser Arg Gly Arg Ser Val Leu Gly Gly Asp Cys Leu Leu Lys
                100                 105                 110

Phe Ser Leu Asp Val Cys Glu Ala Met Glu Tyr Leu Glu Gly Asn Asn
            115                 120                 125

Phe Val His Arg Asp Leu Ala Ala Arg Asn Val Leu Val Ser Glu Asp
        130                 135                 140

Asn Val Ala Lys Val Ser Asp Phe Gly Leu Thr Lys Glu Ala Ser Ser
145                 150                 155                 160

Thr Gln Asp Thr Gly Lys Leu Pro Val Lys Trp Thr Ala Pro Glu Ala
                165                 170                 175

Leu Arg Glu Lys Lys Phe Ser Thr Lys Ser Asp Val Trp Ser Phe Gly
            180                 185                 190

Ile Leu Leu Trp Glu Ile Tyr Ser Phe Gly Arg Val Pro Tyr Pro Arg
        195                 200                 205

Ile Pro Leu Lys Asp Val Val Pro Arg Val Glu Lys Gly Tyr Lys Met
    210                 215                 220

Asp Ala Pro Asp Gly Cys Pro Pro Ala Val Tyr Glu Val Met Lys Asn
225                 230                 235                 240

Cys Trp His Leu Asp Ala Ala Met Arg Pro Ser Phe Leu Gln Leu Arg
                245                 250                 255

Glu Gln Leu Glu His Ile Lys Thr His Glu Leu His Leu
            260                 265

<210> SEQ ID NO 36
<211> LENGTH: 275
<212> TYPE: PRT
<213> ORGANISM: Homo sapiens

<400> SEQUENCE: 36
```

```
Ser Pro Asn Tyr Asp Lys Trp Glu Met Glu Arg Thr Asp Ile Thr Met
  1               5                  10                  15

Lys His Lys Leu Gly Gly Gly Gln Tyr Gly Glu Val Tyr Glu Gly Val
             20                  25                  30

Trp Lys Lys Tyr Ser Leu Thr Val Ala Val Lys Thr Leu Lys Glu Asp
         35                  40                  45

Thr Met Glu Val Glu Glu Phe Leu Lys Glu Ala Ala Val Met Lys Glu
     50                  55                  60

Ile Lys His Pro Asn Leu Val Gln Leu Leu Gly Val Cys Thr Arg Glu
 65              70                  75                  80

Pro Pro Phe Tyr Ile Ile Thr Glu Phe Met Thr Tyr Gly Asn Leu Leu
             85                  90                  95

Asp Tyr Leu Arg Glu Cys Asn Arg Gln Glu Val Asn Ala Val Val Leu
            100                 105                 110

Leu Tyr Met Ala Thr Gln Ile Ser Ser Ala Met Glu Tyr Leu Glu Lys
            115                 120                 125

Lys Asn Phe Ile His Arg Asp Leu Ala Ala Arg Asn Cys Leu Val Gly
        130                 135                 140

Glu Asn His Leu Val Lys Val Ala Asp Phe Gly Leu Ser Arg Leu Met
145                 150                 155                 160

Thr Gly Asp Thr Tyr Thr Ala His Ala Gly Ala Lys Phe Pro Ile Lys
                165                 170                 175

Trp Thr Ala Pro Glu Ser Leu Ala Tyr Asn Lys Phe Ser Ile Lys Ser
            180                 185                 190

Asp Val Trp Ala Phe Gly Val Leu Leu Trp Glu Ile Ala Thr Tyr Gly
        195                 200                 205

Met Ser Pro Tyr Pro Gly Ile Asp Leu Ser Gln Val Tyr Glu Leu Leu
    210                 215                 220

Glu Lys Asp Tyr Arg Met Glu Arg Pro Glu Gly Cys Pro Glu Lys Val
225                 230                 235                 240

Tyr Glu Leu Met Arg Ala Cys Trp Gln Trp Asn Pro Ser Asp Arg Pro
                245                 250                 255

Ser Phe Ala Glu Ile His Gln Ala Phe Glu Thr Met Phe Gln Glu Ser
            260                 265                 270

Ser Ile Ser
275

<210> SEQ ID NO 37
<211> LENGTH: 279
<212> TYPE: PRT
<213> ORGANISM: Homo sapiens

<400> SEQUENCE: 37

Leu Lys Asp Lys Lys Leu Phe Leu Lys Arg Asp Asn Leu Leu Ile Ala
  1               5                  10                  15

Asp Ile Glu Leu Gly Cys Gly Asn Phe Gly Ser Val Arg Gln Gly Val
             20                  25                  30

Tyr Arg Met Arg Lys Lys Gln Ile Asp Val Ala Ile Lys Val Leu Lys
         35                  40                  45

Gln Gly Thr Glu Lys Ala Asp Thr Glu Glu Met Met Arg Glu Ala Gln
     50                  55                  60

Ile Met His Gln Leu Asp Asn Pro Tyr Ile Val Arg Leu Ile Gly Val
 65              70                  75                  80

Cys Gln Ala Glu Ala Leu Met Leu Val Met Glu Met Ala Gly Gly Gly
```

```
                    85                  90                  95
Pro Leu His Lys Phe Leu Val Gly Lys Arg Glu Ile Pro Val Ser
            100                 105                 110
Asn Val Ala Glu Leu Leu His Gln Val Ser Met Gly Met Lys Tyr Leu
            115                 120                 125
Glu Glu Lys Asn Phe Val His Arg Asp Leu Ala Ala Arg Asn Val Leu
130                 135                 140
Leu Val Asn Arg His Tyr Ala Lys Ile Ser Asp Phe Gly Leu Ser Lys
145                 150                 155                 160
Ala Leu Gly Ala Asp Asp Ser Tyr Tyr Thr Ala Arg Ser Ala Gly Lys
                165                 170                 175
Trp Pro Leu Lys Trp Tyr Ala Pro Glu Cys Ile Asn Phe Arg Lys Phe
            180                 185                 190
Ser Ser Arg Ser Asp Val Trp Ser Tyr Gly Cys Thr Met Trp Glu Ala
            195                 200                 205
Leu Ser Tyr Gly Gln Lys Pro Tyr Lys Lys Met Lys Gly Pro Glu Val
            210                 215                 220
Met Ala Phe Ile Glu Gln Gly Lys Arg Met Glu Cys Pro Pro Glu Cys
225                 230                 235                 240
Pro Pro Glu Leu Tyr Ala Leu Met Ser Asp Cys Trp Ile Tyr Lys Trp
                245                 250                 255
Glu Asp Arg Pro Asp Phe Leu Thr Val Glu Gln Arg Met Arg Ala Cys
                260                 265                 270
Tyr Tyr Ser Leu Ala Ser Lys
                275

<210> SEQ ID NO 38
<211> LENGTH: 275
<212> TYPE: PRT
<213> ORGANISM: Homo sapiens

<400> SEQUENCE: 38

Ala Val Pro Lys Asp Lys Trp Val Leu Asn His Glu Asp Leu Val Leu
1               5                   10                  15
Gly Glu Gln Ile Gly Arg Gly Asn Phe Gly Glu Val Phe Ser Gly Arg
            20                  25                  30
Leu Arg Ala Asp Asn Thr Leu Val Ala Val Lys Ser Cys Arg Glu Thr
        35                  40                  45
Leu Pro Pro Asp Leu Lys Ala Lys Phe Leu Gln Glu Ala Arg Ile Leu
    50                  55                  60
Lys Gln Tyr Ser His Pro Asn Ile Val Arg Leu Ile Gly Val Cys Thr
65                  70                  75                  80
Gln Lys Gln Pro Ile Tyr Ile Val Met Glu Leu Val Gln Gly Gly Asp
                85                  90                  95
Phe Leu Thr Phe Leu Arg Thr Glu Gly Ala Arg Leu Arg Val Lys Thr
            100                 105                 110
Leu Leu Gln Met Val Gly Asp Ala Ala Ala Gly Met Glu Tyr Leu Glu
            115                 120                 125
Ser Lys Cys Cys Ile His Arg Asp Leu Ala Ala Arg Asn Cys Leu Val
            130                 135                 140
Thr Glu Lys Asn Val Leu Lys Ile Ser Asp Phe Gly Met Ser Arg Glu
145                 150                 155                 160
Glu Ala Asp Gly Val Tyr Ala Ala Ser Gly Gly Ser Arg Gln Val Pro
                165                 170                 175
```

```
Val Lys Trp Thr Ala Pro Glu Ala Leu Asn Tyr Gly Arg Tyr Ser Ser
            180                 185                 190

Glu Ser Asp Val Trp Ser Phe Gly Ile Leu Leu Trp Glu Thr Phe Ser
        195                 200                 205

Leu Gly Ala Ser Pro Tyr Pro Asn Leu Ser Asn Gln Gln Thr Arg Glu
    210                 215                 220

Phe Val Glu Lys Gly Gly Arg Leu Pro Cys Pro Glu Leu Cys Pro Asp
225                 230                 235                 240

Ala Val Phe Arg Leu Met Glu Gln Cys Trp Ala Tyr Glu Pro Gly Gln
                245                 250                 255

Arg Pro Ser Phe Ser Thr Ile Tyr Gln Glu Leu Gln Ser Ile Arg Lys
            260                 265                 270

Arg His Arg
        275

<210> SEQ ID NO 39
<211> LENGTH: 278
<212> TYPE: PRT
<213> ORGANISM: Homo sapiens

<400> SEQUENCE: 39

Met Pro Ser Thr Arg Asp Tyr Glu Ile Gln Arg Glu Arg Ile Glu Leu
  1               5                  10                  15

Gly Arg Cys Ile Gly Glu Gly Gln Phe Gly Asp Val His Gln Gly Ile
             20                  25                  30

Tyr Met Ser Pro Glu Asn Pro Ala Leu Ala Val Ala Ile Lys Thr Cys
         35                  40                  45

Lys Asn Cys Thr Ser Asp Ser Val Arg Glu Lys Phe Leu Gln Glu Ala
     50                  55                  60

Leu Thr Met Arg Gln Phe Asp His Pro His Ile Val Lys Leu Ile Gly
 65                  70                  75                  80

Val Ile Thr Glu Asn Pro Val Trp Ile Ile Met Glu Leu Cys Thr Leu
                 85                  90                  95

Gly Glu Leu Arg Ser Phe Leu Gln Val Arg Lys Tyr Ser Leu Asp Leu
            100                 105                 110

Ala Ser Leu Ile Leu Tyr Ala Tyr Gln Leu Ser Thr Ala Leu Ala Tyr
        115                 120                 125

Leu Glu Ser Lys Arg Phe Val His Arg Asp Ile Ala Ala Arg Asn Val
    130                 135                 140

Leu Val Ser Ser Asn Asp Cys Val Lys Leu Gly Asp Phe Gly Leu Ser
145                 150                 155                 160

Arg Tyr Met Glu Asp Ser Thr Tyr Tyr Lys Ala Ser Lys Gly Lys Leu
                165                 170                 175

Pro Ile Lys Trp Met Ala Pro Glu Ser Ile Asn Phe Arg Arg Phe Thr
            180                 185                 190

Ser Ala Ser Asp Val Trp Met Phe Gly Val Cys Met Trp Glu Ile Leu
        195                 200                 205

Met His Gly Val Lys Pro Phe Gln Gly Val Lys Asn Asn Asp Val Ile
    210                 215                 220

Gly Arg Ile Glu Asn Gly Glu Arg Leu Pro Met Pro Asn Cys Pro
225                 230                 235                 240

Pro Thr Leu Tyr Ser Leu Met Thr Lys Cys Trp Ala Tyr Asp Pro Ser
                245                 250                 255

Arg Arg Pro Arg Phe Thr Glu Leu Lys Ala Gln Leu Ser Thr Ile Leu
            260                 265                 270
```

Glu Glu Glu Lys Ala Gln
        275

<210> SEQ ID NO 40
<211> LENGTH: 292
<212> TYPE: PRT
<213> ORGANISM: Homo sapiens

<400> SEQUENCE: 40

Pro Thr Glu Val Asp Pro Thr His Phe Glu Lys Arg Phe Leu Lys Arg
 1               5                  10                  15

Ile Arg Asp Leu Gly Glu Gly His Phe Gly Lys Val Glu Leu Cys Arg
                20                  25                  30

Tyr Asp Pro Glu Asp Asn Thr Gly Glu Gln Val Ala Val Lys Ser Leu
            35                  40                  45

Lys Pro Glu Ser Gly Gly Asn His Ile Ala Asp Leu Lys Lys Glu Ile
        50                  55                  60

Glu Ile Leu Arg Asn Leu Tyr His Glu Asn Ile Val Lys Tyr Lys Gly
 65                  70                  75                  80

Ile Cys Thr Glu Asp Gly Gly Asn Gly Ile Lys Leu Ile Met Glu Phe
                85                  90                  95

Leu Pro Ser Gly Ser Leu Lys Glu Tyr Leu Pro Lys Asn Lys Asn Lys
            100                 105                 110

Ile Asn Leu Lys Gln Gln Leu Lys Tyr Ala Val Gln Ile Cys Lys Gly
        115                 120                 125

Met Asp Tyr Leu Gly Ser Arg Gln Tyr Val His Arg Asp Leu Ala Ala
130                 135                 140

Arg Asn Val Leu Val Glu Ser Glu His Gln Val Lys Ile Gly Asp Phe
145                 150                 155                 160

Gly Leu Thr Lys Ala Ile Glu Thr Asp Lys Glu Tyr Tyr Thr Val Lys
                165                 170                 175

Asp Asp Arg Asp Ser Pro Val Phe Trp Tyr Ala Pro Glu Cys Leu Met
            180                 185                 190

Gln Ser Lys Phe Tyr Ile Ala Ser Asp Val Trp Ser Phe Gly Val Thr
        195                 200                 205

Leu His Glu Leu Leu Thr Tyr Cys Asp Ser Asp Ser Ser Pro Met Ala
    210                 215                 220

Leu Phe Leu Lys Met Ile Gly Pro Thr His Gly Gln Met Thr Val Thr
225                 230                 235                 240

Arg Leu Val Asn Thr Leu Lys Glu Gly Lys Arg Leu Pro Cys Pro Pro
                245                 250                 255

Asn Cys Pro Asp Glu Val Tyr Gln Leu Met Arg Lys Cys Trp Glu Phe
            260                 265                 270

Gln Pro Ser Asn Arg Thr Ser Phe Gln Asn Leu Ile Glu Gly Phe Glu
        275                 280                 285

Ala Leu Leu Lys
    290

<210> SEQ ID NO 41
<211> LENGTH: 283
<212> TYPE: PRT
<213> ORGANISM: Homo sapiens

<400> SEQUENCE: 41

Pro Leu Gln Ser Leu Thr Cys Leu Ile Gly Glu Lys Asp Leu Arg Leu
 1               5                  10                  15

-continued

```
Leu Glu Lys Leu Gly Asp Gly Ser Phe Gly Val Val Arg Arg Gly Glu
             20                  25                  30

Trp Asp Ala Pro Ser Gly Lys Thr Val Ser Val Ala Val Lys Cys Leu
             35                  40                  45

Lys Pro Asp Val Leu Ser Gln Pro Glu Ala Met Asp Asp Phe Ile Arg
             50                  55                  60

Glu Val Asn Ala Met His Ser Leu Asp His Arg Asn Leu Ile Arg Leu
 65                  70                  75                  80

Tyr Gly Val Val Leu Thr Pro Pro Met Lys Met Val Thr Glu Leu Ala
             85                  90                  95

Pro Leu Gly Ser Leu Leu Asp Arg Leu Arg Lys His Gln Gly His Phe
            100                 105                 110

Leu Leu Gly Thr Leu Ser Arg Tyr Ala Val Gln Val Ala Glu Gly Met
            115                 120                 125

Gly Tyr Leu Glu Ser Lys Arg Phe Ile His Arg Asp Leu Ala Ala Arg
            130                 135                 140

Asn Leu Leu Leu Ala Thr Arg Asp Leu Val Lys Ile Gly Asp Phe Gly
145                 150                 155                 160

Leu Met Arg Ala Leu Pro Gln Asn Asp Asp His Tyr Val Met Gln Glu
            165                 170                 175

His Arg Lys Val Pro Phe Ala Trp Cys Ala Pro Glu Ser Leu Lys Thr
            180                 185                 190

Arg Thr Phe Ser His Ala Ser Asp Thr Trp Met Phe Gly Val Thr Leu
            195                 200                 205

Trp Glu Met Phe Thr Tyr Gly Gln Glu Pro Trp Ile Gly Leu Asn Gly
            210                 215                 220

Ser Gln Ile Leu His Lys Ile Asp Lys Glu Gly Glu Arg Leu Pro Arg
225                 230                 235                 240

Pro Glu Asp Cys Pro Gln Asp Ile Tyr Asn Val Met Val Gln Cys Trp
                245                 250                 255

Ala His Lys Pro Glu Asp Arg Pro Thr Phe Val Ala Leu Arg Asp Phe
                260                 265                 270

Leu Leu Glu Ala Gln Pro Thr Asp Met Arg Ala
            275                 280
```